United States Patent
Delisle et al.

(10) Patent No.: US 11,633,455 B2
(45) Date of Patent: Apr. 25, 2023

(54) SILK-BASED PRODUCT FORMULATIONS AND METHODS OF USE

(71) Applicant: Cocoon Biotech Inc., Mansfield, MA (US)

(72) Inventors: Scott Delisle, Mansfield, MA (US); Lindsey Easthon, Salem, MA (US); Michael Santos, Mansfield, MA (US); Ailis Tweed-Kent, Mansfield, MA (US)

(73) Assignee: COCOON BIOTECH INC., Mansfield, MA (US)

( * ) Notice: Subject to any disclaimer, the term of this patent is extended or adjusted under 35 U.S.C. 154(b) by 0 days.

(21) Appl. No.: 16/972,021

(22) PCT Filed: Jun. 4, 2019

(86) PCT No.: PCT/US2019/035306
§ 371 (c)(1),
(2) Date: Dec. 4, 2020

(87) PCT Pub. No.: WO2019/236525
PCT Pub. Date: Dec. 12, 2019

(65) Prior Publication Data
US 2021/0228684 A1   Jul. 29, 2021

Related U.S. Application Data

(60) Provisional application No. 62/757,995, filed on Nov. 9, 2018, provisional application No. 62/757,984, filed on Nov. 9, 2018, provisional application No. 62/717,025, filed on Aug. 10, 2018, provisional application No. 62/680,376, filed on Jun. 4, 2018.

(51) Int. Cl.
| | |
|---|---|
| *A61K 38/17* | (2006.01) |
| *A61P 27/04* | (2006.01) |
| *A61K 9/00* | (2006.01) |
| *A61K 9/08* | (2006.01) |
| *A61K 45/06* | (2006.01) |
| *A61K 47/10* | (2017.01) |
| *A61K 47/26* | (2006.01) |

(52) U.S. Cl.
CPC ........ *A61K 38/1767* (2013.01); *A61K 9/0048* (2013.01); *A61K 9/08* (2013.01); *A61K 45/06* (2013.01); *A61K 47/10* (2013.01); *A61K 47/26* (2013.01); *A61P 27/04* (2018.01)

(58) Field of Classification Search
None
See application file for complete search history.

(56) References Cited

U.S. PATENT DOCUMENTS

| | | | |
|---|---|---|---|
| 2007/0297981 A1* | 12/2007 | Ousler, III | A61K 31/21 514/420 |
| 2014/0235554 A1* | 8/2014 | Lawrence | A61K 47/26 514/20.8 |
| 2016/0095695 A1 | 4/2016 | Altman et al. | |
| 2016/0215103 A1 | 7/2016 | Omenetto et al. | |
| 2016/0331815 A1 | 11/2016 | Lawrence et al. | |

FOREIGN PATENT DOCUMENTS

| | | |
|---|---|---|
| KR | 20170062028 A | 6/2017 |
| WO | 2017139684 A1 | 8/2017 |
| WO | 2019094702 A1 | 5/2019 |

OTHER PUBLICATIONS

Cole "Artificial Tears: What Matters and Why" Review of Optometry, Nov. 15, 2020 (Year: 2020).*
Volkov et al. "On the Routines of Wild-Type Silk Fibroin Processing Toward Silk-Inspired Materials: A Review," Macromol. Mater. Eng. 2015, 12, 1199-1216 (Year: 2015).*
Tran et al. "A Review of the Emerging Role of Silk for the Treatment of the Eye," Pharm Res (2018) 35: 248 (Year: 2018).*
International Search Report and Written Opinion dated Sep. 4, 2019 in application No. PCT/US2019/035306 entitled "Silk-Based Product Formulations and Methods of Use".
European Search Report for Application #19816014.5 [PCT/US2019/035306] dated Mar. 29, 2022; 8 pages.

* cited by examiner

*Primary Examiner* — Christina Bradley
(74) *Attorney, Agent, or Firm* — Cantor Colburn LLP

(57) ABSTRACT

Embodiments of the present disclosure include formulations of silk-based product (SBP) formulations and related methods of preparation and use in a variety of applications in the fields of human therapeutics, veterinary medicine, agriculture, and material science.

18 Claims, No Drawings

SILK-BASED PRODUCT FORMULATIONS AND METHODS OF USE

CROSS REFERENCE TO RELATED APPLICATIONS

This application is a 35 U.S.C. § 371 U.S. National Stage Entry of International Application No. PCT/US2019/035306 filed Jun. 4, 2019, which claims the benefit of priority to 62/680,376 filed on Jun. 4, 2018 entitled Silk-Based Products for Ocular Lubrication; 62/717,025 filed Aug. 10, 2018, entitled Silk-Based Product Formulations and Methods of Use; 62/757,984 filed Nov. 9, 2018, entitled Silk-Based Products for Ocular Lubrication; and 62/757,995 filed Nov. 9, 2018, entitled Silk-Based Product Formulations and Methods of Use, the contents of each of which are herein incorporated by reference in their entirety.

FIELD OF DISCLOSURE

The present disclosure relates to formulations and methods. Specifically provided are silk-based product formulations.

BACKGROUND OF THE DISCLOSURE

Silk is a naturally occurring polymer. Most silk fibers are derived from silkworm moth (*Bombyx mori*) cocoons and include silk fibroin and sericin proteins. Silk fibroin is a fibrous material that forms a polymeric matrix bonded together with sericin. In nature, silk is formed from a concentrated solution of these proteins that are extruded through silkworm spinnerets to produce a highly insoluble fiber. These fibers have been used for centuries to form threads used in garments and other textiles.

Many properties of silk make it an attractive candidate for products serving a variety of industries. Polymer strength and flexibility has supported classical uses of silk in textiles and materials, while silk biocompatibility has gained attention more recently for applications in the fields of medicine and agriculture. Additional uses for silk in applications related to material science are being explored as technologies for producing and processing silk advance.

Although a variety of products and uses related to silk are being developed, there remains a need for methods of producing and processing silk and silk-based products that can meet the demands of modern medicine. Additionally, there remains a need for silk-based products that can leverage silk polymer strength, flexibility, and biocompatibility to meet needs in the fields of medicine, agriculture, and material sciences. The present disclosure addresses these needs by providing methods for producing and processing silk as well as formulations of silk-based products useful in a variety of industries.

SUMMARY OF THE DISCLOSURE

In some embodiments, the present disclosure provides silk-based product (SBP) formulations that comprise processed silk and at least one excipient, wherein the processed silk comprises or is derived from one or more articles, said one or more articles is selected from the group consisting of raw silk, silk fiber, silk fibroin, and a silk fibroin fragment. The SBP formulation may comprises or may be combined with one or more members selected from the group consisting of: (a) a therapeutic agent; (b) a cargo; (c) a microorganism; and (d) a biological system.

The processed silk and/or other SBP component (excipient, therapeutic agent, microbe, cargo, and/or biological system) may be present in SBP formulations at a concentration (by weight, volume, or concentration) of from about 0.0001% to about 0.001%, from about 0.001% to about 0.01%, from about 0.01% to about 1%, from about 0.05% to about 2%, from about 1% to about 5%, from about 2% to about 10%, from about 4% to about 16%, from about 5% to about 20%, from about 8% to about 24%, from about 10% to about 30%, from about 12% to about 32%, from about 14% to about 34%, from about 16% to about 36%, from about 18% to about 38%, from about 20% to about 40%, from about 22% to about 42%, from about 24% to about 44%, from about 26% to about 46%, from about 28% to about 48%, from about 30% to about 50%, from about 35% to about 55%, from about 40% to about 60%, from about 45% to about 65%, from about 50% to about 70%, from about 55% to about 75%, from about 60% to about 80%, from about 65% to about 85%, from about 70% to about 90%, from about 75% to about 95%, from about 80% to about 96%, from about 85% to about 97%, from about 90% to about 98%, from about 95% to about 99%, from about 96% to about 99.2%, from about 97% to about 99.5%, from about 98% to about 99.8%, from about 99% to about 99.9%, or greater than 99.9%.

The SBP formulation may have processed silk and/or other SBP components (excipient, therapeutic agent, microbe, cargo, and/or biological system) present at a concentration of from about 0.01 pg/mL to about 1 pg/mL, from about 0.05 pg/mL to about 2 pg/mL, from about 1 pg/mL to about 5 pg/mL, from about 2 pg/mL to about 10 pg/mL, from about 4 pg/mL to about 16 pg/mL, from about 5 pg/mL to about 20 pg/mL, from about 8 pg/mL to about 24 pg/mL, from about 10 pg/mL to about 30 pg/mL, from about 12 pg/mL to about 32 pg/mL, from about 14 pg/mL to about 34 pg/mL, from about 16 pg/mL to about 36 pg/mL, from about 18 pg/mL to about 38 pg/mL, from about 20 pg/mL to about 40 pg/mL, from about 22 pg/mL to about 42 pg/mL, from about 24 pg/mL to about 44 pg/mL, from about 26 pg/mL to about 46 pg/mL, from about 28 pg/mL to about 48 pg/mL, from about 30 pg/mL to about 50 pg/mL, from about 35 pg/mL to about 55 pg/mL, from about 40 pg/mL to about 60 pg/mL, from about 45 pg/mL to about 65 pg/mL, from about 50 pg/mL to about 75 pg/mL, from about 60 pg/mL to about 240 pg/mL, from about 70 pg/mL to about 350 pg/mL, from about 80 pg/mL to about 400 pg/mL, from about 90 pg/mL to about 450 pg/mL, from about 100 pg/mL to about 500 pg/mL, from about 0.01 ng/mL to about 1 ng/mL, from about 0.05 ng/mL to about 2 ng/mL, from about 1 ng/mL to about 5 ng/mL, from about 2 ng/mL to about 10 ng/mL, from about 4 ng/mL to about 16 ng/mL, from about 5 ng/mL to about 20 ng/mL, from about 8 ng/mL to about 24 ng/mL, from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 µg/mL to about 1 µg/mL, from about 0.05 µg/mL to about 2 µg/mL, from about 1 µg/mL to about 5 µg/mL, from about 2 µg/mL to about 10 µg/mL, from about 4 µg/mL to about 16 µg/mL, from about 5 µg/mL to about 20 µg/mL, from about 8 µg/mL to about 24 µg/mL, from about 10 µg/mL to about 30 µg/mL, from about 12 µg/mL to about 32 µg/mL, from about 14 µg/mL to about 34 µg/mL, from about 16 µg/mL to about 36 µg/mL, from about 18 µg/mL to about 38 µg/mL, from about 20 µg/mL to about 40 µg/mL, from about 22 µg/mL to about 42 µg/mL, from about 24 µg/mL to about 44 µg/mL, from about 26 µg/mL to about 46 µg/mL, from about 28 µg/mL to about 48 µg/mL, from about 30 µg/mL to about 50 µg/mL, from about 35 µg/mL to about 55 µg/mL, from about 40 µg/mL to about 60 µg/mL, from about 45 µg/mL to about 65 µg/mL, from about 50 µg/mL to about 75 µg/mL, from about 60 µg/mL to about 240 µg/mL, from about 70 µg/mL to about 350 µg/mL, from about 80 µg/mL to about 400 µg/mL, from about 90 µg/mL to about 450 µg/mL, from about 100 µg/mL to about 500 µg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL, from about 0.05 g/mL to about 2 g/mL, from about 1 g/mL to about 5 g/mL, from about 2 g/mL to about 10 g/mL, from about 4 g/mL to about 16 g/mL, or from about 5 g/mL to about 20 g/mL.

The SBP formulation may have processed silk and/or other SBP components (excipient, therapeutic agent, microbe, cargo, and/or biological system) present in SBPs at a concentration of from about 0.01 pg/kg to about 1 pg/kg, from about 0.05 pg/kg to about 2 pg/kg, from about 1 pg/kg to about 5 pg/kg, from about 2 pg/kg to about 10 pg/kg, from about 4 pg/kg to about 16 pg/kg, from about 5 pg/kg to about 20 pg/kg, from about 8 pg/kg to about 24 pg/kg, from about 10 pg/kg to about 30 pg/kg, from about 12 pg/kg to about 32 pg/kg, from about 14 pg/kg to about 34 pg/kg, from about 16 pg/kg to about 36 pg/kg, from about 18 pg/kg to about 38 pg/kg, from about 20 pg/kg to about 40 pg/kg, from about 22 pg/kg to about 42 pg/kg, from about 24 pg/kg to about 44 pg/kg, from about 26 pg/kg to about 46 pg/kg, from about 28 pg/kg to about 48 pg/kg, from about 30 pg/kg to about 50 pg/kg, from about 35 pg/kg to about 55 pg/kg, from about 40 pg/kg to about 60 pg/kg, from about 45 pg/kg to about 65 pg/kg, from about 50 pg/kg to about 75 pg/kg, from about 60 pg/kg to about 240 pg/kg, from about 70 pg/kg to about 350 pg/kg, from about 80 pg/kg to about 400 pg/kg, from about 90 pg/kg to about 450 pg/kg, from about 100 pg/kg to about 500 pg/kg, from about 0.01 ng/kg to about 1 ng/kg, from about 0.05 ng/kg to about 2 ng/kg, from about 1 ng/kg to about 5 ng/kg, from about 2 ng/kg to about 10 ng/kg, from about 4 ng/kg to about 16 ng/kg, from about 5 ng/kg to about 20 ng/kg, from about 8 ng/kg to about 24 ng/kg, from about 10 ng/kg to about 30 ng/kg, from about 12 ng/kg to about 32 ng/kg, from about 14 ng/kg to about 34 ng/kg, from about 16 ng/kg to about 36 ng/kg, from about 18 ng/kg to about 38 ng/kg, from about 20 ng/kg to about 40 ng/kg, from about 22 ng/kg to about 42 ng/kg, from about 24 ng/kg to about 44 ng/kg, from about 26 ng/kg to about 46 ng/kg, from about 28 ng/kg to about 48 ng/kg, from about 30 ng/kg to about 50 ng/kg, from about 35 ng/kg to about 55 ng/kg, from about 40 ng/kg to about 60 ng/kg, from about 45 ng/kg to about 65 ng/kg, from about 50 ng/kg to about 75 ng/kg, from about 60 ng/kg to about 240 ng/kg, from about 70 ng/kg to about 350 ng/kg, from about 80 ng/kg to about 400 ng/kg, from about 90 ng/kg to about 450 ng/kg, from about 100 ng/kg to about 500 ng/kg, from about 0.01 µg/kg to about 1 µg/kg, from about 0.05 µg/kg to about 2 µg/kg, from about 1 µg/kg to about 5 µg/kg, from about 2 µg/kg to about 10 µg/kg, from about 4 µg/kg to about 16 µg/kg, from about 5 µg/kg to about 20 µg/kg, from about 8 µg/kg to about 24 µg/kg, from about 10 µg/kg to about 30 µg/kg, from about 12 µg/kg to about 32 µg/kg, from about 14 µg/kg to about 34 µg/kg, from about 16 µg/kg to about 36 µg/kg, from about 18 µg/kg to about 38 µg/kg, from about 20 µg/kg to about 40 µg/kg, from about 22 µg/kg to about 42 µg/kg, from about 24 µg/kg to about 44 µg/kg, from about 26 µg/kg to about 46 µg/kg, from about 28 µg/kg to about 48 µg/kg, from about 30 µg/kg to about 50 µg/kg, from about 35 µg/kg to about 55 µg/kg, from about 40 µg/kg to about 60 µg/kg, from about 45 µg/kg to about 65 µg/kg, from about 50 µg/kg to about 75 µg/kg, from about 60 µg/kg to about 240 µg/kg, from about 70 µg/kg to about 350 µg/kg, from about 80 µg/kg to about 400 µg/kg, from about 90 µg/kg to about 450 µg/kg, from about 100 µg/kg to about 500 µg/kg, from about 0.01 mg/kg to about 1 mg/kg, from about 0.05 mg/kg to about 2 mg/kg, from about 1 mg/kg to about 5 mg/kg, from about 2 mg/kg to about 10 mg/kg, from about 4 mg/kg to about 16 mg/kg, from about 5 mg/kg to about 20 mg/kg, from about 8 mg/kg to about 24 mg/kg, from about 10 mg/kg to about 30 mg/kg, from about 12 mg/kg to about 32 mg/kg, from about 14 mg/kg to about 34 mg/kg, from about 16 mg/kg to about 36 mg/kg, from about 18 mg/kg to about 38 mg/kg, from about 20 mg/kg to about 40 mg/kg, from about 22 mg/kg to about 42 mg/kg, from about 24 mg/kg to about 44 mg/kg, from about 26 mg/kg to about 46 mg/kg, from about 28 mg/kg to about 48 mg/kg, from about 30 mg/kg to about 50 mg/kg, from about 35 mg/kg to about 55 mg/kg, from about 40 mg/kg to about 60 mg/kg, from about 45 mg/kg to about 65 mg/kg, from about 50 mg/kg to about 75 mg/kg, from about 60 mg/kg to about 240 mg/kg, from about 70 mg/kg to about 350 mg/kg, from about 80 mg/kg to about 400 mg/kg, from about 90 mg/kg to about 450 mg/kg, from about 100 mg/kg to about 500 mg/kg, from about 0.01 g/kg to about 1 g/kg, from about 0.05 g/kg to about 2 g/kg, from about 1 g/kg to about 5 g/kg, from about 2 g/kg to about 10 g/kg, from about 4 g/kg to about 16 g/kg, or from about 5 g/kg to about 20 g/kg, from about 10 g/kg to about 50 g/kg, from about 15 g/kg to about 100 g/kg, from about 20 g/kg to about 150 g/kg, from about 25 g/kg to about 200 g/kg, from about 30 g/kg to about 250 g/kg, from about 35 g/kg to about 300 g/kg, from about 40 g/kg to about 350 g/kg, from about 45 g/kg to about 400 g/kg, from about 50 g/kg to about 450 g/kg, from about 55 g/kg to about 500 g/kg, from about 60 g/kg to about 550 g/kg, from about 65 g/kg to about 600 g/kg, from about 70 g/kg to about 650 g/kg, from about 75 g/kg to about 700 g/kg, from about 80 g/kg to about 750 g/kg, from about 85 g/kg to about 800 g/kg, from about 90 g/kg to about 850 g/kg, from about 95 g/kg to about 900 g/kg, from about 100 g/kg to about 950 g/kg, or from about 200 g/kg to about 1000 g/kg.

The SBP formulation may comprise processed silk and/or other SBP components (excipient, therapeutic agent, microbe, cargo, and/or biological system) present in SBPs at a concentration of from about 0.1 pM to about 1 pM, from about 1 pM to about 10 pM, from about 2 pM to about 20 pM, from about 3 pM to about 30 pM, from about 4 pM to about 40 pM, from about 5 pM to about 50 pM, from about 6 pM to about 60 pM, from about 7 pM to about 70 pM, from about 8 pM to about 80 pM, from about 9 pM to about 90 pM, from about 10 pM to about 100 pM, from about 11 pM to about 110 pM, from about 12 pM to about 120 pM, from about 13 pM to about 130 pM, from about 14 pM to about 140 pM, from about 15 pM to about 150 pM, from about 16 pM to about 160 pM, from about 17 pM to about 170 pM, from about 18 pM to about 180 pM, from about 19 pM to about 190 pM, from about 20 pM to about 200 pM, from about 21 pM to about 210 pM, from about 22 pM to about 220 pM, from about 23 pM to about 230 pM, from about 24 pM to about 240 pM, from about 25 pM to about 250 pM, from about 26 pM to about 260 pM, from about 27 pM to about 270 pM, from about 28 pM to about 280 pM, from about 29 pM to about 290 pM, from about 30 pM to about 300 pM, from about 31 pM to about 310 pM, from about 32 pM to about 320 pM, from about 33 pM to about 330 pM, from about 34 pM to about 340 pM, from about 35 pM to about 350 pM, from about 36 pM to about 360 pM, from about 37 pM to about 370 pM, from about 38 pM to about 380 pM, from about 39 pM to about 390 pM, from about 40 pM to about 400 pM, from about 41 pM to about 410 pM, from about 42 pM to about 420 pM, from about 43 pM to about 430 pM, from about 44 pM to about 440 pM, from about 45 pM to about 450 pM, from about 46 pM to about 460 pM, from about 47 pM to about 470 pM, from about 48 pM to about 480 pM, from about 49 pM to about 490 pM, from about 50 pM to about 500 pM, from about 51 pM to about 510 pM, from about 52 pM to about 520 pM, from about 53 pM to about 530 pM, from about 54 pM to about 540 pM, from about 55 pM to about 550 pM, from about 56 pM to about 560 pM, from about 57 pM to about 570 pM, from about 58 pM to about 580 pM, from about 59 pM to about 590 pM, from about 60 pM to about 600 pM, from about 61 pM to about 610 pM, from about 62 pM to about 620 pM, from about 63 pM to about 630 pM, from about 64 pM to about 640 pM, from about 65 pM to about 650 pM, from about 66 pM to about 660 pM, from about 67 pM to about 670 pM, from about 68 pM to about 680 pM, from about 69 pM to about 690 pM, from about 70 pM to about 700 pM, from about 71 pM to about 710 pM, from about 72 pM to about 720 pM, from about 73 pM to about 730 pM, from about 74 pM to about 740 pM, from about 75 pM to about 750 pM, from about 76 pM to about 760 pM, from about 77 pM to about 770 pM, from about 78 pM to about 780 pM, from about 79 pM to about 790 pM, from about 80 pM to about 800 pM, from about 81 pM to about 810 pM, from about 82 pM to about 820 pM, from about 83 pM to about 830 pM, from about 84 pM to about 840 pM, from about 85 pM to about 850 pM, from about 86 pM to about 860 pM, from about 87 pM to about 870 pM, from about 88 pM to about 880 pM, from about 89 pM to about 890 pM, from about 90 pM to about 900 pM, from about 91 pM to about 910 pM, from about 92 pM to about 920 pM, from about 93 pM to about 930 pM, from about 94 pM to about 940 pM, from about 95 pM to about 950 pM, from about 96 pM to about 960 pM, from about 97 pM to about 970 pM, from about 98 pM to about 980 pM, from about 99 pM to about 990 pM, from about 100 pM to about 1 nM, from about 0.1 nM to about 1 nM, from about 1 nM to about 10 nM, from about 2 nM to about 20 nM, from about 3 nM to about 30 nM, from about 4 nM to about 40 nM, from about 5 nM to about 50 nM, from about 6 nM to about 60 nM, from about 7 nM to about 70 nM, from about 8 nM to about 80 nM, from about 9 nM to about 90 nM, from about 10 nM to about 100 nM, from about 11 nM to about 110 nM, from about 12 nM to about 120 nM, from about 13 nM to about 130 nM, from about 14 nM to about 140 nM, from about 15 nM to about 150 nM, from about 16 nM to about 160 nM, from about 17 nM to about 170 nM, from about 18 nM to about 180 nM, from about 19 nM to about 190 nM, from about 20 nM to about 200 nM, from about 21 nM to about 210 nM, from about 22 nM to about 220 nM, from about 23 nM to about 230 nM, from about 24 nM to about 240 nM, from about 25 nM to about 250 nM, from about 26 nM to about 260 nM, from about 27 nM to about 270 nM, from about 28 nM to about 280 nM, from about 29 nM to about 290 nM, from about 30 nM to about 300 nM, from about 31 nM to about 310 nM, from about 32 nM to about 320 nM, from about 33 nM to about 330 nM, from about 34 nM to about 340 nM, from about 35 nM to about 350 nM, from about 36 nM to about 360 nM, from about 37 nM to about 370 nM from about 38 nM to about 380 nM from about 39 nM to about 390 nM, from about 40 nM to about 400 nM, from about 41 nM to about 410 nM, from about 42 nM to about 420 nM, from about 43 nM to about 430 nM, from about 44 nM to about 440 nM, from about 45 nM to about 450 nM, from about 46 nM to about 460 nM, from about 47 nM to about 470 nM, from about 48 nM to about 480 nM, from about 49 nM to about 490 nM, from about 50 nM to about 500 nM, from about 51 nM to about 510 nM, from about 52 nM to about 520 nM, from about 53 nM to about 530 nM, from about 54 nM to about 540 nM, from about 55 nM to about 550 nM, from about 56 nM to about 560 nM, from about 57 nM to about 570 nM, from about 58 nM to about 580 nM, from about 59 nM to about 590 nM, from about 60 nM to about 600 nM, from about 61 nM to about 610 nM, from about 62 nM to about 620 nM, from about 63 nM to about 630 nM, from about 64 nM to about 640 nM, from about 65 nM to about 650 nM, from about 66 nM to about 660 nM, from about 67 nM to about 670 nM, from about 68 nM to about 680 nM, from about 69 nM to about 690 nM, from about 70 nM to about 700 nM, from about 71 nM to about 710 nM, from about 72 nM to about 720 nM, from about 73 nM to about 730 nM, from about 74 nM to about 740 nM, from about 75 nM to about 750 nM, from about 76 nM to about 760 nM, from about 77 nM to about 770 nM, from about 78 nM to about 780 nM, from about 79 nM to about 790 nM, from about 80 nM to about 800 nM, from about 81 nM to about 810 nM, from about 82 nM to about 820 nM, from about 83 nM to about 830 nM, from about 84 nM to about 840 nM, from about 85 nM to about 850 nM, from about 86 nM to about 860 nM, from about 87 nM to about 870 nM, from about 88 nM to about 880 nM, from about 89 nM to about 890 nM, from about 90 nM to about 900 nM, from about 91 nM to about 910 nM, from about 92 nM to about 920 nM, from about 93 nM to about 930 nM, from about 94 nM to about 940 nM, from about 95 nM to about 950 nM, from about 96 nM to about 960 nM, from about 97 nM to about 970 nM, from about 98 nM to about 980 nM, from about 99 nM to about 990 nM, from about 100 nM to about 1 μM, from about 0.1 μM to about 1 μM, from about 1 μM to about 10 μM, from about 2 μM to about 20 μM, from about 3 μM to about 30 μM, from about 4 µM to about 40 µM, from about 5 µM to about 50 µM, from about 6 µM to about 60 µM, from about 7 µM to about 70 µM, from about 8 µM to about 80 µM, from about 9 µM to about 90 µM, from about 10 µM to about 100 µM, from about 11 µM to about 110 µM, from about 12 µM to about 120 µM, from about 13 µM to about 130 µM, from about 14 µM to about 140 µM, from about 15 µM to about 150 µM, from about 16 µM to about 160 µM, from about 17 µM to about 170 µM, from about 18 µM to about 180 µM, from about 19 µM to about 190 µM, from about 20 µM to about 200 µM, from about 21 µM to about 210 µM, from about 22 µM to about 220 µM, from about 23 µM to about 230 µM, from about 24 µM to about 240 µM, from about 25 µM to about 250 µM, from about 26 µM to about 260 µM, from about 27 µM to about 270 µM, from about 28 µM to about 280 µM, from about 29 µM to about 290 µM, from about 30 µM to about 300 µM, from about 31 µM to about 310 µM, from about 32 µM to about 320 µM, from about 33 µM to about 330 µM, from about 34 µM to about 340 µM, from about 35 µM to about 350 µM, from about 36 µM to about 360 µM, from about 37 µM to about 370 µM, from about 38 µM to about 380 µM, from about 39 µM to about 390 µM, from about 40 µM to about 400 µM, from about 41 µM to about 410 µM, from about 42 µM to about 420 µM, from about 43 µM to about 430 µM, from about 44 µM to about 440 µM, from about 45 µM to about 450 µM, from about 46 µM to about 460 µM, from about 47 µM to about 470 µM, from about 48 µM to about 480 µM, from about 49 µM to about 490 µM, from about 50 µM to about 500 µM, from about 51 µM to about 510 µM, from about 52 µM to about 520 µM, from about 53 µM to about 530 µM, from about 54 µM to about 540 µM, from about 55 µM to about 550 µM, from about 56 µM to about 560 µM, from about 57 µM to about 570 µM, from about 58 µM to about 580 µM, from about 59 µM to about 590 µM, from about 60 µM to about 600 µM, from about 61 µM to about 610 µM, from about 62 µM to about 620 µM, from about 63 µM to about 630 µM, from about 64 µM to about 640 µM, from about 65 µM to about 650 µM, from about 66 µM to about 660 µM, from about 67 µM to about 670 µM, from about 68 µM to about 680 µM, from about 69 µM to about 690 µM, from about 70 µM to about 700 µM, from about 71 µM to about 710 µM, from about 72 µM to about 720 µM, from about 73 µM to about 730 µM, from about 74 µM to about 740 µM, from about 75 µM to about 750 µM, from about 76 µM to about 760 µM, from about 77 µM to about 770 µM, from about 78 µM to about 780 µM, from about 79 µM to about 790 µM, from about 80 µM to about 800 µM, from about 81 µM to about 810 µM, from about 82 µM to about 820 µM, from about 83 µM to about 830 µM, from about 84 µM to about 840 µM, from about 85 µM to about 850 µM, from about 86 µM to about 860 µM, from about 87 µM to about 870 µM, from about 88 µM to about 880 µM, from about 89 µM to about 890 µM, from about 90 µM to about 900 µM, from about 91 µM to about 910 µM, from about 92 µM to about 920 µM, from about 93 µM to about 930 µM, from about 94 µM to about 940 µM, from about 95 µM to about 950 µM, from about 96 µM to about 960 µM, from about 97 µM to about 970 µM, from about 98 µM to about 980 µM, from about 99 µM to about 990 µM, from about 100 µM to about 1 mM, from about 0.1 mM to about 1 mM, from about 1 mM to about 10 mM from about 2 mM to about 20 mM, from about 3 mM to about 30 mM, from about 4 mM to about 40 mM, from about 5 mM to about 50 mM, from about 6 mM to about 60 mM, from about 7 mM to about 70 mM, from about 8 mM to about 80 mM, from about 9 mM to about 90 mM, from about 10 mM to about 100 mM, from about 11 mM to about 110 mM, from about 12 mM to about 120 mM, from about 13 mM to about 130 mM, from about 14 mM to about 140 mM from about 15 mM to about 150 mM, from about 16 mM to about 160 mM from about 17 mM to about 170 mM, from about 18 mM to about 180 mM, from about 19 mM to about 190 mM, from about 20 mM to about 200 mM, from about 21 mM to about 210 mM, from about 22 mM to about 220 mM, from about 23 mM to about 230 mM, from about 24 mM to about 240 mM, from about 25 mM to about 250 mM, from about 26 mM to about 260 mM, from about 27 mM to about 270 mM, from about 28 mM to about 280 mM, from about 29 mM to about 290 mM, from about 30 mM to about 300 mM, from about 31 mM to about 310 mM, from about 32 mM to about 320 mM, from about 33 mM to about 330 mM, from about 34 mM to about 340 mM, from about 35 mM to about 350 mM, from about 36 mM to about 360 mM, from about 37 mM to about 370 mM, from about 38 mM to about 380 mM, from about 39 mM to about 390 mM, from about 40 mM to about 400 mM, from about 41 mM to about 410 mM, from about 42 mM to about 420 mM, from about 43 mM to about 430 mM, from about 44 mM to about 440 mM, from about 45 mM to about 450 mM, from about 46 mM to about 460 mM from about 47 mM to about 470 mM from about 48 mM to about 480 mM from about 49 mM to about 490 mM, from about 50 mM to about 500 mM, from about 51 mM to about 510 mM, from about 52 mM to about 520 mM, from about 53 mM to about 530 mM, from about 54 mM to about 540 mM, from about 55 mM to about 550 mM, from about 56 mM to about 560 mM, from about 57 mM to about 570 mM, from about 58 mM to about 580 mM, from about 59 mM to about 590 mM, from about 60 mM to about 600 mM, from about 61 mM to about 610 mM, from about 62 mM to about 620 mM, from about 63 mM to about 630 mM, from about 64 mM to about 640 mM, from about 65 mM to about 650 mM from about 66 mM to about 660 mM, from about 67 mM to about 670 mM from about 68 mM to about 680 mM, from about 69 mM to about 690 mM, from about 70 mM to about 700 mM, from about 71 mM to about 710 mM, from about 72 mM to about 720 mM, from about 73 mM to about 730 mM, from about 74 mM to about 740 mM, from about 75 mM to about 750 mM, from about 76 mM to about 760 mM, from about 77 mM to about 770 mM, from about 78 mM to about 780 mM, from about 79 mM to about 790 mM, from about 80 mM to about 800 mM, from about 81 mM to about 810 mM, from about 82 mM to about 820 mM from about 83 mM to about 830 mM, from about 84 mM to about 840 mM from about 85 mM to about 850 mM, from about 86 mM to about 860 mM, from about 87 mM to about 870 mM, from about 88 mM to about 880 mM, from about 89 mM to about 890 mM, from about 90 mM to about 900 mM, from about 91 mM to about 910 mM, from about 92 mM to about 920 mM, from about 93 mM to about 930 mM, from about 94 mM to about 940 mM, from about 95 mM to about 950 mM, from about 96 mM to about 960 mM, from about 97 mM to about 970 mM, from about 98 mM to about 980 mM, from about 99 mM to about 990 mM from about 100 mM to about 1 M, from about 1 M to about 10 M, from about 2 M to about 20 M, from about 3 M to about 30 M, from about 4 M to about 40 M, from about 5 M to about 50 M, from about 6 M to about 60 M, from about 7 M to about 70 M, from about 8 M to about 80 M, from about 9 M to about 90 M, from about 10 M to about 100 M, from about 11 M to about 110 M, from about 12 M to about 120 M, from about 13 M to about 130 M, from about 14 M to about 140 M, from about 15 M to about 150 M, from about 16 M to about 160 M, from about 17 M to about 170 M, from about 18 M to about 180

M, from about 19 M to about 190 M, from about 20 M to about 200 M, from about 21 M to about 210 M, from about 22 M to about 220 M, from about 23 M to about 230 M, from about 24 M to about 240 M, from about 25 M to about 250 M, from about 26 M to about 260 M, from about 27 M to about 270 M, from about 28 M to about 280 M, from about 29 M to about 290 M, from about 30 M to about 300 M, from about 31 M to about 310 M, from about 32 M to about 320 M, from about 33 M to about 330 M, from about 34 M to about 340 M, from about 35 M to about 350 M, from about 36 M to about 360 M, from about 37 M to about 370 M, from about 38 M to about 380 M, from about 39 M to about 390 M, from about 40 M to about 400 M, from about 41 M to about 410 M, from about 42 M to about 420 M, from about 43 M to about 430 M, from about 44 M to about 440 M, from about 45 M to about 450 M, from about 46 M to about 460 M, from about 47 M to about 470 M, from about 48 M to about 480 M, from about 49 M to about 490 M, or from about 50 M to about 500 M.

The processed silk of the SBP formulation may comprise silk fibroin, wherein the silk fibroin comprises a beta-sheet, an alpha-helix, a coiled coil, and/or a random coil. Silk fibroin may comprise a silk fibroin polymer, a silk fibroin monomer, and/or a silk fibroin fragment. The processed silk may comprise a silk fibroin fragment, wherein the silk fibroin fragment comprises a silk fibroin heavy chain fragment and/or a silk fibroin light chain fragment. The processed silk may comprise silk fibroin, wherein the silk fibroin comprises a plurality of silk fibroin fragments. The plurality of silk fibroin fragments may comprise a molecular weight of from about 1 kDa to about 350 kDa.

The SBP may comprise one or more formats selected from the group consisting of adhesives, capsules, cakes, coatings, cocoons, combs, cones, cylinders, discs, emulsions, fibers, films, foams, gels, grafts, hydrogels, implants, mats, membranes, microspheres, nanofibers, nanoparticles, nanospheres, nets, organogels, particles, patches, powders, rods, scaffolds, sheets, solids, solutions, sponges, sprays, spuns, suspensions, tablets, threads, tubes, vapors, and yarns. The format may be a solution. The format may be a hydrogel. The format may be a cake. The format may be a powder. The format may be a film.

The processed silk of the SBP formulation may comprise silk fibroin at a concentration between 0.5% and 5%. In one aspect, the silk fibroin is present at a concentration of 0.5%. In one aspect, the silk fibroin is present at a concentration of 1%. In one aspect, the silk fibroin is present at a concentration of 2.5%. In one aspect, the silk fibroin is present at a concentration of 3%. In one aspect, the silk fibroin is present at a concentration of 5%.

The SBP formulation is in a solution which may be, but is not limited to, phosphate buffer, borate buffer, and phosphate buffered saline. The solution may further comprise propylene glycol, sucrose and/or trehalose. Propylene glycol may be present in a concentration of 1%. Sucrose may be present in a concentration such as, but not limited to, 10 mM, 50 mM, 100 mM and 150 mM. Trehalose may be present in a concentration such as, but not limited to, 10 mM, 50 mM, 100 mM and 150 mM.

In some embodiments, the present disclosure provides a silk-based product (SBP) for ocular lubrication that includes processed silk and an ocular therapeutic agent. The processed silk may be silk fibroin. The SBP may include from about 0.0001% to about 35% (w/v) of silk fibroin. The silk fibroin may be prepared by degumming for a time of a 30-minute boil, a 60-minute boil, a 90-minute boil, a 120-minute boil, and a 480-minute boil. The SBP may be stressed. The SBP may be stressed by one or more methods which includes heating the SBP to 60° C. and autoclaving the SBP. The SBP may include one or more excipients. The one or more excipients may include one or more of sucrose, lactose, phosphate salts, sodium chloride, potassium phosphate monobasic, potassium phosphate dibasic, sodium phosphate dibasic, sodium phosphate monobasic, polysorbate 80, phosphate buffer, phosphate buffered saline, sodium hydroxide, sorbitol, mannitol, lactose USP, Starch 1500, microcrystalline cellulose, potassium chloride, sodium borate, boric acid, sodium borate decahydrate, magnesium chloride hexahydrate, calcium chloride dihydrate, sodium hydroxide, Avicel, dibasic calcium phosphate dehydrate, tartaric acid, citric acid, fumaric acid, succinic acid, malic acid, hydrochloric acid, polyvinylpyrrolidone, copolymers of vinylpyrrolidone and vinylacetate, hydroxypropylcellulose, hydroxyethylcellulose, hydroxypropylmethylcellulose, polyvinyl alcohol, polyethylene glycol, acacia, trehalose, and sodium carboxymethylcellulose. One or more of the excipients may include phosphate buffer. One or more of the excipients may include phosphate buffered saline. One or more of the excipients may include sucrose. The excipients may include boric acid, sodium borate decahydrate, sodium chloride, potassium chloride, magnesium chloride hexahydrate, calcium chloride dihydrate, sodium hydroxide, and hydrochloric acid. The SBP may include at least one excipient selected from one or more members of the group consisting of sorbitol, triethylamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol, glycerol formal, hydroxypropyl beta-cyclodextrin, kolliphor 124, kolliphor 181, kolliphor 188, kolliphor 407, kolliphor EL (cremophor EL), cremophor RH 40, cremophor RH 60, dalpha-tocopherol, PEG 1000 succinate, polysorbate 20, polysorbate 80, solutol HS 15, sorbitan monooleate, poloxamer-407, poloxamer-188, Labrafil M-1944CS, Labrafil M-2125CS, Labrasol, Gellucire 44/14, Softigen 767, mono- and di-fatty acid esters of PEG 300, PEG 400, or PEG 1750, kolliphor RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, medium chain triglycerides of coconut oil, medium chain triglycerides of palm seed oil, beeswax, d-alpha-tocopherol, oleic acid, medium-chain mono-glycerides, medium-chain di-glycerides, alpha-cyclodextrin, beta-cyclodextrin, hydroxypropyl-beta-cyclodextrin, sulfo-butylether-beta-cyclodextrin, hydrogenated soy phosphatidylcholine, distearoylphosphatidylglycerol, L-alphadimyristoylphosphatidylcholine, L-alpha-dimyristoylphosphatidylglycerol, PEG 300, PEG 300 caprylic/capric glycerides (Softigen 767), PEG 300 linoleic glycerides (Labrafil M-2125CS), PEG 300 oleic glycerides (Labrafil M-1944CS), PEG 400, PEG 400 caprylic/capric glycerides (Labrasol), polyoxyl 40 stearate (PEG 1750 monosterate), polyoxyl 8 stearate (PEG 400 monosterate), polysorbate 20, polysorbate 80, polyvinyl pyrrolidone, propylene carbonate, propylene glycol, solutol HS15, sorbitan monooleate (Span 20), sulfobutylether-beta-cyclodextrin, transcutol, triacetin, 1-dodecylazacyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, glycerin, and PEG 4 kDa. The SBP may be formulated, and the formulation may be as hydrogels and solutions. The formulation may be a hydrogel. The formulation may be a solution. The silk fibroin concentration in the solution may be below 1% (w/v). The SBP may be a solution, and the SBP may be stressed. The SBP may be a hydrogel, and the SBP may be stressed. The SBP may be a solution, and the solution may shear thin. The solutions may have the viscosity of a gel at a lower shear rate. The solutions may have the viscosity of a fluid at higher shear rates. The ocular therapeutic agent may be a nonsteroidal anti-inflammatory drug (NSAID) or protein. The SBP may be formulated for topical administration. The SBP may be formulated for ocular administration. The SBP may be biocompatible. The SBP may include any of the samples listed in any of the Tables 1-4.

In some embodiments, the present disclosure provides a method of preparing the SBP formulations comprising: (a) preparing the processed silk, wherein the processed silk comprises or is derived from one or more articles selected from the group consisting of raw silk, silk fiber, silk fibroin, and a silk fibroin fragment; and (b) preparing the SBP formulation using the processed silk. In some embodiments, the present disclosure provides a method of treating an ocular indication of a subject that includes administering to the subject any of the SBPs described herein. The ocular indication may be dry eye disease. The SBP may be administered to the eye. The SBP may be administered via topical administration. The topical administration of SBP may be as drops or sprays. The SBP may shear thin. The shear thinning of the SBPs may tune the residence time in the eye. The residence time of the SBP may be increased.

DETAILED DESCRIPTION OF THE DISCLOSURE

Embodiments of the present disclosure relate to silk-based products (SBPs), formulations and their methods of use. The term "silk" generally refers to a fibrous material formed by insects and some other species that includes tightly bonded protein filaments. Herein, the term "silk" is used in the broadest sense and may embrace any forms, variants, or derivatives of silk discussed.

Silk fibers from silkworm moth (Bombyx mori) cocoons include two main components, sericin (usually present in a range of 20-30%) and silk fibroin (usually present in a range of 70-80%). Structurally, silk fibroin forms the center of the silk fibers and sericin acts as the gum coating the fibers. Sericin is a gelatinous protein that holds silk fibers together with many of the characteristic properties of silk (see Qi et al. (2017) Int J Mol Sci 18:237 and Deptuch et al. (2017) Materials 10:1417, the contents of each of which are herein incorporated by reference in their entireties). Silk fibroin is an insoluble fibrous protein consisting of layers of antiparallel beta sheets. Its primary structure mainly consists of recurrent serine, alanine, and glycine repeating units. The isoelectric point of silk fibroin has been determined to be around 4.2. Silk fibroin monomers include a complex of heavy chain (around 350 kDa) and light chain (around 25 kDa) protein components. Typically, the chains are joined by a disulfide bond. With some forms, heavy chain and light chain segments are non-covalently bound to a glycoprotein, p25. Polymers of silk fibroin monomers may form through hydrogen bonding between monomers, typically increasing mechanical strength (see Qi et 7. (2017) Int J Mol Sci 18:237). During silk processing, fragments of silk fibroin monomers may be produced, including, but not limited to, fragments of heavy and/or light chains. These fragments may retain the ability to form hydrogen bonds with silk fibroin monomers and fragments thereof. Herein, the term "silk fibroin" is used in its broadest sense and embraces silk fibroin polymers, silk fibroin monomers, silk fibroin heavy and light chains, silk fibroin fragments, and variants, derivatives, or mixtures thereof from any of the wild type, genetically modified, or synthetic sources of silk described herein.

The present disclosure includes methods of preparing processed silk and SBPs, different forms of SBP formulations, and a variety of applications for utilizing processed silk, SBPs, and SBP formulations alone or in combination with various compounds, compositions, and devices.

I. Silk-Based Products and Formulations

As used herein, the term "silk-based product" or "SBP" refers to any compound, mixture, or other entity that is made up of or that is combined with processed silk. "Processed silk," as used herein, refers to any forms of silk harvested, obtained, synthesized, formatted, manipulated, or altered through at least one human intervention. SBPs may include a variety of different formats suited for a variety of different applications. Examples of SBP formats include, but are not limited to, fibers, nanofibers, mats, films, foams, membranes, rods, tubes, gels, hydrogels, microspheres, nanospheres, solutions, patches, grafts, adhesives, capsules, cones, cylinders, cakes, discs, emulsions, nanoparticles, nets, organogels, particles, scaffolds, sheets, solids, sponges, sprays, spuns, suspensions, tablets, threads, vapors, yarns, and powders. Additional formats are described herein.

SBPs may find utility in variety of fields and for a variety of applications. Such utility may be due to the unique physical and chemical properties of silk. These physical and chemical properties include, but are not limited to, biocompatibility, biodegradability, bioresorbability, solubility, crystallinity, porosity, mechanical strength, thermal stability, hydrophobicity, and transparency. In some embodiments, SBPs may be used for one or more therapeutic applications, agricultural applications, and/or material science applications. Such SBPs may include processed silk, wherein the processed silk is or is derived from one or more of raw silk, silk fibers, silk fibroin, and silk fibroin fragments. Processed silk present in some SBPs may include one or more silk fibroin polymers, silk fibroin monomers, and/or silk fibroin fragments. In some embodiments, silk fibroin fragments include silk fibroin heavy chain fragments and/or silk fibroin light chain fragments. Some silk fibroin present in SBPs include a plurality of silk fibroin fragments. Each of the plurality of silk fibroin fragments may have a molecular weight of from about 1 kDa to about 400 kDa.

In some embodiments, SBPs may be formulations (e.g., SBP formulations). As used herein, the term "formulation" refers to a mixture of two or more components or the process of preparing such mixtures. In some embodiments, the formulations are low cost and eco-friendly. In some embodiments, the preparation or manufacturing of formulations is low cost and eco-friendly. In some embodiments, the preparation or manufacturing of formulations is scalable. In some embodiments, SBPs are prepared by extracting silk fibroin via degumming silk yarn. In some embodiments, the yarn is medical grade. In some embodiments the yarn may be silk sutures. The extracted silk fibroin may then be dissolved in a solvent (e.g. water, aqueous solution, organic solvent). The dissolved silk fibroin may then be dried (e.g., oven dried, air dried, or freeze-dried). In some embodiments, dried silk fibroin is formed into formats described herein. In some embodiments, that format is a solution. In some embodiments, that format is a powder. In some embodiments, that format is a hydrogel. In some embodiments, formulations include one or more excipients, carriers, additional components, and/or therapeutic agents to generate SBPs. In some embodiments, formulations of processed silks are prepared during the manufacture of SBPs.

Formulation components and/or component ratios may be modulated to affect one or more SBP properties, effects, and/or applications. Variations in the concentration of silk fibroin, choice of excipient, the concentration of excipient, the osmolarity of the formulation, and the method of formulation represent non-limiting examples of differences in formulation that may alter properties, effects, and applications of SBPs. In some embodiments, the formulation of SBPs may modulate their physical properties. Examples of physical properties include solubility, density, and thickness. In some embodiments, the formulation of SBPs may modulate their mechanical properties. Examples of mechanical properties that may be modulated include, but are not limited to, mechanical strength, tensile strength, elongation capabilities, elasticity, compressive strength, stiffness, shear strength, toughness, torsional stability, temperature stability, moisture stability, viscosity, and reeling rate.

In some embodiments, the formulations are prepared to be sterile. As used herein, the term "sterile" refers to something that is aseptic. In some embodiments, SBPs are prepared from sterile materials. In some embodiments, SBPs are prepared and then sterilized. In some embodiments, processed silk is degummed and then sterilized. In some embodiments, processed silk is sterilized and then degummed. Processed silk and/or SBPs may be sterilized via gamma radiation, autoclave (e.g., autoclave sterilization), filtration, electron beam, and any other method known to those skilled in the art.

A pharmaceutical composition (e.g., SBP formulation) in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of therapeutic agent or other compounds. The amount of therapeutic agent may generally be equal to the dosage of therapeutic agent administered to a subject and/or a convenient fraction of such dosage including, but not limited to, one-half or one-third of such a dosage.

Sources of Silk

SBP formulations may include processed silk obtained from one or more of a variety of sources. Processed silk may include raw silk. "Raw silk," as used herein, refers to silk that has been harvested, purified, isolated, or otherwise collected from silk producers. The term "silk producer," as used herein, refers to any organism capable of producing silk. Raw silk has been processed in large quantities for thousands of years, primarily from silkworms (*Bombyx mori*), which use silk to form their cocoon. Raw silk from silkworm cocoons includes silk fibroin and sericin that is secreted onto silk fibroin during cocoon formation. Raw silk may be harvested as a silk fiber. As used herein, the term "silk fiber" refers to any silk that is in the form of a filament or thread. Silk fibers may vary in length and width and may include, but are not limited to, yarns, strings, threads, and nanofibers. In some embodiments, raw silk may be obtained in the form of a yarn.

SBPs may include processed silk obtained from any one of a variety of sources. Processed silk may include raw silk. "Raw silk," as used herein, refers to silk that has been harvested, purified, isolated, or otherwise collected from silk producers. The term "silk producer," as used herein, refers to any organism capable of producing silk. Raw silk has been processed in large quantities for thousands of years, primarily from silkworms (*Bombyx mori*), which use silk to form their cocoon. Raw silk from silkworm cocoons includes silk fibroin and sericin that is secreted onto silk fibroin during cocoon formation. Raw silk may be harvested as a silk fiber. As used herein, the term "silk fiber" refers to any silk that is in the form of a filament or thread. Silk fibers may vary in length and width and may include, but are not limited to, yarns, strings, threads, and nanofibers. In some embodiments, raw silk may be obtained in the form of a yarn.

In some embodiments, processed silk includes silk obtained from a silk producer. Silk producers may be organisms found in nature (referred to herein as "wild type organisms") or they may be genetically modified organisms. There are many species of silk producers in nature capable of producing silk. Silk producers may be insect species, such as silkworms. Some silk producers include arachnid species. In some embodiments, silk producers include species of mollusk. Silk produced by different silk producing species may vary in physical and/or chemical properties. Such properties may include amino acid content, secondary structure (e.g. beta-sheet content), mechanical properties (e.g. elasticity), and others. In some embodiments, the present disclosure provides blends of processed silk from multiple silk producers or other sources (e.g., recombinant or synthetic silk). Such blends may have synergistic properties that are absent from processed silk obtained from single sources or from alternative blends. For example, Janani G et al. describe a silk scaffold fabricated by blending *Bombyx mori* silk fibroin with cell adhesion motif (RGD) rich *Antheraea assamensis* silk fibroin which displays enhanced liver-specific functions of cultured hepatocytes (Acta Biomater. 2018 February; 67:167-182, the contents of which are herein incorporated by reference in their entirety).

In some embodiments, processed silk may be obtained from the silkworm species *Bombyx mori*. Other examples of silk producer species include, but are not limited to, *Bombyx mandarina, Bombyx sinesis, Anaphe moloneyi, Anaphe panda, Anaphe reticulate, Anaphe ambrizia, Anaphe carteri, Anaphe venata, Anapha inacta, Antheraea assamensis, Antheraea assama, Antheraea mylitta, Antheraea pernyi, Antheraea lumamai, Antheraea polyphemus, Antheraea oculea, Anisota senatoria, Apis mellifera, Araneus diademaus, Araneus cavaticus, Automeris io, Atticus alas, Copaxa multifenestrata, Coscinocera hercules, Callosamia promethea, Eupackardia calleta, Eurprosthenops australis, Gonometa postica, Gonometa rufobrunnea, Hyalophora cecropia, Hyulophora eurnulus, Hiulophora gloveri, Miranda auretia, Nephila madagascarensis, Nephila clavipes, Pachypasa otus, Pachypasa atus, Philosamia ricini, Pinna squamosa, Rothschildia hesperis, Rothschildia lebeau, Samia Cynthia,* and *Samia ricini*.

Genetically Modified Organisms

In some embodiments, silk producers are genetically modified organisms. As used herein, the term "genetically modified organism" or "GMO" refers to any living entity that includes or is derived from some form of genetic manipulation. The genetic manipulation may include any human intervention that alters the genetic material of an organism. In some embodiments, the genetic manipulation is limited to selecting organisms for reproduction based on genotype or phenotype. In some embodiments, genetic manipulation includes adding, deleting, and/or substituting one or more nucleotides of a wild type DNA sequence. The genetic manipulation may include the use of recombinant DNA technology. Recombinant DNA technology involves the exchange of DNA sections between DNA molecules. Some genetic manipulation involves the transfer of genetic material from another organism to the GMO. GMOs including such transferred genetic material are referred to as "transgenic organisms." Some genetic materials may be synthetically produced (see e.g., Price et al. (2014) J Control Release 190:304-313; and Deptuch et al. (2017) Materials 10:1417, the contents of each of which are herein incorporated by reference in their entirety). The genetic material may be transferred by way of a vector. The vector may be a plasmid. In some embodiments the vector is a virus. Some genetic manipulations involve the use of inhibitory RNA. In some embodiments, genetic manipulations are carried out using clustered regularly interspaced short palindromic repeats (CRISPR) technology.

GMO silk producers may be species generally known to produce silk (e.g., any of those described above). Some GMO silk producers are species not generally known to produce silk, but that are genetically manipulated to produce silk. Such organisms may be genetically modified to include at least one nucleic acid encoding at least one silk protein (e.g., silk fibroin, silk fibroin heavy chains, silk fibroin light chains, sericin, or fragments or derivates thereof). Some GMO silk producers are genetically manipulated to produce silk with one or more altered silk properties (e.g., strength, stability, texture, etc.). Some genetic manipulations affect characteristics of the GMO that are not directly related to silk production or silk properties (e.g., disease resistance, reproduction, etc.).

In some embodiments, GMO silk producers include genetically modified silkworms (e.g., *Bombyx mori*). Genetically modified silkworms may include genetic manipulations that result in silkworm production of silk fibroin strands that include degradable linkers. In some embodiments, GMOs are arachnids (e.g., spiders).

In some embodiments, GMO silk producers are cells. Such cells may be grown in culture and may include any type of cell capable of expressing protein. The cells may be prokaryotic or eukaryotic cells. In some embodiments, silk producer cells include bacterial cells, insect cells, yeast cells, mammalian cells, or plant cells. Cells may be transformed or transduced with nucleic acids encoding one or more silk proteins (e.g., silk fibroin, sericin, or fragments or derivates thereof).

In some embodiments, GMO silk producers may include, but are not limited to, *Bombyx mori*, soybeans, *Arabidopsis*, *Escherichia coli*, *Pichia pastoris*, potato, tobacco, baby hamster kidney cells, mice, and goats (e.g., see Tokareva et al. (2013) Microb Biotechnol 6(6):651-63 and Deptuch et al. (2017) Materials 10:1417). In some embodiments, silk may be produced in green plants (e.g., see International Publication Number WO2001090389, the contents of which are herein incorporated by reference in their entirety).

Recombinant Silk

As used herein, the term "recombinant silk" refers to any form of silk produced using recombinant DNA technology. Recombinant silk proteins may include amino acid sequences corresponding to silk proteins produced by wild type organisms; amino acid sequences not found in nature; and/or amino acid sequences found in nature, but not associated with silk. Some recombinant silk includes amino acid sequences with repetitive sequences that contribute to polymer formation and/or silk properties (e.g., see Deptuch et al. (2017) Materials 10:1417). Nucleic acid segments encoding repetitive sequences may be incorporated into plasmids after self-ligation into multimers (e.g., see Price et al. (2014) J Control Release 190:304-313).

In some embodiments, recombinant silk may be encoded by expression plasmids.

In some embodiments, recombinant silk may be expressed as a monomer. The monomers may be combined with other monomers or other silk proteins to obtain multimers (e.g., see Deptuch et al (2017) Materials 10:1417). Some monomers may be combined according to methods known in the art. Such methods may include, but are not limited to, ligation, step-by-step ligation, recursive directional ligation, native chemical ligation, and concatemerization.

In some embodiments, recombinant silk may be expressed using the "PiggyBac" vector. The PiggyBac vector includes a spider transposon that is compatible with expression in silkworms.

In some embodiments, recombinant silk may be produced in a silk producing species. Examples of silk producing species include, but are not limited to, *Bombyx mori*, *Bombyx mandarina*, *Bombyx sinesis*, *Anaphe moloneyi*, *Anaphe panda*, *Anaphe reticulate*, *Anaphe ambrizia*, *Anaphe carteri*, *Anaphe venata*, *Anapha infacta*, *Antheraea assamensis*, *Antheraea paphis*, *Antheraea assama*, *Antheraea mylitta*, *Antheraea perny*, *Antheraea yamamai*, *Antheraea polyphemus*, *Antheraea oculea*, *Anisota senatoria*, *Apis mellifera*, *Araneus diadematus*, *Araneus cavaticus*, *Automeris io*, *Atticus atlas*, *Coscinocera hercules*, *Callosamia promethea*, *Copaxa multifenestrata*, *Eupackardia calleta Eurprosthenops australis*, *Gonometa postica*, *Gonometa rufobrunnea*, *Hyalophora cecropia*, *Hyalophora euryalus*, *Hwulophora gloveri*, *Miranda auretia*, *Nephila madagascarensis*, *Nephila clavipes*, *Pachypasa otus*, *Pachypasa atus*, *Philosamia ricini*, *Pinna squamosa*, *Rothschildia hesperis*, *Rothschildia lebeau*, *Samia Cynthia*, and *Samia ricini*.

Synthetic Silk

In some embodiments, SBP formulations include synthetic silk. As used herein, the term "synthetic silk" refers to silk prepared without the aid of a silk producer. Synthetic silk may be prepared using standard methods of peptide synthesis. Such methods typically include the formation of amino acid polymers through successive rounds of polymerization. Amino acids used may be obtained through commercial sources and may include natural or non-natural amino acids. In some embodiments, synthetic silk polypeptides are prepared using solid-phase synthesis methods. The polypeptides may be linked to resin during synthesis. In some embodiments, polypeptide synthesis may be conducted using automated methods.

Synthetic silk may include polypeptides that are identical to wild type silk proteins (e.g., silk fibroin heavy chain, silk fibroin light chain, or sericin) or fragments thereof. In some embodiments, synthetic silk includes polypeptides that are variants of silk proteins or silk protein fragments. Some synthetic silk includes polypeptides with repeating units that correspond with or are variations of those found in silk fibroin heavy chain proteins.

Processed Silk

In some embodiments, SBP formulations include processed silk. Various processing methods may be used to obtain specific forms or formats of processed silk. Such processing methods may include, but are not limited to, acidifying, air drying, alkalinizing, annealing, autoclaving, chemical crosslinking, chemical modification, concentration, cross-linking, degumming, diluting, dissolving, dry spinning, drying, electrifying, electrospinning, electrospraying, emulsifying, encapsulating, extraction, extrusion, gelation, harvesting, heating, lyophilization, molding, oven drying, pH alteration, precipitation, purification, shearing, sonication, spinning, spray drying, spray freezing, spraying, vapor annealing, vortexing, and water annealing. The processing steps may be used to prepare final SBPs or they may be used to generate processed silk preparations. As used herein, the term "processed silk preparation" is generally used to refer to processed silk or compositions that include processed silk that are prepared for or obtained during or after one or more processing steps. Processed silk preparations may be SBPs, may be components of SBPs, SBP formulations or may be used as a starting or intermediate composition in the preparation of SBPs. Processed silk preparations may include other components related to processing (e.g., solvents, solutes, impurities, catalysts, enzymes, intermediates, etc.). Processed silk preparations that include silk fibroin may be referred to as silk fibroin preparations. In some embodiments, processed silk manufacturing is simple, scalable, and/or cost effective.

In some embodiments, processed silk may be prepared as, provided as, or included in a yarn, thread, string, a nanofiber, a textile, a cloth, a fabric, a particle, a nanoparticle, a microsphere, a nanosphere, a powder, a solution, a gel, a hydrogel, an organogel, a mat, a film, a foam, a membrane, a rod, a tube, a patch, a sponge, a scaffold, a capsule, an excipient, an implant, a solid, a coating, and/or a graft.

In some embodiments, processed silk may be stored frozen or dried to a stable soluble form. Processed silk may be frozen with cryoprotectants. Cryoprotectants may include, but are not limited to, phosphate buffer, sucrose, trehalose, histidine, and any other cryoprotectant known to one of skill in the art. In some embodiments, SBPs may be stored frozen or dried to a stable soluble form. In some embodiments, the SBPs may be solutions.

In some embodiments, preparation of processed silk and/or SBP formulations may be scaled up for manufacturing at a large scale. In some embodiments, production of processed silk and/or SBP formulations may be accomplished with automated machinery.

Any of the methods known in the art and/or described herein may be used to extract silk fibroin. The yield of silk fibroin from extraction may be, but is not limited to, 1%, 2%, 3%, 4%, 5%, 6%, 7%, 8%, 9% 10%, 15%, 20% 25%, 30%, 35%, 40%, 45%, 50%, 55%, 60%, 65%, 70%, 75%, 80%, 85%, 90%, 95%, 99% or greater than 99%.

Silk Properties

In some embodiments, processed silk may be selected based on or prepared to include features affecting one or more properties of the processed silk. Such properties may include, but are not limited to, stability, complex stability, composition stability, payload retention or release, payload release rate, wettability, mechanical strength, tensile strength, elongation capabilities, elasticity, compressive strength, stiffness, shear strength, toughness, hydrophobicity, torsional stability, temperature stability, moisture stability, strength, flexibility, solubility, crystallinity, viscosity, and porosity. Features affecting one or more processed silk properties may include silk secondary structure. Secondary structure refers to three-dimensional arrangements of polypeptide chains based on local interactions between neighboring residues. Common secondary structures include β-pleated sheets and α-helices. Silk secondary structure may enhance or attenuate solubility. In some embodiments, β-sheet secondary structure content may enhance processed silk crystallinity. "Crystallinity" refers to the degree of structure and arrangement between atoms or molecules in a compound, with increased structure yielding greater crystallinity. β-sheet structures may be antiparallel β-sheets. In some embodiments, processed silk includes polypeptides with random coil secondary structure. Some processed silk includes polypeptides with coiled coil secondary structure.

In some embodiments, processed silk includes a combination of two or more forms of secondary structure. In some embodiments, processed silk may include polypeptides with multiple repeats. As used herein when referring to polypeptides, the term "multiple repeat" refers to an amino acid sequence that is duplicated two or more times in succession within a polypeptide. Silk fibroin heavy chains include multiple repeats that enable static interactions between parallel silk fibroin heavy chains. Multiple repeats may include repeats of the sequences GAGAGS (SEQ ID NO: 1) and/or GA. In some embodiments, the A of GA dipeptides may be replaced with S or Y. In some embodiments, multiple repeats may include any of those presented in Qi et al. (2017) Int J Mol Sci 18:237, the contents of which are herein incorporated by reference in their entirety. Multiple repeats may enable formation of stable, crystalline regions of antiparallel β-sheets.

Processed silk may include silk fibroin forms described by Qi et a. (2017) Int J Mol Sci 18:237 and Cao et a. (2009) Int J Mol Sci 10:1514-1524, the contents of each of which are herein incorporated by reference in their entirety. These silk fibroin forms are referred to as silk I, silk II, and silk III. Silk I and silk II forms are commonly found in nature. Silk I predominantly includes random coil secondary structures. Silk II predominantly includes β-sheet secondary structure. Silk III predominantly includes an unstable structure.

Processed silk may be treated to modulate β-sheet content and/or crystallinity. In some embodiments these treatments are used to reduce the solubility and/or hydrophobicity of the silk fibroin or silk fibroin composition. Treatments may include, but are not limited to, alteration of the pH, sonication of the silk fibroin, incorporation of an excipient, increasing or decreasing the temperature, treatment with acid, treatment with formic acid, treatment with glycerol, treatment with an alcohol, treatment with methanol, treatment with ethanol, treatment with isopropanol, and/or treatment with a mixture of alcohol and water. In some embodiments, treatments result in transition between forms of silk I, II, or III. Such methods may include any of those described in Cao et a. (2009) Int J Mol Sci 10:1514-1524).

Strength and Stability

Processed silk strength and stability are important factors for many applications. In some embodiments, processed silk may be selected based on or prepared to maximize mechanical strength, tensile strength, elongation capabilities, elasticity, flexibility, compressive strength, stiffness, shear strength, toughness, torsional stability, biological stability, resistance to degradation, and/or moisture stability. In some embodiments, processed silk had a non-acidic microenvironment. In some embodiments, the non-acidic microenvironment enhances the stability of processed silk and or SBPs. In some embodiments, the non-acidic microenvironment enhances the stability of therapeutic agents formulated with the processed silk and/or SBP.

Biocompatibility

In some embodiments, processed silk may be selected based on or prepared to maximize biocompatibility. As used herein, the term "biocompatibility" refers to the degree with which a substance avoids provoking a negative biological response in an organism exposed to the substance. The negative biological response may include an inflammatory response and/or local sensitization, hemorrhage, and/or other complications known to those skilled in the art. In some embodiments, administration of processed silk or an SBP does not induce an inflammatory response, local sensitization, hemorrhage, and/or other complications known to those skilled in the art. In some embodiments, contact with processed silk or an SBP does not induce an inflammatory response, local sensitization, hemorrhage, and/or other complications known to those skilled in the art. In some embodiments, no inflammatory response, local sensitization, hemorrhage, and/or other complications occur after up to 7 months of contact with processed silk or an SBP. In some embodiments, processed silk biocompatibility is enhanced through preparations that produce only non-toxic byproducts during degradation. In some embodiments, exposure to an SBP generates a tolerable biological response, within an acceptable threshold known to those skilled in the art. In some embodiments, processed silk is biocompatible in humans and human whole blood. In some embodiments, processed silk is biocompatible in animals. In some embodiments, processed silk produces no adverse reactions, no acute inflammation, and no immunogenicity in vivo. In some embodiments, the processed silk or SBP is safe to use in vivo. In some embodiments, processed silk or SBPs are biocompatible and/or tolerable m vitro. In some embodiments, processed silk or SBPs are biocompatible and/or tolerable in vivo. In some embodiments, no inflammatory response, local sensitization, hemorrhage, and/or other complications occur after up to 1 day, up to 3 days, up to 1 week, up to 1 month, up to 2 months, up to 3 months, up to 4 months, up to 5 months, up to 6 months, up to 7 months, up to 8 months, up to 9 months, up to 10 months, up to 11 months, or up to 1 year of contact with processed silk or an SBP.

Biodegradability

In some embodiments, processed silk may be selected based on or prepared to maximize biodegradability. As used herein, the term "biodegradability" refers to the degree with which a substance avoids provoking a negative response to an environment exposed to the substance as it deteriorates. The negative environmental response may include a response to toxic byproducts generated as a substance deteriorates. In some embodiments, processed silk biodegradability is enhanced through preparations that produce only non-toxic byproducts during degradation. In some embodiments, processed silk biodegradability is enhanced through preparations that produce only inert amino acid byproducts. In some embodiments, the SBP and/or SBP by products are considered naturally derived and environmentally and/or eco-friendly.

Anti-Evaporative Properties

In some embodiments, processed silk may be selected based on or prepared to reduce the evaporation of a solution. In some embodiments, processed silk may reduce the evaporation of a solution. In some embodiments, an SBP may demonstrate anti-evaporative properties by creating a water and/or water vapor barrier, as taught in Marelli et al. (2008) Sci Rep 6:25263, the contents of which are herein incorporated by reference in their entirety. In some embodiments, processed silk may extend the lifetime or residence time of an SBP product due to its ability to prevent evaporation. In some embodiments, processed silk may increase the amount of time required for a solution to evaporate. In some embodiments, processed silk may be selected based on or prepared to reduce the evaporation of a solution. In some embodiments, processed silk may reduce the evaporation of a solution. In some embodiments, processed silk may extend the lifetime or residence time of an SBP product due to its ability to prevent evaporation. In some embodiments, processed silk may increase the amount of time required for a solution to evaporate.

Demulcent

In some embodiments, processed silk and/or SBPs may act as demulcents. As used herein, the term "demulcent" refers to a substance that relieves irritation or inflammation of the mucous membranes by forming a protective film. This film may mimic a mucous membrane. Demulcents may also provide lubrication. Demulcents may include non-polymeric demulcents and polymer demulcents. Added demulcents may modulate the viscosity of an SBP or product containing an SBP.

Surfactant

In some embodiments, processed silk and/or SBPs may act as a surfactant. As used herein, the term "surfactant" refers to a substance that reduces the surface tension between two materials. In some embodiments, the SBP is a solution. In some embodiments, the SBP is a hydrogel. In some embodiments, the SBP has a surface tension similar to that of water. In some embodiments, the SBP has a surface tension similar to that of human tears. Human tears have been reported to have a surface tension of 43.6 mN/m, as described in Sweeney et al. (2013) Experimental Eye Research 117: 28-38, the contents of which are herein incorporated by reference in their entirety. In some embodiments, the surface tension of the SBP may be controlled by the concentration of processed silk. In some embodiments, the surface tension is about 30-60 mN/m. In some embodiments, the surface tension of an SBP is about 35-55 mN/m. In some embodiments, the surface tension of an SBP is about 40-50 mN/m.

Antimicrobial and Bacteriostatic Properties

In some embodiments, processed silk may be based on or prepared to maximize antimicrobial properties. As used herein, the term "antimicrobial" properties refer to the ability of processed silk or SBPs to inhibit, deter the growth of microorganisms and/or kill the microorganisms. Microorganisms may include bacteria, fungi, protozoans, and viruses. In some embodiments, the antimicrobial properties may include but are not limited to antibacterial, antifungal, antiseptic, and/or disinfectant properties. In some embodiments, antimicrobial properties of silk may be modulated during one or more processing steps or during fabrication of a SBP. In some embodiments, antimicrobial properties may be modulated by the varying the source of silk utilized for the preparation of SBPs (Mirghani, M et al. 2012, Investigation of the spider web of antibacterial activity, (MICOTRiBE) 2012; the contents of which are incorporated by reference in their entirety). In some embodiments, processed silk and SBPs described herein may possess antimicrobial properties against gram positive bacteria. In some embodiments, processed silk and SBPs described herein may possess antimicrobial properties against gram negative bacteria.

In some embodiments, processed silk may be based on or prepared to maximize bacteriostatic properties. As used herein, the term "bacteriostatic" refers to a substance that prevents bacterial reproduction and may or may not kill said bacteria. Bacteriostatic agents prevent the growth of bacteria. In some embodiments, bacteriostatic properties of silk may be modulated during one or more processing steps or during fabrication of a SBP. In some embodiments, bacteriostatic properties may be modulated by the varying the source of silk utilized for the preparation of SBPs. In some embodiments, processed silk and SBPs described herein may possess bacteriostatic properties against gram positive bacteria. In some embodiments, processed silk and SBPs described herein may possess bacteriostatic properties against gram negative bacteria.

Anti-Inflammatory Properties

In some embodiments, processed silk or SBPs may have or be prepared to maximize anti-inflammatory properties. It has been reported that silk fibroin peptide derived from silkworm *Bombyx mori* exhibited anti-inflammatory activity in a mice model of inflammation (Kim et al., (2011) BMB Rep 44(12):787-92; the contents of which are incorporated by reference in their entirety). In some embodiments, processed silk or SBPs may be administered to a subject alone or in combination with other therapeutic agents to elicit anti-inflammatory effects. It is contemplated that processed silk or SBPs alone or combination with other therapeutic agents may be used to treat various inflammatory diseases. For example, processed silk or SBPs may reduce signs and symptoms of inflammation, such as but not limited to, swelling, redness, tenderness, rashes, fever, and pain.

Harvesting Silk

In some embodiments, processed silk is harvested from silk producer cocoons. Cocoons may be prepared by cultivating silkworm moths and allowing them to pupate. Once fully formed, cocoons may be treated to soften sericin and allow for unwinding of the cocoon to form raw silk fiber. The treatment may include treatment with hot air, steam, and/or boiling water. Raw silk fibers may be produced by unwinding multiple cocoons simultaneously. The resulting raw silk fibers include both silk fibroin and sericin. Subsequent processing may be carried out to remove sericin from the raw silk fibers or from later forms of processed silk or SBPs. In some embodiments, raw silk may be harvested directly from the silk glands of silk producers. Raw silk may be harvested from wild type or GMO silk producers.

Extraction of Sericin/Degumming

In some embodiments, sericin may be removed from processed silk, a process referred to herein as "degumming." The processed silk may include raw silk, which includes sericin secreted during cocoon formation. Methods of degumming may include heating (e.g., boiling) in a degumming solution. As used herein, the term "degumming solution" refers to a composition used for sericin removal that includes at least one degumming agent. As used herein, a "degumming agent" refers to any substance that may be used for sericin removal. Heating in degumming solution may reduce or eliminate sericin from processed silk. In some embodiments, heating in degumming solution includes boiling. Heating in degumming solution may be followed by rinsing to enhance removal of sericin that remains after heating. In some embodiments, raw silk is degummed before further processing or utilization in SBPs. In other embodiments, raw silk is further processed or otherwise incorporated into a SBP prior to degumming. Such methods may include any of those presented in European Patent No. EP2904134 or United States Patent Publication No. US2017031287, the contents of each of which are herein incorporated by reference in their entirety.

Degumming agents and/or degumming solutions may include, but are not limited to water, alcohols, soaps, acids, alkaline solutions, and enzyme solutions. In some embodiments, degumming solutions may include salt-containing alkaline solutions. Such solutions may include sodium carbonate. Sodium carbonate concentration may be from about 0.01 M to about 0.3 M. In some embodiments, sodium carbonate concentration may be from about 0.01 M to about 0.05 M, about 0.05 M to about 0.1 M, from about 0.1 M to about 0.2 M, or from about 0.2 M to about 0.3 M. In some embodiments, sodium carbonate concentration may be 0.02 M. In some embodiments, degumming solutions may include from about 0.01% to about % (w/v) sodium carbonate. In some embodiments, degumming solutions may include from about 0.01% to about 10% (w/v) sodium carbonate. In some embodiments, degumming solutions may include from about 0.01% (w/v) to about 1% (w/v), from about 1% (w/v) to about 2% (w/v), from about 2% (w/v) to about 3% (w/v), from about 3% (w/v) to about 4% (w/v), from about 4% (w/v) to about 5% (w/v), or from about 5% (w/v) to about 10% (w/v) sodium carbonate. In some embodiments, degumming solutions may include sodium dodecyl sulfate (SDS). Such degumming solutions may include any those described in Zhang el al. (2012) J Translational Med 10:117, the contents of which are herein incorporated by reference in their entirety. In some embodiments, degumming solutions include boric acid. Such solutions may include any of those taught in European Patent No. EP2904134, the contents of which are herein incorporated by reference in their entirety. In some embodiments, the degumming solution may have a pH of from about 0 to about 5, from about 2 to about 7, from about 4 to about 9, from about 5 to about 11, from about 6 to about 12, from about 6.5 to about 8.5, from about 7 to about 10, from about 8 to about 12, and from about 10 to about 14. In some embodiments, processed silk is present in degumming solutions at concentrations of from about 0.1% to about 2%, from about 0.5% to about 3%, from about 1% to about 4%, or from about 2% to about 5% (w/v). In some embodiments, processed silk is present in degumming solutions at concentrations of greater than 5% (w/v).

Degumming may be carried out by "boiling" in degumming solutions at or near atmospheric boiling temperatures. As used herein, "boiling" does not necessarily mean at or above 100° C. Boiling may be properly used to describe heating the solution at a temperature that is less than or greater than 100° C. Some boiling temperatures may be from about 60° C. to about 115° C. In some embodiments, boiling is carried out at 100° C. In some embodiments, boiling is carried out at about 60° C., about 65° C., about 70° C., about 75° C., about 80° C., about 85° C., about 86° C., about 87° C., about 88° C., about 89° C., about 90° C., about 91° C., about 92° C., about 93° C., about 94° C., about 95° C., about % C, about 97° C., about 98° C., about 99° C., about 100° C., about 101° C., about 102° C., about 103° C., about 104° C., about 105° C., about 106° C., about 107° C., about 108° C., about 109° C., about 110° C., about 111° C., about 112° C., about 113° C., about 114° C., about 115° C. or greater than 115° C.

In some embodiments, degumming includes heating in degumming solution for a period of from about 10 seconds to about 45 seconds, from about 30 seconds to about 90 seconds, from about 1 min to about 5 min, from about 2 min to about 10 min, from about 5 min to about 15 min, from about 10 min to about 25 min, from about 20 min to about 35 min, from about 30 min to about 50 min, from about 45 min to about 75 min, from about 60 min to about 95 min, from about 90 min to about 125 min, from about 120 min to about 175 min, from about 150 min to about 200 min, from about 180 min to about 250 min, from about 210 min to about 350 min, from about 240 min to about 400 min, from about 270 min to about 450 min, from about 300 min to about 500 min, from about 330 min to about 550 min, from about 360 min to about 600 min, from about 390 min to about 700 min, from about 420 min to about 800 min, from about 450 min to about 900 min, from about 480 min to about 1000 min, from about 510 min to about 1100 min, from about 540 min to about 1200 min, from about 570 min to about 1300 min, from about 600 min to about 1400 min, from about 630 min to about 1500 min, from about 660 min to about 1600 min, from about 690 min to about 1700 min, from about 720 min to about 1800 min, from about 1440 min to about 1900 min, from about 1480 min to about 2000 min, or longer than 2000 min.

In some embodiments, processed silk preparations are characterized by the number of minutes boiling was carried out for preparation, a value referred to herein as "minute boil" or "mb." The minute boil value of a preparation may be associated with known or presumed characteristics of similar preparations with the same minute boil value. Such characteristics may include concentration and/or molecular weight of preparation compounds, proteins, or protein fragments altered during boiling. In some embodiments, processed silk preparations (e.g., silk fibroin preparations) have an mb value of from about 1 mb to about 5 mb, from about 2 mb to about 10 mb, from about 5 mb to about 15 mb, from about 10 mb to about 25 mb, from about 20 mb to about 35 mb, from about 30 mb to about 50 mb, from about 45 mb to about 75 mb, from about 60 mb to about 95 mb, from about 90 mb to about 125 mb, from about 120 mb to about 175 mb, from about 150 mb to about 200 mb, from about 180 mb to about 250 mb, from about 210 mb to about 350 mb, from about 240 mb to about 400 mb, from about 270 mb to about 450 mb, from about 300 mb to about 480 mb, or greater than 480 mb.

In some embodiments, degumming may be carried out by treatment with high temperatures and/or pressures. Such methods may include any of those presented International Patent Application Publication No. WO2017200659, the contents of which are herein incorporated by reference in their entirety.

Silk Fibroin Boiling Time

SBP formulations may comprise processed silk with varying molecular weights. SBP formulations may include low molecular weight silk fibroin. As used herein, the term "low molecular weight silk fibroin" refers to silk fibroin with a molecular weight below 200 kDa. Some SBP formulations may include high molecular weight silk fibroin. As used herein, the term "high molecular weight silk fibroin" refers to silk fibroin with a molecular weight equal to or greater than 200 kDa. In some embodiments, the silk fibroin molecular weight is defined by the degumming boiling time. In some embodiments, silk fibroin with a 480-minute boil, or "mb" may produce be a low molecular weight silk fibroin when compared to a silk fibroin produced with a 120-minute boil, or "mb". In some aspects, the 120 mb silk fibroin is considered to be high molecular weight silk fibroin in comparison to the 480 mb silk fibroin. In some embodiments, a longer boiling time is considered to be lower molecular weight silk fibroin. In some embodiments, a shorter boiling time is considered to be a higher molecular weight silk fibroin. In some embodiments, the boiling time is about 15 minutes, about 30 minutes, about 60 minutes, about 90 minutes, about 120 minutes, or about 480 minutes. In some embodiments, an SBP is prepared with processed silk with a single boiling time. In some embodiments, an SBP contains a blend of processed silk with different boiling times.

In one embodiment, the SBP formulation includes 30 mb silk fibroin.

In one embodiment, the SBP formulation includes 60 mb silk fibroin.

In one embodiment, the SBP formulation includes 90 mb silk fibroin.

In one embodiment, the SBP formulation includes 120 mb silk fibroin.

In one embodiment, the SBP formulation includes 480 mb silk fibroin.

Processed Silk Preparation Characterization

Preparations of processed silk sometimes include mixtures of silk fibroin polymers, silk fibroin monomers, silk fibroin heavy chains, silk fibroin light chains, sericin, and/or fragments of any of the foregoing. Where the exact contents and ratios of components in such processed silk preparations are unknown, the preparations may be characterized by one or more properties of the preparation or by conditions or methods used to obtain the preparations.

Solubility and Concentration

Processed silk preparations may include solutions that include processed silk (also referred to herein as "processed silk solutions"). Processed silk solutions may be characterized by processed silk concentration. For example, processed silk may be dissolved in a solvent after degumming to generate a processed silk solution of silk fibroin for subsequent use. Solvent used to dissolve processed silk may be a buffer. In some embodiments, solvent used is an organic solvent. Organic solvents may include, but are not limited to hexafluoroisopropanol (HFIP), methanol, isopropanol, ethanol, or combinations thereof. In some embodiments, solvents include a mixture of an organic solvent and water or an aqueous solution. Solvents may include water or aqueous solutions. Aqueous solutions may include aqueous salt solutions that include one or more salts. Such salts may include but are not limited to lithium bromide (LiBr), lithium thiocyanate, Ajisawa's reagent, a chaotropic agent, calcium nitrate, or other salts capable of solubilizing silk, including any of those disclosed in U.S. Pat. No. 9,623,147 (the content of which is herein incorporated by reference in its entirety). In some embodiments, solvents used in processed silk solutions include high salt solutions. In some embodiments, the solution comprises 5 to 13 M LiBr. The concentration of LiBr may be 9.3 M. In some embodiments, solvents used in processed silk solutions may include Ajisawa's reagent, as described in Zheng et al. (2016) Journal of Biomaterials Applications 31:450-463, the content of which is herein incorporated by reference in its entirety. Ajisawa's reagent comprises a mixture of calcium chloride, ethanol, and water in a molar ratio of 1:2:8 respectively.

In some embodiments, processed silk may be present in processed silk solutions at a concentration of from about 0.01% (w/v) to about 1% (w/v), from about 0.05% (w/v) to about 2% (w/v), from about 1% (w/v) to about 5% (w/v), from about 2% (w/v) to about 10% (w/v), from about 4% (w/v) to about 16% (w/v), from about 5% (w/v) to about 20% (w/v), from about 8% (w/v) to about 24% (w/v), from about 10% (w/v) to about 30% (w/v), from about 12% (w/v) to about 32% (w/v), from about 14% (w/v) to about 34% (w/v), from about 16% (w/v) to about 36% (w/v), from about 18% (w/v) to about 38% (w/v), from about 20% (w/v) to about 40% (w/v), from about 22% (w/v) to about 42% (w/v), from about 24% (w/v) to about 44% (w/v), from about 26% (w/v) to about 46% (w/v), from about 28% (w/v) to about 48% (w/v), from about 30% (w/v) to about 50% (w/v), from about 35% (w/v) to about 55% (w/v), from about 40% (w/v) to about 60% (w/v), from about 45% (w/v) to about 65% (w/v), from about 50% (w/v) to about 70% (w/v), from about 55% (w/v) to about 75% (w/v), from about 60% (w/v) to about 80% (w/v), from about 65% (w/v) to about 85% (w/v), from about 70% (w/v) to about 90% (w/v), from about 75% (w/v) to about 95% (w/v), from about 80% (w/v) to about 96% (w/v), from about 85% (w/v) to about 97% (w/v), from about 90% (w/v) to about 98% (w/v), from about 95% (w/v) to about 99% (w/v), from about 96% (w/v) to about 99.2%

(w/v), from about 97% (w/v) to about 99.5% (w/v), from about 98% (w/v) to about 99.8% (w/v), from about 99% (w/v) to about 99.9% (w/v), or greater than 99.9% (w/v). In some embodiments, the processed silk is silk fibroin.

Processed silk solutions may be characterized by the length of time and/or temperature needed for processed silk to dissolve. The length of time used to dissolve processed silk in solvent is referred to herein as "dissolution time." Dissolution times for dissolution of processed silk in various solvents may be from about 1 min to about 5 min, from about 2 min to about 10 min, from about 5 min to about 15 min, from about 10 min to about 25 min, from about 20 min to about 35 min, from about 30 min to about 50 min, from about 45 min to about 75 min, from about 60 min to about 95 min, from about 90 min to about 125 min, from about 120 min to about 175 min, from about 150 min to about 200 min, from about 180 min to about 250 min, from about 210 min to about 350 min, from about 240 min to about 360 min, from about 270 min to about 420 min, from about 300 min to about 480 min, or longer than 480 minutes.

The temperature used to dissolve processed silk in solvent is referred to herein as "dissolution temperature." Dissolution temperatures used for dissolution of processed silk in solvent may include room temperature. In some embodiments, dissolution temperature may be from about 0° C. to about 10° C., from about 4° C. to about 25° C., from about 20° C. to about 35° C., from about 30° C. to about 45° C., from about 40° C. to about 55° C., from about 50° C. to about 65° C., from about 60° C. to about 75° C., from about 70° C. to about 85° C., from about 80° C. to about 95° C., from about 90° C. to about 105° C., from about 100° C. to about 115° C., from about 110° C. to about 125° C., from about 120° C. to about 135° C., from about 130° C. to about 145° C., from about 140° C. to about 155° C., from about 150° C. to about 165° C., from about 160° C. to about 175° C., from about 170° C. to about 185° C., from about 180° C. to about 200° C., or greater than 200° C. In some embodiments, the processed silk is silk fibroin. Dissolution of some processed silk solutions may use a dissolution temperature of 60° C. Dissolution of some processed silk solutions may use a dissolution temperature of 80° C., as described in Zheng et 71. (2016) Journal of Biomaterials Applications 31:450-463. In some embodiments, dissolution includes boiling. In some embodiments, dissolution may be carried out by autoclaving. In some embodiments, silk fibroin solutions may be prepared according to any of the methods described in International Patent Application Publication No. WO2017200659 or Abdel-Naby (2017) PLoS One 12(11):e0188154), the contents of each of which are herein incorporated by reference in their entirety.

In some embodiments, one or more of sucrose, phosphate buffer, tris buffer, trehalose, mannitol, citrate buffer, ascorbate, histidine, and/or a cryoprotective agent is added to processed silk solutions.

Chaotropic Agents

In some embodiments, processed silk may be dissolved with the aid of a chaotropic agent. As used herein, a "chaotropic agent" refers to a substance that disrupts hydrogen bonding networks in aqueous solutions to facilitate dissolution of a solute. Chaotropic agents typically modify the impact of hydrophobicity on dissolution. Chaotropic agents may be organic compounds. Such compounds may include, but are not limited to, sodium dodecyl sulfate, ethanol, methanol, phenol, 2-propanol, thiourea, urea, n-butanol, and any other chemicals capable of solubilizing silk. In some embodiments, the chaotropic agent is a salt, including, but not limited to, zinc chloride, calcium nitrate, lithium perchlorate, lithium acetate, sodium thiocyanate, calcium thiocyanate, magnesium thiocyanate, calcium chloride, magnesium chloride, guanidinium chloride, lithium bromide, lithium thiocyanate, copper salts, and other salts capable of solubilizing silk. Such salts typically create high ionic strength in the aqueous solutions which destabilizes the beta-sheet interactions in silk fibroin. In some embodiments, a combination of chaotropic agents is used to facilitate the dissolution of silk fibroin. In some embodiments, a chaotropic agent is used to dissolve raw silk during processing.

Molecular Weight

In some embodiments, processed silk preparations may be characterized by the molecular weight of proteins present in the preparations. Different molecular weights may be present as a result of different levels of silk fibroin dissociation and/or fragmentation during degumming or other processing. When referring to silk fibroin molecular weight herein, it should be understood that the molecular weight may be associated with silk fibroin polymers, silk fibroin monomers, silk fibroin heavy and/or light chains, silk fibroin fragments, or variants, derivates, or mixtures thereof. Accordingly, silk fibroin molecular weight values may vary depending on the nature of the silk fibroin or silk fibroin preparation. In some embodiments, processed silk preparations are characterized by average molecular weight of silk fibroin fragments present in the preparation; by a range of silk fibroin fragment molecular weights; by a threshold of silk fibroin fragment molecular weights; or by combinations of averages, ranges, and thresholds.

In some embodiments, processed silk preparation may include silk fibroin, fibroin fragments, or a plurality of fibroin fragments with a molecular weight of, average molecular weight of, upper molecular weight threshold of, lower molecular weight threshold of, or range of molecular weights with an upper or lower range value of from about 1 kDa to about 4 kDa, from about 2 kDa to about 5 kDa, from about 3.5 kDa to about 10 kDa, from about 5 kDa to about 20 kDa, from about 10 kDa to about 35 kDa, from about 15 kDa to about 40 kDa, from about 20 kDa to about 45 kDa, from about 25 kDa to about 50 kDa, from about 30 kDa to about 55 kDa, from about 35 kDa to about 60 kDa, from about 40 kDa to about 65 kDa, from about 45 kDa to about 70 kDa, from about 50 kDa to about 75 kDa, from about 55 kDa to about 80 kDa, from about 60 kDa to about 85 kDa, from about 65 kDa to about 90 kDa, from about 70 kDa to about 95 kDa, from about 75 kDa to about 100 kDa, from about 80 kDa to about 105 kDa, from about 85 kDa to about 110 kDa, from about 90 kDa to about 115 kDa, from about 95 kDa to about 120 kDa, from about 100 kDa to about 125 kDa, from about 105 kDa to about 130 kDa, from about 110 kDa to about 135 kDa, from about 115 kDa to about 140 kDa, from about 120 kDa to about 145 kDa, from about 125 kDa to about 150 kDa, from about 130 kDa to about 155 kDa, from about 135 kDa to about 160 kDa, from about 140 kDa to about 165 kDa, from about 145 kDa to about 170 kDa, from about 150 kDa to about 175 kDa, from about 160 kDa to about 200 kDa, from about 170 kDa to about 210 kDa, from about 180 kDa to about 220 kDa, from about 190 kDa to about 230 kDa, from about 200 kDa to about 240 kDa, from about 210 kDa to about 250 kDa, from about 220 kDa to about 260 kDa, from about 230 kDa to about 270 kDa, from about 240 kDa to about 280 kDa, from about 250 kDa to about 290 kDa, from about 260 kDa to about 300 kDa, from about 270 kDa to about 310 kDa, from about 280 kDa to about 320 kDa, from about 290 kDa to about 330 kDa, from about 300 kDa to about 340 kDa, from about 310 kDa to about 350 kDa, from about 320 kDa to about 360 kDa, from about 330 kDa to about 370 kDa, from about 340 kDa to about 380 kDa, from about 350 kDa to about 390 kDa, from about 360 kDa to about 400 kDa, from about 370 kDa to about 410 kDa, from about 380 kDa to about 420 kDa, from about 390 kDa to about 430 kDa, from about 400 kDa to about 440 kDa, from about 410 kDa to about 450 kDa, from about 420 kDa to about 460 kDa, from about 430 kDa to about 470 kDa, from about 440 kDa to about 480 kDa, from about 450 kDa to about 490 kDa, from about 460 kDa to about 500 kDa, or greater than 500 kDa.

In one embodiment, the silk preparation may include silk fibroin with a molecular weight of or an average molecular weight of 5-60 kDa.

In one embodiment, the silk preparation may include silk fibroin with a molecular weight of or an average molecular weight of 30-60 kDa. In one aspect, silk fibroin in this range maybe referred to as low molecular weight.

In one embodiment, the silk preparation may include silk fibroin with a molecular weight of or an average molecular weight of 100-300 kDa. In one aspect, silk fibroin in this range maybe referred to as high molecular weight.

In one embodiment, the silk preparation may include silk fibroin with a molecular weight of or an average molecular weight of 361 kDa.

Processed silk preparations may be analyzed, for example, by polyacrylamide gel electrophoresis (PAGE) alongside molecular weight standards to determine predominate molecular weights of proteins and/or polymers present. Additional methods for determining the molecular weight range or average molecular weight for a processed silk preparation may include, but are not limited to, sodium dodecyl sulfate (SDS)-PAGE, size-exclusion chromatography (SEC), high pressure liquid chromatography (HPLC), non-denaturing PAGE, and mass spectrometry (MS).

In some embodiments, silk fibroin molecular weight is modulated by the method of degumming used during processing. In some embodiments, longer heating times during degumming are used (e.g., see International Patent Application Publication No. WO2014145002, the contents of which are herein incorporated by reference in their entirety). Longer heating (e.g., boiling) time may be used during the degumming process to prepare silk fibroin with lower average molecular weights. In some embodiments, heating times may be from about 1 min to about 5 min, from about 2 min to about 10 min, from about 5 min to about 15 min, from about 10 min to about 25 min, from about 20 min to about 35 min, from about 30 min to about 50 min, from about 45 min to about 75 min, from about 60 min to about 95 min, from about 90 min to about 125 min, from about 120 min to about 175 min, from about 150 min to about 200 min, from about 180 min to about 250 min, from about 210 min to about 350 min, from about 240 min to about 400 min, from about 270 min to about 450 min, from about 300 min to about 480 min, or more than 480 min. Additionally, the sodium carbonate concentration used in the degumming process, as well as the heating temperature, may also be altered to modulate the molecular weight of silk fibroin.

In some embodiments, silk fibroin molecular weight is presumed, without actual analysis, based on methods used to prepare the silk fibroin. For example, silk fibroin may be presumed to be low molecular weight silk fibroin or high molecular weight silk fibroin based on the length of time that heating is carried out (e.g., by minute boil value). In some embodiments, the molecular weight range for silk fibroin with a 480 mb is between 5-20 kDa. In some embodiments, the molecular weight as defined by the minute boil is as described in International Patent Application Publication No. WO2017139684.

In some embodiments, SBPs include a plurality of silk fibroin fragments generated using a dissociation procedure. The dissociation procedure may include one or more of heating, acid treatment, chaotropic agent treatment, sonication, and electrolysis. Some SBPs include a plurality of silk fibroin fragments dissociated from raw silk, silk fiber, and/or silk fibroin by heating. The heating may be carried out at a temperature of from about 30° C. to about 1,000° C. In some embodiments, heating is carried out by boiling. The raw silk, silk fiber, and/or silk fibroin may be boiled for from about 1 second to about 24 hours.

Bond and Amino Acid Content

In some embodiments, processed silk preparations may be characterized by the content of various amino acids present in the preparations. Different ratios and/or percentages of one or more amino acids may be present as a result of degumming or other processing. Such amino acids may include serine, glycine, and alanine. Amino acid content of processed silk preparations may be measured by any method known to one of skill in the art, including, but not limited to amino acid analysis and mass spectrometry. In some embodiments, the amino acid content of a processed silk preparation is measured for one amino acid (e.g. serine). In some embodiments, the amino acid content of a processed silk preparation may be measured for a combination of two or more amino acids (e.g. serine, glycine, and alanine). In some embodiments, processed silk preparations of the present disclosure may contain from about 0% to about 1%, from about 1% to about 5%, from about 5% to about 10%, from about 10% to about 15%, from about 15% to about 20%, from about 20% to about 25%, from about 25% to about 30%, from about 30% to about 35%, from about 35% to about 40%, or from about 40% to about 45% of any of the one or more amino acids described herein.

In some embodiments, the amino acid content of silk fibroin may be altered after processing (e.g. degumming). In some embodiments, the serine content of silk fibroin may decrease after processing (e.g. degumming). The serine content of silk fibroin in processed silk preparations may decrease by about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or about 25%.

In some embodiments, processed silk preparations may be characterized by the content of disulfide bonds present in the preparations. Different ratios and/or percentages of disulfide bonds may be present as a result of degumming or other processing. Disulfide bond content of processed silk preparations may be measured by any method known to one of skill in the art. In some embodiments, the disulfide bond content of silk fibroin may be altered after processing (e.g. degumming and/or boiling). In some embodiments, the disulfide bond content of silk fibroin may decrease after processing (e.g. degumming and/or boiling). The disulfide bond content of silk fibroin in processed silk preparations may decrease by about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100%.

Purification and Concentration

In some embodiments, processed silk preparations may be purified. Purification, as used herein, refers to any process used to segregate or extract one entity from another. In some embodiments, purification is manual or automated. Purification may include the removal of salts, impurities, or contaminants from processed silk preparations.

In some embodiments, processed silk may be purified by concentration from a processed silk solution. Methods of concentrating silk fibroin from processed silk solutions may include any of those described in the International Patent Application Publication No. WO2017139684, the contents of which are incorporated herein by reference in their entirety. In some embodiments, purification and/or concentration may be carried out by one or more of dialysis, centrifugation, air drying, vacuum drying, filtration, and/or Tangential Flow Filtration (TFF).

In some embodiments, processed silk solutions are purified by dialysis. Dialysis may be carried out to remove undesired salts and/or contaminants. In some embodiments, processed silk solutions are concentrated via dialysis. Purification and/or concentration of processed silk by dialysis may be carried out as described in International Patent Application Publication No. WO2005012606, the contents of which are herein incorporated by reference in their entirety. In some embodiments, the dialysis is performed against a hygroscopic polymer to concentrate the silk fibroin solution. In some embodiments the dialysis is manual, with the use of a membrane and manual solvent changes. In some embodiments, the solvent is changed between 1 and 10 times over the course of the procedure. In some embodiments, the membrane is a dialysis cassette. The dialysis cassette may be a slide-a-lyzer dialysis cassette. In some embodiments, the membrane is dialysis tubing. The dialysis tubing may be regenerated cellulose dialysis tubing and/or snake skin. The dialysis tubing or cassette may be rinsed in distilled water for 30 minutes to prepare the membrane for use. In some embodiments, the dialysis tubing has a molecular weight cutoff of 3.5 kDa. In some embodiments, the dialysis is performed at a temperature of from about 1° C. to about 30° C. In some embodiments, dialysis is performed at room temperature. In other embodiments, the dialysis is performed at 4° C. Dialysis may be performed until desired concentrations of silk fibroin and salt are obtained from processed silk solutions. Dialysis may be performed for periods of time from about 30 minutes to about 24 hours or beyond. For example, dialysis may be carried out for from about 30 minutes to about 2 hours, from about 1 hour to about 6 hours, from about 3 hours to about 10 hours, from about 5 hours, to about 12 hours, from about 7 hours to about 15 hours, from about 11 hours to about 20 hours, or from about 16 hours to about 24 hours.

In some embodiments, dialysis may be automated. The dialysis may use an automated water change system. Such systems may include tanks of up to 10 L and may be able to hold multiple dialysis cassettes (e.g., see International Patent Application Publication No. WO2017106631, the contents of which are herein incorporated by reference in their entirety). Automated equipment may enable purification of larger volumes of solution with greater efficiency. Automated controllers, programmed with the proper times and volumes, may be used to facilitate changes of solvent or buffer over the course of dialysis. The solvent may be replaced from about 1 to about 20 times or more during dialysis. In some embodiments, automated dialysis may be completed in about 48 hours.

Dialysis may be performed with various solvents depending on the nature of the preparation being processed. In some embodiments the solvent is water. In some embodiments, the solvent is an aqueous solution. In some embodiments the solvent includes a hygroscopic polymer. Hygroscopic polymers may include, but are not limited to, polyethylene glycol (PEG), polyethylene oxide (PEO), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, and polyanhydrides. Additional examples of polymers, hygroscopic polymers, and related dialysis methods that may be employed include any of those found in International Patent Application Publication Nos. WO2005012606, WO2005012606, and WO2017106631, and U.S. Pat. Nos. 6,302,848; 6,395,734; 6,127,143; 5,263,992; 6,379,690; 5,015,476; 4,806,355; 6,372,244; 6,310,188; 5,093,489; 6,325,810; 6,337,198; 6,267,776; 5,576,881; 6,245,537; 5,902,800; and 5,270,419; the contents of each of which are herein incorporated by reference in their entirety. Hygroscopic polymer concentrations may be from about 20% (w/v) to about 50% (w/v). In some embodiments, dialysis may be performed in a stepwise manner in a urea solution, and the urea solution may be subsequently be replaced with urea solutions of a lower concentration during buffer changes, until it is ultimately replaced with water, as described in Zheng et al. (2016) Journal of Biomaterials Applications 31:450-463.

In some embodiments, processed silk preparations may be purified by filtration. Such filtration may include trans flow filtration (TFF), also known as tangential flow filtration. During TFF, solutions may be passed across a filter membrane. Anything larger than the membrane pores is retained, and anything smaller passes through the membrane (e.g., see International Patent Application Publication No. WO2017106631, the contents of which are herein incorporated by reference in their entirety). With the positive pressure and flow along the membrane, instead of through it, particles trapped in the membrane may be washed away. TFF may be carried out using an instrument. The instrument may be automated. The membranes may be housed in TFF tubes with vertical inlets and outlets. The flow of solvent may be controlled by peristaltic pumps. Some TFF tubes may include a dual chamber element. The dual chamber element may enable TFF filtration of processed silk solutions at higher concentrations, while reducing aggregation via the reduction of shear forces.

In some embodiments, processed silk solutions are purified and/or concentrated by centrifugation. Centrifugation may be performed before or after other forms of purification, which include, but are not limited to dialysis and tangential flow filtration. Centrifugation times and speeds may be varied to optimize purification and/or concentration according to optimal time frames. Purification and/or concentration by centrifugation may include pelleting of the processed silk and removal of supernatant. In some cases, centrifugation is used to push solvent through a filter, while retaining processed silk. Centrifugation may be repeated as many times as needed. In some embodiments, silk fibroin solutions are centrifuged two or more times during concentration and/or purification.

In some embodiments, processed silk may be purified by any method known to one of skill in the art. In some embodiments, processed silk is purified to remove salts (e.g.

lithium bromide). In some embodiments, processed silk is purified to isolate processed silk of a desired molecular weight. In some embodiments, processed silk is purified by chromatography. Chromatography may include preparatory-scale, gravity, size exclusion chromatography (SEC). In some embodiments, processed silk is purified by gel permeation chromatography. Processed silk may be purified at any scale. In some embodiments, processed silk is purified on a milligram scale. In some embodiments, processed silk is purified on a gram scale. In some embodiments, processed silk is purified on a kilogram scale.

In some embodiments, SBP formulations may be directly prepared from dialyzed silk fibroin. In some embodiments, SBP formulations may be directly prepared from dialyzed and filtered silk fibroin.

Drying Methods

In some embodiments, processed silk preparations are dried to remove solvent. In some embodiments, SBP formulations may be rinsed prior to drying. Methods of drying may include, but are not limited to, air drying, oven drying, lyophilization, spray drying, spray freezing, and vacuum drying. Drying may be carried out to alter the consistency and/or other properties of processed silk preparations. One or more compounds or excipients may be combined with processed silk preparations to improve processed silk recovery and/or reconstitution after the drying process. For example, sucrose may be added to improve silk fibroin recovery and reconstitution from dried solutions. In some embodiments, drying may be carried out in the fabrication of a processed silk format or a SBP. Examples include, but are not limited to fabrication of fibers, nanofibers, mats, films, foams, membranes, rods, tubes, gels, hydrogels, microspheres, nanospheres, solutions, patches, grafts and powders. In some embodiments, drying processed silk is carried out by oven drying, lyophilizing, and/or air drying.

Oven drying refers to any drying method that uses an oven. According to some methods, ovens are maintained at temperatures of from about 30° C. to about 90° C. or more. In some embodiment, oven drying is carried out at a temperature of 60° C. Processed silk preparations may be placed in ovens for a period of from about 1 hour to about 24 hours or more. In one embodiment, SBP formulations are oven dried at 60° C. for 2 hours. Oven drying may be used to dry silk fibroin preparations. In some embodiments, silk fibroin preparations are oven dried for 16 hours at 60° C. to obtain a desired format. In some cases, silk fibroin solutions are oven dried overnight. Examples of formats obtained by oven drying may include, but are not limited to, fibers, nanofibers, mats, films, foams, membranes, rods, tubes, gels, hydrogels, microspheres, nanospheres, solutions, patches, grafts, and powders.

In some embodiments, processed silk preparations are freeze dried. Freeze drying may be carried out by lyophilization. Freeze drying may require processed silk preparations to be frozen prior to freeze drying. Freezing may be carried out at temperatures of from about 5° C. and about −85° C. In some embodiments, freeze drying is carried out by lyophilization for up to 75 hours. In some embodiments, lyophilization is used to prepare processed silk formats or SBPs. Such formats may include, but are not limited to, fibers, nanofibers, mats, films, foams, membranes, rods, tubes, gels, hydrogels, microspheres, nanospheres, solutions, patches, grafts and powders. The use of lyophilization to fabricate SBPs may be carried out according to any of the methods described in Zhou e al. (2017) Acta Biomater S1742-7061(17)30569; Yang et al. (2017) Int J Nanomedicine 12:6721-6733; Seo et al. (2017) J Biomater Appl 32(4):484-491; Ruan et al. (2017) Biomed Pharmacother 97:600-606; Wu et al. (2017) J Mech Behav Biomed Mater 77:671-682; Zhao et al. (2017) Materials Letters 211:110-113; Chen et a. (2017) PLoS One 12(11):e0187880; Min et a. (2017) Int J Biol Macromol 17: 32855-8; Sun et al. Journal of Materials Chemistry B 5:8770; and Thai et al. J Biomed Mater (2017) 13(1):015009, the contents of each of which are herein incorporated by reference in their entirety.

In some embodiments, processed silk preparations may be dried by air drying. "Air drying," as used herein refers to the removal of moisture by exposure to ambient or circulated gasses. Air drying may include exposing a preparation to air at room temperature (from about 18° C. to about 29° C.). Air drying may be carried out for from about 30 minutes to about 24 hours or more. In some embodiments, silk fibroin preparations are air dried to prepare SBPs. SBP formats that may be prepared may include, but are not limited to, fibers, nanofibers, mats, films, foams, membranes, rods, tubes, gels, hydrogels, microspheres, nanospheres, solutions, patches, grafts and powders. Some examples of the use of air drying for fabrication of SBPs are presented in Susanin et al. (2017) Fibre Chemistry 49(2):88-96; Lo et al. J Tissue Eng Regen Med (2017) doi.10.1002/term.2616; and Mane et al. Scientific Reports 7:15531, the contents of each of which are herein incorporated by reference in their entirety.

Spinning

In some embodiments, processed silk may be prepared by spinning. As used herein, the term "spinning" refers to a process of twisting materials together. Spinning may include the process of preparing a silk fiber by twisting silk proteins as they are secreted from silk producers. Other forms of spinning include spinning one or more forms of processed silk together to form a thread, filament, fiber, or yarn. The processed silk may already consist of a filamentous format prior to spinning. In some embodiments, processed silk is processed by spinning from a non-filamentous format (e.g., from a film, mat, or solution).

In some embodiments, spinning includes the technique of electrospinning. Electrospinning may be used to prepare silk fibers from silk fibroin. The silk fibroin may be dissolved in water or an aqueous solution before electrospinning. In other embodiments, silk fibroin is dissolved in an organic solvent before electrospinning. The organic solvent may be hexafluoroisopropanol (HFIP). In some embodiments, electrospinning may be carried out as described in Yu et al. (2017) Biomed Mater Res A doi. 10.1002/jbm.a.36297 or Chantawong et al. (2017) Mater Sci Mater Med 28(12):191, the contents of each of which are herein incorporated by reference in their entirety.

Electrospinning typically includes the use of an electrospinning apparatus. Processed silk may be added to the apparatus to produce silk fiber. The processed silk may be silk fibroin in solution. Electrospinning apparatus components may include one or more of a spinneret (also referred to spinnerette), needle, mandrel, power source, pump, and grounded collector. The apparatus may apply voltage to the dissolved silk fibroin, causing electrostatic repulsion that generates a charged liquid that is extruded from the end. Electrostatic repulsion also enables fiber elongation as it forms, and charged liquid cohesion prevents it from breaking apart. Resulting fiber may be deposited on the collector. In some embodiments, electrospinning methods may be carried out according to those described in European Patent No. EP3206725; Manchineella et al. (2017) European Journal of Organic Chemistry 30:4363-4369; Park et al. (2017) Int J Biomacromol S0141-8130(17):32645-4; Wang et al. (2017) J Biomed Mater Res A doi.10.1002/jbm.a.36225;

Chendang et a. (2017) J Biomaterials and Tissue Engineering 7:858-862; Kambe et al. (2017) Materials (Basel) 10(10):E1153; Chouhan et al. (2017) J Tissue Eng Reneg Med doi.10.1002/term.2581; Genovese et al. (2017) ACS Appl Mater Interfaces doi.10.1021acsami.7b13372; Yu et al. (2017) Biomed Mater Res A doi.10.1002/jbm.a.36297; Chantawong et al. (2017) Mater Sci Mater Med 28(12):191, the contents of each of which are herein incorporated by reference in their entirety.

In some embodiments, spinning may be carried out as dry spinning. Dry spinning may be carried out using a dry spinning apparatus. Dry spinning may be used to prepare silk fibers from SBP formulations. The preparations may include silk fibroin solutions. The preparations may be aqueous solutions. Dry spinning apparatuses typically use hot air to dry processed silk as it is extruded. In some embodiments, dry spinning may be carried out according to any of the methods presented in Zhang et al. (2017) Int J Biol Macromol pii:S0141-8130(17):32857, the contents of which are herein incorporated by reference in their entirety.

Processing Methods: Spraying

In some embodiments, processing methods include spraying. As used herein, the term "spraying" refers to the sprinkling or showering of a compound or composition in the form of small drops or particles. Spraying may be used to prepare SBPs by spraying processed silk. Spraying may be carried out using electrospraying. Processed silk used for spraying may include processed silk in solution. The solution may be a silk fibroin solution. Solutions may be aqueous solutions. Some solutions may include organic solvents. Electrospraying may be carried out in a manner similar to that of electrospinning, except that the charged liquid lacks cohesive force necessary to prevent extruding material from breaking apart. In some embodiments, spraying methods may include any of those presented in United States Publication No. US2017/333351 or Cao et al. (2017) Scientific Reports 7:11913, the contents of each of which are herein incorporated by reference in their entirety. In some embodiments, electrospray methods include a coaxial system for coaxial spraying.

In some embodiments, spraying is carried out as spray drying. Spray drying is a method of producing a dry powder from a liquid or slurry by rapidly drying with a hot gas. For example, the silk fibroin solution may be introduced as a fine spray or mist into a tower or chamber with heated air. The large surface ara of the spray droplets causes evaporation of the water to occur rapidly, converting the droplets into dry powder particles. The heat and drying process may induce beta-sheet formation in the silk fibroin. Additional advantages of spray drying may include low heat, speed, reproducibility, and scalability.

In one embodiment, the spraying is carried out as spray drying using the electrostatic spray drying methods known in the art.

In some embodiments, spraying is carried out as spray coating. For example, SBP formulations may be sprayed onto the surface of a substance to form a coating. The spray coating processing may be a thermal spray coating process where SBP formulations are heated or melted by a heat source, for example, by electrical means (plasma or arc) or chemical means (combustion flame). Thermal spraying techniques that may be used herein include, but are not limited to, plasma spraying, detonation spraying, wire arc spraying, flame spraying, high velocity oxy-fuel coating spraying (HVOF), high velocity air fuel (HVAF), warm spraying, and cold spraying.

In one embodiment, the spray coating may be used for enteric capsules.

Processing Methods: Precipitation

In some embodiments, processing methods include precipitation. As used herein, the term "precipitation" refers to the deposition of a substance in solid form from a solution. Precipitation may be used to obtain solid processed silk from processed silk solutions. The processed silk may be silk fibroin. Processed silk may be precipitate from a solution. The solvent may be aqueous. In some embodiments, the solvent is organic. Examples of organic solvents include, but are not limited to, HFIP, methanol, ethanol, and other alcohols. In some embodiments, the solvent is water. In some embodiments the solvent is a mixture of an organic solvent and water. Aqueous solvents may contain one or more salts. Processed silk may be precipitated from processed silk solutions by modulating one or more components of the solution to alter the solubility of the processed silk and promote precipitation. Additional processing steps may be employed to initiate or speed precipitation. Such methods may include, but are not limited to sonication, centrifugation, increasing the concentration of processed silk, altering the concentration of salt, adding additional salt or salts, altering the pH, applying shear stress, adding excipients, or applying chemical modifications.

Processing Methods: Milling

In some embodiments, processing methods include milling. As used herein, "milling" generally refers to the process of breaking down a solid substance into smaller pieces using physical forces such as grinding, crushing, pressing and/or cutting. As a non-limiting example, SBP formulations may be milled to create powders. The density of powder formulations may be controlled during the milling process. As another non-limiting example, solid encapsulation of a therapeutic agent or cargo with another substance (e.g., SBPs) may be prepared by milling. The therapeutic agent or cargo may include any one of those described herein. In some embodiments, the therapeutic agent or cargo to be encapsulated by another substance may include SBPs.

Altering Mechanical Properties

In some embodiments, the mechanical properties of processed silk may be altered by modulating physical and/or chemical properties of the processed silk. The mechanical properties include, but are not limited to, mechanical strength, tensile strength, elongation capabilities, elasticity, compressive strength, stiffness, shear strength, toughness, torsional stability, temperature stability, moisture stability, viscosity and reeling rate. In some embodiments, the tensile strength of processed silk is stronger than steel. In some embodiments, the tensile strength of SBPs is stronger than steel. Examples of the physical and chemical properties used to tune the mechanical properties of processed silk include, but are not limited to, the temperature, formulations, silk concentration, β-sheet content, crosslinking, the molecular weight of the silk, the storage of the silk, storage, methods of preparation, dryness, methods of drying, purity, and degumming. Methods of tuning the mechanical strength of processed silk are taught in International Patent Application Publication No. WO2017123383, European Patent No. EP2904134, European Patent No. EP3212246, Fang et al., Wu et al., Susanin et al., Zhang et al., Jiang et al., Yu et al., Chantawong et al., and Zhang et al. (Fang et al. (2017) Journal of Materials Chemistry B 5(30):6042-6048; Wu et al. (2017) J Mech Behav Biomed Mater 77:671-682; Susanin et al. (2017) Fibre Chemistry 49(2):88-96; Zhang et al. (2017) Fibers and Polymers 203:9-16; Jiang et al. (2017) J Biomater Sci Polym Ed 15:1-36; Yu et a (2017) Biomed Mater Res A doi. 10.1002/jbm.a.36297; Chantawong et al. (2017) Mater Sci Mater Med 28(12):191; Zhang et al. (2017) Int J Biomacromol S0141-8310(17):32857), the contents of each of which are herein incorporated by reference in their entirety.

In some embodiments, the excipients which may be incorporated in a formulation may be used to control the modulus of SBP formulations. In some embodiments, these SBP formulations are hydrogels.

In some embodiments, processed silk hydrogels are prepared with different excipients and tested for their mechanical properties, including the modulus. SBP formulations may be assessed for modulus, shear storage modulus, shear loss modulus, phase angle, and viscosity using a rheometer, and/or any other method known to one skilled in the art. Rheometer geometry may be selected based on sample viscosity, shear rates, and shear stresses desired, as well as sample volumes. Geometries that are suitable for measuring the rheological properties of SBP formulations include, not are not limited to, cone and plate, parallel plates, concentric cylinders (or Bob and Cup), and double gap cylinders. In one embodiment, a cone and plate geometry is used. In another embodiment, a concentric cylinder geometry is used. SBP formulations may be tested both before and after gelation. In some embodiments, SBP formulations are prepared, optionally with different excipients, and tested for their mechanical properties, including the shear storage modulus, the shear loss modulus, phase angle, and viscosity. As used herein, the term "shear storage modulus" refers to the measure of a material's elasticity or reversible deformation as determined by the material's stored energy. As used herein, the term "shear loss modulus" refer to the measure of a material's ability to dissipate energy, usually in the form of heat. As used herein, the term "phase angle" refers to the difference in the stress and strain applied to a material during the application of oscillating shear stress. As used herein, the term "viscosity" refers to a material's ability to resist deformation due to shear forces, and the ability of a fluid to resist flow. In some embodiments, processed silk hydrogels may possess similar viscosities, but vary in the modulus.

In some embodiments, the concentration of processed silk may enable silk preparations to shear thin. In some embodiments the silk preparation is an SBP. In some embodiments, the SBP is a hydrogel. In some embodiments, the molecular weight of processed silk hydrogels may enable hydrogels to shear thin. In some embodiments, hydrogels prepared with low molecular weight silk fibroin may be injected with much less force than hydrogels of similar viscosity that are prepared with higher molecular weight silk fibroin. In some embodiments, hydrogels with low molecular weight silk fibroin display higher viscosity than hydrogels with high molecular weight silk fibroin.

In some embodiments, the concentration of silk fibroin may be used to control the shear storage modulus and/or the shear loss modulus of processed silk preparations. In some embodiments, a preparation with stressed silk may be used to control the shear storage modulus and the shear loss modulus. In some embodiments, the excipients incorporated in a formulation may be used to control the shear storage modulus and/or the shear loss modulus of processed silk preparations. In some embodiments, these processed silk preparations are hydrogels. In some embodiments, these processed silk preparations are solutions. In some embodiments, processed silk preparations are prepared, optionally with different excipients, and tested for their mechanical and physical properties, including the shear storage modulus, the shear loss modulus, phase angle, and viscosity. As used herein, the term "shear storage modulus" refers to the measure of a material's elasticity or reversible deformation as determined by the material's stored energy. As used herein, the term "shear loss modulus" refers to the measure of a material's ability to dissipate energy, usually in the form of heat. As used herein, the term "phase angle" refers to the difference in the stress and strain applied to a material during the application of oscillating shear stress. As used herein, the term "viscosity" refers to a material's ability to resist deformation due to shear forces, and the ability of a material to resist flow. Processed silk preparations may be assessed for shear storage modulus, shear loss modulus, phase angle, and viscosity using a rheometer, and/or any other method known to one skilled in the art. Rheometer geometry may be selected based on sample viscosity, shear rates, and shear stresses desired, as well as sample volumes. Geometries that are suitable for measuring the rheological properties of SBP formulations include, not are not limited to, cone and plate, parallel plates, concentric cylinders (or Bob and Cup), and double gap cylinders. In one embodiment, a cone and plate geometry is used. In another embodiment, a concentric cylinder geometry is used. Processed silk preparations may be tested both before and after gelation. In some embodiments, processed silk preparations may possess similar viscosities, but vary in the modulus. In some embodiments, the processed silk preparations may have the viscosity of a liquid. In some embodiments, the processed silk preparations may have the viscosity of a gel.

In some embodiments, the processed silk preparations may shear thin or display shear thinning properties. As used herein, the term "shear thinning" refers to a decrease in viscosity at increasing shear rates. As used herein, the term "shear rate" refers to the rate of change in the ratio of displacement of material upon the application of a shear force to the height of the material. This ratio is also known as strain. In some embodiments, the boiling time during degumming of processed silk may enable processed silk preparations to shear thin. In some embodiments, the concentration of processed silk may enable silk preparations to shear thin. In some embodiments, the processed silk preparations may have the viscosity of a liquid at higher shear rates. In some embodiments, the processed silk preparations may have the viscosity of a gel at lower shear rates.

In some embodiments, the mechanical properties of processed silk preparations may be tuned by a preparation with stressed silk. As used herein, the term "stress" or "stressed" refers to a treatment that may alter the shelf life and/or stability of processed silk and/or an SBP. In some embodiments, processed silk is stressed by treatment with heat. In some embodiments, processed silk is stressed by heating to 60° C. In some embodiments, processed silk is stressed by heating overnight. In some embodiments, processed silk is stressed by autoclave. In some embodiments, processed silk is stressed by overnight heating to 60° C. followed by autoclave. In some embodiments, silk is stressed during the preparation of processed silk. In some embodiments, processed silk is stressed during the preparation of SBPs. In some embodiments, SBPs are stressed. Stressed silk or SBPs may be used in any of the embodiments described in the present disclosure.

In some embodiments, boiling silk fibroin in 0.02M sodium carbonate for 480 minutes may result in a polydisperse mixture of peptides ranging in molecular weight from about 200,000 Da to about 7000 Da, with an average molecular weight of about 35.000 Da. In some embodiments, the molecular weight of polymers (e.g. processed silk) may have a dramatic effect on properties such as stability, viscosity, surface tension, gelation and bioactivity. In some embodiments, polydisperse processed silk (e.g. silk fibroin degummed with a 480 minute boil) may be separated into narrow molecular weight fractions. In some embodiments, the separation of polydisperse processed silk may optimize one or more properties of an SBP (e.g. stability, viscosity, surface tension, gelation and bioactivity). Polydisperse mixtures of processed silk may be separated into fractions by any method known to one of skill in the art. In some embodiments, fractionation of processed silk may be used to isolate processed silk with narrower polydispersity. In some embodiments, processed silk is fractionated by preparatory-scale, gravity, size exclusion chromatography (SEC). In some embodiments, processed silk is fractionated by gel permeation chromatography. Processed silk may be fractionated at any scale. In some embodiments, processed silk is fractionated on a milligram scale. In some embodiments, processed silk is fractionated on a gram scale. In some embodiments, processed silk is fractionated on a kilogram scale.

Modulating Degradation and Resorption

In some embodiments, processed silks are, or are processed to be, biocompatible. As used herein, a "biocompatible" substance is any substance that is not harmful to most living organisms or tissues. With some processed silk, degradation may result in products that are biocompatible, making such processed silk attractive for a variety of applications. Some processed silk may degrade into smaller proteins or amino acids. Some processed silk may be resorbable under physiological conditions. In some embodiments, products of silk degradation may be resorbable in vivo. In some embodiments, the rate of degradation of processed silk may be tuned by altering processed silk properties. Examples of these properties include, but are not limited to, type and concentration of certain proteins, β-sheet content, crosslinking, silk fibroin molecular weight, and purity. In some embodiments, rate of processed silk degradation may be modulated by method of storage, methods of preparation, dryness, methods of drying, reeling rate, and degumming process.

In some embodiments, the bioresorbability and degradation of processed silk is modulated by the addition of sucrose, as taught in Li el al. (Li el al. (2017) Biomacromolecules 18(9):2900-2905), the contents of which are herein incorporated by reference in their entirety. Processed silk may be formulated with sucrose to enhance thermal stability. Furthermore, processed silk with sucrose may also be formulated with antiplasticizing agents to further enhance thermal stability of processed silk, SBPs, and/or therapeutic agents included in SBPs. Methods of increasing thermal stability using antiplasticizing agents may include any of those described in Li el al. (Li el al. (2017) Biomacromolecules 18(9):2900-2905), the contents of which are herein incorporated by reference in their entirety. In some embodiments, the addition of sucrose to processed silk preparations prior to lyophilization leads to an increased reconstitution efficiency. In some embodiments, the addition of sucrose may be used to create higher molecular weight processed silk preparations as well as to maintain long term storage stability. In some embodiments, the incorporation of sucrose into processed silk preparations described herein enables slower freezing during lyophilization cycle.

In some embodiments, an SBP maintains and or improves stability by at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, at least 3 months, at least 14 weeks, at least 4 months, at least 18 weeks, at least 5 months, at least 22 weeks, at least 6 months, at least 7 months, at least 8 months, at least 9 months, at least 10 months, at least 11 months, at least a year, at least 2 years, at least 3 years, at least 4 years, at least 5 years, or more than 5 years. In some embodiments, an SBP preparation reduces stability by In some embodiments, an SBP maintains and or improves stability by at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, at least 3 months, at least 14 weeks, at least 4 months, at least 18 weeks, at least 5 months, at least 22 weeks, at least 6 months, at least 7 months, at least 8 months, at least 9 months, at least 10 months, at least 11 months, at least a year, at least 2 years, at least 3 years, at least 4 years, at least 5 years, or more than 5 years. In some embodiments, an SBP may have a shelf life of least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, at least 3 months, at least 14 weeks, at least 4 months, at least 18 weeks, at least 5 months, at least 22 weeks, at least 6 months, at least 7 months, at least 8 months, at least 9 months, at least 10 months, at least 11 months, at least a year, at least 2 years, at least 3 years, at least 4 years, at least 5 years, or more than 5 years.

In some embodiments, the bioresorbability and degradation of processed silk may be tuned through formulation with additional bioresorbable polymer matrices, as taught in International Patent Application Publication Numbers WO2017177281 and WO2017179069, the contents of each of which are herein incorporated by reference in their entirety. In some embodiments, the polymer matrix is polyurethane. In some embodiments, these polymer matrices may be polycaprolactone and a ceramic filler. The ceramic filler may include MgO.

In some embodiments, the bioresorbability and degradation of processed silk is tuned through the fabrication of a composite scaffold. Composite scaffolds, combinations of scaffolds or scaffolds formed from more than one material, may be formed from two or more SBP formulations. In some embodiments, processed silk scaffolds comprising a combination of silk fibroin microspheres within a larger processed silk preparation may demonstrate slower degradation in comparison with other scaffolds, as taught in European Patent No. EP3242967, the contents of which are herein incorporated by reference in their entirety.

Analytics

In some embodiments, processed silk products may be analyzed for properties such as molecular weight, aggregation, amino acid content, lithium content, heavy metal content, bromide content and endotoxin level. Such properties may be evaluated via any analytical methods known in the art. As a non-limiting example, the Ultra-Performance Liquid Chromatography (UPLC)-Size Exclusion Chromatography (SEC) method may be used to assess the molecular weight and/or aggregation of the silk fibroin proteins in the processed silk products.

In some embodiments, processed silk products may be analyzed for silk fibroin concentration. Such properties may be evaluated via any analytical methods known in the art. As a non-limiting example, gravimetry and/or ultraviolet-visible spectroscopy (UV-Vis) may be used.

In some embodiments, silk fibroin molecular weight is modulated by the method of degumming used during processing. In some embodiments, longer heating times during degumming are used (e.g., see International Publication No. WO2014145002, the contents of which are herein incorporated by reference in their entirety). Longer heating (e.g., boiling) time may be used during the degumming process to prepare silk fibroin with lower average molecular weights. In some embodiments, heating times may be from about 1 min to about 5 min, from about 2 min to about 10 min, from about 5 min to about 15 min, from about 10 min to about 25 min, from about 20 min to about 35 min, from about 30 min to about 50 min, from about 45 min to about 75 min, from about 60 min to about 95 min, from about 90 min to about 125 min, from about 120 min to about 175 min, from about 150 min to about 200 min, from about 180 min to about 250 min, from about 210 min to about 350 min, from about 240 min to about 400 min, from about 270 min to about 450 min, from about 300 min to about 480 min, or more than 480 min. Additionally, the sodium carbonate concentration used in the degumming process, as well as the heating temperature, may also be altered to modulate the molecular weight of silk fibroin. In one embodiment, the alteration may cause an increase in the molecular weight of silk fibroin. As compared to silk fibroin where the sodium carbonate concentration and/or the heating temperature was not altered, the increase of the molecular weight may be 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% higher. In one embodiment, the alteration may cause a decrease in the molecular weight of silk fibroin. As compared to silk fibroin where the sodium carbonate concentration and/or the heating temperature was not altered, the decrease of the molecular weight may be 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or greater than 99% lower.

In some embodiments, silk fibroin molecular weight may be presumed, without actual analysis, based on methods used to prepare the silk fibroin. For example, silk fibroin may be presumed to be low molecular weight silk fibroin or high molecular weight silk fibroin based on the length of time that heating is carried out (e.g., by minute boil value).

In some embodiments, SBP formulations include a plurality of silk fibroin fragments generated using a dissociation procedure. The dissociation procedure may include one or more of heating, acid treatment, base treatment, chaotropic agent treatment, sonication, and electrolysis. Some SBPs include a plurality of silk fibroin fragments dissociated from raw silk, silk fiber, and/or silk fibroin by heating. The heating may be carried out at a temperature of from about 30° C. to about 1,000° C. In some embodiments, heating is carried out by boiling. The raw silk, silk fiber, and/or silk fibroin may be boiled for from about 1 second to about 24 hours.

Porosity

In some embodiments, processed silk may include variations in porosity. As used herein, the term "porosity" refers to the frequency with which holes, pockets, channels, or other spaces occur in a material, in some cases influencing the movement of elements to and/or from the material. Processed silk porosity may influence one or more other silk properties or properties of an SBP that includes the processed silk. These properties may include, but are not limited to, stability, payload retention or release, payload release rate, wettability, mechanical strength, tensile strength, elongation capabilities, density, thickness, elasticity, compressive strength, stiffness, shear strength, toughness, torsional stability, temperature stability, and moisture stability. In some embodiments, processed silk porosity may control the diffusion or transport of agents from, within, or into the processed silk or SBP. Such agents may include, but are not limited to, therapeutics, biologics, chemicals, small molecules, oxidants, antioxidants, macromolecules, microspheres, nanospheres, cells, or any payloads described herein.

Processed silk porosity may be modulated during one or more processing steps or during fabrication of a SBP (e.g., see International Publication No. WO2014125505 and U.S. Pat. No. 8,361,617, the contents of each of which are herein incorporated by reference in their entirety). In some embodiments, processed silk porosity may be modulated by one or more of sonication, centrifugation, modulating silk fibroin concentration, modulating salt concentration, modulating pH, modulating secondary structural formats, applying shear stress, modulating excipient concentration, chemical modification, crosslinking, or combining with cells, bacteria, and/or viral particles.

Strength and Stability

Processed silk strength and stability are important factors for many applications. In some embodiments, processed silk may be selected based on or prepared to maximize mechanical strength, tensile strength, elongation capabilities, elasticity, flexibility, compressive strength, stiffness, shear strength, toughness, torsional stability, biological stability, resistance to degradation, and/or moisture stability. In some embodiments, processed silk has a non-acidic microenvironment. In some embodiments, the non-acidic microenvironment enhances the stability of processed silk and or SBPs. In some embodiments, the non-acidic microenvironment enhances the stability of therapeutic agents formulated with processed silk and/or SBP. In some embodiments, the tensile strength of processed silk is stronger than steel. In some embodiments, the tensile strength of an SBP is stronger than steel.

In some embodiments, processed silk may demonstrate stability and/or is determined to be stable under various conditions. As used herein, "stability" and "stable" refers to the capacity of a substance (e.g. an SBP) to remain unchanged over time under the described conditions. Those conditions may be in vitro, in vivo, or ex vivo. In some embodiments, an SBP may be stable for up to 1 hour, up to 3 days, up to 1 week, up to 1 month, up to 3 months, up to 4 months, up to 6 months, up to 7 months, up to 1 year, up to 2 years, or up to 5 years.

Injectability

In some embodiments, processed silk may be selected based on or prepared to modulate the injectability of an SBP formulation. As used herein, the term "injectability" refers to the force required to push a composition through a syringe or syringe and needle. Injections may be used to administer SBP formulations. The SBP formulations may be administered via syringe to a subject. Injectability may be measured by the force required to push the composition through the desired syringe. The force may be, but is not limited to 10, 20, 30, 40, 50, 60, 70, 80, 90, 100, 110, 120, 130, 140, 150, 160, 170, 180, 190, or 200 N. or a range of 10-50, 10-60, 10-90, 10-100, 10-110, 10-150, 10-200, 20-50, 20-70, 20-100, 20-120, 20-150, 20-200, 30-50, 30-80, 30-100, 30-110, 30-130, 30-150, 30-200, 40-50, 40-90, 40-100, 40-120, 40-140, 40-150, 40-200, 50-100, 50-130, 50-150, 50-200, 60-100, 60-110, 60-140, 60-150, 60-160, 60-200, 70-100, 70-120, 70-150, 70-170, 70-200, 80-100, 80-130, 80-150, 80-160, 80-180, 80-200, 90-100, 90-140, 90-150, 90-170, 90-190, 90-200, 100-150, 100-180, 100-200, 110-150, 110-160, 110-190, 110-200, 120-150, 120-170, 120-200, 130-150, 130-180, 130-200, 140-150, 140-190, 140-200, 150-200, 160-200, 170-200, 180-200, or 190-200 N.

In some embodiments, the SBP formulations described herein may be injected with a force of 200 N or less.

In some embodiments, the SBP formulations described herein may be injected with a force of 150 N or less.

In some embodiments, the SBP formulations described herein may be injected with a force of 100 N or less.

In some embodiments, the SBP formulations described herein may be injected with a force of 50 N or less.

In some embodiments, the SBP formulations described herein may be injected with a force of 20 N or less.

In some embodiments, the SBP formulations described herein may be injected with a force of 10 N or less.

In some embodiments, the SBP formulations described herein may be injected with a force of 5 N or less.

In some embodiments, injectability may also be analyzed by maximum force. As used herein, the term "maximum force" refers to the highest force achieved during injection. The maximum force may occur at the beginning of an injection. The maximum force may be, but is not limited to, 5, 10, 20, 25, 30, 40, 50, 60, 70, 75, 80, 90, 100, 110, 120, 125, 130, 140, 150, 160, 170, 175, 180, 190, or 200 N, or 5-10, 5-25, 10-50, 10-60, 10-90, 10-100, 10-110, 10-150, 10-200, 20-50, 20-70, 20-100, 20-120, 20-150, 20-200, 25-50, 30-50, 30-80, 30-100, 30-110, 30-130, 30-150, 30-200, 40-50, 40-90, 40-100, 40-120, 40-140, 40-150, 40-200, 50-100, 50-130, 50-150, 50-200, 60-100, 60-110, 60-140, 60-150, 60-160, 60-200, 70-100, 70-120, 70-150, 70-170, 70-200, 75-100, 80-100, 80-130, 80-150, 80-160, 80-180, 80-200, 90-100, 90-140, 90-150, 90-170, 90-190, 90-200, 100-150, 100-180, 100-200, 110-150, 110-160, 110-190, 110-200, 120-150, 120-170, 120-200, 125-150, 130-150, 130-180, 130-200, 140-150, 140-190, 140-200, 150-175, 150-200, 160-200, 170-200, 175-200, 180-200, or 190-200 N.

In some embodiments, the maximum force is from about 5 N to about 200 N. In some embodiments, the maximum force may be from about 0.001 N to about 5 N, from about 5 N to about 25 N, from about 25 N to about 50 N, from about 50 N to about 75 N, from about 75 N to about 100 N, from about 100 N to about 125 N, from about 125 N to about 150 N, from about 150 N to about 175 N, or from about 175 N to about 200 N.

In some embodiments, the SBP formulation may be delivered using a syringe with a 1, 2, 3, 4, 5, 6, 7, 8, 9, 10, 15, 20, 25, 30, 35, 40, 45, 50, 60, 70, 80, 90, 100 mL syringe which has an applicator which is 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, or more than 10 mm.

In one embodiment, the SBP formulation may be delivered using a 3 mL syringe with a 1.5 mm applicator.

pH

In some embodiments, the SBP formulation may be optimized for a specific pH. The pH of the SBP formulation may be, but is not limited, to 0, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, and 14.

In one embodiment, the SBP formulation may be optimized for a specific pH range. The pH range may be, but is not limited to, 0-4, 1-5, 2-6, 3-7, 4-8, 5-9, 6-10, 7-11, 8-12, 9-13, 10-14, 0-4, 1-5, 2-6, 3-7, 4-8, 5-9, 6-10, 7-11, 8-12, 9-13, 10-14, 0-4.5, 1-5.5, 2-6.5, 3-7.5, 4-8.5, 5-9.5, 6-10.5, 7-11.5, 8-12.5, 9-13.5, 0-1.5, 1-2.5, 2-3.5, 3-4.5, 4-5.5, 5-6.5, 6-7.5, 7-8.5, 8-9.5, 9-10.5, 10-11.5, 11-12.5, 12-13.5, 0-1, 1-2, 2-3, 3-4, 4-5, 5-6, 6-7, 6.5-7.5, 7-8, 8-9, 9-10, 10-11, 11-12, 12-13, 13-14, 0-0.5, 0.5-1, 1-1.5, 1.5-2, 2-2.5, 2.5-3, 3-3.5, 3.5-4, 4-4.5, 4.5-5, 5-5.5, 5.5-6, 6-6.5, 6.5-7, 7-7.5, 7.5-8, 8-8.5, 8.5-9, 9-9.5, 9.5-10, 10-10.5, 10.5-11, 11-11.5, 11.5-12, 12-12.5, 12.5-13, 13-13.5, or 13.5-14.

In one embodiment, the pH of the SBP formulation is between 4-8.5.

In one embodiment, the pH of the SBP formulation is between 6.5-7.5

In one embodiment, the pH of the SBP formulation is between 7-7.5.

Specific Gravity

In some embodiments, the SBP formulation may be optimized for a specific gravity. The specific gravity of the SBP formulation may be, but is not limited, to 0, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and 5.

In some embodiments, the specific gravity of the SBP formulation may be, but is not limited to, 0.1-5 g/ml, 0.2-5 g/ml, 0.3-5 g/ml, 0.4-5 g/ml, 0.5-5 g/ml, 0.6-5 g/ml, 0.7-5 g/ml, 0.8-5 g/ml, 0.9-5 g/ml, 1-5 g/ml, 1.1-5 g/ml, 1.2-5 g/ml, 1.3-5 g/ml, 1.4-5 g/ml, 1.5-5 g/ml, 1.6-5 g/ml, 1.7-5 g/ml, 1.8-5 g/ml, 1.9-5 g/ml, 2-5 g/ml, 2.1-5 g/ml, 2.2-5 g/ml, 2.3-5 g/ml, 2.4-5 g/ml, 2.5-5 g/ml, 2.6-5 g/ml, 2.7-5 g/ml, 2.8-5 g/ml, 2.9-5 g/ml, 3-5 g/ml, 3.1-5 g/ml, 3.2-5 g/ml, 3.3-5 g/ml, 3.4-5 g/ml, 3.5-5 g/ml, 3.6-5 g/ml, 3.7-5 g/ml, 3.8-5 g/ml, 3.9-5 g/ml, 4-5 g/ml, 4.1-5 g/ml, 4.2-5 g/ml, 4.3-5 g/ml, 4.4-5 g/ml, 4.5-5 g/ml, 4.6-5 g/ml, 4.7-5 g/ml, 4.8-5 g/ml, 4.9-5 g/ml, 0.1-0.3 g/ml, 0.2-0.4 g/ml, 0.3-0.5 g/ml, 0.4-0.6 g/ml, 0.5-0.7 g/ml, 0.6-0.8 g/ml, 0.7-0.9 g/ml, 0.8-1 g/ml, 0.9-1.1 g/ml, 1-1.2 g/ml, 1.1-1.3 g/ml, 1.2-1.4 g/ml, 1.3-1.5 g/ml, 1.4-1.6 g/ml, 1.5-1.7 g/ml, 1.6-1.8 g/ml, 1.7-1.9 g/ml, 1.8-2 g/ml, 1.9-2.1 g/ml, 2-2.2 g/ml, 2.1-2.3 g/ml, 2.2-2.4 g/ml, 2.3-2.5 g/ml, 2.4-2.6 g/ml, 2.5-2.7 g/ml, 2.6-2.8 g/ml, 2.7-2.9 g/ml, 2.8-3 g/ml, 2.9-3.1 g/ml, 3-3.2 g/ml, 3.1-3.3 g/ml, 3.2-3.4 g/ml, 3.3-3.5 g/ml, 3.4-3.6 g/ml, 3.5-3.7 g/ml, 3.6-3.8 g/ml, 3.7-3.9 g/ml, 3.8-4 g/ml, 3.9-4.1 g/ml, 4-4.2 g/ml, 4.1-4.3 g/ml, 4.2-4.4 g/ml, 4.3-4.5 g/ml, 4.4-4.6 g/ml, 4.5-4.7 g/ml, 4.6-4.8 g/ml, 4.7-4.9 g/ml, 4.8-5 g/ml, 0.1-0.4 g/ml, 0.2-0.5 g/ml, 0.3-0.6 g/ml, 0.4-0.7 g/ml, 0.5-0.8 g/ml, 0.6-0.9 g/ml, 0.7-1 g/ml, 0.8-1.1 g/ml, 0.9-1.2 g/ml, 1-1.3 g/ml, 1.1-1.4 g/ml, 1.2-1.5 g/ml, 1.3-1.6 g/ml, 1.4-1.7 g/ml, 1.5-1.8 g/ml, 1.6-1.9 g/ml, 1.7-2 g/ml, 1.8-2.1 g/ml, 1.9-2.2 g/ml, 2-2.3 g/ml, 2.1-2.4 g/ml, 2.2-2.5 g/ml, 2.3-2.6 g/ml, 2.4-2.7 g/ml, 2.5-2.8 g/ml, 2.6-2.9 g/ml, 2.7-3 g/ml, 2.8-3.1 g/ml, 2.9-3.2 g/ml, 3-3.3 g/ml, 3.1-3.4 g/ml, 3.2-3.5 g/ml, 3.3-3.6 g/ml, 3.4-3.7 g/ml, 3.5-3.8 g/ml, 3.6-3.9 g/ml, 3.7-4 g/ml, 3.8-4.1 g/ml, 3.9-4.2 g/ml, 4-4.3 g/ml, 4.1-4.4 g/ml, 4.2-4.5 g/ml, 4.3-4.6 g/ml, 4.4-4.7 g/ml, 4.5-4.8 g/ml, 4.6-4.9 g/ml, 4.7-5 g/ml, 0.1-0.5 g/ml, 0.2-0.6 g/ml, 0.3-0.7 g/ml, 0.4-0.8 g/ml, 0.5-0.9 g/ml, 0.6-1 g/ml, 0.7-1.1 g/ml, 0.8-1.2 g/ml, 0.9-1.3 g/ml, 1-1.4 g/ml, 1.1-1.5 g/ml, 1.2-1.6 g/ml, 1.3-1.7 g/ml, 1.4-1.8 g/ml, 1.5-1.9 g/ml, 1.6-2 g/ml, 1.7-2.1 g/ml, 1.8-2.2 g/ml, 1.9-2.3 g/ml, 2-2.4 g/ml, 2.1-2.5 g/ml, 2.2-2.6 g/ml, 2.3-2.7 g/ml, 2.4-2.8 g/ml, 2.5-2.9 g/ml, 2.6-3 g/ml, 2.7-3.1 g/ml, 2.8-3.2 g/ml, 2.9-3.3 g/ml, 3-3.4 g/ml, 3.1-3.5 g/ml, 3.2-3.6 g/ml, 3.3-3.7 g/ml, 3.4-3.8 g/ml, 3.5-3.9 g/ml, 3.6-4 g/ml, 3.7-4.1 g/ml, 3.8-4.2 g/ml, 3.9-4.3 g/ml, 4-4.4 g/ml, 4.1-4.5 g/ml, 4.2-4.6 g/ml, 4.3-4.7 g/ml, 4.4-4.8 g/ml, 4.5-4.9 g/ml, 4.6-5 g/ml, 0.1-0.6 g/ml, 0.2-0.7 g/ml, 0.3-0.8 g/ml, 0.4-0.9 g/ml, 0.5-1 g/ml, 0.6-1.1 g/ml, 0.7-1.2 g/ml, 0.8-1.3 g/ml, 0.9-1.4 g/ml, 1-1.5 g/ml, 1.1-1.6 g/ml, 1.2-1.7 g/ml, 1.3-1.8 g/mi, 1.4-1.9 g/ml, 1.5-2 g/ml, 1.6-2.1 g/ml, 1.7-2.2 g/ml, 1.8-2.3 g/ml, 1.9-2.4 g/ml, 2-2.5 g/ml, 2.1-2.6 g/ml, 2.2-2.7 g/ml, 2.3-2.8 g/ml, 2.4-2.9 g/ml, 2.5-3 g/ml, 2.6-3.1 g/ml, 2.7-3.2 g/ml, 2.8-3.3 g/ml, 2.9-3.4 g/ml, 3-3.5 g/ml, 3.1-3.6 g/ml, 3.2-3.7 g/ml, 3.3-3.8 g/ml, 3.4-3.9 g/ml, 3.5-4 g/ml, 3.6-4.1 g/ml, 3.7-4.2 g/ml, 3.8-4.3 g/ml, 3.9-4.4 g/ml, 4-4.5 g/ml, 4.1-4.6 g/ml, 4.2-4.7 g/ml, 4.3-4.8 g/ml, 4.4-4.9 g/ml, 4.5-5 g/ml, 0.1-0.7 g/ml, 0.2-0.8 g/ml, 0.3-0.9 g/ml, 0.4-1 g/ml, 0.5-1.1 g/ml, 0.6-1.2 g/ml, 0.7-1.3 g/ml, 0.8-1.4 g/ml, 0.9-1.5 g/ml, 1-1.6 g/ml, 1.1-1.7 g/ml, 1.2-1.8 g/ml, 1.3-1.9 g/ml, 1.4-2 g/ml, 1.5-2.1 g/ml, 1.6-2.2 g/ml, 1.7-2.3 g/ml, 1.8-2.4 g/ml, 1.9-2.5 g/ml, 2-2.6 g/ml, 2.1-2.7 g/ml, 2.2-2.8 g/ml, 2.3-2.9 g/ml, 2.4-3 g/ml, 2.5-3.1 g/ml, 2.6-3.2 g/ml, 2.7-3.3 g/ml, 2.8-3.4 g/ml, 2.9-3.5 g/ml, 3-3.6 g/ml, 3.1-3.7 g/ml, 3.2-3.8 g/ml, 3.3-3.9 g/ml, 3.4-4 g/ml, 3.5-4.1 g/ml, 3.6-4.2 g/ml, 3.7-4.3 g/ml, 3.8-4.4 g/ml, 3.9-4.5 g/ml, 4-4.6 g/ml, 4.1-4.7 g/ml, 4.2-4.8 g/ml, 4.3-4.9 g/ml, 4.4-5 g/ml, 0.1-0.8 g/ml, 0.2-0.9 g/ml, 0.3-1 g/ml, 0.4-1.1 g/ml, 0.5-1.2 g/ml, 0.6-1.3 g/ml, 0.7-1.4 g/ml, 0.8-1.5 g/ml, 0.9-1.6 g/ml, 1-1.7 g/ml, 1.1-1.8 g/ml, 1.2-1.9 g/ml, 1.3-2 g/ml, 1.4-2.1 g/ml, 1.5-2.2 g/ml, 1.6-2.3 g/ml, 1.7-2.4 g/ml, 1.8-2.5 g/ml, 1.9-2.6 g/ml, 2-2.7 g/ml, 2.1-2.8 g/ml, 2.2-2.9 g/ml, 2.3-3 g/ml, 2.4-3.1 g/ml, 2.5-3.2 g/ml, 2.6-3.3 g/ml, 2.7-3.4 g/ml, 2.8-3.5 g/ml, 2.9-3.6 g/mi, 3-3.7 g/ml, 3.1-3.8 g/ml, 3.2-3.9 g/ml, 3.3-4 g/ml, 3.4-4.1 g/ml, 3.5-4.2 g/ml, 3.6-4.3 g/ml, 3.7-4.4 g/ml, 3.8-4.5 g/ml, 3.9-4.6 g/ml, 4-4.7 g/ml, 4.1-4.8 g/ml, 4.2-4.9 g/ml, 4.3-5 g/ml, 0.1-0.9 g/ml, 0.2-1 g/ml, 0.3-1.1 g/ml, 0.4-1.2 g/ml, 0.5-1.3 g/ml, 0.6-1.4 g/ml, 0.7-1.5 g/ml, 0.8-1.6 g/ml, 0.9-1.7 g/ml, 1-1.8 g/ml, 1.1-1.9 g/ml, 1.2-2 g/ml, 1.3-2.1 g/ml, 1.4-2.2 g/ml, 1.5-2.3 g/ml, 1.6-2.4 g/ml, 1.7-2.5 g/ml, 1.8-2.6 g/ml, 1.9-2.7 g/ml, 2-2.8 g/ml, 2.1-2.9 g/ml, 2.2-3 g/ml, 2.3-3.1 g/ml, 2.4-3.2 g/ml, 2.5-3.3 g/ml, 2.6-3.4 g/ml, 2.7-3.5 g/ml, 2.8-3.6 g/ml, 2.9-3.7 g/ml, 3-3.8 g/ml, 3.1-3.9 g/ml, 3.2-4 g/ml, 3.3-4.1 g/ml, 3.4-4.2 g/ml, 3.5-4.3 g/ml, 3.6-4.4 g/ml, 3.7-4.5 g/ml, 3.8-4.6 g/ml, 3.9-4.7 g/ml, 4-4.8 g/ml, 4.1-4.9 g/ml, 4.2-5 g/ml, 0.1-1 g/ml, 0.2-1.1 g/m, 0.3-1.2 g/ml, 0.4-1.3 g/ml, 0.5-1.4 g/ml, 0.6-1.5 g/ml, 0.7-1.6 g/ml, 0.8-1.7 g/ml, 0.9-1.8 g/ml, 1-1.9 g/ml, 1.1-2 g/ml, 1.2-2.1 g/ml, 1.3-2.2 g/ml, 1.4-2.3 g/ml, 1.5-2.4 g/ml, 1.6-2.5 g/ml, 1.7-2.6 g/ml, 1.8-2.7 g/ml, 1.9-2.8 g/ml, 2-2.9 g/ml, 2.1-3 g/ml, 2.2-3.1 g/ml, 2.3-3.2 g/ml, 2.4-3.3 g/ml, 2.5-3.4 g/ml, 2.6-3.5 g/ml, 2.7-3.6 g/ml, 2.8-3.7 g/ml, 2.9-3.8 g/ml, 3-3.9 g/ml, 3.1-4 g/ml, 3.2-4.1 g/ml, 3.3-4.2 g/ml, 3.4-4.3 g/ml, 3.5-4.4 g/ml, 3.6-4.5 g/ml, 3.7-4.6 g/ml, 3.8-4.7 g/ml, 3.9-4.8 g/ml, 4-4.9 g/ml, 4.1-5 g/ml, 0.1-1.1 g/ml, 0.2-1.2 g/ml, 0.3-1.3 g/ml, 0.4-1.4 g/ml, 0.5-1.5 g/ml, 0.6-1.6 g/ml, 0.7-1.7 g/ml, 0.8-1.8 g/ml, 0.9-1.9 g/ml, 1-2 g/ml, 1.1-2.1 g/ml, 1.2-2.2 g/ml, 1.3-2.3 g/ml, 1.4-2.4 g/ml, 1.5-2.5 g/ml, 1.6-2.6 g/ml, 1.7-2.7 g/ml, 1.8-2.8 g/ml, 1.9-2.9 g/ml, 2-3 g/ml, 2.1-3.1 g/ml, 2.2-3.2 g/ml, 2.3-3.3 g/ml, 2.4-3.4 g/ml, 2.5-3.5 g/ml, 2.6-3.6 g/ml, 2.7-3.7 g/ml, 2.8-3.8 g/ml, 2.9-3.9 g/ml, 3-4 g/ml, 3.1-4.1 g/ml, 3.2-4.2 g/ml, 3.3-4.3 g/ml, 3.4-4.4 g/ml, 3.5-4.5 g/ml, 3.6-4.6 g/ml, 3.7-4.7 g/ml, 3.8-4.8 g/ml, 3.9-4.9 g/ml, 4-5 g/ml, 0.1-1.6 g/ml, 0.2-1.7 g/ml, 0.3-1.8 g/ml, 0.4-1.9 g/ml, 0.5-2 g/ml, 0.6-2.1 g/ml, 0.7-2.2 g/ml, 0.8-2.3 g/ml, 0.9-2.4 g/ml, 1-2.5 g/ml, 1.1-2.6 g/ml, 1.2-2.7 g/ml, 1.3-2.8 g/ml, 1.4-2.9 g/ml, 1.5-3 g/ml, 1.6-3.1 g/ml, 1.7-3.2 g/ml, 1.8-3.3 g/ml, 1.9-3.4 g/ml, 2-3.5 g/ml, 2.1-3.6 g/ml, 2.2-3.7 g/ml, 2.3-3.8 g/ml, 2.4-3.9 g/ml, 2.5-4 g/ml, 2.6-4.1 g/ml, 2.7-4.2 g/ml, 2.8-4.3 g/ml, 2.9-4.4 g/ml, 3-4.5 g/ml, 3.1-4.6 g/ml, 3.2-4.7 g/ml, 3.3-4.8 g/ml, 3.4-4.9 g/ml, 3.5-5 g/ml, 0.1-2.1 g/ml, 0.2-2.2 g/ml, 0.3-2.3 g/ml, 0.4-2.4 g/ml, 0.5-2.5 g/ml, 0.6-2.6 g/ml, 0.7-2.7 g/ml, 0.8-2.8 g/ml, 0.9-2.9 g/ml, 1-3 g/ml, 1.1-3.1 g/ml, 1.2-3.2 g/ml, 1.3-3.3 g/ml, 1.4-3.4 g/ml, 1.5-3.5 g/ml, 1.6-3.6 g/ml, 1.7-3.7 g/ml, 1.8-3.8 g/ml, 1.9-3.9 g/ml, 2-4 g/ml, 2.1-4.1 g/ml, 2.2-4.2 g/ml, 2.3-4.3 g/ml, 2.4-4.4 g/ml, 2.5-4.5 g/ml, 2.6-4.6 g/ml, 2.7-4.7 g/ml, 2.8-4.8 g/ml, 2.9-4.9 g/ml, 3-5 g/ml, 0.1-2.6 g/ml, 0.2-2.7 g/ml, 0.3-2.8 g/ml, 0.4-2.9 g/ml, 0.5-3 g/ml, 0.6-3.1 g/ml, 0.7-3.2 g/ml, 0.8-3.3 g/ml, 0.9-3.4 g/ml, 1-3.5 g/ml, 1.1-3.6 g/ml, 1.2-3.7 g/ml, 1.3-3.8 g/ml, 1.4-3.9 g/ml, 1.5-4 g/ml, 1.6-4.1 g/ml, 1.7-4.2 g/ml, 1.8-4.3 g/ml, 1.9-4.4 g/ml, 2-4.5 g/ml, 2.1-4.6 g/ml, 2.2-4.7 g/ml, 2.3-4.8 g/ml, 2.4-4.9 g/ml, 2.5-5 g/ml, 0.1-3.1 g/ml, 0.2-3.2 g/ml, 0.3-3.3 g/ml, 0.4-3.4 g/ml, 0.5-3.5 g/ml, 0.6-3.6 g/ml, 0.7-3.7 g/ml, 0.8-3.8 g/ml, 0.9-3.9 g/ml, 1-4 g/ml, 1.1-4.1 g/ml, 1.2-4.2 g/ml, 1.3-4.3 g/ml, 1.4-4.4 g/ml, 1.5-4.5 g/ml, 1.6-4.6 g/ml, 1.7-4.7 g/ml, 1.8-4.8 g/ml, 1.9-4.9 g/ml, and 2-5 g/ml.

In one embodiment, the specific gravity of the SBP formulation may be between 1.2-2 g/ml.

In one embodiment, the specific gravity of the SBP formulation may be 1.8-2 g/ml.

Shear Recovery

In some embodiments, the SBP formulation may optimized for shear recovery. As described herein, "shear recovery" describes the ability of a physical property of an SBP formulation to recover to a specific percent of its original measure within a specified time post-shear application. Properties that can be measured by methods known in the art may include, but are not limited to, G', G", phase angle, and/or viscosity.

In one embodiment, the shear recovery of the SBP formulation is greater than 75% at 1 second, 2 seconds, 3 seconds, 4 seconds, 5 seconds, 6 seconds, 7 seconds, 8 seconds, 9 seconds, 10 seconds, 11, seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes 17 minutes, 18 minutes, 19 minutes, 20 minutes, 25 minutes, 30 minutes, 35 minutes, 40 minutes, 45 minutes, 50 minutes, 55 minutes, 60 minutes or more than 60 minutes. As a non-limiting example, the shear recovery of the SBP formulation is greater than 75% at 1 minute. As a non-limiting example, the shear recovery of the SBP formulation is greater than 75% at 10 seconds.

In one embodiment, the shear recovery of the SBP formulation is greater than 80% at 1 second, 2 seconds, 3 seconds, 4 seconds, 5 seconds, 6 seconds, 7 seconds, 8 seconds, 9 seconds, 10 seconds, 11, seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes 17 minutes, 18 minutes, 19 minutes, 20 minutes, 25 minutes, 30 minutes, 35 minutes, 40 minutes, 45 minutes, 50 minutes, 55 minutes, 60 minutes or more than 60 minutes. As a non-limiting example, the shear recovery of the SBP formulation is greater than 80% at 1 minute. As a nonlimiting example, the shear recovery of the SBP formulation is greater than 80% at 10 seconds.

In one embodiment, the shear recovery of the SBP formulation is greater than 85% at 1 second, 2 seconds, 3 seconds, 4 seconds, 5 seconds, 6 seconds, 7 seconds, 8 seconds, 9 seconds, 10 seconds, 11, seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes 17 minutes, 18 minutes, 19 minutes, 20 minutes, 25 minutes, 30 minutes, 35 minutes, 40 minutes, 45 minutes, 50 minutes, 55 minutes, 60 minutes or more than 60 minutes. As a non-limiting example, the shear recovery of the SBP formulation is greater than 85% at 1 minute. As a non-limiting example, the shear recovery of the SBP formulation is greater than 85% at 10 seconds.

In one embodiment, the shear recovery of the SBP formulation is greater than 90% at 1 second, 2 seconds, 3 seconds, 4 seconds, 5 seconds, 6 seconds, 7 seconds, 8 seconds, 9 seconds, 10 seconds, 11, seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes 17 minutes, 18 minutes, 19 minutes, 20 minutes, 25 minutes, 30 minutes, 35 minutes, 40 minutes, 45 minutes, 50 minutes, 55 minutes, 60 minutes or more than 60 minutes. As a non-limiting example, the shear recovery of the SBP formulation is greater than 90% at 1 minute. As a non-limiting example, the shear recovery of the SBP formulation is greater than 90% at 10 seconds.

In one embodiment, the shear recovery of the SBP formulation is greater than 95% at 1 second, 2 seconds, 3 seconds, 4 seconds, 5 seconds, 6 seconds, 7 seconds, 8 seconds, 9 seconds, 10 seconds, 11, seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes 17 minutes, 18 minutes, 19 minutes, 20 minutes, 25 minutes, 30 minutes, 35 minutes, 40 minutes, 45 minutes, 50 minutes, 55 minutes, 60 minutes or more than 60 minutes. As a non-limiting example, the shear recovery of the SBP formulation is greater than 95% at 1 minute. As a non-limiting example, the shear recovery of the SBP formulation is greater than 95% at 10 seconds.

In one embodiment, the shear recovery of the SBP formulation is greater than 99% at 1 second, 2 seconds, 3 seconds, 4 seconds, 5 seconds, 6 seconds, 7 seconds, 8 seconds, 9 seconds, 10 seconds, 11, seconds, 12 seconds, 13 seconds, 14 seconds, 15 seconds, 16 seconds, 17 seconds, 18 seconds, 19 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes 17 minutes, 18 minutes, 19 minutes, 20 minutes, 25 minutes, 30 minutes, 35 minutes, 40 minutes, 45 minutes, 50 minutes, 55 minutes, 60 minutes or more than 60 minutes. As a non-limiting example, the shear recovery of the SBP formulation is greater than 99% at 1 minute. As a non-limiting example, the shear recovery of the SBP formulation is greater than 99% at 10 seconds.

Stability and Degradation

In some embodiments, the SBP formulation may optimized for stability.

In one embodiment, the SBP formulation may have an in vivo degradation rate of greater than 10 days, 20 days, 30 days, 40 days, 50 days, 60 days, 70 days, 80 days, 90 days, 100 days, 120 days, 140 days, 160 days, 180 days, 200 days, 250 days, 300 days, 350 days, or 400 days. As a non-limiting example, the in vivo degradation rate is greater than 60 days. As another non-limiting example, the in vivo degradation rate is greater than 120 days.

In one embodiment, the SBP formulation may have an in vivo degradation rate of greater than 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7, 8, 9, 10, 11, 12, 13, 14 days, 1, 2, 3, 4 weeks, or 1, 2, 3, 4, 5, 6, 7, 8, 9, 10, 11, 12 months. In some instances, there is no change in weight of the sample over the period. As a non-limiting example, the SBP formulation may have an in vivo degradation rate of greater than 7 days and there is no change in weight in the sample. As a non-limiting example, the SBP formulation may have an in vivo degradation rate of greater than 14 days and there is no change in weight in the sample.

In one embodiment, the SBP formulation may be stable at room temperature for at least 1 month, 2 months, 3 months, 4 months, 5 months, 6 months, 7 months, 8 months, 9 months, 10 months, 11 months, 12 months, 18 months, 1 year, 2 years, 3 years, 4 years, 5 years, 6 years, 7 years, 8 years, 9 years or more than 9 years. As a non-limiting example, the SBP formulation is stable at room temperature for 2 years. As another non-limiting example, the SBP formulation is stable at room temperature for 3 years.

Endotoxin

In some embodiments, the SBP formulation may optimized for a lower endotoxin level.

In one embodiment, the endotoxin level in the SBP formulation is less than 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or 100 EU/g. As a non-limiting example, the endotoxin level is less than 100 EU/g.

In one embodiment, the endotoxin level in the SBP formulation is less than 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, or 100 EU/mL. As a non-limiting example, the endotoxin level is less than 1 EU/mL by the Limulus amebocyte lysate (LAL) method.

In one embodiment, the endotoxin level in the SBP formulation is between 0.5-5, 1-10, 5-10, 5-15, 10-20, 10-25, 10-30, 10-40, 10-50, 10-60, 10-70, 10-80, 10-90, 10-100, 25-50, 25-75, 25-100, 50-75, 50-100, or 75-100 EU/g. As a non-limiting example, the endotoxin level of the SBP formulation is between 0.5-5 EU/g.

Rheological Properties

In some embodiments, SBP formulations may be optimized to modulate SBP rheological properties, including, but not limited to, viscosity, storage modulus (G'), loss modulus, and phase angle. As used herein, the term "viscosity" refers to a measure of a material's resistance to flow and may include shear viscosity or interfacial viscosity. As used herein, the term "shear storage modulus" refers to the measure of a material's elasticity or reversible deformation as determined by the material's stored energy. As used herein, the term "shear loss modulus" refers to the measure of a material's ability to dissipate energy, usually in the form of heat. As used herein, the term "phase angle" refers to the difference in the stress and strain applied to a material during the application of oscillating shear stress. The viscosity and other rheological properties of a composition (e.g., a gel, e.g., hydrogel or organogel) provided herein can be determined using a rotational viscometer or rheometer. Additional methods for determining the rheological properties of a composition (e.g., gel, e.g., hydrogel or organogel) and other properties of the composition are known in the art. In some embodiments, SBP rheological properties may be altered by the incorporation of an excipient that is a gelling agent. In some embodiments, the identity of the excipient (e.g. PEG or poloxamer) may be altered to tune the rheological properties of SBPs. In some embodiments, the rheological properties of SBPs may be tuned for the desired application (e.g. tissue engineering scaffold, drug delivery system, surgical implant, etc.).

In some embodiments, the viscosity of SBPs is tunable between 1-1000 centipoise (cP). In some embodiments, the viscosity of an SBP is tunable from about 0.0001 to about 1000 Pascal seconds (Pa*s). In some embodiments, the viscosity of an SBP is from about 1 cP to about 10 cP, from about 2 cP to about 20 cP, from about 3 cP to about 30 cP, from about 4 cP to about 40 cP, from about 5 cP to about 50 cP, from about 6 cP to about 60 cP, from about 7 cP to about 70 cP, from about 8 cP to about 80 cP, from about 9 cP to about 90 cP, from about 10 cP to about 100 cP, from about 100 cP to about 150 cP, from about 150 cP to about 200 cP, from about 200 cP to about 250 cP, from about 250 cP to about 300 cP, from about 300 cP to about 350 cP, from about 350 cP to about 400 cP, from about 400 cP to about 450 cP, from about 450 cP to about 500 cP, from about 500 cP to about 600 cP, from about 550 cP to about 700 cP, from about 600 cP to about 800 cP, from about 650 cP to about 900 cP, or from about 700 cP to about 1000 cP. In some embodiments, the viscosity of an SBP is from about 0.0001 Pa*s to about 0.001 Pa*s, from about 0.001 Pa*s to about 0.01 Pa*s, from about 0.01 Pa*s to about 0.1 Pa*s, from about 0.1 Pa*s to about 1 Pa*s, from about 1 Pa*s to about 10 Pa*s, from about 2 Pa*s to about 20 Pa*s, from about 3 Pa*s to about 30 Pa*s, from about 4 Pa*s to about 40 Pa*s, from about 5 Pa*s to about 50 Pa*s, from about 6 Pa*s to about 60 Pa*s, from about 7 Pa*s to about 70 Pa*s, from about 8 Pa*s to about 80 Pa*s, from about 9 Pa*s to about 90 Pa*s, from about 10 Pa*s to about 100 Pa*s, from about 100 Pa*s to about 150 Pa*s, from about 150 Pa*s to about 200 Pa*s, from about 200 Pa*s to about 250 Pa*s, from about 250 Pa*s to about 300 Pa*s, from about 300 Pa*s to about 350 Pa*s, from about 350 Pa*s to about 400 Pa*s, from about 400 Pa*s to about 450 Pa*s, from about 450 Pa*s to about 500 Pa*s, from about 500 Pa*s to about 600 Pa*s, from about 550 Pa*s to about 700 Pa*s, from about 600 Pa*s to about 800 Pa*s, from about 650 Pa*s to about 900 Pa*s, from about 700 Pa*s to about 1000 Pa*s or from about 10 Pa*s to about 2500 Pa*s.

In some embodiments, the SBP formulations may shear thin or display shear thinning properties. As used herein, the term "shear thinning" refers to a decrease in viscosity at increasing shear rates. As used herein, the term "shear rate" refers to the rate of change in the ratio of displacement of material upon the application of a shear force to the height of the material. This ratio is also known as strain.

In some embodiments, the storage modulus and/or the loss modulus (G' and G" respectively) of SBPs is tunable between 0.0001-20000 Pascals (Pa). In some embodiments, the storage modulus and/or the loss modulus of SBPs is from about 0.0001 Pa to about 0.001 Pa, from about 0.001 Pa to about 0.01 Pa, from about 0.01 Pa to about 0.1 Pa, from about 0.1 Pa to about 1 Pa, from about 1 Pa to about 10 Pa, from about 2 Pa to about 20 Pa from about 3 Pa to about 30 Pa, from about 4 Pa to about 40 Pa, from about 5 Pa to about 50 Pa, from about 6 Pa to about 60 Pa, from about 7 Pa to about 70 Pa, from about 8 Pa to about 80 Pa from about 9 Pa to about 90 Pa, from about 10 Pa to about 100 Pa, from about 100 Pa to about 150 Pa, from about 150 Pa to about 200 Pa, from about 200 Pa to about 250 Pa, from about 250 Pa to about 300 Pa, from about 300 Pa to about 350 Pa, from about 350 Pa to about 400 Pa, from about 400 Pa to about 450 Pa, from about 450 Pa to about 500 Pa from about 500 Pa to about 600 Pa, from about 550 Pa to about 700 Pa, from about 600 Pa to about 800 Pa, from about 650 Pa to about 900 Pa, from about 700 Pa to about 1000 Pa, from about 1000 Pa to about 1500 Pa, from about 1500 Pa to about 2000 Pa, from about 2000 Pa to about 2500 Pa, from about 2500 Pa to about 3000 Pa, from about 3000 Pa to about 3500 Pa, from about 3500 Pa to about 4000 Pa, from about 4000 Pa to about 4500 Pa, from about 4500 Pa to about 5000 Pa, from about 5000 Pa to about 5500 Pa, from about 5500 Pa to about 6000 Pa, from about 6000 Pa to about 6500 Pa, from about 6500 Pa to about 7000 Pa, from about 7000 Pa to about 7500 Pa, from about 7500 Pa to about 8000 Pa, from about 8000 Pa to about 8500 Pa, from about 8500 Pa to about 9000 Pa, from about 9000 Pa to about 9500 Pa, from about 9500 Pa to about 10000 Pa, from about 10000 Pa to about 11000 Pa, from about 11000 Pa to about 12000 Pa, from about 12000 Pa to about 13000 Pa, from about 13000 Pa to about 14000 Pa, from about 14000 Pa to about 15000 Pa, from about 15000 Pa to about 16000 Pa, from about 16000 Pa to about 17000 Pa, from about 17000 Pa to about 18000 Pa, from about 18000 Pa to about 19000 Pa. or from about 19000 Pa to about 20000 Pa.

In some embodiments, the phase angle of SBPs is tunable between 1°-90°). In some embodiments, the phase angle of SBPs is from about 1° to about 2°, from about 2° to about 3°, from about 3° to about 4°, from about 4° to about 5°, from about 5° to about 6°, from about 6° to about 7°, from about 7° to about 8°, from about 8° to about 9° from about 9° to about 10°, from about 10° to about 15°, from about 15° to about 20°, from about 20° to about 25°, from about 25° to about 30°, from about 30° to about 35°, from about 35° to about 40°, from about 40° to about 45°, from about 45° to about 50°, from about 50° to about 55°, from about 55° to about 60°, from about 60° to about 65°, from about 65° to about 70°, from about 70° to about 75°, from about 75° to about 80° from about 80° to about 85°, or from about 85° to about 90°.

Stress Resistance

In some embodiments, SBPs may be formulated to modulate SBP resistance to stress. Resistance to stress may be measured using one or more rheological measurements. Such measurements may include, but are not limited to tensile elasticity, shear or rigidity, volumetric elasticity, and compression. Additional rheological measurements and properties may include any of those taught in Zhang et al. (2017) Fiber and Polymers 18(10):1831-1840; McGill et al. (2017) Acta Biomaterialia 63:76-84; and Choi et al. (2015) In-Situ Gelling Polymers, Series in BioEngineering doi. 10.1007/978-981-287-152-7_2, the contents of each of which are herein incorporated by reference in their entirety. In some embodiments, stress resistance may be modulated through incorporation of excipients (e.g., PEG or poloxamer). In some embodiments. SBP stress-resistance properties may be modulated to suit a specific application (e.g., tissue engineering scaffold, drug delivery system, surgical implant, etc.).

In some embodiments, stress resistance may be measured by shear recovery experiments. In some embodiments, the SBPs recover 100% of their viscosity from before the application of shear forces. In some embodiments, the SBPs recover from 0.1%-5%, from 5%-10%, from 10% to 25%, from 25% to 50%, from 50% to 75%, or from 75% to 100% of their viscosity from before the application of shear forces. Shear recovery may be measured via any method known to one skilled in the art. In some embodiments, shear recovery occurs over the course of 1 second, 10 seconds, 30 seconds, or one minute.

Osmolarity

In some embodiments, SBP formulations may include processed silk with or without other components (e.g., excipients and cargo). The SBP formulations may contain an from about 1 mOsm to about 10 mOsm, from about 2 mOsm to about 20 mOsm, from about 3 mOsm to about 30 mOsm, from about 4 mOsm to about 40 mOsm, from about 5 mOsm to about 50 mOsm, from about 6 mOsm to about 60 mOsm, from about 7 mOsm to about 70 mOsm, from about 8 mOsm to about 80 mOsm, from about 9 mOsm to about 90 mOsm, from about 10 mOsm to about 100 mOsm, from about 15 mOsm to about 150 mOsm, from about 25 mOsm to about 200 mOsm, from about 35 mOsm to about 250 mOsm, from about 45 mOsm to about 300 mOsm, from about 55 mOsm to about 350 mOsm, from about 65 mOsm to about 400 mOsm, from about 75 mOsm to about 450 mOsm, from about 85 mOsm to about 500 mOsm, from about 125 mOsm to about 600 mOsm, from about 175 mOsm to about 700 mOsm, from about 225 mOsm to about 800 mOsm, from about 275 mOsm to about 285 mOsm, from about 280 mOsm to about 900 mOsm, or from about 325 mOsm to about 1000 mOsm. The SBPs may have an osmolarity of from about 1 mOsm/L to about 10 mOsm/L, from about 2 mOsm/L to about 20 mOsm/L, from about 3 mOsm/L to about 30 mOsm/L, from about 4 mOsm/L to about 40 mOsm/L, from about 5 mOsm/L to about 50 mOsm/L, from about 6 mOsm/L to about 60 mOsm/L, from about 7 mOsm/L to about 70 mOsm/L, from about 8 mOsm/L to about 80 mOsm/L, from about 9 mOsm/L to about 90 mOsm/L, from about 10 mOsm/L to about 100 mOsm/L, from about 15 mOsm/L to about 150 mOsm/L, from about 25 mOsm/L to about 200 mOsm/L, from about 35 mOsm/L to about 250 mOsm/L, from about 45 mOsm/L to about 300 mOsm/L, from about 55 mOsm/L to about 350 mOsm/L, from about 65 mOsm/L to about 400 mOsm/L, from about 75 mOsm/L to about 450 mOsm/L, from about 85 mOsm/L to about 500 mOsm/L, from about 125 mOsm/L to about 600 mOsm/L, from about 175 mOsm/L to about 700 mOsm/L, from about 225 mOsm/L to about 800 mOsm/L, from about 275 mOsm/L to about 285 mOsm/L, from about 280 mOsm/L to about 900 mOsm/L, or from about 325 mOsm/L to about 1000 mOsm/L.

In some embodiments, the SBP formulation has an osmolarity from about 290-320 mOsm/L.

In some embodiment, the SBP formulation has an osmolarity of 280 mOsm/L.

In some embodiment, the SBP formulation has an osmolarity of 290 mOsm/L.

Concentrations and Ratios of SBP Components

SBP formulations may include formulations of processed silk with other components (e.g., excipient, therapeutic agent, microbe, cargo, and/or biological system), wherein each component is present at a specific concentration, ratio, or range of concentrations or ratios, depending on application. In some embodiments, the concentration of processed silk or other SBP component (e.g., excipient, therapeutic agent, microbe, cargo, and/or biological system) is present in SBP formulations at a concentration (by weight, volume, or concentration) of from about 0.0001% to about 0.001%, from about 0.001% to about 0.01%, from about 0.01% to about 1%, from about 0.05% to about 2%, from about 1% to about 5%, from about 2% to about 10%, from about 4% to about 16%, from about 5% to about 20%, from about 8% to about 24%, from about 10% to about 30%, from about 12% to about 32%, from about 14% to about 34%, from about 16% to about 36%, from about 18% to about 38%, from about 20% to about 40%, from about 22% to about 42%, from about 24% to about 44%, from about 26% to about 46%, from about 28% to about 48%, from about 30% to about 50%, from about 35% to about 55%, from about 40% to about 60%, from about 45% to about 65%, from about 50% to about 70%, from about 55% to about 75%, from about 60% to about 80%, from about 65% to about 85%, from about 70% to about 90%, from about 75% to about 95%, from about 80% to about 96%, from about 85% to about 97%, from about 90% to about 98%, from about 95% to about 99%, from about 96% to about 99.2%, from about 97% to about 99.5%, from about 98% to about 99.8%, from about 99% to about 99.9%, or greater than 99.9%.

In some embodiments, the concentration of processed silk or other SBP component (e.g., excipient, therapeutic agent, microbe, cargo, and/or biological system) is present in SBP formulations at a concentration of from about 0.0001% (w/v) to about 0.001% (w/v), from about 0.001% (w/v) to about 0.01% (w/v), from about 0.01% (v/v) to about 1% (w/v), from about 0.05% (w/v) to about 2% (w/v), from about 1% (w/v) to about 5% (w/v), from about 2% (w/v) to about 10% (w/v), from about 4% (w/v) to about 16% (w/v), from about 5% (w/v) to about 20% (w/v), from about 8% (w/v) to about 24% (w/v), from about 10% (w/v) to about 30% (w/v), from about 12% (w/v) to about 32% (w/v), from about 14% (w/v) to about 34% (w/v), from about 16% (w/v) to about 36% (w/v), from about 18% (w/v) to about 38% (w/v), from about 20% (w/v) to about 40% (w/v), from about 22% (w/v) to about 42% (w/v), from about 24% (w/v) to about 44% (w/v), from about 26% (w/v) to about 46% (w/v), from about 28% (w/v) to about 48% (w/v), from about 30% (w/v) to about 50% (w/v), from about 35% (w/v) to about 55% (w/v), from about 40% (w/v) to about 60% (w/v), from about 45% (w/v) to about 65% (w/v), from about 50% (w/v) to about 70% (w/v), from about 55% (w/v) to about 75% (w/v), from about 60% (w/v) to about 80% (w/v), from about 65% (w/v) to about 85% (w/v), from about 70% (w/v) to about 90% (w/v), from about 75% (w/v) to about 95% (w/v), from about 80% (w/v) to about 96% (w/v), from about 85% (w/v) to about 97% (w/v), from about 90% (w/v) to about 98% (w/v), from about 95% (w/v) to about 99% (w/v), from about 96% (w/v) to about 99.2% (w/v), from about 97% (w/v) to about 99.5% (w/v), from about 98% (w/v) to about 99.8% (w/v), from about 99% (w/v) to about 99.9% (w/v), or greater than 99.9% (w/v).

In some embodiments, the concentration of processed silk or other SBP component (e.g., excipient, therapeutic agent, microbe, cargo, and/or biological system) is present in SBP formulations at a concentration of from about 0.0001% (v/v) to about 0.001% (v/v), from about 0.001% (v/v) to about 0.01% (v/v), from about 0.01% (v/v) to about 1% (v/v), from about 0.05% (v/v) to about 2% (v/v), from about 1% (v/v) to about 5% (v/v), from about 2% (v/v) to about 10% (v/v), from about 4% (v/v) to about 16% (v/v), from about 5%

(v/v) to about 20% (v/v), from about 8% (v/v) to about 24% (v/v), from about 10% (v/v) to about 30% (v/v), from about 12% (v/v) to about 32% (v/v), from about 14% (v/v) to about 34% (v/v), from about 16% (v/v) to about 36% (v/v), from about 18% (v/v) to about 38% (v/v), from about 20% (v/v) to about 40% (v/v), from about 22% (v/v) to about 42% (v/v), from about 24% (v/v) to about 44% (v/v), from about 26% (v/v) to about 46% (v/v), from about 28% (v/v) to about 48% (v/v), from about 30% (v/v) to about 50% (v/v), from about 35% (v/v) to about 55% (v/v), from about 40% (v/v) to about 60% (v/v), from about 45% (v/v) to about 65% (v/v), from about 50% (v/v) to about 70% (v/v), from about 55% (v/v) to about 75% (v/v), from about 60% (v/v) to about 80% (v/v), from about 65% (v/v) to about 85% (v/v), from about 70% (v/v) to about 90% (v/v), from about 75% (v/v) to about 95% (v/v), from about 80% (v/v) to about 96% (v/v), from about 85% (v/v) to about 97% (v/v), from about 90% (v/v) to about 98% (v/v), from about 95% (v/v) to about 99% (v/v), from about 96% (v/v) to about 99.2% (v/v), from about 97% (v/v) to about 99.5% (v/v), from about 98% (v/v) to about 99.8% (v/v), from about 99% (v/v) to about 99.9% (v/v), or greater than 99.9% (v/v).

In some embodiments, the concentration of processed silk or other SBP component (e.g., excipient, therapeutic agent, microbe, cargo, and/or biological system) is present in SBP formulations at a concentration of from about 0.0001% (w/w) to about 0.001% (w/w), from about 0.001% (w/w) to about 0.01% (w/w), from about 0.01% (w/w) to about 1% (w/w), from about 0.05% (w/w) to about 2% (w/w), from about 1% (w/w) to about 5% (w/w), from about 2% (w/w) to about 10% (w/w), from about 4% (w/w) to about 16% (w/w), from about 5% (w/w) to about 20% (w/w), from about 8% (w/w) to about 24% (w/w), from about 10% (w/w) to about 30% (w/w), from about 12% (w/w) to about 32% (w/w), from about 14% (w/w) to about 34% (w/w), from about 16% (w/w) to about 36% (w/w), from about 18% (w/w) to about 38% (w/w), from about 20% (w/w) to about 40% (w/w), from about 22% (w/w) to about 42% (w/w), from about 24% (w/w) to about 44% (w/w), from about 26% (w/w) to about 46% (w/w), from about 28% (w/w) to about 48% (w/w), from about 30% (w/w) to about 50% (w/w), from about 35% (w/w) to about 55% (w/v), from about 40% (w/w) to about 60% (w/w), from about 45% (w/w) to about 65% (w/w), from about 50% (w/w) to about 70% (w/w), from about 55% (w/w) to about 75% (w/w), from about 60% (w/w) to about 80% (w/w), from about 65% (w/w) to about 85% (w/w), from about 70% (w/w) to about 90% (w/w), from about 75% (w/w) to about 95% (w/w), from about 80% (w/w) to about 96% (w/w), from about 85% (w/w) to about 97% (w/v), from about 90% (w/w) to about 98% (w/w), from about 95% (w/v) to about 99% (w/w), from about 96% (w/w) to about 99.2% (w/w), from about 97% (w/w) to about 99.5% (w/w), from about 98% (w/w) to about 99.8% (w/w), from about 99% (w/w) to about 99.9% (w/w), or greater than 99.9% (w/w).

In one embodiment, the concentration of processed silk or other SBP component (e.g., excipient or cargo) is present in SBPs at a concentration of 1% (w/v).

In one embodiment, the concentration of processed silk or other SBP component (e.g., excipient or cargo) is present in SBPs at a concentration of 2% (w/v).

In one embodiment, the concentration of processed silk or other SBP component (e.g., excipient or cargo) is present in SBPs at a concentration of 3% (w/v).

In one embodiment, the concentration of processed silk or other SBP component (e.g., excipient or cargo) is present in SBPs at a concentration of 4% (w/v).

In one embodiment, the concentration of processed silk or other SBP component (e.g., excipient or cargo) is present in SBPs at a concentration of 5% (w/v).

In one embodiment, the concentration of processed silk or other SBP component (e.g., excipient or cargo) is present in SBPs at a concentration of 6% (w/v).

In one embodiment, the concentration of processed silk or other SBP component (e.g., excipient or cargo) is present in SBPs at a concentration of 10% (w/v).

In one embodiment, the concentration of processed silk or other SBP component (e.g., excipient or cargo) is present in SBPs at a concentration of 20% (w/v).

In one embodiment, the concentration of processed silk or other SBP component (e.g., excipient or cargo) is present in SBPs at a concentration of 30% (w/v).

In one embodiment, the concentration of processed silk or other SBP component (e.g., excipient or cargo) is present in SBPs at a concentration of 16.7% (w/w).

In one embodiment, the concentration of processed silk or other SBP component (e.g., excipient or cargo) is present in SBPs at a concentration of 20% (w/w).

In one embodiment, the concentration of processed silk or other SBP component (e.g., excipient or cargo) is present in SBPs at a concentration of 23% (w/w).

In one embodiment, the concentration of processed silk or other SBP component (e.g., excipient or cargo) is present in SBPs at a concentration of 25% (w/w).

In one embodiment, the concentration of processed silk or other SBP component (e.g., excipient or cargo) is present in SBPs at a concentration of 27.3% (w/w).

In one embodiment, the concentration of processed silk or other SBP component (e.g., excipient or cargo) is present in SBPs at a concentration of 28.6% (w/w).

In one embodiment, the concentration of processed silk or other SBP component (e.g., excipient or cargo) is present in SBPs at a concentration of 33.3% (w/w).

In one embodiment, the concentration of processed silk or other SBP component (e.g., excipient or cargo) is present in SBPs at a concentration of 40% (w/w).

In one embodiment, the concentration of processed silk or other SBP component (e.g., excipient or cargo) is present in SBPs at a concentration of 50% (w/w).

In some embodiments, the concentration of processed silk (e.g., silk fibroin) or other SBP component (e.g., excipient, therapeutic agent, microbe, cargo, and/or biological system) is present in SBP formulations at a concentration of from about 0.01 pg/mL to about 1 pg/mL, from about 0.05 pg/mL to about 2 pg/mL, from about 1 pg/mL to about 5 pg/mL, from about 2 pg/mL to about 10 pg/mL, from about 4 pg/mL to about 16 pg/mL, from about 5 pg/mL to about 20 pg/mL, from about 8 pg/mL to about 24 pg/mL, from about 10 pg/mL to about 30 pg/mL, from about 12 pg/mL to about 32 pg/mL, from about 14 pg/mL to about 34 pg/mL, from about 16 pg/mL to about 36 pg/mL, from about 18 pg/mL to about 38 pg/mL, from about 20 pg/mL to about 40 pg/mL, from about 22 pg/mL to about 42 pg/mL, from about 24 pg/mL to about 44 pg/mL, from about 26 pg/mL to about 46 pg/mL, from about 28 pg/mL to about 48 pg/mL, from about 30 pg/mL to about 50 pg/mL, from about 35 pg/mL to about 55 pg/mL, from about 40 pg/mL to about 60 pg/mL, from about 45 pg/mL to about 65 pg/mL, from about 50 pg/mL to about 75 pg/mL, from about 60 pg/mL to about 240 pg/mL, from about 70 pg/mL to about 350 pg/mL, from about 80 pg/mL to about 400 pg/mL, from about 90 pg/mL to about 450 pg/mL, from about 100 pg/mL to about 500 pg/mL, from about 0.01 ng/mL to about 1 ng/mL, from about 0.05 ng/mL to about 2 ng/mL, from about 1 ng/mL to about 5 ng/mL, from about 2 ng/mL to about 10 ng/mL, from about 4 ng/mL to about 16 ng/mL, from about 5 ng/mL to about 20 ng/mL, from about 8 ng/mL to about 24 ng/mL, from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 µg/mL to about 1 µg/mL, from about 0.05 µg/mL to about 2 µg/mL, from about 1 µg/mL to about 5 µg/mL, from about 2 µg/mL to about 10 µg/mL, from about 4 µg/mL to about 16 µg/mL, from about 5 µg/mL to about 20 µg/mL, from about 8 µg/mL to about 24 µg/mL, from about 10 µg/mL to about 30 µg/mL, from about 12 µg/mL to about 32 µg/mL, from about 14 µg/mL to about 34 µg/mL, from about 16 µg/mL to about 36 µg/mL, from about 18 µg/mL to about 38 µg/mL, from about 20 µg/mL to about 40 µg/mL, from about 22 µg/mL to about 42 µg/mL, from about 24 µg/mL to about 44 µg/mL, from about 26 µg/mL to about 46 µg/mL, from about 28 µg/mL to about 48 µg/mL, from about 30 µg/mL to about 50 µg/mL, from about 35 µg/mL to about 55 µg/mL, from about 40 µg/mL to about 60 µg/mL, from about 45 µg/mL to about 65 µg/mL, from about 50 µg/mL to about 75 µg/mL, from about 60 µg/mL to about 240 µg/mL, from about 70 µg/mL to about 350 µg/mL, from about 80 µg/mL to about 400 µg/mL, from about 90 µg/mL to about 450 µg/mL, from about 100 µg/mL to about 500 µg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL, from about 0.05 g/mL to about 2 g/mL, from about 1 g/mL to about 5 g/mL, from about 2 g/mL to about 10 g/mL, from about 4 g/mL to about 16 g/mL, or from about 5 g/mL to about 20 g/mL.

In some embodiments, the concentration of processed silk (e.g., silk fibroin) or other SBP component (e.g., excipient, therapeutic agent, microbe, cargo, and/or biological system) is present in SBP formulations at a concentration of from about 0.01 pg/kg to about 1 pg/kg, from about 0.05 pg/kg to about 2 pg/kg, from about 1 pg/kg to about 5 pg/kg, from about 2 pg/kg to about 10 pg/kg, from about 4 pg/kg to about 16 pg/kg, from about 5 pg/kg to about 20 pg/kg, from about 8 pg/kg to about 24 pg/kg, from about 10 pg/kg to about 30 pg/kg, from about 12 pg/kg to about 32 pg/kg, from about 14 pg/kg to about 34 pg/kg, from about 16 pg/kg to about 36 pg/kg, from about 18 pg/kg to about 38 pg/kg, from about 20 pg/kg to about 40 pg/kg, from about 22 pg/kg to about 42 pg/kg, from about 24 pg/kg to about 44 pg/kg, from about 26 pg/kg to about 46 pg/kg, from about 28 pg/kg to about 48 pg/kg, from about 30 pg/kg to about 50 pg/kg, from about 35 pg/kg to about 55 pg/kg, from about 40 pg/kg to about 60 pg/kg, from about 45 pg/kg to about 65 pg/kg, from about 50 pg/kg to about 75 pg/kg, from about 60 pg/kg to about 240 pg/kg, from about 70 pg/kg to about 350 pg/kg, from about 80 pg/kg to about 400 pg/kg, from about 90 pg/kg to about 450 pg/kg, from about 100 pg/kg to about 500 pg/kg, from about 0.01 ng/kg to about 1 ng/kg, from about 0.05 ng/kg to about 2 ng/kg, from about 1 ng/kg to about 5 ng/kg, from about 2 ng/kg to about 10 ng/kg, from about 4 ng/kg to about 16 ng/kg, from about 5 ng/kg to about 20 ng/kg, from about 8 ng/kg to about 24 ng/kg, from about 10 ng/kg to about 30 ng/kg, from about 12 ng/kg to about 32 ng/kg, from about 14 ng/kg to about 34 ng/kg, from about 16 ng/kg to about 36 ng/kg, from about 18 ng/kg to about 38 ng/kg, from about 20 ng/kg to about 40 ng/kg, from about 22 ng/kg to about 42 ng/kg, from about 24 ng/kg to about 44 ng/kg, from about 26 ng/kg to about 46 ng/kg, from about 28 ng/kg to about 48 ng/kg, from about 30 ng/kg to about 50 ng/kg, from about 35 ng/kg to about 55 ng/kg, from about 40 ng/kg to about 60 ng/kg, from about 45 ng/kg to about 65 ng/kg, from about 50 ng/kg to about 75 ng/kg, from about 60 ng/kg to about 240 ng/kg, from about 70 ng/kg to about 350 ng/kg, from about 80 ng/kg to about 400 ng/kg, from about 90 ng/kg to about 450 ng/kg, from about 100 ng/kg to about 500 ng/kg, from about 0.01 µg/kg to about 1 µg/kg, from about 0.05 µg/kg to about 2 µg/kg, from about 1 µg/kg to about 5 µg/kg, from about 2 µg/kg to about 10 µg/kg, from about 4 µg/kg to about 16 µg/kg, from about 5 µg/kg to about 20 µg/kg, from about 8 µg/kg to about 24 µg/kg, from about 10 µg/kg to about 30 µg/kg, from about 12 µg/kg to about 32 µg/kg, from about 14 µg/kg to about 34 µg/kg, from about 16 µg/kg to about 36 µg/kg, from about 18 µg/kg to about 38 µg/kg, from about 20 µg/kg to about 40 µg/kg, from about 22 µg/kg to about 42 µg/kg, from about 24 µg/kg to about 44 µg/kg, from about 26 µg/kg to about 46 µg/kg, from about 28 µg/kg to about 48 µg/kg, from about 30 µg/kg to about 50 µg/kg, from about 35 µg/kg to about 55 µg/kg, from about 40 µg/kg to about 60 µg/kg, from about 45 µg/kg to about 65 µg/kg, from about 50 µg/kg to about 75 µg/kg, from about 60 µg/kg to about 240 µg/kg, from about 70 µg/kg to about 350 µg/kg, from about 80 µg/kg to about 400 µg/kg, from about 90 µg/kg to about 450 µg/kg, from about 100 µg/kg to about 500 µg/kg, from about 0.01 mg/kg to about 1 mg/kg, from about 0.05 mg/kg to about 2 mg/kg, from about 1 mg/kg to about 5 mg/kg, from about 2 mg/kg to about 10 mg/kg, from about 4 mg/kg to about 16 mg/kg, from about 5 mg/kg to about 20 mg/kg, from about 8 mg/kg to about 24 mg/kg, from about 10 mg/kg to about 30 mg/kg, from about 12 mg/kg to about 32 mg/kg, from about 14 mg/kg to about 34 mg/kg, from about 16 mg/kg to about 36 mg/kg, from about 18 mg/kg to about 38 mg/kg, from about 20 mg/kg to about 40 mg/kg, from about 22 mg/kg to about 42 mg/kg, from about 24 mg/kg to about 44 mg/kg, from about 26 mg/kg to about 46 mg/kg, from about 28 mg/kg to about 48 mg/kg, from about 30 mg/kg to about 50 mg/kg, from about 35 mg/kg to about 55 mg/kg, from about 40 mg/kg to about 60 mg/kg, from about 45 mg/kg to about 65 mg/kg, from about 50 mg/kg to about 75 mg/kg, from about 60 mg/kg to about 240 mg/kg, from about 70 mg/kg to about 350 mg/kg, from about 80 mg/kg to about 400 mg/kg, from about 90 mg/kg to about 450 mg/kg, from about 100 mg/kg to about 500 mg/kg, from about 0.01 g/kg to about 1 g/kg, from about 0.05 g/kg to about 2 g/kg, from about 1 g/kg to about 5 g/kg, from about 2 g/kg to about 10 g/kg, from about 4 g/kg to about 16 g/kg, or from about 5 g/kg to about 20 g/kg, from about 10 g/kg to about 50 g/kg, from about 15 g/kg to about 100 g/kg, from about 20 g/kg to about 150 g/kg, from about 25 g/kg to about 200 g/kg, from about 30 g/kg to about 250 g/kg, from about 35 g/kg to about 300 g/kg, from about 40 g/kg to about 350 g/kg, from about 45 g/kg to about 400 g/kg, from about 50 g/kg to about 450 g/kg, from about 55 g/kg to about 500 g/kg, from about 60 g/kg to about 550 g/kg, from about 65 g/kg to about 600 g/kg, from about 70 g/kg to about 650 g/kg, from about 75 g/kg to about 700 g/kg, from about 80 g/kg to about 750 g/kg, from about 85 g/kg to about 800 g/kg, from about 90 g/kg to about 850 g/kg, from about 95 g/kg to about 900 g/kg, from about 100 g/kg to about 950 g/kg, or from about 200 g/kg to about 1000 g/kg.

In some embodiments, the concentration of processed silk or other SBP component (e.g., excipient, therapeutic agent, microbe, cargo, and/or biological system) is present in SBP formulations at a concentration of from about 0.1 pM to about 1 pM, from about 1 pM to about 10 pM, from about 2 pM to about 20 pM, from about 3 pM to about 30 pM, from about 4 pM to about 40 pM, from about 5 pM to about 50 pM, from about 6 pM to about 60 pM, from about 7 pM to about 70 pM, from about 8 pM to about 80 pM, from about 9 pM to about 90 pM, from about 10 pM to about 100 pM, from about 11 pM to about 110 pM, from about 12 pM to about 120 pM, from about 13 pM to about 130 pM, from about 14 pM to about 140 pM, from about 15 pM to about 150 pM, from about 16 pM to about 160 pM, from about 17 pM to about 170 pM, from about 18 pM to about 180 pM, from about 19 pM to about 190 pM, from about 20 pM to about 200 pM, from about 21 pM to about 210 pM, from about 22 pM to about 220 pM, from about 23 pM to about 230 pM, from about 24 pM to about 240 pM, from about 25 pM to about 250 pM, from about 26 pM to about 260 pM, from about 27 pM to about 270 pM, from about 28 pM to about 280 pM, from about 29 pM to about 290 pM, from about 30 pM to about 300 pM, from about 31 pM to about 310 pM, from about 32 pM to about 320 pM, from about 33 pM to about 330 pM, from about 34 pM to about 340 pM, from about 35 pM to about 350 pM, from about 36 pM to about 360 pM, from about 37 pM to about 370 pM, from about 38 pM to about 380 pM, from about 39 pM to about 390 pM, from about 40 pM to about 400 pM, from about 41 pM to about 410 pM, from about 42 pM to about 420 pM, from about 43 pM to about 430 pM, from about 44 pM to about 440 pM, from about 45 pM to about 450 pM, from about 46 pM to about 460 pM, from about 47 pM to about 470 pM, from about 48 pM to about 480 pM, from about 49 pM to about 490 pM, from about 50 pM to about 500 pM, from about 51 pM to about 510 pM, from about 52 pM to about 520 pM, from about 53 pM to about 530 pM, from about 54 pM to about 540 pM, from about 55 pM to about 550 pM, from about 56 pM to about 560 pM, from about 57 pM to about 570 pM, from about 58 pM to about 580 pM, from about 59 pM to about 590 pM, from about 60 pM to about 600 pM, from about 61 pM to about 610 pM, from about 62 pM to about 620 pM, from about 63 pM to about 630 pM, from about 64 pM to about 640 pM, from about 65 pM to about 650 pM, from about 66 pM to about 660 pM, from about 67 pM to about 670 pM, from about 68 pM to about 680 pM, from about 69 pM to about 690 pM, from about 70 pM to about 700 pM, from about 71 pM to about 710 pM, from about 72 pM to about 720 pM, from about 73 pM to about 730 pM, from about 74 pM to about 740 pM, from about 75 pM to about 750 pM, from about 76 pM to about 760 pM, from about 77 pM to about 770 pM, from about 78 pM to about 780 pM, from about 79 pM to about 790 pM, from about 80 pM to about 800 pM, from about 81 pM to about 810 pM, from about 82 pM to about 820 pM, from about 83 pM to about 830 pM, from about 84 pM to about 840 pM, from about 85 pM to about 850 pM, from about 86 pM to about 860 pM, from about 87 pM to about 870 pM, from about 88 pM to about 880 pM, from about 89 pM to about 890 pM, from about 90 pM to about 900 pM, from about 91 pM to about 910 pM, from about 92 pM to about 920 pM, from about 93 pM to about 930 pM, from about 94 pM to about 940 pM, from about 95 pM to about 950 pM, from about 96 pM to about 960 pM, from about 97 pM to about 970 pM, from about 98 pM to about 980 pM, from about 99 pM to about 990 pM, from about 100 pM to about 1 nM, from about 0.1 nM to about 1 nM, from about 1 nM to about 10 nM, from about 2 nM to about 20 nM, from about 3 nM to about 30 nM, from about 4 nM to about 40 nM, from about 5 nM to about 50 nM, from about 6 nM to about 60 nM, from about 7 nM to about 70 nM, from about 8 nM to about 80 nM, from about 9 nM to about 90 nM, from about 10 nM to about 100 nM, from about 11 nM to about 110 nM, from about 12 nM to about 120 nM, from about 13 nM to about 130 nM, from about 14 nM to about 140 nM, from about 15 nM to about 150 nM, from about 16 nM to about 160 nM, from about 17 nM to about 170 nM, from about 18 nM to about 180 nM, from about 19 nM to about 190 nM, from about 20 nM to about 200 nM, from about 21 nM to about 210 nM, from about 22 nM to about 220 nM, from about 23 nM to about 230 nM, from about 24 nM to about 240 nM, from about 25 nM to about 250 nM, from about 26 nM to about 260 nM, from about 27 nM to about 270 nM, from about 28 nM to about 280 nM, from about 29 nM to about 290 nM, from about 30 nM to about 300 nM, from about 31 nM to about 310 nM, from about 32 nM to about 320 nM, from about 33 nM to about 330 nM, from about 34 nM to about 340 nM, from about 35 nM to about 350 nM, from about 36 nM to about 360 nM, from about 37 nM to about 370 nM, from about 38 nM to about 380 nM, from about 39 nM to about 390 nM, from about 40 nM to about 400 nM, from about 41 nM to about 410 nM, from about 42 nM to about 420 nM, from about 43 nM to about 430 nM, from about 44 nM to about 440 nM, from about 45 nM to about 450 nM, from about 46 nM to about 460 nM, from about 47 nM to about 470 nM, from about 48 nM to about 480 nM, from about 49 nM to about 490 nM, from about 50 nM to about 500 nM, from about 51 nM to about 510 nM, from about 52 nM to about 520 nM, from about 53 nM to about 530 nM, from about 54 nM to about 540 nM, from about 55 nM to about 550 nM, from about 56 nM to about 560 nM, from about 57 nM to about 570 nM, from about 58 nM to about 580 nM, from about 59 nM to about 590 nM, from about 60 nM to about 600 nM, from about 61 nM to about 610 nM, from about 62 nM to about 620 nM, from about 63 nM to about 630 nM, from about 64 nM to about 640 nM, from about 65 nM to about 650 nM, from about 66 nM to about 660 nM, from about 67 nM to about 670 nM, from about 68 nM to about 680 nM, from about 69 nM to about 690 nM, from about 70 nM to about 700 nM, from about 71 nM to about 710 nM, from about 72 nM to about 720 nM, from about 73 nM to about 730 nM, from about 74 nM to about 740 nM, from about 75 nM to about 750 nM, from about 76 nM to about 760 nM, from about 77 nM to about 770 nM, from about 78 nM to about 780 nM, from about 79 nM to about 790 nM, from about 80 nM to about 800 nM, from about 81 nM to about 810 nM, from about 82 nM to about 820 nM, from about 83 nM to about 830 nM, from about 84 nM to about 840 nM, from about 85 nM to about 850 nM, from about 86 nM to about 860 nM, from about 87 nM to about 870 nM, from about 88 nM to about 880 nM, from about 89 nM to about 890 nM, from about 90 nM to about 900 nM, from about 91 nM to about 910 nM, from about 92 nM to about 920 nM, from about 93 nM to about 930 nM, from about 94 nM to about 940 nM, from about 95 nM to about 950 nM, from about 96 nM to about 960 nM, from about 97 nM to about 970 nM, from about 98 nM to about 980 nM, from about 99 nM to about 990 nM, from about 100 nM to about 1 µM, from about 0.1 µM to about 1 µM, from about 1 µM to about 10 µM, from about 2 µM to about 20 µM, from about 3 µM to about 30 µM, from about 4 µM to about 40 µM, from about 5 µM to about 50 µM, from about 6 µM to about 60 µM, from about 7 µM to about 70 µM, from about 8 µM to about 80 µM, from about 9 µM to about 90 µM, from about 10 µM to about 100 µM, from about 11 µM to about 110 µM, from about 12 µM to about 120 µM, from about 13 µM to about 130 µM, from about 14 µM to about 140 µM, from about 15 µM to about 150 µM, from about 16 µM to about 160 µM, from about 17 µM to about 170 µM, from about 18 µM to about 180 µM from about 19 µM to about 190 µM, from about 20 µM to about 200 µM, from about 21 µM to about 210 µM, from about 22 µM to about 220 µM, from about 23 µM to about 230 µM, from about 24 µM to about 240 µM, from about 25 µM to about 250 µM, from about 26 µM to about 260 µM, from about 27 µM to about 270 µM, from about 28 µM to about 280 µM, from about 29 µM to about 290 µM, from about 30 µM to about 300 µM, from about 31 µM to about 310 µM, from about 32 µM to about 320 µM, from about 33 µM to about 330 µM, from about 34 µM to about 340 µM, from about 35 µM to about 350 µM, from about 36 µM to about 360 µM, from about 37 µM to about 370 µM, from about 38 µM to about 380 µM, from about 39 µM to about 390 µM, from about 40 µM to about 400 µM, from about 41 µM to about 410 µM, from about 42 µM to about 420 µM, from about 43 µM to about 430 µM, from about 44 µM to about 440 µM from about 45 µM to about 450 µM, from about 46 µM to about 460 µM, from about 47 µM to about 470 µM, from about 48 µM to about 480 µM, from about 49 µM to about 490 µM, from about 50 µM to about 500 µM, from about 51 µM to about 510 µM, from about 52 µM to about 520 µM, from about 53 µM to about 530 µM from about 54 µM to about 540 µM, from about 55 µM to about 550 µM, from about 56 µM to about 560 µM, from about 57 µM to about 570 µM, from about 58 µM to about 580 µM, from about 59 µM to about 590 µM, from about 60 µM to about 600 µM, from about 61 µM to about 610 µM, from about 62 µM to about 620 µM from about 63 µM to about 630 µM, from about 64 µM to about 640 µM, from about 65 µM to about 650 µM, from about 66 µM to about 660 µM, from about 67 µM to about 670 µM, from about 68 µM to about 680 µM, from about 69 µM to about 690 µM, from about 70 µM to about 700 µM, from about 71 µM to about 710 µM, from about 72 µM to about 720 µM, from about 73 µM to about 730 µM, from about 74 µM to about 740 µM from about 75 µM to about 750 µM, from about 76 µM to about 760 µM, from about 77 µM to about 770 µM, from about 78 µM to about 780 µM, from about 79 µM to about 790 µM, from about 80 µM to about 800 µM, from about 81 µM to about 810 µM, from about 82 µM to about 820 µM, from about 83 µM to about 830 µM, from about 84 µM to about 840 µM, from about 85 µM to about 850 µM, from about 86 µM to about 860 µM, from about 87 µM to about 870 µM, from about 88 µM to about 880 µM, from about 89 µM to about 890 µM, from about 90 µM to about 900 µM, from about 91 µM to about 910 µM, from about 92 µM to about 920 µM, from about 93 µM to about 930 µM, from about 94 µM to about 940 µM, from about 95 µM to about 950 µM, from about 96 µM to about 960 µM, from about 97 µM to about 970 µM, from about 98 µM to about 980 µM, from about 99 µM to about 990 µM, from about 100 µM to about 1 mM, from about 0.1 mM to about 1 mM, from about 1 mM to about 10 mM, from about 2 mM to about 20 mM, from about 3 mM to about 30 mM, from about 4 mM to about 40 mM, from about 5 mM to about 50 mM, from about 6 mM to about 60 mM, from about 7 mM to about 70 mM, from about 8 mM to about 80 mM, from about 9 mM to about 90 mM, from about 10 mM to about 100 mM, from about 11 mM to about 110 mM, from about 12 mM to about 120 mM, from about 13 mM to about 130 mM, from about 14 mM to about 140 mM, from about 15 mM to about 150 mM, from about 16 mM to about 160 mM, from about 17 mM to about 170 mM, from about 18 mM to about 180 mM, from about 19 mM to about 190 mM, from about 20 mM to about 200 mM, from about 21 mM to about 210 mM, from about 22 mM to about 220 mM, from about 23 mM to about 230 mM, from about 24 mM to about 240 mM, from about 25 mM to about 250 mM, from about 26 mM to about 260 mM, from about 27 mM to about 270 mM, from about 28 mM to about 280 mM, from about 29 mM to about 290 mM, from about 30 mM to about 300 mM, from about 31 mM to about 310 mM, from about 32 mM to about 320 mM, from about 33 mM to about 330 mM, from about 34 mM to about 340 mM, from about 35 mM to about 350 mM, from about 36 mM to about 360 mM, from about 37 mM to about 370 mM, from about 38 mM to about 380 mM, from about 39 mM to about 390 mM, from about 40 mM to about 400 mM, from about 41 mM to about 410 mM, from about 42 mM to about 420 mM, from about 43 mM to about 430 mM, from about 44 mM to about 440 mM, from about 45 mM to about 450 mM, from about 46 mM to about 460 mM, from about 47 mM to about 470 mM, from about 48 mM to about 480 mM, from about 49 mM to about 490 mM from about 50 mM to about 500 mM, from about 51 mM to about 510 mM, from about 52 mM to about 520 mM, from about 53 mM to about 530 mM, from about 54 mM to about 540 mM from about 55 mM to about 550 mM, from about 56 mM to about 560 mM, from about 57 mM to about 570 mM, from about 58 mM to about 580 mM, from about 59 mM to about 590 mM, from about 60 mM to about 600 mM, from about 61 mM to about 610 mM, from about 62 mM to about 620 mM, from about 63 mM to about 630 mM, from about 64 mM to about 640 mM, from about 65 mM to about 650 mM, from about 66 mM to about 660 mM, from about 67 mM to about 670 mM, from about 68 mM to about 680 mM, from about 69 mM to about 690 mM, from about 70 mM to about 700 mM, from about 71 mM to about 710 mM from about 72 mM to about 720 mM, from about 73 mM to about 730 mM, from about 74 mM to about 740 mM, from about 75 mM to about 750 mM, from about 76 mM to about 760 mM, from about 77 mM to about 770 mM, from about 78 mM to about 780 mM, from about 79 mM to about 790 mM, from about 80 mM to about 800 mM, from about 81 mM to about 810 mM, from about 82 mM to about 820 mM, from about 83 mM to about 830 mM, from about 84 mM to about 840 mM, from about 85 mM to about 850 mM, from about 86 mM to about 860 mM, from about 87 mM to about 870 mM, from about 88 mM to about 880 mM, from about 89 mM to about 890 mM, from about 90 mM to about 900 mM, from about 91 mM to about 910 mM, from about 92 mM to about 920 mM, from about 93 mM to about 930 mM, from about 94 mM to about 940 mM, from about 95 mM to about 950 mM, from about 96 mM to about 960 mM, from about 97 mM to about 970 mM, from about 98 mM to about 980 mM, from about 99 mM to about 990 mM, from about 100 mM to about 1 M, from about 1 M to about 10 M, from about 2 M to about 20 M, from about 3 M to about 30 M, from about 4 M to about 40 M, from about 5 M to about 50 M, from about 6 M to about 60 M, from about 7 M to about 70 M, from about 8 M to about 80 M, from about 9 M to about 90 M, from about 10 M to about 100 M, from about 11 M to about 110 M, from about 12 M to about 120 M from about 13 M to about 130 M, from about 14 M to about 140 M, from about 15 M to about 150 M, from about 16 M to about 160 M, from about 17 M to about 170 M, from about 18 M to about 180 M, from about 19 M to about 190 M, from about 20 M to about 200 M, from about 21 M to about 210 M, from about 22 M to about 220 M, from about 23 M to about 230 M, from about 24 M to about 240 M, from about 25 M to about 250 M, from about 26 M to about 260 M, from about 27 M to about 270 M, from about 28 M to about 280 M, from about 29 M to about 290 M, from about 30 M to about 300 M, from about 31 M to about 310 M, from about 32 M to about 320 M from about 33 M to about 330 M, from about 34 M to about 340 M, from about 35 M to about 350 M, from about 36 M to about 360 M, from about 37 M to about 370 M, from about 38 M to about 380 M, from about 39 M to about 390 M, from about 40 M to about 400 M, from about 41 M to about 410 M, from about 42 M to about 420 M, from about 43 M to about 430 M, from about 44 M to about 440 M, from about 45 M to about 450 M, from about 46 M to about 460 M, from about 47 M to about 470 M, from about 48 M to about 480 M, from about 49 M to about 490 M, or from about 50 M to about 500 M.

SBPs may include a ratio of silk fibroin (by weight, volume, or concentration) to at least one excipient and/or therapeutic agent (by weight, volume, or concentration) of from about 0.001:1 to about 1:1, from about 0.005:1 to about 5:1, from about 0.01:1 to about 0.5:1, from about 0.01:1 to about 10:1, from about 0.02:1 to about 20:1, from about 0.03:1 to about 30:1, from about 0.04:1 to about 40:1, from about 0.05:1 to about 50:1, from about 0.06:1 to about 60:1, from about 0.07:1 to about 70:1, from about 0.08:1 to about 80:1, from about 0.09:1 to about 90:1, from about 0.1:1 to about 100:1, from about 0.2:1 to about 150:1, from about 0.3:1 to about 200:1, from about 0.4:1 to about 250:1, from about 0.5:1 to about 300:1, from about 0.6:1 to about 350:1, from about 0.7:1 to about 400:1, from about 0.8:1 to about 450:1, from about 0.9:1 to about 500:1, from about 1:1 to about 550:1, from about 2:1 to about 600:1, from about 3:1 to about 650:1, from about 4:1 to about 700:1, from about 5:1 to about 750:1, from about 6:1 to about 800:1, from about 7:1 to about 850:1, from about 8:1 to about 900:1, from about 9:1 to about 950:1, from about 10:1 to about 960:1, from about 50:1 to about 970:1, from about 100:1 to about 980:1, from about 200:1 to about 990:1, or from about 500:1 to about 1000:1. In some embodiments, SBP formulations contain trace amounts of excipient.

In some embodiments, the concentration processed silk and/or other components may be determined by absorbance. In some embodiments, the concentration of processed silk and/or other components may be determined by their absorbance at 280 nm.

Appearance: Transparent, Opaque, Translucent

In some embodiments, the appearance of SBP formulations described in the present disclosure may be tuned for the application for which they were designed. In some embodiments, SBP formulations may be transparent. In some embodiments, SBP formulations may be translucent. In some embodiments, SBP formulations may be opaque. In some embodiments, SBP preparation methods may be used to modulate clarity, as taught in International Patent Application Publication No. WO2012170655, the contents of which are herein incorporated by reference in their entirety. In some embodiments, the incorporation of excipients may be used to tune the clarity of processed silk preparations. In some embodiments, the excipient is sucrose. In some embodiments, the sucrose may also increase protein reconstitution during lyophilization. In some embodiments, sucrose may improve processed silk hydrogel clarity (optically transparent). The transparency of SBP formulations, as well as other properties, may render resulting labels edible, biodegradable, and/or holographic.

Solubility

In some embodiments, SBP formulations or components thereof are water soluble. The water solubility, along with the rate of degradation, of SBPs may modulate payload (e.g., therapeutic agent) release rate and/or release period. An increasing amount of payload may be released into surrounding medium as surrounding matrix dissolves (e.g., see International Publication Numbers WO2013126799 and WO2017165922; and U.S. Pat. No. 8,530,625, the contents of each of which are herein incorporated by reference in their entirety). Longer time periods required to dissolve SBPs or components thereof may result in longer release periods. In some embodiments, SBP solubility may be modulated in order to control the rate of payload release in the surrounding medium. The solubility of SBPs may be modulated via any method known to those skilled in the art. In some embodiments, SBP solubility may be modulated by altering included silk fibroin secondary structure (e.g., increasing beta-sheet content and/or crystallinity). In some embodiments, SBP solubility may be modulated by altering SBP format. In some embodiments, SBP solubility and/or rate of degradation may be modulated to facilitate extended release of therapeutic agent payloads in vitro and/or in vivo.

Residence Time

In some embodiments, SBP formulations may be prepared to have desired residence time according to the application for which they are designed. As used herein, the term "residence time" refers to the average length of time during which a substance (e.g., SBP formulations) is in a given location or condition. In some embodiments, residence time of SBP formulations described herein may vary from a few hours to several months. For example, residence time of SBP formulations may be about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, or longer than 1 year.

Excipients

In some embodiments, SBP formulations include one or more excipients. In some embodiments, SBP formulation may not include an excipient. As used herein, the term "excipient" refers to any substance included in a composition with an active agent or primary component, often serving as a carrier, diluent, or vehicle for the active agent or primary component. In some embodiments, excipients may be compounds or compositions approved for use by the US Food and Drug Administration (FDA). In some embodiments, SBPs may include excipients that increase SBP stability or stability of one or more other SBP components. Some SBPs may include an excipient that modulates payload release. Excipients may include, but are not limited to, solvents, diluents, liquid vehicles, dispersion or suspension media or aids, surfactants, thickening agents, emulsifying agents, lipids, liposomes, isotonic agents, buffers, and preservatives. In some embodiments, excipients include lipidoids, lipid nanoparticles, polymers, lipoplexes, particles, core-shell nanoparticles, peptides, proteins, cells, hyaluronidase, and/or nanoparticle mimics. In some embodiments, processed silk and/or SBPs may be used as an excipient. In some embodiments, excipients included in SBPs are selected from one or more of sucrose, lactose, phosphate salts, sodium chloride, potassium phosphate monobasic, potassium phosphate dibasic, sodium phosphate dibasic, sodium phosphate monobasic, polysorbate 80, phosphate buffer, phosphate buffered saline, sodium hydroxide, sorbitol, mannitol, lactose USP, Starch 1500, microcrystalline cellulose, potassium chloride, sodium borate, boric acid, sodium borate decahydrate, magnesium chloride hexahydrate, calcium chloride dihydrate, sodium hydroxide, Avicel, dibasic calcium phosphate dehydrate, tartaric acid, citric acid, fumaric acid succinic acid, malic acid, hydrochloric acid, polyvinylpyrrolidone, copolymers of vinylpyrrolidone and vinylacetate, hydroxypropylcellulose, hydroxyethylcellulose, hydroxypropylmethylcellulose, polyvinyl alcohol, polyethylene glycol, acacia, and sodium carboxymethylcellulose. Excipients may include phosphate buffered saline. Excipients may be present in SBPs at any concentration. In some embodiments, excipients are present at a concentration of from about 0.0001% weight per weight (w/w) of excipient to total SBP weight to about 20% (w/w). In some embodiments, excipients are present at a concentration of from about 0.0001% weight per weight (w/w) of excipient to total SBP weight to about 50% (w/w).

In some embodiments, excipients included in SBPs may be selected from one or more of sorbitol, triethylamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol, glycerol formal, hydroxypropyl beta-cyclodextrin, kolliphor 124, kolliphor 181, kolliphor 188, kolliphor 407, kolliphor EL (cremophor EL), cremophor RH 40, cremophor RH 60, dalpha-tocopherol, PEG 1000 succinate, polysorbate 20, polysorbate 80, solutol HS 15, sorbitan monooleate, poloxamer-407, poloxamer-188, Labrafil M-1944CS, Labrafil M-2125CS, Labrasol, Gellucire 44/14, Softigen 767, mono- and di-fatty acid esters of PEG 300, PEG 400, or PEG 1750, kolliphor RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, medium chain triglycerides of coconut oil, medium chain triglycerides of palm seed oil, beeswax, d-alpha-tocopherol, oleic acid, medium-chain mono-glycerides, medium-chain di-glycerides, alpha-cyclodextrin, betacyclodextrin, hydroxypropyl-beta-cyclodextrin, sulfo-butylether-beta-cyclodextrin, hydrogenated soy phosphatidylcholine, distearoylphosphatidylglycerol, L-alphadimyristoylphosphatidylcholine, L-alpha-dimyristoylphosphatidylglycerol, PEG 300, PEG 300 caprylic/capric glycerides (Softigen 767), PEG 300 linoleic glycerides (Labrafil M-2125CS), PEG 300 oleic glycerides (Labrafil M-1944CS), PEG 400, PEG 400 caprylic/capric glycerides (Labrasol), polyoxyl 40 stearate (PEG 1750 monosterate), polyoxyl 8 stearate (PEG 400 monosterate), polysorbate 20, polysorbate 80, polyvinyl pyrrolidone, propylene carbonate, propylene glycol, solutol HS15, sorbitan monooleate (Span 20), sulfobutylether-beta-cyclodextrin, transcutol, triacetin, 1-dodecylazaeyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, glycerin, and PEG 4 kDa. Such SBPs may include hydrogels. In some embodiments, SBP hydrogels include one or more of polysorbate 80, poloxamer-188, PEG 4 kDa, and glycerol.

In some embodiments, excipients included in SBPs are selected from one or more of those listed in Table 1. In the Table, example categories are indicated for each excipient. These categories are not limiting and each excipient may fall under multiple categories (e.g., any of the categories of excipients described herein).

TABLE 1

Excipients

| Excipient | Example Category |
| --- | --- |
| Avicel | bulking agent |
| bulking agent | bulking agent |
| copolymers of vinylpyrrolidone and vinylacetate | bulking agent |
| dibasic calcium phosphate dehydrate | bulking agent |
| fumaric acid | bulking agent |
| hydroxypropylmethylcellulose | bulking agent |
| lactose USP | bulking agent |
| malic acid | bulking agent |
| microcrystalline cellulose | bulking agent |
| polyvinylpyrrolidone | bulking agent |
| tartaric acid | bulking agent |
| (12Z,15Z)-N,N-dimethyl-2-nonylhenicosa-12,15-dien-1-amine | cationic lipid |
| (12Z,15Z)-N,N-dimethylhenicosa-12,15-dien-4-amine | cationic lipid |
| (13Z,16Z)-N,N-dimethyl-3-nonyldocosa-13,16-dien-1-amine | cationic lipid |
| (13Z,16Z)-N,N-dimethyldocosa-13,16-dien-5-amine | cationic lipid |
| (14Z)-N,N-dimethylnonacos-14-en-l0-amine | cationic lipid |
| (14Z,17Z)-N,N-dimethyltricosa-14,17-dien-4-amine | cationic lipid |
| (14Z,17Z)-N,N-dimethyltricosa-14,17-dien-6-amine | cationic lipid |
| (15Z)-N,N-dimethyl eptacos-15-en-l 0-amine | cationic lipid |
| (15Z,18Z)-N N-dimethyltetracosa-15,18-dien-7-amine | cationic lipid |
| (15Z,18Z)-N,N-dimethyltetracosa-15,18-dien-5-amine | cationic lipid |
| (16Z)-N,N-dimethylpentacos-16-en-8-amine | cationic lipid |
| (16Z,19Z)-N,N-dimethylpentacosa-16,19-dien-6-amine | cationic lipid |
| (17Z)-N,N-dimethylhexacos-17-en-9-amine | cationic lipid |
| (17Z)-N,N-dimethylnonacos-17-en-l0-amine | cationic lipid |
| (17Z,20Z)-N,N-dimemylhexacosa-17,20-dien-9-amine | cationic lipid |
| (17Z,20Z)-N,N-dimethylhexacosa-17,20-dien-7-amine | cationic lipid |

TABLE 1-continued

| Excipient | Example Category |
|---|---|
| (18Z)-N,N-dimetylheptacos-18-en-10-amine | cationic lipid |
| (18Z,21 Z)-N,N-dimethylheptacosa-18,21-dien-8-amine | cationic lipid |
| (18Z,21Z)-N,N-dimethylheptacosa-18,21-dien-10-amine | cationic lipid |
| (19Z,22Z)-N,N-dimethyloctacosa-19,22-dien-9-amine | cationic lipid |
| (19Z,22Z)-N,N-dimethyloctacosa-19,22-dien-7-amine | cationic lipid |
| (11E,20Z,23Z)-N,N-dimethylnonacosa-l1,20,2-trien-10-amine | cationic lipid |
| (1Z,19Z)-N5N-dimethylpentacosa-16,19-dien-8-amine | cationic lipid |
| (20Z)-N,N-dimethylheptacos-20-en-10-amine | cationic lipid |
| (202)-N,N-dimethylnonacos-20-en-10-amine | cationic lipid |
| (20Z,23Z)-N,N-dimethylnonacosa-20,23-dien-10-amine | cationic lipid |
| (20Z,23Z)-N-ethyl-N-methylnonacosa-20,23-dien-l0-amine | cationic lipid |
| (21Z,24Z)-N,N-dimethyltriaconta-21,24-dien-9-amine | cationic lipid |
| (22Z)-N,N-dimethylhentriacont-22-en-10-amine | cationic lipid |
| (22Z,25Z)-N,N-dimethylhentriaconta-22,25-dien-10-amine | cationic lipid |
| (24Z)-N,N-dimethyltritriacont-24-en-l0-amine | cationic lipid |
| (2R)-1-[(3,7-dimethyloctyl)oxy]-N,N-dimethyl-3-[(9Z$_s$12Z)-octadeca-9,12-dien-1-yloxy]propan-2-amine | cationic lipid |
| (2R)-N,N-dimethyl-H(1-metoylo ctyl)oxy]-3-[(9Z,12Z)-octadeca-9,12-dien-1-yloxy]propan-2-amine | cationic lipid |
| (2S)-1-(heployxy)-N,N-dimethyl-3-[(9Z,12Z)-octadeca-9,12-dien-1-yloxy]propan-2-amine | cationic lipid |
| (2S)-1-(hexyloxy)-3-[(11Z,14Z)-icosa-11,14-dien-1-yloxy]-N,N-dimethylpropan-2-amine | cationic lipid |
| (2S)-1-(hexyloxy)-N,N-dimethyl-3-[(9Z,12Z)-octadeca-9,12-dien-1-yloxy]propan-2-amine | cationic lipid |
| (2S)-1-(1Z,14Z)-icosa-11,14-dien-1-yloxy]-N,N-dimethyl-3-(pentyloxy)propan-2-amine | cationic lipid |
| (2S)-1-[(13Z)-docos-13-en-1-yloxy]-3-(hexyloxy)-N,N-dimethylpropan-2-amine | cationic lipid |
| (2S)-1-[(13Z,16Z)-docosa-13,16-dien-1-yloxy]-3-(hexyloxy)-N,N-dimethylpropan-2-amine | cationic lipid |
| (2S)-N,N-dimethyl-1-[(6Z,9Z,12Z)-octadeca-6,9,12-trien-1-yloxy]-3-(octyloxy)propan-2-amine | cationic lipid |
| (2S)-N,N-dimethyl-1-[(9Z,12Z)-octadeca-9,12-dien-1-yloxy]-3-[(5Z)-oct-5-en-1-yloxy]propan-2-amine | cationic lipid |
| 1,2-dilinolenyloxy-3-dimethylaminopropane (DLenDMA) | cationic lipid |
| 1,2-distearloxy-N,N-dimethylaminopropane (DSDMA) | cationic lipid |
| 1-[(11Z,14Z)-icosa-11,14-dien-1-yloxy]-N,N-dimethyl-3-(octyloxy)propan-2-amine | cationic lipid |
| 1-[(11Z,14Z)-1-nonylicosa-11,14-dien-1-yl]pyrrolidine | cationic lipid |
| 1-[(13Z)-docos-13-en-1-yloxy]-N,N-dimethyl-3-(octyloxy)propan-2-amine | cationic lipid |
| 1-[(13Z,16Z)-docosa-13,16-dien-1-yloxy]-N,N-dimethyl-3-(octyloxy)propan-2-amine | cationic lipid |
| 1-[(1R,2S)-2-hepty lcyclopropyl]-N,N-dimethyloctadecan-9-amine | cationic lipid |
| 1-[(1S,2R)-2-decylcyclopropyl]-N,N-dimethylpentadecan-6-amine | cationic lipid |
| 1-[(1S,2R)-2-hexylcyclopropyl]-N,N-dimethylnonadecan-10-amine | cationic lipid |
| 1-[(9Z)-hexadec-9-en-1-yloxy]-N,N-dimethyl-3-(octyloxy)propan-2-amine | cationic lipid |
| 1-{2-[(9Z,12Z)-octadeca-9,12-dien-1-yloxy]-1-[(octyloxy)methyl]ethyl}azetidine | cationic lipid |
| 1-{2-[(9Z,12Z)-octadeca-9,12-dien-1-yloxy]-1-[(octyloxy)methyl]ethyl}pyrrolidine | cationic lipid |
| cationic lipid | cationic lipid |
| CLI-CLXXIX of International Publication No. WO2008103276 | cationic lipid |
| DLin-DMA | cationic lipid |
| DODMA | cationic lipid |
| formula CLI-CLXXIX of U.S. Pat. No. US7893302 | cationic lipid |
| formula CLI-CLXXXXII of U.S. Pat. No. US7404969 | cationic lipid |
| formula I-VI of U.S. Pat. Publication No. US20100036115 | cationic lipid |
| N,N-dimethyl-1-(octyloxy)-3-({8-[(1S,2S)-2-{[(1R,2R)-2-pentylcyclopropyl]methyl}cyclopropyl]octyl}oxy)propan-2-amine | cationic lipid |
| N,N-dimethyl-1-{[8-(2-oclylcyclopropyl)octyl]oxy}-3-(octyloxy)propan-2-amine | cationic lipid |
| N,N-dimethyl-21-[(1S,2R)-2-octylcyclopropyl]henicosan-l0-amine | cationic lipid |
| N,N-dimethyl-3-{7-[(1S.2R)-2-octylcyclopropyl]heptyl} dodecan-1-amine | cationic lipid |
| N,N-dimethylheptacosan-10-amine | cationic lipid |
| N,N-dimethyl-1-[(1S,2R)-2-octylcyclopropyl]eptadecan-8-amine | cationic lipid |
| N,N-dimethyl-1-((1S,2R)-2-octylcyclopropyl)pentadecan-8-amine | cationic lipid |
| R-N,N-dimethyl-1-[(9Z,12Z)-octadeca-9,12-dien-1-yloxy]-3-(octyloxy)propan-2-amine | cationic lipid |
| S-N,N-dimethyl-1-[(9Z,12Z)-octadeca-9,12-dien-1-yloxy]-3-(octyloxy)propan-2-amine | cationic lipid |
| N,N-dimethyl-[(1R,2S)-2-undecylcyclopropyl]tetradecan-5-amine | cationic lipid |
| N,N-dimethyl-1-(nonyloxy)-3-[(9Z,12Z)-octadeca-9,12-dien-1-yloxy]propan-2-amine | cationic lipid |
| N,N-dimethyl-1-(1S,2R)-2-octylcyclopropyl]nonadecan-10-amine | cationic lipid |
| N,N-dimethyl-1-[(1S,2R)-2-octylcyclopropyl]hexadecan-8-amine | cationic lipid |
| N,N-dimethyl-1-[(1S,2S)-2-{[(1R,2R)-2-pentylcydopropyl]methyl}cyclopropyl]nonadecan-10-amine | cationic lipid |
| N,N-dimethyl-1-[(9Z)-oetadec-9-en-1-yloxy]-3-(octyloxy)propan-2-amine | cationic lipid |
| coating agents | coating agent |
| poly(alkyl)(meth)acrylate | coating agent |
| poly(ethylene-co-vinyl acetate) | coating agent |
| zein | coating agent |
| apocarotenal | colorant |
| apocatotenal derivative | colorant |
| astaxanthin | colorant |
| astaxanthin derivative | colorant |
| bixin | colorant |
| canthaxanthin | colorant |
| canthaxanthin derivative | colorant |
| capsanthin | colorant |
| capsanthin derivative | colorant |
| capsorubin derivative | colorant |
| capso rubin occurring in paprika ole-oresin | colorant |
| caretinoids | colorant |
| colorant | colorant |
| crocin | colorant |
| crocin derivative | colorant |
| dyes | colorant |
| FD&C Blue No. 2 (indigotine) | colorant |
| FD&C colorant | colorant |
| FD&C Red No. 3 (ervthrosine) | colorant |

TABLE 1-continued

| Excipient | Example Category |
|---|---|
| FD&C Red No. 40 (allura red AC) | colorant |
| food coloring | colorant |
| inks | colorant |
| lutein | colorant |
| lutein derivative | colorant |
| lycopene | colorant |
| pigments | colorant |
| rhodoxanthin | colorant |
| rubixanthin | colorant |
| saffron | colorant |
| saffron derivative | colorant |
| turmeric | colorant |
| violaxanthin | colorant |
| β-carotene | colorant |
| β-carotene derivative | colorant |
| flowability agents | flowability agent |
| 1-dodecylazacyclo-heptan-2-one | gelling agent |
| 2-pyrrolidone | gelling agent |
| acacia | gelling agent |
| alginic acid | gelling agent |
| alpha-cyclodextrin | gelling agent |
| beeswax | gelling agent |
| bentonite | gelling agent |
| benzyl alcohol | gelling agent |
| beta-cyclodextrin | gelling agent |
| caprolactam | gelling agent |
| CARBOPOL ® (also known as carbomer) | gelling agent |
| carboxymethyl cellulose | gelling agent |
| castor oil | gelling agent |
| corn oil | gelling agent |
| cottonseed oil | gelling agent |
| cremaphor RH 40 | gelling agent |
| cremaphor RH 60 | gelling agent |
| d-alpha-tocopherol | gelling agent |
| di-fatty acid ester of PEG 1750 | gelling agent |
| di-fatty acid ester of PEG 300 | gelling agent |
| di-fatty acid ester of PEG 400 | gelling agent |
| dimethyl sulfoxide | gelling agent |
| dimethylacetamide (DMA) | gelling agent |
| dimethylformamide | gelling agent |
| distearoylphosphatidylglycerol | gelling agent |
| ethanol | gelling agent |
| ethyl acetate | gelling agent |
| ethylcellulose | gelling agent |
| gamma-cyclodextrin | gelling agent |
| gelatin | gelling agent |
| Gellucire 44/14 | gelling agent |
| glycerin | gelling agent |
| glycerol | gelling agent |
| glycerol formal | gelling agent |
| glycerophosphate | gelling agent |
| hydrogenated soy phosphatidylcholine | gelling agent |
| hydrogenated soybean oil | gelling agent |
| hydrogenated vegetable oils | gelling agent |
| hydroxy ethyl cellulose | gelling agent |
| hydroxyethyl cellulose | gelling agent |
| hydroxypropyl beta-cyclodextrin | gelling agent |
| hydroxypropyl cellulose | gelling agent |
| hydroxypropyl-beta-cyclodextrin | gelling agent |
| kolliphor 124 | gelling agent |
| kolliphor 181 | gelling agent |
| kolliphor 188 | gelling agent |
| kolliphor 407 | gelling agent |
| kolliphor EL (cremaphor EL) | gelling agent |
| kolliphor RH60 | gelling agent |
| Labrafil M-1944CS | gelling agent |
| Labrafil M-2125CS | gelling agent |
| Labrasol | gelling agent |
| L-alpha-dimyristoylphosphatidylcholine | gelling agent |
| L-alphadimyristoylphosphatidylglycerol | gelling agent |
| magnesium aluminum silicate | gelling agent |
| medium chain triglyceride | gelling agent |
| medium-chain diglyceride | gelling agent |
| medium-chain mono-glyceride | gelling agent |
| medium-chain triglyceride of coconut oil | gelling agent |
| medium-chain triglyceride of palm seed oil | gelling agent |
| methyl acetate | gelling agent |
| methylcellulose | gelling agent |
| mono-fatty acid ester of PEG 1750 | gelling agent |
| mono-fatty acid ester of PEG 300 | gelling agent |
| mono-fatty acid ester of PEG 400 | gelling agent |
| N-methyl-2-pyrrolidone | gelling agent |
| oleic acid | gelling agent |
| olive oil | gelling agent |
| peanut oil | gelling agent |
| PEG 1000 succinate | gelling agent |
| PEG 1750 | gelling agent |
| PEG 300 | gelling agent |
| PEG 300 caprylic/capric glyceride (Softigen 767) | gelling agent |
| PEG 300 linoleic glyceride (Labrafil M-2125CS) | gelling agent |
| PEG 300 oleic glyceride (Labrafil M-1944CS) | gelling agent |
| PEG 400 | gelling agent |
| PEG 400 caprylic/capric glyceride (Labrasol) | gelling agent |
| PEG 4000 (PEG 4kDa) | gelling agent |
| peppermint oil | gelling agent |
| polaxamer | gelling agent |
| poloxamer-188 | gelling agent |
| poloxamer-407 | gelling agent |
| polyoxyl 40 stearate (PEG 1750 monsterate) | gelling agent |
| polyoxyl 8 stearate (PEG 400 monosterate) | gelling agent |
| polysorbate 20 | gelling agent |
| polysorbate-80 (tween-80) | gelling agent |
| polysorbate-SO | gelling agent |
| polyvinyl alcohol | gelling agent |
| polyvinyl pyrrolidone | gelling agent |
| polyvinyl pyrrolidone-12 | gelling agent |
| polyvinyl pyrrolidone-17 | gelling agent |
| propylene carbonate | gelling agent |
| propylene glycol | gelling agent |
| safflower oil | gelling agent |
| sesame oil | gelling agent |
| sodium alginate | gelling agent |
| Softigen 767 | gelling agent |
| solutol HS 15 | gelling agent |
| sorbitan monooleate | gelling agent |
| sorbitan monooleate (Span 20) | gelling agent |
| sorbitol | gelling agent |
| soybean oil | gelling agent |
| sulfobutylether-beta-cydodextrin | gelling agent |
| sulfo-butylether-beta-cyclodextrin | gelling agent |
| tetrahydrofuran | gelling agent |
| tragacanth | gelling agent |
| transcutol | gelling agent |
| triacetin | gelling agent |
| triethanolamine | gelling agent |
| triethylamine | gelling agent |
| xanthan gum | gelling agent |
| (50:50, Poly(D1-Lactic-Co-Glycolic Acid) | general |
| (50:50, Polyacrylic Acid (250000 Mw) | general |
| 1,2,6-Hexanetriol | general |
| 1.2-Dimyristoyl-Sn-Glycero-3-(Phospho-S-(1-Glycerol)) | general |
| 1,2-Dimyristoyl-Sn-Glycero-3-Phosphocholine | general |
| 1,2-Dioleoyl-Sn-Glycero-3-Phosphocholine | general |
| 1,2-Dipalimtoyl-Sn-Glycero-3-(Phospho-Rac-(1-Glycerol)) | general |
| 1,2-Distearoyl-Sn-Glycero-3-(Phospho-Rac-(1-Glycerol)) | general |
| 1,2-Distearoyl-Sn-Glycero-3-Phosphocholine | general |
| 1-O-Tolylbiguanide | general |
| 2-Ethyl-1,6-Hexanediol | general |
| Acetic Acid | general |
| Acetic Anhydride | general |
| Acetone | general |
| Acetone Sodium Bisulfite | general |
| Acetylated Lanolin Alcohol | general |
| Acetylated Monoglyceride | general |
| Acetylcysteine | general |
| Acetyltryptophan (DL-) | general |

TABLE 1-continued

| Excipient | Example Category |
|---|---|
| Acrylates Copolymer | general |
| Acrylic Acid-Isooctyl Acrylate Copolymer | general |
| Acrylic Adhesive 788 | general |
| Activated Charcoal | general |
| Adcote 72A103 | general |
| Adhesive Tape | general |
| Adipic Acid | general |
| Aerotex Resin 3730 | general |
| Alanine | general |
| albumin | general |
| Albumin Aggregated | general |
| Albumin Colloidal | general |
| Albumin Human | general |
| Alcohol | general |
| Alfadex | general |
| Alkyl Ammonium Sulfonic Acid Betaine | general |
| Alkyl Aryl Sodium Sulfonate | general |
| Allantoin | general |
| Allyl Alpha-Ionone | general |
| Almond Oil | general |
| Alpha Terpineol | general |
| Alpha-Tocopherol (DL-) | general |
| Alpha-Tocopherol Acetate (DL-) | general |
| Aluminum Acetate | general |
| Aluminum Chlorhydroxy Allantoinate | general |
| Aluminum Hydroxide | general |
| Aluminum Hydroxide - Sucrose | general |
| Aluminum Hydroxide Gel | general |
| Aluminum Hydroxide Gel F 500 | general |
| Aluminum Hydroxide Gel F 5000 | general |
| Aluminum Monostearate | general |
| Aluminum Oxide | general |
| Aluminum Polyester | general |
| Aluminum Silicate | general |
| Aluminum Starch Octenyl succinate | general |
| Aluminum Stearate | general |
| Aluminum Subacetate | general |
| Aluminum Sulfate Anhydrous | general |
| Amerchol C | general |
| Amerchol-Cab | general |
| Aminomethylpropanol | general |
| Ammonia | general |
| Ammonia Solution | general |
| Ammonium Acetate | general |
| Ammonium Hydroxide | general |
| Ammonium Lauryl Sulfate | general |
| Ammonium Nonoxynol-4 Sulfate | general |
| Ammonium Salt Of C-12-C-15 Linear Primary Alcohol Ethoxylate | general |
| Ammonium Sulfate | general |
| Ammonyx | general |
| Amphoteric-2 | general |
| Amphoteric-9 | general |
| Anethole | general |
| Anhydrous Citric Acid | general |
| Anhydrous Dextrose | general |
| Anhydrous Lactose | general |
| Anhydrous Trisodium Citrate | general |
| Aniseed Oil | general |
| Artoxid Sbn | general |
| Antifoam | general |
| Antipyrine | general |
| Apaflurane | general |
| Apricot Kernel Oil Peg-6 Esters | general |
| Aquaphor | general |
| Arginine | general |
| Arlacel | general |
| Ascorbic Acid | general |
| Ascorbyl Palmitate | general |
| Aspartic Acid | general |
| Bacteriostatic | general |
| Balsam Peru | general |
| Barium Sulfate | general |
| Beheneth-10 | general |
| Benzalkonium Chloride | general |
| Benzenesulfonic Acid | general |
| Benzethonium Chloride | general |
| Benzododecinium Bromide | general |
| Benzoic Acid | general |
| Benzyl Benzoate | general |
| Benzyl Chloride | general |
| Betadex | general |
| Bibapcitide | general |
| Bismuth Subgallate | general |
| Boric Acid | general |
| Brocrinat | general |
| Butane | general |
| Butyl Alcohol | general |
| Butyl Ester Of Vinyl Methyl Ether/Maleic Anhydride Copolymer (125000 Mw) | general |
| Butyl Stearate | general |
| Butylated Hydroxyanisole | general |
| Butylated Hydroxytoluene | general |
| Butylene Glycol | general |
| Butylparaben | general |
| Butyric Acid | general |
| C20-40 Pareth-24 | general |
| Caffeine | general |
| Calcium | general |
| Calcium Carbonate | general |
| Calcium Chloride | general |
| Calcium Gluceptate | general |
| Calcium Hydroxide | general |
| Calcium Lactate | general |
| Calcobutrol | general |
| Caldiamide Sodium | general |
| Caloxetate Trisodium | general |
| Calteridol Calcium | general |
| Canada Balsam | general |
| Caprylic/Capric Triglyceride | general |
| Caprylic/Capric/Stearic Triglyceride | general |
| Caplan | general |
| Captisol | general |
| Caramel | general |
| Carbomer 1342 | general |
| Carbomer 1382 | general |
| Carbomer 934 | general |
| Carbomer 934p | general |
| Carbomer 940 | general |
| Carbomer 941 | general |
| Carbomer 980 | general |
| Carbomer 981 | general |
| Carbomer Homopolymer Type B (Allyl Pentaerythritol Crosslinked) | general |
| Carbomer Homopolymer Type C (Allyl Pentaerythritol Crosslinked) | general |
| Carbon Dioxide | general |
| Carboxy Vinyl Copolymer | general |
| Carboxymethylcellulose (CMC) | general |
| Carboxymethylcellulose Sodium | general |
| Carboxypoly methylene | general |
| Carrageenan | general |
| Carrageenan Salt | general |
| Cedar Leaf Oil | general |
| Cellobiose | general |
| Cellulose | general |
| Cerasynt-Se | general |
| Ceresin | general |
| Ceteareth-12 | general |
| Ceteareth-15 | general |
| Ceteareth-30 | general |
| Cetearyl Alcohol/Ceteareth-20 | general |
| Cetearyl Ethylhexanoate | general |
| Ceteth-10 | general |
| Ceteth-2 | general |
| Ceteth-20 | general |
| Ceteth-23 | general |
| Cetostearyl Alcohol | general |
| Cetrimonium Chloride | general |
| Cetyl Alcohol | general |

TABLE 1-continued

Excipients

| Excipient | Example Category |
|---|---|
| Cetyl Esters Wax | general |
| Cetyl Palmitate | general |
| Cetylpyridinium Chloride | general |
| Chlorobutanol | general |
| Chlorobutanol Hemihydrate | general |
| Chlorocresol | general |
| Chloroutanol anhydrous | general |
| Chloroxylenol | general |
| Cholesterol | general |
| Choleth | general |
| Choleth-24 | general |
| Citrate | general |
| Citric Acid | general |
| citric acid (hydrous) | general |
| Citric Acid Monohydrate | general |
| Cocamide Ether Sulfate | general |
| Cocamine Oxide | general |
| Coco Betaine | general |
| Coco Diethanolamide | general |
| Coco Monoethanolamide | general |
| Cocoa Butter | general |
| Coco-Glycerides | general |
| Coconut Oil | general |
| Coconut Oil glycerides | general |
| Cocoyl Caprylocaprate | general |
| Cola Nitida Seed Extract | general |
| Collagen | general |
| Colloidal | general |
| Coloring Suspension | general |
| Corn | general |
| Cream Base | general |
| Creatine | general |
| Creatinine | general |
| Cresol | general |
| Croscarmellose Sodium | general |
| Crospovidone | general |
| Cupric Sulfate | general |
| Cupric Sulfate Anhydrous | general |
| Cyclomethicone | general |
| Cyclo methicone/Dimethicone Copolyol | general |
| Cysteine | general |
| Cysteine (DL-) | general |
| Cysteine Hydrochloride | general |
| Cysteine Hydrochloride Anhydrous | general |
| D&C Red No. 28 | general |
| D&C Red No. 33 | general |
| D&C Red No. 36 | general |
| D&C Red No. 39 | general |
| D&C Yellow No. 10 | general |
| Dalfampridine | general |
| Dauber 1-5 Pestr (Matte) 164z | general |
| Decyl Methyl Sulfoxide | general |
| Dehydag Wax Sx | general |
| Dehydrated | general |
| Dehydroacetic Acid | general |
| Dehymuls E | general |
| Denatonium Benzoate | general |
| Denatured | general |
| Dental | general |
| Deoxycholic Acid | general |
| Dextran | general |
| Dextran 40 | general |
| Dextrin | general |
| Dextrose | general |
| Dextrose Monohydrate | general |
| Dextrose Solution | general |
| Diatrizoic Acid | general |
| Diazolidinyl Urea | general |
| Dichlorobenzyl Alcohol | general |
| Dichlorodifluoromethane | general |
| Dichlorotetrafluoroethane | general |
| Diethanolamine | general |
| Diethyl Pyrocarbonate | general |
| Diethyl Sebacate | general |
| Diethylene Glycol Monoethyl Ether | general |
| Diethylhexyl Phthalate | general |
| Dihydroxyaluminum Aminoacetate | general |
| Diisopropanolamine | general |
| Diisopropyl Adipate | general |
| Diisopropyl Dilinoleate | general |
| Dimethicone 350 | general |
| Dimethicone Copolyol | general |
| Dimethicone Mdx4-4210 | general |
| Dimethicone Medical Fluid .360 | general |
| Dimethyl Isosorbide | general |
| Dimethylaminoethyl Methacrylate - Butyl Methacrylate - Methyl Methacrylate Copolymer | general |
| Dimethyldioctadecylammonium Bentonite | general |
| Dimethylsiloxane/Methylvinylsiloxane Copolymer | general |
| Dinoseb Ammonium Salt | general |
| Dipalmitoylphosphatidylglycerol (DL-) | general |
| Dipropylene Glycol | general |
| Disodium Cocoamphodiacetate | general |
| Disodium Laureth Sulfosuccinate | general |
| Disodium Lauryl Sulfosuccinate | general |
| Disodium Sulfosalicylate | general |
| Disofenin | general |
| Divinylbenzene Styrene Copolymer | general |
| Dmdm Hydantoin | general |
| Docosanol | general |
| Docusate Sodium | general |
| Duro-Tak 280-2516 | general |
| Duro-Tak 387-2516 | general |
| Duro-Tak 80-1196 | general |
| Duro-Tak 87-2070 | general |
| Duro-Tak 87-2194 | general |
| Duro-Tak 87-2287 | general |
| Duro-Tak 87-2296 | general |
| Duro-Tak 87-2888 | general |
| Duro-Tak 87-2979 | general |
| Edetate Calcium Disodium | general |
| Edetate Disodium | general |
| Edetate Disodium Anhydrous | general |
| Edetate Sodium | general |
| Edetic Acid | general |
| Egg | general |
| Egg Phospholipid | general |
| Entsufon | general |
| Entsufon Sodium | general |
| Epilactose | general |
| Epitetracycline Hydrochloride | general |
| Essence Bouquet 9200 | general |
| Ethanolamine Hydrochloride | general |
| Ethoxylated | general |
| Ethyl Ester Terminated | general |
| Ethyl Oleate | general |
| Ethylene Glycol | general |
| Ethylene Vinyl Acetate Copolymer | general |
| Ethylenediamine | general |
| Ethylenediamine Dihydrochloride | general |
| Ethylenediaminetetracetic acid (EDTA) | general |
| Ethylene-Propylene Copolymer | general |
| Ethylene-Vinyl Acetate Copolymer (28% Vinyl Acetate) | general |
| Ethylene-Vinyl Acetate Copolymer (9% Vinylacetate) | general |
| Ethylhexyl Hydroxystearate | general |
| Ethylparaben | general |
| Eucalyptol | general |
| Exametazime | general |
| F&C Red No. 40 | general |
| Fat (Edible) | general |
| Fat (Hard) | general |
| Fatty Acid | general |
| Fatty Acid Ester | general |
| Fatty Acid Pentaerythriol Ester | general |
| Fatty Alcohol | general |
| Fatty Alcohol Citrate | general |

TABLE 1-continued

| Excipient | Example Category |
|---|---|
| FD&C Blue No. 1 (brilliant blue FCF) | general |
| FD&C Green No. 3 (fast green FCF) | general |
| FD&C Red No. 4 | general |
| FD&C Yellow No. 10 (Delisted) | general |
| FD&C Yellow No. 5 (tartrazine) | general |
| FD&C Yellow No. 6 (sunset yellow) | general |
| Ferric Chloride | general |
| Ferric Oxide | general |
| Flavor 89-186 | general |
| Flavor 89-259 | general |
| Flavor Df-119 | general |
| Flavor Df-1530 | general |
| Flavor Enhancer | general |
| Flavor Fig 827118 | general |
| Flavor Raspberry Pfc-8407 | general |
| Flavor Rhodia Pharmaceutical No. Rf 451 | general |
| Fluorochlorohydrocarbon | general |
| Formaldehyde | general |
| Formaldehyde Solution | general |
| Fractionated Coconut Oil | general |
| Fragrance 3949-5 | general |
| Fragrance 520a | general |
| Fragrance 6.007 | general |
| Fragrance 91-122 | general |
| Fragrance 9128-Y | general |
| bragrance 93498g | general |
| Fragrance Balsam Pine No. 5124 | general |
| Fragrance Bouquet 10328 | general |
| Fragrance Chemoder 6401-B | general |
| Fragrance Chemoderm 6411 | general |
| Fragrance Cream No. 73457 | general |
| Fragrance Cs-28197 | general |
| Fragrance Felton 066m | general |
| Fragrance Firmenich 47373 | general |
| Fragrance Givaudan Ess 9090/1c | general |
| Fragrance H-6540 | general |
| Fragrance Herbal 10396 | general |
| Fragrance Nj-1085 | general |
| Fragrance P O Fl-147 | general |
| Fragrance Pa 52805 | general |
| Fragrance Pera Derm D | general |
| Fragrance Rbd-9819 | general |
| Fragrance Shaw Mudge U-7776 | general |
| Fragrance Tf 044078 | general |
| Fragrance Ungerer Honeysuckle K 2771 | general |
| Fragrance Ungerer N5195 | general |
| Fructose | general |
| Gadolinium Oxide | general |
| Galactose | general |
| Gamma Cyclodextrin | general |
| Gelatin (Crosslinked) | general |
| Gelfoam Sponge | general |
| Gellan Gum (Low Acyl) | general |
| Gelva 737 | general |
| Gentisic Acid | general |
| Gentisic Acid Ethanolamide | general |
| Glacial acetic acid | general |
| Gluceptate Sodium | general |
| Gluceptate Sodium Dihydrate | general |
| Gluconolactone | general |
| Glucuronic Acid | general |
| Glutamic Acid (DL-) | general |
| Glutathione | general |
| Glycerol Ester Of Hydrogenated Rosin | general |
| Glyceryl Citrate | general |
| Glyceryl Isostearate | general |
| Glyceryl Laurate | general |
| Glyceryl Monostearate | general |
| Glyceryl Oleate | general |
| Glyceryl Oleate/Propylene Glycol | general |
| Glyceryl Palmitate | general |
| Glyceryl Ricinoleate | general |
| Glyceryl Stearate | general |
| Glyceryl Stearate - Laureth-23 | general |
| Glyceryl Stearate/Peg, Stearate | general |
| Glyceryl Stearate/Peg-100 Stearate | general |
| Glycervi Stearate/Peg-40 Stearate | general |
| Glyceryl Stearate-Stearamidoethyl Diethylamine | general |
| Glyceryl Trioleate | general |
| Glycine | general |
| Glycine Hydrochloride | general |
| Glycol Distearate | general |
| Glycol Stearate | general |
| Guanidine Hydrochloride | general |
| Guar Gum | general |
| Hair Conditioner (18n195-1m) | general |
| Heptane | general |
| Hetastarch | general |
| Hexylene Glycol | general |
| High Density Polyethylene | general |
| Histidine | general |
| Human Albumin Microspheres | general |
| Hyaluronate Sodium | general |
| Hydrocarbon | general |
| Hydrocarbon Gel | general |
| Hydrochloric Acid | general |
| Hydrocortisone | general |
| Hydrogel Polymer | general |
| Hydrogen Peroxide | general |
| Hydrogenated Castor Oil | general |
| Hydrogenated coconut oil | general |
| Hydrogenated Coconut Oil Glyceride | general |
| Hydrogenated palm kernel oil | general |
| Hydrogenated Palm Kernel Oil glyceride | general |
| Hydrogenated Palm Oil | general |
| Hydrogenated Palm/Palm Kernel Oil Peg-6 Ester | general |
| Hydrogenated Polvbutene 635-690 | general |
| Hydrogenated Soy | general |
| Hydrogenated soy phosphotidylcholine | general |
| Hydroxide Ion | general |
| Hydroxyethylpiperazine Ethane Sulfonic Acid | general |
| Hydroxymethyl Cellulose | general |
| Hydroxyoctacosanyl Hydroxystearate | general |
| Hydroxypropyl Methylcellulose 2906 | general |
| Hydroxypropyl-B-cyclodextrin | general |
| Hypromellose | general |
| Hypromellose 2208 (15000 Mpa.S) | general |
| Hypromellose 2910 (15000 Mpa.S) | general |
| Imidurea | general |
| Iodine | general |
| Iodoxamic Acid | general |
| Iofetamine Hydrochloride | general |
| Irish Moss Extract | general |
| Isobutane | general |
| Isoceteth-20 | general |
| Isoleucine | general |
| Isooctyl Acrylate | general |
| Isopropyl Alcohol | general |
| Isopropyl Isostearate | general |
| Isopropyl Myristate | general |
| Isopropyl Palmitate | general |
| Isopropyl Stearate | general |
| Isostearic Acid | general |
| Isostearyl Alcohol | general |
| Isotonic Sodium Chloride Solution | general |
| Jelene | general |
| Kaolin | general |
| Kathon Cg | general |
| Kathon Cg II | general |
| Lactate | general |
| Lactic Acid | general |
| Lactic Acid (DL-) | general |
| Lactobionic Acid | general |
| Lactose | general |
| Lactose hydrous | general |
| Lactose Monohydrate | general |
| Laneth | general |

TABLE 1-continued

Excipients

| Excipient | Example Category |
|---|---|
| Lanolin | general |
| Lanolin (ethoxylated) | general |
| Lanolin (hydrogenated) | general |
| Lanolin Alcohol | general |
| Lanolin Anhydrous | general |
| Lanolin Cholesterol | general |
| Lanolin Nonionic Derivatives | general |
| Lauralkonium Chloride | general |
| Lauramine Oxide | general |
| Laurdimonium Hydrolyzed Animal Collagen | general |
| Laureth Sulfete | general |
| Laureth-2 | general |
| Laureth-23 | general |
| Laureth-4 | general |
| Laurie Diethanolamide | general |
| Lauric Myristic Diethanolamide | general |
| Lauroyl Sarcosine | general |
| Lauryl Lactate | general |
| Lauryl Sulfate | general |
| Lavandula Angustifolia Flowering Top | general |
| Lecithin | general |
| Lecithin (hydrogenated) | general |
| Lecithin Unbleached | general |
| Lemon Oil | general |
| Leucine | general |
| Levulinic Acid | general |
| Lidofenin | general |
| Light Mineral Oil | general |
| Light Mineral Oil (85 Ssu) | general |
| Limonene (+/−) | general |
| Lipocol Sc-15 | general |
| Lysine | general |
| Lysine Acetate | general |
| Lysine Monohydrate | general |
| Magnesium Aluminum Silicate Hydrate | general |
| Magnesium Chloride | general |
| Magnesium Nitrate | general |
| Magnesium Stearate | general |
| Maleic Acid | general |
| Maltitol | general |
| Maltodextrin | general |
| Mannitol | general |
| Mannose | general |
| Maprofix | general |
| Mebrofenin | general |
| Medical Adhesive Modified 5-15 | general |
| Medical Antiform A-F Emulsion | general |
| Medium Chain | general |
| Medronate Disodium | general |
| Medronic Acid | general |
| Meglumine | general |
| Melezitose | general |
| Menthol | general |
| Metacresol | general |
| Metaphosphoric Acid | general |
| Methanesulfonic Acid | general |
| Methionine | general |
| Methyl Alcohol | general |
| Methyl Gluceth-10 | general |
| Methyl Gluceth-20 | general |
| Methyl Gluceth-20 Sesquistearate | general |
| Methyl Glucose Sesquistearate | general |
| Methyl Laurate | general |
| Methyl Pyrrolidone | general |
| Methyl Salicylate | general |
| Methyl Stearate | general |
| Methylboronic Acid | general |
| Methylcellulose (4000 Mpa.S) | general |
| Methylchloroisothiazolinone | general |
| Methylene Blue | general |
| Methylisothiazolinone | general |
| Methylparaben | general |
| Microcry stalline | general |
| Microcrystalline Wax | general |
| Mineral Oil | general |
| Monostearyl Citrate | general |
| Monothioglycerol | general |
| Multisterol Extract | general |
| Myristyl Alcohol | general |
| Myristyl Lactate | general |
| Myristyl-.Gamma.-Picolinium Chloride | general |
| N-(Carbamoyl-Methoxy Peg-40)-1,2-Distearoyl-Cephalin Sodium | general |
| N,N-Dimethylacetamide | general |
| Niacinamide | general |
| Nioxime | general |
| Nitric Acid | general |
| Nitrogen | general |
| Nonoxynol Iodine | general |
| Nonoxynol-15 | general |
| Nonoxynol-9 | general |
| Norflurane | general |
| Oatmeal | general |
| Octadecene-1/Maleic Acid Copolymer | general |
| Octanoic Acid | general |
| Octisalate | general |
| Octoxynol-1 | general |
| Octoxynol-40 | general |
| Octoxynol-9 | general |
| Octyldodecanol | general |
| Octylphenol Polymethylene | general |
| Oleth-10/Oleth-5 | general |
| Oleth-2 | general |
| Oleth-20 | general |
| Oleyl Alcohol | general |
| Oleyl Oleate | general |
| Oxidronate Disodium | general |
| Oxyquinoline | general |
| Palm Kernel Oil | general |
| Palm Kernel Oil Glyceride | general |
| Palmitamine Oxide | general |
| Parabens | general |
| Paraffin | general |
| Parfum Creme 45/3 | general |
| Peanut Oil (Refined) | general |
| Pectin | general |
| Peg 6-32 Stearate/Glycol Stearate | general |
| Peg Vegetable Oil | general |
| Peg-100 Stearate | general |
| Peg-12 Glyceryl Laurate | general |
| Peg-120 Glyceryl Stearate | general |
| Peg-120 Methyl Glucose Dioleate | general |
| Peg-15 Cocamine | general |
| Peg-150 Distearate | general |
| Peg-2 Stearate | general |
| Peg-20 Sorbitan Isostearate | general |
| Peg-22 Methyl Ether/Dodecyl Glycol Copolymer | general |
| Peg-25 Propylene Glycol Stearate | general |
| Peg-4 Dilaurate | general |
| Peg-4 Laurate | general |
| Peg-40 Castor Oil | general |
| Peg-40 Sorbitan Diisostearate | general |
| Peg-45/Dodecyl Glycol Copolymer | general |
| Peg-5 Oleate | general |
| Peg-50 Stearate | general |
| Peg-54 Hydrogenated Castor Oil | general |
| Peg-6 Isostearate | general |
| Peg-60 Castor Oil | general |
| Peg-60 Hydrogenated Castor Oil | general |
| Peg-7 Methyl Ether | general |
| Peg-75 Lanolin | general |
| Peg-8 Laurate | general |
| Peg-8 Stearate | general |
| Pegoxol 7 Stearate | general |
| Pentadecalactone | general |
| Pentaerythritol Cocoate | general |
| Pentasodium Pentetate | general |
| Pentetate Calcium Trisodium | general |
| Pentetic Acid | general |

TABLE 1-continued

Excipients

| Excipient | Example Category |
|---|---|
| Perflutren | general |
| Perfume 25677 | general |
| Perfume Bouquet | general |
| Perfume E-1991 | general |
| Perfume Gd 5604 | general |
| Perfume Tana 90/42 Scba | general |
| Perfume W-1952-1 | general |
| Petrolatum | general |
| Petroleum Distillate | general |
| Phenol | general |
| Phenol (Liquefied) | general |
| Phenonip | general |
| Phenoxyethanol | general |
| Phenylalanine | general |
| Phenylethyl Alcohol | general |
| Phenylmercuric Acetate | general |
| Phenylmercuric Nitrate | general |
| Phosphate buffer | general |
| Phosphate buffered saline | general |
| Phosphate salts | general |
| Phosphatidyl Glycerol | general |
| Phospholipid | general |
| Phospholipid (Egg) | general |
| Phospholipon 90g | general |
| Phosphoric Acid | general |
| Pine Needle Oil (Pinus Sylvestris) | general |
| Piperazine Hexahydrate | general |
| Plastibase-50w | general |
| Polacrilin | general |
| Polidromum Chloride | general |
| Poloxamer 124 | general |
| Poloxamer 181 | general |
| Poloxamer 182 | general |
| Poloxamer-188 | general |
| Poloxamer 237 | general |
| Poloxamer-407 | general |
| Poly(Bis(P-Catboxyphenoxy)Propane Anhydride):Sebacic Acid | general |
| Poly(Dimethylsiloxane/Methylvinylsiloxane/Methylhydrogensiloxane) Dimethylvinyl Or Dimethylhydroxy Or Trimethyl Endblocked | general |
| Poly(Dl-Lactic-Co-Glycolic Acid) | general |
| Polybutene (1400 Mw) | general |
| Polycarbophil | general |
| Polyester Polyamine Copolymer | general |
| Polyester Rayon | general |
| Polyethylene Glycol 1000 | general |
| Polyethylene Glycol 1450 | general |
| Polyethylene Glycol 1500 | general |
| Polyethylene Glycol 1540 | general |
| Polyethylene Glycol 200 | general |
| Polyethylene Glycol 300 | general |
| Polyethylene Glycol 300-1600 | general |
| Polyethylene Glycol 3350 | general |
| Polyethylene Glycol 400 (PEG 400) | general |
| Polyethylene Glycol 4000 (PEG 4000, PEG 4kDa) | general |
| Polyethylene Glycol 540 | general |
| Polyethylene Glycol 600 | general |
| Polyethylene Glycol 6000 | general |
| Polyethylene Glycol 8000 | general |
| Polyethylene Glycol 900 | general |
| Polyethylene High Density Containing Ferric Oxide Black (<1%) | general |
| Polyethylene Low Density Containing Barium Sulfate (20-24%) | general |
| Polyethylene T | general |
| Polyethylene Terephthalate | general |
| Polyglactin | general |
| Polyglyceryl-3 Oleate | general |
| Polyglyceryl-4 Oleate | general |
| Polyhydroxymethyl Methacrylate | general |
| Polyisobutylene | general |
| Polyisobutylene (1100000 Mw) | general |
| Polyisobutylene (35000 Mw) | general |
| Polyisobutylene 178-236 | general |
| Polyisobutylene 241-294 | general |
| Polyisobutylene 35-39 | general |
| Polyisobutylene Low Molecular Weight | general |
| Polyisobutylene Medium Molecular Weight | general |
| Polyisobutylene/Polybutene Adhesive | general |
| Polylactide | general |
| Polyol | general |
| Polyoxyethylene | general |
| Polyoxyethylene Alcohol | general |
| Polyoxyethylene Fatly Acid Ester | general |
| Polyoxyethylene Propylene | general |
| Polyoxyl 20 Cetostearyl Ether | general |
| Polyoxyl 32 Palmitostearate | general |
| Polyoxyl 35 Castor Oil | general |
| Polyoxyl 40 Hydrogenated Castor Oil | general |
| Polyoxyl 40 Stearate | general |
| Polyoxyl 400 Stearate | general |
| Polyoxyl 6 | general |
| Polyoxyl Distearate | general |
| Polyoxyl Glyceryl Stearate | general |
| Polyoxyl Lanolin | general |
| Polyoxyl Palmitate | general |
| Polyoxyl Stearate | general |
| Polyoxylpropylene 1800 | general |
| Polypropylene | general |
| Polypropylene Glycol | general |
| Polyquaternium-10 | general |
| Polyquaternium-7 (70/30) Acrylamide/Dadmac | general |
| Polysiloxane | general |
| Polysorbate 40 | general |
| Polysorbate 60 | general |
| Polysorbate 65 | general |
| Polyurethane | general |
| Polyvinyl Acetate | general |
| Polyvinyl Chloride | general |
| Polyvinyl Chloride-Polyvinyl Acetate Copolymer | general |
| Polyvinylpyridine | general |
| Poppy Seed Oil | general |
| Potash | general |
| Potassium Acetate | general |
| Potassium Alum | general |
| Potassium Bicarbonate | general |
| Potassium Bisulfite | general |
| Potassium Chloride | general |
| Potassium Citrate | general |
| Potassium Hydroxide | general |
| Potassium Metabisulfite | general |
| Potassium Phosphate (Dibasic) | general |
| Potassium Phosphate (Monobasic) | general |
| Potassium Soap | general |
| Povidone | general |
| Povidone Acrylate Copolymer | general |
| Povidone Hydrogel | general |
| Povidone K17 | general |
| Povidone K25 | general |
| Povidone K29/32 | general |
| Povidone K30 | general |
| Povidone K90 | general |
| Povidone K90f | general |
| Povidone/Eicosene Copolymer | general |
| Ppg-12/Smdi Copolymer | general |
| Ppg-15 Stearyl Ether | general |
| Ppg-20 Methyl Glucose Ether Distearate | general |
| Ppg-26 Oleate | general |
| Pregelatinized | general |
| Product Wat | general |
| Proline | general |
| Promulgen D | general |
| Promulgen G | general |
| Propane | general |
| Propellant A-46 | general |

TABLE 1-continued

Excipients

| Excipient | Example Category |
|---|---|
| Propyl Gallate | general |
| Propylene Glycol Diacetate | general |
| Propylene Glycol Dicaprylate | general |
| Propylene Glycol Monolaurate | general |
| Propylene Glycol Monopalmitostearate | general |
| Propylene Glycol Palmito stearate | general |
| Propylene Glycol Ricinoleate | general |
| Propylene Glycol/Diazolidinyl Urea/ Methylparaben/Propylparben | general |
| Propylparaben | general |
| Protamine Sulfate | general |
| Protein Hydrolysate | general |
| Pvm/Ma Copolymer | general |
| Quaternium-15 | general |
| Quaternium-15 Cis-Form | general |
| Quaternium-52 | general |
| Ra-2397 | general |
| Ra-3011 | general |
| Raffinose | general |
| Saccharin | general |
| Saccharin Sodium | general |
| Saccharin Sodium Anhydrous | general |
| Sd Alcohol 3a | general |
| Sd Alcohol 40 | general |
| Sd Alcohol 40-2 | general |
| Sd Alcohol 40b | general |
| Sepineo P 600 | general |
| Serine | general |
| Shea Butter | general |
| Silastic Brand Medical Grade Tubing | general |
| Silastic Medical Adhesive | general |
| Silica | general |
| Silicon | general |
| Silicon Dioxide | general |
| Silicone | general |
| Silicone Adhesive 4102 | general |
| Silicone Adhesive 4502 | general |
| Silicone Adhesive Bio-Psa Q7-4201 | general |
| Silicone Adhesive Bio-Psa Q7-4301 | general |
| Silicone Emulsion | general |
| Silicone Type A | general |
| Silicone/Polyester Film Strip | general |
| Simethicone | general |
| Simethicone Emulsion | general |
| Sipon Ls 20np | general |
| Soda Ash | general |
| Sodium Acetate | general |
| Sodium Acetate Anhydrous | general |
| Sodium Alkyl Sulfate | general |
| Sodium Ascorbate | general |
| Sodium Benzoate | general |
| Sodium Bicarbonate | general |
| Sodium Bisulfate | general |
| Sodium Borate | general |
| Sodium Borate Decahydrate | general |
| Sodium Carbonate | general |
| Sodium Carbonate Decahydrate | general |
| Sodium Carbonate Monohydrate | general |
| Sodium Cetostearyl Sulfate | general |
| Sodium Chlorate | general |
| Sodium Chloride | general |
| Sodium Chloride Injection | general |
| Sodium Cholesteryl Sulfate | general |
| Sodium Citrate | general |
| Sodium Citrate Dihydrate | general |
| Sodium Cocoyl Sarcosinate | general |
| Sodium Desoxycholate | general |
| Sodium Dithionite | general |
| Sodium Dodecylbenzenesulfonate | general |
| Sodium Formaldehyde Sulfoxylate | general |
| Sodium Gluconate | general |
| Sodium Hydroxide | general |
| Sodium Hypochlorite | general |
| Sodium Iodide | general |
| Sodium Lactate | general |
| Sodium Lactate (L-) | general |
| Sodium Laureth-2 Sulfate | general |
| Sodium Laureth-3 Sulfate | general |
| Sodium Laureth-5 Sulfate | general |
| Sodium Lauroyl Sarcosinate | general |
| Sodium Lauryl Sulfate | general |
| Sodium Laurel Sulfoacetate | general |
| Sodium Metabisulfite | general |
| Sodium Phosphate | general |
| Sodium Phosphate (Dibasic) | general |
| Sodium Phosphate (Dibasic, Anhydrous) | general |
| Sodium Phosphate (Dibasic, Dihydrate) | general |
| Sodium Phosphate (Dibasic, Dodecahydrate) | general |
| Sodium Phosphate (Dibasic, Heptahydrate) | general |
| Sodium Phosphate (Monobasic) | general |
| Sodium Phosphate (Monobasic, Anhydrous) | general |
| Sodium Phosphate (Monobasic, Dihydrate) | general |
| Sodium Phosphate (Monobasic, Monohydrate) | general |
| Sodium Phosphate Dihydrate | general |
| Sodium Polyacrylate (2500000 Mw) | general |
| Sodium Pyrophosphate | general |
| Sodium Pyrrolidone Carboxylate | general |
| Sodium Starch Glycolate | general |
| Sodium Succinate Hexahydrate | general |
| Sodium Sulfate | general |
| Sodium Sulfate Anhydrous | general |
| Sodium Sulfate Decahydrate | general |
| Sodium Sulfite | general |
| Sodium Sulfosuccinated Undecyclenic Monoalkylolamide | general |
| Sodium Tartrate | general |
| Sodium Thioglycolate | general |
| Sodium Thiomalate | general |
| Sodium Thiosulfate | general |
| Sodium Thiosulfate Anhydrous | general |
| Sodium Trimetaphosphate | general |
| Sodium Xylenesulfonate | general |
| Somay 44 | general |
| Sorbic Acid | general |
| Sorbitan | general |
| Sorbitan Isostearate | general |
| Sorbitan Monolaurate | general |
| Sorbitan Monopalmitate | general |
| Sorbitan Monostearate | general |
| Sorbitan Sesquioleate | general |
| Sorbitan Trioleate | general |
| Sorbitan Tristearale | general |
| Sorbitol Solution | general |
| Sorbose | general |
| Soybean | general |
| Soybean Flour | general |
| Spearmint Oil | general |
| Spermaceti | general |
| Squalane | general |
| Stabilized Oxychloro Complex | general |
| Stannous 2-Ethylhexanoate | general |
| Stannous Chloride | general |
| Stannous Chloride Anhydrous | general |
| Stannous Fluoride | general |
| Stannous Tartrate | general |
| Starch | general |
| Starch 1500 | general |
| Stearalkonium Chloride | general |
| Stearalkonium Hectorite/Propylene Carbonate | general |
| Stearamidoethyl Diethylamine | general |
| Steareth-10 | general |
| Steareth-100 | general |
| Steareth-2 | general |
| Steareth-20 | general |
| Steareth-21 | general |
| Steareth-40 | general |
| Stearic Acid | general |
| Stearic Diethanolamide | general |
| Stearoxytrimethylsilane | general |
| Steartrimonum Hydrolyzed Animal Collagen | general |

TABLE 1-continued

Excipients

| Excipient | Example Category |
|---|---|
| Stearyl Alcohol | general |
| Styrene/Isoprene/Styrene Block Copolymer | general |
| Succimer | general |
| Succinic Acid | general |
| Sucralose | general |
| Sucrose | general |
| Sucrose Distearate | general |
| Sucrose Polyester | general |
| Sugar | general |
| Sulfacetamide Sodium | general |
| Sulfobutylether.Beta.-Cyclodextrin | general |
| Sulfur Dioxide | general |
| Sulfuric Acid | general |
| Sulfurous Acid | general |
| Surfactol Qs | general |
| Lagatose (D-) | general |
| Talc | general |
| Tall Oil | general |
| Tallow Glycerides | general |
| Tartaric Acid (DL-) | general |
| Tenox | general |
| Tenox-2 | general |
| Tert-Butyl Alcohol | general |
| Tert-Butyl Hydroperoxide | general |
| Tert-Butylhydroquinone | general |
| Tetrakis(2-Methoxyisobutylisocyanide) Copper(I) Tetrafluoroborate | general |
| Tetrapropyl Orthosilicate | general |
| Tetrofosmin | general |
| Theophylline | general |
| Thimerosal | general |
| Threonine | general |
| Thymol | general |
| Tin | general |
| Titanium Dioxide | general |
| Tocopherol | general |
| Tocophersolan | general |
| Trehalose | general |
| Tricaprylin | general |
| Trichloromonofluoromethane | general |
| Trideceth-10 | general |
| Triethanolamine Lauryl Sulfate | general |
| Trifluoroacetic Acid | general |
| Triglycerides | general |
| Trihalose | general |
| Trihydroxystearin | general |
| Trilaneth-4 Phosphate | general |
| Trilaureth-4 Phosphate | general |
| Trisodium Citrate Dihydrate | general |
| Trisodium Hedta | general |
| Triton 720 | general |
| Triton X-200 | general |
| Trolamine | general |
| Tromantadine | general |
| Tromethamine | general |
| Tryptophan | general |
| Tyloxapol | general |
| Tyrosine | general |
| Undecylenic Acid | general |
| Union 76 Amsco-Res 6038 | general |
| Urea | general |
| Valine | general |
| Vegetable Oil | general |
| Vegetable Oil Glyceride | general |
| Versetamide | general |
| Viscarin | general |
| Viscose/Cotton | general |
| Vitamin E | general |
| Water | general |
| Wax | general |
| Wecobee P | general |
| White | general |
| White Ceresin Wax | general |
| White Soft | general |
| White Wax | general |
| Zinc | general |
| Zinc Acetate | general |
| Zinc Carbonate | general |
| Zinc Chloride | general |
| Zinc Oxide | general |
| DSPC | lipid nanoparticle |
| lipid nanoparticle | lipid nanoparticle |
| PEG-DMG 2000 (1,2-dimyristoyl-sn-glycero-3-phophoethanolamine-N-[methoxy(polyethylene glycol)-2000] | lipid nanoparticle |
| 1,2-dilauroyl-sn-glycero-3-phosphocholine (DLPC) | lipids |
| 1,2-dimyristoyl-sn-glycero-3-phosphocholine (DMPC)phosphatidylinositol | lipids |
| 1,2-dioleoyl-sn-glycero-3-phophoethanolamine (DOPE) | lipids |
| 1,2-dioleoyl-sn-glycero-3-phosphocholine (DOPC) | lipids |
| diglyceride | lipids |
| dilinoleoylphosphatidylcholine | lipids |
| dioleoylphosphatidylcholine | lipids |
| dipalmitoylphosphatidylcholine | lipids |
| distearoylphosphatidylcholine | lipids |
| fats | lipids |
| lysolipids | lipids |
| lysophosphatidylethanolamine | lipids |
| lysophospholipid | lipids |
| monoglyceride | lipids |
| mono-myristoyl-phosphatidylethanolamine (MMPE) | lipids |
| mono-oleoyl-phosphatidic acid (MOPA) | lipids |
| mono-oleoyl-phosphatidylethanolamine (MOPE) | lipids |
| mono-oleoyl-phosphatidylglycerol (MOPG) | lipids |
| mono-oleoyl-phosphatidylserine (MOPS) | lipids |
| palmitoyloleoyl | lipids |
| palmitoyloleoyl phosphatidylcholine | lipids |
| palmitoyl-oleoyl-phosphatidylethanolamine (POPE) | lipids |
| phosphatidic acid | lipids |
| phosphatidylcholines | lipids |
| phosphatidylethanolamine | lipids |
| phosphatidylserine | lipids |
| phosphotidylglycerol | lipids |
| sterol | lipids |
| 1,2-dilinoleyloxy-3-dimethylaminopropane (DLin-DMA) | liposomes |
| 1,2-dioleyloxy-N,N-dimethylaminopropane (DODMA) liposomes | liposomes |
| 2,2-dilinoleyl-4-(2-dimethylaminoethyl)-[1,3]-dioxolane (DLin-KC2-DMA) | liposomes |
| DiLa2 liposomes from Marina Biotech (Bothell, WA) | liposomes |
| hyaluronan-coated liposomes | liposomes |
| liposome | liposomes |
| MC3 | liposomes |
| neutral DOPC (1,2-dioleoyl-sn-glycero-3-phosphocholine) based liposome | liposomes |
| SMARTICLES ® (Marina Biotech, Bothell, WA) | liposomes |
| stabilized nucleic acid lipid particle (SNALP) | liposomes |
| stabilized plasmid-lipid particles (SPLP) | liposomes |
| alkali salt | lubricant |
| alkaline earth salt | lubricant |
| aqueous solution | lubricant |
| calcium stearate | lubricant |
| fumed silica | lubricant |
| high molecular weight polyalkylene ghxol | lubricant |
| high molecular weight polyethylene glycol | lubricant |
| hyaluronic acid | lubricant |
| hydrogenated vegetable oil | lubricant |
| hydrous magnesium silicate | lubricant |
| lipids | lubricant |
| lubricants | lubricant |

TABLE 1-continued

Excipients

| Excipient | Example Category |
|---|---|
| lubricin | lubricant |
| micelle | lubricant |
| microsphere | lubricant |
| monoester of propylene glycol | lubricant |
| oils | lubricant |
| polymer | lubricant |
| saturated fatty acid containing about 16-20 carbon atoms | lubricant |
| saturated fatty acid containing about 8-22 carbon atoms | lubricant |
| solvents | lubricant |
| stearate salts | lubricant |
| transition metal salt | lubricant |
| vegetable oil derivative | lubricant |
| acrylic acid | nanoparticles |
| acrylic polymer | nanoparticles |
| amino alkyl methacrylate copolymer | nanoparticles |
| anhydride-modified material | nanoparticles |
| anhydride-modified phytoglycogen beta-dextrin | nanoparticles |
| carbon nanoparticles | nanoparticles |
| ceramic silicon carbide nanoparticle | nanoparticles |
| cerium oxide nanoparticle | nanoparticles |
| curcumin nanoparticle | nanoparticles |
| cyanoethyl methacrylate | nanoparticles |
| DLin-KC2-DMA | nanoparticles |
| DLin-M C3 -DMA | nanoparticles |
| ethoxyethyl methacrylate | nanoparticles |
| glycogen-type material | nanoparticles |
| gold nanoparticle | nanoparticles |
| iron nanoparticles | nanoparticles |
| iron oxide nanoparticle | nanoparticles |
| magnetic nano particle | nanoparticles |
| methacrylic acid | nanoparticles |
| methacrylic acid copolymer | nanoparticles |
| methyl methacrylate copolymer | nanoparticles |
| nanodiamond | nanoparticles |
| nickel nanoparticle | nanoparticles |
| phytoglvcogen beta-dextrin | nanoparticles |
| phytoglycogen octenyl succinate | nanoparticles |
| platinum nanoparticles | nanoparticles |
| poly(4-hydroxy-L-proline ester) | nanoparticles |
| poly(acrylic acid) | nanoparticles |
| poly(ethylene imine) | nanoparticles |
| poly(L-lactide-co-L-lysine) | nanoparticles |
| poly(methacrylic acid) | nanoparticles |
| poly(orthoesters) | nanoparticles |
| poly(serine ester) | nanoparticles |
| polyacetal | nanoparticles |
| polyacrylate | nanoparticles |
| polycyanoacrylate | nanoparticles |
| polyester | nanoparticles |
| polyether | nanoparticles |
| polyethylene | nanoparticles |
| polyhydroxyacid | nanoparticles |
| polylysine | nanoparticles |
| polymer coated iron oxide nanoparticle | nanoparticles |
| polymeric mycelle | nanoparticles |
| polymethacrylate | nanoparticles |
| polyphosphazene | nanoparticles |
| polypropylfumerate | nanoparticles |
| polyureas | nanoparticles |
| protein filled nanoparticle | nanoparticles |
| silica nanoparticle | nanoparticles |
| silicon dioxide crystalline nanoparticle | nanoparticles |
| silver nanoparticles | nanoparticles |
| silver oxide nanoparticle | nanoparticles |
| titanium dioxide nanoparticle | nanoparticles |
| natural polymers | natural polymers |
| natural rubbers | natural polymers |
| ceramic | other |
| cobalt-chromum-molydenum composite | other |
| duck's feet collagen | other |
| ionic liquids | other |
| magnesium oxide | other |
| melanin | other |
| metal scaffold | other |
| nano-hydroxyapatite | other |
| poly(α-estef) | other |
| SBA15 | other |
| alginate | polymers |
| alkyl cellulose | polymers |
| amber | polymers |
| bacterial cellulose | polymers |
| bioplastic | polymers |
| bioresorbable polymer matrix | polymers |
| carbohydrate polymers | polymers |
| cellulose acetate | polymers |
| cellulose ester | polymers |
| cellulose ether | polymers |
| chitin | polymers |
| chitosan | polymers |
| copolymers of acrylic and methacrylic acid esters | polymers |
| derivatized cellulose | polymers |
| elastin | polymers |
| ethylene vinyl acetate polymer (EVA) | polymers |
| EUDRAGIT ® RL | polymers |
| EUDRAGIT ® RS | polymers |
| fibrin | polymers |
| genetically modified bioplastics | polymers |
| glycogen | polymers |
| high-density polyethylene (HOPE) | polymers |
| hydroxypropyl methylcellulose (HPMC) | polymers |
| hydroxyalkyl celluloses | polymers |
| hydroxypropyl ethylcellulose (HEC) | polymers |
| hydroxypropyl methacrylate (HPMA) | polymers |
| hy droxypropylcellulose | polymers |
| keratins | polymers |
| lignin | polymers |
| lipid-derived polymer | polymers |
| low-density polyethylene (LDPE) | polymers |
| methacrylates | polymers |
| natural rubber | polymers |
| neoprene | polymers |
| nitro cellulose | polymers |
| nucleic acid | polymers |
| nylon | polymers |
| nylon 6 | polymers |
| nylon 6.6 | polymers |
| nylone | polymers |
| phenol formaldehyde resin | polymers |
| poloxamer | polymers |
| poly(butyl(meth)acrylate) | polymers |
| poly(butyric acid) | polymers |
| poly(caprolactone) (PCL) | polymers |
| poly(D,L-lactide) (PDLA) | polymers |
| poly(D,L-lactide-co-caprolactone) | polymers |
| poly(D,L-lactide-co-caprolactone-co-glycolide) | polymers |
| poly(D,L-lactide-co-PPO-co-D,L-lactide) | polymers |
| poly(ester amides) | polymers |
| poly(ester ethers) | polymers |
| poly(ethyl(meth)acrylate) | polymers |
| poly(ethylene terephthalate) | polymers |
| poly(glycolic acid) (PGA) | polymers |
| poly(hexyl(meth)acrylate) | polymers |
| poly(hydroxy acids) | polymers |
| poly(isobutyl acrylate) | polymers |
| poly(isobutyl(meth)acrylate) | polymers |
| poly(isodecyl(meth)acrylate) | polymers |
| poly(isopropyl acrylate) | polymers |
| poly(lactic acid) (PLA) | polymers |
| poly(lactic acid-co-glycolic acid) (PLGA) | polymers |
| poly(lactide-co-caprolactone) | polymers |
| poly(lactide-co-glycolide) | polymers |
| poly(lauryl(meth)acrylate) | polymers |
| poly(L-lactic acid) (PLLA) | polymers |
| poly(L-lactic acid-co-glycolic acid) (PLLGA) | polymers |
| poly(L-lactide) (PLLA) | polymers |
| poly(methyl acrylate) | polymers |

TABLE 1-continued

| Excipient | Example Category |
|---|---|
| poly(methyl(meth)acrylate) (PMMA) | polymers |
| poly(octadecyl acrylate) | polymers |
| poly(ortho)esters | polymers |
| poly(phenyl(meth)acrylate) | polymers |
| poly(valeric acid) | polymers |
| poly(vinyl acetate) | polymers |
| polyacrylonitrile | polymers |
| polyalkyl cyanoacralate | polymers |
| polyalkylene | polymers |
| polyalkylene glycol | polymers |
| polyalkylene oxide | polymers |
| polyalkylene terephthalate | polymers |
| polyamide | polymers |
| polyamino acid | polymers |
| polyanhydride | polymers |
| polyaniline | polymers |
| polycaprolactone | polymers |
| polycarbonate | polymers |
| polydioxanone | polymers |
| polydioxanone copolymer | polymers |
| polyethtylene glycol diglycidl ester | polymers |
| polyethylene glycol | polymers |
| polyethylene oxide | polymers |
| polyethyleneglycol | polymers |
| polyglycolide | polymers |
| polyhydroxyalkanoate | polymers |
| polyhydroxybutyrate (also known as polyhydroxyalkanoate) | polymers |
| polyhydroxyurethane | polymers |
| polyisoprene | polymers |
| polyketal | polymers |
| polylactic acid | polymers |
| poly-L-glutamic acid | polymers |
| poly-L-lysine (PLL) | polymers |
| polymer of acrylic acid | polymers |
| polyorthoester | polymers |
| polyoxymethylene | polymers |
| polypeptides | polymers |
| polyphosphoester | polymers |
| polypropylene fumarate | polymers |
| polysaccharide | polymers |
| polystyrene | polymers |
| polytetrafluoroethylene | polymers |
| polyvinyl butyral | polymers |
| polyvinyl ester | polymers |
| polyvinyl ether | polymers |
| polyvinyl halides such as poly(vinyl chloride) (PVC) | polymers |
| poyphosphazene | polymers |
| quarternary ammonium chitosan | polymers |
| shellac | polymers |
| sodium carboxymethylcellulose | polymers |
| synthetic polyether | polymers |
| synthetic rubber | polymers |
| thermoplastic polyurethane | polymers |
| trimethylene carbonate | polymers |
| ultra-high-molecular-weight-polyethylene (UHMWPE) | polymers |
| wool | polymers |
| β-keratin | polymers |
| alkylparaben | preservative |
| amino acids | preservative |
| Antioxidant | preservative |
| BHA | preservative |
| BHT | preservative |
| calcium propionate | preservative |
| disodium EDTA | preservative |
| glutaraldehyde | preservative |
| magnesium chloride hexahydrate | preservative |
| m-cresol | preservative |
| methyl paraben | preservative |
| o-cresol | preservative |
| p-cresol | preservative |
| phenylmercuric nitrite | preservative |
| potassium hydrogen sulfite | preservative |
| potassium sorbate | preservative |
| preservative | preservative |
| propyl paraben | preservative |
| selenium | preservative |
| sodium dehydroacetate | preservative |
| sodium nitrate | preservative |
| sodium nitrite | preservative |
| sulfites | preservative |
| vitamin A | preservative |
| vitamin C | preservative |
| acesulfame potassium | sweetener |
| advantame | sweetener |
| artificial sweetener | sweetener |
| aspartame | sweetener |
| brazzein | sweetener |
| curculin | sweetener |
| cyclamates | sweetener |
| erythritol | sweetener |
| glucose | sweetener |
| glycyrrhizin | sweetener |
| hydrogenated starch hydrolysate | sweetener |
| inulin | sweetener |
| ismalt | sweetener |
| isomaltooligosaccharide | sweetener |
| isomaltulose | sweetener |
| lactitol | sweetener |
| lead acetate | sweetener |
| mabinlin | sweetener |
| miraculin | sweetener |
| mogroside | sweetener |
| monantin | sweetener |
| neotame | sweetener |
| osladin | sweetener |
| pentadin | sweetener |
| polydextrose | sweetener |
| psicose | sweetener |
| stevia | sweetener |
| sweetener | sweetener |
| tagatose | sweetener |
| thaumatin | sweetener |
| xylitol | sweetener |
| xylose | sweetener |
| elastomer | synthetic polymer |
| synthetic fiber | synthetic polymer |
| synthetic polymer | synthetic polymer |
| thermoplastic | synthetic polymer |
| thermoset | synthetic polymer |
| Non-polymeric diol | Demulcent |
| Non-polymeric glycol | Demulcent |
| Cellulose derivative | Demulcent |
| Dextran 70 | Demulcent |
| Cationic cellulose derivative | Demulcent |

Some excipients may include pharmaceutically acceptable excipients. The phrase "pharmaceutically acceptable" as used herein, refers to suitability within the scope of sound medical judgment for contacting subject (e.g., human or animal) tissues and/or bodily fluids with toxicity, irritation, allergic response, or other complication levels yielding reasonable benefit/risk ratios. As used herein, the term "pharmaceutically acceptable excipient" refers to any ingredient, other than active agents, that is substantially nontoxic and non-inflammatory in a subject. Pharmaceutically acceptable excipients may include, but are not limited to, solvents, dispersion media, diluents, inert diluents, buffering agents, lubricating agents, oils, liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins. Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of pharmaceutical compositions.

In one embodiment, the excipient is sorbitol.

In one embodiment, the excipient is mannitol.

Polymers

In some embodiments, excipients may include polymers. As used herein, the term "polymer" refers to any substance formed through linkages between similar modules or units. Individual units are referred to herein as "monomers." Common polymers found in nature include, but are not limited to, carbon chains (e.g., lipids), polysaccharides, nucleic acids, and proteins. In some embodiments, polymers may be synthetic (e.g., thermoplastics, thermosets, elastomers, and synthetic fibers), natural (e.g., chitosan, cellulose, polysaccharides, glycogen, chitin, polypeptides, β-keratins, nucleic acids, natural rubber, etc.), or a combination thereof. In some embodiments, polymers may be irradiated. Non limiting examples of polymers include ethylcellulose and co-polymers of acrylic and methacrylic acid esters (EUDRAGIT® RS or RL), alginates, sodium carboxymethylcellulose, carboxypolymethylene, hydroxpropyl methylcellulose, hydroxypropyl cellulose, collagen, hydroxypropyl ethylcellulose, hydroxyethylcellulose, methylcellulose, xanthum gum, polyethylene oxide, polyethylene glycol, polysiloxane, poyphosphazene, low-density polyethylene (LDPE), high-density polyethylene (HDPE), polyvinyl chloride, polystyrene, nylon, nylon 6, nylon 6.6, polytetrafluoroethylene, thermoplastic polyurethanes, polycaprolactone, polyamide, polycarbonate, chitosan, cellulose, polysaccharides, glycogen, starch, chitin, polypeptides, keratins, β-keratins, nucleic acids, natural rubber, hyaluronan, polylactic acid, methacrylates, polyisoprene, shellac, amber, wool, synthetic rubber, silk, phenol formaldehyde resin, neoprene, nylon, polyacrylonitrile, silicone, polyvinyl butyral, polyhydroxybutyrate (also known as polyhydroxyalkanoate), polyhydroxyurethanes, bioplastics, genetically modified bioplastics, lipid-derived polymers, lignin, carbohydrate polymers, ultra-high-molecular-weight-polyethylene (UHMWPE), gelatin, dextrans, and polyamino acids.

Specific non-limiting examples of specific polymers include, but are not limited to poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D, L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly (vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) and copolymers and mixtures thereof polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), and trimethylene carbonate, polyvinylpyrrolidone. In some embodiments, polymer excipients may include any of those presented in Table 1, above.

Particles

In some embodiments, excipients may include particles. Such particles may be of any size and shape, depending on the nature of associated SBPs. In some embodiments, excipient particles are nanoparticles. Non-limiting examples of nanoparticles include gold nanoparticles, silver nanoparticles, silver oxide nanoparticles, iron nanoparticles, iron oxide nanoparticles, platinum nanoparticles, silica nanoparticles, titanium dioxide nanoparticles, magnetic nanoparticles, cerium oxide nanoparticles, protein filled nanoparticles, carbon nanoparticles, nanodiamonds, curcumin nanoparticles, polymeric micelles, polymer coated iron oxide nanoparticles, ceramic silicon carbide nanoparticles, nickel nanoparticles, and silicon dioxide crystalline nanoparticles.

In some embodiments, nanoparticles may include carbohydrate nanoparticles. Carbohydrate nanoparticles may include carbohydrate carriers. As a non-limiting example, carbohydrate carriers may include, but are not limited to, anhydride-modified or glycogen-type materials, phytoglycogen octenyl succinate, phytoglycogen beta-dextrin, or anhydride-modified phytoglycogen beta-dextrin. (See e.g., International Publication Number WO2012109121, the contents of which are herein incorporated by reference in their entirety).

In some embodiments, excipient nanoparticles may include lipid nanoparticles. Lipid nanoparticle excipients may be carriers in some embodiments. In some embodiments, lipid nanoparticles may be formulated with cationic lipids. In some embodiments, cationic lipids may be biodegradable cationic lipids. Such cationic lipids may be used to form rapidly eliminated lipid nanoparticles. Cationic lipids may include, but are not limited, DLinDMA, DLin-KC2-DMA, and DLin-MC3-DMA. Biodegradable lipid nanoparticles may be used to avoid toxicity associated with accumulation of more stable lipid nanoparticles in plasma and tissues over time.

In some embodiments, nanoparticles include polymeric matrices. As used herein, the term "polymeric matrix" refers to a network of polymer fibers that are bound together to form a material. The polymer fibers may be uniform or may include different lengths or monomer subunits. In some embodiments, polymer matrices may include one or more of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester), or combinations thereof.

In some embodiments, polymers include diblock copolymers. As used herein, the term "diblock copolymer" refers to polymers with two different monomer chains grafted to form a single chain. Diblock polymers may be designed to aggregate in different ways, including aggregation as a particle. In some embodiments, diblock copolymers include polyethylene glycol (PEG) in combination with polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), or poly(4-hydroxy-L-proline ester).

In some embodiments, nanoparticles include acrylic polymers. As used herein, the term "acrylic polymer" refers to a polymer made up of acrylic acid monomers or derivatives or variants of acrylic acid. Monomers included in acrylic polymers may include, but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), and polycyanoacrylates.

In some embodiments, particle excipients may include any of those presented in Table 1, above.

Lipids

In some embodiments, excipients include lipids. As used herein, the term "lipid" refers to members of a class of organic compounds that include fatty acids and various derivatives of fatty acids that are soluble in organic solvents, but not in water. Examples of lipids include, but are not limited to, fats, triglycerides, oils, waxes, sterols (e.g. cholesterol, ergosterol, hopanoids, hydroxysteroids, phytosterol, and steroids), stearin, palmitin, triolein, fat-soluble vitamins (e.g., vitamins A, D, E, and K), monoglycerides (e.g. monolaurin, glycerol monostearate, and glyceryl hydroxystearate), diglycerides (e.g. diacylglycerol), phospholipids, glycerophospholipids (e.g., phosphatidic acid, phosphatidylethanolamine, phosphatidylcholine, phosphatidylserine, phosphoinositides), sphingolipids (e.g., sphingomyelin), and phosphosphingolipids. In some embodiments, lipids may include, but are not limited to, any of those listed (e.g., fats and fatty acids) in Table 1, above.

In some embodiments, lipid excipients include amphiphilic lipids (e.g., phospholipids). As used herein, the term "amphiphilic lipid" refers to a class of lipids with both hydrophilic and hydrophobic domains. Amphiphilic lipids may be used to prepare vesicles as these molecules typically form layers along water:lipid interfaces. Non-limiting examples of amphiphilic lipids include, but are not limited to, phospholipids, phosphatidylcholines, phosphatidylethanolamines, palmitoyl-oleoyl-phosphatidylethanolamine (POPE), phosphatidylserines, phosphotidylglycerols, lysophospholipids such as lysophosphatidylethanolamines, mono-oleoyl-phosphatidylethanolamine (MOPE), mono-myristoyl-phosphatidylethanolamine (MMPE), lysolipids, mono-oleoyl-phosphatidic acid (MOPA), mono-oleoyl-phosphatidylserine (MOPS), mono-oleoyl-phosphatidylglycerol (MOPG), palmitoyloleoyl phosphatidylcholine, lysophosphatidylethanolamine, dipalmitoylphosphatidylcholine, dioleoylphosphatidylcholine; distearoylphosphatidylcholine, dilinoleoylphosphatidylcholine, 1,2-dioleoyl-sn-glycero-3-phosphocholine (DOPC), 1,2-dioleoyl-sn-glycero-3-phophoethanolamine (DOPE), 1,2-dilauroyl-sn-glycero-3-phosphocholine (DLPC), 1,2-dimyristoyl-sn-glycero-3-phosphocholine (DMPC)phosphatidylinositol, phosphatidic acid, palmitoyloleoyl phosphatidylcholine, lysophosphatidylethanolamines, monoglycerides, diglycerides, triglycerides.

Lipid Vesicles

In some embodiments, excipients may include lipid vesicles or components of lipid vesicles. As used herein, the term "lipid vesicle" refers to a particle enveloped by an amphiphilic lipid membrane. Examples of lipid vesicles include, but are not limited to, liposomes, lipoplexes, and lipid nanoparticles. SBPs may include lipid vesicles as cargo or payloads. In some embodiments, SBPs are or encompassed by lipid vesicles. Such lipid vesicles may be used to deliver SBPs as a payload. Such SBPs may themselves include cargo or payload. As used herein, the term "liposome" refers generally to any vesicle that includes a phospholipid bilayer and aqueous core. Liposomes may be artificially prepared and may be used as delivery vehicles. Liposomes can be of different sizes. Multilamellar vesicles (MLVs) may be hundreds of nanometers in diameter and contain two or more concentric bilayers separated by narrow aqueous compartments. Small unicellular vesicles (SUVs) may be smaller than 50 nm in diameter. Large unilamellar vesicles (LUVs) may be between 50 and 500 nm in diameter. Liposomes may include opsonins or ligands to improve liposome attachment to unhealthy tissue or to activate events (e.g., endocytosis). Liposome core pH may be modulated to improve payload delivery. In some embodiments, lipid vesicle excipients may include, but are not limited to, any of those listed in Table 1, above.

In some embodiments, liposomes may include 1,2-dioleyloxy-N,N-dimethylaminopropane (DODMA) liposomes, DiLa2 liposomes (Marina Biotech, Bothell, Wash.), 1,2-dilinoleyloxy-3-dimethylaminopropane (DLin-DMA) liposomes, 2,2-dilinoleyl-4-(2-dimethylaminoethyl)-[1,3]-dioxolane (DLin-KC2-DMA) liposomes, and MC3 liposomes (e.g., see US Publication Number US20100324120, the contents of which are herein incorporated by reference in their entirety). In some embodiments, liposomes may include small molecule drugs (e.g., DOXIL® from Janssen Biotech, Inc., Horsham, Pa.).

Liposomes may be formed from the synthesis of stabilized plasmid-lipid particles (SPLP) or stabilized nucleic acid lipid particle (SNALP) that have been previously described and shown to be suitable for delivery of oligonucleotides in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles *Hum Gene Ther.* 2008 19:125-132). These liposomes are designed for the delivery of DNA, RNA, and other oligonucleotide constructs, and they may be adapted for the delivery of SBPs with oligonucleotides. These liposome formulations may be composed of 3 to 4 lipid components in addition to SBPs. As an example, a liposome may contain 55% cholesterol, 20% disteroylphosphatidyl choline (DSPC), 10% PEG-S-DSG, and 15% 1,2- dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, SBPs may be encapsulated within liposomes and/or contained in an encapsulated aqueous liposome core. In another embodiment. SBPs may be formulated in an oil-in-water emulsion where the emulsion particle comprises an oil core and a cationic lipid which can interact with SBPs, anchoring them to emulsion particles (e.g., see International Publication. Number WO2012006380, the contents of which are herein incorporated by reference in their entirety. In another embodiment. SBPs may be formulated in lipid vesicles which may have crosslinks between functionalized lipid bilayers (e.g., see United States Publication Number US20120177724, the contents of which are herein incorporated by reference in their entirety).

In some embodiments, lipid vesicles may include cationic lipids selected from one or more of formula CLI-CLXXIX of International Publication Number WO2008103276; formula CLI-CLXXIX of U.S. Pat. No. 7,893,302; formula CLI-CLXXXXII of U.S. Pat. No. 7,404,969; and formula I-VI of United States Publication Number US20100036115, the contents of each of which are herein incorporated by reference in their entirety. As non-limiting examples, cationic lipids may be selected from (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-16, 19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimethyloctacosa-19,22-dien-9-amine, (18Z,21 Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21 Z,24Z)—N,N-dimethyltriaconta-21,24-dien-9-amine, (18Z)—N,N-dimethylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl] pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-6-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl] heptyl} dodecan-1-amine, 1-[(1R,2S)-2-heptylcyclopropyl]-N,N-dimethyloctadecan-9-anine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy) propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl] ethyl}azetidine, (2S)-1-(hexyloxy)-N,N-dimethyl-3-[(9Z, 12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(octyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy) propan-2-amine, (2S)-1-[(13Z,16Z)-docosa-13,16-dien-1-yloxy]-3-(hexyloxy)-N,N-dimethylpropan-2-amine. (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoylotyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z, 12Z)-octadeca-9,12-dien-1-yloxy]propan-2-amine, N,N-dimethyl-1-(octyloxy)-3-({8-[(1S,2S)-2-{[(1R2R)-2-pentylcyclopropyl]methyl}cyclopropyl]octyl}oxy)propan-2-amine, N,N-dimethyl-1-{[8-(2-octylcyclopropyl)octyl]oxy}-3-(octyloxy)propan-2-amine, (11E,20Z,23Z)—N,N-dimethylnonacosa-11,20,2-trien-10-amine, or pharmaceutically acceptable salts or steroisomers thereof.

In some embodiments, lipids may be cleavable lipids. Such lipids may include any of those described in International Publication Number WO2012170889, the contents of which are herein incorporated by reference in their entirety. In some embodiments, SBPs may be formulated with at least one of the PEGylated lipids described in International Publication Number WO2012099755, the contents of which are herein incorporated by reference in their entirety.

In some embodiments, excipients include lipid nanoparticles. As used herein, the term "lipid nanoparticle" or "LNP" refers to a tiny colloidal particle of solid lipid and surfactant, typically ranging in size of from about 10 nm in diameter to about 1000 nm in diameter. LNPs may contain PEG-DMG 2000 (1,2-dimyristoyl-sn-glycero-3-phophoethanolamine-N-[methoxy(polyethylene glycol)-2000). In some embodiments, LNPs may contain PEG-DMG 2000, a cationic lipid known in the art and at least one other component. LNPs may contain PEG-DMG 2000, a cationic lipid known in the art, DSPC and cholesterol. As a nonlimiting example, LNPs may contain PEG-DMG 2000, DLin-DMA, DSPC, and cholesterol.

In some embodiments, excipients may include DiLa2 liposomes (Marina Biotech, Bothell, Wash.), SMARTICLES® (Marina Biotech, Bothell. Wash.), neutral DOPC (1,2-dioleoyl-sn-glycero-3-phosphocholine) based liposomes, and hyaluronan-coated liposomes (Quiet Therapeutics, Israel).

In some embodiments, excipients may include lipidoids. As used herein, the term "lipidoid" refers to any non-lipid material that mimics lipid properties. The synthesis of lipidoids may be carried out as described by others (e.g., see Mahon et al., Bioconjug Chem. 2010 21:1448-1454; Schroeder et al., J Intern Med. 2010 267:9-21, Akine et al., Nat Biotechnol. 2008 26:561-569; Love et al., Proc Natl Acad Sci USA. 2010 107:1864-1869; and Siegwart et al., Proc Natl Acad Sci USA. 2011 108:12996-3001, the contents of each of which are herein incorporated by reference in their entireties). Lipidoids may be included in complexes, micelles, liposomes, or particles. In some embodiments, SBPs may include lipidoids.

In some embodiments, lipidoids may be combined with lipids to form particles. Such lipids may include cholesterol. Some lipidoids may be combined with PEG (e.g., C14 alkyl chain length). As another example, formulations with certain lipidoids, include, but are not limited to, C12-200 and may contain a combination of lipidoid, disteroylphosphatidyl choline, cholesterol, and PEG-DMG.

Coating Agents

In some embodiments, excipients may include coating agents. Polymers are commonly used as coating agents and may be layered over SBPs. Non-limiting examples of polymers for use as coating agents include polyethylene glycol, methylcellulose, hypromellose, ethylcellulose, gelatin, hydroxypropyl cellulose, titanium dioxide, zein, poly(alkyl) (meth)acrylate, poly(ethylene-co-vinyl acetate), and combinations thereof. In some embodiments, coating agents may include one or more compounds listed in Table 1, above.

Bulking Agents

In some embodiments, excipients include bulking agents. As used herein, the term "bulking agent" refers to a substance that adds weight and volume to a composition. Examples of bulking agents include, but are not limited to, lactose, sorbitol, sucrose, mannitol, lactose USP, Starch 1500, microcrystalline cellulose, Avicel, dibasic calcium phosphate dehydrate, sucrose, tartaric acid, citric acid, fumaric acid, succinic acid, malic acid, polyvinylpyrrolidone, copolymers of vinylpyrrolidone and vinylacetate, hydroxypropylcellulose, hydroxyethylcellulose, hydroxypropylmethylcellulose, polyvinyl alcohol, polyethylene glycol, acacia, sodium carboxymethylcellulose, and combinations thereof. In some embodiments, bulking agents may include any of those presented in Table 1, above.

Lubricants

In some embodiments, excipients may include lubricants. As used herein, the term "lubricant" refers to any substance used to reduce friction between two contacting materials. Lubricants may be natural or synthetic. Lubricants may comprise oils, lipids, microspheres, polymers, water, aqueous solutions, liposomes, solvents, alcohols, micelles, stearate salts, alkali, alkaline earth, and transition metal salts thereof (e.g., calcium, magnesium, or zinc), stearic acid, polyethylene oxide, talc, hydrogenated vegetable oil, and vegetable oil derivatives, fumed silica, silicones, high molecular weight polyalkylene glycol (e.g. high molecular weight polyethylene glycol), monoesters of propylene glycol, saturated fatty acids containing about 8-22 carbon atoms and/or 16-20 carbon atoms, and any other component known to one skilled in the art. Other examples of lubricants include, but are not limited to, hyaluronic acid, magnesium stearate, calcium stearate, and lubricin. In some embodiments, lubricant excipients may include any of those presented in Table 1, above.

Sweeteners and Colorants

In some embodiments, excipients may include sweeteners and/or colorants. As used herein, a "sweetener" refers to a substance that adds a sweet taste to or improves the sweetness of a composition. Sweeteners may be natural or artificial. Non-limiting examples of sweeteners include glucose, aspartame, sucralose, neotame, acesulfame potassium, saccharin, advantame, cyclamates, sorbitol, xylitol, lactitol, xylose, *stevia*, lead acetate, mogrosides, brazzein, curculin, erythritol, glycyrrhizin, glycerol, hydrogenated starte hydrolysates, inulin, ismalt, isomaltooligosaccharide, isomaltulose, mabinlin, maltodextrin, miraculin, monantin, osladin, pentadin, polydextrose, psicose, tagatose, thaumatin, mannitol, lactose, and sucrose. In some embodiments, sweetener excipients may include any of those presented in Table 1, above.

As used herein, the term "colorant" refers to any substance that adds color to a composition (e.g., a dye). Non-limiting examples of colorants include dyes, inks, pigments, food coloring, turmeric, titanium dioxide, caretinoids (e.g., bixin, β-carotene, apocarotenals, canthaxanthin, saffron, crocin, capsanthin and capsorubin occurring in paprika ole-oresin, lutein, astaxanthin, rubixanthin, violaxanthin, rhodoxanthin, lycopenc, and derivatives thereof), and FD&C colorants [e.g., FD&C Blue No. 1 (brilliant blue FCF); FD&C Blue No. 2 (indigotine); FD&C Green No. 3 (fast green FCF); FD&C Red No. 40 (allura red AC); FD&C Red No. 3 (erythrosine); FD&C Yellow No. 5 (tartrazine); and FD&C Yellow No. 6 (sunset yellow)]. In some embodiments, colorant excipients may include any of those presented in Table 1, above.

Preservatives

In some embodiments, excipients may include preservatives. As used herein a "preservative" is any substance that protects against decay, decomposition, or spoilage. Preservatives may be natural or synthetic. They may be antimicrobial preservatives, which inhibit the growth of bacteria or fungi, including mold, or antioxidants such as oxygen absorbers, which inhibit the oxidation of food constituents. Common antimicrobial preservatives include calcium propionate, sodium nitrate, sodium nitrite, sulfites (sulfur dioxide, sodium bisulfite, potassium hydrogen sulfite, etc.) and disodium EDTA. Antioxidants include BHA and BHT. Other preservatives include formaldehyde (usually in solution), glutaraldehyde (kills insects), vitamin A, vitamin C, vitamin E selenium, amino acids, methyl paraben, propyl paraben, potassium sorbate, sodium chloride, ethanol, phenol, m-cresol, p-cresol, o-cresol, chlorocresol, benzyl alcohol, phenylmercuric nitrite, phenoxyethanol, methylchloroisothiazolinone, chlorobutanol, magnesium chloride (e.g., hexahydrate), alkylparaben (methyl, ethyl, propyl, butyl and the like), benzalkonium chloride, benzethonium chloride, sodium dehydroacetate, thimerosal, and combinations thereof. In some embodiments, preservative excipients may include any of those presented in Table 1, above.

Flowability Agents

In some embodiments, excipients may include flowability agents. As used herein, the term "flowability agent" refers to a substance used to reduce viscosity and/or aggregation in a composition. Flowability agents are particularly useful for the formulation of powders, particles, solutions, gels, polymers, and any other form of matter capable of flow from one area to another. Flowability agents have been used to improve powder flowability for the manufacture of therapeutics, as taught in Morin et al. (2013) AAPS PharmSciTech 14(3):1158-1168, the contents of which are herein incorporated by reference in their entirety. In some embodiments, flowability agents are used to modulate SBP viscosity. In some embodiments, flowability agents may be lubricants. Non-limiting examples of flowability agents include magnesium stearate, stearic acid, hydrous magnesium silicate, and any other lubricant used to promote flowability known to one skilled in the art. In some embodiments, flowability agent excipients may include any of those presented in Table 1, above.

Gelling Agents

In some embodiments, excipients may include gelling agents. As used herein, the term "gelling agent" refers to any substance that promotes viscosity and/or polymer cross-linking in compositions. Non-limiting examples of gelling agents include glycerol, glycerophosphate, sorbitol, hydroxyethyl cellulose, carboxymethyl cellulose, triethylamine, triethanolamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol formal, hydroxypropyl beta-cyclodextrin, kolliphor 124, kolliphor 181, kolliphor 188, kolliphor 407, kolliphor EL (cremaphor EL), cremaphor RH 40, cremaphor RH 60, d-alpha-tocopherol, PEG 1000 succinate, polysorbate 20, polysorbate-80, solutol HS 15, sorbitan monooleate, poloxamer-407, poloxamer-188, Labrafil M-1944CS, Labrafil M-2125CS, Labrasol, Gellucire 44/14, Softigen 767, mono- and di-fatty acid esters of PEG 300, PEG 400, or PEG 1750, kolliphor RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil and palm seed oil, beeswax, d-alpha-tocopherol, oleic acid, medium-chain mono- and diglycerides, alpha-cyclodextrin, beta-cyclodextrin, hydroxypropyl-beta-cyclodextrin, sulfo-butylether-beta-cyclodextrin, hydrogenated soy phosphatidylcholine, distearoylphosphatidylglycerol, L-alpha-dimyristoylphosphatidylcholine, L-alphadimyristoylphosphatidylglycerol, PEG 300, PEG 300 caprylic/capric glycerides (Softigen 767), PEG 300 linoleic glycerides (Labrafil M-2125CS), PEG 300 oleic glycerides (Labrafil M-1944CS), PEG 400, PEG 400 caprylic/capric glycerides (Labrasol), polyoxyl 40 stearate (PEG 1750 monosterate), PEG 4000 (PEG 4 kDa), polyoxyl 8 stearate (PEG 400 monosterate), polysorbate 20, polysorbate-SO, polyvinyl pyrrolidone, polyvinyl pyrrolidone-12, polyvinyl pyrrolidone-17, propylene carbonate, propylene glycol, solutol HS 15, sorbitan monooleate (Span 20), sulfobutylether-beta-cyclodextrin, transcutol, triacetin, 1-dodecylazacyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, and glycerin. Additional examples of gelling agents include acacia, alginic acid, bentonite, CARBOPOLS® (also known as carbomers), carboxymethyl cellulose, ethylcellulose, gelatin, hydroxy ethyl cellulose, hydroxypropyl cellulose, magnesium aluminum silicate, methylcellulose, poloxamers, polyvinyl alcohol, sodium alginate, tragacanth, and xanthan gum. In some embodiments, gelling agent excipients may include any of those presented in Table 1, above.

PEGs which may be used as gelling agents and/or excipients may be selected from a variety of chain lengths and molecular weights. These compounds are typically prepared through ethylene oxide polymerization. In some embodiments, PEGs may have a molecular weight of from about 300 g/mol to about 100,000 g/mol. In some embodiments, PEGs may have a molecular weight of from about 3600 g/mol to about 4400 g/mol. In some embodiments, PEGs with a molecular weight of from about 300 g/mol to about 3000 g/mol, from about 350 g/mol to about 3500 g/mol, from about 400 g/mol to about 4000 g/mol, from about 450 g/mol to about 4500 g/mol, from about 500 g/mol to about 5000 g/mol, from about 550 g/mol to about 5500 g/mol, from about 600 g/mol to about 6000 g/mol, from about 650 g/mol to about 6500 g/mol, from about 700 g/mol to about 7000 g/mol, from about 750 g/mol to about 7500 g/mol, from about 800 g/mol to about 8000 g/mol, from about 850 g/mol to about 8500 g/mol, from about 900 g/mol to about 9000 g/mol, from about 950 g/mol to about 9500 g/mol, from about 1000 g/mol to about 10000 g/mol, from about 1100 g/mol to about 12000 g/mol, from about 1200 g/mol to about 14000 g/mol, from about 1300 g/mol to about 16000 g/mol, from about 1400 g/mol to about 18000 g/mol, from about 1500 g/mol to about 20000 g/mol, from about 1600 g/mol to about 22000 g/mol, from about 1700 g/mol to about 24000 g/mol, from about 1800 g/mol to about 26000 g/mol, from about 1900 g/mol to about 28000 g/mol, from about 2000 g/mol to about 30000 g/mol, from about 2200 g/mol to about 35000 g/mol, from about 2400 g/mol to about 40000 g/mol, from about 2600 g/mol to about 45000 g/mol, from about 2800 g/mol to about 50000 g/mol, from about 3000 g/mol to about 55000 g/mol, from about 10000 g/mol to about 60000 g/mol, from about 13000 g/mol to about 65000 g/mol, from about 16000 g/mol to about 70000 g/mol, from about 19000 g/mol to about 75000 g/mol, from about 22000 g/mol to about 80000 g/mol, from about 25000 g/mol to about 85000 g/mol, from about 28000 g/mol to about 90000 g/mol, from about 31000 g/mol to about 95000 g/mol, or from about 34000 g/mol to about 100000 g/mol are utilized.

Demulcents

In some embodiments, excipients may include demulcents. As used herein, the term "demulcent" refers to a substance that relieves irritation or inflammation of the mucous membranes by forming a protective film. Demulcents may include non-polymeric demulcents and polymer demulcents. Non-limiting examples of non-polymeric demulcents include glycerin, gelatin, propylene glycol, and other non-polymeric diols and glycols. Non-limiting examples of polymer demulcents include polyvinyl alcohol (PVA), povidone or polyvinyl pyrrolidone (PVP), cellulose derivatives, polyethylene glycol (e.g., PEG 300, PEG 400), polysorbate 80, and dextran (e.g., dextran 70). Specific cellulose derivatives may include hydroxypropyl methyl cellulose, carboxymethyl cellulose, carboxymethylcellulose sodium, methyl cellulose, hydroxyethyl cellulose, hypromellose, and cationic cellulose derivatives. In some embodiments, demulcent excipients may include any of those presented in Table 1, above.

Formats

SBPs may include or be prepared to conform to a variety of formats. In some embodiments, such formats include formulations of processed silk with various excipients and/or cargo. In some embodiments, SBP formats include, but are not limited to, gels, hydrogels, drops, creams, microspheres, implants, and solutions. In some embodiments, the formats are formulated with a therapeutic agent.

Formulations

In some embodiments, SBPs may be formulations. As used herein, the term "formulation" refers to a mixture of two or more components or the process of preparing such mixtures. In some embodiments, the formulations are low cost and eco-friendly. In some embodiments, the preparation or manufacturing of formulations is low cost and eco-friendly. In some embodiments, the preparation or manufacturing of formulations is scalable. In some embodiments, SBPs are prepared by extracting silk fibroin via degumming silk yarn. In some embodiments, the yarn is medical grade. In some embodiments the yarn may be silk sutures. The extracted silk fibroin may then be dissolved in a solvent (e.g. water, aqueous solution, organic solvent). The dissolved silk fibroin may then be dried (e.g., oven dried, air dried, or freeze-dried). In some embodiments, dried silk fibroin is formed into formats described herein. In some embodiments, that format is a solution. In some embodiments, that format is a hydrogel. In some embodiments, formulations include one or more excipients, carriers, additional components, and/or therapeutic agents to generate SBPs. In some embodiments, formulations of processed silk are prepared during the manufacture of SBPs. In some embodiments, the silk is graded from 3-6, wherein the higher graded silk denotes higher quality silk. Grades of silk may vary in several properties, including, but not limited to, color, number of knots, lustrousness, and cleanliness. In some embodiments, the silk is grade 3 (grade AAA). In some embodiments, the silk is grade 4 (grade AAAA). In some embodiments, the silk is grade 5 (grade AAAAA). In some embodiments, the silk is grade 6 (grade AAAAAA). Formulations, preparations, and SBPs of the present disclosure may use silk of any grade. In some embodiments, properties of SBPs and ocular SBPs may not be affected or altered by the grade of silk (e.g. clarity, solubility, rheology, viscosity, hydrogel formation, and SEC results). In some embodiments, properties of SBPs and ocular SBPs may be affected or altered by the grade of silk (e.g. clarity, solubility, rheology, viscosity, hydrogel formation, and SEC results).

Formulation components and/or component ratios may be modulated to affect one or more SBP properties, effects, and/or applications. Variations in the concentration of silk fibroin, choice of excipient, the concentration of excipient, the osmolarity of the formulation, and the method of formulation represent non-limiting examples of differences in formulation that may alter properties, effects, and applications of SBPs. In some embodiments, the formulation of SBPs may modulate their mechanical properties. Examples of mechanical properties that may be modulated include, but are not limited to, mechanical strength, tensile strength, elongation capabilities, elasticity, compressive strength, stiffness, shear strength, toughness, torsional stability, temperature stability, moisture stability, viscosity, and reeling rate.

Cargo

In some embodiments, SBPs and SBP formulations are or include cargo. As used herein, the term "cargo" refers to any substance that is embedded in, enclosed within, attached to, or otherwise associated with a carrier. SBP formulations may be carriers for a large variety of cargo. Such cargo may include, but are not limited to, compounds, compositions, therapeutic agents, biological agents, materials, cosmetics, devices, agricultural compositions, particles, lipids, liposomes, sweeteners, colorants, preservatives, carbohydrates, small molecules, supplements, tranquilizers, ions, metals, minerals, nutrients, pesticides, herbicides, fungicides, and cosmetics.

In some embodiments, the cargo is or includes a payload. As used herein, the term "payload" refers to cargo that is delivered from a source or carrier to a target. Payloads may be released from SBP formulations, where SBP formulations serve as a carrier. Where SBPs are the payload, the SBPs may be released from a source or carrier. In some embodiments, payloads remain associated with carriers upon delivery. Payloads may be released in bulk or may be released over a period of time, also referred to herein as the "delivery period." In some embodiments, payload release is by way of controlled release. As used herein, the term "controlled release" refers to distribution of a substance from a source or carrier to a surrounding area, wherein the distribution occurs in a manner that includes or is affected by some manipulation, some property of the carrier, or some carrier activity.

In some embodiments, controlled release may include a steady rate of release of payload from carrier. In some embodiments, payload release may include an initial burst, wherein a substantial amount of payload is released during an initial release period followed by a period where less payload is released. As used herein, the term "initial burst" refers to a rate of payload release from a source or depot over an initial release period (e.g., after administration or other placement, for example in solution during experimental analysis) that is higher than rates during one or more subsequent release periods. In some embodiments, release rate slows over time. Payload release may be measured by assessing payload concentration in a surrounding area and comparing to initial payload concentration or remaining payload concentration in a carrier or source area. Payload release rate may be expressed as a quantity or mass of payload released over time (e.g., mg/min). Payload release rate may be expressed as a percentage of payload released from a source or carrier over a period of time (e.g., 5%/hour). Controlled release of a payload that extends the delivery period is referred to herein as "sustained release." Sustained release may include delivery periods that are extended over a period of hours, days, months, or years.

Some controlled release may be mediated by interactions between payload and carrier. Some controlled release is mediated by interactions between payload or carrier with surrounding areas where payload is released. With sustained payload release, payload release may be slowed or prolonged due to interactions between payload and carrier or payload and surrounding areas where payload is released. Payload release from SBPs may be controlled by SBP viscosity. Where the SBP includes processed silk gel, gel viscosity may be adjusted to modulate payload release.

In some embodiments, payload delivery periods may be from about 1 second to about 20 seconds, from about 10 seconds to about 1 minute, from about 30 seconds to about 10 minutes, from about 2 minutes to about 20 minutes, from about 5 minutes to about 30 minutes, from about 15 minutes to about 1 hour, from about 45 minutes to about 2 hours, from about 90 minutes to about 5 hours, from about 3 hours to about 20 hours, from about 10 hours to about 50 hours, from about 24 hours to about 100 hours, from about 48 hours to about 2 weeks, from about 72 hours to about 4 weeks, from about 1 week to about 3 months, from about 1 month to about 6 months, from about 3 months to about 1 year, from about 9 months to about 2 years, or more than 2 years.

In some embodiments, payload release may be consistent with near zero-order kinetics. In some embodiments, payload release may be consistent with first-order kinetics. In some embodiments, payload release may be modulated based on the density, loading, molecular weight, and/or concentration of the payload. Where the carrier is an SBP, payload release may be modulated by one or more of SBP drying method, silk fibroin molecular weight, and silk fibroin concentration.

In some embodiments. SBP formulations maintain and/or improve cargo stability, purity, and/or integrity. For example, SBP formulations may be used to protect therapeutic agents or macromolecules during lyophilization. The maintenance and/or improvement of stability during lyophilization may be determined by comparing SBP cargo stability to formulations lacking processed silk or to standard formulations in the art.

Viscosity

In some embodiments, SBPs may be formulated to modulate SBP viscosity. The viscosity of a composition (e.g., a solution, a gel or hydrogel) provided herein can be determined using a rotational viscometer or rheometer. Additional methods for determining the viscosity of a composition and other rheological properties may include any of those known in the art. In some embodiments, the SBP viscosity may be controlled via the concentration of processed silk. In some embodiments, the SBP viscosity may be controlled via the molecular weight of processed silk. In some embodiments, the SBP viscosity may be controlled via the boiling time or mb of the processed silk. In some embodiments, the SBP viscosity may be altered by the incorporation of stressed silk. In some embodiments, SBP viscosity is altered by the incorporation of an excipient. In some embodiments, SBP viscosity may be altered by the incorporation of an excipient that is a gelling agent. In some embodiments, the identity of the excipient (e.g., PEG or poloxamer) may be altered to modulate SBP viscosity. In some embodiments, the viscosity of SBPs may be tuned for the desired application (e.g., drug delivery system, surgical implant, lubricant, etc.). In some embodiments, the viscosity of SBPs is tunable between 1-1000 centipoise (cP). In some embodiments, the viscosity of an SBP is tunable from about 0.0001 to about 1000 Pascal seconds (Pa*s). In some embodiments, the viscosity of an SBP is from about 1 cP to about 10 cP, from about 2 cP to about 20 cP, from about 3 cP to about 30 cP, from about 4 cP to about 40 cP, from about 5 cP to about 50 cP, from about 6 cP to about 60 cP, from about 7 cP to about 70 cP, from about 8 cP to about 80 cP, from about 9 cP to about 90 cP, from about 10 cP to about 100 cP, from about 100 cP to about 150 cP, from about 150 cP to about 200 cP, from about 200 cP to about 250 cP, from about 250 cP to about 300 cP, from about 300 cP to about 350 cP, from about 350 cP to about 400 cP, from about 400 cP to about 450 cP, from about 450 cP to about 500 cP, from about 500 cP to about 600 cP, from about 550 cP to about 700 cP, from about 600 cP to about 800 cP, from about 650 cP to about 900 cP, or from about 700 cP to about 1000 cP. In some embodiments, the viscosity of an SBP is from about 0.0001 Pa*s to about 0.001 Pa*s, from about 0.001 Pa*s to about 0.01 Pa*s, from about 0.01 Pa*s to about 0.1 Pa*s, from about 0.1 Pa*s to about 1 Pa*s, from about 1 Pa*s to about 10 Pa*s, from about 2 Pa*s to about 20 Pa*s, from about 3 Pa*s to about 30 Pa*s, from about 4 Pa*s to about 40 Pa*s, from about 5 Pa*s to about 50 Pa*s, from about 6 Pa*s to about 60 Pa*s, from about 7 Pa*s to about 70 Pa*s, from about 8 Pa*s to about 80 Pa*s, from about 9 Pa*s to about 90 Pa*s, from about 10 Pa*s to about 100 Pa*s, from about 100 Pa*s to about 150 Pa*s, from about 150 Pa*s to about 200 Pa*s, from about 200 Pa*s to about 250 Pa*s, from about 250 Pa*s to about 300 Pa*s, from about 300 Pa*s to about 350 Pa*s, from about 350 Pa*s to about 400 Pa*s, from about 400 Pa*s to about 450 Pa*s, from about 450 Pa*s to about 500 Pa*s, from about 500 Pa*s to about 600 Pa*s, from about 550 Pas to about 700 Pa*s, from about 600 Pa*s to about 800 Pa*s, from about 650 Pa*s to about 900 Pa*s, or from about 700 Pa*s to about 1000 Pa*s.

Interfacial Viscosity

In some embodiments, silk fibroin may preferentially partition to the air-water interface when in solution. Similar to a surfactant, hydrophobic regions of hydrophobic proteins (e.g. silk fibroin) may exclude themselves from solution. The protein may migrate to the air-water boundary, resulting in an increase in the local concentration at this interface. This increase in the local concentration of a high molecular weight, hydrophobic protein may lead to an increase in local viscosity, as described in Sharma et al. (2011) Soft Matter 7(11): 5150-5160 and in Jaishankar et al. (2011) Soft Matter 7: 7623-7634, the contents of each of which are herein incorporated by reference in their entirety. This effect is termed “interfacial viscosity”. In some embodiments, processed silk may demonstrate the effects of interfacial viscosity. In some embodiments, the interfacial viscosity is independent of the concentration of processed silk. As long as there is sufficient protein in solution to create a film at the air-water interface, the viscosity of this film will increase to a similar effect.

This phenomenon may be observed with the use of a rotational rheometer fit with a cone and plate configuration. This setup allows for an air-water interface located at the edges of the cone and plate. If protein migrates and leads to local concentration build-up at the edges of the plate, increasing shear viscosity will be observed due the increased local viscosity on the torque of the rotating cone spindle. Viscosity may increase with decreasing shear rate, as the decreasing shear allows for more efficient stacking of proteins, increased protein concentration, and more stable film of protein at the air-water interface.

Incorporation of a surfactant, a molecule that can better and more efficiently associate to the air-water interface, may block the hydrophobic protein association and may negate increase in viscosity due to the protein buildup at the boundary. When a competing surfactant is added to the formulations, preventing the silk fibroin from partitioning this interface, the viscosity may be reduced; formulations may have shear viscosity properties similar to controls (without silk fibroin).

In some embodiments, the viscosity of an SBP as measured by a rotational rheometer fit with a cone and plate configuration may be the interfacial viscosity. Unlike the rotational rheometer, a capillary rheometer has a very low air-water interface. This may greatly reduce if not eliminate interfacial viscosity effects that are observed using other rheologic methods (cone and plate rotational rheology). In some embodiments, the viscosity of an SBP may be measured by a capillary rheometer to measure the viscosity without measuring the interfacial viscosity. In some embodiments, the viscosity of an SBP may be measured with a surfactant incorporated to negate the effects of interfacial viscosity.

Stress Resistance

In some embodiments, SBPs may be formulated to modulate SBP resistance to stress. Resistance to stress may be measured using one or more rheological measurements. Such measurements may include, but are not limited to tensile elasticity, shear or rigidity, volumetric elasticity, and compression. Additional rheological measurements and properties may include any of those taught in Zhang et al. (2017) Fiber and Polymers 18(10):1831-1840; McGill et al. (2017) Acta Biomaterialia 63:76-84; and Choi et al. (2015) In-Situ Gelling Polymers. Series in BioEngineering doi.

10.1007/978-981-287-152-7_2, the contents of each of which are herein incorporated by reference in their entirety. In some embodiments, stress resistance may be modulated through incorporation of excipients (e.g., PEG or poloxamer). In some embodiments, SBP stress-resistance properties may be modulated to suit a specific application (e.g., lubricant, etc.).

Concentrations and Ratios of SBP Components

SBPs may include formulations of processed silk with other components (e.g., excipients and cargo), wherein each SBP component is present at a specific concentration, ratio, or range of concentrations or ratios, depending on SBP format and/or application. In some embodiments, the concentration of processed silk (e.g. silk fibroin) or other SBP component (e.g., excipient or cargo) is present in SBPs and SBP formulations at a concentration of from about 0.0001% (w/v) to about 0.001% (w/v), from about 0.001% (w/v) to about 0.01% (w/v), from about 0.01% (w/v) to about 1% (w/v), from about 0.05% (w/v) to about 2% (w/v), from about 1% (w/v) to about 5% (w/v), from about 2% (w/v) to about 10% (w/v), from about 4% (w/v) to about 16% (w/v), from about 5% (w/v) to about 20% (w/v), from about 8% (w/v) to about 24% (w/v), from about 10% (w/v) to about 30% (w/v), from about 12% (w/v) to about 32% (w/v), from about 14% (w/v) to about 34% (w/v), from about 16% (w/v) to about 36% (w/v), from about 18% (w/v) to about 38% (w/v), from about 20% (w/v) to about 40% (w/v), from about 22% (w/v) to about 42% (w/v), from about 24% (w/v) to about 44% (w/v), from about 26% (w/v) to about 46% (w/v), from about 28% (w/v) to about 48% (w/v), from about 30% (w/v) to about 50% (w/v), from about 35% (w/v) to about 55% (w/v), from about 40% (w/v) to about 60% (w/v), from about 45% (w/v) to about 65% (w/v), from about 50% (w/v) to about 70% (w/v), from about 55% (w/v) to about 75% (w/v), from about 60% (w/v) to about 80% (w/v), from about 65% (w/v) to about 85% (w/v), from about 70% (w/v) to about 90% (w/v), from about 75% (w/v) to about 95% (w/v), from about 80% (w/v) to about 96% (w/v), from about 85% (w/v) to about 97% (w/v), from about 90% (w/v) to about 98% (w/v), from about 95% (w/v) to about 99% (w/v), from about 96% (w/v) to about 99.2% (w/v), from about 97% (w/v) to about 99.5% (w/v), from about 98% (w/v) to about 99.8% (w/v), from about 99% (w/v) to about 99.9% (w/v), or greater than 99.9% (w/v).

In some embodiments, the concentration of processed silk (e.g. silk fibroin) or other SBP component (e.g., excipient or cargo) may be present in SBPs or SBP formulations at a concentration of from about 0.0001% (v/v) to about 0.001% (v/v), from about 0.001% (v/v) to about 0.01% (v/v), from about 0.01% (v/v) to about 1% (v/v), from about 0.05% (v/v) to about 2% (v/v), from about 1% (v/v) to about 5% (v/v), from about 2% (v/v) to about 10% (v/v), from about 4% (v/v) to about 16% (v/v), from about 5% (v/v) to about 20% (v/v), from about 8% (v/v) to about 24% (v/v), from about 10% (v/v) to about 30% (v/v), from about 12% (v/v) to about 32% (v/v), from about 14% (v/v) to about 34% (v/v), from about 16% (v/v) to about 36% (v/v), from about 18% (v/v) to about 38% (v/v), from about 20% (v/v) to about 40% (v/v), from about 22% (v/v) to about 42% (v/v), from about 24% (v/v) to about 44% (v/v), from about 26% (v/v) to about 46% (v/v), from about 28% (v/v) to about 48% (v/v), from about 30% (v/v) to about 50% (v/v), from about 35% (v/v) to about 55% (v/v), from about 40% (v/v) to about 60% (v/v), from about 45% (v/v) to about 65% (v/v), from about 50% (v/v) to about 70% (v/v), from about 55% (v/v) to about 75% (v/v), from about 60% (v/v) to about 80% (v/v), from about 65% (v/v) to about 85% (v/v), from about 70% (v/v) to about 90% (v/v), from about 75% (v/v) to about 95% (v/v), from about 80% (v/v) to about 96% (v/v), from about 85% (v/v) to about 97% (v/v), from about 90% (v/v) to about 98% (v/v), from about 95% (v/v) to about 99% (v/v), from about 96% (v/v) to about 99.2% (v/v), from about 97% (v/v) to about 99.5% (v/v), from about 98% (v/v) to about 99.8% (v/v), from about 99% (v/v) to about 99.9% (v/v), or greater than 99.9% (v/v).

In some embodiments, the concentration of processed silk (e.g. silk fibroin) or other SBP component (e.g., excipient or cargo) may be present in SBPs and SBP formulations at a concentration of from about 0.0001% (w/w) to about 0.001% (w/w), from about 0.001% (w/w) to about 0.01% (w/w), from about 0.01% (w/w) to about 1% (w/w), from about 0.05% (w/w) to about 2% (w/w), from about 1% (w/w) to about 5% (w/w), from about 2% (w/w) to about 10% (w/w), from about 4% (w/w) to about 16% (w/w), from about 5% (w/w) to about 20% (w/w), from about 8% (w/w) to about 24% (w/w), from about 10% (w/w) to about 30% (w/w), from about 12% (w/w) to about 32% (w/w), from about 14% (w/w) to about 34% (w/w), from about 16% (w/w) to about 36% (w/w), from about 18% (w/w) to about 38% (w/w), from about 20% (w/w) to about 40% (w/w), from about 22% (w/w) to about 42% (w/w), from about 24% (w/w) to about 44% (w/w), from about 26% (w/w) to about 46% (w/w), from about 28% (w/w) to about 48% (w/w), from about 30% (w/w) to about 50% (w/w), from about 35% (w/w) to about 55% (w/w), from about 40% (w/w) to about 60% (w/w), from about 45% (w/w) to about 65% (w/w), from about 50% (w/w) to about 70% (w/w), from about 55% (w/w) to about 75% (w/w), from about 60% (w/w) to about 80% (w/w), from about 65% (w/w) to about 85% (w/w), from about 70% (w/w) to about 90% (w/w), from about 75% (w/w) to about 95% (w/w), from about 80% (w/w) to about 96% (w/w), from about 85% (w/w) to about 97% (w/w), from about 90% (w/w) to about 98% (w/w), from about 95% (w/w) to about 99% (w/w), from about 96% (w/w) to about 99.2% (w/w), from about 97% (w/w) to about 99.5% (w/w), from about 98% (w/w) to about 99.8% ((w/w), from about 99% (w/w) to about 99.9% (w/w), or greater than 99.9% (w/w).

In one embodiment, the concentration of processed silk or other SBP component (e.g., excipient or cargo) is present in SBPs and SBP formulations at a concentration of 1% (w/v).

In one embodiment, the concentration of processed silk or other SBP component (e.g., excipient or cargo) is present in SBPs at a concentration of 2% (w/v).

In one embodiment, the concentration of processed silk or other SBP component (e.g., excipient or cargo) is present in SBPs at a concentration of 3% (w/v).

In one embodiment, the concentration of processed silk or other SBP component (e.g., excipient or cargo) is present in SBPs at a concentration of 4% (w/v).

In one embodiment, the concentration of processed silk or other SBP component (e.g., excipient or cargo) is present in SBPs at a concentration of 5% (w/v).

In one embodiment, the concentration of processed silk or other SBP component (e.g., excipient or cargo) is present in SBPs at a concentration of 6% (w/v).

In one embodiment, the concentration of processed silk or other SBP component (e.g., excipient or cargo) is present in SBPs at a concentration of 10% (w/v).

In one embodiment, the concentration of processed silk or other SBP component (e.g., excipient or cargo) is present in SBPs at a concentration of 20% (w/v).

In one embodiment, the concentration of processed silk or other SBP component (e.g., excipient or cargo) is present in SBPs at a concentration of 30% (w/v).

In one embodiment, the concentration of processed silk or other SBP component (e.g., excipient or cargo) is present in SBPs at a concentration of 16.7% (w/w).

In one embodiment, the concentration of processed silk or other SBP component (e.g., excipient or cargo) is present in SBPs at a concentration of 20% (w/w).

In one embodiment, the concentration of processed silk or other SBP component (e.g., excipient or cargo) is present in SBPs at a concentration of 23% (w/w).

In one embodiment, the concentration of processed silk or other SBP component (e.g., excipient or cargo) is present in SBPs at a concentration of 25% (w/w).

In one embodiment, the concentration of processed silk or other SBP component (e.g., excipient or cargo) is present in SBPs at a concentration of 27.3% (w/w).

In one embodiment, the concentration of processed silk or other SBP component (e.g., excipient or cargo) is present in SBPs at a concentration of 28.6% (w/w).

In one embodiment, the concentration of processed silk or other SBP component (e.g., excipient or cargo) is present in SBPs at a concentration of 33.3% (w/w).

In one embodiment, the concentration of processed silk or other SBP component (e.g., excipient or cargo) is present in SBPs at a concentration of 40% (w/w).

In one embodiment, the concentration of processed silk or other SBP component (e.g., excipient or cargo) is present in SBPs at a concentration of 50% (w/w).

In some embodiments, the concentration of processed silk (e.g., silk fibroin) or other SBP component (e.g., excipient or cargo) may be present in SBPs and SBP formulations at a concentration of from about 0.01 pg/mL to about 1 pg/mL, from about 0.05 pg/mL to about 2 pg/mL, from about 1 pg/mL to about 5 pg/mL, from about 2 pg/mL to about 10 pg/mL, from about 4 pg/mL to about 16 pg/mL, from about 5 pg/mL to about 20 pg/mL, from about 8 pg/mL to about 24 pg/mL, from about 10 pg/mL to about 30 pg/mL, from about 12 pg/mL to about 32 pg/mL, from about 14 pg/mL to about 34 pg/mL, from about 16 pg/mL to about 36 pg/mL, from about 18 pg/mL to about 38 pg/mL, from about 20 pg/mL to about 40 pg/mL, from about 22 pg/mL to about 42 pg/mL, from about 24 pg/mL to about 44 pg/mL, from about 26 pg/mL to about 46 pg/mL, from about 28 pg/mL to about 48 pg/mL, from about 30 pg/mL to about 50 pg/mL, from about 35 pg/mL to about 55 pg/mL, from about 40 pg/mL to about 60 pg/mL, from about 45 pg/mL to about 65 pg/mL, from about 50 pg/mL to about 75 pg/mL, from about 60 pg/mL to about 240 pg/mL, from about 70 pg/mL to about 350 pg/mL, from about 80 pg/mL to about 400 pg/mL, from about 90 pg/mL to about 450 pg/mL, from about 100 pg/mL to about 500 pg/mL, from about 0.01 ng/mL to about 1 ng/mL, from about 0.05 ng/mL to about 2 ng/mL, from about 1 ng/mL to about 5 ng/mL, from about 2 ng/mL to about 10 ng/mL, from about 4 ng/mL to about 16 ng/mL, from about 5 ng/mL to about 20 ng/mL, from about 8 ng/mL to about 24 ng/mL, from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 µg/mL to about 1 µg/mL, from about 0.05 µg/mL to about 2 µg/mL, from about 1 µg/mL to about 5 µg/mL, from about 2 µg/mL to about 10 µg/mL, from about 4 µg/mL to about 16 µg/mL, from about 5 µg/mL to about 20 µg/mL, from about 8 µg/mL to about 24 µg/mL, from about 10 µg/mL to about 30 µg/mL, from about 12 µg/mL to about 32 µg/mL, from about 14 µg/mL to about 34 µg/mL, from about 16 µg/mL to about 36 µg/mL, from about 18 µg/mL to about 38 µg/mL, from about 20 µg/mL to about 40 µg/mL, from about 22 µg/mL to about 42 µg/mL, from about 24 µg/mL to about 44 µg/mL, from about 26 µg/mL to about 46 µg/mL, from about 28 µg/mL to about 48 µg/mL, from about 30 µg/mL to about 50 µg/mL, from about 35 µg/mL to about 55 µg/mL, from about 40 µg/mL to about 60 µg/mL, from about 45 µg/mL to about 65 µg/mL, from about 50 µg/mL to about 75 µg/mL, from about 60 µg/mL to about 240 µg/mL, from about 70 µg/mL to about 350 µg/mL, from about 80 µg/mL to about 400 µg/mL, from about 90 µg/mL to about 450 µg/mL, from about 100 µg/mL to about 500 µg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL, from about 0.05 g/mL to about 2 g/mL, from about 1 g/mL to about 5 g/mL, from about 2 g/mL to about 10 g/mL, from about 4 g/mL to about 16 g/mL, or from about 5 g/mL to about 20 g/mL.

In one embodiment, the concentration of processed silk (e.g., silk fibroin) or other SBP component (e.g., excipient or cargo) is present in SBPs at a concentration of 5 mg/mL.

In one embodiment, the concentration of processed silk (e.g., silk fibroin) or other SBP component (e.g., excipient or cargo) is present in SBPs at a concentration of 2.5 mg/mL.

In one embodiment, the concentration of processed silk (e.g., silk fibroin) or other SBP component (e.g., excipient or cargo) is present in SBPs at a concentration of 1.25 mg/mL.

In one embodiment, the concentration of processed silk (e.g., silk fibroin) or other SBP component (e.g., excipient or cargo) is present in SBPs at a concentration of 0.625 mg/mL.

In one embodiment, the concentration of processed silk (e.g., silk fibroin) or other SBP component (e.g., excipient or cargo) is present in SBPs at a concentration of 0.3125 mg/mL.

In some embodiments, the concentration of processed silk (e.g., silk fibroin) or other SBP component (e.g., excipient or cargo) is present in SBPs and SBP formulations at a concentration of from about 0.01 pg/kg to about 1 pg/kg, from about 0.05 pg/kg to about 2 pg/kg, from about 1 pg/kg to about 5 pg/kg, from about 2 pg/kg to about 10 pg/kg, from about 4 pg/kg to about 16 pg/kg, from about 5 pg/kg to about 20 pg/kg, from about 8 pg/kg to about 24 pg/kg, from about 10 pg/kg to about 30 pg/kg, from about 12 pg/kg to about 32 pg/kg, from about 14 pg/kg to about 34 pg/kg, from about 16 pg/kg to about 36 pg/kg, from about 18 pg/kg to about 38 pg/kg, from about 20 pg/kg to about 40 pg/kg, from about 22 pg/kg to about 42 pg/kg, from about 24 pg/kg to about 44 pg/kg, from about 26 pg/kg to about 46 pg/kg, from about 28 pg/kg to about 48 pg/kg, from about 30 pg/kg to about 50 pg/kg, from about 35 pg/kg to about 55 pg/kg, from about 40 pg/kg to about 60 pg/kg, from about 45 pg/kg to about 65 pg/kg, from about 50 pg/kg to about 75 pg/kg, from about 60 pg/kg to about 240 pg/kg, from about 70 pg/kg to about 350 pg/kg, from about 80 pg/kg to about 400 pg/kg, from about 90 pg/kg to about 450 pg/kg, from about 100 pg/kg to about 500 pg/kg, from about 0.01 ng/kg to about 1 ng/kg, from about 0.05 ng/kg to about 2 ng/kg, from about 1 ng/kg to about 5 ng/kg, from about 2 ng/kg to about 10 ng/kg, from about 4 ng/kg to about 16 ng/kg, from about 5 ng/kg to about 20 ng/kg, from about 8 ng/kg to about 24 ng/kg, from about 10 ng/kg to about 30 ng/kg, from about 12 ng/kg to about 32 ng/kg, from about 14 ng/kg to about 34 ng/kg, from about 16 ng/kg to about 36 ng/kg, from about 18 ng/kg to about 38 ng/kg, from about 20 ng/kg to about 40 ng/kg, from about 22 ng/kg to about 42 ng/kg, from about 24 ng/kg to about 44 ng/kg, from about 26 ng/kg to about 46 ng/kg, from about 28 ng/kg to about 48 ng/kg, from about 30 ng/kg to about 50 ng/kg, from about 35 ng/kg to about 55 ng/kg, from about 40 ng/kg to about 60 ng/kg, from about 45 ng/kg to about 65 ng/kg, from about 50 ng/kg to about 75 ng/kg, from about 60 ng/kg to about 240 ng/kg, from about 70 ng/kg to about 350 ng/kg, from about 80 ng/kg to about 400 ng/kg, from about 90 ng/kg to about 450 ng/kg, from about 100 ng/kg to about 500 ng/kg, from about 0.01 µg/kg to about 1 µg/kg, from about 0.05 µg/kg to about 2 µg/kg, from about 1 µg/kg to about 5 µg/kg, from about 2 µg/kg to about 10 µg/kg, from about 4 µg/kg to about 16 µg/kg, from about 5 µg/kg to about 20 µg/kg, from about 8 µg/kg to about 24 µg/kg, from about 10 µg/kg to about 30 µg/kg, from about 12 µg/kg to about 32 µg/kg, from about 14 µg/kg to about 34 µg/kg, from about 16 µg/kg to about 36 µg/kg, from about 18 µg/kg to about 38 µg/kg, from about 20 µg/kg to about 40 µg/kg, from about 22 µg/kg to about 42 µg/kg, from about 24 µg/kg to about 44 µg/kg, from about 26 µg/kg to about 46 µg/kg, from about 28 µg/kg to about 48 µg/kg, from about 30 µg/kg to about 50 µg/kg, from about 35 µg/kg to about 55 µg/kg, from about 40 µg/kg to about 60 µg/kg, from about 45 µg/kg to about 65 µg/kg, from about 50 µg/kg to about 75 µg/kg, from about 60 µg/kg to about 240 µg/kg, from about 70 µg/kg to about 350 µg/kg, from about 80 µg/kg to about 400 µg/kg, from about 90 µg/kg to about 450 µg/kg, from about 100 µg/kg to about 500 µg/kg, from about 0.01 mg/kg to about 1 mg/kg, from about 0.05 mg/kg to about 2 mg/kg, from about 1 mg/kg to about 5 mg/kg, from about 2 mg/kg to about 10 mg/kg, from about 4 mg/kg to about 16 mg/kg, from about 5 mg/kg to about 20 mg/kg, from about 8 mg/kg to about 24 mg/kg, from about 10 mg/kg to about 30 mg/kg, from about 12 mg/kg to about 32 mg/kg, from about 14 mg/kg to about 34 mg/kg, from about 16 mg/kg to about 36 mg/kg, from about 18 mg/kg to about 38 mg/kg, from about 20 mg/kg to about 40 mg/kg, from about 22 mg/kg to about 42 mg/kg, from about 24 mg/kg to about 44 mg/kg, from about 26 mg/kg to about 46 mg/kg, from about 28 mg/kg to about 48 mg/kg, from about 30 mg/kg to about 50 mg/kg, from about 35 mg/kg to about 55 mg/kg, from about 40 mg/kg to about 60 mg/kg, from about 45 mg/kg to about 65 mg/kg, from about 50 mg/kg to about 75 mg/kg, from about 60 mg/kg to about 240 mg/kg, from about 70 mg/kg to about 350 mg/kg, from about 80 mg/kg to about 400 mg/kg, from about 90 mg/kg to about 450 mg/kg, from about 100 mg/kg to about 500 mg/kg, from about 0.01 g/kg to about 1 g/kg, from about 0.05 g/kg to about 2 g/kg, from about 1 g/kg to about 5 g/kg, from about 2 g/kg to about 10 g/kg, from about 4 g/kg to about 16 g/kg, or from about 5 g/kg to about 20 g/kg, from about 10 g/kg to about 50 g/kg, from about 15 g/kg to about 100 g/kg, from about 20 g/kg to about 150 g/kg, from about 25 g/kg to about 200 g/kg, from about 30 g/kg to about 250 g/kg, from about 35 g/kg to about 300 g/kg, from about 40 g/kg to about 350 g/kg, from about 45 g/kg to about 400 g/kg, from about 50 g/kg to about 450 g/kg, from about 55 g/kg to about 500 g/kg, from about 60 g/kg to about 550 g/kg, from about 65 g/kg to about 600 g/kg, from about 70 g/kg to about 650 g/kg, from about 75 g/kg to about 700 g/kg, from about 80 g/kg to about 750 g/kg, from about 85 g/kg to about 800 g/kg, from about 90 g/kg to about 850 g/kg, from about 95 g/kg to about 900 g/kg, from about 100 g/kg to about 950 g/kg, or from about 200 g/kg to about 1000 g/kg.

Appearance: Transparent, Opaque, Translucent

In some embodiments, the appearance of SBPs described in the present disclosure may be tuned for the application for which they were designed. In some embodiments. SBPs may be transparent. In some embodiments, SBPs may be translucent. In some embodiments, SBPs may be opaque. In some embodiments, SBP preparation methods may be used to modulate clarity, as taught in International Patent Application Publication No. WO2012170655, the contents of which are herein incorporated by reference in their entirety. In some embodiments, the incorporation of excipients may be used to tune the clarity of processed silk preparations. In some embodiments, the excipient is sucrose. In some embodiments, the sucrose may also increase protein reconstitution during lyophilization. In some embodiments, sucrose may improve processed silk hydrogel clarity (optical transparency).

The optical clarity of an SBP may be measured by any method known to one of skill in the art. SBPs may be determined to be optically clear because silk materials may be naturally optically clear, as described in Lawrence et al (2009) Biomaterials 30(7): 1299-1308, the contents of which are herein incorporated by reference in their entirety. In some embodiments, the optical clarity of an SBP is measured by absorbance. As used herein, the term "absorbance" refers to a measurement of a substance's ability to take in light. Absorbance may be measured at any wavelength. In some embodiments, the absorbance of an SBP is measured from 200 nm-850 nm. The absorbance of an SBP may optionally be converted to transmittance. As used herein, the term "transmittance" refers to a measurement of the amount of light that has passed through a substance unchanged, without absorbance, reflection, or scattering. Transmittance may be determined by the ratio of the intensity of transmitted light to the ratio of the intensity of the incident light. In some embodiments, an SBP absorbs light at around 280 nm, which is the range of light absorbed for a protein. Said SBP may be otherwise determined to be optically clear. In some embodiments, the optical clarity of an SBP is measured with any of the methods described in Toytziaridis et al. (2016) International Journal of Molecular Sciences 17: 1897, the contents of which are herein incorporated by reference in their entirety.

In some embodiments, optically transparent SBPs may be used for ocular applications. e.g., treatment of ocular conditions, diseases, and/or indications.

Combinations

In some embodiments, SBP formulations are presented in a combinatorial format. A combinatorial format may consist of two or more different materials that have been combined to form a single composition. In some embodiments, two or more SBPs of different formats (e.g. rod, hydrogel etc.) are combined to form a single composition (e.g., see European Publication Number EP3212246, the contents of which are herein incorporated by reference in their entirety). In some embodiments, one or more SBP is combined with a different material (e.g. a polymer, a mat, a particle, a microsphere, a nanosphere, a metal, a scaffold, etc.) to form a single composition (e.g., see International Publication Number WO2017179069, the contents of which are herein incorporated by reference in their entirety. In some embodiments, combinatorial formats are prepared by formulating two or more SBPs of different formats as a single composition (e.g., see Kambe et al. (2017) Materials (Basel) 10(10):1153, the contents of which are herein incorporated by reference in their entirety). In some embodiments, combinatorial formats are prepared by formulating two or more SBPs of different formats, along with another material, as a single composition (e.g., see International Publication Number WO2017177281, the contents of which are herein incorporated by reference in their entirety). In some embodiments, combinatorial formats include adding one or more SBPs to a first SBP of a different format (e.g., see European Patent Number EP3212246, the contents of which are herein incorporated by reference in their entirety). In some embodiments, combinatorial formats include adding one or more SBPs to a first composition comprising a different material (e.g., see Jiang et al. (2017) J Biomater Sci Polym Ed 15:1-36, the contents of which are herein incorporated by reference in their entirety). In some embodiments, the combinatorial formats are prepared by adding one or more materials to one or more first formed SBPs (e.g., see Babu et 71. (2017) J Colloid Interface Sci 513:62-72, the contents of which are herein incorporated by reference in their entirety).

In some embodiments, SBP formulations may be administered in combination with other therapeutic agent and/or methods of treatment, e.g., with known pharmaceuticals and/or known therapeutic methods, such as, for example, those which are currently employed for treating these disorders. For example, SBP formulations used to treat cancer may be administered in combination with other anti-cancer treatments (e.g., biological, chemotherapy, or radiotherapy treatments).

Distribution

SBP components may be distributed equally or unequally, depending on format and application. Non-limiting examples of unequal distribution include component localization in SBP regions or compartments, on SBP surfaces, etc. In some embodiments, components include cargo. Such cargo may include payloads, for example, therapeutic agents. In some embodiments, therapeutic agents are present on the surface of an SBP (e.g., see Han et al. (2017) Biomacromolecules 18(11):3776-3787; Ran et al. (2017) Biomacromolecules 18(11):3788-3801, the contents of each of which are herein incorporated by reference in their entirety). In some embodiments, components (e.g., therapeutic agents) are homogenously mixed with processed silk to generate a desired distribution (e.g., see United States Publication No. US20170333351; Sun et al. (2017) Journal of Materials Chemistry B 5:8770-8779; and Du el al. (2017) Nanocale Res Lett 12(1):573, the contents of each of which are herein incorporated by reference in their entirety). In some embodiments, components (e.g., therapeutic agents) are encapsulated in SBPs (e.g., see Shi et al (2017) Nanoscale 9:14520, the contents of which are herein incorporated by reference in their entirety).

Rods

In some embodiments, SBP formulation includes rods. As used herein when referring to SBPs, the term "rod" refers to an elongated format, typically cylindrical, that may have blunted or tapered ends. Rods may be suitable for implantation or similar administration methods as it may be possible to deliver rods by injection. Rods may also be obtained simply by passing suitably viscous SBP formulations through a needle, cannula, tube, or opening. In some embodiments, rods are prepared by one or more of injection molding, heated or cooled extrusion, extrusion through a coating agent, milling with a therapeutic agent, and combining with a polymer followed by extrusion.

In some embodiments, SBP rods include processed silk (e.g., silk fibroin) rods. Some rods may include coterminous luminal cavities in whole or in part running through the rod. Rods may be of any cross-sectional shape, including, but not limited to, circular, square, oval, triangular, irregular, or combinations thereof.

In some embodiments, rods are prepared from silk fibroin preparations. The silk fibroin preparations may include lyophilized silk fibroin. The lyophilized silk fibroin may be dissolved in water to form silk fibroin solutions used in rod preparation. Silk fibroin solutions may be prepared as stock solutions to be combined with additional components prior to rod preparation. In some embodiments silk fibroin stock solutions have a silk fibroin concentration of between 10% (w/v) and 40% (w/v). In some embodiments, the silk fibroin stock solution for the preparation of silk fibroin rods has a concentration of at least 10% (w/v), at least 20% (w/v), at least 30% (w/v), at least 40% (w/v), or at least 50% (w/v).

In some embodiments, silk fibroin stock solution prepared for rod formation are mixed with one or more other components intended to be include in the final processed silk rods. Examples of such other components include, but are not limited to, excipients, salts, therapeutic agents, biological agents, proteins, small molecules, and polymers. In some embodiments, processed silk rods may include between 20 to 55% (w/w) silk fibroin. In some embodiments, processed silk rods may include between 40 to 80% (w/w) therapeutic agent. In some embodiments, processed silk rods may include 35% (w/w) silk fibroin and 65% (w/w) therapeutic agent. In some embodiments, processed silk rods may include 30% (w/w) silk fibroin and 70% (w/w) therapeutic agent. In some embodiments, processed silk rods may include 40% (w/w) silk fibroin and 60% (w/w) therapeutic agent. In some embodiments, processed silk rods may include 26% (w/w) silk fibroin and 74% (w/w) therapeutic agent. In some embodiments, processed silk rods may include 37% (w/w) silk fibroin and 63% (w/w) therapeutic agent. In some embodiments, processed silk rods may include 33% (w/w) silk fibroin and 66% (w/w) therapeutic agent. In some embodiments, processed silk rods may include 51% (w/w) silk fibroin and 49% (w/w) therapeutic agent. In some embodiments, silk fibroin may be included at a concentration (w/w) of 0.01% to about 1%, from about 0.05% to about 2%, from about 0.1% to about 30%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 96%, from about 32% to about 97%, from about 34% to about 98%, from about 36% to about 98.5%, from about 38% to about 99%, from about 40% to about 99.5%, from about 42% to about 99.6%, from about 44% to about 99.7%, from about 46% to about 99.8%, or from about 50% to about 99.9%.

In some embodiments, processed silk rods are prepared by extrusion. As used herein, the term "extrusion" refers to a process by which a substance is forced through an opening, tube, or passage. In some embodiments, processed silk rods are formed by extruding SBP formulations through a needle or cannula. SBP formulations used for rod formation may have varying levels of viscosity. Preparation viscosity may depend on the presence and/or identity of excipients present. In some embodiments, SBP formulations may include compounds or compositions intended to be embedded in rods prepared by extrusion. Excipients, compounds, or compositions included in SBP formulations used for extrusion may include, but are not limited to, salts, therapeutic agents, biological agents, proteins, small molecules, and polymers. Extrusion may be carried out manually or by an automated process.

In some embodiments, extrusion may be carried out using a syringe. The syringe may be fitted with a needle, tube, or cannula. The needle, tube, or cannula may have a sharpened end or a blunt end. The needle may have a diameter of from about 0.1 mm to about 0.3 mm, from about 0.2 mm to about 0.7 mm, from about 0.4 mm to about 1.1 mm, from about 0.6 mm to about 1.5 mm, from about 0.8 mm to about 1.9 mm, from about 1 mm to about 2.3 mm, from about 1.2 mm to about 2.7 mm, from about 1.6 mm to about 3.1 mm, or from about 2 mm to about 3.5 mm. SBP formulations may be used to fill tubes, wherein the SBP formulations are incubated in the tubes for various periods of time under various conditions (e.g., various temperatures). In some embodiments, tubing filled with processed silk preparation may be incubated at 37° C. for from about 2 hours to about 36 hours or more. In some embodiments, processed silk filled tubing is incubated for 24 hours. In some embodiments, SBP formulations remain in tubing after the 37° C. incubation. In some embodiments, SBP formulations are removed from the tubing after the incubation at 37° C. SBP formulations removed from tubing may maintain a rod-shaped format. Such preparations may be dried after removal from tubing. In some embodiments, SBP formulations may be encased in tubing while drying. Rods may be dried by one or more of freeze-drying, oven drying, and air drying. Some SBP formulations may be removed tubing after drying.

Tubing used for extrusion may be composed of various materials. In some embodiments, tubing is made from one or more of silicone, polyetheretherketone (PEEK), polytetrafluoroethylene (PTFE), amorphous fluoroplastics, fluorinated ethylene propylene, perfluoroalkoxy copolymers, ethylene-tetrafluoroethylene, polyolefins, and nylon.

In some embodiments, rods may have a diameter of from about 0.05 µm to about 10 µm, from about 1 µm to about 20 µm, from about 2 µm to about 30 µm, from about 5 µm to about 40 µm, from about 10 µm to about 50 µm, from about 20 µm to about 60 µm, from about 30 µm to about 70 µm, from about 40 µm to about 80 µm, from about 50 µm to about 90 µm, from about 0.05 mm to about 2 mm, from about 0.1 mm to about 3 mm, from about 0.2 mm to about 4 mm, from about 0.5 mm to about 5 mm, from about 1 mm to about 6 mm, from about 2 mm to about 7 mm, from about 5 mm to about 10 mm, from about 8 mm to about 16 mm, from about 10 mm to about 50 mm, from about 20 mm to about 100 mm, from about 40 mm to about 200 mm, from about 60 mm to about 300 mm, from about 80 mm to about 400 mm, from about 250 mm to about 750 mm, or from about 500 mm to about 1000 mm. In some embodiments, rods include a diameter of at least 0.5 µm, at least 1 µm, at least 10 µm, at least 100 µm, at least 500 µm, at least 1 mm, at least 10 mm, or at least 100 mm. In one embodiment, the rods have a diameter of 1 mm. In another embodiment, the rods have a diameter of 0.5 mm. In another embodiment, the rods have a diameter of 400 sm. In another embodiment, the rods have a diameter of 430 µm.

In some embodiments, the rods described herein may have a density of from about 0.01 µg/mL to about 1 µg/mL, from about 0.05 µg/mL to about 2 µg/mL, from about 1 µg/mL to about 5 µg/mL, from about 2 µg/mL to about 10 µg/mL, from about 4 µg/mL to about 16 µg/mL, from about 5 µg/mL to about 20 µg/mL, from about 8 µg/mL to about 24 µg/mL, from about 10 µg/mL to about 30 µg/mL, from about 12 µg/mL to about 32 µg/mL, from about 14 µg/mL to about 34 µg/mL, from about 16 µg/mL to about 36 µg/mL, from about 18 µg/mL to about 38 µg/mL, from about 20 µg/mL to about 40 µg/mL, from about 22 µg/mL to about 42 µg/mL, from about 24 µg/mL to about 44 µg/mL, from about 26 µg/mL to about 46 µg/mL, from about 28 µg/mL to about 48 µg/mL, from about 30 µg/mL to about 50 µg/mL, from about 35 µg/mL to about 55 µg/mL, from about 40 µg/mL to about 60 µg/mL, from about 45 µg/mL to about 65 µg/mL, from about 50 µg/mL to about 75 µg/mL, from about 60 µg/mL to about 240 µg/mL, from about 70 µg/mL to about 350 µg/mL, from about 80 µg/mL to about 400 µg/mL, from about 90 µg/mL to about 450 µg/mL, from about 100 µg/mL to about 500 µg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL, from about 0.05 g/mL to about 2 g/mL, from about 1 g/mL to about 5 g/mL, from about 2 g/mL to about 10 g/mL, from about 4 g/mL to about 16 g/mL, or from about 5 g/mL to about 20 g/mL.

Gels and Hydrogels

In some embodiments, SBP formulations include gels or hydrogels. As used herein, the term "gel" refers to a dispersion of liquid molecules in a solid medium. Gels in which the dispersed liquid molecules include water are referred to herein as "hydrogels." Gels in which the dispersed liquid molecules include an organic phase are referred to herein as "organogels." The solid medium may include polymer networks. Hydrogels may be formed with silk of any grade (e.g. grade 3, grade 4, grade 5, and/or grade 6).

In some embodiments, SBP gels or hydrogels are prepared with processed silk. In processed silk gels, polymer networks may include silk fibroin. In some embodiments, gels are prepared with one or more therapeutic agents. In some embodiments, gels include one or more excipients. The excipients may be selected from any of those described herein. In some embodiments, excipients may include salts. In some embodiments, the excipients may include gelling agents. In some embodiments, gels are prepared with one or more therapeutic agents, biological agents, proteins, small molecules, and/or polymers. In some embodiments, gels may be prepared by mixing a solution comprising processed silk with a gelling agent. The gelling agent may be in a second solution. In some embodiments, the therapeutic agent may be in solution with processed silk. In some embodiments, the therapeutic agent may be in solution with the gelling agent. In some embodiments, a stock solution of therapeutic agent may be used to dissolve processed silk for the preparation of a hydrogel. The ratio of the solution comprising processed silk to the gelling agent or solution comprising the gelling agent may be from about 5:1 to about 4.5:1, from about 4.5:1 to about 4:1, from about 4:1 to about 3.5:1, from about 3.5:1 to about 3:1, from about 3:1 to about 2.5:1, from about 2.5:1 to about 2:1, from about 2:1 to about 1.5:1, from about 1.5:1 to about 1:1, from about 1:1 to about 1:1.5, from about 1:1.5 to about 1:2, from about 1:2 to about 1:2.5, from about 1:2.5 to about 1:3, from about 1:3 to about 1:3.5, from about 1:3.5 to about 1:4, from about 1:4 to about 1:4.5, or from about 1:4.5 to about 1:5.

Gel preparation may require varying temperatures and incubation times for gel polymer networks to form. In some embodiments, SBP formulations are heated to 37° C. to prepare gels. In some embodiments, SBP formulations are incubated at 4° C. to prepare gels. In some embodiments, SBP formulations are incubated for from about 2 hours to about 36 hours or more to promote gel formation. In some embodiments, gel formation requires mixing with one or more gelling agents or excipients. Mixing may be carried out under various temperatures and lengths of time to allow gel polymer networks to form. Gel formation may require homogenous dispersion of gelling agents or excipients. In some embodiments, SBP formulations used to prepare gels include silk fibroin. Gel formation for processed silk gels may require incubation at 37° C. for up to 24 hours. Gel formation for processed silk gels may require incubation at 4° C. for up to 24 hours. Some gels may be stored for later use or processing. In some embodiments, gels are stored at 4° C.

In some embodiments, processed silk gels include one or more excipients and/or gelling agents at a concentration of from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v).

In some embodiments, processed silk gels (e.g., hydrogels or organogels) include silk fibroin at a concentration of from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v).

Silk fibroin included may be from a silk fibroin preparation with an average silk fibroin molecular weight or range of molecular weights of from about 3.5 kDa to about 10 kDa, from about 5 kDa to about 20 kDa, from about 10 kDa to about 30 kDa, from about 15 kDa to about 40 kDa, from about 20 kDa to about 50 kDa, from about 25 kDa to about 60 kDa, from about 30 kDa to about 70 kDa, from about 35 kDa to about 80 kDa, from about 40 kDa to about 90 kDa, from about 45 kDa to about 100 kDa, from about 50 kDa to about 110 kDa, from about 55 kDa to about 120 kDa, from about 60 kDa to about 130 kDa, from about 65 kDa to about 140 kDa, from about 70 kDa to about 150 kDa, from about 75 kDa to about 160 kDa, from about 80 kDa to about 170 kDa, from about 85 kDa to about 180 kDa, from about 90 kDa to about 190 kDa, from about 95 kDa to about 200 kDa, from about 100 kDa to about 210 kDa, from about 115 kDa to about 220 kDa, from about 125 kDa to about 240 kDa, from about 135 kDa to about 260 kDa, from about 145 kDa to about 280 kDa, from about 155 kDa to about 300 kDa, from about 165 kDa to about 320 kDa, from about 175 kDa to about 340 kDa, from about 185 kDa to about 360 kDa, from about 195 kDa to about 380 kDa, from about 205 kDa to about 400 kDa, from about 215 kDa to about 420 kDa, from about 225 kDa to about 440 kDa, from about 235 kDa to about 460 kDa, or from about 245 kDa to about 500 kDa.

In some embodiments, hydrogels include one or more therapeutic agents at a concentration of from about 0.0001% (w/v) to about 0.001% (w/v), from about 0.001% (w/v) to about 0.01% (w/v), from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v).

Gelling agents may be used to facilitate sol-gel transition. As used herein, the term "sol-gel transition" refers to the shift of a formulation from a solution to a gel. In some embodiments, the use of gelling agents may be carried out according to any of such methods described in International Publication No. WO2017139684, the contents of which are herein incorporated by reference in their entirety. Gelling agents may be water-soluble, waxy solids. In some embodiments, gelling agents may be water-soluble and hygroscopic in nature. In some embodiments, gelling agents may include polar molecules. Gelling agents may have net positive, net negative, or net neutral charges at a physiological pH (e.g., pH of about 7.4). Some gelling agents may be amphipathic. Additional examples of gelling agents include oils (e.g., castor, corn oil, cottonseed oil, olive oil, peanut oil, peppermint oil, safflower oil, sesame oil, soybean oil, hydrogenated vegetable oil, hydrogenated soybean oil, and medium-chain triglycerides of coconut oil and/or palm seed oil), emulsifiers [e.g., polyoxyl 40 stearate (PEG 1750 monosterate), polyoxyl 8 stearate (PEG 400 monosterate), polysorbate 20, polysorbate 80, polysorbate-SO, or poloxamer], surfactants (e.g., polysorbate, poloxamer, sodium dodecyl sulfate. Triton X100, or tyloxapol), and suspending agents (e.g., polyvinyl pyrrolidone, polyvinyl pyrrolidone-12, polyvinyl pyrrolidone-17, hydroxyethyl cellulose, or carboxymethyl cellulose). Any gelling agent listed in Table 1 may be used.

In some embodiments, gel formation is induced by applying one or more of the following to processed silk preparations: ultrasound, sonication, shear forces, temperature change (e.g., heating), addition of precipitants, modulation of pH, changes in salt concentration, chemical cross-linking, chemical modification, seeding with preformed hydrogels, increasing silk fibroin concentration, modulating osmolarity, use of electric fields, or exposure to electric currents. In some embodiments, methods of inducing gel formation may include, but are not limited to any of those described in International Patent Application Publication No. WO2005012606 or United States Patent Publication No. US2011/0171239, the contents of each of which are herein incorporated by reference in their entirety.

In some embodiments, processed silk gel preparation may be carried with the aid of sonication. As used herein, the term "sonication" refers to a process of agitation using sound energy. Sonication conducted at frequencies greater than 20 kHz is referred to as ultrasonication. Sonication may aid in gel formation by dispersing and/or agitating polymer components within a solution to foster an arrangement that favors polymer network formation. The polymer network may include silk fibroin. In some embodiments, the use of sonication for gel preparation may be carried out according to any of the methods described in Zhao el al. (2017) Materials Letters 211:110-113 or Mao et al. (2017) Colloids Surf B Biointerfaces 160:704-714), the contents of each of which are herein incorporated by reference in their entirety.

In some embodiments, processed silk gel formation may be carried out using shear forces. As used herein, the term "shear forces" refers to unaligned forces that apply pressure to two or more different parts of an object or medium from different and/or opposing directions. Shear forces are distinct from compression forces, which are directed toward each other. Shear forces may be applied during processed silk gel preparation using a syringe, tubing, needle, or other apparatus capable of increasing shear forces. Processed silk preparation may be pushed through a syringe, tubing, needle, or other apparatus to generate shear forces. The use of shear forces in gel formation may include any of those described in United States Patent Publication No. US2011/0171239, the contents of which are herein incorporated by reference in their entirety.

In some embodiments, changes in temperature may be used to aid in processed silk gel formation. Changes in temperature may be used to disperse or align polymer components in an arrangement that promotes gel polymer network formation. The polymer components may include silk fibroin. In some embodiments, gel formation may be carried out by raising or lowering the temperature of a processed silk preparation to from about 0° C. to about 5° C., from about 2° C. to about 6° C., from about 4° C. to about 12° C., from about 8° C. to about 16° C., from about 10° C. to about 26° C., from about 15° C. to about 28° C., from about 20° C. to about 32° C., from about 25° C. to about 34° C., from about 30° C. to about 45° C., from about 35° C. to about 55° C., from about 37° C. to about 65° C., from about 40° C. to about 75° C., from about 50° C. to about 100° C., from about 60° C. to about 120° C., from about 70° C. to about 140° C., from about 80° C. to about 160° C., or from about 100° C. to about 300° C. In some embodiments, one or more excipients or gelling agents may be included to lower the temperature necessary for gel formation to occur. Such embodiments may be employed to protect temperature-sensitive components embedded within gels. In some embodiments, gel formation is carried out at 4° C. Glycerol, polyethylene glycol (PEG), and/or polymers of PEG (e.g., PEG400) may be included in SBP formulations as excipients to lower the temperature necessary to form a gel. The gel may be a silk fibroin gel. Excipient concentration may be about 30% (w/v). Silk fibroin concentration may be from about 2% to about 30%.

In some embodiments, gel formation is carried out by applying an electric current, also referred to as "electrogelation." Electrogelation may be carried out according to any of the methods presented in International Publication No. WO2010036992, the contents of which are herein incorporated by reference in their entirety. In some embodiments, a reverse voltage may be applied to reverse gel formation and regenerate a processed silk solution.

In some embodiments, gel formation is carried out by modulating the pH of processed silk preparations. Gel formation through pH modulation may be carried out according to the methods described in International Patent Application Publication No. WO2005012606, United States Patent Publication No. US2011/0171239, and Dubey et a (2017) Materials Chemistry and Physics 203:9-16, the contents of each of which are herein incorporated by reference in their entirety.

In some embodiments, gel formation is carried out in association with modulating the osmolarity of a processed silk preparation. As used herein, the term "osmolarity" or "osmotic concentration" refers to the number of osmoles of solute in solution on a per liter basis (Osm/L). Unlike molarity, which is a measure of the number of moles solute per liter of solvent (M), osmolarity factors in the effect of ions on osmotic pressure. For example, a 1 M solution of NaCl would have an osmolarity of 2 Osm/L while a 1 M solution of $MgCl_2$ would have an osmolarity of 3 Osm/L. Hypo- or hyper-osmotic formulations can lead to local tissue damage and reduced biocompatibility. In some embodiments, the osmolarity of processed silk gels is modulated by controlling the type, molecular weight, and/or concentration of excipients included. Osmolarity may be modulated by varying the concentration and/or molecular weight of salts used in processed silk preparations. In some embodiments, osmolarity is reduced by using lower molecular weight gelling agents. For example, 4 kDa PEG may be used in place of PEG400. The use of Poloxamer-188 at 10% (w/v) may reduce osmolarity in comparison to lower molecular weight species such as glycerol. In some embodiments, sodium chloride may be added to increase osmolarity. In some embodiments, osmolarity is adjusted to fall between 280 and 320 mOsm/L.

In some embodiments, gel formation is carried out through seeding. As used herein when referring to gel formation, "seeding" refers to a process of inducing gel formation using a small amount of pre-formed gel. Seeding may promote gel formation by encouraging polymer network formation to build off of the pre-formed gel introduced. In some embodiments the gel includes silk fibroin. Seeding with a pre-formed silk fibroin hydrogel may be used to promote transition of a silk fibroin solution into a silk fibroin gel. In some embodiments, seeding reduces the need for gelling agents and/or excipients to form gels.

In some embodiments, gel formation is carried out using chemical cross-linking. As used herein, the term "chemical cross-linking" refers to a process of forming covalent bonds between chemical groups from different molecules or between chemical groups present on different parts of the same molecule. In some embodiments, chemical cross-linking may be carried out by contacting SBP formulations with ethanol. Such methods may be carried out according to those described in Shi el al. (2017) Advanced Material 29(29):1701089, the contents of which are herein incorporated by reference in their entirety. In some embodiments, cross-linking may be carried out using enzymes. Methods of enzyme cross-linking using horse radish peroxidase may include any of those described in McGill et al. (2017) Acta Biomaterialia 63:76-84 or Guo et al. (2017) Biomaterials 145:44-55, the contents of each of which are herein incorporated by reference in their entirety. In some embodiments, chemical cross-linking may be photo-initiated, as disclosed in International Publication No. WO2017123383 and in Zhang el al. (2017) Fibers and Polymers 18(10):1831-1840, the contents of each of which are herein incorporated by reference in their entirety.

In some embodiments, other chemical modifications may be used during processed silk gel preparation. Some chemical modifications may be used to induce silk fibroin β-sheet conformations. In some embodiments, this process involves contact with a chemical. Chemicals may include, but are not limited to, ethanol. In some embodiments, silk fibroin may be chemically crosslinked with other materials during gel preparation. Such materials may include other peptides (e.g., see Guo et al. (2017) Biomaterials 145:44-55, the contents of which are herein incorporated by reference in their entirety). In some embodiments, processed silk gels are prepared by formation of internal chemical cross-links. These crosslinks may be dityrosine crosslinks (e.g., see International Patent Application Publication No. WO2017123383, the contents of which are herein incorporated by reference in their entirety). In some embodiments, photosensitive materials may be used to promote chemical modifications. Such materials may include riboflavin (e.g., see International Publication No. WO2017123383). In some embodiments, processed silk gels may be functionalized with particles. These particles may be microspheres and/or nanospheres (e.g., see Ciocci et al. (2017) Int J Biol Macromol S0141-8130(17):32839-8, the contents of which are herein incorporated by reference in their entirety).

In some embodiments, the SBPs are prepared as hydrogels. In some embodiments, the hydrogels have a concentration between about 3% (w/v) to about 15% (w/v) silk fibroin. In some embodiments the silk fibroin has a boiling time of 90 mb, 120 mb, or 480 mb. In some embodiments, the hydrogels are prepared from silk fibroin lyophilized in phosphate buffer. In some embodiments, the hydrogels have trace amounts of phosphate salts (e.g. potassium phosphate dibasic and potassium phosphate monobasic). In some embodiments, the hydrogels comprise between about 10% (w/v) to about 50% (w/v) excipient. In some embodiments, the excipient is poloxamer-188 (P188), in some embodiments, the excipient is glycerol. In some embodiments, the excipient is PEG 4000 (PEG 4 kDa) and the formulation may optionally include hydrochloric acid. In some embodiments, the excipient is PEG400 and the formulation may optionally include hydrochloric acid. In some embodiments, the hydrogels comprise 15 mM hydrochloric acid. In some embodiments, the formulations are as described in Table 2. In the sample named 90 mb; hyd; 5% SFf; 10% P188f, "90 mb" refers to silk degummed with a 90-minute boil, "hyd" refers to the formulation of the sample as a hydrogel, "5% SFf" refers to a formulation with 5% (w/v) silk fibroin, and "40% Glycf" refers to a formulation with 40% (w/v) glycerol.

TABLE 2

Hydrogel formulations

| Sample | Boil Time (mb) | [Silk] (%) | Excipient | [Excipient] (%) | Sample Name |
|---|---|---|---|---|---|
| 1 | 90 | 5 | P188 | 10 | 90mb; hyd; 10%st; 5%SFf; 10%P188f |
| 2 | 90 | 5 | PEG 4kDa | 40 | 90mb; hyd; 10%st; 5%SFf; 40%PEG4kf |
| 3 | 90 | 5 | Glycerol | 40 | 90mb; hyd; 10%st; 5%SFf; 40%Glycf |
| 4 | 90 | 10 | P188 | 10 | 90mb; hyd; 20%st; 10%SFf; 10%P188f |
| 5 | 90 | 10 | PEG 4kDa | 40 | 90mb; hyd; 20%st; 10%SFf; 40%PEG4kf |
| 6 | 90 | 10 | Glycerol | 40 | 90mb; hyd; 20%st; 10%SFf; 40%Glycf |
| 7 | 480 | 5 | P188 | 10 | 480mb; hyd; 10%st; 5%SFf; 10%P188f |
| 8 | 480 | 5 | PEG 4kDa | 40 | 480mb; hyd; 10%st; 5%SFf; 40%PEG4kf |
| 9 | 480 | 5 | Glycerol | 40 | 480mb; hyd; 10%st; 5%SFf; 40%Glycf |
| 10 | 480 | 10 | P188 | 10 | 480mb; hyd; 120%st; 0%SFf; 10%P188f |
| 11 | 480 | 10 | PEG 4kDa | 40 | 480mb; hyd; 20%st; 10%SFf; 40%PEG4kf |
| 12 | 480 | 10 | Glycerol | 40 | 480mb; hyd; 20%st; 10%SFf; 40%Glycf |
| 13 | 480 | 15 | P188 | 10 | 480mb; hyd; 30%st; 15%SFf; 10%P188f |
| 14 | 480 | 15 | PEG 4kDa | 40 | 480mb; hyd; 30%st; 15%SFf; 40%PEG4kf |
| 15 | 480 | 15 | Glycerol | 40 | 480mb; hyd; 30%st; 15%SFf; 40%Glycf |

In some embodiments, SBP gels or hydrogels have sufficient internal strength to maintain themselves as a cohesive matrix without the need for mechanical reinforcement. The cohesive property of SBP gels or hydrogels may be tuned according to their intended applications. As a non-limiting example, SBP gels or hydrogels may be capable of tolerating physiological concentrations of ionized salt without breakdown of the gel.

Solutions

In some embodiments, SBPs, SBP formulations are or include solutions. As used herein, the term "solution" refers to a dispersion of molecules or solute in a liquid medium or solvent. In some embodiments, the solute is a processed silk or an SBP. In some embodiments, the solvent is water. In some embodiments, the solvent is an aqueous buffer. Non-limiting examples of buffer include citrate buffer, phosphate buffer, phosphate buffer saline, borate buffer, sodium borate, glycine-HCl, sodium acetate, citrate buffered saline, Tris buffer, HEPES buffer, MOPS buffer, and cacodylate buffer. In some embodiments, SBP formulations may be prepared as a solution, as taught in International Patent Application Publication No. WO2005012606 and Cheng et al. (2015) J. App. Polym. Sci. 132(22): 41959. In some embodiments, an SBP is prepared as a solution using any of the methods described herein. In some embodiments, the solution is prepared by dissolving processed silk in water or buffer. In some embodiments the solution is mixed to facilitate dissolution. In some embodiments, the solution is heated to facilitate dissolution. In some embodiments, solutions are prepared with one or more therapeutic agents. In some embodiments, solutions include one or more excipients. The excipients may be selected from any of those described herein. In some embodiments, excipients may include salts. In some embodiments, the excipients may be any of those described in Table 1. In some embodiments, solutions are prepared with one or more therapeutic agents, biological agents, proteins, small molecules, and/or polymers. In some embodiments, a stock solution of the therapeutic agent may be used to dissolve processed silk in the preparation of a solution. In some embodiments, a stock solution of the therapeutic agent may be mixed with a stock solution of processed silk to prepare the SBP. In some embodiments, a solution may be diluted to obtain additional solutions with processed silk at varying concentrations.

In some embodiments, processed silk solutions include one or more excipients at a concentration of from about 0.0001% (w/v) to about 0.001% (w/v), from about 0.001% (w/v) to about 0.01% (w/v), from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v).

In some embodiments, processed silk solutions include silk fibroin at a concentration of 0.0001% (w/v) to about 0.001% (w/v), from about 0.001% (w/v) to about 0.01% (w/v), from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v). Silk fibroin included may be from a silk fibroin preparation with an average silk fibroin molecular weight or range of molecular weights of from about 3.5 kDa to about 10 kDa, from about 5 kDa to about 20 kDa, from about 10 kDa to about 30 kDa, from about 15 kDa to about 40 kDa, from about 20 kDa to about 50 kDa, from about 25 kDa to about 60 kDa, from about 30 kDa to about 70 kDa, from about 35 kDa to about 80 kDa, from about 40 kDa to about 90 kDa, from about 45 kDa to about 100 kDa, from about 50 kDa to about 110 kDa, from about 55 kDa to about 120 kDa, from about 60 kDa to about 130 kDa, from about 65 kDa to about 140 kDa, from about 70 kDa to about 150 kDa, from about 75 kDa to about 160 kDa, from about 80 kDa to about 170 kDa, from about 85 kDa to about 180 kDa, from about 90 kDa to about 190 kDa from about 95 kDa to about 200 kDa, from about 100 kDa to about 210 kDa, from about 115 kDa to about 220 kDa, from about 125 kDa to about 240 kDa, from about 135 kDa to about 260 kDa, from about 145 kDa to about 280 kDa, from about 155 kDa to about 300 kDa, from about 165 kDa to about 320 kDa, from about 175 kDa to about 340 kDa, from about 185 kDa to about 360 kDa, from about 195 kDa to about 380 kDa, from about 205 kDa to about 400 kDa, from about 215 kDa to about 420 kDa, from about 225 kDa to about 440 kDa, from about 235 kDa to about 460 kDa, or from about 245 kDa to about 500 kDa.

In some embodiments, processed silk solutions include one or more therapeutic agents at a concentration of from about 0.0001% (w/v) to about 0.001% (w/v), from about 0.001% (w/v) to about 0.01% (w/v), from about 0.01% (w/v) to about 0.1% (w/v), from about 0.1% (w/v) to about 1% (w/v), from about 0.5% (w/v) to about 5% (w/v), from about 1% (w/v) to about 10% (w/v), from about 5% (w/v) to about 15% (w/v), from about 10% (w/v) to about 30% (w/v), from about 15% (w/v) to about 45% (w/v), from about 20% (w/v) to about 55% (w/v), from about 25% (w/v) to about 65% (w/v), from about 30% (w/v) to about 70% (w/v), from about 35% (w/v) to about 75% (w/v), from about 40% (w/v) to about 80% (w/v), from about 50% (w/v) to about 85% (w/v), from about 60% (w/v) to about 90% (w/v), from about 75% (w/v) to about 95% (w/v), from about 90% (w/v) to about 96% (w/v), from about 92% (w/v) to about 98% (w/v), from about 95% (w/v) to about 99% (w/v), from about 98% (w/v) to about 99.5% (w/v), or from about 99% (w/v) to about 99.9% (w/v). In some embodiments, the solutions have a concentration between about 0.25% (w/v) to about 2% (w/v) silk fibroin. In some embodiments the silk fibroin has a boiling time of 90 mb, 120 mb, or 480 mb. In some embodiments, the solutions are prepared from silk fibroin lyophilized in phosphate buffer. In some embodiments, the solutions have trace amounts of phosphate salts (e.g. potassium phosphate dibasic and potassium phosphate monobasic). In some embodiments, the solutions are formulated with one or more therapeutic agents. In some embodiments, one or more therapeutic agents may be a biological agent. In some embodiments, the biological agent is a protein.

In some embodiments, the solutions have a concentration between about 0.25% (w/v) to about 2% (w/v) silk fibroin. In some embodiments the silk fibroin has a boiling time of 90 mb, 120 mb, or 480 mb. In some embodiments, the solutions are prepared from silk fibroin lyophilized in phosphate buffer. In some embodiments, the solutions have trace amounts of phosphate salts (e.g. potassium phosphate dibasic and potassium phosphate monobasic). In some embodiments, the solutions are formulated with one or more therapeutic agents. In some embodiments, one or more therapeutic agents may be a biological agent. In some embodiments, the biological agent is a protein.

In some embodiments, silk fibroin may be prepared as a stock solution.

In one embodiment, the silk fibroin stock solution has a concentration of 10% (w/v).

In one embodiment, the silk fibroin stock solution has a concentration of 20% (w/v).

In one embodiment, the silk fibroin stock solution has a concentration of 30% (w/v).

In one embodiment, the silk fibroin stock solution has a concentration of 40% (w/v).

In one embodiment, the silk fibroin stock solution has a concentration of 50% (w/v).

In some embodiments, processed silk formulations may be prepared as solutions. In these solutions, the processed silk may be silk fibroin. Silk fibroin may be degummed with any minute boil (mb) described herein, including, but not limited to, 15, 30, 60, 90, 120 and 480 mb. These solutions may be prepared in water. These solutions may also be prepared with any buffer or excipient described herein, including, but not limited to, phosphate buffer (PB), borate buffer (DED), and propylene glycol (PG). Buffers and excipients may be present at any concentration described herein (e.g. 10 mM PB). Phosphate buffer may be prepared as 10 mM PB. Borate buffer (DED) may be prepared as 6 mg/mL boric acid, 0.45 mg/mL sodium borate, 3.4 mg/mL sodium chloride, 1.4 mg/mL potassium chloride, 0.06 mg/mL magnesium chloride, and 0.06 mg/mL calcium chloride, pH 7.3. In some embodiments, the solutions may comprise 1% PG. In some embodiments, the solution has a pH between 7.0 and 8.0. In some embodiments, the solution has a pH of 7.3. In some embodiments, the solution has a pH of 7.4. In some embodiments, these solutions may comprise silk fibroin at a concentration of from about 0.01% to about 30% (w/v). In some embodiments, these solutions may comprise silk fibroin at a concentration of from about 0.01% to about 0.1%, about 0.1% to about 1%, about 1% to about 2%, about 2% to about 3%, about 3% to about 4%, about 4% to about 5%, about 5% to about 10%, about 10% to about 15%, about 15% to about 20%, or about 20% to about 30% (w/v) silk fibroin.

In some embodiments, the solution comprises 1% (w/v) silk fibroin.

In some embodiments, the solution comprises 2% (w/v) silk fibroin.

In some embodiments, the solution comprises 3% (w/v) silk fibroin.

In some embodiments, the solution comprises 1% (w/v) silk fibroin and 1% (w/v) PG.

In some embodiments, the solutions may be any of those described in Table 3.

TABLE 3

Solution formulations

| Sample No. | Description | Silk % | Buffer |
| --- | --- | --- | --- |
| 82-1 | 3% Water, Baseline | 3 | Water |
| 82-2 | 3% PB, Baseline | 3 | 10 mMPB |
| 82-3 | 3% DED Baseline | 3 | DED |
| 82-4 | 1% PBS, Baseline | 1 | PBS |
| 82-5 | 1% DED, Baseline | 1 | DED |
| 82-6 | 1% PBS + PG, Baseline | 1 | PBS + 1% PG |
| 82-7 | 1% DED + PG, Baseline | 1 | DED + 1% PG |
| 83-1 | 0.5% SF in 10 mM phosphate, pH 7.4 | 5 | 10 mMPB |
| 83-2 | 1% SF in 10 mM phosphate, pH 7.4 | 10 | 10 mMPB |
| 83-3 | 2.5% SF in 10 mM phosphate, pH 7.4 | 25 | 10 mM PB |
| 83-4 | 5% SF in 10 mM phosphate, pH 7.4 | 50 | 10 mMPB |

TABLE 3-continued

Solution formulations

| Sample No. | Description | Silk % | Buffer |
| --- | --- | --- | --- |
| 83-5 | 5% SF, 10 mM sucrose in 10 mM phosphate, pH 7.4 | 50 | 10 mM PB + 10 mM sucrose |
| 83-6 | 5% SF, 50 mM sucrose in 10 mM phosphate, pH 7.4 | 50 | 10 mMPB + 50 mM sucrose |
| 83-7 | 5% SF, 100 mM sucrose in 10 mM phosphate, pH 7.4 | 50 | 10 mMPB + 100 mM sucrose |
| 83-8 | 5% SF, 150 mM sucrose in 10 mM phosphate, pH 7.4 | 50 | 10 mMPB + 150 mM sucrose |
| 83-9 | 5% SF, 10 mM trehalose in 10 mM phosphate, pH 7.4 | 50 | 10 mMPB + 10 mM trehalose |
| 83-10 | 5% SF, 50 mM trehalose in 10 mM phosphate, pH 7.4 | 50 | 10 mM PB + 50 mM trehalose |
| 83-11 | 5% SF, 100 mM trehalose in 10 mM phosphate, pH 7.4 | 50 | 10 mMPB + 100 mM trehalose |
| 83-12 | 5% SF, 150 mM trehalose in 10 mM phosphate, pH 7.4 | 50 | 10 mMPB + 150 mM trehalose |

Particles

In some embodiments, SBP formulation include SBP particles. As used herein, the term "particle" refers to a minute portion of a substance. SBP particles may include particles of processed silk. Processed silk particles may include silk fibroin particles. Silk fibroin particles may be tiny clusters of silk fibroin or they may be arranged as more ordered structures. Particles may vary in size. Processed silk particles may be visible or may be too tiny to view easily with the naked eye. Particles with a width of from about 0.1 μm to about 100 μm are referred to herein as "microparticles." Particles with a width of about 100 nm or less are referred to herein as "nanoparticles." Microparticles and nanoparticles that are spherical in shape are termed microspheres and nanospheres respectively. Processed silk particle preparations may include particles with uniform width or with ranges of widths. In some embodiments, processed silk particle preparations include average particle widths of or ranges of particle widths of from about 10 nm to about 25 nm, from about 20 nm to about 50 nm, from about 30 nm to about 75 nm, from about 40 nm to about 80 nm, from about 50 nm to about 100 nm, from about 0.05 μm to about 10 μm, from about 1 μm to about 20 μm, from about 2 μm to about 30 μm, from about 5 μm to about 40 μm, from about 10 μm to about 50 μm, from about 20 μm to about 60 μm, from about 30 μm to about 70 μm, from about 40 μm to about 80 μm, from about 50 μm to about 90 μm, from about 0.05 mm to about 2 mm, from about 0.1 mm to about 3 mm, from about 0.2 mm to about 4 mm, from about 0.5 mm to about 5 mm, from about 1 mm to about 6 mm, from about 2 mm to about 7 mm, from about 5 mm to about 10 mm, from about 10 nm to about 100 μm, from about 10 μm to about 10 mm, from about 50 nm to about 500 μm, from about 50 μm to about 5 mm, from about 100 nm to about 10 mm, or from about 1 μm to about 10 mm. In some embodiments, processed silk particle preparations include average particle widths of at least 10 nm, at least 100 nm, at least 0.5 μm, at least 1 μm, at least 10 μm, at least 100 μm, at least 500 μm, at least 1 mm, or at least 10 mm.

Processed silk particles may be formed through spraying of a processed silk preparation. In some embodiments, electrospraying is used. Electrospraying may be carried out using a coaxial electrospray apparatus (e.g., see Cao et al. (2017) Scientific Reports 7:11913, the contents of which are herein incorporated by reference in their entirety). In some embodiments, silk fibroin microspheres or nanospheres may be obtained by electrospraying a silk fibroin preparation into a collector and flash freezing the sprayed particles (e.g., see United States Publication No. US2017/0333351, the contents of which are herein incorporated by reference in their entirety). The flash frozen silk fibroin particles may then be lyophilized. In some embodiments, processed silk particles may be prepared using centrifugal washing, followed by lyophilization, as taught in United States Publication No. US2017/0340575, the contents of which are herein incorporated by reference in their entirety. In some embodiments, processed silk microspheres may be formed through the use of a microfluidic device (e.g., see Sun et al. (2017) Journal of Materials Chemistry B 5:8770-8779, the contents of which are herein incorporated by reference in their entirety). In some embodiments, microspheres are formed via coagulation in a methanol bath, as taught in European Patent No. EP3242967, the contents of which are herein incorporated by reference in their entirety.

Devices

In some embodiments, SBP formulations may be included as or in device components. As used herein, the term "device" refers to any article constructed or modified to suit a particular purpose. Devices may be designed for a variety of purposes, including, but not limited to, therapeutic applications, material science applications, and agricultural applications. In some embodiments, SBPs are embedded or incorporated into devices. Some devices include SBPs as coatings or lubricants. In some embodiments, devices include implants, patches, mesh, sponges, grafts, insulators, pipes, prosthetics, resistors, bedding, blankets, liners, ropes, plugs, fillers, electronic devices, mechanical devices, medical devices, surgical devices, veterinary devices, and agricultural devices. Additional devices are described herein.

In some embodiments, SBPs may be or may be included in therapeutic devices. In some embodiments, therapeutic devices may be coated with SBPs described herein. Some therapeutic devices may include therapeutic agents. In some embodiments, the use of SBPs within therapeutic devices may enable the delivery of therapeutic agents via such therapeutic devices. Some therapeutic devices may include synthetic materials. In some embodiments, therapeutic devices include, but are not limited to, artificial blood vessels, artificial organ, bandage, cartilage replacement, filler, hemostatic sponge, implant, silk contact lens, contact lens solution, stem cell, surgical mesh, surgical suture, tissue replacement, vascular patch, wound dressing, antenna, applier, assembly, balloon, barrier, biosensor, biotransducer, cable assembly, caliper, capacitor, carrier, clamp, connector, corneal implant, coronary stent, cryotome, degradable device, delivery device, dermatome, detector, diagnostic device, dilator, diode, discharge device, display technology, distractor, drill bit, electronic device, graft, grasper, harmonic scalpel, hemostatic device, imaging apparatus, implant, implant for continuous drug delivery, integrated circuit, intraocular lens, lancet, LIGASURE™, liner, magnetic or inductive device, magnetic resonance imaging apparatus, mechanical assembly, medical device, memristor, module, needle, nerve stimulator, network, neurostimulator, occluder, optoelectronic device, pacemaker, patch, pen, piezoelectric device, pin, pipe, plate, positioner, power source, probe, prosthesis, prosthetic, protection device, removable device, resistor, retractor, rod, rongeur, rope, ruler, scalpel, scope, screw, semiconductor, sensor, solution, specula, stent, stent, sterotactic device, suction tip, suction tube, surgical device, surgical mesh, surgical scissor, surgical staple, suture, switch, temperature sensor, terminal, tie, tip, transducer, transistor, tube, ultrasound tissue disruptor, vacuum tube, vacuum valve, ventilation system, water balloon, wire, bleb, gel, gel that hardens after implantation, implant, lacrimal plug, lens, plug, punctal plug, rod, slurry, slurry that hardens after implantation, and solids.

Solid Implants

In some embodiments, SBP formulations may be included as or in solid implants. SBP solid implants may be prepared by gelation of processed silk followed by drying and/or injection molding. Methods of drying may include any of those described herein, such as heat, air drying or lyophilization. The drying process may induce beta-sheet formation. Density of the SBP formulation is properly controlled during this process. SBP formulations may also be formatted as a film that is applied to the exterior of a solid implant. Alternatively, SBP formulations may be included into solid implants by spray-drying, spray-coating, and/or milling.

Solid implants prepared with SBP formulations may be of any size and shape. As a non-limiting example, solid implants may be shaped as forceps, speculum, bands, stoppers, screws, tubes, rods, cones, cylinders, teardrops, etc. Solid implants prepared with SBP formulations may be prepared via aqueous processing. The pH of solid implants prepared with SBP formulations may be controlled during preparation and degradation. Solid implants prepared with SBP formulations may comprise a hydrophobic matrix. Solid implants prepared with SBP formulations prepared with high loading of active pharmaceutical ingredient (e.g. at least 50% (w/w)). Delivery of the active pharmaceutical ingredient may be sustained (e.g. for weeks to months). Solid implants prepared with SBP formulations may be biocompatible and/or biodegradable.

Controlled Release

In some embodiments, SBP formulations and related methods described herein be may be used for controlled release of therapeutic agents. As used herein, the term "controlled release" refers to regulated movement of factors from specific locations to surrounding areas. In some embodiments, the specific location is a depot. Controlled release of factors from depots may be regulated by interactions between therapeutic agents and depot components. Such interactions may, for example, modulate therapeutic agent diffusion rate and/or affect therapeutic agent stability and/or degradation. In some embodiments, the depot is an SBP formulation. In some embodiments, factors subject to controlled release from depots are SBP formulations. In some embodiments, therapeutic agents are subject to controlled release from SBP depots.

In some embodiments, SBP formulations may control payload release by extending payload half-life. As used herein, the term "half-life" refers to the length of time necessary for levels of a factor to be reduced (e.g., through clearance or degradation) by 50%. In some embodiments, SBP depots may be used for therapeutic agents, wherein release is facilitated by diffusion. In some embodiments, SBP formulations may be lyophilized together with therapeutic agents. In some embodiments, combined lyophilization may induce further interactions between therapeutic agents and SBP formulations. These interactions may be maintained through SBP preparation and support extended payload release. Payload release may be dependent on SBP degradation and/or dissolution. In some embodiments, SBP β-sheet content is increased (e.g., via water annealing), thereby increasing SBP insolubility in water. Such SBPs may exhibit increased payload release periods. In some embodiments, these SBP formulations may include therapeutic agent stabilizing properties to extend administration periods and/or therapeutic agent half-life.

In some embodiments, methods of increasing payload half-life using SBPs may include any of those described in United States Patent Publication US20100028451, the contents of which are herein incorporated by reference in their entirety. Methods of improving payload half-life may be carried out in vitro or in vivo. In some embodiments, SBP-based methods of improving payload half-life may enable therapeutic indication treatment with fewer doses and/or treatments. Such methods may include any of those described in International Patent Application Publication No. WO2017139684, the contents of which are herein incorporated by reference in their entirety. In some embodiments, payload half-life may be extended by from about 0.01% to about 1%, from about 0.05% to about 2%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 100%, from about 32% to about 105%, from about 34% to about 110%, from about 36% to about 115% from about 38% to about 120%, from about 40% to about 125%, from about 42% to about 130%, from about 44% to about 135%, from about 46% to about 14%, from about 48% to about 145%, from about 50% to about 150%, from about 60% to about 175%, from about 70% to about 200%, from about 80% to about 225%, from about 90% to about 250%, from about 100% to about 275%, from about 110% to about 300%, from about 120% to about 325%, from about 130% to about 350%, from about 140% to about 375%, from about 150% to about 400%, from about 170% to about 450%, from about 190% to about 500%, from about 210% to about 550%, from about 230% to about 600%, from about 250% to about 650%, from about 270% to about 700%, from about 290% to about 750%, from about 310% to about 800%, from about 330% to about 850%, from about 350% to about 900%, from about 370% to about 950%, from about 390% to about 1000%, from about 410% to about 1050%, from about 430% to about 1100%, from about 450% to about 1500%, from about 480% to about 2000%, from about 510% to about 2500%, from about 540% to about 3000%, from about 570% to about 3500%, from about 600% to about 4000%, from about 630% to about 4500%, from about 660% to about 5000%, from about 690% to about 5500%, from about 720% to about 6000%, from about 750% to about 6500%, from about 780% to about 7000%, from about 810% to about 7500%, from about 840% to about 8000%, from about 870% to about 8500%, from about 900% to about 9000%, from about 930% to about 9500%, from about 960% to about 10000%, or more than 10000%.

Ocular SBPs

SBPs described herein may include ocular SBPs. As used herein, the term "ocular SBP" refers to an SBP used in any application related to the eye. Ocular SBPs may be used in therapeutic applications. Such therapeutic applications may include treating or otherwise addressing one or more ocular indications.

In further embodiments, ocular SBPs may be prepared as eye drops for the treatment of dry eye disease, as described in U.S. Pat. No. 9,394,355, the contents of which are hereby incorporated by reference in their entirety, or formulated for the treatment of corneal injury, as described in International Patent Application Publication Nos. WO2017200659 and WO2018031973; Abdel-Naby et al. (2017) Invest Ophthalmol Vis Sci; 58(3):1425-1433; and Abdel-Naby et al. (2017) PLoS One; 12(11):e0188154, the contents of each of which are hereby incorporated by reference in their entirety.

Ocular SBPs may be prepared in a variety of formats. Some ocular SBPs are in the form of a hydrogel. These hydrogels may vary in viscosity and appear runny. Other ocular SBPs may be in the form of a solution. Some ocular SBPs may be devices. These devices may include medical devices. In some embodiments, solutions may include silk fibroin micelles, as described in Wongpanit et al (2007) Macromolecular Bioscience 7: 1258-1271, the contents of which are herein incorporated by reference in their entirety. Silk fibroin micelles may be of any size (e.g. between 100 to 200 nm). In some embodiments, ocular SBPs may act as demulcents. The ocular SBPs described herein may relieve irritation or inflammation of the mucous membranes by forming a protective film. In some embodiments, the ocular SBPs of the present disclosure may contain one or more demulcents (e.g. propylene glycol, gelatin, glycerin, carboxymethylcellulose. Dextran 70, methylcellulose, PEG 300, PEG 400, hydroxyethyl cellulose, hydroxypropyl methylcellulose, povidone, polyvinyl alcohol, and polysorbate 80). This film may mimic a mucous membrane. In some embodiments, ocular SBPs may act as a surfactant.

Ocular SBPs may include ocular therapeutic agents. Ocular therapeutic agents may be delivered to subject eyes by release from SBPs while SBPs are in contact with the eyes. Release of ocular therapeutic agents from SBPs may be modulated by one or more of silk fibroin concentration, silk fibroin molecular weight. SBP volume, method used to dry SBPs, ocular therapeutic agent molecular weight, and inclusion of at least one excipient. The ocular therapeutic agents may include any of those described herein. In some embodiments, ocular therapeutic agents include one or more of processed silk, biological agents, small molecules, analgesics, proteins, anti-inflammatory agents, steroids, opiates, sodium channel blockers (e.g. lidocaine and proparacaine), ciclosporin, corticosteroids, tetracyclines, fatty acids, NSAIDs, and VEGF-related agents. Ocular therapeutic agent proteins may include, but are not limited to, lysozyme, bovine serum albumin (BSA), bevacizumab, or VEGF-related agents. NSAIDs may include, but are not limited to, aspirin, carprofen, celecoxib, deracoxib, diclofenac, diflunisal, etodolac, fenoprofen, firocoxib, flurbirofen, ibuprofen, indomethacin, ketoprofen, ketorolac, mefenamic acid, meloxicam, nabumetone, naproxen, oxaprozin, piroxicam, robenacoxib, salsalate, sulindac, and tolmetin. In some embodiments, the SBPs stabilize ocular therapeutic agents included. Ocular SBPs may include ocular therapeutic agent concentrations [expressed as percentage of ocular therapeutic agent weight contributing to total SBP volume] of from about 0.0001% (w/v) to about 98% (w/v). For example, SBPs may include ocular therapeutic agents at a concentration of from about 0.0001% (w/v) to about 0.001% (w/v), from about 0.001% (w/v) to about 0.01% (w/v), from about 0.01% (w/v) to about 1% (w/v), from about 0.05% (w/v) to about 2% (w/v), from about 1% (w/v) to about 5% (w/v), from about 2% (w/v) to about 10% (w/v), from about 4% (w/v) to about 16% (w/v), from about 5% (w/v) to about 20% (w/v), from about 5% (w/v) to about 85% (w/v), from about 8% (w/v) to about 24% (w/v), from about 10% (w/v) to about 30% (w/v), from about 12% (w/v) to about 32% (w/v), from about 14% (w/v) to about 34% (w/v), from about 15% (w/v) to about 95% (w/v), from about 16% (w/v) to about 36% (w/v), from about 18% (w/v) to about 38% (w/v), from about 20% (w/v) to about 40% (w/v), from about 22% (w/v) to about 42% (w/v), from about 24% (w/v) to about 44% (w/v), from about 26% (w/v) to about 46% (w/v), from about 28% (w/v) to about 48% (w/v), from about 30% (w/v) to about 50% (w/v), from about 35% (w/v) to about 55% (w/v), from about 40% (w/v) to about 60% (w/v), from about 45% (w/v) to about 65% (w/v), from about 50% (w/v) to about 70% (w/v), from about 55% (w/v) to about 75% (w/v), from about 60% (w/v) to about 80% (w/v), from about 65% (w/v) to about 85% (w/v), from about 70% (w/v) to about 90% (w/v), from about 75% (w/v) to about 95% (w/v), from about 80% (w/v) to about 96% (w/v), from about 85% (w/v) to about 97% (w/v), from about 90% (w/v) to about 98% (w/v), from about 95% (w/v) to about 99% (w/v), from about 96% (w/v) to about 99.2% (w/v), or from about 97% (w/v) to about 98% (w/v).

Ocular SBPs may have a pH from about 3 to about 10. In some embodiments, the pH is from about 3 to about 6, from about 6 to about 8, or from about 8 to about 10. In some embodiments, the pH of the SBP is about 7.4.

In some embodiments, the ocular SBP is a solution. In some embodiments the ocular SBP is a hydrogel. In some embodiments, the SBP comprises from about 0.0001% to about 35% (w/v) of silk fibroin. In some embodiments the silk fibroin may be included at a concentration (w/w or w/v) of from about 0.0001% to about 0.001%, from about 0.001% to about 0.01%, from about 0.01% to about 1%, from about 0.05% to about 2%, from about 0.1% to about 30%$_6$, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 96%, from about 32% to about 97%, from about 34% to about 98%, from about 36% to about 98.5%, from about 38% to about 99%, from about 40% to about 99.5%, from about 42% to about 99.6%, from about 44% to about 99.7%, from about 46% to about 99.8%, or from about 50% to about 99.9%.

Ocular SBPs may include one or more excipients. The excipients may include any of those described herein. In some embodiments, the excipients include one or more of sucrose, lactose, phosphate salts, sodium chloride, potassium phosphate monobasic, potassium phosphate dibasic, sodium phosphate dibasic, sodium phosphate monobasic, polysorbate 80, phosphate buffer, phosphate buffered saline, sodium hydroxide, sorbitol, mannitol, lactose USP, Starch 1500, microcrystalline cellulose, potassium chloride, sodium borate, boric acid, sodium borate decahydrate, magnesium chloride hexahydrate, calcium chloride dihydrate, sodium hydroxide. Avicel, dibasic calcium phosphate dehydrate, tartaric acid, citric acid, fumaric acid, succinic acid, malic acid, hydrochloric acid, polyvinylpyrrolidone, copolymers of vinylpyrrolidone and vinylacetate, hydroxypropylcellulose, hydroxyethylcellulose, hydroxypropylmethylcellulose, polyvinyl alcohol, polyethylene glycol, acacia, and sodium carboxymethylcellulose. In some embodiments, excipients may include phosphate buffered saline. In some embodiments, excipients may include phosphate buffer. In some embodiments, excipients may include sucrose. In some embodiments, excipients may include boric acid, sodium borate decahydrate, sodium chloride, potassium chloride, magnesium chloride hexahydrate, calcium chloride dihydrate, sodium hydroxide, and hydrochloric acid. SBPs may include at least one excipient at a concentration of from about 0.0001% to about 50% (w/w or w/v). In some embodiments, SBPs include at least one excipient at a concentration of from about 0.01% to about 1%, from about 0.05% to about 2%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 96%, from about 32% to about 97%, from about 34% to about 98%, from about 36% to about 98.5%, from about 38% to about 99%, from about 40% to about 99.5%, from about 42% to about 99.6%, from about 44% to about 99.7%, from about 46% to about 99.8%, or from about 50% to about 99.9%.

In some embodiments, less than 1% of silk fibroin in an ocular SBP aggregates In some embodiments, less than 0.1% of silk fibroin in an ocular SBP aggregates.

Ocular SBPs may be hydrogels. Such SBPs may include at least one excipient selected from one or more of sorbitol, triethylamine, 2-pyrrolidone, alpha-cyclodextrin, benzyl alcohol, beta-cyclodextrin, dimethyl sulfoxide, dimethylacetamide (DMA), dimethylformamide, ethanol, gamma-cyclodextrin, glycerol, glycerol formal, hydroxypropyl beta-cyclodextrin, kolliphor 124, kolliphor 181, kolliphor 188, kolliphor 407, kolliphor EL (cremophor EL), cremophor RH 40, cremophor RH 60, dalpha-tocopherol, PEG 1000 succinate, polysorbate 20, polysorbate 80, solutol HS 15, sorbitan monooleate, poloxamer-407, poloxamer-188, Labrafil M-1944CS, Labrafil M-2125CS, Labrasol, Gellucire 44/14, Softigen 767, mono- and di-fatty acid esters of PEG 300, PEG 400, or PEG 1750, kolliphor RH60, N-methyl-2-pyrrolidone, castor oil, corn oil, cottonseed oil, olive oil, peanut oil, peppermint oil, safflower oil, sesame oil, soybean oil, hydrogenated vegetable oils, hydrogenated soybean oil, medium chain triglycerides of coconut oil, medium chain triglycerides of palm seed oil, beeswax, d-alpha-tocopherol, oleic acid, medium-chain mono-glycerides, medium-chain di-glycerides, alpha-cyclodextrin, betacyclodextrin, hydroxypropyl-beta-cyclodextrin, sulfo-butylether-beta-cyclodextrin, hydrogenated soy phosphatidylcholine, distearoylphosphatidylglycerol, L-alphadimyristoylphosphatidylcholine, L-alpha-dimyristoylphosphatidylglycerol, PEG 300, PEG 300 caprylic/capric glycerides (Softigen 767), PEG 300 linoleic glycerides (Labrafil M-2125CS), PEG 300 oleic glycerides (Labrafil M-1944CS), PEG 400, PEG 400 caprylic/capric glycerides (Labrasol), polyoxyl 40 stearate (PEG 1750 monosterate), polyoxyl 8 stearate (PEG 400 monosterate), polysorbate 20, polysorbate 80, polyvinyl pyrrolidone, propylene carbonate, propylene glycol, solutol HS15, sorbitan monooleate (Span 20), sulfobutylether-beta-cyclodextrin, transcutol, triacetin, 1-dodecylazacyclo-heptan-2-one, caprolactam, castor oil, cottonseed oil, ethyl acetate, medium chain triglycerides, methyl acetate, oleic acid, safflower oil, sesame oil, soybean oil, tetrahydrofuran, glycerin, and PEG 4 kDa. The SBPs may have an osmolarity of from about 1 mOsm to about 10 mOsm, from about 2 mOsm to about 20 mOsm, from about 3 mOsm to about 30 mOsm, from about 4 mOsm to about 40 mOsm, from about 5 mOsm to about 50 mOsm, from about 6 mOsm to about 60 mOsm, from about 7 mOsm to about 70 mOsm, from about 8 mOsm to about 80 mOsm, from about 9 mOsm to about 90 mOsm, from about 10 mOsm to about 100 mOsm, from about 15 mOsm to about 150 mOsm, from about 25 mOsm to about 200 mOsm, from about 35 mOsm to about 250 mOsm, from about 45 mOsm to about 300 mOsm, from about 55 mOsm to about 350 mOsm, from about 65 mOsm to about 400 mOsm, from about 75 mOsm to about 450 mOsm, from about 85 mOsm to about 500 mOsm, from about 125 mOsm to about 600 mOsm, from about 175 mOsm to about 700 mOsm, from about 225 mOsm to about 800 mOsm, from about 275 mOsm to about 285 mOsm, from about 280 mOsm to about 900 mOsm, or from about 325 mOsm to about 1000 mOsm.

In some embodiments, the viscosity and/or complex viscosity of SBPs is tunable between 1-1000 centipoise (cP). In some embodiments, the viscosity of an SBP is tunable from about 0.0001 to about 1000 Pascal seconds (Pa*s). In some embodiments, the viscosity of an SBP is from about 1 cP to about 10 cP, from about 2 cP to about 20 cP, from about 3 cP to about 30 cP, from about 4 cP to about 40 cP, from about 5 cP to about 50 cP, from about 6 cP to about 60 cP, from about 7 cP to about 70 cP, from about 8 cP to about 80 cP, from about 9 cP to about 90 cP, from about 10 cP to about 100 cP, from about 100 cP to about 150 cP, from about 150 cP to about 200 cP, from about 200 cP to about 250 cP, from about 250 cP to about 300 cP, from about 300 cP to about 350 cP, from about 350 cP to about 400 cP, from about 400 cP to about 450 cP, from about 450 cP to about 500 cP, from about 500 cP to about 600 cP, from about 550 cP to about 700 cP, from about 600 cP to about 800 cP, from about 650 cP to about 900 cP, from about 700 cP to about 1000 cP, from about 1000 cP to about 5000 cP, from about 5000 cP to about 10000 cP, from about 10000 cP to about 20000 cP, from about 20000 cP to about 30000 cP, from about 30000 cP to about 4000 cP, from about 40000 cP to about 50000 cP, from about 50000 cP to about 60000 cP, from about 60000 cP to about 80000 cP, from about 80000 cP to about 90000 cP, or from about 90000 cP to about 100000 cP. In some embodiments, the viscosity of an SBP is from about 0.0001 Pa*s to about 0.001 Pa*s, from about 0.001 Pa*s to about 0.01 Pa*s, from about 0.01 Pa*s to about 0.1 Pa*s, from about 0.1 Pa*s to about 1 Pa*s, from about 1 Pa*s to about 10 Pa*s, from about 2 Pa*s to about 20 Pa*s, from about 3 Pa*s to about 30 Pa*s, from about 4 Pa*s to about 40 Pa*s, from about 5 Pa*s to about 50 Pa*s, from about 6 Pa*s to about 60 Pa*s, from about 7 Pa*s to about 70 Pa*s, from about 8 Pa*s to about 80 Pa*s, from about 9 Pa*s to about 90 Pa*s, from about 10 Pa*s to about 100 Pa*s, from about 100 Pa*s to about 150 Pa*s, from about 150 Pa*s to about 200 Pa*s, from about 200 Pa*s to about 250 Pa*s, from about 250 Pa*s to about 300 Pa*s, from about 300 Pa*s to about 350 Pa*s, from about 350 Pa*s to about 400 Pa*s, from about 400 Pa*s to about 450 Pa*s, from about 450 Pa*s to about 500 Pa*s, from about 500 Pa*s to about 600 Pa*s, from about 550 Pa*s to about 700 Pa*s, from about 600 Pa*s to about 800 Pa*s, from about 650 Pa*s to about 900 Pa*s, from about 700 Pa*s to about 1000 Pa*s, from about 1000 Pa*s to about 2500 Pa*s, from about 2500 Pa*s to about 5000 Pa*s, from about 5000 Pa*s to about 7500 Pa*s, from about 7500 Pa*s to about 10000 Pa*s, from about 10000 Pa*s to about 20000 Pa*s, from about 20000 Pa*s to about 30000 Pa*s, from about 30000 Pa*s to about 40000 Pa*s, or from about 40000 Pa*s to about 50000 Pa*s. In some embodiments, the SBP formulations may shear thin or display shear thinning properties. As used herein, the term "shear thinning" refers to a decrease in viscosity at increasing shear rates. As used herein, the term "shear rate" refers to the rate of change in the ratio of displacement of material upon the application of a shear force to the height of the material. This ratio is also known as strain.

In some embodiments, the storage modulus and/or the loss modulus (G' and G" respectively) of SBPs is tunable between 0.0001-20000 Pascals (Pa). In some embodiments, the storage modulus and/or the loss modulus of SBPs is from about 0.0001 Pa to about 0.001 Pa, from about 0.001 Pa to about 0.01 Pa, from about 0.01 Pa to about 0.1 Pa, from about 0.1 Pa to about 1 Pa, from about 1 Pa to about 10 Pa, from about 2 Pa to about 20 Pa, from about 3 Pa to about 30 Pa, from about 4 Pa to about 40 Pa, from about 5 Pa to about 50 Pa, from about 6 Pa to about 60 Pa, from about 7 Pa to about 70 Pa, from about 8 Pa to about 80 Pa, from about 9 Pa to about 90 Pa, from about 10 Pa to about 100 Pa, from about 100 Pa to about 150 Pa, from about 150 Pa to about 200 Pa, from about 200 Pa to about 250 Pa, from about 250 Pa to about 300 Pa, from about 300 Pa to about 350 Pa, from about 350 Pa to about 400 Pa, from about 400 Pa to about 450 Pa, from about 450 Pa to about 500 Pa, from about 500 Pa to about 600 Pa, from about 550 Pa to about 700 Pa, from about 600 Pa to about 800 Pa, from about 650 Pa to about 900 Pa, from about 700 Pa to about 1000 Pa, from about 1000 Pa to about 1500 Pa, from about 1500 Pa to about 2000 Pa, from about 2000 Pa to about 2500 Pa, from about 2500 Pa to about 3000 Pa, from about 3000 Pa to about 3500 Pa, from about 3500 Pa to about 4000 Pa, from about 4000 Pa to about 4500 Pa, from about 4500 Pa to about 5000 Pa, from about 5000 Pa to about 5500 Pa, from about 5500 Pa to about 6000 Pa, from about 6000 Pa to about 6500 Pa, from about 6500 Pa to about 7000 Pa, from about 7000 Pa to about 7500 Pa, from about 7500 Pa to about 8000 Pa, from about 8000 Pa to about 8500 Pa, from about 8500 Pa to about 9000 Pa, from about 9000 Pa to about 9500 Pa, from about 9500 Pa to about 10000 Pa, from about 10000 Pa to about 11000 Pa, from about 11000 Pa to about 12000 Pa, from about 12000 Pa to about 13000 Pa, from about 13000 Pa to about 14000 Pa, from about 14000 Pa to about 15000 Pa, from about 15000 Pa to about 16000 Pa, from about 16000 Pa to about 17000 Pa, from about 17000 Pa to about 18000 Pa, from about 18000 Pa to about 19000 Pa, or from about 19000 Pa to about 20000 Pa.

In some embodiments, the phase angle of SBPs is tunable between 1°-90°) In some embodiments, the phase angle of SBPs is from about 1° to about 2° from about 2° to about 3°, from about 3° to about 4°, from about 4° to about 5°, from about 5° to about 6 from about 6° to about 7°, from about 7° to about 8°, from about 8° to about 9°, from about 9° to about 10°, from about 10° to about 15°, from about 15° to about 20°, from about 20° to about 25°, from about 25° to about 30°, from about 30° to about 35°, from about 35° to about 40°, from about 40° to about 45° from about 45° to about 50°, from about 50° to about 55°, from about 55° to about 60°, from about 60° to about 650 from about 65° to about 70° from about 70° to about 75°, from about 75° to about 80°, from about 80° to about 85°, or from about 85° to about 90°.

In some embodiments, ocular SBPs may demonstrate the effects of interfacial viscosity. In some embodiments, the processed silk of an ocular SBP may migrate to the air-water boundary. In some embodiments this migration may result in an increase in the local concentration at this interface and ultimately generate the effects of interfacial viscosity. The effects of interfacial viscosity may be independent of the concentration of processed silk. In some embodiments, the effects of interfacial viscosity may be mitigated through the incorporation of a surfactant. The surfactant may be any surfactant described herein. In some embodiments, the surfactant is polysorbate 80. In some embodiments, the SBPs are topical ocular drops. In some embodiments these topical ocular drops show the effects of interfacial viscosity, as the thin tear film allows for a large air-water interface. In some embodiments, the processed silk in the ocular SBP and/or topical ocular drops may migrate to the air-water interface. In some embodiments, the ocular SBP and/or topical ocular drops create a viscous film-like layer at the tear film surface. In some embodiments, the effects interfacial viscosity in an ocular SBP and/or topical ocular drops may prevent evaporation of tears. In some embodiments, the effects interfacial viscosity in an ocular SBP and/or topical ocular drops may extend silk residence dwell time on the surface of the eye. In some embodiments, the effects of interfacial viscosity of an ocular SBP and/or topical ocular drops may lead to a reduction in the frequency of application. In some embodiments, ocular SBPs and/or topical ocular drops may have viscosities similar to that of saline (1 cP). In some embodiments, ocular SBPs and/or topical ocular drops may have viscosities similar to that of saline at high shear rates (e.g. greater than or equal to 500 l/s). These shear rates may be similar or identical to those produced during blinking. In some embodiments, the ocular SBPs and/or topical ocular drops may not elicit any unwanted effects with comfort due to the effects of interfacial viscosity.

In some embodiments, ocular SBPs may comprise a solution with a demulcent. In some embodiments, the demulcent is propylene glycol. In some embodiments, ocular SBPs may comprise a solution with 0.001%-10% propylene glycol. In some embodiments, ocular SBPs may comprise a solution with 1% propylene glycol.

In some embodiments, ocular SBPs may comprise a solution in borate (DED) buffer.

In some embodiments, ocular SBPs may comprise a solution in borate (DED) buffer with 1% 480 mb silk fibroin at pH 7.5 with an osmolarity of 150 mOsm/L. These ocular SBPs may be prepared with silk fibroin lyophilized in 50 mM sucrose.

In some embodiments, ocular SBPs may comprise a solution in borate (DED) buffer with 1% 120 mb silk fibroin at pH 7.5 with an osmolarity of 150 mOsm/L These ocular SBPs may be prepared with silk fibroin lyophilized in 50 mM sucrose.

In some embodiments, ocular SBPs may comprise a solution in borate (DED) buffer with 1% 480 mb silk fibroin at pH 7.5 with an osmolarity of 150 mOsm/L and 1% propylene glycol. These ocular SBPs may be prepared with silk fibroin lyophilized in 50 mM sucrose.

In some embodiments, the ocular SBP may be formulated for topical administration. In some embodiments, ocular SBPs may be formulated for ocular administration. In some embodiments, ocular SBPs are formulated for intraocular administration. In some embodiments, ocular SBPs are formulated for one or more of intravitreal administration, intraretinal administration, intracorneal administration, intrascleral administration, lacrimal administration, punctal administration, administration to the anterior sub-Tenon's, suprachoroidal administration, administration to the posterior sub-Tenon's, subretinal administration, administration to the fornix, administration to the lens, administration to the anterior segment, administration to the posterior segment, macular administration, and intra-aqueous humor administration. Ocular SBPs may be biocompatible, well tolerated, and/or non-immunogenic. Ocular SBPs may be administered as eye drops. Ocular SBPs may be administered as sprays. Ocular SBPs may be biocompatible. Ocular SBPs may be tolerable.

In some embodiments, ocular SBPs may be used as artificial tears. In some embodiments, ocular SBPs may be used in the management of glaucoma. In some aspects, the ocular SBPs useful for the management of glaucoma may be in the format of drops. Eye drops used in managing glaucoma help the eye's fluid to drain better and decrease the amount of fluid made by the eye which decreases eye pressure. Ocular SBPs formatted as eye drops may include prostaglandin analogs, beta blockers, alpha agonists, and carbonic anhydrase inhibitors.

In some embodiments, SBPs formatted as drops may be used to treat ocular allergies. Drops may contain histamine antagonists or nonsteroidal anti-inflammatory drug (NSAIDs), which suppress the optical mast cell responses to allergens including (but not limited to) aerosolized dust particles.

In some embodiments, SBPs formatted as drops may be used to treat conjunctivitis or pink eye. In some embodiments ocular SBPs comprising antibiotics as therapeutic agents may be prescribed when the conjunctivitis is caused by bacteria. In some embodiments, pharmaceutical compositions comprising ocular SBPs may be prepared as artificial tears to help dilute irritating allergens present in the tear film.

In some embodiments, ocular SBPs formatted as drops may include mydriatics, an agent that causes pupil dilation. Mydriatics include but are not limited to phenylephrine, cyclopentolate, tropicamide, hydroxyamphetamine/tropicamide, atropine, cyclopentolate/phenylephrine ophthalmic, homatropine ophthalmic, and scopolamine. Such SBPs may be used in the treatment of ocular indications or in preparation for the diagnosis of ocular conditions.

In some embodiments, ocular SBPs formatted as solutions may be used as contact lens solution. Contact lens solutions are solutions used for the storage of contact lenses in between use of said contact lenses. Contact lenses may be used for vision correction and/or for cosmetic purposes. In some embodiments, the anti-microbial and/or bacteriostatic properties of an SBP may enable the storage of contact lenses while prohibiting the growth of microbes and/or bacteria.

In some embodiments, the ocular SBPs of the present disclosure are biocompatible in the ocular space. In some embodiments, administration of the ocular SBP does not cause local inflammation in the ocular space. In some embodiments, ocular SBP is tolerable in the ocular space. In some embodiments, the retinal tissue remains normal after the administration of the ocular SBP. In some embodiments, the SBPs are biocompatible and tolerable in the ocular space for at least 1 day, at least 3 days, at least 1 week, at least 2 weeks, at least 1 month, at least 3 months, at least 4 months, at least 6 months, or at least 1 year.

In some embodiments, the present disclosure provides methods of treating subjects by contacting them with ocular SBPs. The subjects may have, may be suspected of having, and/or may be at risk for developing one or more ocular indications. Such ocular indications may include any of those described herein. In some embodiments, ocular indications include dry eye disease. In some embodiments, ocular indications include one or more of an infection, refractive errors, age related macular degeneration, cystoid macular edema, cataracts, diabetic retinopathy (proliferative and non-proliferative), glaucoma, amblyopia, strabismus, color blindness, cytomegalovirus retinitis, keratoconus, diabetic macular edema (proliferative and non-proliferative), low vision, ocular hypertension, retinal detachment, eyelid twitching, inflammation, uveitis, bulging eyes, dry eye disease, floaters, xerophthalmia, diplopia, Graves' disease, night blindness, eye strain, red eyes, nystagmus, presbyopia, excess tearing, retinal disorder, conjunctivitis, cancer, corneal ulcer, corneal abrasion, snow blindness, scleritis, keratitis, Thygeson's superficial punctate keratopathy, corneal neovascularization, Fuch's dystrophy, keratoconjunctivitis sicca, iritis, cyclitis, cycloplegia, chorioretinal inflammation (e.g. chorioretinitis, choroiditis, retinitis, retinochoroiditis, pars planitis, Harada's disease, aniridia, macular scars, solar retinopathy, choroidal degeneration, choroidal dystrophy, chorioderemia, gyrate atrophy, choroidal hemorrhage, choroidal detachment, retinoschisis, hypertensive retinopathy, Bull's eye maculopathy, epiretinal membrane, peripheral retinal degeneration, hereditary retinal dystrophy, retinitis pigmentosa, retinal hemorrhage, retinal vein occlusion, and separation of retinal layers.

In some embodiments, the present disclosure provides methods of delivering ocular therapeutic agents to subjects by contacting subject eyes with ocular SBPs. Such ocular SBPs may be prepared by combining processed silk with ocular therapeutic agents. The SBPs may be prepared as solutions. The SBPs may be prepared by dissolving processed silk in water or buffer. In some embodiments, the processed silk is silk fibroin. In some embodiments, the processed silk is prepared by degummed degumming for a boiling time selected from a 30-minute boil, a 60-minute boil, a 90-minute boil, a 120-minute boil, and a 480-minute boil. In some embodiments the processed silk is freeze dried in phosphate buffer. In some embodiments, the processed silk is freeze dried with sucrose. In some embodiments, the SBP is stressed. In some embodiments, the SBP is stressed by one or more methods including heating to 60° C. and autoclaving. In some embodiments, the SBP contains phosphate salts. In some embodiments, the SBP is formulated as a hydrogel. In some embodiments the SBP is formulated as a solution. In some embodiments, the SBP solution comprises phosphate buffered saline and trace amounts of phosphate buffer. In some embodiments, the SBP solution comprises sucrose, phosphate buffered saline and/or trace amounts of phosphate buffer.

In some embodiments, the viscosity of an ocular SBP may be tuned by preparation with silk fibroin of different boiling times. In some embodiments, a preparation of an ocular SBP from silk fibroin with a longer boiling time (e.g. 480 mb) may increase the viscosity of the SBP. In some embodiments, a preparation of an ocular SBP from silk fibroin with a shorter boiling time (e.g. 30 mb) may increase the viscosity of the SBP. In some embodiments, the viscosity of an ocular SBP may be tuned by preparation with different concentrations of silk fibroin. In some embodiments, a preparation of an ocular SBP with a lower concentration of silk fibroin may increase the viscosity of the SBP. In some embodiments, a preparation of an ocular SBP with a silk fibroin concentration of below 1% (w/v) may increase viscosity. In some embodiments, a preparation of an ocular SBP with a concentration between 0.005% and 0.5% (w/v) may increase viscosity. In some embodiments, both the boiling time of silk fibroin and the concentration of silk fibroin may be used to tune the viscosity of the SBP. In some embodiments, the viscosity of an ocular SBP may be tuned by preparation with stressed silk fibroin. In some embodiments, both the preparation of an SBP with stressed silk and the concentration of silk fibroin may be used to tune the viscosity of the SBP.

In some embodiments, the shear storage modulus and/or the shear loss modulus of an ocular SBP are tuned by the concentration of silk fibroin. In some embodiments, the shear storage modulus and/or the shear loss modulus of an ocular SBP are tuned by preparation with stressed silk fibroin. In some embodiments, both the preparation of an SBP with stressed silk and the concentration of processed silk may be used to tune the shear storage modulus and the shear loss modulus of the SBP. In some embodiments, the phase angle of the ocular SBP is tuned by preparation with stressed silk fibroin. In some embodiments, the phase angle of the ocular SBP is tuned by the concentration of processed silk.

In some embodiments, the viscosity of an ocular SBP may remain consistent across a range of silk fibroin concentrations. In some embodiments the viscosity of an ocular SBP may remain within 50%, 40%, 30% 20%, 10%, 5%, or 1% upon dilution. An ocular SBP may be diluted between 0 and 20-fold while maintaining a consistent viscosity.

In some embodiments, the ocular SBPs shear thin, or demonstrate shear thinning properties. In some embodiments, the ocular SBPs demonstrate greater shear thinning than commercially available treatments for dry eye disease. In some embodiments, the ocular SBPs of the present disclosure have a higher viscosity at a lower shear rate. In some embodiments, the ocular SBPs of the present disclosure have the viscosity of a gel at a lower shear rate. In some embodiments, the higher viscosity at a lower shear rate tunes the residence time of the SBP. In some embodiments, the residence time is increased. In some embodiments, the ocular SBPs of the present disclosure have a lower viscosity at a higher shear rate. In some embodiments, the ocular SBPs of the present disclosure have the viscosity of a fluid (e.g. liquid) at a higher shear rate. In some embodiments, the lower viscosity at a higher shear rate increases the comfort in the eye. In some embodiments, the shear thinning of tolerable ocular SBPs promotes differentiation.

In some embodiments, the ocular SBPs of the present disclosure are used to treat a subject. In some embodiments, ocular SBPs are used to treat a subject by contacting the subject with an ocular SBP. In some embodiments, the subject has an ocular indication. In some embodiments, the ocular condition is dry eye disease (DED). In some embodiments, the ocular SBP is administered for ocular lubrication. In some embodiments, the ocular SBP acts as artificial tears and/or a tear replacement. In some embodiments, the ocular SBP alleviates the symptoms of DED after administration. These symptoms may include, but are not limited to, ocular discomfort, dryness, grittiness, and pain. These symptoms may be associated with any grade of DED, including mild, moderate, and/or severe DED. In some embodiments, administration of an ocular SBP of the present disclosure may reduce signs of DED. These signs include, but are not limited to, ocular surface staining and/or tear film break-up time. In some embodiments, the ocular SBP improves comfort in the eye. In some embodiments, the ocular SBP is a hydrogel. In some embodiments, the ocular SBP is a solution. In some embodiments, the ocular SBP is hydrophobic. In some embodiments, the ocular SBP is administered to the eye. In some embodiments, the ocular SBP is administered via topical administration. In some embodiments, the ocular SBP is administered as drops. In some embodiments, the ocular SBP is administered as a spray. In some embodiments, the ocular SBP adheres to the ocular surface. In some embodiments, the ocular SBP adheres to the ocular surface in a manner similar to a mucin layer. In some embodiments, the hydrophobicity of the ocular SBP may improve tear film formation and enhance tear production. In some embodiments, the hydrophobicity of the ocular SBP may prevent evaporation. In some embodiments, the residence time of an ocular SBP will be analyzed after ocular SBP administration, using any method known to one skilled in the art. In some embodiments, the efficacy of an ocular SBP will be analyzed after ocular SBP administration, using any method known to one skilled in the art. In some embodiments, the pharmacokinetics of an ocular SBP will be analyzed after ocular SBP administration, using any method known to one skilled in the art. In some embodiments, the irritability of an ocular SBP will be analyzed after ocular SBP administration, using any method known to one skilled in the art. In some embodiments, the use of an ocular SBP to treat irritation will be analyzed after ocular SBP administration, using any method known to one skilled in the art. In some embodiments, the toxicity of an ocular SBP will be analyzed after ocular SBP administration, using any method known to one skilled in the art.

In some embodiments, the ocular SBP has a surface tension similar to that of water. In some embodiments, the ocular SBP has a surface tension similar to that of human tears. In some embodiments, the surfactant properties of ocular SBPs reduce surface tension to magnitude similar to human tears. Human tears have been reported to have a surface tension of 43.6 mN/m, as described in Sweeney et al (2013) Experimental Eye Research 117: 28-38. In some embodiments, ocular SBPs have a surface tension of about 40-50 mN/m.

Ocular SBPs with a surface tension similar to human tears may allow optimal spreading and tear reformation after blinking. In some embodiments, the surface tension of an ocular SBP may be optimizing to allow for improved spreading and/or tear reformation following blinking. In some embodiments, the surface tension of the ocular SBP may be controlled by the concentration of processed silk. In some embodiments, the surfactant and/or demulcent properties of an ocular SBP may reduce surface tension and provide optimal spreading and/or coating of the ocular surface. In some embodiments, the spreading and/or wetting capabilities of an ocular SBP may be modulated via the surface tension of the ocular SBP. In some embodiments, spreading and/or wetting is improved in ocular SBPs with lower surface tension. In some embodiments, the coating of the ocular surface may be improved in ocular SBPs with lower surface tension.

In some embodiments, ocular SBPs may display a coefficient of friction lower than that of water, as measured by the experimental sliding speeds. In some embodiments, the coefficient of friction of an ocular SBP is slightly lower than that of water. In some embodiments, the ocular SBP is more lubricating that water. In some embodiments, the ocular SBP is slightly more lubricating that water.

In some embodiments, silk fibroin solutions described herein may be prepared by dissolving lyophilized processed silk. That processed silk may be silk fibroin. Silk fibroin may be lyophilized in water, phosphate buffer, sucrose, and any other cryoprotectant and/or buffer described herein. In some embodiments, the formulations with lower molecular weight silk fibroin (480 mb) may be more viscous than the formulations with higher molecular weight silk fibroin (120 mb). Preparation from silk fibroin lyophilized in PB may not affect the viscosity of the formulations.

In some embodiments, silk fibroin may be conjugated with a fluorescent label (e.g. fluorescein isothiocyanate (FITC)). Conjugation may be performed by any method known to one of skill in the art. In some embodiments, the silk fibroin may be conjugated to FITC by mixing the two components together in a sodium bicarbonate solution at a basic pH (e.g. 9.0). The reaction may be performed under light protection at room temperature for at least 1 hour, 2 hours, 3 hours, 4 hours, 5 hours, 6 hours, or overnight. The resulting labeled silk fibroin (FITC-SF) may be dialyzed to remove any impurities. The FITC-SF may be stored at 4° C. until use.

In some embodiments, FITC-SF may be added to solutions of silk fibroin. In the resulting solution, FITC-SF may comprise at 10%, 20%, 300, or 40% of the total silk fibroin in solution. The total concentration of silk fibroin, with and without FITC-SF, may be any concentration described herein. In some embodiments, formulations of silk fibroin solutions may comprise 1% (w/v) silk fibroin of which 10%, 20%, 30%, or 40% of the total silk fibroin is FITC-SF. In some embodiments, formulations with higher percentages of FITC-SF may have lower complex viscosities. In some embodiments, formulations comprising silk fibroin in which 30% of the silk fibroin is FITC-SF have the most similar rheological properties to solutions of unlabeled silk fibroin.

In some embodiments, silk fibroin solutions may be prepared in any buffer described herein. In some embodiments, silk fibroin solutions may be prepared in a borate (DED) buffer. This buffer may comprise 6 mg/mL boric acid, 0.45 mg/mL sodium borate, 3.4 mg/mL sodium chloride, 1.4 mg/mL potassium chloride, 0.06 mg/mL magnesium chloride, and 0.06 mg/mL calcium chloride, pH 7.3. Silk fibroin solutions may further comprise polyethylene glycol (PG). PG may be present at any concentration described herein. In some embodiments, silk solutions comprise 1% PG. In some embodiments, G' and G" may be measured to be lower for formulations with higher molecular weight silk fibroin. G' and G" may also be increased by the preparation from silk fibroin lyophilized in PB or formulations with PG. The phase angle may be higher for formulations with higher molecular weight silk fibroin.

The irritability and/or tolerability of any silk fibroin solution described herein may be analyzed after administration to the eye of a subject. In some embodiments, topical administration of the solution of silk fibroin may be well tolerated for at least 1 hour, 2 hours, 1 day, 2 days, 3 days, 4 days, 5 days, 6 days, 1 week, 2 weeks, 3 weeks, or 1 month. In some embodiments, no deleterious effects (e.g. to the corneal surface) are detected after administration of an ocular SBP.

In some embodiments, the silk fibroin solutions described herein may be stable under storage. Storage conditions may include, but are not limited to, 4° C. room temperature, and 40° C. Silk fibroin solutions may be stable under the storage conditions for at least 1 hour, 2 hours, 1 day, 2 days, 3 days, 4 days, 5 days, 6 days, 1 week, 2 weeks, 3 weeks, 1 month, 6 months, 1 year, 2 years, 3 years, 4 years, 5 years, or 10 years. In some embodiments, an ocular SBP may have a shelf life of least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, at least 3 months, at least 14 weeks, at least 4 months, at least 18 weeks, at least 5 months, at least 22 weeks, at least 6 months, at least 7 months, at least 8 months, at least 9 months, at least 10 months, at least 11 months, at least a year, at least 2 years, at least 3 years, at least 4 years, at least 5 years, or more than 5 years. In some embodiments, ocular SBPs may have a shelf life of about 1 year at room temperature. In some embodiments, ocular SBPs may have a shelf life of about 2 years at room temperature. In some embodiments, ocular SBPs may have a shelf life of about 3 years at room temperature. In some embodiments, ocular SBPs may have a shelf life of about 4 years at room temperature. In some embodiments, ocular SBPs may have a shelf life of about 5 years at room temperature.

In some embodiments, ocular SBPs may be prepared to have desired residence time for their intended use. As used herein, the term "residence time" refers to the average length of time during which a substance (e.g., SBPs) is in a given location or condition. In some embodiments, enhanced residence time may enable convenient dosing for patients, as described in Zhu et al. (2008) Optometry and Vision Science 85(8): E715-E725, the contents of which are herein incorporated by reference in their entirety. The residence time may be modulated via the viscosity of the SBP. In some embodiments the viscosity is about 10-100 cP. In some embodiments, the viscosity is about 20-80 cP. In some embodiments, the viscosity is about 30-60 cP. In some embodiments, higher viscosity of an ocular SBP may lead to a longer residence time of said ocular SBP, as described in Zhu et al. (2007) Current Eye Research 32(3): 177-179, the contents of which are herein incorporated by reference in their entirety. These longer residence times may improve the symptoms benefit of an ocular indication (e.g. DED). In some embodiments, residence time of ocular SBP formulations described herein may vary from a few hours to several weeks. For example, residence time of SBP formulations may be about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 day, about 2 days, about 3 days, about 4 days, about 5 days, about 6 days, about 1 week, about 2 weeks, about 3 weeks, about 4 weeks, one month, 2 months, 6 months, 1 year, or longer than two years. In some embodiments, residence time of ocular SBP may be from about 4 hours to about 10 hours, from about 8 hours to about 12 hours, from about 10 hours to about 14 hours, from about 12 hours to about 16 hours, from about 15 hours to about 20 hours, from about 18 hours to about 22 hours, from about 20 to about 25 hours, from about 22 hours to about 26 hours, from about 24 hour to about 30 hours, from about 20 hour to about 28 hours, or from about 30 hours to about 40 hours. In one embodiment, residence time of an ocular SBP is about 24 hours. In some embodiments, sustained viscosity of an ocular SBP upon dilution may enable longer residence times and enhanced retention.

In some embodiments, ocular SBPs may be prepared to have desired degradation time for their intended use. As used herein, the term "degradation time" refers to the amount of time required for a substance to break down. In some embodiments, degradation times of ocular SBP formulations described herein may vary from a few hours to several weeks. For example, degradation time of ocular SBP formulations may be about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 day, about 2 days, about 3 days, about 4 days, about 5 days, about 6 days, about 1 week, about 2 weeks, about 3 weeks, about 4 weeks, one month, 2 months, 6 months, 1 year, or longer than two years. In some embodiments, degradation time of ocular SBPs may be from about 4 hours to about 10 hours, from about 8 hours to about 12 hours, from about 10 hours to about 14 hours, from about 12 hours to about 16 hours, from about 15 hours to about 20 hours, from about 18 hours to about 22 hours, from about 20 to about 25 hours, from about 22 hours to about 26 hours, from about 24 hour to about 30 hours, from about 20 hour to about 28 hours, or from about 30 hours to about 40 hours.

Delivery

SBPs may be delivered to cells, tissues, organs and/or organisms in naked form. As used herein in, "naked" delivery refers to delivery of an active agent with minimal or with no additional formulation or modification. Naked SBPs may be delivered to cells, tissues, organs and/or organisms using routes of administration known in the art and described herein. In some embodiments, naked delivery may include formulation in a simple buffer such as saline or PBS.

In some embodiments, SBPs may be prepared with one or more cell penetration agents, pharmaceutically acceptable carriers, delivery agents, bioerodible or biocompatible polymers, solvents, and/or sustained-release delivery depots. SBPs may be delivered to cells using routes of administration known in the art and described herein. In some embodiments, SBPs may be formulated for direct delivery to organs or tissues in any of several ways in the art including, but not limited to, direct soaking or bathing, via a catheter, by gels, powder, ointments, creams, gels, lotions, and/or drops, or by using substrates (e.g., fabric or biodegradable materials) coated or impregnated with SBPs.

Routes of Delivery

In some embodiments, SBP formulations may be administered by any route to achieve a therapeutically effective outcome.

These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intra-arterial (into an artery), intramuscular (into a muscle), intracranial (into the heart), intraosseous infusion (into the bone marrow), intrathecal (into the spinal canal), intraperitoneal, (infusion or injection into the peritoneum), intrasinal infusion, intravitreal, (through the eye), intravenous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intra-cartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavemosum (within the dilatable spaces of the corpus cavemosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal.

As a non-limiting example, the SBP is in the form of a hydrogel and the route of delivery is topical.

In one embodiment, the amount of the SBP in the formulation can be optimized for a particular Cmax value. When used for delivery (e.g., oral delivery) for small molecules or biologics, the Cmax may be decreased.

Detectable Agents and Labels

In some embodiments, SBP formulations may include detectable labels. As used herein, the term "detectable label" refers to any incorporated compound or entity that facilitates some form of identification. Detectable labels may include, but are not limited to various organic small molecules, inorganic compounds, nanoparticles, enzymes or enzyme substrates, fluorescent materials, luminescent materials (e.g., luminol), bioluminescent materials (e.g., luciferase, luciferin, and aequorin), chemiluminescent materials, radioactive materials (e.g., $^{18}F$, $^{67}Ga$, $^{81m}Kr$, $^{82}Rb$, $^{111}In$, $^{123}I$, $^{133}Xe$, $^{201}Tl$, $^{125}I$, $^{35}S$, $^{14}C$, $^{3}H$, or $^{99}mTc$ (e.g. as pertechnetate (technetate(VII), $TcO^{4-}$)), contrast agents (e.g., gold, gold nanoparticles, gadolinium, chelated Gd, iron oxides, superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexol), microbubbles, or perfluorocarbons). Such optically-detectable labels include for example, without limitation, 4-acetamido-4'-isothiocyanatostilbene-2,2'disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid 5-[dimethylamino]-naphthalene-1-sulfonyl chloride (DNS, dansylchloride) 4-dimethylaminophenylazopheny-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, X-rhodamine-5-(and -6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with n,ndiethylethanamine(1:1) (1R144); 5-chloro-2-[2-[3-[(5-chloro-3-ethyl-2(3H)-benzothiazolylidene) ethylidene]-2-(diphenylamino)-1-cyclopenten-1-yl]ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrne and derivatives (e.g., pyrene, pyrene butyrate, and succinimidyl 1-pyrene); butyrate quantum dots; Reactive Red 4 (CIBA-CRON™ Brilliant Red 3B-A); rhodamine and derivatives (e.g., 6-carboxy-Xrhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In some embodiments, the detectable labels may include non-detectable precursors that becomes detectable upon activation (e.g., fluorogenic tetrazine-fluorophore constructs, tetrazine-BODIPY FL, tetrazine-Oregon Green 488, or tetrazine-BODIPY TMR-X) or enzyme activatable fluorogenic agents (e.g., PROSENSE® (VisEn Medical)). In vitro assays in which enzyme labeled compositions can be used include, but are not limited to, enzyme linked immunosorbent assays (ELISAs), immunoprecipitation assays, immunofluorescence, enzyme immunoassays (EIA), radioimmunoassays (RIA), and Western blot analysis.

In some embodiments, SBP formulations may include may fluorescein isothiocyanate (FITC) as a detectable label. In some embodiments, FITC is conjugated to processed silk. In some embodiments, the processed silk conjugated to FITC is silk fibroin. Conjugation of FITC to silk fibroin may be performed using the standard isothiocyanate coupling protocol. FITC can be attached to silk fibroin via the amine group. The labeled silk fibroin may be purified from the unconjugated fluorescein by gel filtration. The final ratio of labeled and unlabeled silk fibroin can be determined by measuring the absorbance at 280 nm and at 495 nm.

SBP formulations may contain both labeled SBP and free (unlabeled) SBP. In some embodiments, the ratio of labeled SBP to free (unlabeled) SBP may be about 50:1, about 20:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 7:3, about 2.5:1, about 2:1, about 1.5:1, about 1:1, about 1:1.5, about 1:2, about 1:2.5, about 3:7, about 1:3, about 1:3.5, about 1:4, about 1:4, about 1:4.5, about 1:5, about 1:5.5, about 1:6, about 1:7, about 1:7.5, about 1:8, about 1:8.5, about 1:9, about 1:9.5, about 1:10, about 1:20, or about 1:50. In some embodiments, the ratio of labeled SBP to free (unlabeled) SBP may be from about 10:1 to about 7:1, from about 8:1 to about 5:1, from about 6:1 to about 4:1, from about 5:1 to about 3:1, from about 4:1 to about 2:1, from about 3:1 to about 1.5:1, from about 2:1 to about 1:1, from about 1:1 to about 1:2, from about 1:1.5 to about 1:3, about 1:2 to about 1:4, from about 1:3 to about 1:5, from about 1:4 to about 1:6, from about 1:5 to about 1:8, or from about 1:7 to about 1:10.

In one embodiment, the SBP formulation contains 1% silk fibroin, wherein the ratio of FITC labeled silk fibroin and unlabeled silk fibroin is 4:6.

In one embodiment, the SBP formulation contains 1% silk fibroin, wherein the ratio of FITC labeled silk fibroin and unlabeled silk fibroin is 3:7.

In one embodiment, the SBP formulation contains 1% silk fibroin, wherein the ratio of FITC labeled silk fibroin and unlabeled silk fibroin is 2:8.

In one embodiment, the SBP formulation contains 1% silk fibroin, wherein the ratio of FITC labeled silk fibroin and unlabeled silk fibroin is 1:9.

Depot Administration

In some embodiments, SBPs may be administered by or be used to administer therapeutic agents by depot administration. As used herein, the term "depot" refers to a concentration of one or more agents in a particular region or in association with a composition or device. With depot administration, the one or more agents exit or diffuse from the concentration into surrounding areas. Agents administered by depot administration may be SBPs. In some embodiments, SBPs are depots for therapeutic agents, wherein the therapeutic agents exit or diffuse from the SBPs. In some embodiments, depots are solutions. In some embodiments, depots are gels or hydrogels. In some embodiments, depots are eye drops. In some embodiments, depot administration of an SBP may reduce the number of times a therapeutic agent needs to be administered. In some embodiments, depot administration of an SBP may replace oral administration of a therapeutic agent.

In some embodiments, SBP depots may be used for controlled release of therapeutic agents, wherein release is facilitated by diffusion. Such methods may include any of those described in United States Patent Publication Number US20170333351, the contents of which are herein incorporated by reference in their entirety. Therapeutic agent diffusion may be slowed (i.e., controlled) by SBP depots leading to extended release periods. Extended therapeutic agent release periods may enable longer administration periods. In some embodiments, administration periods are extended by from about 0.01% to about 1%, from about 0.05% to about 2%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55%, from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 100%, from about 32% to about 105%, from about 34% to about 110%, from about 36% to about 115%, from about 38% to about 120%, from about 40% to about 125%, from about 42% to about 130%, from about 44% to about 135%, from about 46% to about 140%, from about 48% to about 145%, from about 50% to about 150%, from about 60% to about 175%, from about 70% to about 200%, from about 80% to about 225%, from about 90% to about 250%, from about 100% to about 275%, from about 110% to about 300%, from about 120% to about 325%, from about 130% to about 350%, from about 140% to about 375%, from about 150% to about 400%, from about 170% to about 450%, from about 190% to about 500%, from about 210% to about 550%, from about 230% to about 600%, from about 250% to about 650%, from about 270% to about 700%, from about 290% to about 750%, from about 310% to about 800%, from about 330% to about 850%, from about 350% to about 900%, from about 370% to about 950%, from about 390% to about 1000%, from about 410% to about 1050%, from about 430% to about 1100%, from about 450% to about 1500%, from about 480% to about 2000%, from about 510% to about 2500%, from about 540% to about 3000%, from about 570% to about 3500%, from about 600% to about 40000, from about 630% to about 4500%, from about 660% to about 5000%, from about 690% to about 5500%, from about 720% to about 6000%, from about 750% to about 6500%, from about 780% to about 7000%, from about 810% to about 7500%, from about 840% to about 8000%, from about 870% to about 8500%, from about 900% to about 9000%, from about 930% to about 9500%, from about 960% to about 10000%, In some embodiments, the controlled release of a therapeutic agent for the treatment of a condition, disease, or indication may be facilitated by the degradation and/or dissolution of SBPs. Such methods may be carried according to those described in International Patent Application Publication Nos. WO2013126799, WO2017165922, and U.S. Pat. No. 8,530,625, the contents of each of which are herein incorporated by reference in their entirety. SBP degradation and/or dissolution may expose increasing amounts of therapeutic agents over time for treatment of therapeutic indications.

In some embodiments, therapeutic agent release from SBPs may be monitored via high performance liquid chromatography (HPLC), ultra-performance liquid chromatography (UPLC), and/or other methods known to those skilled in the art.

SBP hydrogels may be used to extend payload release periods (e.g., as shown for extended release of small molecule in International Patent Application Publication No. WO2017139684, the contents of which are herein incorporated by reference in their entirety. In some embodiments, SBP hydrogels are used to provide extended release of therapeutic agents (e.g., biological agents). Hydrogel networks may stabilize such agents and support their release as the hydrogel degrades. This effect serves to extend agent release and may be modulated by varying factors including processed silk molecular weight, concentration, excipient type, pH, and temperature. In some embodiments, processed silk molecular weight, concentration, excipient type, pH, and processing temperature used to prepare SBPs may be modulated to achieve desired payload release periods for specific therapeutic agents.

In some embodiments, SBPs may be lyophilized together with therapeutic agents. In some embodiments, combined lyophilization may induce further interactions between therapeutic agents and SBPs. These interactions may be maintained through SBP preparation and support extended payload release. Payload release may be dependent on SBP degradation and/or dissolution. In some embodiments, SBP i-sheet content is increased (e.g., via water annealing), thereby increasing SBP insolubility in water. Such SBPs may exhibit increased payload release periods. In some embodiments, these SBPs may include therapeutic agent stabilizing properties to extend administration periods and/or therapeutic agent half-life.

In some embodiments, SBPs described herein maintain and/or improve the controlled delivery of a therapeutic agent. In some embodiments, SBPs lengthen payload release period and/or administration period by at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours. In some embodiments, SBPs lengthen payload release period and/or administration period by at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, or at least 3 months.

In some embodiments, SBPs may be used to modulate depot release of therapeutic agents. Some SBPs may release therapeutic agents according to near zero-order kinetics. In some embodiments, SBPs may release therapeutic agents according to first-order kinetics. In some embodiments, therapeutic agent release rate may be modulated by preparing SBP depots with modification of one or more of density, loading, drying method, silk fibroin molecular weight, and silk fibroin concentration.

In some embodiments, SBPs are prepared to release from about 0.01% to about 1%, from about 0.05% to about 2%, from about 1% to about 5%, from about 2% to about 10%, from about 3% to about 15%, from about 4% to about 20%, from about 5% to about 25%, from about 6% to about 30%, from about 7% to about 35%, from about 8% to about 40%, from about 9% to about 45%, from about 10% to about 50%, from about 12% to about 55% from about 14% to about 60%, from about 16% to about 65%, from about 18% to about 70%, from about 20% to about 75%, from about 22% to about 80%, from about 24% to about 85%, from about 26% to about 90%, from about 28% to about 95%, from about 30% to about 100% of the total amount of therapeutic or macromolecular therapeutic agent to be delivered.

II. Therapeutic Applications

In some embodiments, SBP formulations may be used in a variety of therapeutic applications. As used herein, the term "therapeutic application" refers to any method related to restoring or promoting the health, nutrition, and/or well-being of a subject; supporting or promoting reproduction in a subject; or treating, preventing, mitigating, alleviating, curing, or diagnosing a disease, disorder, or condition. As used herein, the term "condition" refers to a physical state of wellbeing. Therapeutic applications may include, but are not limited to, medical applications, surgical applications, and veterinary applications. As used herein, the term "medical application" refers to any method or use that involves treating, diagnosing, and/or preventing disease according to the science of medicine. "Surgical applications" refer to methods of treatment and/or diagnosis that involve operation on a subject, typically requiring incision and the use of instruments. "Veterinary applications" refer to therapeutic applications where the subject is a non-human animal. In some embodiments, therapeutic applications may include, but are not limited to, experimental, diagnostic, or prophylactic applications. In some embodiments, therapeutic applications include preparation and/or use of therapeutic devices. As used herein, the term "therapeutic device" refers to any article prepared or modified for therapeutic use.

SBP formulations used for therapeutic applications may include or may be combined with one or more pharmaceutical compositions, implants, therapeutic agents, coatings, excipients, or devices. In some embodiments, SBP formulations facilitate the delivery and/or controlled release of therapeutic agent payloads. In some embodiments, SBP formulations described herein may be used to stabilize therapeutic agents. Some SBP formulations may be used as tools, materials, or devices in therapeutic applications. Such SBP formulations may include, but are not limited to, delivery vehicles, and scaffolds. In some embodiments, therapeutic applications utilizing SBP formulations may include gene therapy. As used herein, the term "gene therapy" refers to the use of genetic transplantation to address disease and/or genetic disorders. In some embodiments, therapeutic applications utilizing SBP formulations may include gene editing. As used herein, the term "gene editing" refers to any process used to alter a DNA gene sequence at the level of individual nucleotides. In some embodiments, therapeutic applications utilizing SBP formulations may include immunotherapy. As used herein, the term "immunotherapy" refers to treatment of a disease, condition, or indication by modulating the immune system. In some embodiments, therapeutic applications utilizing SBP formulations may include diagnostic applications. In some embodiments, SBP formulations are used as diagnostic tools. In some embodiments, therapeutic applications utilizing SBP formulations may include tissue engineering. In some embodiments, therapeutic applications utilizing SBP formulations may include cell culture. In some embodiments, therapeutic applications utilizing SBP formulations may include surgical applications (e.g. incorporation into surgical tools, devices, and fabrics). In some embodiments, SBP formulations may be or may be included in therapeutic devices. In some embodiments, therapeutic devices may be coated with SBP formulations described herein.

Therapeutic applications of the present disclosure may be applied to a variety of subjects. As used herein, the term "subject" refers to any entity to which a particular process or activity relates to or is applied. Subjects of therapeutic applications described herein may be human or non-human. Human subjects may include humans of different ages, genders, races, nationalities, or health status. Non-human subjects may include non-human animal subjects (also simply referred to herein as "animal subjects"). Animal subjects may be non-human vertebrates or invertebrates. Some animal subjects may be wild type or genetically modified organisms (e.g., transgenic). In some embodiments, subjects include patients. As used herein, the term "patient" refers to a subject seeking treatment, in need of treatment, requiring treatment, receiving treatment, expecting treatment, or who is under the care of a trained (e.g., licensed) professional for a particular disease, disorder, and/or condition.

In some embodiments, SBP formulations may be used to address one or more therapeutic indications. As used herein, the term "therapeutic indication" refers to a disease, disorder, condition, or symptom that may be cured, reversed, alleviated, stabilized, improved, or otherwise addressed through some form of therapeutic intervention (e.g., administration of a therapeutic agent or method of treatment). As a non-limiting example, the therapeutic indication is ophthalmology, ophthalmology-related disease and/or disorder, otology, or an otology-related disease and/or disorder. As a non-limiting example, the ophthalmology-related disease and/or disorder is dry eye disease.

SBP formulation treatment of therapeutic indications may include contacting subjects with SBPs. SBP formulations may include therapeutic agents (e.g., any of those described herein) as cargo or payloads for treatment. In some embodiments, payload release may occur over a period of time (the "payload release period"). The payload release rate and/or length of the payload release period may be modulated by SBP components or methods of preparation.

In some embodiments, ocular SBPs may be used as an anti-inflammatory treatment for dry eye disease, as described in Kim e al. (2017) Scientific Reports 7: 44364, the contents of which are herein incorporated by reference in their entirety. It has been demonstrated that the administration of 0.1 to 0.5% silk fibroin solutions in a mouse model of dry eye disease enhances corneal smoothness and tear production, while reducing the amount of inflammatory markers detected.

Therapeutic Agents

In some embodiments, therapeutic applications involve the use of SBP formulations that are therapeutic agents or are combined with one or more therapeutic agents. As used herein, the term "therapeutic agent" refers to any substance used to restore or promote the health and/or wellbeing of a subject and/or to treat, prevent, alleviate, cure, or diagnose a disease, disorder, or condition. Examples of therapeutic agents include, but are not limited to, adjuvants, analgesic agents, antiallergic agents, antiangiogenic agents, antiarrhythmic agents, antibacterial agents, antibiotics, antibodies, anticancer agents, anticoagulants, antidementia agents, antidepressants, antidiabetic agents, antigens, antihypertensive agents, anti-infective agents, anti-inflammatory agents, antioxidants, antipyretic agents, anti-rejection agents, antiseptic agents, antitumor agents, antiulcer agents, antiviral agents, biological agents, birth control medication, carbohydrates, cardiotonics, cells, chemotherapeutic agents, cholesterol lowering agents, cytokines, endostatins, enzymes, fats, fatty acids, genetically engineered proteins, glycoproteins, growth factors, health supplements, hematopoietics, herbal preparations, hormones, hypotensive diuretics, immunological agents, inorganic synthetic pharmaceutical drugs, ions, lipoproteins, metals, minerals, nanoparticles, naturally derived proteins, NSAIDs, nucleic acids, nucleotides, organic synthetic pharmaceutical drugs, oxidants, peptides, pills, polysaccharides, proteins, protein-small molecule conjugates or complexes, psychotropic agents, small molecules, sodium channel blockers, statins, steroids, stimulants, therapeutic agents for osteoporosis, therapeutic combinations, thrombopoietics, tranquilizers, vaccines, vasodilators, VEGF-related agents, veterinary agents, viruses, virus particles, and vitamins. In some embodiments, SBP therapeutics and methods of delivery may include any of those taught in International Publication Numbers WO2017139684, WO2010123945, WO2017123383, or United States Publication Numbers US20170340575, US20170368236, and US20110171239 the contents of each of which are herein incorporated by reference in their entirety. In some embodiments, SBPs may be used to encapsulate, store, stabilize, preserve, and/or release, in a controlled manner, therapeutic agents. For example, using silk fibroin micrococoons as delivery vehicles for small molecules has been described in Shimanovich et al (Shimanovich et al (2015) Nature Communications 8:15902, the contents of which are herein incorporated by reference in their entirety). In some embodiments, SBP formulations may be prepared with therapeutic agents selected from any of those listed in Table 4. In the Table, example categories are indicated for each therapeutic agent. These categories are not limiting and each therapeutic agent may fall under multiple categories (e.g., any of the categories of therapeutic agents described herein).

TABLE 4

Therapeutic agents

| Agent | Category |
| --- | --- |
| opium | analgesic agent |
| opiate | analgesic agent |
| doxycycline monohydrate | antibacterial agent |
| tigecycline | antibacterial agent |
| doxycycline hyclate | antibacterial agent |
| vibramycin | antibacterial agent |
| doxycycline hydrochloride hemiethanolate hemihydrate | antibacterial agent |
| doxycycline calcium | antibacterial agent |
| abciximab | antibody |
| adalimumab | antibody |
| adalimumab-atto | antibody |
| alefacept | antibody |
| alemtuzumab | antibody |
| antibody fragment | antibody |
| antibody-drug conjugate | antibody |
| atezolizumab | antibody |
| basiliximab | antibody |
| belimumab | antibody |
| bezlotoxumab | antibody |
| bivalent antibody | antibody |
| canakinumab | antibody |
| certolizumab pegol | antibody |
| cetuximab | antibody |
| daclizumab | antibody |
| denosumab | antibody |
| efalizumab | antibody |
| golimumab | antibody |
| inflectra | antibody |
| ipilimumab | antibody |
| ixekizumab | antibody |
| monoclonal antibody | antibody |
| monovalent antibody | antibody |
| multivalent antibody | antibody |
| natalizumab | antibody |
| nivolumab | antibody |
| obiltoxaxamab | antibody |
| olaratumab | antibody |
| omalizumab | antibody |
| palivizumab | antibody |
| panitumumab | antibody |
| pembrolizumab | antibody |
| polyclonal antibody | antibody |
| reslizumab | antibody |
| rituximab | antibody |
| secukimmab | antibody |
| tocilizumab | antibody |
| trastuzumab | antibody |
| ustekinumab | antibody |
| autoantigen | antigen |
| endogenous antigen | antigen |
| exogenous antigen | antigen |

TABLE 4-continued

Therapeutic agents

| Agent | Category |
|---|---|
| neoantigen | antigen |
| tumor antigen | antigen |
| viral antigen | antigen |
| exogenous antigen | antigen |
| endogenous antigen | antigen |
| autoantigen | antigen |
| neoantigen | antigen |
| viral antigen | antigen |
| tumor antigen | antigen |
| xenogenus (heterologous) antigen | antigen |
| autologous antigen | antigen |
| idiotypic antigen | antigen |
| allogenic (homologous) antigen | antigen |
| epilope | antigen |
| tumor-specific antigen | antigen |
| tumor-associated antigen | antigen |
| neo-epitope | antigen |
| allergen | antigen |
| superantigen | antigen |
| tolerogen | antigen |
| immanoglobulin -binding protein | antigen |
| t-dependent antigen | antigen |
| t-independent antigen | antigen |
| immunodominant antigen | antigen |
| COX-1 inhibitor | anti-inflammatory agent |
| COX-2 inhibitor | anti-inflammatory agent |
| bisbiguanides polymeric quaternary ammonium compound | antiseptic agent |
| chlorhexidine | antiseptic agent |
| chlorinated phenol | antiseptic agent |
| ethanol | antiseptic agent |
| hydrogen peroxide | antiseptic agent |
| lower alcohol | antiseptic agent |
| peroxides | antiseptic agent |
| propanol | antiseptic agent |
| quaternary amine surfactant | antiseptic agent |
| silver complex | antiseptic agent |
| small molecule quaternary ammonium compound | antiseptic agent |
| 5-FU Enhancer | anticancer agent |
| 9-AC | anticancer agent |
| abraxane | anticancer agent |
| actinomycin | anticancer agent |
| AG2037 | anticancer agent |
| AG3340 | anticancer agent |
| Aggrecanase Inhibitor | anticancer agent |
| alitretinoin | anticancer agent |
| alkylating agent | anticancer agent |
| Aminoglutethimide | anticancer agent |
| Amsacrine (m-AMSA) | anticancer agent |
| anthracycline | anticancer agent |
| antimicrobial peptide | anticancer agent |
| Asparaginase | anticancer agent |
| Azacitidine | anticancer agent |
| azathioprine | anticancer agent |
| Batimastat (BB94) | anticancer agent |
| BAY 12-9566 | anticancer agent |
| BCH-4556 | anticancer agent |
| bexarotene | anticancer agent |
| Bis-Naphtalimide | anticancer agent |
| bleomycin | anticancer agent |
| Busulfan | anticancer agent |
| Capecitabine | anticancer agent |
| Carboplatin | anticancer agent |
| Carmustaine + Polifepr Osan | anticancer agent |
| cdk4/cdk2 inhibitor | anticancer agent |
| chlorambucil | anticancer agent |
| CI-994 | anticancer agent |
| Cisplatin | anticancer agent |
| Cladribine | anticancer agent |
| CS-682 | anticancer agent |
| cyclophosphamide | anticancer agent |
| cytarabine | anticancer agent |
| Cytarabine HCl | anticancer agent |
| cytoskeletal disruptor | anticancer agent |
| D2163 | anticancer agent |

TABLE 4-continued

Therapeutic agents

| Agent | Category |
|---|---|
| dacarbazine | anticancer agent |
| Dactinomycin | anticancer agent |
| daunorubicin | anticancer agent |
| Daunorubicin HCl | anticancer agent |
| DepoCyt | anticancer agent |
| Dexifosamide | anticancer agent |
| Docetaxel | anticancer agent |
| Dolastain | anticancer agent |
| Doxifluridine | anticancer agent |
| Doxorubicin | anticancer agent |
| DX8951f | anticancer agent |
| E 7070 | anticancer agent |
| EGFR | anticancer agent |
| Epirubicin | anticancer agent |
| epothilone | anticancer agent |
| erlotinib | anticancer agent |
| Estramustine phosphate sodium | anticancer agent |
| Etoposide (VP16-213) | anticancer agent |
| Farnesyl Transferase Inhibitor | anticancer agent |
| FK 317 | anticancer agent |
| Flavopiridol | anticancer agent |
| Floxuridine | anticancer agent |
| Fludarabine | anticancer agent |
| Fluorouracil (5-FU) | anticancer agent |
| Flutamide | anticancer agent |
| Fragyline | anticancer agent |
| gefitinib | anticancer agent |
| Gemcitabine | anticancer agent |
| Hexamethylmelamine (HMM) | anticancer agent |
| histone deacetylase inhibitor | anticancer agent |
| hydroxyurea | anticancer agent |
| Hydroxyurea (hydroxycarbanride) | anticancer agent |
| idarubicin | anticancer agent |
| Ifosfamide | anticancer agent |
| imatinib | anticancer agent |
| Interferon Alfa-2a | anticancer agent |
| Interferon Alfa-2b | anticancer agent |
| Irinotecan | anticancer agent |
| ISI 641 | anticancer agent |
| kinase inhibitor | anticancer agent |
| Krestin | anticancer agent |
| Lemonal DP 2202 | anticancer agent |
| Leuptolide acetate (LHRH-releasing factor analogue) | anticancer agent |
| Levamisole | anticancer agent |
| LiGLA (lithium-gamma linolenate) | anticancer agent |
| Lodine Seed | anticancer agent |
| Lometexol | anticancer agent |
| Lomustine (CCNU) | anticancer agent |
| Marimistat | anticancer agent |
| mechlorethamine | anticancer agent |
| Mechlorethamine HCl (nitrogen mustard) | anticancer agent |
| Megestrol acetate | anticancer agent |
| Megi amine GLA | anticancer agent |
| melphalan | anticancer agent |
| Mercaptopurine | anticancer agent |
| Mesna | anticancer agent |
| methotrexate | anticancer agent |
| methyl glyoxal bis-guanylhydrazone (MGBG) | anticancer agent |
| Mitoguazone (methyl-GAG | anticancer agent |
| Mitotane (o.p'-DDD) | anticancer agent |
| Mitoxantrone HCl | anticancer agent |
| mitozantrone | anticancer agent |
| MMI 270 | anticancer agent |
| W | anticancer agent |
| MTA/LY 231514 | anticancer agent |
| MTX | anticancer agent |
| nitrosourea | anticancer agent |
| nucleotide analogue | anticancer agent |
| nucleotide precursor analogue | anticancer agent |
| ODN 698 | anticancer agent |
| OK-432 | anticancer agent |
| Oral Platinum | anticancer agent |
| Oral Taxoid | anticancer agent |

TABLE 4-continued

Therapeutic agents

| Agent | Category |
|---|---|
| oxaliplatin | anticancer agent |
| paclitaxel | anticancer agent |
| PARP Inhibitor | anticancer agent |
| PD 183805 | anticancer agent |
| Pentostatin (2 deoxycoformycin) | anticancer agent |
| PKC 412 | anticancer agent |
| platinum based chemotherapeutic | anticancer agent |
| Plicamycin | anticancer agent |
| Procarbazine HCl | anticancer agent |
| PSC 833 | anticancer agent |
| Ralitrexed | anticancer agent |
| RAS Farnesyl Transferase Inhibitor | anticancer agent |
| RAS Oncogene Inhibitor | anticancer agent |
| retinoids | anticancer agent |
| romidepsin | anticancer agent |
| Semustine (methyl-CCNU) | anticancer agent |
| Streptozocin | anticancer agent |
| Suramin | anticancer agent |
| tafluposide | anticancer agent |
| Tamoxifen citrate | anticancer agent |
| taxane | anticancer agent |
| Taxane Analog | anticancer agent |
| taxotere | anticancer agent |
| Temozolomide | anticancer agent |
| Teniposide (VM-26) | anticancer agent |
| Thioguanine | anticancer agent |
| Thiotepa | anticancer agent |
| tioguanine | anticancer agent |
| topoisomerase I inhibitor | anticancer agent |
| topoisomerase II inhibitor | anticancer agent |
| Topotecan | anticancer agent |
| tretinoin | anticancer agent |
| Tyrosine Kinase | anticancer agent |
| UFT (Tegafur/Uracil) | anticancer agent |
| Valtubicin | anticancer agent |
| vemurafenib | anticancer agent |
| vinblastine | anticancer agent |
| Vinblastine sulfate | anticancer agent |
| vinca alkaloid | anticancer agent |
| vinca alkaloid derivative | anticancer agent |
| vincristine | anticancer agent |
| vindesine | anticancer agent |
| Vindesine sulfate | anticancer agent |
| vinorelbine | anticancer agent |
| vismodegib | anticancer agent |
| vorinostat | anticancer agent |
| VX-710 | anticancer agent |
| VX-853 | anticancer agent |
| YM 116 | anticancer agent |
| ZD 0101 | anticancer agent |
| ZD 0473/Anormed | anticancer agent |
| ZD 1839 | anticancer agent |
| ZD 9331 | anticancer agent |
| 2-dimensional tissue | biological |
| 3-dimensional tissue | biological |
| adenovirus | biological |
| adipose tissue-derived mesenchymal stem cell | biological |
| bacteria | biological |
| bone mesenchymal stem cell | biological |
| cardiac mesenchymal stem cell | biological |
| cells | biological |
| chicken dorsal root ganglion | biological |
| complex carbohydrate | biological |
| deoxyribonucleic acid | biological |
| embryonic stem cell | biological |
| fibroblast | biological |
| fungi | biological |
| gene | biological |
| hematopoietic stem cell | biological |
| human corneal epithelial cell | biological |
| human corneal stromal stem cell | biological |
| human small intestinal enteroids | biological |
| lentivirs | biological |
| limbal epithelial stem cell | biological |
| lipids | biological |
| macromolecule | biological |
| mesenchymal stem cell | biological |
| microbe | biological |
| microbiome | biological |
| microorganism | biological |
| neural stem cells | biological |
| oligonucleotide | biological |
| oral keratinocyte | biological |
| organ | biological |
| organism | biological |
| periodontal ligament stem cells | biological |
| polymer | biological |
| probiotic | biological |
| proteins | biological |
| ribonucleic acid | biological |
| spore | biological |
| stem cell | biological |
| symbiote | biological |
| T cell | biological |
| tissue | biological |
| transfected fibroblast | biological |
| vesicle | biological |
| viral particle | biological |
| virus | biological |
| abequose | carbohydrate |
| arabinose | carbohydrate |
| cellobiose | carbohydrate |
| derivative of a monosaccharide | carbohydrate |
| di saccharide | carbohydrate |
| fructose | carbohydrate |
| fucose | carbohydrate |
| galactosamine | carbohydrate |
| galactose | carbohydrate |
| glucosamine | carbohydrate |
| glucose | carbohydrate |
| glucuronic acid | carbohydrate |
| iduronic acid | carbohydrate |
| lactose | carbohydrate |
| maltose | carbohydrate |
| mannose | carbohydrate |
| monosaccharide | carbohydrate |
| muramic acid | carbohydrate |
| N-acetylgalactosamine | carbohydrate |
| N-acetylglucosamine | carbohydrate |
| N-acetylmuramic acid | carbohydrate |
| N-acetylneuraminic acid | carbohydrate |
| oligosaccharide | carbohydrate |
| rhamnose | carbohydrate |
| ribose | carbohydrate |
| sialic acid | carbohydrate |
| sucrose | carbohydrate |
| trehalose | carbohydrate |
| xylose | carbohydrate |
| adipose tissue-derived mesenchymal stem cell | cell |
| periodontal ligament stem cell | cell |
| human small intestinal enteroid | cell |
| oral keratinocyte | cell |
| fibroblast | cell |
| transfected fibroblast | cell |
| 2-dimensional tissue | cell |
| 3-dimensional tissue | cell |
| T cell | cell |
| embryonic stem cell | cell |
| neural stem cell | cell |
| mesenchymal stem cell | cell |
| hematopoietic stem ceil | cell |
| osteoblast | cell |
| osteoclast | cell |
| osteocyte | cell |
| neuron | cell |
| glial cell | cell |
| chondrocyte | cell |
| photoreceptor cell | cell |
| cone cell | cell |
| rod cell | cell |

TABLE 4-continued

Therapeutic agents

| Agent | Category |
|---|---|
| corneal cell | cell |
| keratocyte | cell |
| corneal endothelial cell | cell |
| brain-derived neurotrophic factor (BDNF) | cytokine |
| cardiotrophin 1 (CTF1) | cytokine |
| cardiotrophin-like cytokine factor 1 (CLCF1) | cytokine |
| cell signal molecule | cytokine |
| chemokine | cytokine |
| ciliary neurotrophic factor (CNTF) | cytokine |
| erythropoietin (EPO) | cytokine |
| fibroblast growth factor acidic (FGFa) | cytokine |
| fibroblast growth factor basic (FGFb) | cytokine |
| IL-18 | cytokine |
| IL-10 | cytokine |
| IL-11 | cytokine |
| IL-12 | cytokine |
| IL-13 | cytokine |
| IL-14 | cytokine |
| IL-15 | cytokine |
| IL-16 | cytokine |
| IL-17 | cytokine |
| IL-19 | cytokine |
| IL-1α | cytokine |
| IL-1β | cytokine |
| IL-2 | cytokine |
| IL-20 | cytokine |
| IL-21 | cytokine |
| IL-22 | cytokine |
| IL-23 | cytokine |
| IL-27 | cytokine |
| IL-3 | cytokine |
| IL-4 | cytokine |
| IL-5 | cytokine |
| IL-6 | cytokine |
| IL-7 | cytokine |
| IL-8 | cytokine |
| IL-9 | cytokine |
| interferon | cytokine |
| interferon-α1 | cytokine |
| interleukin | cytokine |
| interleukin-1 receptor antagonist (IL-IRA) | cytokine |
| keratinocyte growth factor 1 | cytokine |
| keratinocyte growth factor 2 (KGF) | cytokine |
| kit ligand/stem cell factor (KITLG) | cytokine |
| leptin (LEP) | cytokine |
| leukemia inhibitory factor (LIF) | cytokine |
| lymphokine | cytokine |
| matrix metalloproteinase (MMP) | cytokine |
| monokine | cytokine |
| nerve growth factor (NGF) | cytokine |
| oncostatin M (OSM) | cytokine |
| prolactin (PRL) | cytokine |
| TGFβ | cytokine |
| tissue inhibitor of metalloproteinase (TIMP) | cytokine |
| transforming growth factor (TGF) α (TGFα) | cytokine |
| tumor necrosis factor α (TNFα) | cytokine |
| diacylglycerol | fat |
| diglycerides | fat |
| ergosterol | fat |
| fat-soluble vitamin | fat |
| glycerol monostearate | fat |
| glycerophospholipid | fat |
| glyceryl hydroxystearate | fat |
| hopanoid | fat |
| hydroxy-steroid | fat |
| monoglyceride | fat |
| monolaurin | fat |
| oil | fat |
| palmitin | fat |
| phosphatidic acid | fat |
| phosphatidylcholine | fat |
| phosphatidylethanolamine | fat |
| phosphatidylserine | fat |
| phosphoinositides | fat |
| phospholipids | fat |
| phosphosphingolipids | fat |
| phytosterol | fat |
| sphingolipid | fat |
| sphingomyelin | fat |
| stearin | fat |
| sterol | fat |
| triglyceride | fat |
| triolein | fat |
| wax | fat |
| fatty acid | fatty acid |
| essential fatty acid | fatty acid |
| omega-3 fatty acid | fatty acid |
| lincoleic acid | fatty acid |
| omega-6 fatty acid | fatty acid |
| docosahezaenoic acid | fatty acid |
| arachidonic acid | fatty acid |
| omega-9 fatty acid | fatty acid |
| Hexadecatrienoic acid (HTA) | fatty acid |
| α-Linolenic acid (ALA) | fatty acid |
| Stearidonic acid (SDA) | fatty acid |
| Eicosatrienoic acid (ETE) | fatty acid |
| Eicosatetraenoic acid (ETA) | fatty acid |
| Eicosapentaenoic acid (EPA) | fatty acid |
| Heneicosapentaenoic acid (HPA) | fatty acid |
| Docosapentaenoic acid (DPA), Clupanodonic acid | fatty acid |
| Docosahexaenoic acid (DHA) | fatty acid |
| Tetracosapentaenoic acid | fatty acid |
| Tetracosahexaenoic acid (Nisinic acid) | fatty acid |
| 5-Dodecenoic acid | fatty acid |
| 7-Tetradecenoic acid | fatty acid |
| 9-Hexadecenoic acid | fatty acid |
| 11-Octadecenoic acid | fatty acid |
| 13-Eicosenoic acid | fatty acid |
| 15-Docosenoic acid | fatty acid |
| 17-Tetracosenoic acid | fatty acid |
| Linoleic acid (LA) | fatty acid |
| Gamma-linolenic acid (GLA) | fatty acid |
| Calendic acid | fatty acid |
| Eicosadienoic acid | fatty acid |
| Dihomo-gamma-linolenic acid (DGLA) | fatty acid |
| Arachidonic acid (AA, ARA) | fatty acid |
| Docosadienoic acid | fatty acid |
| Adrenic acid | fatty acid |
| Osbond acid | fatty acid |
| Tetracosatetraenoic acid | fatty acid |
| Tetracosapentaenoic acid | fatty acid |
| oleic acid | fatty acid |
| elaidic acid | fatty acid |
| gondoic acid | fatty acid |
| mead acid | fatty acid |
| erucic acid | fatty acid |
| nervonic acid | fatty acid |
| ximenic acid | fatty acid |
| bone morphogenic protein | protein |
| bone morphogenic-like protein | protein |
| epidermal growth factor | protein |
| fibroblast growth factor | protein |
| insulin like growth factor I | protein |
| insulin like growth factor II | protein |
| transforming growth factor | protein |
| biotin (vitamin B7) | health supplement |
| iodine | health supplement |
| niacin (vitamin B3) | health supplement |
| pantothenic acid (vitamin B5) | health supplement |
| phosphorus | health supplement |
| riboflavin (vitamin B2) | health supplement |
| selenium | health supplement |
| thiamine (vitamin B1) | health supplement |

TABLE 4-continued

Therapeutic agents

| Agent | Category |
| --- | --- |
| vanadium | health supplement |
| vitamin A | health supplement |
| vitamin B | health supplement |
| vitamin B12 | health supplement |
| vitamin B6 | health supplement |
| vitamin B9 | health supplement |
| vitamin C | health supplement |
| vitamin D | health supplement |
| vitamin E | health supplement |
| vitamin K | health supplement |
| allspice berry essential oil | herbal preparation |
| angelica seed essential oil | herbal preparation |
| anise seed essential oil | herbal preparation |
| basil | herbal preparation |
| basil essential oil | herbal preparation |
| bay essential oil | herbal preparation |
| bay laurel | herbal preparation |
| bay laurel essential oil | herbal preparation |
| bergamot essential oil | herbal preparation |
| blood orange essential oil | herbal preparation |
| borage | herbal preparation |
| camphor essential oil | herbal preparation |
| caraway | herbal preparation |
| caraway seed essential oil | herbal preparation |
| cardamom seed essential oil | herbal preparation |
| carrot seed essential oil | herbal preparation |
| cassia essential oil | herbal preparation |
| catnip | herbal preparation |
| catnip essential oil | herbal preparation |
| cedarwood essential oil | herbal preparation |
| celery seed essential oil | herbal preparation |
| chamomile german essential oil | herbal preparation |
| chamomile roman essential oil | herbal preparation |
| chervil | herbal preparation |
| chives | herbal preparation |
| cilantro | herbal preparation |
| cinnamon bark essential oil | herbal preparation |
| cinnamon leaf essential oil | herbal preparation |
| citronella essential oil | herbal preparation |
| clary sage essential oil | herbal preparation |
| clove bud essential oil | herbal preparation |
| cold infusion | herbal preparation |
| compresses | herbal preparation |
| cordial | herbal preparation |
| coriander seed essential oil | herbal preparation |
| cumin | herbal preparation |
| cypress essential oil | herbal preparation |
| decoctions | herbal preparation |
| dill | herbal preparation |
| elemi essential oil | herbal preparation |
| epazote | herbal preparation |
| essential oils | herbal preparation |
| eucalyptus essential oil | herbal preparation |
| fennel | herbal preparation |
| fennel essential oil | herbal preparation |
| fir needle essential oil | herbal preparation |
| flower essence | herbal preparation |
| frankincense essential oil | herbal preparation |
| garlic | herbal preparation |
| geranium essential oil | herbal preparation |
| ginger essential oil | herbal preparation |
| granule | herbal preparation |
| grapefruit pink essential oil | herbal preparation |
| helichrysum essential oil | herbal preparation |
| herbal wine | herbal preparation |
| hop essential oil | herbal preparation |
| hyssop essential oil | herbal preparation |
| jasmine absolute oil | herbal preparation |
| juniper berry essential oil | herbal preparation |
| labdanum essential oil | herbal preparation |
| lavender | herbal preparation |
| lavender absolute oil | herbal preparation |
| lemon balm | herbal preparation |
| lemon essential oil | herbal preparation |
| lemon verbena | herbal preparation |
| lemongrass | herbal preparation |
| lemongrass essential oil | herbal preparation |
| time essential oil | herbal preparation |
| lovage | herbal preparation |
| magnolia essential oil | herbal preparation |
| mandarin essential oil | herbal preparation |
| margoram essential oil | herbal preparation |
| marjoram | herbal preparation |
| Melissa essential oil | herbal preparation |
| mints | herbal preparation |
| mugward essential oil | herbal preparation |
| myrrh essential oil | herbal preparation |
| myrtle essential oil | herbal preparation |
| nasturtium | herbal preparation |
| neroli essential oil | herbal preparation |
| niaouli essential oil | herbal preparation |
| nutmeg essential oil | herbal preparation |
| ointment | herbal preparation |
| orange sweet essential oil | herbal preparation |
| oregano | herbal preparation |
| oregano essential oil | herbal preparation |
| palmarosa essential oil | herbal preparation |
| parsley | herbal preparation |
| patchouli essential oil | herbal preparation |
| pennyroyal essential oil | herbal preparation |
| pepper black essential oil | herbal preparation |
| peppermint essential oil | herbal preparation |
| petitgram essential oil | herbal preparation |
| pine needle essential oil | herbal preparation |
| pink lotus absolute oil | herbal preparation |
| poultice | herbal preparation |
| radiata essential oil | herbal preparation |
| ravensara essential oil | herbal preparation |
| rose absolute oil | herbal preparation |
| rose essential oil | herbal preparation |
| rosemary | herbal preparation |
| rosemary essential oil | herbal preparation |
| rosewood essential oil | herbal preparation |
| sage | herbal preparation |
| sage essential oil | herbal preparation |
| salad burnet | herbal preparation |
| salve | herbal preparation |
| sambac absolute oil | herbal preparation |
| sandalwood essential oil | herbal preparation |
| savory | herbal preparation |
| scented geranium | herbal preparation |
| sitz bath | herbal preparation |
| soak | herbal preparation |
| sorrel | herbal preparation |
| spearmint essential oil | herbal preparation |
| spikenard essential oil | herbal preparation |
| spruce essential oil | herbal preparation |
| star anise essential oil | herbal preparation |
| suppository | herbal preparation |
| sweet annie essential oil | herbal preparation |
| syrup | herbal preparation |
| tangerine essential oil | herbal preparation |
| tarragon | herbal preparation |
| tea | herbal preparation |
| tea tree essential oil | herbal preparation |
| thyme | herbal preparation |
| thyme red essential oil | herbal preparation |
| tincture | herbal preparation |
| verbena essential oil | herbal preparation |
| vetiver essential oil | herbal preparation |
| white lotus absolute oil | herbal preparation |
| wintergreen essential oil | herbal preparation |
| wormwood essential oil | herbal preparation |
| varrow essential oil | herbal preparation |
| ylang essential oil | herbal preparation |
| 3-ketodesogestrel | hormone |
| allopregnanolone | hormone |
| androgen | hormone |
| androstenediol | hormone |
| androstenedione | hormone |
| chlormadinone acetate | hormone |
| cholesterol | hormone |

TABLE 4-continued

Therapeutic agents

| Agent | Category |
|---|---|
| conjugated estrogen | hormone |
| dehydroepiandrosterone | hormone |
| dexamethasone | hormone |
| dihydrotestosterone | hormone |
| drospirorenone | hormone |
| estradiol ester | hormone |
| estradiols | hormone |
| estriol | hormone |
| estriol succinate | hormone |
| estrogen | homone |
| estrone | hormone |
| estrone sulfate | hormone |
| ethinyl estradiol | hormone |
| gestodene | hormone |
| glucocoriticoid | hormone |
| levonorgestrel | hormone |
| mestranol | hormone |
| mineralocorticoid | hormone |
| norethisterone acetate | hormone |
| norgestrel | hormone |
| polyestriol phosphate | hormone |
| progesterone | hormone |
| progestogen | hormone |
| testosterone | hormone |
| calcium oxide | ion, metal, or mineral |
| iron oxide | ion, metal, or mineral |
| phosphorus oxide | ion, metal, or mineral |
| iodine oxide | ion, metal, or mineral |
| magnesium oxide | ion, metal, or mineral |
| zinc oxide | ion, metal, or mineral |
| selenium oxide | ion, metal, or mineral |
| copper oxide | ion, metal, or mineral |
| manganese oxide | ion, metal, or mineral |
| chromium oxide | ion, metal, or mineral |
| molybdenum oxide | ion, metal, or mineral |
| gold oxide | ion, metal, or mineral |
| potassium oxide | ion, metal, or mineral |
| nickel oxide | ion, metal, or mineral |
| silicon oxide | ion, metal, or mineral |
| vanadium oxide | ion, metal, or mineral |
| tin oxide | ion, metal, or mineral |
| calcium | ion, metal, or mineral |
| chloride | ion, metal, or mineral |
| chromium | ion, metal, or mineral |
| copper | ion, metal, or mineral |
| gold | ion, metal, or mineral |
| iron | ion, metal, or mineral |
| magnesium | ion, metal, or mineral |
| manganese | ion, metal, or mineral |
| metal oxide | ion, metal, or mineral |
| molybdenum | ion, metal, or mineral |
| nickel | ion, metal, or mineral |
| potassium | ion, metal, or mineral |
| silicon | ion, metal, or mineral |
| silver | ion, metal, or mineral |
| silver oxide | ion, metal, or mineral |
| tin | ion, metal, or mineral |
| zinc | ion, metal, or mineral |
| nano-hydroxyapatite | nanoparticle |
| acetominophen | NSAID |
| carprofen | NSAID |
| deracoxib | NSAID |
| fenoprofen | NSAID |
| firocoxib. | NSAID |
| flurbirofen | NSAID |
| mefenamic acid | NSAID |
| meloxicam | NSAID |
| robenacoxib | NSAID |
| aptamer | nucleic acid |
| antisense nucleic acid | nucleic acid |
| small interfering RNA (siRNA) | nucleic acid |
| exon skipping nucleic acid | nucleic acid |
| RNA editing nucleic acid | nucleic acid |
| microRNA therapeutic inhibitor (antimiR) | nucleic acid |
| microRNA therapeutic inhibitor mimic (promiR) | nucleic acid |
| long non-coding RNA modulator | nucleic acid |
| mRNA | nucleic acid |
| plasmid | nucleic acid |
| DNA aptamer | nucleic acid |
| deoxyribonucleic acidzyme | nucleic acid |
| RNA aptamer | nucleic acid |
| RNA decoy | nucleic acid |
| antisense DNA | nucleic acid |
| antisense RNA | nucleic acid |
| ribozyme | nucleic acid |
| micro ribonucleic acid | nucleic acid |
| fomivirsen | nucleic acid |
| viral nucleic acid | nucleic acid |
| Gendicine (Shenzhen SiBiono GeneTech) | nucleic acid |
| Advexin (Intro gen) | nucleic acid |
| nucleic acid vaccines | nucleic acid |
| fomivirsen sodium (Isis Pharmaceuticals) | nucleic acid |
| MG98 | nucleic acid |
| ISIS 5132 | nucleic acid |
| DNAzyme | nucleic acid |
| 2,5-diketopiperazine | oxidant or antioxidant |
| antioxidant | oxidant or antioxidant |
| melanin | oxidant or antioxidant |
| oxidants | oxidant or antioxidant |
| quarternary ammonium chitosan ion | oxidant or antioxidant |
| mineral | oxidant or antioxidant |
| vitamin | oxidant or antioxidant |
| protein | oxidant or antioxidant |
| hydrogen peroxide | oxidant or antioxidant |
| ozone | oxidant or antioxidant |
| nitric acid | oxidant or antioxidant |
| sulfuric acid | oxidant or antioxidant |
| oxygen | oxidant or antioxidant |
| sodium perborate | oxidant or antioxidant |
| nitrous oxide | oxidant or antioxidant |
| potassium nitrate | oxidant or antioxidant |
| sodium bismuthate | oxidant or antioxidant |
| hypochlorite | oxidant or antioxidant |
| bleach | oxidant or antioxidant |
| halogen | oxidant or antioxidant |
| Cl2 | oxidant or antioxidant |
| F2 | oxidant or antioxidant |
| endogenous oxidant | oxidant or antioxidant |
| exogenous oxidant | oxidant or antioxidant |
| hydroxide | oxidant or antioxidant |
| singlet oxygen | oxidant or antioxidant |
| superoxide anion | oxidant or antioxidant |
| hydroxy one radical | oxidant or antioxidant |
| reactive oxygen species | oxidant or antioxidant |
| vitamin A | oxidant or antioxidant |
| beta-carotene | oxidant or antioxidant |
| carotenoid | oxidant or antioxidant |
| vitamin C | oxidant or antioxidant |
| ascorbic acid | oxidant or antioxidant |
| vitamin E | oxidant or antioxidant |
| tocopherol | oxidant or antioxidant |
| tocotrienol | oxidant or antioxidant |
| selenium | oxidant or antioxidant |
| glutatione peroxidase | oxidant or antioxidant |
| zinc | oxidant or antioxidant |
| catalase | oxidant or antioxidant |
| superoxide dismutase | oxidant or antioxidant |
| copper | oxidant or antioxidant |
| manganese | oxidant or antioxidant |
| glutathione | oxidant or antioxidant |
| polyphenol | oxidant or antioxidant |
| tirilazad | oxidant or antioxidant |
| allupurinol | oxidant or antioxidant |
| acetylcysteine | oxidant or antioxidant |
| lipoic acid | oxidant or antioxidant |
| carotene | oxidant or antioxidant |

TABLE 4-continued

Therapeutic agents

| Agent | Category |
|---|---|
| ubiquinol | oxidant or antioxidant |
| BHA | oxidant or antioxidant |
| BHT | oxidant or antioxidant |
| Anidulafungin | peptide |
| Atosiban acetate | peptide |
| Bacitracin | peptide |
| Bivalirudin | peptide |
| Bortezomib | peptide |
| Buserelin | peptide |
| Calcitonin | peptide |
| Captopril | peptide |
| Carbetocin acetate | peptide |
| Caspofungin | peptide |
| Cetrorelix acetate | peptide |
| Colistin | peptide |
| cyclic dipeptide | peptide |
| cyclic peptide | peptide |
| Cyclosporine | peptide |
| Daptomycin | peptide |
| Degarelix acetate | peptide |
| Enalapril maleate | peptide |
| Enfuvittide | peptide |
| Eptifibatide | peptide |
| Exenatide | peptide |
| Glutathione | peptide |
| Goserelin | peptide |
| Human calcitonin | peptide |
| Ianreotide acetate | peptide |
| Icatibant acetate | peptide |
| Lepirdin | peptide |
| Liraglutide | peptide |
| Lisinopril | peptide |
| Lypressin | peptide |
| Nafarelin acetate | peptide |
| Nesiritide | peptide |
| Oxytocin | peptide |
| RGD peptide | peptide |
| r-hirudin | peptide |
| Salmon calcitonin | peptide |
| Saralasin acetate | peptide |
| Somatostatin acetate | peptide |
| Spaglumat magnesium | peptide |
| Thymalfasin | peptide |
| Tirofib an | peptide |
| Vapreotide acetate | peptide |
| Ziconotide | peptide |
| adrenocorticotropic hormone (ACTH) | protein |
| Alpha interferon | protein |
| antibody | protein |
| Anakinra | protein |
| antigen | protein |
| Beta interferon | protein |
| Bone morphogenetic protein (BMP) | protein |
| bone-motphogenic protein 2 | protein |
| chimeric protein | protein |
| Coagulation Factor IX | protein |
| Colony stimulating growth factor (CSF) | protein |
| Desmopressin | protein |
| Etanercept | protein |
| Factor IX | protein |
| Factor VII | protein |
| Factor VIII | protein |
| Follicle stimulating hormone (FSH) | protein |
| Gamma interferon | protein |
| gastrin prolactin | protein |
| Granulocyte colony-stimulating factor (G-CSF) | protein |
| Granulocyte macrophage colony stimulating factor (GM-CSF) | protein |
| growth hormone (GH) | protein |
| Human chorionic gonadotropin (HCG) | protein |
| infliximab | protein |
| insulin | protein |
| Insulin glargine | protein |
| Insulin-like growth factor (IGF) | protein |
| kallikrein | protein |
| kerantinocyte growth factor (KGF) | protein |
| Luteinizing hormone (LH) | protein |
| Macrophage colony stimulating factor (M-CSF) | protein |
| Neurotrophic growth factor (NGF) | protein |
| obesity protein (leptin) | protein |
| Octreotide | protein |
| Osteoprotegerin (OPG) | protein |
| pancreatic RNAase | protein |
| Pegfilgrastim | protein |
| peptides | protein |
| platelet activating factor acetyl hydrolase | protein |
| Platelet-derived growth factor (PDGF) | protein |
| processed silk | protein |
| sene in | protein |
| silk | protein |
| silk fibroin | protein |
| Stem cell factor (SCF) | protein |
| streptokinase | protein |
| Superoxide dismutase (SOD) | protein |
| synthetic protein | protein |
| thrombopoietin | protein |
| Thyroid stimulating hormone (TSH) | protein |
| tissue plasminogen activator (TPA) | protein |
| Tumor necrosis factor (TNF) | protein |
| tumor necrosis factor binding protein (TNFbp) | |
| urokinase | protein |
| Vascular endothelial growth factor (VEGF) | protein |
| antibacterial agent | small molecule |
| antifungal agent | small molecule |
| antimalarial agent | small molecule |
| antiseptic | small molecule |
| nonsteroidal anti-inflammatory drugs (NSAIDs) | small molecule |
| stimulant | small molecule |
| tranquilizers | small molecule |
| acetaminophen | small molecule - analgesic agent |
| alcohols | small molecule - analgesic agent |
| alcuronium | small molecule - analgesic agent |
| alfentanyl | small molecule - analgesic agent |
| amethocaine | small molecule - analgesic agent |
| amobarbital | small molecule - analgesic agent |
| anileridine | small molecule - analgesic agent |
| atracurium | small molecule - analgesic agent |
| bupivacaine | small molecule - analgesic agent |
| buprenorphine | small molecule - analgesic agent |
| butorphanol | small molecule - analgesic agent |
| cannabinoid | small molecule - analgesic agent |
| cannabis | small molecule - analgesic agent |
| cisatracurium | small molecule - analgesic agent |
| cocaine | small molecule - analgesic agent |
| codiene | small molecule - analgesic agent |
| COX-2 inhibitor | small molecule - analgesic agent |
| decamethonium | small molecule - analgesic agent |
| diacetyl morphine | small molecule - analgesic agent |
| diamorphine | small molecule - analgesic agent |
| diazepam | small molecule - analgesic agent |
| dibucaine | small molecule - analgesic agent |
| doxacurium | small molecule - analgesic agent |
| etomidate | small molecule - analgesic agent |
| fentanyl | small molecule - analgesic agent |
| gallamine | small molecule - analgesic agent |
| hydrocodone | small molecule - analgesic agent |
| hydromorphone | small molecule - analgesic agent |
| ketamine | small molecule - analgesic agent |
| levobupivacaine | small molecule - analgesic agent |
| levorphanol | small molecule - analgesic agent |
| lidocaine | small molecule - analgesic agent |
| lorazepam | small molecule - analgesic agent |

TABLE 4-continued

Therapeutic agents

| Agent | Category |
|---|---|
| meperidine (pethidine) | small molecule - analgesic agent |
| mepivacaine | small molecule - analgesic agent |
| methadone | small molecule - analgesic agent |
| methohexital | small molecule - analgesic agent |
| metocurine | small molecule - analgesic agent |
| midazolam | small molecule - analgesic agent |
| morphine | small molecule - analgesic agent |
| morphine glucuronide | small molecule - analgesic agent |
| morphine sulfate | small molecule - analgesic agent |
| nalbuphine | small molecule - analgesic agent |
| NSAID | small molecule - analgesic agent |
| opioid agonist | small molecule - analgesic agent |
| opioid antagonist | small molecule - analgesic agent |
| opioids | small molecule - analgesic agent |
| oxycodone | small molecule - analgesic agent |
| oxymorphone | small molecule - analgesic agent |
| pancuronium | small molecule - analgesic agent |
| pentazocine | small molecule - analgesic agent |
| pipecuronium | small molecule - analgesic agent |
| prilocaine | small molecule - analgesic agent |
| procaine | small molecule - analgesic agent |
| propoxyphene | small molecule - analgesic agent |
| rapacuronium | small molecule - analgesic agent |
| remifentanil | small molecule - analgesic agent |
| rocuronium | small molecule - analgesic agent |
| ropivacaine | small molecule - analgesic agent |
| succinylcholine | small molecule - analgesic agent |
| sufentanil | small molecule - analgesic agent |
| thiamylal | small molecule - analgesic agent |
| thiopental | small molecule - analgesic agent |
| tubocurarine | small molecule - analgesic agent |
| vecuronium | small molecule - analgesic agent |
| amikacin | small molecule - antibacterial agent |
| amoxicillin | small molecule - antibacterial agent |
| ampicillin | small molecule - antibacterial agent |
| azithromycin | small molecule - antibacterial agent |
| azlocillin | small molecule - antibacterial agent |
| aztreonam | small molecule - antibacterial agent |
| capreomycin | small molecule - antibacterial agent |
| carbenicillin | small molecule - antibacterial agent |
| cefaclor | small molecule - antibacterial agent |
| cefadroxil | small molecule - antibacterial agent |
| cefalexin | small molecule - antibacterial agent |
| cefalotin | small molecule - antibacterial agent |
| cefamandole | small molecule - antibacterial agent |
| cefazolin | small molecule - antibacterial agent |
| cefdinir | small molecule - antibacterial agent |
| cefditoren | small molecule - antibacterial agent |
| cefepime | small molecule - antibacterial agent |
| cefixime | small molecule - antibacterial agent |
| cefoperazone | small molecule - antibacterial agent |
| cefotaxime | small molecule - antibacterial agent |
| cefoxitin | small molecule - antibacterial agent |
| cefpodoxime | small molecule - antibacterial agent |
| cefprozil | small molecule - antibacterial agent |
| ceftaroline fosamil | small molecule - antibacterial agent |
| ceftazidime | small molecule - antibacterial agent |
| ceftibuten | small molecule - antibacterial agent |
| ceftizoxime | small molecule - antibacterial agent |
| ceftobiprole | small molecule - antibacterial agent |
| ceftriaxone | small molecule - antibacterial agent |
| cefuroxime | small molecule - antibacterial agent |
| cilastatin | small molecule - antibacterial agent |
| ciprofolaxin | small molecule - antibacterial agent |
| clarithromycin | small molecule - antibacterial agent |
| clindamycin | small molecule - antibacterial agent |
| clofazimine | small molecule - antibacterial agent |
| cloxacillin | small molecule - antibacterial agent |
| cycloserine | small molecule - antibacterial agent |
| dalbavancin | small molecule - antibacterial agent |
| dapsone | small molecule - antibacterial agent |
| demeclocycline | small molecule - antibacterial agent |
| dicloxacillin | small molecule - antibacterial agent |
| dirithromycin | small molecule - antibacterial agent |
| doripenem | small molecule - antibacterial agent |
| doxycycline | small molecule - antibacterial agent |
| enoxacin | small molecule - antibacterial agent |
| ertapenem | small molecule - antibacterial agent |
| erythromycin | small molecule - antibacterial agent |
| ethambutol | small molecule - antibacterial agent |
| ethionamide | small molecule - antibacterial agent |
| flucloxacillin | small molecule - antibacterial agent |
| furazolidone | small molecule - antibacterial agent |
| gatifloxacin | small molecule - antibacterial agent |
| geldanamycin | small molecule - antibacterial agent |
| gemifloxacin | small molecule - antibacterial agent |
| gentamicin | small molecule - antibacterial agent |
| grepafloxacin | small molecule - antibacterial agent |
| herbimycin | small molecule - antibacterial agent |
| imipeneum | small molecule - antibacterial agent |
| isoniazid | small molecule - antibacterial agent |
| kanamycin | small molecule - antibacterial agent |

TABLE 4-continued

Therapeutic agents

| Agent | Category |
|---|---|
| levofloxacin | small molecule - antibacterial agent |
| linezolid | small molecule - antibacterial agent |
| linomycin | small molecule - antibacterial agent |
| lomefloxacin | small molecule - antibacterial agent |
| loracarbef | small molecule - antibacterial agent |
| mafenide | small molecule - antibacterial agent |
| meropenem | small molecule - antibacterial agent |
| methicillin | small molecule - antibacterial agent |
| mezlocillin | small molecule - antibacterial agent |
| minocycline | small molecule - antibacterial agent |
| moxifloxacin | small molecule - antibacterial agent |
| nafcillin | small molecule - antibacterial agent |
| nalidixic acid | small molecule - antibacterial agent |
| neomycin | small molecule - antibacterial agent |
| netilmicin | small molecule - antibacterial agent |
| nitrofurantoin | small molecule - antibacterial agent |
| norfloxacin | small molecule - antibacterial agent |
| ofloxacin | small molecule - antibacterial agent |
| oritavancin | small molecule - antibacterial agent |
| oxacillin | small molecule - antibacterial agent |
| oxytetracycline | small molecule - antibacterial agent |
| paromomycin | small molecule - antibacterial agent |
| penicillin | small molecule - antibacterial agent |
| penicillin G | small molecule - antibacterial agent |
| penicillin V | small molecule - antibacterial agent |
| piperacillin | small molecule - antibacterial agent |
| posizolid | small molecule - antibacterial agent |
| pyrazinamide | small molecule - antibacterial agent |
| radezolid | small molecule - antibacterial agent |
| rifampicin | small molecule - antibacterial agent |
| rifaximin | small molecule - antibacterial agent |
| roxithromycin | small molecule - antibacterial agent |
| sparfloxacin | small molecule - antibacterial agent |
| spectinomycin | small molecule - antibacterial agent |
| spiramycin | small molecule - antibacterial agent |
| streptomycin | small molecule - antibacterial agent |
| sulfacetamide | small molecule - antibacterial agent |
| sulfadiazine | small molecule - antibacterial agent |
| sulfadimethoxine | small molecule - antibacterial agent |
| sulfamethizole | small molecule - antibacterial agent |
| sulfamethoxazole | small molecule - antibacterial agent |
| sulfanilimide | small molecule - antibacterial agent |
| sulfasalazine | small molecule - antibacterial agent |
| sulfisoxazole | small molecule - antibacterial agent |
| teicoplanin | small molecule - antibacterial agent |
| telavancin | small molecule - antibacterial agent |
| telithromycin | small molecule - antibacterial agent |
| temafloxacin | small molecule - antibacterial agent |
| temocillin | small molecule - antibacterial agent |
| tetracycline | small molecule - antibacterial agent |
| ticarcillin | small molecule - antibacterial agent |
| tobramycin | small molecule - antibacterial agent |
| torezolid | small molecule - antibacterial agent |
| troleandomycin | small molecule - antibacterial agent |
| trovafloxacin | small molecule - antibacterial agent |
| vancomycin | small molecule - antibacterial agent |
| 5-flnorocytosine | small molecule - antifungal |
| abafungin | small molecule - antifungal |
| albaconazole | small molecule - antifungal |
| amorolfin | small molecule - antifungal |
| amphotericin B | small molecule - antifungal |
| benzoic acid | small molecule - antifungal |
| bifonazole | small molecule - antifungal |
| butenafine | small molecule - antifungal |
| butoconazole | small molecule - antifungal |
| candicidin | small molecule - antifungal |
| caspofungin | small molecule - antifungal |
| ciclopirox | small molecule - antifungal |
| clotrimazole | small molecule - antifungal |
| crystal violet | small molecule - antifungal |
| econazole | small molecule - antifungal |
| efinaconazole | small molecule - antifungal |
| epexiconazole | small molecule - antifungal |
| fenticonazole | small molecule - antifungal |
| filipin | small molecule - antifungal |
| fluconazole | small molecule - antifungal |
| flucytosine | small molecule - antifungal |
| griseofulvin | small molecule - antifungal |
| haloprogin | small molecule - antifungal |
| hamycin | small molecule - antifungal |
| isavuconazole | small molecule - antifungal |
| isoconazole | small molecule - antifungal |
| itraconazole | small molecule - antifungal |
| ketoconazole | small molecule - antifungal |
| luliconazole | small molecule - antifungal |
| micafungin | small molecule - antifungal |
| miconazole | small molecule - antifungal |
| naftifine | small molecule - antifungal |
| natamycin | small molecule - antifungal |
| nystatin | small molecule - antifungal |
| omoconazole | small molecule - antifungal |
| oxiconazole | small molecule - antifungal |
| posaconazole | small molecule - antifungal |
| propiconazole | small molecule - antifungal |
| ravuconazole | small molecule - antifungal |
| rimocidin | small molecule - antifungal |

TABLE 4-continued

Therapeutic agents

| Agent | Category |
|---|---|
| sertaconazole | small molecule - antifungal |
| sulconazole | small molecule - antifungal |
| terbinafine | small molecule - antifungal |
| terconazole | small molecule - antifungal |
| tioconazole | small molecule - antifungal |
| tolnaftate | small molecule - antifungal |
| undecylenic acid | small molecule - antifungal |
| voriconazole | small molecule - antifungal |
| aminoquinoline | small molecule - antimalarial |
| amodiaquine | small molecule - antimalarial |
| antifolate | small molecule - antimalarial |
| artemether | small molecule - antimalarial |
| artemisinin derivative | small molecule - antimalarial |
| artemotil | small molecule - antimalarial |
| artesunate | small molecule - antimalarial |
| atovaquone | small molecule - antimalarial |
| biguanide | small molecule - antimalarial |
| bisphosphonate | small molecule - antimalarial |
| chloroguanil | small molecule - antimalarial |
| chloroquine | small molecule - antimalarial |
| cinchona alkaloid | small molecule - antimalarial |
| dermaseptin | small molecule - antimalarial |
| DHA-piperaquine | small molecule - antimalarial |
| diaminopyrimidine | small molecule - antimalarial |
| dihydroartemisinin | small molecule - antimalarial |
| doxycillin | small molecule - antimalarial |
| halofantrine | small molecule - antimalarial |
| lumefantrine | small molecule - antimalarial |
| melfoquine | small molecule - antimalarial |
| N-acetyl cysteine | small molecule - antimalarial |
| piperaquine | small molecule - antimalarial |
| primaquine | small molecule - antimalarial |
| proguanil | small molecule - antimalarial |
| pyremethamine | small molecule - antimalarial |
| pyronaridine | small molecule - antimalarial |
| quercitin | small molecule - antimalarial |
| quinidine | small molecule - antimalarial |
| quinine | small molecule - antimalarial |
| sulfadoxine-pyrimethamine | small molecule - antimalarial |
| sulfonamide | small molecule - antimalarial |
| tafenoquine | small molecule - antimalarial |
| trimethoprim | small molecule - antimalarial |
| choline salicylate | small molecule - antipyretic |
| magnesium salicylate | small molecule - antipyretic |
| metamizole | small molecule - antipyretic |
| nimesulide | small molecule - antipyretic |
| phenazone | small molecule - antipyretic |
| salicylate | small molecule - antipyretic |
| sodium salicylate | small molecule - antipyretic |
| aspirin | small molecule - NSAID |
| celecoxib | small molecule - NSAID |
| diclofenac | small molecule - NSAID |
| diflunisal | small molecule - NSAID |
| etodolac | small molecule - NSAID |
| fenoprofen | small molecule - NSAID |
| flurbiprofen | small molecule - NSAID |
| ibuprofen | small molecule - NSAID |
| indomethacin | small molecule - NSAID |
| ketoprofen | small molecule - NSAID |
| ketorolac | small molecule - NSAID |
| mechlofenamic acid | small molecule - NSAID |
| nabumetone | small molecule - NSAID |
| naproxen | small molecule - NSAID |
| oxaprozin | small molecule - NSAID |
| piroxicam | small molecule - NSAID |
| roficoxib | small molecule - NSAID |
| salsalate | small molecule - NSAID |
| sulindac | small molecule - NSAID |
| tolfenamic acid | small molecule - NSAID |
| tolmetin | small molecule - NSAID |
| sodium channel blocker | sodium channel blocker |
| alkaloid | sodium channel blocker |
| saxitoxin | sodium channel blocker |
| neosaxitoxin | sodium channel blocker |
| tetrodoxin | sodium channel blocker |
| class I antiarrhythmic agent | sodium channel blocker |
| quinidine | sodium channel blocker |
| procainamide | sodium channel blocker |
| disopryamide | sodium channel blocker |
| tocainide | sodium channel blocker |
| mexiletine | sodium channel blocker |
| proparacaine | sodium channel blocker |
| flecainide | sodium channel blocker |
| propafenone | sodium channel blocker |
| moricizine | sodium channel blocker |
| atorvastatin | statin |
| cerivastatin | statin |
| fluvastatin | statin |
| lovastatin | statin |
| mevastatin | statin |
| pitavastatin | statin |
| pravastatin | statin |
| rosuvastatin | statin |
| simvastatin | statin |
| statin | statin |
| steroid | steroid |
| corticosteroid | steroid |
| triamcinolone | steroid |
| cortisone | steroid |
| prednisone | steroid |
| methylprenisolone | steroid |
| prednisolone | steroid |
| betamethasone | steroid |
| dexamethasone | steroid |
| hydrocortisone | steroid |
| deflazacort | steroid |
| fludrocortisone | steroid |
| Anadrol | steroid |
| Anavar | steroid |
| Clenbuterol | steroid |
| Clomid | steroid |
| Cytomel | steroid |
| Deca Durabolin | steroid |
| Dianabol | steroid |
| Equipoise | steroid |
| Halotestin | steroid |
| Human Growth Hormone | steroid |
| Insulin | steroid |
| Lasix | steroid |
| Methyltestosterone | steroid |
| Nolvadex | steroid |
| Omnadren | steroid |
| Primobolan | steroid |
| Sustanon | steroid |
| Cypionate | steroid |
| Enanthate | steroid |
| Propionate | steroid |
| Testosterone | steroid |
| Trenbolone | steroid |
| Winstrol | steroid |
| Flunisolide | steroid |
| Budesonide | steroid |
| Mometasone | steroid |
| Ciclesonide | steroid |
| Fluticasone | steroid |
| Beclomethasone | steroid |
| glutocorticoid | steroid |
| minerolocorticoid | steroid |
| corticosterone | steroid |
| aldosterone | steroid |
| Hydrocortisone | steroid |
| methylprednisolone | steroid |
| prednisolone | steroid |
| prednisone | steroid |
| triamcinolone | steroid |
| Amcinonide | steroid |
| budesonide | steroid |
| desonide | steroid |
| fluocinolone acetonide | steroid |
| fluocinonide | steroid |
| halcinonide | steroid |
| triamcinolone acetonide | steroid |

TABLE 4-continued

Therapeutic agents

| Agent | Category |
|---|---|
| Beclometasone | steroid |
| betamethasone | steroid |
| dexamethasone | steroid |
| fluocortolone | steroid |
| halometasone | steroid |
| mometasone | steroid |
| Alclometasone dipropionate | steroid |
| betamethaso ne dipropionate | steroid |
| betamethasone valerate | steroid |
| clobetasol propionate | steroid |
| clobetasone butyrate | steroid |
| fluprednidene acetate | steroid |
| mometasone furoate | steroid |
| Ciclesonide | steroid |
| cortisone acetate | steroid |
| hydrocortisone aceponate | steroid |
| hydrocortisone acetate | steroid |
| hydrocortisone buteprate | steroid |
| hydrocortisone butyrate | steroid |
| hydrocortisone valerate | steroid |
| prednicarbate | steroid |
| tixocottol pivalate | steroid |
| 3,4-methylenedioxymethamphetamine | stimulant |
| amphetamines | stimulant |
| caffeine | stimulant |
| ephedrine | stimulant |
| mephedrone | stimulant |
| methamphetamine | stimulant |
| methylenedioxy pyrovalerone | stimulant |
| methylphenidate | stimulant |
| nicotine | stimulant |
| phenylpropanolamine | stimulant |
| propylhexedrine | stimulant |
| pseudoephedrine | stimulant |
| imatinib (Gleevac) | therapeutic combination |
| all-trans-retinoic acid | therapeutic combination |
| monoclonal antibody treatment | therapeutic combination |
| gemtuzumab | therapeutic combination |
| ozogamicin | therapeutic combination |
| chemotherapy | therapeutic combination |
| chlorambucil | therapeutic combination |
| prednisone | therapeutic combination |
| prednisolone | therapeutic combination |
| vincristine | therapeutic combination |
| cytarabine | therapeutic combination |
| clofarabine | therapeutic combination |
| farnesyl transferase inhibitor | therapeutic combination |
| decitabine | therapeutic combination |
| inhibitor of MDR1 | therapeutic combination |
| rituximab | therapeutic combination |
| interferon-α | therapeutic combination |
| anthracy cline drug | therapeutic combination |
| daunorubicin | therapeutic combination |
| idambicin | therapeutic combination |
| L-asparaginase | therapeutic combination |
| doxorubicin | therapeutic combination |
| cyclophosphamide | therapeutic combination |
| bleomycin | therapeutic combination |
| fludarabine | therapeutic combination |
| etoposide | therapeutic combination |
| pentostatin | therapeutic combination |
| cladribine | therapeutic combination |
| bone marrow transplant | therapeutic combination |
| stem cell transplant | therapeutic combination |
| radiation therapy | therapeutic combination |
| anti-metabolite drug | therapeutic combination |
| methotrexate | therapeutic combination |
| 6-mercapto purine | therapeutic combination |
| acepromazine | tranquilizer |
| alpha blockers | tranquilizer |
| alpha-adrenergic agonist | tranquilizer |
| antihistamine | tranquilizer |
| azapirone | tranquilizer |
| barbiturate | tranquilizer |
| benperidol | tranquilizer |
| benzamidine | tranquilizer |
| benzodiazepine | tranquilizer |
| beta-blocker | tranquilizer |
| bromantane | tranquilizer |
| bromperidol | tranquilizer |
| butyrophenone | tranquilizer |
| carbamates | tranquilizer |
| carpipramine | tranquilizer |
| chlorpromazine | tranquilizer |
| chlorprothixene | tranquilizer |
| clocapramine | tranquilizer |
| clopenthixol | tranquilizer |
| clorotepine | tranquilizer |
| cyamemazine | tranquilizer |
| diphenylbutylpiperidine | tranquilizer |
| dixyrazine | tranquilizer |
| droperidol | tranquilizer |
| emoxypine | tranquilizer |
| fabomotizole | tranquilizer |
| flupentixol | tranquilizer |
| fluphenazine | tranquilizer |
| fluspirilene | tranquilizer |
| gamma aminobutyric acid | tranquilizer |
| haloperidol | tranquilizer |
| inhalants | tranquilizer |
| levomepromazine | tranquilizer |
| loxapine | tranquilizer |
| mebicar | tranquilizer |
| mentyl isovalerate | tranquilizer |
| meso ridazine | tranquilizer |
| molindone | tranquilizer |
| monoamine oxidase inhibitors | tranquilizer |
| moperone | tranquilizer |
| mosapramine | tranquilizer |
| penfluridol | tranquilizer |
| perazine | tranquilizer |
| periciazine | tranquilizer |
| perphenazine | tranquilizer |
| phenothiazine | tranquilizer |
| pimozide | tranquilizer |
| pipamperone | tranquilizer |
| pipotiazine | tranquilizer |
| pregabalin | tranquilizer |
| prochlorperazine | tranquilizer |
| promazine | tranquilizer |
| promethazine | tranquilizer |
| propofol | tranquilizer |
| prothipendyl | tranquilizer |
| racetam | tranquilizer |
| selank | tranquilizer |
| selective serotonin reuptake inhibitors | tranquilizer |
| serotonin-norepinephrine reuptake inhibitor | tranquilizer |
| sulpiride | tranquilizer |
| sultopride | tranquilizer |
| sympatholytic | tranquilizer |
| thioproperazine | tranquilizer |
| thioridazine | tranquilizer |
| thiothixene | tranquilizer |
| thioxanthene | tranquilizer |
| timiperone | tranquilizer |
| tricyclic | tranquilizer |
| trifluoperazine | tranquilizer |
| triflupromazine | tranquilizer |
| veralipride | tranquilizer |
| zuclopenthixol | tranquilizer |
| 3-(4-Bromo-2,6-difluoro-benzyloxy)-5-[3-(4-pyrrolidin 1-yl-butyl)-ureido]-isothiazole-4-carboxylic acid amide hydrochloride | VEGF-related agent |
| 5-((7- Benzyloxyquinazolin-4-yl) amino)-4-fluoro-2 -methyl phenol hydrochloride | VEGF-related agent |
| aflibercept | VEGF-related agent |
| AG-013958 (Pfizer Inc.) | VEGF-related agent |
| Angiogenesis inhibitor | VEGF-related agent |
| angiostatin | VEGF-related agent |

TABLE 4-continued

Therapeutic agents

| Agent | Category |
|---|---|
| angiozyme | VEGF-related agent |
| anti-VEGF antibody | VEGF-related agent |
| arresten | VEGF-related agent |
| AVASTIN ® | VEGF-related agent |
| axitinib | VEGF-related agent |
| bevacizumab | VEGF-related agent |
| canstatin | VEGF-related agent |
| cediranib | VEGF-related agent |
| combretastatin | VEGF-related agent |
| Combretastatin A4 Prodrug (CA4P) | VEGF-related agent |
| combstatin | VEGF-related agent |
| endogenous peptide | VEGF-related agent |
| EVIZON ™ (squalamine lactate) | VEGF-related agent |
| Fumagillin | VEGF-related agent |
| Fumagillin analogtie | VEGF-related agent |
| glufanide disodium | VEGF-related agent |
| JSM6427 (Jerini AG) | VEGF-related agent |
| LUCENTIS ® | VEGF-related agent |
| MACUGEN ® | VEGF-related agent |
| multitargeted human epidermal receptor (HER) 1/2 and vascular endothelial growth factor receptor (VEGFR) 1/2 receptor family tyrosine kinases inhibitor | VEGF-related agent |
| N-(4-bromo-2- fluorophenyl)-6-methoxy-7-[(1-methylpiperidin-4-yl)methoxy]quinazolin-4-amine | VEGF-related agent |
| N-(4-bromo-2-fluorophenyl)-6-methoxy-7-[(1-methylpiperidin-4-yl)methoxy]quinazol in-4-amine | VEGF-related agent |
| N,2-dimethyl-6-(2-(1-methyl-1H-imidazol-2- yl)thieno[3,2-b]pyridin-7-yloxy)benzo[b]thiophene-3-carboxamide | VEGF-related agent |
| pan-VEGF-R-kinase inhibitor | VEGF-related agent |
| pegaptanib | VEGF-related agent |
| protein kinase inhibitor | VEGF-related agent |
| ranibizumab | VEGF-related agent |
| shark cartilage | VEGF-related agent |
| shark cartilage derivative | VEGF-related agent |
| short interfering RNA (siRNA) | VEGF-related agent |
| siRNA-based VEGFR 1 inhibitor | VEGF-related agent |
| soluble ectodomain of the VEGP receptor | VEGF-related agent |
| sorafenib | VEGF-related agent |
| synthetic peptide | VEGF-related agent |
| thalidomide | VEGF-related agent |
| thalidomide derivative | VEGF-related agent |
| thrombospondin | VEGF-related agent |
| tivozanib | VEGF-related agent |
| toll-like receptor agonist | VEGF-related agent |
| tumstatin | VEGF-related agent |
| tyrosine kinase inhibitor of the RET/PTC oncogenic kinase | VEGF-related agent |
| vatalanib | VEGF-related agent |
| VEGF agonist | VEGF-related agent |
| VEGF antagonist | VEGF-related agent |
| VEGF nucleic acid ligand | VEGF-related agent |
| VEGF therapeutic agent | VEGF-related agent |
| VEGF-R1 inhibitor | VEGF-related agent |
| VEGF-R2 inhibitor | VEGF-related agent |
| VEGFR2-selective monoclonal antibody | VEGF-related agent |
| VEGF-Trap | VEGF-related agent |
| β2-glycoprotein 1 | VEGF-related agent |

Processed Silk

In some embodiments, SBP formulations may include processed silk as an active therapeutic component. The processed silk may include, but is not limited to one or more of silk fibroin, fragments of silk fibroin, chemically altered silk fibroin, and mutant silk fibroin. Therapeutic applications including such SBPs may include any of those taught in International Publication Number WO2017200659; Aykac et al. (2017) Gene s0378-1119(17)30865-8; and Abdel-Naby (2017) PLoS One 12(11):e0188154 the contents of each of which are herein incorporated by reference in their entirety. Processed silk may be administered as a therapeutic agent for treatment of a localized indication or for treatment of an indication further from the SBP application site. In some embodiments, therapeutic agents are combinations of processed silk and some other active component. In some embodiments, therapeutic agent activity requires cleavage or dissociation from silk. Therapeutic agents may include silk fibroin and/or chemically modified silk fibroin. In some embodiments, such therapeutic agents may be used to treat burn injury, inflammation, wound healing, or corneal injury. These and other treatments may be carried out according to any of the methods described in International Publication Number WO2017200659; United States Publication Number US20140235554; Aykac et al. (2017) Gene s0378-1119 (17)30868-30865; or Abdel-Naby (2017) PLoS One 12(11): e0188154, the contents of each of which are herein incorporated by reference in their entirety. In some embodiments, SBPs are silk fibroin solutions used to facilitate wound healing, as described in Park et al. (2017) Acta Biomater 67:183-195, the contents of which are herein incorporated by reference in their entirety. These SBPs may enhance wound healing via a nuclear factor kappa enhancer binding protein (NF-κB) signaling pathway. In some embodiments, SBPs are therapeutic agents used to facilitate delivery and/or release of therapeutic agent payloads. Such therapeutic agents and/or methods of use may include, but are not limited to, any of those described in International Publication Number WO2017139684, the contents of which are herein incorporated by reference in their entirety.

Lubricants

In some embodiments, processed silk and/or SBPs may be used as a lubricant. In some embodiments, processed silk may be selected base on or prepared to maximize its use as a lubricant. As used herein, the term "lubricant" refers to a substance that reduces the friction between two or more surfaces. In some embodiments, the surfaces in need of lubrication may be part of a subject. In some embodiments, surfaces in need of lubrication include, but are not limited to, the body, eyes, ears, skin, scalp, mouth, vagina, nose, hands, feet, and lips. In some embodiments, SBPs are used for ocular lubrication. As used herein, the term "ocular lubrication" refers to a method of the reduction of friction and/or irritation in the eye. In some embodiments, processed silk and/or SBPs may be used to reduce friction caused by dryness, as taught in U.S. Pat. No. 9,907,836 (the content of which is herein incorporated by reference in its entirety). This dryness may be dryness in the eye.

In some embodiments, the coefficient of friction of an SBP is approximately that of naturally occurring, biological, and/or protein lubricants (e.g. lubricin). In some embodiments, SBPs may display a coefficient of friction lower than that of water, as measured by the experimental sliding speeds. In some embodiments, the coefficient of friction of an SBP is slightly lower than that of water. In some embodiments, the SBP is more lubricating that water. In some embodiments, the SBP is slightly more lubricating that water. In some embodiments, SBPs may be incorporated into a lubricant. Such methods may include any of those presented in International Patent Application Publication No. WO2013163407, the contents of which are herein incorporated by reference in their entirety. In some embodiments, processed silk and/or SBPs may be used as an excipient. In some embodiments, processed silk and/or SBPs may be used as an excipient to prepare a lubricant.

Lubricants comprising SBPs may be prepared in any format described herein. Non-limiting examples include solutions, gels, hydrogels, creams, drops, and sprays.

In some embodiments, an SBP is a lubricant prepared in the format of a nasal spray.

In some embodiments, an SBP is a lubricant prepared in the format of eye drops.

In some embodiments, an SBP is a lubricant prepared in the format of ear drops.

Biological Agents

In some embodiments, therapeutic agents include biological agents (also referred to as "biologics" or "biologicals"). As used herein, a "biological agent" refers to a therapeutic substance that is or is derived from an organism or virus. Examples of biological agents include, but are not limited to, proteins, organic polymers and macromolecules, carbohydrates, complex carbohydrates, nucleic acids, cells, tissues, organs, organisms, DNA, RNA, oligonucleotides, genes, and lipids. Biological agents may include processed silk. In some embodiments, biological agents may include any of the biologicals and compounds associated with specific categories of biological agents listed in Table 4, above. In some embodiments, biological agents may include any of those taught in International Publication Numbers WO2010123945 or WO2017123383, the contents of each of which are herein incorporated by reference in their entirety.

In some embodiments, SBP formulations may be used to deliver or administer biological agents. In some embodiments, delivery may include controlled release of one or more biological agents. Delivery may be carried out in vivo. In some embodiments, delivery is in vitro. Processed silk may be used to facilitate delivery and/or maintain stability of biological agents.

Antibodies

In some embodiments, SBP formulations may include one or more antibodies. As used herein, the term "antibody" refers to a class of immune proteins that bind to specific target antigens or epitopes. Herein, "antibody" is used in the broadest sense and embraces various natural and derivative formats that include, but are not limited to monoclonal antibodies, polyclonal antibodies, multispecific antibodies (e.g., bispecific antibodies that bind to two different epitopes), antibody conjugates (e.g., antibodies conjugates with therapeutic agents, cytotoxic agents, or detectable labels), antibody variants [e.g., antibody mimetics, chimeric antibodies (e.g., having components from two or more antibody types or species), and synthetic variants], and antibody fragments. Antibodies are typically amino acid-based but may include post-translational or synthetic modifications. In some embodiments, SBPs may be used to facilitate antibody delivery, as taught in International Publication Number WO2017139684 and Guziewicz et 71. (2011) Biomaterials 32(10):2642-2650, the contents of each of which are herein incorporated by reference in their entirety. In some embodiments, SBPs may be used to improve antibody stability.

In some embodiments, antibodies are VEGF antagonist or agonists. Non-limiting examples of monoclonal antibody therapeutic agents include canakinumab, palivizumab, panitumumab, inflectra, adalimumab-atto, alemtuzumab, nivolumab, ustekinumab, alefacept, ixekizumab, obiltoxaxamab, golimumab, pembrolizumab, atezolizumab, tocilizumab, basiliximab, abciximab, denosumab, omalizumab, belimumab, efalizumab, natalizumab, ustekinumab, trastuzumab, bezlotoxumab, adalimumab, rituximab, daclizumab, secukinumab, cetuximab, reslizumab, olaratumab, ipilimumab, ixekizumab, certolizumab pegol, and daclizumab. In some embodiments, antibodies may include, but are not limited to, any of those listed in Table 4, above.

Antigens

In some embodiments, SBP formulations include antigens. As used herein, the term "antigen" refers to any substance capable of provoking an immune response. In some embodiments, antigens include processed silk. In some embodiments, antigens include any of those presented in Table 4, above. In some embodiments, SBPs may be used to facilitate antigen delivery. In some embodiments, SBPs may stabilize included antigens. In some embodiments, SBPs are or are included in vaccines. Vaccines that include processed silk and methods of using such vaccines may include any of those taught in United States Publication Number US20170258889 or in Zhang et al. (2012) PNAS 109(30):11981-6 (retracted), the contents of each of which are herein incorporated by reference in their entirety. In some embodiments, formulation of an antigen with processed silk may be used to facilitate the delivery of said antigen in a vaccine, as taught in Zhang et al. (2012) PNAS 109(30):11981-6 (retracted).

Carbohydrates

In some embodiments, SBP formulations include carbohydrates. As used herein, the term "carbohydrate" refers to any members of a class of organic compounds that typically have carbon, oxygen, and hydrogen atoms and include, but are not limited to, simple and complex sugars. In some embodiments, carbohydrates may be monosaccharides or derivatives of a monosaccharides (e.g., ribose, glucose, fructose, galactose, mannose, abequose, arabinose, fucose, rhamnose, xylose, glucuronic acid, galactosamine, glucosamine, N-acetylgalactosamine, N-acetylglucosamine, iduronic acid, muramic acid, sialic acid, N-acetylmuramic acid, and N-acetylneuraminic acid). In some embodiments, carbohydrates may include disaccharides (e.g., sucrose, lactose, maltose, trehalose, and cellobiose). In some embodiments, carbohydrates are oligosaccharides or polysaccharides. In some embodiments, incorporation of carbohydrates may be used to stabilize SBPs. Such methods of use may include any of those taught in Li et al. (2017) Biomacromolecules 18(9):2900-5, the contents of which are herein incorporated by reference in their entirety. In some embodiments, carbohydrates may include, but are not limited to, any of those listed in Table 4, above.

Cells, Tissues, Microorganisms, and Microbiomes

In some embodiments, SBP formulations include cells, tissues, organs, and/or organisms. In some embodiments, such agents are used for direct treatment. In other embodiments, cell- or tissue-based therapeutic agents are incorporated into SBPs to prepare model systems. Such methods may include any of those taught in International Publication Number WO2017189832; Chen et al. (2017) PLoS One, 12(11):e0187880; or Chen et al. (2017) Stem Cell Research and Therapy 8:260, the contents of each of which are herein incorporated by reference in their entirety. In some embodiments, incorporated cells are stem cells (e.g., see International Publication Number WO2017189832; Chendang et al. (2017) J Biomaterials and Tissue Engineering 7:858-862; Xiao et al (2017) Oncotarget 8(49):86471-89487; Ciocci et al. (2017) Int J Biol Macromol S0141-8130(17):32839-8; Li et al. (2017) Stem Cell Res Ther 8(1):256; or Ruan et al. (2017) Biomed Pharmacother 97:600-6, the contents of each of which are herein incorporated by reference in their entirety). Examples of cell- or tissue-based therapeutic agents include, but are not limited to, human corneal stromal stem cells, human corneal epithelial cells, chicken dorsal root ganglions, bone mesenchymal stem cells, limbal epithelial stem cells, cardiac mesenchymal stem cells, adipose tissue-derived mesenchymal stem cells, periodontal ligament stem cells, human small intestinal enteroids, oral keratinocytes, fibroblasts, transfected fibroblasts, any 2-dimensional tissue, and any 3-dimensional tissue, T cells, embryonic stem cells, neural stem cells, mesenchymal stem cells, and hematopoietic stem cells. In some embodiments, cells used as therapeutic agents may include, but are not limited to, any of those listed in Table 4, above.

In some embodiments, therapeutic agents include bacteria or other microorganisms. Such therapeutic agents may be used to alter a microbiome. Examples of bacteria or other microorganisms that may be used as therapeutic agents in SBPs include any of those described in U.S. Pat. Nos. 9,688,967 and 9,688,967; US Publication Numbers US20170136073, US20170128499, US20160206666, US20170067065, and US20170014457; and International Publication Numbers WO2017123676, WO2017123675, WO2017123610, WO2017123592, WO2017123418, WO2016210384, WO2017075485, WO2017023818, WO2016210373, WO2017040719, WO2016210378, and WO2016106343, the contents of each of which are herein incorporated by reference in their entirety.

In some embodiments, SBP formulations include cellular therapeutics, such as bacteria and/or other microorganisms. As used herein, the term "microorganism" refers to a microscopic living thing (e.g. bacteria and/or fungi). In some embodiments, SBPs may be used to deliver cellular therapeutics (e.g., bacteria and/or other microorganisms) to alter or improve the microbiome of a subject or patient. In some embodiments, bacteria and/or other microorganisms used as therapeutic agents may include, but are not limited to, any of those described in U.S. Pat. No. 9,688,967, or 9,688,967; in US Patent Publication Numbers US20170136073, US20170128499, US20160206666, US20170067065, or US20170014457; or in International Publication Numbers WO2017123676, WO2017123675, WO2017123610, WO2017123592, WO2017123418, WO2016210384, WO2017075485, WO2017023818, WO2016210373, WO2017040719, WO2016210378, WO2016200614, WO2017087580, or WO2016106343, the contents of each of which are herein incorporated by reference in their entirety. In some embodiments, said bacteria and/or microorganisms are formulated as a part of SBPs. In some embodiments, the bacteria and/or microorganisms may be supported during delivery using SBPs. In some embodiments, bacteria and/or other microorganisms used as therapeutic agents may be engineered. e.g., by any method described in the U.S. Pat. No. 9,688,967 or 9,487,764; or in International Publication Numbers WO2016200614 and WO2017087580, the contents of each of which are herein incorporated by reference in their entirety.

In some embodiments, SBPs described herein maintain and/or improve the stability of bacteria and/or other microorganisms. The maintenance and/or improvement of stability may be determined by comparing stability with SBP compositions to stability with compositions lacking SBPs or to standard compositions in the art. Maintenance and/or improvement of stability may be found or appreciated where superior or durational benefits are observed with SBPs. In some embodiments, SBPs maintain and/or improve the stability of bacteria and/or other microorganisms that can be used in bacterial or microbial therapy.

In some embodiments, bacteria and/or other microorganisms may be used as biopesticides. As used herein, the term "biopesticide" refers to a composition with a bacteria, microorganisms, or biological cargo used to harm, kill, or prevent the spread of pests. Biopesticides have been used in agricultural development, as described in U.S. Pat. No. 6,417,163, the contents of which are herein incorporated by reference in their entirety. In some embodiments, SBPs that include bacteria, microorganisms, and/or microbiomes, may be used as biopesticides to support agricultural applications.

In some embodiments, bacteria and/or other microorganisms formulated as a part of SBPs may include one or more of the following microbes: *Abiotrophia, Abiotrophia dejectiva, Acetanaerobacterium, Acetanaerobacterium elongatum, Acetivibrio, Acetivibrio bacterium, Acetobacterium, Acetobacternum woodi, Acholeplasma Acidaminococcus, Acidaminococcus fermentans, Acidianus, Acidianus brierleyi, Acidovorax, Acinetobacter, Acinetobacter guillouiae, Acinetobacter juni, Actinobacillus, Actinobacillus* M1933/96/1, *Actinomyces, Actinomyces* ICM34, *Actinomyces* ICM41, *Actinomyces* ICM54, *Actinomyces lingnae, Actinomyces odontolyticus, Actinomyces oral, Actinomyces* ph3, *Adlercreutzia, Adlercreutzia equolifaciens, Adlercreutzia intestinal, Aerococcus, Aeromonas, Aeromonas* 165C, *Aeromonas hydrophila, Aeromonas* RC50, *Aeropyrum, Aeropyrum pernix, agglomerans, Aggregatibacter, Agreia, Agreia bicolorata Agromonas, Agromonas* CS30, *Akkermansia, Akkermansia muciniphila, Alistipes, Alistipes* ANH, *Alistipes* AP11, *Alistipes bacterium, Alistipes* CCUG, *Alistipes* DJF B185, *Alistipes* DSM, *Alistipes* EBA6-25c12, *Alistipes finegoldii, Alisdpes indistinctus, Alistipes* JC136, *Alistipes* NML05A004, *Alistipes onderdonkii, Alistipes putredinis, Alistipes* RMA, *Alistipes senegalensis, Alisipes shahii, Alistipes Smarlab, Alkalibaculum, Alkaliflexus, Allisonella, Allisonella histaminiformans, Alloscardovia, Alloscardovia omnicolens, Anaeroilum, Anaerofustis, Anaerofustis stercorihominis, Anaeroplasma, Anaerostipes, Anaerostipes* 08964, *Anaerosdpes* 494a, *Anaerostipes* 5_1_63FAA, *Anaerostipes* AIP, *Anaerostipes bacterium, Anaerostipes butyraticus, Anaerostipes caccae, Anaerostipes hadrum, Anaerostipes* IE4, *Anaerostipes indolis, Anaerostipes* ly-2, *Anaerotruncus, Anaerotruncus colihominis, Anaerotruncus* NML, *Aquincola, Arcobacter, Arthrobacter, Arthrobacter* FV-1, *Asaccharobacter, Asaccharobacter celatus, Asteroleplasma, Atopobacter, Atopobacter phocae, Atopobium, Atopobium parvulum, Atopobium rimae, Bacteriovorax, Bacteroides, Bacteroides* 31SF18, *Bacteroides* 326-8, *Bacteroides* 35AE3, *Bacteroides* 35AE37, *Bacteroides* 35BE34, *Bacteroides* 4072, *Bacteroides* 7853, *Bacteroides acidifaciens, Bacteroides* API, *Bacteroides* AR20, *Bacteroides* AR29, *Bacteroides* B2, *Bacteroides bacterium, Bacteroides barnesiae, Bacteroides* BLBE-6, *Bacteroides* BV-1, *Bacteroides caccae, Bacteroides* CannelCatfish9, *Bacteroides cellulosilyticus, Bacteroides chinchillae, Bacteroides* CIP 103040, *Bacteroides clarus, Bacteroides coprocola, Bacteroides coprophilus, Bacteroides* D8, *Bacteroides* DJF_B097, *Bacteroides* dnLKV2, *Bacteroides* dnLKV7, *Bacteroides* dnLKV9, *Bacteroides dorei, Bacteroides* EBA5-17, *Bacteroides eggerthii, Bacteroides enrichment, Bacteroides* F-4, *Bacteroides faecichinchillae, Bacteroides faecis, Bacteroides fecal, Bacteroides finegoldii, Bacteroides fraglis, Bacteroides gallinarum, Bacteroides helcogenes, Bacteroides* c1292, *Bacteroides intestinalis, Bacteroides massiliensis, Bacteroides mpnisolate, Bacteroides* NB-8, *Bacteroides* new, *Bacteroides* NLAE-zl-c204, *Bacteroides* NLAE-zl-c205, *Bacteroides* NLAE-zl-c206, *Bacteroides* NLAE-zl-c207, *Bacteroides* NLAE-zl-c211, *Bacteroides* NLAE-zl-c218, *Bacteroides* NLAE-zl-c257, *Bacteroides* NLAE-zl-c260 *Bacteroides* NLAE-zl-c261, *Bacteroides* NLAE-zl-c263, *Bacteroides* NLAE-zl-c308, *Bacteroides* NLAE-zl-c315, *Bacteroides* NLAE-zl-c322,

*Bacteroides* NLAE-zl-c324, *Bacteroides* NLAE-zl-c331, *Bacteroides* NLAE-zl-c339 *Bacteroides* NLAE-zl-c36, *Bacteroides* NLAE-zl-c367, *Bacteroides* NLAE-zl-c375, *Bacteroides* NLAE-zl-c376, *Bacteroides* NLAE-zl-c380, *Bacteroides* NLAE-zl-c391, *Bacteroides* NLAE-zl-c459, *Bacteroides* NLAE-zl-c484, *Bacteroides* NLAE-zl-c501, *Bacteroides* NLAE-zl-c504, *Bacteroides* NLAE-zl-c515, *Bacteroides* NLAE-zl-c519, *Bacteroides* NLAE-zl-c532 *Bacteroides* NLAE-zl-c557, *Bacteroides* NLAE-zl-c57, *Bacteroides* NLAE-zl-c574, *Bacteroides* NLAE-zl-c592, *Bacteroides* NLAE-zl-c13, *Bacteroides* NLAE-zl-c158, *Bacteroides* NLAE-zl-c159, *Bacteroides* NLAE-zl-c161, *Bacteroides* NLAE-zl-c163, *Bacteroides* NLAE-zl-c167, *Bacteroides* NLAE-zl-c172, *Bacteroides* NLAE-zl-c18, *Bacteroides* NLAE-zl-c182, *Bacteroides* NLAE-zl-c190, *Bacteroides* NLAE-zl-c198, *Bacteroides* NLAE-zl-g209, *Bacteroides* NLAE-zl-g212, *Bacteroides* NLAE-zl-g213, *Bacteroides* NLAE-zl-g218, *Bacteroides* NLAE-zl-g221, *Bacteroides* NLAE-zl-g228, *Bacteroides* NLAE-zl-g234, *Bacteroides* NLAE-zl-g237, *Bacteroides* NLAE-zl-g24, *Bacteroides* NLAE-zl-g245, *Bacteroides* NLAE-zl-g257, *Bacteroides* NLAE-zl-g27, *Bacteroides* NLAE-zl-g285, *Bacteroides* NLAE-zl-g288, *Bacteroides* NLAE-zl-g295, *Bacteroides* NLAE-zl-g296, *Bacteroides* NLAE-zl-g303, *Bacteroides* NLAE-zl-g310, *Bacteroides* NLAE-zl-g312, *Bacteroides* NLAE-zl-g327, *Bacteroides* NLAE-zl-g329, *Bacteroides* NLAE-zl-g336, *Bacteroides* NLAE-zl-g338, *Bacteroides* NLAE-zl-g347, *Bacteroides* NLAE-zl-g356, *Bacteroides* NLAE-zl-g373, *Bacteroides* NLAE-zl-g376, *Bacteroides* NLAE-zl-g380, *Bacteroides* NLAE-zl-g382, *Bacteroides* NLAE-zl-g385, *Bacteroides* NLAE-zl-g4, *Bacteroides* NLAE-zl-g422, *Bacteroides* NLAE-zl-g437, *Bacteroides* NLAE-zl-g454, *Bacteroides* NLAE-zl-g455, *Bacteroides* NLAE-zl-g456, *Bacteroides* NLAE-zl-g458, *Bacteroides* NLAE-zl-g459, *Bacteroides* NLAE-zl-g46, *Bacteroides* NLAE-zl-g461, *Bacteroides* NLAE-zl-g475, *Bacteroides* NLAE-zl-g481, *Bacteroides* NLAE-zl-g484, *Bacteroides* NLAE-zl-g5, *Bacteroides* NLAE-zl-g502, *Bacteroides* NLAE-zl-g515, *Bacteroides* NLAE-zl-g518, *Bacteroides* NLAE-zl-g521, *Bacteroides* NLAE-zl-g54, *Bacteroides* NLAE-zl-g6, *Bacteroides* NLAE-zl-g8, *Bacteroides* NLAE-zl-g80, *Bacteroides* NLAE-zl-g98, *Bacteroides* NLAE-zl-g117, *Bacteroides* NLAE-zl-g105, *Bacteroides* NLAE-zl-g127, *Bacteroides* NLAE-zl-g136, *Bacteroides* NLAE-zl-g143, *Bacteroides* NLAE-zl-g157, *Bacteroides* NLAE-zl-g167, *Bacteroides* NLAE-zl-g171, *Bacteroides* NLAE-zl-g187, *Bacteroides* NLAE-zl-g194, *Bacteroides* NLAE-zl-g195, *Bacteroides* NLAE-zl-g199, *Bacteroides* NLAE-zl-h207, *Bacteroides* NLAE-zl-h22, *Bacteroides* NLAE-zl-h250, *Bacteroides* NLAE-zl-h251, *Bacteroides* NLAE-zl-h28, *Bacteroides* NLAE-zl-h313, *Bacteroides* NLAE-zl-h319, *Bacteroides* NLAE-zl-h321, *Bacteroides* NLAE-zl-h328, *Bacteroides* NLAE-zl-h334, *Bacteroides* NLAE-zl-h390, *Bacteroides* NLAE-zl-h391, *Bacteroides* NLAE-zl-h414, *Bacteroides* NLAE-zl-h416, *Bacteroides* NLAE-zl-h419, *Bacteroides* NLAE-zl-h429, *Bacteroides* NLAE-zl-h439, *Bacteroides* NLAE-zl-h444, *Bacteroides* NLAE-zl-h45, *Bacteroides* NLAE-zl-h46, *Bacteroides* NLAE-zl-h462, *Bacteroides* NLAE-zl-h463, *Bacteroides* NLAE-zl-h465 *Bacteroides* NLAE-zl-h468, *Bacteroides* NLAE-zl-h471, *Bacteroides* NLAE-zl-h472, *Bacteroides* NLAE-zl-h474, *Bacteroides* NLAE-zl-h479, *Bacteroides* NLAE-zl-h482, *Bacteroides* NLAE-zl-h49, *Bacteroides* NLAE-zl-h493, *Bacteroides* NLAE-zl-h496, *Bacteroides* NLAE-zl-h497, *Bacteroides* NLAE-zl-h499, *Bacteroides* NLAE-zl-h50, *Bacteroides* NLAE-zl-h531, *Bacteroides* NLAE-zl-h535, *Bacteroides* NLAE-zl-h8, *Bacteroides* NLAE-zl-h120, *Bacteroides* NLAE-zl-h15, *Bacteroides* NLAE-zl-h62, *Bacteroides* NLAE-zl-h17, *Bacteroides* NLAE-zl-h174, *Bacteroides* NLAE-zl-h18, *Bacteroides* NLAE-zl-h188, *Bacteroides* NLAE-zl-h192, *Bacteroides* NLAE-zl-h94 *Bacteroides* NLAE-zl-h195, *Bacteroides* NLAE-zl-p208, *Bacteroides* NLAE-zl-p213, *Bacteroides* NLAE-zl-p228, *Bacteroides* NLAE-zl-p233, *Bacteroides* NLAE-zl-p267, *Bacteroides* NLAE-zl-p278, *Bacteroides* NLAE-zl-p282, *Bacteroides* NLAE-zl-p286, *Bacteroides* NLAE-zl-p295, *Bacteroides* NLAE-zl-p299 *Bacteroides* NLAE-zl-p301, *Bacteroides* NLAE-zl-p302, *Bacteroides* NLAE-zl-p304, *Bacteroides* NLAE-zl-p317, *Bacteroides* NLAE-zl-p319, *Bacteroides* NLAE-zl-p32, *Bacteroides* NLAE-zl-p332 *Bacteroides* NLAE-zl-p349, *Bacteroides* NLAE-zl-p35, *Bacteroides* NLAE-zl-p356 *Bacteroides* NLAE-zl-p370, *Bacteroides* NLAE-zl-p371, *Bacteroides* NLAE-zl-p376, *Bacteroides* NLAE-zl-p395, *Bacteroides* NLAE-zl-p402 *Bacteroides* NLAE-zl-p403, *Bacteroides* NLAE-zl-p409, *Bacteroides* NLAE-zl-p412, *Bacteroides* NLAE-zl-p436, *Bacteroides* NLAE-zl-p438, *Bacteroides* NLAE-zl-p440 *Bacteroides* NLAE-zl-p447, *Bacteroides* NLAE-zl-p448, *Bacteroides* NLAE-zl-p451, *Bacteroides* NLAE-zl-p476, *Bacteroides* NLAE-zl-p478, *Bacteroides* NLAE-zl-p483, *Bacteroides* NLAE-zl-p489, *Bacteroides* NLAE-zl-p493, *Bacteroides* NLAE-zl-p557, *Bacteroides* NLAE-zl-p559, *Bacteroides* NLAE-zl-p564, *Bacteroides* NLAE-zl-p565, *Bacteroides* NLAE-zl-p572, *Bacteroides* NLAE-zl-p573, *Bacteroides* NLAE-zl-p576, *Bacteroides* NLAE-zl-p591, *Bacteroides* NLAE-zl-p592, *Bacteroides* NLAE-zl-p631, *Bacteroides* NLAE-zl-p633, *Bacteroides* NLAE-zl-p696 *Bacteroides* NLAE-zl-p7, *Bacteroides* NLAE-zl-p720, *Bacteroides* NLAE-zl-p730, *Bacteroides* NLAE-zl-p736, *Bacteroides* NLAE-zl-p737, *Bacteroides* NLAE-zl-p754, *Bacteroides* NLAE-zl-p759, *Bacteroides* NLAE-zl-p774, *Bacteroides* NLAE-zl-p828, *Bacteroides* NLAE-zl-p854, *Bacteroides* NLAE-zl-p860, *Bacteroides* NLAE-zl-p886, *Bacteroides* NLAE-zl-p887, *Bacteroides* NLAE-zl-p900, *Bacteroides* NLAE-zl-p909, *Bacteroides* NLAE-zl-p913, *Bacteroides* NLAE-zl-p916, *Bacteroides* NLAE-zl-p920, *Bacteroides* NLAE-zl-p96, *Bacteroides* NLAE-zl-p104, *Bacteroides* NLAE-zl-p105, *Bacteroides* NLAE-zl-p08, *Bacteroides* NLAE-zl-p132, *Bacteroides* NLAE-zl-p133, *Bacteroides* NLAE-zl-p151, *Bacteroides* NLAE-zl-p157, *Bacteroides* NLAE-zl-p66, *Bacteroides* NLAE-zl-p167 *Bacteroides* NLAE-zl-p171, *Bacteroides* NLAE-zl-p178, *Bacteroides* NLAE-zl-p187, *Bacteroides* NLAE-zl-p191, *Bacteroides* NLAE-zl-p196, *Bacteroides nordii*, *Bacteroides oleiciplenus*, *Bacteroides ovatus*, *Bacteroides paurosaccharolyticus*, *Bacteroides plebetus*, *Bacteroides* R6, *Bacteroides rodentium*, *Bacteroides* S-17, *Bacteroides* S-18, *Bacteroides salyersiae*, *Bacteroides* SLCl-38, *Bacteroides* Smarlab, *Bacteroides* 'Smarlab, *Bacteroides stercorirosoris*, *Bacteroides stercoris*, *Bacteroides* str, *Bacteroides thetaiotaomicron*, *Bacteroides* TP-5, *Bacteroides uniformis*, *Bacteroides vulgatus*, *Bacteroides* WA1, *Bacteroides* WH2, *Bacteroides* WH302, *Bacteroides* WH305, *Bacteroides* X077B42, *Bacteroides* XB12B, *Bacteroides* XB44A, *Bacteroides xylanisolvens*, *Barnesiella*, *Barnesiella intestinihominis*, *Barnesiella* NSB1, *Barnesiella viscericola*, *Bavariicoccus*, *Bdellovibrio*, *Bdellovibrio* oral, *Bergeriella*, *Bifidobacterium*, *Bifidobacterium* 103, *Bifidobacterium* 108, *Bifidobacterium* 113, *Bifidobacterium* 120, *Bifidobacterium* 138, *Bifidobacterium* 33, *Bifidobacterium* Acbbto5, *Bifidobacterium adolescentis*, *Bifidobacterium* Amsbbt12, *Bifidobacterium angulatum*, *Bifidobacterium animalis*, *Bifidobacterium bacterium*, *Bifidobacterium bifidum* *Bifidobacterium* Bisn6, *Bifidobacte-* rium Bma6, *Bifidobacterium breve*, *Bifidobacterium catenulatum*, *Bifidobacterium choerinum*, *Bifidobacterium coryneforme*, *Bifidobacterium dentium*, *Bifidobacterium* DJF_WC44, *Bifidobacterium* F-10 *Bifidobacterium* F-11, *Bifidobacterium* group, *Bifidobacterium* h12, *Bifidobacterium* HMLN1, *Bifidobacterium* HMLN12, *Bifidobacterium* HMLN5, *Bifidobacterium* iarfr2341d, *Bifidobacterium* iarfr642d48, *Bifidobacterium* 10332, *Bifidobacterium indicum*, *Bifdobacerium kashiwanohense*, *Bifidobacterium* LIS-LUCIII-2, *Bifidobacterium longum*, *Bifidobacterium* M45, *Bifidobacterium merycicum*, *Bifidobacterium minimum*, *Bifidobacterium* MSX5B *Bifidobacterium* oral, *Bifidobacterium* PG12A, *Bifidobacterium* PL1, *Bifidobacterium pseudocatenulatum*, *Bifidobacterium pseudolongum*, *Bifidobacterium pullorum*, *Bifidobacterium ruminantium*, *Bifidobacterium* S-10, *Bifidobacterium saeculare*, *Bifidobacterium saguini*, *Bifidobacterium scardovii*, *Bifidobacterium simiae*, *Bifidobacterium* SLPYG-1, *Bifidobacterium stercoris*, *Bifidobacterium* TM-7, *Bifidobacterium* Trm9, *Bilophila*, *Bilophila* NLAE-zl-h528, *Bilophila wadsworthia*, *Blautia*, *Blautia bacterium*, *Blautia* CE2, *Blautia* CE6, *Blautia coccoides*, *Blautia* DJF_VR52, *Blautia* DJF_VR67, *Blautia* DJF_VR70kl, *Blautia formate*, *Blautia glucerasea*, *Blautia hansenii*, *Blautia* ic272, *Blautia* IE5, *Blautia* K-1, *Blautia luti*, *Blautia* M-1, *Blautia mpnisolate*, *Blautia* NLAE-zl-c25, *Blautia* NLAE-zl-c259, *Blautia* NLAE-zl-c51, *Blautia* NLAE-zl-c520, *Blautia* NLAE-zl-c542, *Blautia* NLAE-zl-c544, *Blautia* NLAE-zl-h27, *Blautia* NLAE-zl-h316, *Blautia* NLAE-zl-h317, *Blautia obeum*, *Blautia producta*, *Blautia productus*, *Blautia schinki*, *Blautia* Ser5, *Blautia* Ser8, *Blautia* WAL, *Blautia wexlerae*, *Blautia* YHC-4, *Brenneria*, *Brevibacterium*, *Brochothrix*, *Brochothrix thermosphacta*, *Buttiauxella*, *Butiauxella* 57916, *Buttiauxella gaviniae*, *Butyricicoccus*, *Butyricicoccus bacterium*, *Butyricimonas*, *Butricimonas* 180-3, *Butyricimonas* 214-4, *Butyricimonas bacterium*, *Butyricimonas* GD2, *Butyricimonas synergisica*, *Butyricimonas virosa*, *Butyrivibrio*, *Butyrivibrio fibrisolvens*, *Butyrivibrio hungatei*, *Caldimicrobium*, *Caldisercum*, *Campylobacter*, *Campylobacter coli*, *Campylobacter hominis*, *Capnocytophaga*, *Carnobactenum*, *Carnobacterium alterfinditum*, *Caryophanon*, *Catenibacterium*, *Catenibacterium mitsuokai*, *Catonella*, *Caulobacter*, *Cellulophaga*, *Cellulosilyicum*, *Cetobacterium*, *Chelatococcus*, *Chlorobium*, *Chryseobacterium*, *Chryseobacterium* A1005, *Chryseobacterium* KJ9C8, *Citrobacter*, *Citrobacter* 1, *Citrobacter* 191-3, *Citrobacter agglomerans*, *Citrobacter amalonaticus*, *Citrobacter ascorbata*, *Citrobacter bacterium*, *Citrobacter* BinzhouCLT, *Citrobacter braakii*, *Citrobacter* enrichment, *Citrobacter* F24, *Citrobacter* F96, *Citrobacter farmeri*, *Citrobacter freundii*, *Citrobacter gillenii*, *Citrobacter* HBKC_SR1, *Citrobacter* HD4.9, *Citrobacter hormaechei*, *Citrobacter* ka55, *Citrobacter lapagei*, *Citrobacter* LAR-1, *Citrobacter ludwigii*, *Citrobacter* MEB5, *Citrobacter* MS36, *Citrobacter murliniae*, *Citrobacter* NLAE-zl-c269, *Citrobacter* P014, *Citrobacter* P042bN, *Citrobacter* P046a, *Citrobacter* P073, *Citrobacter* SR3, *Citrobacter* T1, *Citrobacter* tnt4, *Citrobacter* tnt5, *Citrobacter* trout, *Citrobacter* TSA-1, *Citrobacter werkmanii*, *Cloacibacillus*, *Cloacibacillus* adv66, *Cloacibacillus* NLAE-zl-p702, *Cloacibacillus* NML05A017, *Cloacibacterium*, *Collinsella*, *Collinsella aerofaciens*, *Collinsella* A-1, *Collinsella* AUH-Julong21, *Collinsella bacterium*, *Collinsella* CCUG, *Comamonas*, *Comamonas straminea*, *Comamonas testosteroni*, *Conexibacter*, *Coprobacillus*, *Coprobacillus bacterium*, *Coprobacillus catenitormis*, *Coprobacillus* TM-40, *Coprococcus*, *Coprococcus* 14505, *Coprococcus bacterium*, *Coprococcus catus*, *Coprococcus comes*, *Coprococcus eutactus*, *Coprococcus nexile*, *Coraliomargarita*, *Coraliomargarita fucoidanolyticus*, *Coraliomargarita marisflavi*, *Corynebacterium*, *Corynebacterium amycolatum*, *Cornebacterium durum*, *Coxiella*, *Cronobacter*, *Cronobacter dublinensis*, *Cronobacter sakazakii*, *Cronobacter turicensis*, *Cryptobacterium*, *Cryptobacterium curtum*, *Cupriaviduis*, *Cupriavidus eutropha*, *Dechloromonas*, *Dechloromonas* HZ, *Desulfobacterium*, *Desulfobulbus*, *Desulfopila*, *Desulfopila* La4.1, *Desulfovibrio*, *Desulfovibrio* D4 *Desulfovibrio desulfriricans*, *Desulfovibrio* DSM 2803, *Desulfovibrio* enrichment, *Desulfovibrio fairfieldensis*, *Desulfovibrio* LNB1, *Desulfovibrio piger*, *Dialister*, *Dialister* E2_20, *Dialister* GBA27, *Dialister invisus*, *Dialister* oral, *Dialister succinatiphilus*, *Dorea*, *Dorea* auhjulong64, *Dorea bacterium*, *Dorea formicigenerans*, *Dorea longicatena*, *Dorea mpnisolate*, *Dysgonomonas*, *Dysgonomonas gadei*, *Edwardsiella*, *Edwardsiella tarda*, *Eggerthella*, *Eggerthella* El, *Eggerthella lenta*, *Eggerthella* MLG043, *Eggerthella* MVA1, *Eggerthella* S6-CL *Eggerthella* SDG-2, *Eggerthella sinensis*, *Eggerthella* str, *Enhydrobacter*, *Enterobacter*, *Enterobacter* 1050, *Enterobacter* 112, *Enterobacter* 1122, *Enterobacter* 77000, *Enterobacter* 82353, *Enterobacter* 9C, *Enterobacter* A5C, *Enterobacter adecarboxylata*, *Enterobacter aerogenes*, *Enterobacter agglomerans*, *Enterobacter* AJAR-A2, *Enterobacter amnigenus*, *Enterobacter asbunae*, *Enterobacter* B 1(2012), *Enterobacter* B363, *Enterobacter* B509, *Enterobacter bacterium*, *Enterobacter* Badong3, *Enterobacter* BEC441, *Enterobacter* C8, *Enterobacter cancerogenus*, *Enterobacter cloacae*, *Enterobacter* CO, *Enterobacter* core2 *Enterobacter cowanhi*, *Enterobacter* dc6, *Enterobacter* DRSBII, *Enterobacter* enrichment, *Enterobacter* FLI3-2-1, *Enterobacter* GIST-NKst9, *Enterobacter* GIST-NKstlO, *Enterobacter* GJl-11, *Enterobacter* gx-148, *Enterobacter hormaechei*, *Enterobacter* I-Bh20-21, *Enterobacter* ICB113, *Enterobacter kobei*, *Enterobacter* KW14, *Enterobacter ludwigi*, *Enterobacter* M10_1B, *Enterobacter* M1R3, *Enterobacter* marine, *Enterobacter* NCCP-167, *Enterobacter* of *Enterobacter oryzae*, *Enterobacter oxytoca*, *Enterobacter* P101, *Enterobacter* SEL2, *Enterobacter* SI 1, *Enterobacter* SPh, *Enterobacter* SSASP5, *Enterobacter terrigena*, *Enterobacter* TNT3, *Enterobacter* TP2MC, *Enterobacter* TS4, *Enterobacter* TSSAS2-48, *Enterobacter* ZYXCA1, *Enterococcus*, *Enterococcus* 020824/02-A, *Enterococcus* 1275b, *Enterococcus* 16C, *Enterococcus* 48, *Enterococcus* 6114, *Enterococcus* ABRIINW-H61, *Enterococcus asini*, *Enterococcus avium*, *Enterococcus azikeevi*, *Enterococcus bacterium*, *Enterococcus* BBDP57, *Enterococcus* BPH34, *Enterococcus* Bt, *Enterococcus canis*, *Enterococcus casseflavus*, *Enterococcus* CmNA2, *Enterococcus* Da-20, *Enterococcus devriesei*, *Enterococcus dispar*, *Enterococcus* DJF 030, *Enterococcus* DMB4, *Enterococcus durans*, *Enterococcus* enrichment, *Enterococcus* F81, *Enterococcus faecalis*, *Enterococcus faecium*, *Enterococcus* fcc9, *Enterococcus* fecal, *Enterococcus flavescens*, *Enterococcus fluvialis*, *Enterococcus* FR-3, *Enterococcus* FUA3374, *Enterococcus galinarum*, *Enterococcus* GSC-2, *Enterococcus* GYPB01, *Enterococcus hermanniensis*, *Enterococcus hirae*, *Enterococcus lactis*, *Enterococcus malodoratus*, *Enterococcus* manure, *Enterococcus* marine, *Enterococcus* MNC1, *Enterococcus moraviensis*, *Enterococcus* MS2, *Enterococcus mundtii*, *Enterococcus* NAB 15, *Enterococcus* NBRC, *Enterococcus* NLAE-zl-c434, *Enterococcus* NLAE-zl-g87, *Enterococcus* NLAE-zl-g106, *Enterococcus* NLAE-zl-h339, *Enterococcus* NLAE-zl-h375, *Enterococcus* NLAE-zl-h381, *Enterococcus* NLAE-zl-h383, *Enterococcus* NLAE-zl-h405, *Enterococcus* NLAE-zl-p401, *Enterococcus* NLAE-zl-p650 *Enterococcus*

NLAE-zl-p116, *Enterococcus* NLAE-zl-p148, *Enterococcus pseudoavium*, *Enterococcus* R-25205, *Enterococcus raffinosus*, *Enterococcus rottae*, *Enterococcus* R107, *Enterococcus saccharolyticus*, *Enterococcus saccharominimus*, *Enterococcus sanguinicola*, *Enterococcus* SCA16, *Enterococcus* SCA2, *Enterococcus* SF138, *Enterococcus* SF-1, *Enterococcus sulfureus*, *Enterococcus* SV6, *Enterococcus* te32a, *Enterococcus* te42a, Enterococus te45r, *Enterococcus* te49a, *Enterococcus* te51a, *Enterococcus* te58r, *Enterococcus* te59r, *Enterococcus* te61r, *Enterococcus* te93r, *Enterococcus* te95a, *Enterococcus tela*, *Enterorhabdus*, *Enterorhabdus caecimuris*, entomophaga, *Erwinia*, *Erwinia agglomerans*, *Erwinia enterica*, *Erwinia rhapontici*, *Erwinia tasmaniensis*, Erysipelotrichaceae incertae *sedis*, Erysipelotrichaceae incertae *sedis* aff Erysipelotrichaceae incertae *sedis bacterium*, Erysipelotrichaceae incertae *sedis biforme*, Erysipelotrichaceae incertae *sedis* C-1 Erysipelotrichaceae incertae *sedis cylindroides*, Erysipelotrichaceae incertae *sedis* GK2, Erysipelotrichaceae incertae *sedis innocuum*, Erysipelotrichaceae incertae *sedis* NLAE-zl-c332, Erysipelotrichaceae incertae *sedis* NLAE-zl-c340, Erysipelotrichaceae incertae *sedis* NLAE-zl-g420, Erysipelotrichaceae incertae *sedis* NLAE-zl-g425, Erysipelotrichaceae incertae *sedis* NLAE-zl-g440, Erysipelotrichaceae incertae *sedis* NLAE-zl-g463, Erysipelotrichaceae incertae *sedis* NLAE-zl-h340, Erysipelotrichaceae incertae *sedis* NLAE-zl-h354, Erysipelotrichaceae incertae *sedis* NLAE-zl-h379, Erysipelotrichaceae incertae *sedis* NLAE-zl-h380, Erysipelotrichaceae incertae *sedis* NLAE-zl-h385, Erysipelotrichaceae incertae *sedis* NLAE-zl-h410, Erysipelotrichaceae incertae *sedis tortuosum*, *Escherichia/Shigella*, *Escherichia/Shigella* 29(2010), *Escherichia/Shigella* 4091, *Escherichia/Shigella* 4104, *Escherichia/Shigella* 8gw18, *Escherichia/Shigella* A94, *Escherichia/Shigella albertii*, *Escherichia/Shigella* B-1012, *Escherichia/Shigella* B4, *Escherichia Shigella bacterium*, *Escherichia/Shigella* BBDP15, *Escherichia/Shigella* BBDP80, *Escherichia/Shigella boydii*, *Escherichia/Shigella carotovorum*, *Escherichia/Shigella* CERAR, *Escherichia/Shigella coli*, *Escherichia/Shigella* DBC-1, *Escherichia/Shigella* dc262011, *Escherichia/Shigella dysenteriae*, *Escherichia/Shigella* enrichment, *Escherichia/Shigella escherichia*, *Escherichia/Shigella fecal*, *Escherichia/Shigella fergusonii*, *Escherichia/Shigella flexneri*, *Escherichia/Shigella* GDR05, *Escherichia/Shigella* GDR07, *Escherichia/Shigella* H7, *Escherichia/Shigella marine*, *Escherichia/Shigella* ML2-46, *Escherichia/Shigella mpnisolate*, *Escherichia/Shigella* NA, *Escherichia/Shigella* NLAE-zl-g330, *Escherichia/Shigella* NLAE-zl-g400, *Escherichia/Shigella* NLAE-zl-g441, *Escherichia/Shigella* NLAE-zl-g506, *Escherichia/Shigella* NLAE-zl-h204, *Escherichia/Shigella* NLAE-zl-h208, *Escherichia/Shigella* NLAE-zl-h209, *Escherichia/Shigella* NLAE-zl-h213, *Escherichia/Shigella* NLAE-zl-h214, *Escherichia/Shigella* NLAE-zl-h4, *Escherichia/Shigella* NLAE-zl-h435, *Escherichia/Shigella* NLAE-zl-h81, *Escherichia/Shigella* NLAE-zl-p21 *Escherichia/Shigella* NLAE-zl-p235, *Escherichia/Shigella* NLAE-zl-p237, *Escherichia/Shigella* NLAE-zl-p239, *Escherichia/Shigella* NLAE-zl-p25, *Escherichia/Shigella* NLAE-zl-p252, *Escherichia/Shigella* NLAE-zl-p275, *Escherichia/Shigella* NLAE-zl-p280, *Escherichia/Shigella* NLAE-zl-p51, *Escherichia/Shigella* NLAE-zl-p53, *Escherichia Shigella* NLAE-zl-p669, *Escherichia/Shigella* NLAE-zl-p676, *Escherichia/Shigella* NLAE-zl-p717, *Escherichia/Shigella* NLAE-zl-p731, *Escherichia/Shigella* NLAE-zl-p826, *Escherichia/Shigella* NLAE-zl-p877 *Escherichia/Shigella* NLAE-zl-p884, *Escherichia/Shigella* NLAE-zl-p126, *Escherichia/Shigella* NLAE-zl-p198, *Escherichia/Shigella* NMU-ST2, *Escherichia/Shigella* ocl 82011, *Escherichia Shigella* of, *Escherichia/Shigella proteobacterium*, *Escherichia/Shigella* Q1, *Escherichia/Shigella sakazakii*, *Escherichia/Shigella* SF6, *Escherichia/Shigella* sm1719, *Escherichia/Shigella* SOD-7317, *Escherichia/Shigella sonnei*, *Escherichia/Shigella* SW86, *Escherichia/Shigella vulneris*, *Ethanoligenens*, *Ethanoligenens harbinense*, *Eubacterium*, *Eubacterium* ARC-2, *Eubacterium callanderi*, *Eubacterium* E-1, *Eubacterium* G3(2011), *Eubacterium infirmum*, *Eubacterium limosum*, *Eubacterium methylotrophicum*, *Eubacterium* NLAE-zl-p439, *Eubacterium* NLAE-zl-p4S7, *Eubacterium* NLAE-zl-p458, *Eubacterium* NLAE-zl-p469, *Eubacterium* NLAE-zl-p474, *Eubacterium oral*, *Eubacterium saphenum*, *Eubacterium sulci*, *Eubacterium* WAL, *Euglenida*, *Euglenida longa*, *Faecalibacterium*, *Faecalibacterium bacterium*, *Faecalibacterium canine*, *Faealibacterium* DJF VR20, *Faecalibacterium* ic1379, *Faecalibacterium prausnitzii*, *Filibacter*, *Filibacter globispora*, *Flavobacterium*, *Flavobacterium* SSL03, *Flavonifractor*, *Flavonifractor* AUH-JLC235, *Flavonifractor* enrichment, *Flavonifractor* NLAE-zl-c354, *Flavonifractor orbiscindens*, *Flavonifractor plautil*, *Francisella*, *Francisella piscicida*, *Fusobacterium*, *Fusobacterium nucleatum*, *Gardnerella*, *Gardnerella vaginalis*, *Gemmiger*, *Gemmiger* DJF_VR33k2, *Gemmiger formicilis*, *Geobacter*, GHAPRB1, *Gordonibacter*, *Gordonibacter bacterium*, *Gordonibacter intestinal*, *Gordonibacter pamelaeae*, Gp2, Gp21, Gp4, Gp6, *Granulicatella*, *Granulicutella adiacens*, *Granulicatella* enrichment, *Granulicatella oral*, *Granulicatella paraadiacens*, *Haemophrlus*, *Hafnia*, *Hafnia* 3-12(2010), *Hafnia alvei*, *Hafnia* CC16, *Hafnia proteus*, *Haliea*, *Hallella*, *Hallella seregens*, *Herbaspirillum*, *Herbaspirillum* 02254-11, *Herbaspirillum seropedicae*, *Hespellia*, *Hespellia porcina*, *Hespellia stercorisuis*, *Holdemania*, *Holdemania* AP2, *Holdemania filiormis*, *Howardella*, *Howardella urelytica*, *Hydrogenoanaerobacterium*, *Hydrogenoanaerobacterium saccharovorans*, *Hydrogenophaga*, *Hydrogenophaga bacterium*, *Ilumatobacter*, inulinivorans, *Janthinobacterium*, *Janthinobacterium* C30An7, *Jeotgalicoccus*, *Klebsiella*, *Klebsiella aerogenes*, *Klebsiella bacterium*, *Klebsiella* E1L1, *Klebsiella* EB2-THQ, *Klebsiella* enrichment, *Klebsiella* F83, *Klebsiella* gg160e, *Klebsiella* Gl-6, *Klebsiella gramlomatis*, *Klebsiella* HaNA20, *Klebsiella* HF2, *Klebsiella* ii_3_chl_1, *Klebsiella* KALAICIBA17, *Klebsiella* kpu, *Klebsiella* M3, *Klebsiella* MB45, *Klebsiella milletis*, *Klebsiella* NCCP-138, *Kiebsiella* ok1_1_9_S16, *Klebsiella* ok1_1_9_S54, *Klebsiella planticola*, *Klebsiella pneumoniae*, *Klebsiella poinarii*, *Klebsiella* PSB26 *Klebsiella* RS, *Klebsiella* Sel4, *Klebsiella* SRC_DSD12, *Klebsiella* tdl53s, *Klebsiella* TG-1, *Klebsiella* TPS 5, *Klebsiella varicola*, *Klebsiella* WB-2, *Klebsiella* Y9, *Klebsiella* zlmy, *Kluyvera*, *Kluyvera* An5-1, *Kluvera cryocrescens*, *Kocuria*, *Kocuria* 2216.35.31, *Kurthia*, *Lachnobacterium*, *Lachnobacterium* C12b, Lachnospiracea incertae *sedis*, Lachnospiracea incertae *sedis bacterium*, Lachnospiracea incertae *sedis contortum*, Lachnospiracea incertae *sedis* Eg2 Lachnospiracea incertae *sedis eligens*, Lachnospiracea incertae *sedis ethanolgignens*, Lachnospiracea incertae *sedis galacturonicus*, Lachnospiracea incertae *sedis gnavus*, Lachnospiracea incertae *sedis halli*, Lachnospiracea incertae *sedis hydrogenotrophica*, Lachnospiracea incertae *sedis* ID5, Lachnospiracea incertae *sedis intestinal*, Lachnospiracea incertae *sedis mpnisolate*, Lachnospiracea incertae *sedis pectinoschiza*, Lachnospiracea incertae *sedis ramulus*, Lachnospiracea incertae *sedis rectale*, Lachnospiracea incertae *sedis*

RLB1, Lachnospiracea incertae *sedis rumen*, Lachnospiracea incertae *sedis* SY8519, Lachnospiracea incertae *sedis torques*, Lachnospiracea incertae *sedis uniforme*, Lachnospiracea incertae *sedis ventriosum*, Lachnospiracea incertae *sedis xylanophilum*, Lachnospiracea incertae *sedis* ye62, *Lactobacillus, Lactobacillus* 5-1-2, *Lactobacillus* 66c, *Lactobacillus acidophilus, Lactobacillus arizonensis, Lactobacillus* B5406, *Lactobacillus brevis, Lactobacillus casei, Lactobacillus crispatus, Lactobacillus curvatus, Lactobacillus delbrueckii, Lactobacillus fermentum, Lactobacillus gasseri, Lactobacillus helveticus, Lactobacillus hominis, Lactobacillus* ID9203 *Lactobacillus* IDSAc, *Lactobacillus intestinal, Lactobacillus johnsonii, Lactobacillus lactis, Lactobacillus manihotivorans, Lactobacillus mucosae, Lactobacillus* NA, *Lactobacillus oris, Lactobacillus* P23, *Lactobacillus* P8, *Lactobacillus paracasei, Lactobacillus paraplantarum, Lactobacillus pentosus, Lactobacillus plantarum, Lactobacillus pontis, Lactobacillus rennanqilfy*14, *Lactobacillus rennanqilfyl*9, *Lactobacillus reuteri, Lactobacillus rhamnosus, Lactobacillus salivarius, Lactobacillus sanfranciscensis, Lactobacillus suntoryeus, Lactobacillus* T3R1C1, *Lactobacillus vaginalis, Lactobacillus zeae, Lactococcus, Lactococcus* 56, *Lactococcus* CR-317S, *Lactococcus* CW-1, *Lactococcus* D8, *Lactococcus* Da-18, *Lactococcus* DAP39, *Lactococcus delbrueckii, Lactococcis* F116*Lactococcus fujiensis, Lactococcis* G22, *Lactococcus garvieae, Lactococcus lactis, Lactococcus manure, Lactococcus* RT5, *Lactococcus* SXVIII1(2011), *Lactococcus* TP2MJ, *Lactococcus* TP2ML, *Lactococcus* TP2MN, *Lactococcus* U5-1, *Lactonifactor, Lactonifactor bacterium, Lactonifactor longoviformis, Lactonifactor* NLAE-zl-c533, *Leclercia, Lentisphaera, Leuconostoc, Leuconostoc carnosum, Leuconostoc citreum, Leuconostoc garlicum, Leuconostoc gasicomitatum, Leuconostoc gelidum, Leuconostoc inhae, Leuconostoc lactis, Leuconostoc* MFBF2, *Leuconostoc mesenteroides, Leuconostoc pseudomesenteroides, Limnobacter, Limnobacter* spf3, *Luteolibacter, Luteolibacter bacterium, Lutispora, Marinifilum, Marinobacter, Marinobacter arcticus, Mariprofundus, Marvinbryantia, Megamonas, Megasphaera, Melissococcus, Melissococcus faecalis, Methanobacterium, Methanobacterium subterraneum, Methanobrevibacter, Methanobrevibacter arboriphilus, Methanobrevibacter millerae, Methanobrevibacter olleyae, Methanobrevibacter oralis, Methanobrevibacter* SM9, *Methanobrevibacter smithii, Methanosphaera, Methanosphaera stadtmanae, Methylobacterium, Methylobacterium adhaesivum, Methylobacterium bacterium, Methylobacterium* iEID, *Methylobacterium* MP3, *Methylobacterium oryzae, Methylobacterium* PB132, *Methylobacterium* PB20, *Methylobacterium* PB280, *Methylobacterium* PDD-23b-14, *Methylobacterium radiotolerans, Methylobacterium* SKJH-1, *Mitsuokella, Mitsuokella jalaludinii, Morganella, Aforganella morganii, Moritella, Moritella* 2D2, *Morvella, Aloryella indoligenes, Morvella naviforme, Mycobacterium, Mycobacterum tuberculosis, Negativicoccus, Nitrosomonas, Nitrosomonas eutropha, Novosphingobium, Odoribacter, Odoribacter laneus, Odonbacter splanchnicus Olsenella, Olsenella* 1832, *Olsenella* F0206, *Orbus, Orbus gilliamella, Oribacterium, Oscillibacter, Oscillibacter bacterium, Oscillibacter enrichment, Owenweeksia, Oxalobacter, Oxalobacter formigenes, Paludibacter, Pantoea, Pantoea eucaljpti, Papillibacter, Papillibacter cinnamivorans, Parabacteroides, Parabacteroides* ASF519, *Parabacteroides* CR-34, *Parabacteroides distasonis, Parabacteroides* DJF B084, *Parabacteroides* DJF B086, *Parabacteroides* dnLKV8, *Parabacteroides* enrichment, *Parabacteroides fecal, Parabacteroides goldsteinii, Parabacteroides gordonii Parabacteroides johnsonii, Parabacteroides merdae, Parabacteroides mpnisolate, Parabacteroides* NLAE-zl-p340, *Paraeggerthella, Paraeggerthella hongkongensis, Paraeggerthella* NLAE-zl-p797, *Paraeggerthella* NLAE-zl-p896, *Paraprevotella, Paraprevotella clara, Paraprevotella xylaniphda, Parasutterella, Parasutterella excrementihominis, Pectobacterium, Pectobacterium carotovorum, Pectobacterium wasabiae, Pediococcus, Pediococcus* te2r *Pedobacter, Pedobacter* b3Nlb-b5, *Pedobacter daechungensis, Peptostreptococcus, Peptostreptococcus anaerobius, Peptostreptococcus stomatis, Phascolarcobacterium, Phascolarctobacterium faecium, Photobacterum, Photobacterium* MIE, *Pilibacter Planctomyces*, Planococcaceae incertae *sedis, Planomicrobium, Plesiomonas, Porphyrobacter, Porphyrobacter* KK348, *Porphyromonas, Porphyromonas asaccharolytica, Porphyromonas bennonis, Porphyromonas canine, Porphyromonas somerae, Prevotella, Prevotella bacterium, Prevotella* BI-42, *Prevotella bivia, Prevotella buccalis, Prevotella copri, Prevotella* DJF_B112, *Prevotella mpnisolate, Prevotella oral, Propionibacterium, Propionibacterium acnes, Propionibacterium freudenreichii, Propionibacterium* LG, *Proteiniborus, Proteniphilum, Proteus, Proteus* HS7514 *Providencia, Pseudobutyrivibrio, Pseudobutyrivibrio bacterium, Pseudobutyrivibrio fibrisolvens, Pseudobutyrivibrio ruminis, Pseudochrobactrum, Pseudoflavonifractor, Pseudoflavonifractor* asf500, *Pseudoflavonifractor bacterium, Pseudoflavonifractor capillosus Pseudoflavonfractor* NML, *Pseudomonas, Pseudomonas* 1043, *Pseudomonas* 10569, *Pseudomonas* 11-44, *Pseudomonas* 127(39-zx), *Pseudomonas* 12A_19, *Pseudomonas* 145(38zx), *Pseudomonas* 22010, *Pseudomonas* 32010, *Pseudomonas* 34t20, *Pseudomonas* 3C_10, *Pseudomonas* 4-5(2010), *Pseudomonas* 4-9(2010), *Pseudomonas* 6-13.J. *Pseudomonas* 63596, *Pseudomonas* 82010, *Pseudomonas* a001-142L, *Pseudomonas aeruginosa, Pseudomonas agarici, Pseudomonas* al 11-5, *Pseudomonas* alOl-18-2, *Pseudomonas* amspl, *Pseudomonas* AU2390, *Pseudomonas* AZ8R1, *Pseudomonas azotoformans, Pseudomonas* B122, *Pseudomonas* B65(2012), *Pseudomonas bacterium, Pseudomonas* BJS, *Pseudomonas* BLH-8D5, *Pseudomonas* BWDY-29, *Pseudomonas* CA18, *Pseudomonas* Cantas12, *Pseudomonas* CB11, *Pseudomonas* CBZ-4, *Pseudomonas cedrina, Pseudomonas* CGMCC, *Pseudomonas* CL16, *Pseudomonas* CNE, *Pseudomonas corrugata, Pseudomonas cuatroienegasensis, Pseudomonas* CYEB-7, *Pseudomonas* D5, *Pseudomonas* DAP37, *Pseudomonas* DB48, *Pseudomonas deceptionensis, Pseudomonas* Den-05, *Pseudomonas* DF7EH1, *Pseudomonas* DhA-91, *Pseudomonas* DVS44a, *Pseudomonas* DYJK4-9, *Pseudomonas* DZQ5, *Pseudomonas* E11_ICE19B, *Pseudomonas* E2.2, *Pseudomonas* e2-CDC-TB4D2, *Pseudomonas* EM189, *Pseudomonas* enrichment, *Pseudomonas extremorientalis Pseudomonas* FAIR/BE/F/GH37, *Pseudomonas* FAIR/BE/F/GH39, *Pseudomonas* FAIR/BE/F/GH94, *Pseudomonas* FLM05-3, *Pseudomonas fluorescens, Pseudomonas fragi, Pseudomonas* TSL, *Pseudomonas* G1013, *Pseudomonas gingeri, Pseudomonas* HC2-2, *Pseudomonas* HC2-4, *Pseudomonas* HC2-5, *Pseudomonas* HC4-8, *Pseudomonas* HC6-6, *Pseudomonas* Hg4-06, *Pseudomonas* HLB8-2, *Pseudomonas* HISI 2-1, *Pseudomonas* HSF20-13, *Pseudomonas* HW08, *Pseudomonas* IpA-92, *Pseudomonas* IV, *Pseudomonas* JCM, *Pseudomonas jessenii, Pseudomonas* JSPB5, *Pseudomonas* K3R3.1A, *Pseudomonas* KB40, *Pseudomonas* KB42, *Pseudomonas* KB44, *Pseudomonas* KB63, *Pseudomonas* KB73, *Pseudomonas* KK-21-4, *Pseudomonas* KOPRI, *Pseudomonas* L1R3.5, *Pseudomonas* LAB-27,

*Pseudomonas* LAB-44, *Pseudomonas* LclO-2, *Pseudomonas libanensis*, *Pseudomonas* Ln5C.7, *Pseudomonas* LS197, *Pseudomonas lundensis*, *Pseudomonas marginalis*, *Pseudomonas* MFY143, *Pseudomonas* MFY146, *Pseudomonas* MY 1412, *Pseudomonas* MYJ404, *Pseudomonas* AY1416, *Pseudomonas* MY1420, *Pseudomonas* N14zhy, *Pseudomonas* NBRC, *Pseudomonas* NCCP-506, *Pseudomonas* NFU20-14, *Pseudomonas* NJ-22, *Pseudomonas* NJ-24 *Pseudomonas* Nj-3, *Pseudomonas* Nj-55, *Pseudomonas* N-56, *Pseudomonas* Nj-59, *Pseudomonas* Nj-60, *Pseudomonas* Nj-62, *Pseudomonas* Nj-70, *Pseudomonas* NP41, *Pseudomonas* OCW4, *Pseudomonas* OW3-15-3-2, *Pseudomonas* P2(2010), *Pseudomonas* P3(2010), *Pseudomonas* P4(2010), *Pseudomonas* P, *Pseudomonas* PF1B4, *Pseudomonas* PF2M10, *Pseudomonas* PHRI, *Pseudomonas* P1(2010), *Pseudomonas poae*, *Pseudomonas proteobacterium*, *Pseudomonas* ps4-12, *Pseudomonas* ps4-2, *Pseudomonas* ps4-28, *Pseudomonas* ps4-34, *Pseudomonas* ps4-4, *Pseudomonas psychrophila* *Pseudomonas putida*, *Pseudomonas* R-35721, *Pseudomonas* R-37257, *Pseudomonas* R-37265, *Pseudomonas* R-37908, *Pseudomonas* RBE2CD-42, *Pseudomonas* regd9, *Pseudomonas* RKS7-3, *Pseudomonas* S2, *Pseudomonas* seawater, *Pseudomonas* SGb08, *Pseudomonas* SGb396, *Pseudomonas* SGb120, *Pseudomonas* sgn, *Pseudomonas* 'Shk, *Pseudomonas stutzeri*, *Pseudomonas syringae*, *Pseudomonas taetrolens*, *Pseudomonas tolaasii*, *Pseudomonas trivialis*, *Pseudomonas* TUT1023, *Pseudomonas* W15Feb26, *Pseudomonas* W15Feb4, *Pseudomonas* W5Feb6, *Pseudomonas* WD-3, *Pseudomonas* WR4-13, *Pseudomonas* WR7 #2, *Pseudomonas* Y1000, *Pseudomonas* ZS29-8, *Psychrobacter*, *Psychrobacter* umb13d, *Pyramidobacter*, *Pyramidobacter piscolens*, *Rahnella*, *Rahnella aquatilis*, *Rahnella carotovorum*, *Rahnella* GIST-WP4w1, *Rahnella* LR113, *Rahnella* Z2-S1, *Ralstonia*, *Ralstonia bacterium*, *Raoultella*, *Raoultella* B 19, *Raoultella enrichment*, *Raoultella planticola*, *Raoulhella* sv6xvii, *Raoulhella* SZ015, RBElCD-48, *Renibacterium*, *Renibacterium* G20, rennanqilfylO *Rhizobium*, *Rhizobium leguminosarum*, *Rhodococcus*, *Rhodococcus erythropolis*, *Rhodopirellula*, *Riemerella*, *Riemerella anatipestifer*, *Rikenella*, *Robinsoniella*, *Robinsoniella peoriensis*, *Roseburia*, *Roseburia* 11SE37, *Roseburia bacterium*, *Roseburia cecicola*, *Roseburia* DJF_VR77, *Roseburia faecis*, *Roseburia fibrisolvens*, *Roseburia hominis*, *Roseburia intestinalis*, *Roseibaci Uus*, *Rothia*, *Rubritalea*, *Ruminococcus*, *Ruminococcus* 25F6, *Ruminococcus albus*, *Ruminococcus bacterium*, *Ruminococcus bromii*, *Ruminococcus callidus*, *Ruminococcus champanellensis*, *Ruminococcus* DJF_VR87, *Ruminococcus, flavefaciens*, *Ruminococcus gauvreauii*, *Ruminococcus lactaris*, *Ruminococcus* NK3A76, *Ruminococcus* YE71, *Saccharofermentans*, *Salinicoccus*, *Salinimicrobium*, *Salmonella*, *Salmonella agglomerans*, *Salmonella bacterium*, *Salmonella enterica*, *Salmonella freundii*, *Salmonella hermannii*, *Salmonella paratyphi*, *Salmonella* SL0604, *Salmonella subterranea*, *Scardovia*, *Scardovia oral*, *Schwartzia Sedimenticola*, *Sediminibacter*, *Selenomonas*, *Selenomonas fecal*, *Serpens*, *Serratia*, *Serratia* 1135, *Serratia* 136-2, *Serratia* 5.1R, *Serratia* AC-CS-1B, *Serratia* AC-CS-B2, *Serratia aquatilis*, *Serratia bacterium*, *Serratia* BS26, *Serratia carotovorum*, *Serratia* DAP6, *Serratia enrichment*, *Serratia* F2, *Serratia ficaria*, *Serratia fonticola*, *Serratia grimesii*, *Serratia*, J 145, *Serratia* JM983, *Serratia liquefaciens*, *Serratia marcescens*, *Serratia plymuthica*, *Serratia proteamaculans*, *Serratia proteolyticus*, *Serratia* ptz-16s, *Serratia quinivorans*, *Serratia* SBS, *Serratia* SS22, *Serratia* trout, *Serratia* UA-G004, *Serratia* White, *Serratia* yellow, *Shewanella*, *Shewanella baltica*, *Slackia*, *Slackia intestinal*, *Slackia isoflavoniconvertens*, *Slackia* NATTS, *Solibacillus*, *Solobacterium*, *Solobacterium moorei*, *Spartobacteria* genera incertae *sedis*, *Sphingobium*, *Sphingomonas*, *Sporacetigenium*, *Sporobacter*, *Sporobacterium*, *Sporobacterium olearium*, *Staphylococcus*, *Staphylococcus epidermadis*, *Staphylococcus* PCA17, *stellenboschense*, *Stenotrophomonas*, *Streptococcus*, *Streptococcus* 15, *Streptococcus* 1606-02B, *Streptococcus agalactiae*, *Streptococcs alactolyticus*, *Streptococcus anginosus*, *Streptococcus bacterium*, *Streptococcus bovis*, *Streptococcus* ChDC, *Streptococcus constellatus*, *Streptococcus* CR-314S, *Streptococcus criceti*, *Streptococcus cristatus*, *Streptococcus downei*, *Streptococcus dysgalactiae*, *Streptococcus enrichment*, *Streptococcus equi*, *Streptococcus equinus*, *Streptococcus* ES11, *Streptococcus eubacterium*, *Streptococcus fecal*, *Streptococcus gallinaceus*, *Streptococcus gallolyticus*, *Streptococcus gastrococcus*, *Streptococcus genomosp*, *Streptococcus gordoni*, *Streptococcus infantarius*, *Streptococcus intermedius*, *Streptococcus* Je2, *Streptococcus* JS-CD2, *Streptococcus* LRC, *Streptococcus lueciae*, *Streptococcus lutetiensis*, *Streptococcus* M09-11185, *Streptococcus mitis*, *Streptococcus mutans*, *Streptococcus* NA, *Streptococcus* NLAE-zl-c353, *Streptococcus* NLAE-zl-p68 *Streptococcus* NLAE-zl-p758, *Streptococcus* NLAE-zl-p807, *Streptococcus oral*, *Streptococcus oralis*, *Streptococcus parasanguinis*, *Streptococcus phome*, *Streptococcus pneumoniae*, *Streptococcus porcinus*, *Streptococcus pyogenes*, *Streptococcus* S 16-08, *Streptococcus salivarius*, *Streptococcus sanguinis*, *Streptococcus sobrinus*, *Streptococcus suis*, *Streptococcus symbiont*, *Streptococcus thermophilus*, *Streptococcus* TW1, *Streptococcus vestibularis*, *Streptococcus warneri*, *Streptococcus* XJ-RY-3, *Streptomyces*, *Streptomyces malaysiensis*, *Streptomyces* MVCS6, *Streptophyta*, *Streptophyta cordifolium*, *Streptophyta ginseng*, *Streptophyta hirsutum*, *Streptophyta oleracea*, *Streptophyta sativa*, *Streptophyta sativum*, *Streptophyta sativus*, *Streptophyta tabacum*, Subdivision3 genera incertae *sedis*, *Subdoligranulum*, *Subdoligranulum bacterium*, *Subdoligranulum* ic1393, *Subdoligranulum* ic1395, *Subdoligranulum variabile*, *Succinicasticum*, *Sulfiricella*, *Sulfbro spirillum*, *Sutterella*, *Syntrophococcus*, *Syntrophomonas*, *Syntrophomonas biyantii*, *Syntrophus*, *Tannerella*, *Tatumella*, *Thermogmnomonas*, *Thermofilum*, *Thermogymnomonas*, *Thermovirga*, *Thiomonas*, *Thiomonas* ML1-46, *Thorsellia*, *Thorsellia carsonella*, TM7 genera incertae *sedis*, *Trichococcus*, *Turicibacter*, *Turicibacter sanguinis*, *Vagococcus*, *Vagococcus* bfsll-15, *Vampiro vibrio*, *Vampirovibrio*, *Varibacidum*, *Variovorax*, *Variovorax* KS2D-23, *Veillonella*, *Veillonella dispar*, *Veillonella* MSA 12 *Veillonella* OK8, *Veillonella oral*, *Veillonella parvula*, *Veillonella tobetsuensis*, *Vibrio*, *Yibrio* 3C1, *Victivallis*, *Victivallis vadensis*, *Vitellibacter, wadsworthensis*, *Wandonia*, *Wandonia haliotis*, *Weissella*, *Weissella cibaria*, *Weissella confusa*, *Weissella oryae*, *Yersinia*, *Yersinia* 9gw38, *Yersinia* A125, *Yersinia aldovae*, *Yersinia aleksiciae*, *Yersinia* b702011, *Yersinia bacterium*, *Yersinia bercovieri*, *Yersinia enterocolitica*, *Yersinia frederiksenii*, *Yersina intermedia*, *Yersinia kristensenii*, *Yersinia* MAC, *Yersinia massiliensis*, *Yersinia mollaretii*, *Yersnia nurmii*, *Yersinia pekkanenii*, *Yersinia pestis*, *Yersinia pseudotuberculosis*, *Yersinia rohdei*, *Yersinia ruckeri*, *Yersinia* s4fe31, *Yersinia* sl0fe31, *Yersinia* sl7fe31, and *Yersinia* YEM17B.

The names of the microbes provided herein, may optionally include the strain name.

Cytokines

In some embodiments, SBP formulations include cytokines. As used herein, the term "cytokine" refers to a class of biological signaling molecules produced by cells that regulate cellular activity in surrounding or distant cells. In some embodiments, the cytokine is a lymphokine, monokine, growth factor, colony-stimulating factor (CSF), transforming growth factor (TGF), tumor necrosis factor (TNF), chemokine, and/or interleukin. Examples of cytokines include, but are not limited to, brain-derived neurotrophic factor (BDNF), cardiotrophin-like cytokine factor 1 (CLCF1), ciliary neurotrophic factor (CNTF), cardiotrophin 1 (CTF1), epidermal growth factor (EGF), erythropoietin (EPO), fibroblast growth factor acidic (FGFa), fibroblast growth factor basic (FGFb), granulocyte colony stimulating factor (G-CSF), growth hormone, granulocyte-macrophage colony stimulating factor 2 (GM-CSF), interferon-α1, interleukin(IL)-1 (IL-1), IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23. IL-27, interleukin-1 receptor antagonist (IL-1RA), keratinocyte growth factor 1 and 2 (KGF), kit ligand/stem cell factor (KITLG), leptin (LEP), leukemia inhibitory factor (LIF), nerve growth factor (NGF), oncostatin M (OSM), platelet derived growth factors, prolactin (PRL), thrombopoietin (THPO), transforming growth factor (TGF) α (TGFα), TGFβ, tumor necrosis factor α (TNFα), vascular endothelial growth factor (VEGF), tissue inhibitor of metalloproteinase (TIMP), matrix metalloproteinase (MMP), any of the interferons, any of the interleukins, any of the lymphokines, any of the cell signal molecules, and any structural or functional molecule thereof. In some embodiments, cytokines may include, but are not limited to, any of those listed in Table 4, above.

Lipids

In some embodiments, therapeutic agents include lipids. As used herein, the term "lipid" refers to members of a class of organic compounds that include fatty acids and various derivatives of fatty acids that are soluble in organic solvents, but not in water. Examples of lipids include, but are not limited to, fats, triglycerides, oils, waxes, sterols (e.g. cholesterol, ergosterol, hopanoids, hydroxysteroids, phytosterol, and steroids), stearin, palmitin, triolein, fat-soluble vitamins (e.g., vitamins A, D, E, and K), monoglycerides (e.g. monolaurin, glycerol monostearate, and glyceryl hydroxystearate), diglycerides (e.g. diacylglycerol), phospholipids, glycerophospholipids (e.g., phosphatidic acid, phosphatidylethanolamine, phosphatidvlcholine, phosphatidylserine, phosphoinositides), sphingolipids (e.g., sphingomyelin), and phosphosphingolipids. In some embodiments, lipids may include, but are not limited to, any of those listed (e.g., fats and fatty acids) in Table 4, above.

Macromolecules

In some embodiments, therapeutic agents include macromolecules, cells, tissues, organs, and/or organisms. Examples of macromolecules include, but are not limited to, proteins, polymers, carbohydrates, complex carbohydrates, lipids, nucleic acids, oligonucleotides, and genes. Macromolecules may be expressed (e.g. expression in *Escherichia coli*) or they may be chemically synthesized (e.g. solid phase synthesis, and/or polymer forming chain reactions).

Nucleic Acids

In some embodiments, SBP formulations include nucleic acids. As used herein, the term "nucleic acid" refers to any polymer of nucleotides (natural or non-natural) or derivatives or variants thereof. Nucleic acids may include deoxyribonucleic acid (DNA) or ribonucleic acid (RNA). In some embodiments, SBP formulations may enhance the stability of the nucleic acid (e.g. RNA), as taught in He et al. (2018) ACS Biomaterials Science and Engineering/4(5):1708-1715, the contents of which are herein incorporated by reference in their entirety. In some embodiments, nucleic acids may be polynucleotides or oligonucleotides. Some nucleic acids may include aptamers, plasmids, small interfering RNA (siRNA), microRNAs, or viral nucleic acids. In some embodiments, nucleic acids may encode proteins. In some embodiments, SBPs including therapeutic agent nucleic acids may include any of those described in International Publication Number WO2017123383, the contents of which are herein incorporated by reference in their entirety. In some embodiments, nucleic acids may include, but are not limited to, any of those listed in Table 4, above.

In some embodiments, nucleic acids may include a "CELiD" DNA as described in Li et al. (2013) PLoS One. 8(8):e69879, the contents of which are herein incorporated by reference in their entirety. CELiD DNA is a eukaryotic vector DNA that includes an expression cassette flanked by adeno-associated virus (AAV) inverted terminal repeats.

Proteins

In some embodiments, SBP formulations may include biological agents that are or include proteins. As used herein, the term "protein" generally refers to polymers of amino acids linked by peptide bonds and embraces "peptides" and "polypeptides." In some SBPs, the biological agent protein included is processed silk. Classes of proteins used as biological agent may include, but are not limited to, antigens, antibodies, antibody fragments, cytokines, peptides, hormones, enzymes, oxidants, antioxidants, synthetic proteins, and chimeric proteins. In some embodiments, proteins include any of those presented in Table 4, above. In some embodiments, proteins are combined with processed silk to improve protein stability.

In some embodiments, SBP formulations include peptides. The term "peptide" generally refers to shorter proteins of about 50 amino acids or less. Peptides with only two amino acids may be referred to as "dipeptides." Peptides with only three amino acids may be referred to as "tripeptides." Polypeptides generally refer to proteins with from about 4 to about 50 amino acids. SBPs that include peptides may include any of those described in International Publication Numbers WO2017123383 and WO2010123945, the contents of each of which are herein incorporated by reference in their entirety. Peptides may be obtained via any method known to those skilled in the art. In some embodiments, peptides may be expressed in culture. In some embodiments, peptides may be obtained via chemical synthesis (e.g. solid phase peptide synthesis). In some embodiments, peptides are used to functionalize SBPs, for example, as taught in International Publication Number WO2010123945.

In some embodiments, SBP formulations are used to facilitate peptide delivery, for example, according to the methods presented in International Publication Number WO2017123383. In some embodiments, peptides include RGD peptides, for example, as taught in Kambe et al. (2017) Materials 10(10):1153, the contents of which are herein incorporated by reference in their entirety. Non-limiting examples of peptide therapeutic agents include, but are not limited to, Degarelix acetate, Liraglutide, Cyclosporine, Eptifibatide, Dactinomycin, Spaglumat magnesium, Colistin, Nafarelin acetate, Somatostatin acetate, Buserelin, Enfuvirtide, Octreotide, lanreotide acetate, Caspofungin, Nesiritide, Goserelin, Salmon calcitonin, Lepirudin or r-hirudin, Daptomycin, Exenatide, Carbetocin acetate, Tirofiban, Glutathione, Cetrorelix acetate, Enalapril maleate, Bivalirudin, Vapreotide acetate. Icatibant acetate, Human calcitonin, Oxytocin. Atosiban acetate, Bacitracin, Lypressin, Vancomycin, Captopril. Anidulafungin, Bortezomib. Saralasin acetate, Calcitonin, Thymalfasin, Ziconotide, and Lisinopril. In some embodiments, peptides may include any of those presented in Table 4, above.

Synthetic/Chimeric Proteins

In some embodiments, SBP formulations include synthetic proteins. As used herein, the term "synthetic" refers to any article produced through at least some human manipulation. Synthetic proteins may be identical to proteins found in nature or may have one or more distinguishing features. Distinguishing features may include, but are not limited to, differences in amino acid sequences, incorporation of non-natural amino acids, post-translational modifications, and conjugation to non-protein moieties (e.g., some antibody drug conjugates). Synthetic proteins may be expressed in vitro or in vivo. Synthetic proteins may also be chemically synthesized (e.g. by solid phase peptide synthesis). In some embodiments, synthetic proteins are made from a combination of expression and chemical synthesis (e.g. native chemical ligation or enzyme catalyzed protein ligation).

In some embodiments, synthetic proteins include chimeric or fusion proteins. As used herein, the term "fusion protein" refers to a substance that includes two or more protein components that are conjugated through at least one chemical bond. As used herein, the term "chimeric protein" refers to a protein that includes segments from at least two different sources (e.g., from two different species or two different isotypes or variants from a common species). Chimeric proteins may be produced via the expression of two or more ligated genes encoding different proteins. Chimeric proteins may be produced via chemical synthesis. In some embodiments, chimeric proteins are made from a combination of expression and chemical synthesis (e.g. native chemical ligation or enzyme catalyzed protein ligation). In some embodiments, synthetic proteins or chimeric proteins may include, but are not limited to, any of those listed in Table 4, above.

Viruses and Viral Particles

In some embodiments, SBP formulations include viruses or viral particles. Viruses and viral particles may be used to transfer nucleic acid into cells for genetic manipulation, gene therapy, gene editing, protein expression, or to inhibit protein expression. In some embodiments, SBPs be prepared with viral or viral particle payloads. In some embodiments, payload release may occur over a period of time (the payload release period). The payload release rate and/or length of the payload release period may be modulated by SBP components or methods of preparation. Examples of viruses and viral particles may include, but are not limited to, any of those presented in Table 4, above. In some embodiments, SBP formulations with a virus or viral particle may enhance the stability of said virus or viral particle, as taught in WO2018053524A1, the contents of which are herein incorporated by reference in their entirety.

In some embodiments, the virus or viral particle payloads prepared with SBP formulations may include, but are not limited to, adeno-associated virus, lentivirus, alphavirus, enterovirus, pestivirus, baculovirus, herpesvirus, Epstein Barr virus, papovavirus, poxvirus, vaccinia virus, herpes simplex virus, and/or a viral particle thereof.

Oxidants/Antioxidants

In some embodiments, therapeutic agents include oxidants or antioxidants. As used herein, the term "oxidant" refers to a substance that oxidizes (i.e., strips electrons from) another substance. Inhibitors of oxidation are referred to herein as "antioxidants." The use of oxidants and/or antioxidants as therapeutic agents may include any of the methods taught, for example, in International Publication Number WO2017137937; Min et al. (2017) Int J Biol Macromol s0141-8130(17):32855-32856; or Manchineella et al. (2017) European Journal of Organic Chemistry 30:4363-4369, the contents of each of which are herein incorporated by reference in their entirety. Oxidant or antioxidant therapeutic agents may be included in SBPs for treatment of indications requiring localized treatment or for indications requiring activity more distant from an administration site. In some embodiments, incorporation of oxidants or antioxidants may be used to modulate SBPs stability or degradation. In some embodiments, oxidants or antioxidants may be polymers. Such polymers may include quaternary ammonium chitosan and melanin. Examples of such therapeutic agents include those taught in International Publication Number WO2017137937 and Min et al. (2017) Int J Biol Macromol s0141-8130(17):32855-32856, the contents of each of which are herein incorporated by reference in their entirety. In some embodiments, oxidants or antioxidants include small molecules, metals, ions, minerals, vitamins, peptides, and/or proteins. In some embodiments, antioxidants include cyclic dipeptides or 2,5-diketopiperazines. Such antioxidants may include any of those taught in Manchineella et al. (2017) European Journal of Organic Chemistry 30:4363-4369, the contents of which are herein incorporated by refernce in their entirety. In some embodiments, oxidants or antioxidants may include, but are not limited to, any of those listed in Table 4, above.

Small Molecules

In some embodiments, SBP formulations include small molecule therapeutic agents. As used herein, the term "small molecule" refers to a low molecular weight compound, typically less than 900 Daltons. Many small molecules are able to pass through cell membranes, making them attractive candidates for therapeutic applications. SBPs may be combined with any small molecules to carry out a variety of therapeutic applications. Such small molecules may include small molecule drugs approved for human treatment. Some small molecules may be hydrophobic or hydrophilic. Small molecules may include, but are not limited to, antibacterial agents, antifungal agents, anti-inflammatory agents, non-steroidal anti-inflammatory drugs, antipyretics, analgesics, antimalarial agents, antiseptics, hormones, stimulants, tranquilizers, and statins. In some embodiments, small molecules may include any of those listed in Table 4, above.

In some embodiments, SBP formulations may be used to encapsulate, store and/or release, in a controlled manner, small molecules. For example, using silk fibroin micrococoons as delivery vehicles for small molecules has been described in Shimanovich et al. (Shimanovich et al. (2015) Nature Communications 8:15902, the contents of which are herein incorporated by reference in their entirety).

Angiogenesis Moddators

In some embodiments, therapeutic agents include modulators of angiogenesis. Such therapeutic agents may include vascular endothelial growth factor (VEGF)-related agents. As used herein, the term "VEGF-related agent" refers to any substance that affects VEGF expression, synthesis, stability, biological activity, degradation, receptor binding, cellular signaling, transport, secretion, internalization, concentration, or deposition (e.g., in extracellular matrix).

In some embodiments, VEGF-related agents are angiogenesis inhibitors. In some embodiments, the angiogenesis inhibitor includes any of those taught in International Publication Number WO2013126799, the contents of which are herein incorporated by reference in their entirety. In some embodiments, VEGF-related agents may include antibodies. VEGF-related agents may include VEGF agonists, including, but not limited to, toll-like receptor agonists. In some embodiments, the therapeutic agent is a VEGF antagonist. VEGF agonists or antagonists may be small molecules. In some embodiments, VEGF agonists or antagonists may be macromolecules or proteins. Angiogenesis inhibitors may include, but are not limited to, MACUGEN® or another VEGF nucleic acid ligand; LUCENTIS®, AVASTIN®, or another anti-VEGF antibody; combretastatin or a derivative or prodrug thereof such as Combretastatin A4 Prodrug (CA4P); VEGF-Trap (Regeneron); EVIZON™ (squalamine lactate); AG-013958 (Pfizer, Inc.); JSM6427 (Jerini AG); a short interfering RNA (siRNA) that inhibits expression of one or more VEGF isoforms (e.g., $VEGF_{165}$); an siRNA that inhibits expression of a VEGF receptor (e.g., VEGFR1), endogenous or synthetic peptides, angiostatin, combstatin, arresten, tumstatin, thalidomide, thalidomide derivatives, canstatin, endostatin, thrombospondin, and β2-glycoprotein 1. In some embodiments, VEGF-related agents may include, but are not limited to any of those listed in Table 4, above.

Antibacterial Agents

In some embodiments, therapeutic agents include antibacterial agents. As used herein, the term "antibacterial agent" refers to any substance that harms, kills, or otherwise inhibits the growth and/or reproduction of bacteria. Antibacterial agents may include, but are not limited to, any of those listed in Table 4, above.

Antifungal Agents

In some embodiments, therapeutic agents include antifungal agents. As used herein, the term "antifungal agent" refers to any substance that harms, kills, or otherwise inhibits the growth and/or reproduction of fungi. Antifungal agents may include, but are not limited to, any of those listed in Table 4, above.

Analgesic Agents

In some embodiments, therapeutic agents include analgesic agents. As used herein, the term "analgesic agent" refers to any substance used to reduce or alleviate pain. Analgesic agents may include, but are not limited to, any of those listed in Table 4, above.

Antipyretics

In some embodiments, therapeutic agents include antipyretics. As used herein, the term "antipyretic" refers to any substance used to reduce or alleviate fever. Examples of antipyretics include, but are not limited to, any NSAID, acetaminophen, aspirin and related salicylates (e.g. choline salicylate, magnesium salicylate, and sodium salicylate), ibuprofen, naproxen, ketoprofen, nimesulide, phenazone, metamizole, and nabumetone. In some embodiments, antipyretics may include, but are not limited to, any of those listed in Table 4, above.

Antimalarial Agents

In some embodiments, therapeutic agents include antimalarial agents. As used herein, the term "antimalarial agent" refers to any substance that harms, kills, or otherwise inhibits the growth and/or reproduction of *plasmodium* parasites. Examples of antimalarial agents may include, but are not limited to, any of those listed in Table 4, above.

Antiseptic Agents

In some embodiments, therapeutic agents include antiseptic agents. As used herein, the term "antiseptic agent" refers to any substance that harms, kills, or otherwise inhibits the growth and/or reproduction of microorganisms. Examples of antiseptics include, but are not limited to, iodine, lower alcohols (ethanol, propanol, etc.), chlorhexidine, quatemary amine surfactants, chlorinated phenols, biguanides, bisbiguanides polymeric quatemary ammonium compounds, silver and its complexes, small molecule quatemary ammonium compounds, peroxides, and hydrogen peroxide. In some embodiments, antiseptic agents may include any of those listed in Table 4, above.

Hormones

In some embodiments, therapeutic agents include hormones. As used herein, the term "hormone" refers to a cellular signaling molecule that promotes a response in cells or tissues. Hormones may be produced naturally by cells. In some embodiments, hormones are synthetic. Examples of hormones include, but are not limited to, any steroid, dexamethasone, allopregnanolone, any estrogen (e.g. ethinyl estradiol, mestranol, estradiols and their esters, estriol, estriol succinate, polyestriol phosphate, estrone, estrone sulfate and conjugated estrogens), any progestogen (e.g. progesterone, norethisterone acetate, norgestrel, levonorgestrel, gestodene, chlormadinone acetate, drospirorenone, and 3-ketodesogestrel), any androgen (e.g. testosterone, androstenediol, androstenedione, dehydroepiandrosterone, and dihydrotestosterone), any mineralocorticoid, any glucocorticoid, cholesterols, and any hormone known to those skilled in the art. In some embodiments, hormones may include, but are not limited to, any of those listed in Table 4, above.

Non-Steroidal Anti-Inflammatory Drugs

In some embodiments, therapeutic agents include nonsteroidal anti-inflammatory drugs. A nonsteroidal anti-inflammatory drug (NSAID) is a class of non-opioid analgesics used to reduce inflammation and associated pain. NSAIDs may include, but are not limited to, any of those listed in Table 4, above. In some embodiments, the NSAID is celecoxib. Some SBPs include gels or hydrogels that are combined with NSAIDs (e.g., celecoxib). Such SBPs may be used as carriers for NSAID payload delivery. NSAID delivery may include controlled release of the NSAID.

Stimulants

In some embodiments, therapeutic agents include stimulants. As used herein, the term "stimulant" refers to any substance that increases subject physiological or nervous activity. Examples of stimulants include, but are not limited to, amphetamines, caffeine, ephedrine, 3,4-methylenedioxymethamphetamine, methylenedioxypyrovalerone, mephedrone, methamphetamine, methylphenidate, nicotine, phenylpropanolamine, propylhexedrine, pseudoephedrine, and cocaine. In some embodiments, stimulants may include, but are not limited to, any of those listed in Table 4, above.

Tranquilizers

In some embodiments, therapeutic agents include tranquilizers. As used herein, the term "tranquilizer" refers to any substance used to lower subject anxiety or tension. Examples of tranquilizers include, but are not limited to, barbiturates, benzodiazepines, carbamates, antihistamines, opioids, antidepressants (e.g. monoamine oxidase inhibitors, tetracyclic antidepressants, tricyclic antidepressants, selective serotonin reuptake inhibitors, and serotonin-norepinephrine reuptake inhibitors), sympatholytics (e.g. alpha blockers, beta-blockers, and alpha-adrenergic agonists), mebicar, fabomotizole, selank, bromantane, emoxypine, azapirones, pregabalin, mentyl isovalerate, propofol, racetams, alcohols, inhalants, any butyrophenone (e.g. benperidol, bromperidol, droperidol, haloperidol, moperone, pipamperone, and timiperone), any diphenylbutylpiperidine (e.g. fluspirilene, penfluridol, and pimozide), any phenothiazine (e.g. acepromazine, chlorpromazine, cyamemazine, dixyrazine, fluphenazine, levomepromazine, levomepromazine, mesoridazine, perazine, periciazine, perphenazine, pipotiazine, prochlorperazine, promazine, promethazine, prothipendyl, thioproperazine, thioridazine, trifluoperazine, and triflupromazine), any thioxanthene (e.g. chlorprothixene, clopenthixol, flupentixol, thiothixene, and zuclopenthixol), any benzamidine (e.g. sulpiride, sultopride, and veralipride), any tricyclic (e.g. carpipramine, clocapramine, clorotepine, loxapine, and mosapramine), gamma aminobutyric acid, and molindone. In some embodiments, tranquilizers may include, but are not limited to, any of those listed in Table 4, above.

Statins

In some embodiments, therapeutic agents include statins. As used herein, the term "statin" refers to a class of compounds that inhibit hydroxy-methylglutary-coenzyme A reductase (HMG-CoA reductase), a key enzyme in cholesterol biosynthesis. Statins are referred to herein in the broadest sense and include statin derivatives such as ester derivatives or protected ester derivatives. Examples of statins include, but are not limited to, rosuvastatin, pitavastatin, pravastatin, fluvastatin, cerivastatin, atorvastatin, simvastatin, mevastatin, and lovastatin. In some embodiments, statins may include, but are not limited to, any of those listed in Table 4, above.

Anti-Cancer Agents

In some embodiments, therapeutic agents include anticancer agents. As used herein, the term "anticancer agent" refers to any substance used to kill cancer cells or inhibit cancer cell growth and/or cell division. Anticancer agents that target tumor cells are referred to herein as "antitumor agents." Such anticancer agents may reduce tumor mass and/or volume. Anticancer agents that are chemical substances are referred to herein as "chemotherapeutic agents." Examples of antitumor agents include, but are not limited to, busulphan, cisplatin, cyclophosphamide, MTX, daunorubicin, doxorubicin, melphalan, vincristine, vinblastine, chlorabucil, any alkylating agent (e.g. cyclophosphamide, mechlorthamine, chlorambucil, melphalan, dacarbazine, nitrosoureas, and temozolomide), any anthracycline (e.g. daunorubicin, doxorubicin, epirubicin, idarubicin, mitozantrone, and valrubicin), any cytoskeletal disruptors or taxanes (e.g. paclitaxel, docetaxel, abraxane, and taxotere), any epothilones, any histone deacetylase inhibitors (e.g. vorinostat and romidepsin), any topoisomerase I inhibitors (e.g. irinotecan and topotecan), any topoisomerase II inhibitors (e.g. etoposide, teniposide, and tafluposide), kinase inhibitors (e.g. bortezomib, erlotinib, gefitinib, imatinib, vemurafenib, and vismodegib), nucleotide and precursor analogues (e.g. azacitidine, azathioprine, capecitabine, cytarabine, doxifluridine, fluorouracil, gemcitabine, hydroxyurea, mercaptopurine, methotrexate, and tioguanine), antimicrobial peptides (e.g. bleomycin and actinomycin), platinum based chemotherapeutics (e.g. carboplatin, cisplatin, oxaliplatin), retinoids (e.g. tretinoin, alitretinoin, and bexarotene), and *vinca* alkaloids and derivatives (e.g. vinblastine, vincristine, vindesine, and vinorelbine). In some embodiments, anticancer agents may include, but are not limited to, any of those listed in Table 4, above.

Herbal Preparations

In some embodiments, therapeutic agents include herbal preparations. As used herein, the term "herbal preparation" refers to any substance derived or extracted from vegetation. These preparations may include, but are not limited to, tea, decoctions, cold infusions, tinctures, cordials, herbal wines, granules, syrups, essential oils (e.g. allspice berry essential oil, *angelica* seed essential oil, anise seed essential oil, basil essential oil, bay laurel essential oil, bay essential oil, bergamot essential oil, blood orange essential oil, camphor essential oil, caraway seed essential oil, cardamom seed essential oil, carrot seed essential oil, *cassia* essential oil, catnip essential oil, cedarwood essential oil, celery seed essential oil, chamomile german essential oil, chamomile roman essential oil, cinnamon bark essential oil, cinnamon leaf essential oil, citronella essential oil, clary sage essential oil, clove bud essential oil, coriander seed essential oil, cypress essential oil, elemi essential oil, *eucalyptus* essential oil, fennel essential oil, fir needle essential oil, frankincense essential oil, geranium essential oil, ginger essential oil, grapefruit pink essential oil, helichrysum essential oil, hop essential oil, hyssop essential oil, juniper berry essential oil, labdanum essential oil, lemon essential oil, lemongrass essential oil, lime essential oil, *magnolia* essential oil, mandarin essential oil, margoran essential oil, Melissa essential oil, mugward essential oil, myrrh essential oil, myrtle essential oil, neroli essential oil, niaouli essential oil, nutmeg essential oil, orange sweet essential oil, oregano essential oil, palmarosa essential oil, patchouli essential oil, pennyroyal essential oil, pepper black essential oil, peppermint essential oil, petitgram essential oil, pine needle essential oil, *radiata* essential oil, ravensara essential oil, rose essential oil, rosemary essential oil, rosewood essential oil, sage essential oil, sandalwood essential oil, spearmint essential oil, spikenard essential oil, spruce essential oil, star anise essential oil, sweet annie essential oil, tangerine essential oil, tea tree essential oil, thyme red essential oil, *verbena* essential oil, vetiver essential oil, wintergren essential oil, wormwood essential oil, yarrow essential oil, ylang essential oil, jasmine absolute oil, lavender absolute oil, pink lotus absolute oil, rose absolute oil, sambac absolute oil, and white lotus absolute oil), flower essences, sitz baths, soaks, pills, suppositories, poultices, compresses, salves, and ointments. Examples of herbs to be incorporated include, but are not limited to, sage, thyme, cumin, basil, bay laurel, borage, caraway, catnip, chervil, chives, cilantro, dill, epazote, fennel, garlic, lavender, lemongrass, lemon balm, lemon *verbena*, lovage, marjoram, mints, nasturtium, parsley, oregano, rosemary, salad bumet, savory, scented geranium, sorrel, and tarragon. In some embodiments, herbal preparations may include, but are not limited to, any of those listed in Table 4, above.

Health Supplements

In some embodiments, therapeutic agents include health supplements. As used herein, the term "health supplement" refers to any substance used to provide a nutrient, vitamin, or other beneficial compound that is typically lacking from a normal diet or is complimentary to such substances present in a normal diet. Examples of health supplements include, but are not limited to, vitamin A, vitamin B, vitamin C, vitamin D, vitamin E, vitamin K, thiamin, riboflavin, niacin, vitamin B6, vitamin B12, biotin, pantothenic acid, calcium, iron, phosphorus, iodine, magnesium, zinc, selenium, selenium, copper, manganese, chromium, molybdenum, chloride, potassium, nickel, silicon, vanadium, and tin. In some embodiments, health supplements may include, but are not limited to, any of those listed in Table 4, above.

Ions, Metals, Minerals

In some embodiments, therapeutic agents include ions, metals, and/or minerals. Examples include, but are not limited to, calcium, iron, phosphorus, iodine, magnesium, zinc, selenium, selenium, copper, manganese, chromium, molybdenum, gold, silver, chloride, potassium, nickel, silicon, vanadium, and tin. In some embodiments, therapeutic agents include oxides (e.g. silver oxide). In some embodiments, ions, metals, and/or minerals may be present in nanoparticles. Such nanoparticles may include any of those taught in Mane et al. (2017) Scientific Reports 7:15531; and Babu et al. (2017) J Colloid Interface Sci 513:62-72, the contents of each of which are herein incorporated by reference in their entirety. In some embodiments, ions, metals, and/or minerals may include, but are not limited to, any of those listed in Table 4, above.

Vitamins

In some embodiments, therapeutic agents include vitamins or vitamin analogues. As used herein, the term "vitamin" refers to a nutrient that must be obtained through diet (i.e., is not synthesized endogenously or is synthesized endogenously, but in insufficient amounts). Examples of vitamins include, but are not limited to, vitamin A, vitamin B-1, vitamin B-2, vitamin B-3, vitamin B-5, vitamin B-6, vitamin B-7, vitamin B-9, vitamin B-12, vitamin C, vitamin D, vitamin E, and vitamin K. In some embodiments, vitamins may include, but are not limited to, any of those listed in Table 4, above.

Other Therapeutic Agents

Other therapeutic agents may include, but are not limited to, anthocyanidin, anthoxanthin, apigenin, dihydrokaempferol, eriodictyol, fisetin, flavan, flavan-3,4-diol, flavan-3-ol, flavan-4-ol, flavanone, flavanonol, flavonoid, furanoflavonols, galangin, hesperetin, homoeriodictyol, isoflavonoid, isorhamnetin, kaempferol, luteolin, myricetin, naringenin, neoflavonoid, pachypodol, proanthocyanidins, pyranoflavonols, quercetin, rhamnazin, tangeritin, taxifolin, theaflavin, thearubigin, chondrocyte-derived extracellular matrix, macrolide, erythromycin, roxithromycin, azithromycin and clarithromycin. In some embodiments, other therapeutic agents may include, but are not limited to, any of those listed in Table 4, above.

Controlled Degradation

In some embodiments, SBP formulations may be used for controlled degradation, and to modulate the stability and storage of therapeutic agents or other materials (e.g., agricultural compositions, agricultural products, materials, devices, and excipients). As used herein, the term "controlled degradation" refers to regulated loss of structure, function, and/or other physical and chemical properties. Such SBP formulations may be used to stabilize therapeutic agents used in therapeutic applications. In some embodiments, SBP formulations are used to maintain and/or improve the stability of therapeutic agents during storage. In some embodiments SBP formulations may be used to enhance the degradation rate of therapeutic agents. In some embodiments, an SBP formulation may increase the rate of degradation of a therapeutic agent (e.g. a protein) during storage. In some embodiments, preparation of an SBP formulation with a therapeutic agent may increase the rate of degradation of said therapeutic agent (e.g. a protein) during storage.

Use as a Preservation/Stabilizing Agent

In some embodiments, SBP formulations may be used to preserve or stabilize therapeutic agents or other materials (e.g., agricultural compositions, agricultural products, materials, devices, and excipients). Such SBPs may be used to stabilize therapeutic agents used in therapeutic applications. In some embodiments, SBP formulations are used to maintain and/or improve the stability of therapeutic agents during lyophilization. The maintenance and/or improvement of stability during lyophilization may be determined by comparing products lyophilized with SBP formulations to products lyophilized with non-SBP formulation. Maintenance and/or improvement of stability during lyophilization will be found or appreciated by those of skill in the art when products lyophilized with SBP formulations are determined to impart superior or durational benefits over non-SBP formulations or those standard in the art.

In some embodiments, lyophilization may be utilized for long term storage of processed silk formulations. In some embodiments processed silk formulations are stored frozen. In some embodiments, processed silk formulations may be frozen without altering the protein quality. In some embodiments, processed silk formulations may be frozen without altering rheological properties, protein size, and aggregation of said formulations. In some embodiments, processed silk formulations may be prepared as solutions, and then frozen. In some embodiments these solutions may then be thawed. The thawed solutions may exhibit less than 10%, less than 5%, less than 3%, less than 1%, less than 0.1%, less than 0.01%, or less than 0.001% aggregation of protein.

In some embodiments, silk fibroin processing will be more efficient and cheaper if there is no need for lyophilization. In some embodiments, removing a drying condition will require that silk fibroin solutions are stable through a freeze/thaw process. This will allow for aseptic preparation and shipment of drug substance from the manufacturing site to the fill/finish facility. In some embodiments, these silk fibroin solutions may comprise silk fibroin at various concentrations, as well as cryoprotectants (sucrose and trehalose), to improve the freeze-thaw stability of dialyzed drug substance. In some embodiments, these solutions may comprise silk fibroin at a concentration of from about 0.01% to about 0.1%, about 0.1% to about 1%, about 1% to about 2%, about 2% to about 3%, about 3% to about 4%, about 4% to about 5%, about 5% to about 10%, about 10% to about 15%, about 15% to about 20%, or about 20% to about 30% (w/v) silk fibroin. In some embodiments, the cryoprotectant is sucrose or trehalose. Cryoprotectants may be included at a concentration of 0 to about 150 mM. In some embodiments, the rheological properties of the silk fibroin solutions may remain the same following freeze/thaw. In some embodiments, the molecular weight by SEC may not change following freeze/thaw. In some embodiments, the lowest increase in aggregation may be seen in formulations with sucrose as an excipient.

In some embodiments, the SBP formulations maintain and/or improve therapeutic agent stability by at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 2 weeks, at least 3 weeks, at least 1 month, at least 6 weeks, at least 2 months, at least 10 weeks, at least 3 months, at least 14 weeks, at least 4 months, at least 18 weeks, at least 5 months, at least 22 weeks, at least 6 months, at least 7 months, at least 8 months, at least 9 months, at least 10 months, at least 11 months, at least a year, at least 2 years, at least 3 years, at least 4 years, at least 5 years, or more than 5 years.

Ocular Therapeutic Agents

In some embodiments, therapeutic agents include ocular therapeutic agents. As used herein, the term "ocular therapeutic agent" refers to any compound that has a healing, corrective, diagnostic, and/or prophylactic effect and/or elicits a desired biological and/or pharmacological effect on the eye. In some embodiments, ocular therapeutic agents include one or more of processed silk, biological agents, small molecules, proteins, anti-inflammatory agents, steroids, opiates, analgesics, ciclosporin, corticosteroids, tetracyclines, essential fatty acids, sodium channel blockers, nonsteroidal anti-inflammatory drugs, cyclosporine, lifitegrast, and vascular endothelial growth factor-related agents. Ocular therapeutic agent proteins may include, but are not limited to, lysozyme, bovine serum albumin (BSA), bevacizumab, or VEGF-related agents. In some embodiments, ocular therapeutic agents may be used to treat one or more of the ocular therapeutic indications described herein.

Bacteriostatic Agents

In some embodiments, therapeutic agents include bacteriostatic agents. As used herein, the term "bacteriostatic agent" or "bacteriostat" refers to a substance that prevents bacterial reproduction and may or may not kill said bacteria. Bacteriostatic agents prevent the growth of bacteria. Non-limiting examples of bacteriostatic agents include antibiotics, antiseptics, disinfectants, and preservatives. Other non-limiting examples of bacteriostatic agents include tigecycline, trimethoprim, oxazolidinone, tetracyclines, novobiocin, clindamycin, nitrofurantoin, ethambutol, sulfonamides, macrolides, lincosamides, spectinomycin, and chloramphenicol.

Non-Steroidal Anti-Inflammatory Drugs

Therapeutic agents may include nonsteroidal anti-inflammatory drugs. A nonsteroidal anti-inflammatory drug (NSAID) is a class of non-opioid analgesics used to reduce inflammation and associated pain. NSAIDs may include small molecules. NSAIDs may include, but are not limited to, aspirin, carprofen, celecoxib, deracoxib, diclofenac, diflunisal, etodolac, fenoprofen, firocoxib, flurbirofen, ibuprofen, indomethacin, ketoprofen, ketorolac, mefenamic acid, meloxicam, nabumetone, naproxen, oxaprozin, piroxicam, robenacoxib, salsalate, sulindac, and tolmetin. In some embodiments, NSAIDs may be used to treat one or more of the ocular therapeutic indications described herein. In some embodiments, the NSAID is celecoxib. Some SBPs include gels or hydrogels that are combined with NSAIDs (e.g., celecoxib). Such SBPs may be used as carriers for NSAID payload delivery. NSAID delivery may include controlled release of the NSAID.

Therapeutic Indications

In some embodiments, SBPs are used to address one or more therapeutic indications. As used herein, the term "therapeutic indication" refers to a disease, disorder, condition, or symptom that may be cured, reversed, alleviated, stabilized, improved, or otherwise addressed through some form of therapeutic intervention (e.g., administration of a therapeutic agent or method of treatment).

SBP treatment of therapeutic indications may include contacting subjects with SBPs. SBPs may include therapeutic agents (e.g., any of those described herein) as cargo or payloads for treatment. In some embodiments, payload release may occur over a period of time (the "payload release period"). The payload release rate and/or length of the payload release period may be modulated by SBP components or methods of preparation.

Ocular Indications

In some embodiments, therapeutic indications include ocular indications. As used herein, the term "ocular indication" refers to any therapeutic indication related to the eye. Treatment of such indications in subjects may include contacting subjects with SBPs. SBPs and SBP formulations may include therapeutic agents (e.g., any of those described herein) as cargo or payloads for treatment. In some embodiments, payload release may occur over a period of time (the payload release period). The payload release rate and/or length of the payload release period may be modulated by SBP components or methods of preparation. In some embodiments, SBPs may be provided in the form of a solution or may be incorporated into a solution for ocular administration. Such solutions may be administered topically (e.g., in the form of drops, creams, or sprays) or by injection. In some embodiments, SBPs may be provided in the format of a lens or may be incorporated into lenses that are placed on eye. In some embodiments, SBPs are provided in the form of implants or are incorporated into implants that may be placed around the eye, on a surface of the eye, in a periocular space or compartment, or intraocularly. Implants may be solid or gelatinous (e.g., a gel or slurry) and may be in the form of a bleb, rod, or plug. Some gelatinous implants may harden after application. In some embodiments, implants include punctal plugs. Such plugs may be inserted into tear ducts. In some embodiments, SBPs may be used to repair ocular damage. In some embodiments, the SBP adheres to the ocular surface. In some embodiments, the SBP adheres to the ocular surface in a manner similar to a mucin layer.

Non-limiting examples of ocular indications include infection, refractive errors, age related macular degeneration, cataracts, diabetic retinopathy (proliferative and non-proliferative), cystoid macular edema, glaucoma, amblyopia, strabismus, color blindness, cytomegalovirus retinitis, keratoconus, diabetic macular edema (proliferative and non-proliferative), low vision, ocular hypertension, retinal detachment, eyelid twitching, inflammation, uveitis, bulging eyes, dry eye disease, floaters, xerophthalmia, diplopia. Graves' disease, night blindness, eye strain, red eyes, nystagmus, presbyopia, excess tearing, retinal disorders (e.g. age related macular degeneration), conjunctivitis, cancer, corneal ulcer, corneal abrasion, snow blindness, scleritis, keratitis, Thygeson's superficial punctate keratopathy, corneal neovascularization, Fuch's dystrophy, keratoconjuctitivis sicca, iritis, chorioretinal inflammation (e.g. chorioretinitis, choroiditis, retinitis, retinochoroiditis, pars planitis, and Harada's disease), aniridia, macular scars, solar retinopathy, choroidal degeneration, choroidal dystrophy, choroideremia, gyrate atrophy, choroidal hemorrhage, choroidal detachment, retinoschisis, hypertensive retinopathy, Bull's eye maculopathy, epiretinal membrane, peripheral retinal degeneration, hereditary retinal dystrophy, retinitis pigmentosa, retinal hemorrhage, separation of retinal layers, retinal vein occlusion, and other visual impairments. In some embodiments, ocular indications include inflammation of the eye.

Dry Eye

In one embodiment, the ocular indications which may be treated with the SBPs described herein may be dry eye. "Dry eye", "dry eye syndrome," "dry eye disease", or "DED" is a condition involving a lack of hydration on the eye surface that may be caused by one or more of a variety of factors (e.g., cellular/tissue dysfunction or environmental irritants). After the development of symptoms in a subject or patient, an optometrist and/or ophthalmologist may conduct and ocular exam and test for additional signs in the cornea and tears (e.g. ocular surface staining, corneal fluorescein and conjunctival staining, or tear film break-up time). Symptoms of DED may result from lack of tear production, improper tear or film production, alterations in tear or film composition and/or alteration in tear or film clearance. General symptoms of DED include, but are not limited to, ocular discomfort, dryness, conjunctival redness, grittiness, pain, burning, stinging, and any other symptom described in Moshifar et at (2014) Clinical Ophthalmology 8:1419-1433, the contents of which are herein incorporated by reference in their entirety.

Symptoms may vary with the severity level of DED, which is graded on a scale of 1-4, as described in Behrens et al. (2006) Cornea 25: 900-907, the contents of which are herein incorporated by reference in their entirety. Mild and/or episodic DED (grade 1) has signs and symptoms which may include, but are not limited to, no or episodic mild fatigue, a variable Schirmer score, no to mild conjunctival injection, variable tear film break-up time (TFBUT), no to mild conjunctival staining, variable meibomian gland dysfunction (MGD), no to mild corneal staining, and no to mild corneal/and or tear signs. Mild DED may be caused by environmental stress. Moderate episodic and/or chronic DED (grade 2) has signs and symptoms which may include, but are not limited to, episodic visual symptoms that may annoy and/or limit activity, a Schirmer score of less than 10 mm/5 min, no to mild conjunctival injection, variable conjunctival staining, variable MOD, TFBUT of less than 10 minutes, variable corneal staining, and mild debris with a variable meniscus. Moderate DED may be brought on due to stress. Severe DED (grades 3-4) may be frequent, annoying, chronic, activity limiting, disabling, constant, and brought on without stress. Signs and symptoms of severe DED may include, but are not limited to, conjunctival injection (+/– and +/++), a Schirmer score of less than 5 mm/5 min (in some cases less than 2 mm/5 min), moderate to marked conjunctival staining, frequent MGD (optionally including trichiasis, keratinization, and symblepharon), moderate to marked corneal staining (optionally with severe punctate erosions), a TFBUT of less than 5 minutes (in some cases immediate), filamentary keratitis, mucus clumping, increased tear debris, and ulceration.

After diagnosis of DED, a treatment for DED (e.g. artificial tears) may be administered to the subject. Non-limiting examples of current DED treatments include education, counseling, environmental management, tear supplementation (with or without preservatives), prescription drugs (e.g. cyclosporine and lifitegrast), punctal plugs, and surgery. Side effects of current DED treatments include, but are not limited to, burning, redness, discomfort, discharge, pain, blurring, eye irritation, and changes in taste. Current DED treatments may also require frequent administration, as described in Moshifar et al. (2014) Clinical Ophthalmology 8:1419-1433.

In some embodiments, SBPs used to treat dry eye are provided as or included in solutions or devices. Solutions may include silk fibroin micelles, as described in Wongpanit et al (2007) Macromolecular Bioscience 7: 1258-1271, the contents of which are herein incorporated by reference in their entirety. Solutions and SBPs to treat dry eye may be administered topically (e.g., by cream, spray, microspheres, or drops) or by injection to periocular or intraocular areas. Solutions may include viscous solutions, such as gels or slurries. The viscosity of such a solution may modulate properties of a resulting artificial tear replacement. Low viscosity artificial tear replacements may have shorter residence times and less efficacy. High viscosity artificial tear replacements may result in side effects including, but not limited to, blurred vision and discomfort. Devices for the treatment of DED may include, but are not limited to, solutions, implants, microspheres, hydrogels, lenses, artificial tear replacements, contact lens solution, and plugs. Devices may be hardened structures or gelatinous. In some embodiments, devices are gelatinous or prepared as a slurry, but harden after placement. Devices may include lacrimal or punctal plugs that treat dry eye via tear duct insertion. Punctal plugs may be prepared with or without therapeutic agent payloads.

SBPs used to treat dry eye may include therapeutic agent payloads. The therapeutic agents may include any of those described herein. In some embodiments, therapeutic agents include one or more of cyclosporine, corticosteroids, tetracyclines, lifitegast, NSAIDs, anti-inflammatory agents, opiates, analgesics, and essential fatty acids. In some embodiments, processed silk is the therapeutic agent. Therapeutic agent release from SBPs may occur over an extended payload release period. The payload release period may be from about 1 hour to about 48 hours, from about 1 day to about 14 days, or from about 1 week to about 52 weeks, or more than 52 weeks.

In some embodiments, ocular SBPs may be used as an anti-inflammatory treatment for dry eye disease, as described in Kim et al. (2017) Scientific Reports 7: 44364, the contents of which are herein incorporated by reference in their entirety. It has been demonstrated that the administration of 0.1 to 0.5% silk fibroin solutions in a mouse model of dry eye disease enhances corneal smoothness and tear production, while reducing the amount of inflammatory markers detected. In some embodiments, the SBPs described herein may be used to treat dry eye disease in humans. In some embodiments, the SBPs described herein may be used to treat dry eye disease in non-human primates. In some embodiments, the SBPs described herein may be used to treat dry eye disease in canines (e.g. dogs). In some embodiments, the SBPs described herein may be used to treat dry eye disease in felines (e.g. cats).

Combinations

In some embodiments, SBPs may be administered in combination with other therapeutic agent and/or methods of treatment, e.g., with known pharmaceuticals and/or known therapeutic methods, such as, for example, those which are currently employed for treating these disorders. For example, SBPs used to treat ocular indications may be administered in combination with other therapeutic agents used to treat ocular indications.

Pharmaceutical Compositions

In some embodiments, SBPs are or are included in pharmaceutical compositions. As used herein, the term "pharmaceutical composition" refers to a composition designed and/or used for medicinal purposes (e.g., the treatment of a disease).

In some embodiments, pharmaceutical compositions include one or more excipients and/or one or more therapeutic agents. Excipients and/or therapeutic agents included in pharmaceutical compositions may include, but are not limited to, any of those described herein. Relative amounts of therapeutic agents, excipient, and/or any additional ingredients in pharmaceutical compositions may vary, depending upon the identity, size, and/or condition of subjects being treated and further depending upon routes by which compositions are administered. For example, the compositions may include from about 0.0001% to about 99% (w/v) of a therapeutic agent.

Some excipients may include pharmaceutically acceptable excipients. The phrase "pharmaceutically acceptable" as used herein, refers to suitability within the scope of sound medical judgment for contacting subject (e.g., human or animal) tissues and/or bodily fluids with toxicity, irritation, allergic response, or other complication levels yielding reasonable benefit/risk ratios. As used herein, the term "pharmaceutically acceptable excipient" refers to any ingredient, other than active agents, that is substantially nontoxic and non-inflammatory in a subject. Pharmaceutically acceptable excipients may include, but are not limited to, solvents, dispersion media, diluents, inert diluents, buffering agents, lubricating agents, oils, liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of pharmaceutical compositions.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of therapeutic agent or other compound. The amount of therapeutic agent may generally be equal to the dosage of therapeutic agent administered to a subject and/or a convenient fraction of such dosage including, but not limited to, one-half or one-third of such a dosage.

In some embodiments, pharmaceutical compositions may include between 0.0001 to 35% (w/v) silk fibroin. In some embodiments, the pharmaceutical compositions may include silk fibroin in concentrations from about 0.0001% (w/v) to about 0.001% (w/v), from about 0.001% (w/v) to about 0.01% (w/v), from about 0.01% (w/v) to about 0.1% (w/v), from about 0.1% (w/v) to about 1% (w/v), from about 1% (w/v) to about 5% (w/v), from about 5% (w/v) to about 10% (w/v), from about 10% (w/v) to about 20% (w/v), or from about 20% (w/v) to about 35% (w/v).

Dosing

In some embodiments, the present disclosure provides methods of administering pharmaceutical compositions that are or include SBPs to subjects in need thereof. Such methods may include providing pharmaceutical compositions at one or more doses and/or according to a specific schedule. In some embodiments, doses may be determined based on desired amounts of therapeutic agent or SBP to be delivered. Doses may be adjusted to accommodate any route of administration effective for a particular therapeutic application. The exact amount required will vary from subject to subject, depending on the species, age, and general condition of the subject, the severity of the disease, the particular composition, its mode of administration, its mode of activity, and the like. The frequency of dosing required will also vary from subject to subject, depending on the species, age, and general condition of the subject, the severity of the disease, the particular composition, its mode of administration, its mode of activity, and the like.

SBPs may be formulated in dosage unit form. Such forms may allow for ease of administration and uniformity of dosage. Total daily SBP usage may be decided by an attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, pharmaceutical compositions that are or include SBPs may include a therapeutic agent or SBP at a concentration of from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 µg/mL to about 1 µg/mL, from about 0.05 µg/mL to about 2 µg/mL, from about 1 µg/mL to about 5 µg/mL, from about 2 µg/mL to about 10 µg/mL, from about 4 µg/mL to about 16 µg/mL, from about 5 µg/mL to about 20 µg/mL, from about 8 µg/mL to about 24 µg/mL, from about 10 µg/mL to about 30 µg/mL, from about 12 µg/mL to about 32 µg/mL, from about 14 µg/mL to about 34 µg/mL, from about 16 µg/mL to about 36 µg/mL, from about 18 µg/mL to about 38 µg/mL, from about 20 µg/mL to about 40 µg/mL, from about 22 µg/mL to about 42 µg/mL, from about 24 µg/mL to about 44 µg/mL, from about 26 µg/mL to about 46 µg/mL, from about 28 µg/mL to about 48 µg/mL, from about 30 µg/mL to about 50 µg/mL, from about 35 µg/mL to about 55 µg/mL, from about 40 µg/mL to about 60 µg/mL, from about 45 µg/mL to about 65 µg/mL, from about 50 µg/mL to about 75 µg/mL, from about 60 µg/mL to about 240 µg/mL, from about 70 µg/mL to about 350 µg/mL, from about 80 µg/mL to about 400 µg/mL, from about 90 µg/mL to about 450 µg/mL, from about 100 µg/mL to about 500 µg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 40 mg/mL to about 100 mg/mL, from about 100 mg/mL to about 200 mg/mL, from about 200 mg/mL to about 300 mg/mL, from about 300 mg/mL to about 400 mg/mL, or more than 400 mg/mL.

In some embodiments, pharmaceutical compositions that are or include SBPs may be administered at a dose that provides subjects with a mass of therapeutic agent or SBP per unit mass of the subject (e.g., mg therapeutic agent or SBP per kg of subject [mg/kg]). In some embodiments, therapeutic agents or SBPs are administered at a dose of from about 1 ng/kg to about 5 ng/kg, from about 2 ng/kg to about 10 ng/kg, from about 4 ng/kg to about 16 ng/kg, from about 5 ng/kg to about 20 ng/kg, from about 8 ng/kg to about 24 ng/kg, from about 10 ng/kg to about 30 ng/kg, from about 12 ng/kg to about 32 ng/kg, from about 14 ng/kg to about 34 ng/kg, from about 16 ng/kg to about 36 ng/kg, from about 18 ng/kg to about 38 ng/kg, from about 20 ng/kg to about 40 ng/kg, from about 22 ng/kg to about 42 ng/kg, from about 24 ng/kg to about 44 ng/kg, from about 26 ng/kg to about 46 ng/kg, from about 28 ng/kg to about 48 ng/kg, from about 30 ng/kg to about 50 ng/kg, from about 35 ng/kg to about 55 ng/kg, from about 40 ng/kg to about 60 ng/kg, from about 45 ng/kg to about 65 ng/kg, from about 50 ng/kg to about 75 ng/kg, from about 60 ng/kg to about 240 ng/kg, from about 70 ng/kg to about 350 ng/kg, from about 80 ng/kg to about 400 ng/kg, from about 90 ng/kg to about 450 ng/kg, from about 100 ng/kg to about 500 ng/kg, from about 0.01 µg/kg to about 1 µg/kg, from about 0.05 µg/kg to about 2 µg/kg, from about 1 µg/kg to about 5 µg/kg, from about 2 µg/kg to about 10 µg/kg, from about 4 µg/kg to about 16 µg/kg, from about 5 µg/kg to about 20 µg/kg, from about 8 µg/kg to about 24 µg/kg, from about 10 µg/kg to about 30 µg/kg, from about 12 µg/kg to about 32 µg/kg, from about 14 µg/kg to about 34 µg/kg, from about 16 µg/kg to about 36 µg/kg, from about 18 µg/kg to about 38 µg/kg, from about 20 µg/kg to about 40 µg/kg, from about 22 µg/kg to about 42 µg/kg, from about 24 µg/kg to about 44 µg/kg, from about 26 µg/kg to about 46 µg/kg, from about 28 µg/kg to about 48 µg/kg, from about 30 µg/kg to about 50 µg/kg, from about 35 µg/kg to about 55 µg/kg, from about 40 µg/kg to about 60 µg/kg, from about 45 µg/kg to about 65 µg/kg, from about 50 µg/kg to about 75 µg/kg, from about 60 µg/kg to about 240 µg/kg, from about 70 µg/kg to about 350 µg/kg, from about 80 µg/kg to about 400 µg/kg, from about 90 µg/kg to about 450 µg/kg, from about 100 µg/kg to about 500 µg/kg, from about 0.01 mg/kg to about 1 mg/kg, from about 0.05 mg/kg to about 2 mg/kg, from about 1 mg/kg to about 5 mg/kg, from about 2 mg/kg to about 10 mg/kg, from about 4 mg/kg to about 16 mg/kg, from about 5 mg/kg to about 20 mg/kg, from about 8 mg/kg to about 24 mg/kg, from about 10 mg/kg to about 30 mg/kg, from about 12 mg/kg to about 32 mg/kg, from about 14 mg/kg to about 34 mg/kg, from about 16 mg/kg to about 36 mg/kg, from about 18 mg/kg to about 38 mg/kg, from about 20 mg/kg to about 40 mg/kg, from about 22 mg/kg to about 42 mg/kg, from about 24 mg/kg to about 44 mg/kg, from about 26 mg/kg to about 46 mg/kg, from about 28 mg/kg to about 48 mg/kg, from about 30 mg/kg to about 50 mg/kg, from about 35 mg/kg to about 55 mg/kg, from about 40 mg/kg to about 60 mg/kg, from about 45 mg/kg to about 65 mg/kg, from about 50 mg/kg to about 75 mg/kg, from about 60 mg/kg to about 240 mg/kg, from about 70 mg/kg to about 350 mg/kg, from about 80 mg/kg to about 400 mg/kg, from about 90 mg/kg to about 450 mg/kg, from about 100 mg/kg to about 500 mg/kg, from about 0.01 g/kg to about 1 g/kg, from about 0.05 g/kg to about 2 g/kg, from about 1 g/kg to about 5 g/kg, or more than 5 g/kg.

In some embodiments, pharmaceutical compositions that are or include SBPs may be administered at a dose sufficient to yield desired therapeutic agent or SBP concentration levels in subject tissue or fluids (e.g., blood, plasma, urine, etc.). In some embodiments, doses are adjusted to achieve subject therapeutic agent or SBP concentration levels in subject tissues or fluids of from about 1 pg/mL to about 5 pg/mL, from about 2 pg/mL to about 10 pg/mL, from about 4 pg/mL to about 16 pg/mL, from about 5 pg/mL to about 20 pg/mL, from about 8 pg/mL to about 24 pg/mL, from about 10 pg/mL to about 30 pg/mL, from about 12 pg/mL to about 32 pg/mL, from about 14 pg/mL to about 34 pg/mL, from about 16 pg/mL to about 36 pg/mL, from about 18 pg/mL to about 38 pg/mL, from about 20 pg/mL to about 40 pg/mL, from about 22 pg/mL to about 42 pg/mL, from about 24 pg/mL to about 44 pg/mL, from about 26 pg/mL to about 46 pg/mL, from about 28 pg/mL to about 48 pg/mL, from about 30 pg/mL to about 50 pg/mL, from about 35 pg/mL to about 55 pg/mL, from about 40 pg/mL to about 60 pg/mL, from about 45 pg/mL to about 65 pg/mL, from about 50 pg/mL to about 75 pg/mL, from about 60 pg/mL to about 240 pg/mL, from about 70 pg/mL to about 350 pg/mL, from about 80 pg/mL to about 400 pg/mL, from about 90 pg/mL to about 450 pg/mL, from about 100 pg/mL to about 500 pg/mL, from about 0.01 ng/mL to about 1 ng/mL, from about 0.05 ng/mL to about 2 ng/mL, from about 1 ng/mL to about 5 ng/mL, from about 2 ng/mL to about 10 ng/mL, from about 4 ng/mL to about 16 ng/mL, from about 5 ng/mL to about 20 ng/mL, from about 8 ng/mL to about 24 ng/mL, from about 10 ng/mL to about 30 ng/mL, from about 12 ng/mL to about 32 ng/mL, from about 14 ng/mL to about 34 ng/mL, from about 16 ng/mL to about 36 ng/mL, from about 18 ng/mL to about 38 ng/mL, from about 20 ng/mL to about 40 ng/mL, from about 22 ng/mL to about 42 ng/mL, from about 24 ng/mL to about 44 ng/mL, from about 26 ng/mL to about 46 ng/mL, from about 28 ng/mL to about 48 ng/mL, from about 30 ng/mL to about 50 ng/mL, from about 35 ng/mL to about 55 ng/mL, from about 40 ng/mL to about 60 ng/mL, from about 45 ng/mL to about 65 ng/mL, from about 50 ng/mL to about 75 ng/mL, from about 60 ng/mL to about 240 ng/mL, from about 70 ng/mL to about 350 ng/mL, from about 80 ng/mL to about 400 ng/mL, from about 90 ng/mL to about 450 ng/mL, from about 100 ng/mL to about 500 ng/mL, from about 0.01 µg/mL to about 1 µg/mL, from about 0.05 µg/mL to about 2 µg/mL, from about 1 µg/mL to about 5 µg/mL, from about 2 µg/mL to about 10 µg/mL, from about 4 µg/mL to about 16 µg/mL, from about 5 µg/mL to about 20 µg/mL, from about 8 µg/mL to about 24 µg/mL, from about 10 µg/mL to about 30 µg/mL, from about 12 µg/mL to about 32 µg/mL, from about 14 µg/mL to about 34 µg/mL, from about 16 µg/mL to about 36 µg/mL, from about 18 µg/mL to about 38 µg/mL, from about 20 µg/mL to about 40 µg/mL, from about 22 µg/mL to about 42 µg/mL, from about 24 µg/mL to about 44 µg/mL, from about 26 µg/mL to about 46 µg/mL, from about 28 µg/mL to about 48 µg/mL, from about 30 µg/mL to about 50 µg/mL, from about 35 µg/mL to about 55 µg/mL, from about 40 µg/mL to about 60 µg/mL, from about 45 µg/mL to about 65 µg/mL, from about 50 µg/mL to about 75 µg/mL, from about 60 µg/mL to about 240 µg/mL, from about 70 µg/mL to about 350 µg/mL, from about 80 µg/mL to about 400 µg/mL, from about 90 µg/mL to about 450 µg/mL, from about 100 µg/mL to about 500 µg/mL, from about 0.01 mg/mL to about 1 mg/mL, from about 0.05 mg/mL to about 2 mg/mL, from about 1 mg/mL to about 5 mg/mL, from about 2 mg/mL to about 10 mg/mL, from about 4 mg/mL to about 16 mg/mL, from about 5 mg/mL to about 20 mg/mL, from about 8 mg/mL to about 24 mg/mL, from about 10 mg/mL to about 30 mg/mL, from about 12 mg/mL to about 32 mg/mL, from about 14 mg/mL to about 34 mg/mL, from about 16 mg/mL to about 36 mg/mL, from about 18 mg/mL to about 38 mg/mL, from about 20 mg/mL to about 40 mg/mL, from about 22 mg/mL to about 42 mg/mL, from about 24 mg/mL to about 44 mg/mL, from about 26 mg/mL to about 46 mg/mL, from about 28 mg/mL to about 48 mg/mL, from about 30 mg/mL to about 50 mg/mL, from about 35 mg/mL to about 55 mg/mL, from about 40 mg/mL to about 60 mg/mL, from about 45 mg/mL to about 65 mg/mL, from about 50 mg/mL to about 75 mg/mL, from about 60 mg/mL to about 240 mg/mL, from about 70 mg/mL to about 350 mg/mL, from about 80 mg/mL to about 400 mg/mL, from about 90 mg/mL to about 450 mg/mL, from about 100 mg/mL to about 500 mg/mL, from about 0.01 g/mL to about 1 g/mL.

In some embodiments, pharmaceutical compositions that are or include SBPs are provided in one or more doses and are administered one or more times to subjects. Some pharmaceutical compositions are provided in only a single administration. Some pharmaceutical compositions are provided according to a dosing schedule that include two or more administrations. Each administration may be at the same dose or may be different from a previous and/or subsequent dose. In some embodiments, subjects are provided an initial dose that is higher than subsequent doses (referred to herein as a "loading dose"). In some embodiments, doses are decreased over the course of administration. In some embodiments, dosing schedules include pharmaceutical composition administration from about every 2 hours to about every 10 hours, from about every 4 hours to about every 20 hours, from about every 6 hours to about every 30 hours, from about every 8 hours to about every 40 hours, from about every 10 hours to about every 50 hours, from about every 12 hours to about every 60 hours, from about every 14 hours to about every 70 hours, from about every 16 hours to about every 80 hours, from about every 18 hours to about every 90 hours, from about every 20 hours to about every 100 hours, from about every 22 hours to about every 120 hours, from about every 24 hours to about every 132 hours, from about every 30 hours to about every 144 hours, from about every 36 hours to about every 156 hours, from about every 48 hours to about every 168 hours, from about every 2 days to about every 10 days, from about every 4 days to about every 15 days, from about every 6 days to about every 20 days, from about every 8 days to about every 25 days, from about every 10 days to about every 30 days, from about every 12 days to about every 35 days, from about every 14 days to about every 40 days, from about every 16 days to about every 45 days, from about every 18 days to about every 50 days, from about every 20 days to about every 55 days, from about every 22 days to about every 60 days, from about every 24 days to about every 65 days, from about every 30 days to about every 70 days, from about every 2 weeks to about every 8 weeks, from about every 3 weeks to about every 12 weeks, from about every 4 weeks to about every 16 weeks, from about every 5 weeks to about every 20 weeks, from about every 6 weeks to about every 24 weeks, from about every 7 weeks to about every 28 weeks, from about every 8 weeks to about every 32 weeks, from about even 9 weeks to about every 36 weeks, from about every 10 weeks to about every 40 weeks, from about every 11 weeks to about every 44 weeks, from about every 12 weeks to about every 48 weeks, from about every 14 weeks to about every 52 weeks, from about ever 16 weeks to about even 56 weeks, from about every 20 weeks to about every 60 weeks, from about every 2 months to about every 6 months, from about every 3 months to about every 12 months, from about every 4 months to about every 18 months, from about every 5 months to about every 24 months, from about every 6 months to about every 30 months, from about every 7 months to about every 36 months, from about every 8 months to about every 42 months, from about every 9 months to about every 48 months, from about every 10 months to about every 54 months, from about every 11 months to about every 60 months, from about every 12 months to about every 66 months, from about 2 years to about 5 years, from about 3 years to about 10 years, from about 4 years to about 15 years, from about 5 years to about 20 years, from about 6 years to about 25 years, from about 7 years to about 30 years, from about 8 years to about 35 years, from about 9 years to about 40 years, from about 10 years to about 45 years, from about 15 years to about 50 years, or more than every 50 years.

In some embodiments, pharmaceutical compositions that are or include SBPs may be administered at a dose sufficient to provide a therapeutically effective amount of therapeutic agents or SBPs. As used herein, the term "therapeutically effective amount" refers to an amount of an agent sufficient to achieve a therapeutically effective outcome. As used herein, the term "therapeutically effective outcome" refers to a result of treatment where at least one objective of treatment is met. In some embodiments, a therapeutically effective amount is provided in a single dose. In some embodiments, a therapeutically effective amount is administered according to a dosing schedule that includes a plurality of doses. Those skilled in the art will appreciate that in some embodiments, a unit dosage form may be considered to include a therapeutically effective amount of a particular agent or entity if it includes an amount that is effective when administered as part of such a dosage regimen.

Administration

In some embodiments, pharmaceutical compositions that are or include SBPs may be administered according to one or more administration routes. In some embodiments, administration is enteral (into the intestine), transdermal, intravenous bolus, intralesional (within or introduced directly to a localized lesion), intrapulmonary (within the lungs or its bronchi), diagnostic, intraocular (within the eye), transtympanic (across or through the tympanic cavity), intravesical infusion, sublingual, nasogastric (through the nose and into the stomach), spinal, intracartilaginous (within a cartilage), insufflation (snorting), rectal, intravascular (within a vessel or vessels), buccal (directed toward the cheek), dental (to a tooth or teeth), intratesticular (within the testicle), intratympanic (within the aurus media), percutaneous, intrathoracic (within the thorax), submucosal, cutaneous, epicutaneous (application onto the skin), dental intracomal, intramedullary (within the marrow cavity of a bone), intra-abdominal, epidural (into the dura matter), intramuscular (into a muscle), intralymphatic (within the lymph), iontophoresis (by means of electric current where ions of soluble salts migrate into the tissues of the body), subcutaneous (under the skin), intragastric (within the stomach), nasal administration (through the nose), transvaginal, intravenous drip, endosinusial, intraprostatic (within the prostate gland), soft tissue, intradural (within or beneath the dura), subconjunctival, oral (by way of the mouth), peridural, parenteral, intraduodenal (within the duodenum), intracisternal (within the cisterna magna cerebellomedularis), periodontal, periarticular, biliary perfusion, intracoronary (within the coronary arteries), intrathecal (within the cerebrospinal fluid at any level of the cerebrospinal axis), intrameningeal (within the meninges), intracavernous injection (into a pathologic cavity) intracavitary (into the base of the penis), intrabiliary, subarachnoid, intrabursal, ureteral (to the ureter), intratendinous (within a tendon), auricular (in or by way of the ear), intracardiac (into the heart), enema, intraepidermal (to the epidermis), intraventricular (within a ventricle), intramyocardial (within the myocardium), intratubular (within the tubules of an organ), vaginal, sublabial, intracorporus cavemosum (within the dilatable spaces of the corpus cavernosa of the penis), intradermal (into the skin itself), intravitreal (through the eye), perineural, cardiac perfusion, irrigation (to bathe or flush open wounds or body cavities), in ear drops, endotracheal, intraosseous infusion (into the bone marrow), caudal block, intrauterine, transtracheal (through the wall of the trachea), intra-articular, intracorneal (within the cornea), endocervical, extracorporeal, intraspinal (within the vertebral column), transmucosal (diffusion through a mucous membrane), topical, photopheresis, oropharyngeal (directly to the mouth and pharynx), occlusive dressing technique (topical route administration which is then covered by a dressing which occludes the area), transplacental (through or across the placenta), intrapericardial (within the pericardium), intraarterial (into an artery), interstitial, intracerebral (into the cerebrum), intracerebroventricular (into the cerebral ventricles), peridural, intrapleural (within the pleura), infiltration, intrabronchial, intrasinal (within the nasal or periorbital sinuses), intraductal (within a duct of a gland), transdermal (diffusion through the intact skin for systemic distribution), intracaudal (within the cauda equine), nerve block, retrobulbar (behind the pons or behind the eyeball), intravenous (into a vein), intra-amniotic, conjunctival, intrasynovial (within the synovial cavity of a joint), gastroenteral, intraluminal (within a lumen of a tube), intrathecal (into the spinal canal), electro-osmosis, intraileal (within the distal portion of the small intestine), intraesophageal (to the esophagus), extra-amniotic administration, hemodialysis, intragingival (within the gingivae), intratumor (within a tumor), eye drops (onto the conjunctiva), laryngeal (directly upon the larynx), urethral (to the urethra), intravaginal administration, intramyocardial (entering the myocardium), intraperitoneal (infusion or injection into the peritoneum), respiratory (within the respiratory tract by inhaling orally or nasally for local or systemic effect), intradiscal (within a disc), ophthalmic (to the external eye), and/or intraovarian (within the ovary).

In some embodiments, pharmaceutical compositions that are or include SBPs may be administered by auricular administration, intraarticular administration, intramuscular administration, intrathecal administration, extracorporeal administration, buccal administration, intrabronchial administration, conjunctival administration, cutaneous administration, dental administration, endocervical administration, endosinusial administration, endotracheal administration, enteral administration, epidural administration, intra-abdominal administration, intrabiliary administration, intrabursal administration, oropharyngeal administration, interstitial administration, intracardiac administration, intracartilaginous administration, intracaudal administration, intracavernous administration, intracerebral administration, intracorporous cavernosum, intracavitary administration, intracorneal administration, intracisternal administration, cranial administration, intracranial administration, intradermal administration, intralesional administration, intratympanic administration, intragingival administration, intraovarian administration, intraocular administration, intradiscal administration, intraductal administration, intraduodenal administration, ophthalmic administration, intradural administration, intraepidermal administration, intraesophageal administration, nasogastric administration, nasal administration, laryngeal administration, intraventricular administration, intragastric administration, intrahepatic administration, intraluminal administration, intravitreal administration, intravesicular administration, intralymphatic administration, intramammary administration, intramedullary administration, intrasinal administration, intrameningeal administration, intranodal administration, intraovarian administration, intrapulmonary administration, intrapericardial administration, intraperitoneal administration, intrapleural administration, intraprericardial administration, intraprostatic administration, intrapulmonary administration, intraluminal administration, intraspinal administration, intrasynovial administration, intratendinous administration, intratesticular administration, subconjunctival administration, intracerebroventricular administration, epicutanous administration, intravenous administration, retrobulbar administration, periarticular administration, intrathoracic administration, subarachnoid administration, intratubular administration, periodontal administration, transtympanic administration, transtracheal administration, intratumor administration, vaginal administration, urethral administration, intrauterine administration, oral administration, gastroenteral administration, parenteral administration, sublingual administration, ureteral administration, percutaneous administration, peridural administration, transmucosal administration, perineural administration, transdermal administration, rectal administration, soft tissue administration, intraarterial administration, subcutaneous administration, topical administration, extra-amniotic administration, insufflation, enema, eye drops, ear drops, or intravesical infusion. In some embodiments, the SBPs described herein may be administered via injection. Injection site reactions may be monitored via any method known to one skilled in the art.

In some embodiments, SBPs may be administered for localized treatment (e.g., see United States Publication Numbers US20170368236 and US20110171239, the contents of each of which are herein incorporated by reference in their entirety). In some embodiments, SBPs may be administered for treatment of areas located further away from administration sites (e.g., see Aykac et al. (2017) Gene s0378-1119(17)30868-30865, the contents of which are herein incorporated by reference in their entirety).

In some embodiments, administration includes ocular administration. As used herein, the term "ocular administration" refers to delivery of an agent to an eye. Ocular administration may include, but is not limited to, topical administration (e.g., using eye drops, ointments, sprays, or creams), intraocular administration, intravitreal administration, intraretinal administration, intracorneal administration, intrascleral administration, lacrimal administration, punctal administration, administration to the anterior sub-Tenon's, suprachoroidal administration, administration to the posterior sub-Tenon's, subretinal administration, administration to the fornix, administration to the lens, administration to the anterior segment, administration to the posterior segment, macular administration, and intra-aqueous humor administration. Administration may include intravitreal injection.

In some embodiments, the SBPs described herein may be administered as an eye drop. In some embodiments, the SBPs described herein may be administered as a spray. In some embodiments, the SBPs described herein may be administered by injection. In some embodiments, the SBPs described herein may be administered by lens application. In some embodiments, the SBPs described herein may be administered as a plug. In some embodiments, the SBPs are administered as a lacrimal plug. In some embodiments, the SBPs are administered as a punctal plug.

In some embodiments, SBP administration or SBP-based therapeutic agent administration occurs over a period of time, referred to herein as the "administration period." During administration periods, administration may be continuous or may be separated into two or more administrations. In some embodiments, administration periods may be from about 1 min to about 30 min, from about 10 min to about 45 min, from about 20 min to about 60 min, from about 40 min to about 90 min, from about 2 hours to about 10 hours, from about 4 hours to about 20 hours, from about 6 hours to about 30 hours, from about 8 hours to about 40 hours, from about 10 hours to about 50 hours, from about 12 hours to about 60 hours, from about 14 hours to about 70 hours, from about 16 hours to about 80 hours, from about 18 hours to about 90 hours, from about 20 hours to about 100 hours, from about 22 hours to about 120 hours, from about 24 hours to about 132 hours, from about 30 hours to about 144 hours, from about 36 hours to about 156 hours, from about 48 hours to about 168 hours, from about 2 days to about 10 days, from about 4 days to about 15 days, from about 6 days to about 20 days, from about 8 days to about 25 days, from about 10 days to about 30 days, from about 12 days to about 35 days, from about 14 days to about 40 days, from about 16 days to about 45 days, from about 18 days to about 50 days, from about 20 days to about 55 days, from about 22 days to about 60 days, from about 24 days to about 65 days, from about 30 days to about 70 days, from about 2 weeks to about 8 weeks, from about 3 weeks to about 12 weeks, from about 4 weeks to about 16 weeks, from about 5 weeks to about 20 weeks, from about 6 weeks to about 24 weeks, from about 7 weeks to about 28 weeks, from about 8 weeks to about 32 weeks, from about 9 weeks to about 36 weeks, from about 10 weeks to about 40 weeks, from about 11 weeks to about 44 weeks, from about 12 weeks to about 48 weeks, from about 14 weeks to about 52 weeks, from about 16 weeks to about 56 weeks, from about 20 weeks to about 60 weeks, from about 2 months to about 6 months, from about 3 months to about 12 months, from about 4 months to about 18 months, from about about 5 months to about 24 months, from about 6 months to about 30 months, from about 7 months to about 36 months, from about 8 months to about 42 months, from about 9 months to about 48 months, from about 10 months to about 54 months, from about 11 months to about 60 months, from about 12 months to about 66 months, from about 2 years to about 5 years, from about 3 years to about 10 years, from about 4 years to about 15 years, from about 5 years to about 20 years, from about 6 years to about 25 years, from about 7 years to about 30 years, from about 8 years to about 35 years, from about 9 years to about 40 years, from about 10 years to about 45 years, from about 15 years to about 50 years, or more than 50 years.

III. Agricultural Applications and Products

In some embodiments, SBP formulations are prepared for use in agriculture. As used herein, the term "agriculture" refers to the cultivation of plants and animals to produce products useful for individual, communal, industrial, or commercial purposes. SBPs may be agricultural compositions. In some embodiments, SBPs may include an agricultural composition. As used herein, the term "agricultural composition" refers to any substance used in or produced by agriculture. In some embodiments, SBPs may be used to improve the growth, production, the shelf-life and stability of agricultural products. As used herein, the term "agriculture product" refers to any product of agriculture (e.g., food, medicines, materials, biofuels, etc.). In some embodiments, SBP formulations may be used in a variety of agricultural applications (e.g., agricultural SBP formulations). As used herein, the term "agricultural application" refers to any method used to improve, promote or increase the production of products obtained through the cultivation of plants and animals, for the benefit of individuals, communities, or commercial entities.

In some embodiments, agricultural compositions described herein are used for agricultural and environmental development. In some embodiments, SBP formulations may be used to improve the growth and production of agricultural products. These agricultural products may be plants, animals, plant agricultural products, or animal agricultural products. In some embodiments, SBP formulation administration may result in increased weight, biomass, growth, offspring production, product levels, and/or product size of one or more agricultural products. In some embodiments, the agricultural SBP formulations may include soil or locus stabilizers.

Cargo

In some embodiments, agricultural SBP formulations are used to facilitate delivery of cargo that enhance agricultural product health, yield, half-life and/or stability. In some embodiments, SBP formulations may be the cargos. In some embodiments, cargos may include, but are not limited to, therapeutic agents, small molecules, chemicals, nutrients, micronutrients, macronutrients, pest control agents, pesticides, antibiotics, antifungal, fungicide, virus, virus fragment, virus particle, herbicide, insecticide, fertilizers, pH modulators, soil stabilizers, and flowability agents. In some embodiments, the efficacy of the cargo is improved by formulation within an agricultural SBP formulations. In some embodiments, agricultural SBP formulations may encapsulate cargo for extended and/or controlled release.

In some embodiments, cargos for use in SBP formulations may be selected from any of those listed in Table 5.

TABLE 5

| Cargo | |
|---|---|
| Paytoad | Category |
| amikacin | antibiotic |
| amoxicillin | antibiotic |
| ampicillin | antibiotic |
| azithromycin | antibiotic |
| azlocillin | antibiotic |
| aztreonam | antibiotic |
| capreomycin | antibiotic |
| carbenicillin | antibiotic |
| cefaclor | antibiotic |
| cefadroxil | antibiotic |
| cefalexin | antibiotic |
| cefalothin | antibiotic |
| cefamandole | antibiotic |
| cefazolin | antibiotic |
| cefdinir | antibiotic |
| cefditoren | antibiotic |
| cefepime | antibiotic |
| cefixime | antibiotic |
| cefoperazone | antibiotic |
| cefotaxime | antibiotic |
| cefoxitin | antibiotic |
| cefpodoxime | antibiotic |
| cefprozil | antibiotic |
| ceftaroline fosamil | antibiotic |
| ceftazidime | antibiotic |
| ceftibuten | antibiotic |
| ceftizoxime | antibiotic |
| ceftobiprole | antibiotic |
| ceftriaxone | antibiotic |
| cefuroxime | antibiotic |
| cilastatin | antibiotic |
| ciprofolaxin | antibiotic |
| clarithromycin | antibiotic |
| clindamycin | antibiotic |
| clofazimine | antibiotic |
| cloxacillin | antibiotic |
| cycloserine | antibiotic |
| dalbavancin | antibiotic |
| dapsone | antibiotic |
| daptomycin | antibiotic |
| demeclocycline | antibiotic |
| dicloxacillin | antibiotic |
| dirithromycin | antibiotic |
| doripenem | antibiotic |
| doxycycline | antibiotic |
| enoxacin | antibiotic |

TABLE 5-continued

Cargo

| Paytoad | Category |
|---|---|
| ertapenem | antibiotic |
| ethambutol | antibiotic |
| ethionamide | antibiotic |
| flucloxacillin | antibiotic |
| furazolidone | antibiotic |
| gatifloxacin | antibiotic |
| geldanamycin | antibiotic |
| gemifloxacin | antibiotic |
| gentamicin | antibiotic |
| grepafloxacin | antibiotic |
| herbimycin | antibiotic |
| imipeneum | antibiotic |
| isoniazid | antibiotic |
| kanamycin | antibiotic |
| levofloxacin | antibiotic |
| linezolid | antibiotic |
| linomycin | antibiotic |
| lomefloxacin | antibiotic |
| loracarbef | antibiotic |
| mafenide | antibiotic |
| meropenem | antibiotic |
| methicillin | antibiotic |
| mezlocillin | antibiotic |
| minocycline | antibiotic |
| moxifloxacin | antibiotic |
| nafcillin | antibiotic |
| nalidixic acid | antibiotic |
| neomycin | antibiotic |
| netilmicin | antibiotic |
| nitrofurantoin | antibiotic |
| norfloxacin | antibiotic |
| ofloxacin | antibiotic |
| oritavancin | antibiotic |
| oxacillin | antibiotic |
| oxytetracycline | antibiotic |
| paromomycin | antibiotic |
| penicillin G | antibiotic |
| penicillin V | antibiotic |
| piperacillin | antibiotic |
| posizolid | antibiotic |
| pyrazinamide | antibiotic |
| radezolid | antibiotic |
| rifampicin | antibiotic |
| rifaximin | antibiotic |
| roxithromycin | antibiotic |
| sparfloxacin | antibiotic |
| spectinomycin | antibiotic |
| spiramycin | antibiotic |
| sulfacetamide | antibiotic |
| sulfadiazine | antibiotic |
| sulfadimethoxine | antibiotic |
| sulfamethizole | antibiotic |
| sulfamethoxazole | antibiotic |
| sulfanilimide | antibiotic |
| sulfasalazine | antibiotic |
| sulfisoxazole | antibiotic |
| teicoplanin | antibiotic |
| telavancin | antibiotic |
| telithromycin | antibiotic |
| temafloxacin | antibiotic |
| temocillin | antibiotic |
| ticarcillin | antibiotic |
| tobramycin | antibiotic |
| torezolid | antibiotic |
| troleandomycin | antibiotic |
| trovafloxacin | antibiotic |
| vancomycin | antibiotic |
| erythromycin | antibiotic; endoparasiticide |
| penicillin | antibiotic; endoparasiticide |
| streptomycin | antibiotic; endoparasiticide |
| tetracycline | antibiotic; endoparasiticide |
| 5-fluorocytosine | antifungal |
| abafungin | antifungal |
| albaconazole | antifungal |
| allylamine | antifungal |
| amorolfin | antifungal |
| amphotericin B | antifungal |
| anidulafungin | antifungal |
| aurone | antifungal |
| balsam | antifungal |
| benzoic acid | antifungal |
| bifonazole | antifungal |
| butenafine | antifungal |
| butoconazole | antifungal |
| candicidin | antifungal |
| caspofungin | antifungal |
| ciclopirx | antifungal |
| clotrimazole | antifungal |
| crystal violet | antifungal |
| echinocandin | antifungal |
| econazole | antifungal |
| efinaconazole | antifungal |
| epoxiconazole | antifungal |
| tenticonazole | antifungal |
| filipin | antifungal |
| fluconazole | antifungal |
| flucytosine | antifungal |
| griseofulvin | antifungal |
| haloprogin | antifungal |
| hamycin | antifungal |
| imidazole | antifungal |
| isavuconazole | antifungal |
| isoconazole | antifungal |
| itraconazole | antifungal |
| ketoconazole | antifungal |
| luliconazole | antifungal |
| micafungin | antifungal |
| miconazole | antifungal |
| miltefosine | antifungal |
| naftitine | antifungal |
| natamycin | antifungal |
| nystatin | antifungal |
| omoconazole | antifungal |
| orotomide | antifungal |
| oxiconazole | antifungal |
| polyene antifungal | antifungal |
| posaconazole | antifungal |
| propiconazole | antifungal |
| ravuconazole | antifungal |
| rimocidin | antifungal |
| sertaconazole | antifungal |
| sulconazole | antifungal |
| terbinafine | antifungal |
| terconazole | antifungal |
| thiazole | antifungal |
| tioconazole | antifungal |
| tolnaftate | antifungal |
| triazole | antifungal |
| undecylenic acid | antifungal |
| voriconazole | antifungal |
| bacterial cell | biologic |
| microbiome | biologic |
| microorganism | biologic |
| rhizobia bacteria | biologic |
| symbiote | biologic |
| virus | biologic |
| virus fragment | biologic |
| virus particle | biologic |
| fungicide | biologic; pesticide |
| Pour-Ons | ectoparasiticide |
| Sprays | ectoparasiticide |
| Dips | ectoparasiticide |
| Ear Tags | ectoparasiticide |
| Collars | ectoparasiticide |
| Oral Tablets | ectoparasiticide |
| Other Ectoparasiticides | ectoparasiticide |
| Spot-Ons | ectoparasiticide |
| ectoparaciticide | ectoparasiticide |
| pyrethroid | ectoparasiticide |
| carbamate | ectoparasiticide |
| water-insoluble organo-phospphorus compound | ectoparasiticide |

TABLE 5-continued

Cargo

| Paytoad | Category |
|---|---|
| benzoyl urea | ectoparasiticide |
| formamidine | ectoparasiticide |
| triazine | ectoparasiticide |
| avermectin | ectoparasiticide |
| milbemycin | ectoparasiticide |
| flumethrin | ectoparasiticide |
| alphamethrin | ectoparasiticide |
| pirimphos methyl | ectoparasiticide |
| pirimphos ethyl | ectoparasiticide |
| mylbemycin | ectoparasiticide |
| moxidectin | ectoparasiticide; endoparasiticide |
| ivermectin | ectoparasiticide; endoparasiticide; insecticide |
| doramectin | ectoparasiticide; endoparasiticide; insecticide |
| abamectin | ectoparasiticide; insecticide |
| pyrethrin | ectoparasiticide; insecticide |
| cyhalothrin | ectoparasiticide; insecticide |
| amitraz | ectoparasiticide; insecticide |
| deltamethrin | ectoparasiticide; insecticide |
| diazmon | ectoparasiticide; insecticide |
| macrocyclic lactones | endecticide |
| benzimidazole | endecticide |
| pro-benzimidazole | endecticide |
| imidazothiazole | endecticide |
| tetrahydropyrimidine | endecticide |
| organophosphate | endecticide |
| Endoparasiticide | endoparasiticide |
| Oral Liquids | endoparasiticide |
| Oral Solids | endoparasiticide |
| Injectables | endoparasiticide |
| Feed Additives | endoparasiticide |
| Endectocides | endoparasiticide |
| Tetramisole | endoparasiticide |
| dexamisole | endoparasiticide |
| Milbemycin oxime | endoparasiticide |
| Nemadectin | endoparasiticide |
| Albendazole | endoparasiticide |
| Clorsulon | endoparasiticide |
| Cydectin | endoparasiticide |
| Diethyicarbamazine | endoparasiticide |
| Febantel | endoparasiticide |
| Fenbendazole | endoparasiticide |
| Haloxon | endoparasiticide |
| Levamisole | endoparasiticide |
| Mebendazole | endoparasiticide |
| Morantel | endoparasiticide |
| Oxyclozanide | endoparasiticide |
| Oxibendazole | endoparasiticide |
| Oxfendazole | endoparasiticide |
| Oxamniquine | endoparasiticide |
| Pyrantel | endoparasiticide |
| Praziquantel | endoparasiticide |
| Thiabendazole | endoparasiticide |
| cyclosporin | endoparasiticide |
| sulfonamide | endoparasiticide |
| cephalosporin | endoparasiticide |
| cephamycin | endoparasiticide |
| aminoglucosid | endoparasiticide |
| trimethoprim | endoparasiticide |
| dimetridazole | endoparasiticide |
| framycetin | endoparasiticide |
| fruazolidone | endoparasiticide |
| plenromutilin | endoparasiticide |
| a compound active against protozoa | endoparasiticide |
| piperazine | endoparasiticide; endecticide |
| emamectin | endoparasiticide; insecticide |
| eprinomectin | endoparasiticide; insecticide |
| milbemectin | endoparasiticide; insecticide |
| permethrin | endoparasiticide; insecticide |
| selamectin | endoparasiticide, insecticide |
| trichlorfon | endoparasiticide; insecticide |
| ammonium nitrate | fertilizer |
| binary fertilizer | fertilizer |
| compound fertilizer | fertilizer |
| diammonium phosphate | fertilizer |
| fertilizer | fertilizer |
| monoammonium phosphate | fertilizer |
| multinutrient fertilizer | fertilizer |
| natural fertilizer | fertilizer |
| nitrogen fertilizer | fertilizer |
| NK fertilizer | fertilizer |
| NP fertilizer | fertilizer |
| NPK fertilizer | fertilizer |
| organic fertilizer | fertilizer |
| phosphate fertilizer | fertilizer |
| PK fertilizer | fertilizer |
| potassium fertilizer | fertilizer |
| single-nutrient fertilizer | fertilizer |
| superphosphate | fertilizer |
| synthetic fertilizer | fertilizer |
| urea | fertilizer |
| binapacryl | fungicide |
| Bisphenol A | fungicide |
| copper 8-hydroxyquinoline | fungicide |
| copper sulfate | fungicide |
| mercuric chloride | fungicide |
| phenol | fungicide |
| phenylmercuric oleate | fungicide |
| tributyltin chloride | fungicide |
| tributyltin triacetate | fungicide |
| pentachlorophenol | fungicide; insecticide |
| Bupirimate | fungicide; pesticide |
| Captan | fungicide; pesticide |
| Carbendazim | fungicide; pesticide |
| Chloranil | fungicide; pesticide |
| antibiotic | general |
| fertilizer | general |
| nutrient | general |
| pH modulator | general |
| small molecule | general |
| soil stabilizer | general |
| therapeutic agent | general |
| 2,4,5-T | herbicide |
| 2,4-D | herbicide |
| atrazine | herbicide |
| chlorophenoxy acid | herbicide |
| cynazine | herbicide |
| glyphosate | herbicide |
| hexazinone | herbicide |
| MCPA | herbicide |
| metribuzin | herbicide |
| organic phosphorus herbicide | herbicide |
| silvex | herbicide |
| simazine | herbicide |
| triazine herbicide | herbicide |
| bromacil | herbicide, pesticide |
| Chloramben | herbicide; pesticide |
| Chlorfenac | herbicide; pesticide |
| Chlorsulfuron | herbicide; pesticide |
| Abscisic acid | hormone |
| Auxins | hormone |
| Cytokinins | hormone |
| Ethylene | hormone |
| Gibberellins | hormone |
| steroid | hormone |
| dexamethasone | hormone |
| allopregnanolone | hormone |
| estrogen | hormone |
| ethinylestradiol | hormone |
| mestranol | hormone |
| estradiols | hormone |
| estriol | hormone |
| estriolsuccinate | hormone |
| polyestriolphosphate | hormone |
| estrone | hormone |
| estronesulfate | hormone |
| conjugatedesttogens | hormone |
| progesterone | hormone |

TABLE 5-continued

| Cargo | |
|---|---|
| Paytoad | Category |
| norethisteroneacetate | hormone |
| norgestrel | hormone |
| levonorgestrel | hormone |
| gestodene | hormone |
| chiormadinoneacetate | hormone |
| drospirorenone | hormone |
| 3-ketodesogestrel | hormone |
| androgen | hormone |
| testosterone | hormone |
| androstenediol | hormone |
| androstenedione | hormone |
| dehydroepiandrosterone | hormone |
| dihydrotestosterone | hormone |
| anymineralocorticoid | hormone |
| anyglucocoriticoid | hormone |
| cholesterols | hormone |
| 1,2-dichloropropane | insecticide |
| acephate | insecticide |
| acetamiprid | insecticide |
| acethion | insecticide |
| acetoprole | insecticide |
| acrinathrin | insecticide |
| acrylonitrile | insecticide |
| alanycarb | insecticide |
| aldicarb | insecticide |
| aldnm | insecticide |
| aldoxycatb | insecticide |
| allethrin | insecticide |
| allosamidin | insecticide |
| allyxycarb | insecticide |
| alpha-cypermethrin | insecticide |
| amidithion | insecticide |
| aminocarb | insecticide |
| amiton | insecticide |
| anabasine | insecticide |
| athidathion | insecticide |
| azadirachtin | insecticide |
| azamethiphos | insecticide |
| azinphos-ethyl | insecticide |
| azinphos-methyl | insecticide |
| azothoate | insecticide |
| barium hexafluorosilicate | insecticide |
| barthrin | insecticide |
| bendiocarb | insecticide |
| benfuracarb | insecticide |
| bensultap | insecticide |
| beta-cyfluthrin | insecticide |
| beta-cypermethrin | insecticide |
| bifenthrin | insecticide |
| bioallethtin | insecticide |
| bioethanomethrin | insecticide |
| biopermethrin | insecticide |
| bioresmethtin | insecticide |
| bistrifluron | insecticide |
| borax | insecticide |
| botanical insecticide | insecticide |
| bromfenvinfos | insecticide |
| bromo-DDT | insecticide |
| bromophos-ethyl | insecticide |
| bufencarb | insecticide |
| buprofezin | insecticide |
| butacarb | insecticide |
| butathiofos | insecticide |
| butocarboxim | insecticide |
| butonate | insecticide |
| butoxycarboxim | insecticide |
| cadusafos | insecticide |
| calcium arsenate | insecticide |
| calcium polysulfide | insecticide |
| camphechlor | insecticide |
| carbanolate | insecticide |
| carbofuran | insecticide |
| carbon disulfide | insecticide |
| carbon tetrachloride | insecticide |
| carbosulfan | insecticide |
| cartap | insecticide |
| chiorbicyclen | insecticide |
| chlordane | insecticide |
| chlordecone | insecticide |
| chlorethoxyfos | insecticide |
| chlorfenapyr | insecticide |
| chlorfenvinphos | insecticide |
| chiorfluazuton | insecticide |
| chlormephos | insecticide |
| chloroform | insecticide |
| chloropicrin | insecticide |
| chlorphoxim | insecticide |
| chlorprazophos | insecticide |
| chlorpyrifos-methyl | insecticide |
| chlorthiophos | insecticide |
| chromafenozide | insecticide |
| cinerin I | insecticide |
| cinerin II | insecticide |
| cismethrin | insecticide |
| cloethocarb | insecticide |
| closantel | insecticide |
| clothianidin | insecticide |
| copper acetoarsenite | insecticide |
| copper arsenate | insecticide |
| coumaphos | insecticide |
| coumithoale | insecticide |
| crotamiton | insecticide |
| crotoxyphos | insecticide |
| crufomate | insecticide |
| cryolite | insecticide |
| cyanofenphos | insecticide |
| cyanophos | insecticide |
| cyanthoate | insecticide |
| cyclethrin | insecticide |
| cycloprothrin | insecticide |
| cyfluthrin | insecticide |
| cypermethrin | insecticide |
| cyphenothrin | insecticide |
| cyromazine | insecticide |
| cythioate | insecticide |
| DDT | insecticide |
| decatbofuran | insecticide |
| demephion | insecticide |
| demephion-O | insecticide |
| demephion-S | insecticide |
| demeton | insecticide |
| demeton-methyl | insecticide |
| demeton-O | insecticide |
| demeton-O-methyl | insecticide |
| demeton-S | insecticide |
| demeton-S-methyl | insecticide |
| demeton-S-methylsulphon | insecticide |
| diafenthiuron | insecticide |
| dialifos | insecticide |
| dicapthon | insecticide |
| dichlofenthion | insecticide |
| dichlorvos | insecticide |
| dicresyl | insecticide |
| dicrotophos | insecticide |
| dicyclanil | insecticide |
| dieldrin | insecticide |
| diflubenzuron | insecticide |
| dilor | insecticide |
| dimefox | insecticide |
| dimetan | insecticide |
| dimethoate | insecticide |
| dimethrin | insecticide |
| dimethylvinphos | insecticide |
| dimetilan | insecticide |
| dinex | insecticide |
| dinoprop | insecticide |
| dinosam | insecticide |
| dinotefuran | insecticide |
| diofenolan | insecticide |
| dioxabenzofos | insecticide |
| dioxacarb | insecticide |
| dioxathion | insecticide |

TABLE 5-continued

| Cargo | |
|---|---|
| Paytoad | Category |
| disulfoton | insecticide |
| dithicrofos | insecticide |
| d-limonene | insecticide |
| ecdysterone | insecticide |
| empenthtin | insecticide |
| endosulfan | insecticide |
| endothion | insecticide |
| endrin | insecticide |
| epofenonane | insecticide |
| esfenvalerate | insecticide |
| etaphos | insecticide |
| ethiofencarb | insecticide |
| ethion | insecticide |
| ethiprole | insecticide |
| ethoate-methyl | insecticide |
| ethoprophos | insecticide |
| ethyl formate | insecticide |
| ethylene dibromide | insecticide |
| ethylene dichloride | insecticide |
| ethylene oxide | insecticide |
| etofenprox | insecticide |
| etrimfos | insecticide |
| famphur | insecticide |
| fenamiphos | insecticide |
| fenazaflor | insecticide |
| fenchlorphos | insecticide |
| fenethacarb | insecticide |
| fenfluthrin | insecticide |
| fenitrothion | insecticide |
| fenobucarb | insecticide |
| fenoxacrim | insecticide |
| fenoxycarb | insecticide |
| fenpitithrin | insecticide |
| fenpropathrin | insecticide |
| fensulfothion | insecticide |
| fenthion | insecticide |
| fenthion-ethyl | insecticide |
| fenvalerate | insecticide |
| fipronil | insecticide |
| flonicamid | insecticide |
| flucofuron | insecticide |
| flucycloxuron | insecticide |
| flucythrinate | insecticide |
| flufenerim | insecticide |
| flufenoxuron | insecticide |
| flufenprox | insecticide |
| fluvalinate | insecticide |
| fonofos | insecticide |
| formetanate | insecticide |
| formothion | insecticide |
| formparanate | insecticide |
| fosmethilan | insecticide |
| fospirate | insecticide |
| fosthietan | insecticide |
| furathiocarb | insecticide |
| furethtin | insecticide |
| gamma-cyhalothrin | insecticide |
| balfenprox | insecticide |
| halofenozide | insecticide |
| heptachlor | insecticide |
| heptenophos | insecticide |
| heterophos | insecticide |
| hexaflumuron | insecticide |
| hydramethylnon | insecticide |
| hydrogen cyanide | insecticide |
| hydroprene | insecticide |
| hyquincarb | insecticide |
| imidacloprid | insecticide |
| imiprothrin | insecticide |
| indoxacatb | insecticide |
| isazofos | insecticide |
| isobenzan | insecticide |
| isodrin | insecticide |
| isofenphos | insecticide |
| isoprocarb | insecticide |
| isoprothiolane | insecticide |

TABLE 5-continued

| Cargo | |
|---|---|
| Paytoad | Category |
| isothioate | insecticide |
| isoxathion | insecticide |
| isoxazole | insecticide |
| jasmolin I | insecticide |
| jasmolin II | insecticide |
| jodfenphos | insecticide |
| juvenile hormone I | insecticide |
| juvenile hormone II | insecticide |
| juvenile hormone III | insecticide |
| ketevan | insecticide |
| kinoprene | insecticide |
| lambda-cyhalothrin | insecticide |
| lead arsenate | insecticide |
| leptophos | insecticide |
| lirimfos | insecticide |
| lufenuron | insecticide |
| lythidathion | insecticide |
| malathion | insecticide |
| malonoben | insecticide |
| mazidox | insecticide |
| mecarbam | insecticide |
| mecarbon | insecticide |
| menazon | insecticide |
| mephosfolan | insecticide |
| mercurous chloride | insecticide |
| mesulfenfos | insecticide |
| methacrifos | insecticide |
| methamidophos | insecticide |
| methidathion | insecticide |
| methiocarb | insecticide |
| methocrotophos | insecticide |
| methomyl | insecticide |
| methoprene | insecticide |
| methoxychlor | insecticide |
| methoxyfenozide | insecticide |
| methyl bromide | insecticide |
| methy chloroform | insecticide |
| methylene chloride | insecticide |
| metofluthrin | insecticide |
| metolcarb | insecticide |
| metoxadiazone | insecticide |
| mevinphos | insecticide |
| mexacarbate | insecticide |
| mipafox | insecticide |
| mirex | insecticide |
| monocrotophos | insecticide |
| morhothion | insecticide |
| naftalofos | insecticide |
| naled | insecticide |
| naphthalene | insecticide |
| nicotine | insecticide |
| nifluridide | insecticide |
| nitenpyram | insecticide |
| nithiazine | insecticide |
| nitrilacarb | insecticide |
| novaluron | insecticide |
| noviflumuron | insecticide |
| omethoate | insecticide |
| oxamyl | insecticide |
| oxydemeton-methyl | insecticide |
| oxydeprofos | insecticide |
| oxydisulfoton | insecticide |
| para-dichlotobenzene | insecticide |
| parathion | insecticide |
| parathion-methyl | insecticide |
| penfluron | insecticide |
| phenkapton | insecticide |
| phenothrin | insecticide |
| phenthoate | insecticide |
| phorate | insecticide |
| phosalone | insecticide |
| phosfolan pirimetaphos | insecticide |
| phosmet | insecticide |
| phosnichlor | insecticide |
| phosphamidon | insecticide |
| phosphine | insecticide |

TABLE 5-continued

| Cargo | |
|---|---|
| Paytoad | Category |
| phoxim | insecticide |
| phoxim-methyl | insecticide |
| pirimicarb | insecticide |
| pirimiphos-ethyl | insecticide |
| pirimiphos-methyl | insecticide |
| potassium arsenite | insecticide |
| potassium thiocyanate | insecticide |
| pp'-DDT | insecticide |
| prallethrin | insecticide |
| precocene I | insecticide |
| precocene II | insecticide |
| precocene III | insecticide |
| primidophos | insecticide |
| profenofos | insecticide |
| profluthrin | insecticide |
| promacyl | insecticide |
| promecarb | insecticide |
| propaphos | insecticide |
| propetamphos | insecticide |
| propoxur | insecticide |
| prothidathion | insecticide |
| prothiofos | insecticide |
| prothoate | insecticide |
| protrifenbute | insecticide |
| pyraclofos | insecticide |
| pyrazophos | insecticide |
| pyresmethrin | insecticide |
| pyrethrin I | insecticide |
| pyrethrin II | insecticide |
| pyridaben | insecticide |
| pyridalyl | insecticide |
| pyridaphenthion | insecticide |
| pyrimidifen | insecticide |
| pyrimitate | insecticide |
| pyriproxyfen | insecticide |
| quassia | insecticide |
| quinalphos | insecticide |
| quinalphos-methyl | insecticide |
| quinothion | insecticide |
| rafoxanide | insecticide |
| resmethrin | insecticide |
| rotenone | insecticide |
| ryania | insecticide |
| sabadilla | insecticide |
| schradan | insecticide |
| silafluofen | insecticide |
| sodium arsenite | insecticide |
| sodium fluoride | insecticide |
| sodium hexafluorosilicate | insecticide |
| sodium thiocyanate | insecticide |
| sophamide | insecticide |
| spinosad | insecticide |
| spiromesifen | insecticide |
| sulcofuron | insecticide |
| sulfluramid | insecticide |
| sulfotep | insecticide |
| sulfuryl fluoride | insecticide |
| sulprofos | insecticide |
| tau-fluvalinate | insecticide |
| tazimcarb | insecticide |
| tebufenozide | insecticide |
| tebufenpyrad | insecticide |
| tebupirimfos | insecticide |
| teflubenzuron | insecticide |
| tefluthrin | insecticide |
| temephos | insecticide |
| terallethrin | insecticide |
| terbufos | insecticide |
| tetrachlorethane | insecticide |
| tetrachlorvinphos | insecticide |
| tetramethrin | insecticide |
| theta-cypermethrin | insecticide |
| thiacloprid | insecticide |
| thiamethoxam | insecticide |
| thicrofos | insecticide |
| thiocarboxime | insecticide |
| thiocyclam | insecticide |
| thiodicarb | insecticide |
| thiofanox | insecticide |
| thiometon | insecticide |
| thiosultap | insecticide |
| thuringiensin | insecticide |
| tolfenpyrad | insecticide |
| tralomethrin | insecticide |
| transfluthrin | insecticide |
| transpermethrin | insecticide |
| triarathene | insecticide |
| triazamate | insecticide |
| triazophos | insecticide |
| trichlormetaphos-3 | insecticide |
| trichloronat | insecticide |
| trifenofos | insecticide |
| triflumuron | insecticide |
| trimethacarb | insecticide |
| triprene | insecticide |
| vamidothion | insecticide |
| vaniliprole | insecticide |
| xylylcarb | insecticide |
| zeta-cypermethrin | insecticide |
| zolaprofos | insecticide |
| α-ecdysone | insecticide |
| bromophos | insecticide; pesticide |
| chlordimeform | insecticide; pesticide |
| Carbaryl | insecticide; pesticide |
| Carbophenothion | insecticide; pesticide |
| Chlorpyrifos | insecticide; pesticide |
| amino acid | macronutrient |
| amylopectin | macronutrient |
| amylose | macronutrient |
| arachidic acid | macronutrient |
| behenic acid | macronutrient |
| butyric acid | macronutrient |
| capric acid | macronutrient |
| caprioic acid | macronutrient |
| caprylic acid | macronutrient |
| carbohydrate | macronutrient |
| cerotic acid | macronutrient |
| cervonic acid | macronutrient |
| clupanodonic acid | macronutrient |
| eicosen | macronutrient |
| erucic acid | macronutrient |
| essential fatty acid | macronutrient |
| fat | macronutrient |
| fructose | macronutrient |
| galactose | macronutrient |
| glucose | macronutrient |
| heptadecanoic acid | macronutrient |
| lactose | macronutrient |
| lauric acid | macronutrient |
| lignoceric acid | macronutrient |
| linoleic acid | macronutrient |
| Macronutrient | macronutrient |
| maltose | macronutrient |
| margaric acid | macronutrient |
| monounsaturated fat | macronutrient |
| myristic acid | macronutrient |
| myristol | macronutrient |
| nervonic acid | macronutrient |
| oleic acid | macronutrient |
| palmitic acid | macronutrient |
| palmitoyl | macronutrient |
| pentadecanoic acid | macronutrient |
| polyunsaturated fat | macronutrient |
| protein | macronutrient |
| ribose | macronutrient |
| saturated fat | macronutrient |
| stearic acid | macronutrient |
| steridonic acid | macronutrient |
| sucrose | macronutrient |
| timnodonic acid | macronutrient |
| α-linoleic acid | macronutrient |
| calcium | micronutrient |

TABLE 5-continued

| Cargo | |
|---|---|
| Paytoad | Category |
| chloride | micronutrient |
| chromium | micronutrient |
| copper | micronutrient |
| iodine | micronutrient |
| iron | micronutrient |
| magnesium | micronutrient |
| manganese | micronutrient |
| mineral | micronutrient |
| molybdenum | micronutrient |
| nickel | micronutrient |
| phosphorus | micronutrient |
| potassium | micronutrient |
| selenium | micronutrient |
| silicon | micronutrient |
| tin | micronutrient |
| vanadium | micronutrient |
| vitamin | micronutrient |
| vitamin A | micronutrient |
| vitamin B-1 | micronutrient |
| vitamin B-12 | micronutrient |
| vitamin B-2 | micronutrient |
| vitamin B-3 | micronutrient |
| vitamin B-5 | micronutrient |
| vitamin B-6 | micronutrient |
| vitamin B-7 | micronutrient |
| vitamin B-9 | micronutrient |
| vitamin C | micronutrient |
| vitamin D | micronutrient |
| vitamin E | micronutrient |
| vitamin K | micronutrient |
| zinc | micronutrient |
| adhesive | pest control agent |
| allomone | pest control agent |
| anti-disease agent | pest control agent |
| antifeedant | pest control agent |
| antifungal | pest control agent |
| behavior-modifying compound | pest control agent |
| bird repellent | pest control agent |
| black pepper | pest control agent |
| caffeine | pest control agent |
| capsaicin | pest control agent |
| capsaicin oleoresin | pest control agent |
| catnip oil | pest control agent |
| chemosterlant | pest control agent |
| chili powder | pest control agent |
| complex sugar | pest control agent |
| dill | pest control agent |
| ginger | pest control agent |
| gum | pest control agent |
| herbicide | pest control agent |
| insect attractant | pest control agent |
| insect repellent | pest control agent |
| insecticide | pest control agent |
| kairomone | pest control agent |
| mammal repellent | pest control agent |
| mating disrupter | pest control agent |
| monoterpenoid | pest control agent |
| paprika | pest control agent |
| pest control agent | pest control agent |
| pesticide | pest control agent |
| phenolic compound | pest control agent |
| pheromone | pest control agent |
| red pepper | pest control agent |
| acaricide | pesticide |
| algicide | pesticide |
| avicide | pesticide |
| Bacillus thurngiensis endotoxin polypeptide | pesticide |
| bactericide | pesticide |
| Bis(p-chlorophenoxy)methane | pesticide |
| Bitertanol | pesticide |
| Bromadiolone | pesticide |
| Bromethalinlin | pesticide |
| Bromopropylate | pesticide |
| Busulfan | pesticide |
| Butrylin | pesticide |

TABLE 5-continued

| Cargo | |
|---|---|
| Paytoad | Category |
| Cambendazole | pesticide |
| Candicidin | pesticide |
| Candidin | pesticide |
| Chioramphenacol | pesticide |
| Chlorbetamide | pesticide |
| Chlorothion | pesticide |
| Chlorphenesin | pesticide |
| molluscicide | pesticide |
| nematicide | pesticide |
| rodenticide | pesticide |
| virucide | pesticide |
| biopolymer | soil stabilizer |
| chemical | soil stabilizer |
| co-polymer | soil stabilizer |
| enzyme | soil stabilizer |
| fiber reinforcement agent | soil stabilizer |
| flowability agent | soil stabilizer |
| hydrophilic agent | soil stabilizer |
| hydrophobic agent | soil stabilizer |
| ionic stabilizer | soil stabilizer |
| polymer | soil stabilizer |
| resin | soil stabilizer |
| salt | soil stabilizer |
| surfactant | soil stabilizer |
| chelated micronutrient | therapeutic agent |
| microbe | therapeutic agent |
| non-chelated micronutrient | therapeutic agent |
| probiotic | therapeutic agent |

In one embodiment, the cargo for use in SBP formulations may be hormone analogue such as, but not limited to, Deslorelin.

Coating

In some embodiments, agricultural SBP formulations may include one or more coatings. As used herein, the term "coating" refers to any substance that is applied to the surface of another substance. In some embodiments, the coating may be functional, decorative or both. Coatings may be applied to completely cover the surface. Coating may also be applied to partially cover the surface. In some embodiments, coatings may include processed silk. In some aspects, the coating may be an SBP formulation. Coatings may also include but are not limited to any of the cargos described in Table 5. In some embodiments, the coating may be a plant coating. In some embodiments, the coating may be a seed coating. In some embodiments, the coating may be a leaf coating. In some embodiments, agricultural compositions described herein, such as coatings, may be able to penetrate plants, leaves, seeds, roots, and/or any other part of the plant described herein. In some embodiments, the SBP coating may be used for one or more applications, including, but not limited to, protection of a seed, plant, planting substrate, agricultural product, or device; fertilizing and/or promoting germination of a coated seed or plant; encasing a payload; delivering a payload, modulating nutrient and/or water uptake; stabilizing a payload; and/or controlling the release of a payload. In some embodiments, SBP coatings may be applied to a fruit or a vegetable to prevent spoilage.

Agricultural Products

In some embodiments, agricultural SBP formulations may include one or more agricultural products. These agricultural products may be plants, animals, plant agricultural products, and animal agricultural products.

In some embodiments, agricultural SBP formulations may include plants. The methods and SBPs of the present disclosure may have applications in plants. In some embodiments, SBPs will serve as agricultural composition to facilitate the production of plants. In some embodiments the plants are agricultural plants i.e., plants for farming purposes. In some embodiments, the plants are silvicultural plants, i.e. plants for the controlling the growth, health, establishment, composition, and quality of forests. In some embodiments, the plants are ornamental plants. In some embodiments, the plants are edible plants. In some embodiments, the plants are horticultural plants. In some embodiments, the plants are natural or wild-type plants. In other embodiments, the plants are genetically modified plants. In some aspects, the plants are medicinal plants. In some embodiments, the agricultural products may be portions of plants.

In some embodiments, agricultural products may include animals and/or animal agricultural products. In some embodiments, the animals used with agricultural compositions of the present disclosure include but are not limited to cows, bulls, sheep, goat, bison, turkey, buffalo, pigs, poultry, horses, alpaca, llama, camels, rabbits, guinea pigs, fish, shrimps, crustaceans, mollusks, insects, silk worms, bees, and crickets.

In some embodiments, the agricultural SBP formulations may be or may include one or more animal agricultural products. Animal agricultural products may include, but are not limited to milk, butter, cheese, yogurt, whey, curds, meat, oil, fat, blood, amino acids, hormones, enzymes, wax, feathers, fur, hide, bones, gelatin, horns, ivory, wool, venom, tallow, silk, sponges, manure, eggs, pearl culture, honey, and food dye. In some embodiments, the animal agricultural product is a dairy product. Non-limiting examples of dairy products include milk, cream, cheese, clotted cream, sour cream, gelato, ghee, infant formula, powdered milk, butter, crème fraiche, ice cream, yoghurt, curds, whey, custard, dulce de leche, evaporated milk, eggnog, frozen yoghurt, frozen custard, buttermilk, formula, casein, condensed milk, cottage cheese, and cream cheese.

Pest Control Agent

In some embodiments, agricultural SBP formulations may include pest control agents. In some aspects, the SBPs may be a pest control agent. As used herein, the term "pest" refers to any organism that harms, irritates, causes discomfort, or generally annoys another organism. In some embodiments, the pest control agent may optionally include a pesticide. In some embodiments, pesticides used in agricultural compositions may be selected from any of those listed in Table 5. Pesticides may include, but are not limited to parasiticides, insecticides, herbicides, antifungal or fungicide, anti-disease agents, behavior-modifying compounds, adhesives (e.g. gums), acaricide, algicide, avicide, bactericide, molluskicide, biocides, miticides, nematicide, rodenticide, and a virucide.

Biological Systems

In some embodiments, agricultural SBP formulations described herein include biological systems. As used herein, the term "biological system" refers to a network of interrelated substances and/or organisms. These biological systems may include systems of symbiotes, microbiomes and/or probiotics. The compositions provided herein may include a SBPs and an active amount of beneficial microbes/probiotics. In some embodiments, SBP formulations may be used as stabilizers in the microbial compositions. In some embodiments, these microbiomes or symbiotes may incorporate species of fungi or bacteria. In some embodiments, the fungi are from the *Aspergillus* genus. In some embodiments, the bacteria are from the *Streptomyces* genus. In some embodiments, SBP biological systems may be used as biopesticides. As used herein, the term "biopesticide" refers to a composition with a bacteria, microorganism, or biological cargo that displays pesticidal activity. In some embodiments, SBP biological systems may be applied as a coating to a plant. The coating may be applied to the whole plant, or to any part of the plant described in the present disclosure. In some embodiments, the coating may be applied to a seed.

In some embodiments, the biological systems may be used to enable nitrogen fixation. These microbes, microorganisms, and/or microbiomes may incorporate *rhizobia* bacteria. *Rhizobia* bacteria enable nitrogen fixation in plants that do not independently fix nitrogen, such as legumes (Zahran et al. (1999) Microbiology and Molecular Biology Reviews 63(4):968-989, the contents of which are herein incorporated by reference in its entirety). In some embodiments, the biological systems described herein deliver *rhizobia* bacteria for the growth and production of other plants. In some embodiments, the SBP agricultural compositions described herein may be formulated with the nutrients needed to promote the growth of *rhizobia* bacteria. The beneficial microbe and/or probiotic can be any beneficial microbe and/or probiotic known in the art.

In some embodiments, SBP biological systems formulations may include microbes, microorganisms, and/or microbiomes that promote plant growth. SBP biological systems may include one or more microbes, microorganisms and/or microbiomes that promote plant growth. Such microbes, microorganisms, and/or microbiomes may include, but are not limited to, *Algoriphagus ratkowski, Allererythrobacter luteolus, Alternaria thalicfngena, Arthrobacter agilis, Arthrobacter arilaitensis, Arthrobacter aurescens, Arthrobacter citreus, Arthrobacter crstallopoeietes, Arthrobacter globiformis, Arthrobacter humicola, Arthrobacter orvzae, Arthrobacter oxydans, Arthrobacter pascens, Arthrobacter ramosus, Arthrobacter tumbae, Aspergillus jiimigauiaffints, Bacillus aquimars, Bacillus benzoevorans, Bacillus cibi, Bacillus herbersteinensis, Bacillus idriensis, Bacillus licheniformis, Bacillus niacin, Bacillus psyvhordurans, Bacillus simplex, Bacillus simplex 11, Bacillus simplex 237, Bacillus simplex 30N-5, Bacillus subtilis 30VD-1, Bartonella elizabethae, Ctricoccus alkalitolerans, Citricoccus nitrophenolicus, Cladosporium sphaerospermum, Curtobacterium flaccumfaciens, Exiguobacterium aurantiacum, Fusarium equisei, Fusarium oxynporum, Georgenia ruanii, Halomonas aquamarina, Kocuria rosea, Massilia timonae, Mesorhizobium loti, Microbacterium aerolatum, Microbacterium oxydans, Microbacterium paludicola, Microbacterium paraoxydans, Microbacterium phyllosphaerae Microbacterium testaceum, Micrococcus luteus, Mycobacterium sacrum, Nocardiopsis quinghatensis, Oceanobacillus picturae, Ochroconis* sp., *Olivibacter soli, Paenbacillus tundrae, Penicillium chrysogenum, Penicillium commune, Phoma betae, Planococcus maritimus, Planococcus psychrotoleratus, Planomicrobium koreense, Planomicrobium okeanokoites, Promicromonospora kroppenstedii, Pseudomonas brassicacearum, Pseudomonasfluorescens, Pseudomonas frederiksbergensis, Pseudomonas fulva, Pseudomonas geniculata, Pseudomonas gessardii, Pseudomonas libanensis, Pseudomonas mosseli, Pseudomonas plecoglossicida, Pseudomonas puhda, Pseudomonas stutzeri, Pseudomonas syringae, Rhodococcus jostii, Sinorhizobium medicae, Sinorhizobium meliloti, Staphylococcus succinus, Stenotrophomonas maltophilia, Stenotrophomonas rhizophila, Streptomyces althioticus, Streptomyces azureus, Streptomyces bottropensis, Streptomjves candidus, Streptomyces chryseus, Streptomces cirratus, Streptomites coeruleofuscus, Streptomyces durmitorensis, Streptomyces flaveus, Streptomyces fradeiae, Streptomyces griseoruber, Streptomyces griseus,*

*Streptomyces halstedii, Streptomyces marokkonensis, Streptomyces olivoviridis, Streptomyces peucetius, Streptomyces phaeochromogenes, Streptomyces pseudogriseolus, Terribacillus halophilus, Virgibacillus halodenitrificans*, and *Williamensia muralis*. In further embodiments, such plant growth-promoting microbes, microorganisms, and/or microbiomes may be selected from any of those microbial isolates described in US Publication Number US20140342905, and International Publication Number WO2014201044, the contents of which are hereby incorporated by reference in their entirety.

In some embodiments, the SBP biological system formulations contains a mixture of two or more microbes and/or microorganisms. In some embodiments, the mixture might be a mixture of generic microbes. In some embodiments, formulation with one or more microbes enhances the viability of said microbes. In some embodiments, the SBP biological system may also include one or more excipients (e.g. sugar, mannitol, trehalose, buffer salts, PEGs, Poloxamer-188, Poloxamer-407, glycerol, HPMC, HEC, CMC, glycerol formal, propylene glycol, propylene carbonate, sorbitol, and/or polysorbate-80). The excipients may be included at concentrations between 0.1%-50% (w/w or w/v). The concentration of processed silk may be any of those described in the present disclosure. The SBP biological systems may be made from processed silk prepared with any boiling time described in the present disclosure (e.g. 90 mb, 120 mb, and 480 mb) and one or more microbes. In some embodiments, the pH of the SBP biological system is between about 4 and about 6. In some embodiments, the osmolarity of the SBP biological system is between about 200 mOsm/L to about 400 mOsm/L. The osmolarity may also be from about 290 mOsm/L to about 320 mOsm/L.

In some embodiments, the SBP biological system formulations may be prepared as a solution. These solutions may be made from processed silk prepared with any boiling time described in the present disclosure (e.g. 90 mb, 120 mb, and 480 mb) and the bacteria. The solutions may be prepared with any concentration of processed silk described herein (e.g. 0.5%, 1%, 5%). The solutions may be prepared with any solvent and/or buffer described in the present disclosure.

In some embodiments, the SBP biological system formulations may be prepared as a lyophilized powder. These powders may be prepared from processed silk prepared with any boiling time described in the present disclosure (e.g. 90 mb, 120 mb, and 480 mb) and the bacteria. The processed silk may be mixed with one or more microbes and then lyophilized. The lyophilized powder may be prepared from solutions of any concentration of processed silk described herein (e.g. 0.5%, 1%, 5%). The lyophilized powder may be prepared from processed silk formulated with a sugar (e.g. sugar, mannitol, or trehalose) to aid in the stability of bacteria. The lyophilized silk may be reconstituted in a solvent (e.g. water or buffer). The lyophilized powder may be reconstituted in any solvent and/or buffer described in the present disclosure.

In some embodiments, the SBP biological system formulations may be prepared as insoluble powder, particles, cakes and/or films. To prepare the powder, particles, cakes and/or films, gels and/or other SBP formulations may be formed and then dried. In some embodiments, the gels and/or other SBP formulations may be lyophilized to form cakes and/or films. Powders, particles, cakes and films may also utilize excipients (e.g. gelling agents) as well as sonication, or pH changes to induce beta-sheet formation prior to or during drying or lyophilization. These excipients may be powders under typical environmental conditions (e.g. MW PEG's, Poloxamer-188, etc.). The total solid content of the powders, particles, cakes and/or films may be between 3-40% (w/w or w/v). The solid content included buffer, silk, and any excipients included.

In some embodiments, the SBP biological systems formulations may be insoluble. These SBP biological system formulations may be lyophilized powders. The SBP biological system formulations may also be prepared by milling insoluble solids (e.g. cakes or films) into a powder. In some embodiments, the SBP biological system formulations may be digested. In some embodiments, insoluble SBP biological system formulations are formulated for spray drying. The total solid content of the formulations for spray drying may be between 5-40% (w/w or w/v). The solid content included buffer, silk, and any excipients included.

Agricultural Therapeutic Agent

In some embodiments, agricultural applications involve the use of SBP formulations which can be agricultural therapeutic agents or are combined with one or more agricultural therapeutic agents. Examples of SBP therapeutic agents include, but are not limited to, adjuvants, analgesic agents, antiallergic agents, antiangiogenic agents, antiarrhythmic agents, antibacterial agents, antibiotics, antibodies, anticancer agents, anticoagulants, antidementia agents, antidepressants, antidiabetic agents, antigens, antihypertensive agents, anti-infective agents, anti-inflammatory agents, antioxidants, antipyretic agents, anti-rejection agents, antiseptic agents, antitumor agents, antiulcer agents, antiviral agents, biological agents, birth control medication, carbohydrates, cardiotonics, cells, chemotherapeutic agents, cholesterol lowering agents, cytokines, endostatins, enzymes, fats, fatty acids, genetically engineered proteins, glycoproteins, growth factors, health supplements, hematopoictics, herbal preparations, hormones, hypotensive diuretics, immunological agents, inorganic synthetic pharmaceutical drugs, ions, lipoproteins, metals, minerals, nanoparticles, naturally derived proteins, NSAIDs, nucleic acids, nucleotides, organic synthetic pharmaceutical drugs, oxidants, peptides, pills, polysaccharides, proteins, protein-small molecule conjugates or complexes, psychotropic agents, small molecules, sodium channel blockers, statins, steroids, stimulants, therapeutic agents for osteoporosis, therapeutic combinations, thrombopoietics, tranquilizers, vaccines, vasodilators, VEGF-related agents, veterinary agents, viruses, virus particles, and vitamins. In some embodiments, SBP therapeutics and methods of delivery may include any of those taught in International Patent Publication Numbers WO2017139684, WO2010123945, WO2017123383, or United States Publication Numbers US20170340575, US20170368236, and US20110171239 the contents of each of which are herein incorporated by reference in their entirety. In some embodiments, the agricultural therapeutic agent may be a pest control agent. In some embodiments, examples of pest control agents that may be useful as agricultural therapeutic agent include, but are not limited to parasiticides, insecticides, antifungal or fungicide, anti-disease agents, acaricide, algicide, avicide, bactericide, nematicide, and a virucide.

In some embodiments, the subject in the context of an agricultural therapeutic agent may refer to one or more plants.

In some embodiments, the subject in the context of an agricultural therapeutic agent may refer to one or more non-human animals.

In some embodiments, the agricultural therapeutic agent may be nucleic acids. Nucleic acids may include DNA and/or RNA. In some embodiments, nucleic acids may be polynucleotides or oligonucleotides. Exemplary nucleic acids may include, but are not limited to, aptamers, plasmids, siRNA, microRNAs, or viral nucleic acids. In some embodiments, nucleic acids may encode a therapeutic peptide or protein, such as any one of those described herein. In some embodiments, SBPs may be used to improve the stability of composition comprising the nucleic acids. In some embodiments, SBPs may be used to facilitate the delivery of the nucleic acids to a plant.

Agriculture Devices

In some embodiments, agricultural SBP formulations may be or may include may be used to improve the growth and production of agricultural products by utilizing said composition with an agricultural device. An agricultural device is a device or machine that assists in agricultural production. The agricultural SBP formulations may comprise any format described in the present disclosure (e.g. hydrogel). In some embodiments, SBP formulations may be utilized as an agricultural device, as taught in in United States Patent Publication US20030198659 (the contents of which are herein incorporated by reference in its entirety). In some embodiments, SBP formulations may comprise one or more components of an agricultural device. In some embodiments, SBP formulations may be used in conjunction with another agricultural device. Agricultural devices that may incorporate SBP formulations include, but are not limited to, agricultural equipment, crop storage devices (e.g. bale bags), landscaping fabrics (e.g. polypropylene and burlap blankets), and pest control devices. In one embodiments, the agricultural equipment may comprise a silk-coated microporous pipeline, as taught in Chinese Patent Publication, CN102407193, the contents of which are herein incorporated by reference in their entirety.

In some embodiments, SBP formulations are or are used with agricultural devices used for pest control and are referred to as pest control agents. In some embodiments, SBPs that include one or more pest control agents are used as coatings to coat agricultural pest control devices. Devices may be carriers used to spread pest control agents included in carrier coatings. The carriers may be seeds. SBP seed coatings (e.g., seed coating compositions) provided herein may offer advantages with respect to the variety of cargo that can be formulated (small molecules, proteins, DNA, microbes, viruses), the ability to tailor the release rate of the cargo, stabilization of the cargo, efficient seed coating, break-down into non-toxic peptides, and/or a significantly reduced propensity to produce dust that can contaminate surrounding environments. The latter property, along with the controlled and delayed release of the active ingredient significantly reduces the contamination of surrounding environments by the active ingredient. These properties will likely mitigate the collateral damage to important pollinator populations. In addition, the compositions (e.g., seed coating compositions) provided herein impart advantages vs. seed flow and plantability that are due to the physical properties of silk fibroin such as a very low coefficient of friction.

In some embodiments, SBP formulation agricultural devices described herein may be used in the field of animal husbandry. In some embodiments, SBP formulation agricultural devices described herein may be include a component or the whole of animal housing in the field of animal husbandry. SBP formulations may be used in animal housing applications to provide optimal temperature, humidity, radiation, air flow, precipitation and light required to keep the animal safe, healthy and comfortable.

Animals require healthy environments that permit the production, and quality of the non-human animals, as well as that of the animal agricultural products. Examples of animal housing include, but are not limited to, blankets, bedding, clothing, footwear (e.g. horseshoes), feeding equipment (e.g. bowls and water bottles), brushes, bandages, barns, coops, cages, stalls, liners, enclosures, ropes, ties, pens, flooring, shelters, sheds, stalls, ventilations systems, and wires.

In some embodiments, SBP formulation agricultural devices may be used to aid the health and production of animals. In some embodiments. SBP formulations may be used in the treatment of mastitis. Transition from the dry period prior to lactation to lactation is a high-risk period for agricultural animals such as cows. During the period, the mammary gland (udder) may become infected with bacteria resulting in inflammation. In some embodiments, SBPs may be used in the treatment of mastitis. SBP formulations may be or may include antibiotics effective against one or more mastitis causing bacteria. SBP formulations may also be formatted into plugs and inserted into the teat canal (e.g., a teat sealant). In some embodiments, SBP formulations may be prepared as solutions and injected into the teat canal by an injection apparatus (e.g., a syringe, a needle, etc.). Formation of the plug may occur during injection and/or after injection. In some embodiments, SBP formulations may be formatted into films that is applied to the exterior of the teats. SBPs may be useful, both in treating and preventing mastitis. In some embodiments, SBP formulations may be used as a form of birth control, to regulate the production of animals, such as cows In some embodiments, SBP formulations may be or may include hormones and/or birth control agents. SBP formulations may be prepared as implants or depots and injected into the subject (cattle).

Aquaculture Products

In some embodiments, agricultural SBP formulations may be used in the preparation of aquaculture products. As used herein, the term "aquaculture" generally refers to the farming of aquatic animals (e.g., fish, crustaceans, mollusks) or the cultivation of aquatic plants (e.g., algae). As a non-limiting example, agricultural SBP formulations may be used in the preparation of aquaculture feeds for various aquatic animals including, but not limited to, carp, salmon, catfish, tilapia, cod, trout, milkfish, eel, shrimp, crawfish, crab, oyster, mussel, clam, jellyfish, sea cucumbers and sea urchins.

Delivery

In some embodiments, the delivery of the agricultural SBP formulations described herein may occur through controlled release. In some embodiments, the agricultural SBP formulations may be utilized for the local delivery of cargo. In some embodiments, the agent may be a chemical for use in any one agricultural applications described in the present disclosure. In some embodiments, SBP formulations described herein may enable the controlled delivery of cargos that have a shorter half-life when delivered without SBP formulations, therein enhancing the time for which the therapeutic agent may be effective, as taught in United States Patent Publication US20100028451, the contents of which are herein incorporated by reference in its entirety. In some embodiments, SBP formulations may enhance the residence time of a cargo. In some embodiments the SBP formulation delivery may be targeting to the entire plant, or animal; or it may be targeted to a portion of the plant or animal. In some embodiments, the portion of the plant may be leaf, root, bark, phloem, seed, and/or fruit.

In some embodiments, the controlled release of the SBP formulations for agricultural applications may be facilitated by diffusion of SBP formulations into the surrounding environment, his phenomenon has been observed in pharmaceutical compositions for animal subjects, as taught in United States Patent Publication No. US20170333351, the contents of which are herein incorporated by reference in its entirety. In some embodiments, the controlled release of SBPs for an agricultural application may be facilitated by the degradation and/or dissolution of SBPs. The degradation and/or dissolution has been employed for pharmaceutical compositions for animal subjects, as taught in International Patent Publications WO2013126799, WO2017165922, and U.S. Pat. No. 8,530,625, the contents of each of which are herein incorporated by reference in their entirety. In some embodiments, both the diffusion and the degradation and/or dissolution of SBPs may facilitate the controlled release of the agricultural compositions for agricultural applications.

Applications

In some embodiments, the agricultural SBP formulations may be used to increase biomass, increase product yield, and/or enhance offspring production of plants, plant agricultural products, animals, and animal agricultural products. In some embodiments, SBPs may be used in the field of farming. As used herein, "farming" refers to the technique of growing crops or keeping animals for food and materials. Agricultural SBP formulations may be used in arable farming to grow crops, and/or pastoral farming SBP formulations may be utilized to improve one or more aspects of farming such as, but not limited to, plant growth, yield, reproduction, soil properties, weed control, pest control, disease control, product preservation, and/or treatment, environmental factors such as controlling access to water, air, and/or sunlight. In some embodiments, SBPs may be used to mitigate crop damage. In some embodiments, the agricultural SBP formulations of the present disclosure may be used to tune properties of soil. In some embodiments, the agricultural SBP formulations of the present disclosure are used as agents of weed control. In some embodiments, seeds may be treated with agricultural SBP formulations to increase germination, seedling vigor, and seedling size. In some aspects, seeds may be treated with agricultural SBP formulations to increase seed storage, and shelf life of the seed, such that the seedlings produced upon germination of stored seeds are superior to seeds that stored without SBPs. In some embodiments, the agricultural SBP formulations described herein may be used to enhance plant germination. As used herein, the term "germination" refers to growth from a seed or spore. In some embodiments, agricultural products may be treated with agricultural SBP formulations to improve preservation, the shelf life, the physical appearance, and/or freshness of the agricultural products. In some aspects, agricultural products may be treated with SBPs to preserve the products such that they are superior in agricultural SBP formulations and appearance to products untreated agricultural products. In some embodiments, SBPs described herein may be used to control the access of the plant, animal or agricultural product to environmental factors such as water, air and/or sunlight. In some embodiments, agricultural SBP formulations may be used to modulate different aspects of the environment such as, but are not limited to, water air, humidity, and light.

In some embodiments, the agricultural SBP formulations of the present disclosure may be or may include photodegradable film. Agricultural SBP formulations may be prepared to be photosensitive or may include photosensitive agents that degrade upon exposure to light, (see Chinese Patent Publication CN105199353 and International Patent Publication WO2017123383; the contents of each of which are herein incorporated by reference in their entirety). Photosensitive agents may be chemicals, small molecules, or a drug. Photodegradable SBPs may be prepared in any format (e.g. films, microspheres, nanospheres, and any format described in the present disclosure).

Animals

In some embodiments, agricultural SBP formulations may be used to improve characteristics of animal, and/or increase the yield and quality of animal agricultural products. In some embodiments, the agricultural products include, but are not limited to, milk, butter, cheese, yogurt, whey, curds, meat, oil, fat, blood, amino acids, hormones, enzymes, wax, feathers, fur, hide, bones, gelatin, horns, ivory, wool, venom, tallow, silk, sponges, manure, eggs, pearl culture, honey, and food dye.

In some embodiments, agricultural SBP formulations of the present disclosure may be used in animal agricultural products to facilitate the release of fragrance, flavor, or other compounds responsible for odor and/or flavor, as taught in United States Patent Publication No. US20150164117, the contents of which are herein incorporated by reference in their entirety.

In some embodiments, agricultural SBP formulations may incorporate animal feed or beverage. In some embodiments, agricultural SBP formulations may include health supplements, produce supplements, hormone supplements, and/or agricultural therapeutic agents to improve the health and viability of the animals. In some embodiments, agricultural SBP formulations may include animal feed such as forage, fodder, or a combination of forage and fodder. Examples of forage include, but are not limited to, plant derived material (e.g. leaves and stems), hay, grass, silage, herbaceous legumes, tree legumes, and crop residue. Examples of fodder include, but are not limited to, hay, straw, silage, compressed and pelleted feeds, oils, mixed rations, fish meal, meat and bone meal, molasses, oligosaccharides, seaweed, seeds, grains (e.g. maize, soybeans, wheat, oats, barley, rise, peanuts, corn, and sorghum), crop residues (e.g. stover, copra, straw, chaff, and sugar beet waste), sprouted grains and legumes, brewer's spent grains, yeast extract, compounded feeds (e.g. meal type, pellets, nuts, cakes, and crumbles), cut grass and other forage plants, bran, concentrate mix, oilseed prescake (e.g. cottonseed, safflower, soybean peanut, and groundnut), horse gram, clipping waste, and legumes.

In some embodiments, agricultural SBP formulations described herein may be used to improve the yield of animal agricultural products by improving the health of non-human animals. In some embodiments, SBPs described herein may be used to improve the production capabilities of non-human animals. In some embodiments, SBPs described herein may be used to improve the breeding of non-human animals. In some embodiments, SBPs described herein may be used to improve the health, production, breeding, or a combination thereof in non-human animals.

In some embodiments, agricultural SBP formulations of this disclosure may be used to deliver health supplements to a non-human animal. These health supplements may improve the health of said non-human animals. SBPs may deliver said health supplements as a payload. SBPs may be incorporated into the feed, housing, or any other component or tool of animal husbandry that would enable the delivery of the payload. Examples of health supplements include, but are not limited to, vitamin A, vitamin B, vitamin C, vitamin D, vitamin E, vitamin K, thiamin, riboflavin, niacin, vitamin B6, vitamin B12, biotin, pantothenic acid, calcium, iron, phosphorus, iodine, magnesium, zinc, selenium, selenium, copper, manganese, chromium, molybdenum, chloride, potassium, nickel, silicon, vanadium, and tin.

In some embodiments, agricultural SBP formulations of this disclosure may be used to deliver supplements to a non-human animal that improve the yield and/or quality of the animal agricultural products. These health supplements may improve the production capabilities of said non-human animals. SBPs may include said supplements as a payload. Examples of supplements include, but are not limited to, vitamins, minerals, ions, nutrients, and hormones. In some embodiments, the SBPs may be used to stimulate animal appetite.

In some embodiments, agricultural SBP formulations of this disclosure may be used to deliver hormones to a non-human animal. SBPs may deliver said hormones as a payload. Examples of hormones include, but are not limited to, any steroid, dexamethasone, allopregnanolone, any estrogen (e.g. ethinyl estradiol, mestranol, estradiols and their esters, estriol, estriol succinate, polyestriol phosphate, estrone, estrone sulfate and conjugated estrogens), any progestogen (e.g. progesterone, norethisterone acetate, norgestrel, levonorgestrel, gestodene, chlormadinone acetate, drospirorenone, and 3-ketodesogestrel), any androgen (e.g. testosterone, androstenediol, androstenedione, dehydroepiandrosterone, and dihydrotestosterone), any mineralocorticoid, any glucocoriticoid, cholesterols, and any hormone known to those skilled in the art. In some embodiments, any of the hormones described herein.

In some embodiments, agricultural SBP formulations of this disclosure may be used to deliver birth control agents to a non-human animal. These agents of disease control may improve the health, growth, and/or increase the yield of the agricultural product from said non-human animals. SBPs may be or may include birth control as cargo. SBPs may be incorporated into the feed, housing, or any other component or tool of animal husbandry that would enable the delivery of the payload. In some embodiments, SBPs may be used in conjunction with other forms of birth control, such as surgical procedures (e.g. spaying and neutering). Examples of birth control agents, include, but are not limited to, pills, ointments, implants, surgical procedures, hormones, patches, barriers, and injections.

In one embodiment, agricultural SBP formulations may be used to deliver birth control agents to cattle. Cattle birth control is important for producers to maintain herd genetic traits, reduce disease transmission, as well as eliminating the need for separate breeding pastures. The SBPs may provide controlled release of the birth control agent to the cattle. The birth control agents may include, but are not limited to, gonadorelin, gonadorelin acetate, progesterone, dinoprost tromethamine, and cloprostenol sodium, and any combination thereof.

Pest Control

In some embodiments, agricultural SBP formulations may be used in pest control of plants, animals, plant agricultural products, and/or animal agricultural products, agricultural SBP formulations may be or may include pest control agents described herein. In some embodiments, agricultural SBP formulations pest control devices may be used in pest control. Pest control agents and devices described herein may be applied directly to the pest, a pest susceptible surface such as the locus or planting substrate where the plant is growing e.g. soil; a pest habitat and/or the animal affected by the pest. In some embodiments, SBPs may be used to reduce the drift of a pest control agent to a surrounding environment.

Disease Control

In some embodiments, agricultural SBP formulations may be useful in disease control of plants, and/or animals. In some embodiments, disease may be caused by disease agents. As used herein, the term "disease agent" refers to any biological pathogen that causes a disease. In some embodiments, the disease agent may be a parasite.

In some embodiments, the agricultural SBP formulations of the present disclosure may be used to treat plant diseases. In some embodiments, the present disclosure relates to the use SBPs as a matrix for formulations of disease inhibitory agents. In some embodiments, formulations of silk fibroin containing active ingredients with the ability to prevent the infection of plants, or of controlling disease in plants already infected with disease. More specifically, compositions including a silk fibroin and an inhibitory agent (e.g., 10 antibiotics with the ability to prevent the infection of citrus trees with Las, or of controlling citrus greening in citrus trees already infected with Las). In some embodiments, the agricultural SBP formulations may be or may include therapeutic agents and/or agricultural therapeutic agents to enable disease control. SBPs offer advantages for treating plant disease in their ability to tune the release rate, stabilization, and are biodegradable.

In some embodiments, hydrogels or other formats of agricultural SBP formulations described herein may be utilized to inject and form drug depots in the phloem and provide effective and long-term treatment of affected plants or agricultural products, or protection of susceptible plants and agricultural products.

In some embodiments, agricultural SBP formulations of this disclosure may be used to deliver agents of disease control to a non-human animal. These agents of disease control may improve the health of said non-human animals. Agricultural SBP formulations may deliver said agents of disease control as a payload. SBPs may be incorporated into the feed, housing, or any other component or tool of animal husbandry that would enable the delivery of the payload. In some embodiments, SBPs for disease control may be administered to treat a disease. In some embodiments, SBPs for disease control may be administered as a prophylactic to prevent the onset and/or spread of disease. Examples of agents of disease control include, but are not limited to, biologics, small molecules, vitamins, minerals, herbal preparations, health supplements, ions, metals, carbohydrates, fats, hormones, proteins, peptides, antibiotics and other anti-infective agents. Thematopoietics, thrombopoietics, agents, antidementia agents, antiviral agents, antiangiogenic proteins (e.g. endostatin), antitumoral agents (chemotherapeutic agents), antipyretics, analgesics, anti-inflammatory agents, anti-infective, antiulcer agents, antiallergic agents, antidepressants, psychotropic agents, cardiotonics, antiarrhythmic agents, vasodilators, antihypertensive agents such as hypotensive diuretics, antidiabetic agents, anti-rejection agents, anticoagulants, cholesterol lowering agents, therapeutic agents for osteoporosis, bone morphogenic proteins, bone morphogenic-like proteins, enzymes, vaccines, immunological agents and adjuvants, naturally derived proteins, genetically engineered proteins, chemotherapeutic agents, cytokines, growth factors (e.g. epidermal growth factor, fibroblast growth factor, insulin like growth factor I and II, transforming growth factors, and vascular endothelial growth factors), nucleotides and nucleic acids, steroids carbohydrates and polysaccharides, glycoproteins, lipoproteins, viruses and virus particles, conjugates or complexes of small molecules and proteins, or mixtures thereof, and organic or inorganic synthetic pharmaceutical drugs.

IV. Material Science Applications

In some embodiments, SBP formulations may be prepared for use in one or more material science (MS) applications (e.g., MS SBP formulations). As used herein, the term "material science application" refers to any method related to development, production, synthesis, use, degradation, or disposal of materials. As used herein, the term "material" refers to a substance or chemical substance that may be used for the fabrication, production, and/or manufacture of an article. MS SBP formulations may be materials or may be combinations of processed silk with one or more materials. Examples of materials include, but are not limited to, adhesives, aquaculture products, biomaterials, composting agents, conductors, devices, electronics, emulsifiers, fabrics, fibers, fillers, films, filters, food products, heaters, insulators, lubricants, membranes, metal replacements, micelles, microneedles, microneedle arrays, microspheres, nanofibers, nanomaterials, nanoparticles, nanospheres, paper, paper additives, particles, plastics, plastic replacements, polymers, sensors, solar panels, spheres, sun screens, taste-masking agents, textiles, thickening agents, topical creams or ointments, optical devices, vasolines, and composites thereof. In some embodiments, materials comprising SBPs described herein may be used as a plastic, plastic supplement, or a plastic replacement, as taught in Yu et al. and Chantawong et al. (Yu et al. (2017) Biomed Mater Res A doi. 10.1002/jbm.a.36297; Chantawong et al. (2017) Mater Sci Mater Med 28(12):191), the contents of which are herein incorporated by reference in their entirety.

Consumer Products

In some embodiments, MS SBP formulations or materials comprising SBP formulations may be used to produce or may be incorporated into consumer products. As used herein, the term "consumer products" refers to goods or merchandise purchasable by the public. Consumer products may include, but are not limited to, agricultural products, therapeutic products, veterinary products, and products for household use. Non-limiting examples of consumer products include cleaning supplies, sponges, brushes, cloths, protectors, sealant, adhesives, lubricants, protectants, labels, paint, clothing, insulators, devices, bandages, screens, electronics, batteries, and surfactants.

Surfactant Materials

In some embodiments, MS SBP formulations may be used as a surfactant. In some embodiments, SBP materials may reduce the surface tension of liquids. In some embodiments, the SBP materials may be used to tune the surface tension of liquids. In some embodiments, the SBP may be a surfactant. In some embodiments, the surfactant may be prepared from SBPs. In some embodiments, silk is used in the preparation of surfactant using any of the methods described in Chinese patent publication CN105380891, the contents of which are herein incorporated by reference in their entirety. In some embodiments, SBP surfactants may be more environmentally friendly than existing surfactants. In some embodiments, MS SBP formulations have the surface tension of water. In some embodiments, SBPs have the surface tension of tears.

Lubricant

In some embodiments, MS SBP formulations may be used as lubricants, to reduce friction between two or more surfaces. In some embodiments, the SBP is a lubricant. In some embodiments, the SBP is an excipient in a lubricant. In some embodiments, the SBP is prepared from processed silk, oils, water, and other materials as described in Chinese Patent Publication Number CN101725049, the contents of which are herein incorporated by reference in their entirety. Lubricants can be prepared from SBPs in many formats, including, but not limited to, capsules, coatings, emulsions, fibers, films, foams, gels, grafts, hydrogels, membranes, microspheres, nanoparticles, nanospheres, organogels, particles, powders, rods, scaffolds, sheets, solids, solutions, sponges, sprays, suspensions, and vapors. In some embodiments, an SBP lubricant may comprise silk microspheres. In some embodiments, the microspheres may be prepared with a phospholipid coating as described in United States Patent Application Publication Number US20150150993A1, the contents of which are herein incorporated by reference in their entirety. In some embodiments, the lubricants may be used on a material surface, non-limiting examples of which include gears, machinery, vacuums, plastics, threads, wood, furniture, and other items. In some embodiments, the lubricants may be used on a biological surface, non-limiting examples of which include bones, joints, eyes, and mucosal membranes. In some embodiments, the coefficient of friction of an SBP is approximately that of naturally occurring, biological and/or protein lubricants (e.g. lubricin). In some embodiments, SBPs may be incorporated into a lubricant. Such methods may include any of those presented in International Publication No. WO2013163407, the contents of which are herein incorporated by reference in their entirety. In some embodiments, processed silk and/or SBPs may be used as an excipient to prepare a lubricant.

Device Materials

In some embodiments, MS SBP formulations may be used in the fabrication, production, and/or manufacture of a device, e.g., as taught in European Patent Number EP2904133, U.S. Pat. No. 9,802,374, and United States Patent Application Publication Number US20170312387, the contents of each of which are herein incorporated by reference in their entirety. In some embodiments, the device is a medical device (e.g. surgical devices, implants, dental devices, dental implants, diagnostic device, hospital equipment, etc.). In some embodiments, the device is an electronic device (e.g. diagnostic device, hospital equipment, implants, etc.).

The term "medical device" refers to any device, product, equipment or material having surfaces that contact tissue, blood, or other bodily fluids of a subject in the course of their use or operation. Exemplary medical devices include, but are not limited to, absorbable and nonabsorbable sutures, access ports, amniocentesis needles, arterial catheters, arteriovenous shunts, artificial joints, artificial organs, artificial urinary sphincters, bandages, biliary stents, biopsy needles, blood collection tubes, blood filters, blood oxygenators, blood pumps, blood storage bags, bolts, brain and nerve stimulators, calipers, cannulas, cardiac defibrillators, cardioverter defibrillators, castings, catheter introducers, catheter sheaths s, catheters, chemical sensors, clips or fasteners, contraceptive devices, coronary stents, dialysis catheters, dialysis devices, dilators, drain tubes, drainage tubes, drug infusion catheters and guidewires, electrodes, endoscopes, endotracheal tubes, feminine hygiene products, fetal monitors, Foley catheters, forceps, gastroenteric tubes, genitourinary implants, guide wires, halo systems, heart valves, hearing aids, hydrocephalus shunts, implants, infusion needles, inserters, intermittent urinary catheters, intraurethral implants, introducers, introducer needles, irrigators, joint prostheses, knives, long-term central venous catheters, long-term tunneled central venous catheters, long-term urinary devices, monitors, nails, nasogastric tubes, needles, neurological stents, nozzles, nuts, obdurators, orthopedic implants, orthopedic devices, osteoports, pacemaker capsules, pacemaker leads, pacemakers, patches, penile prostheses, peripheral venous catheters, peripherally insertable central venous catheters, peritoneal catheters, peritoneal dialysis catheters, personal hygiene items, pins, plates, probes, prostheses, pulmonary artery Swan-Ganz catheters, pulse generators, retractors, rods, scaffolding, scalpels, screws, sensors, short-term central venous catheters, shunts, small joint replacements, specula, spinal stimulators, stents, stints, stylets, suture needles, suturing materials, syringes, temporary joint replacements, tissue bonding urinary devices, tracheostomy devices, transducers, trocars, tubes, tubing, urethral inserts, urinary catheters, urinary dilators, urinary sphincters, urological stents, valves, vascular catheters, vascular catheter ports, vascular grafts, vascular port catheters, vascular stents, wire guides, wires, wirings, wound drains, wound drain tubes, and wound dressings.

In some embodiments, the medical device may be an ocular device, such as, but not limited to, contact lens (hard or soft), intraocular lens, corneal onlay, ocular inserts, artificial cornea and membranes, eye bandages, and eyeglasses.

In some embodiments, the medical device may be a dental device, such as, but not limited to, dental flossers, dental flossing devices, dental threaders, dental stimulators, dental picks, dental massagers, proxy brushes, dental tapes, dental fillings, dental implants, orthodontic arch wire, and other orthodontic devices or prostodontic devices.

In some embodiments, the device may be any one of the following devices: audio players, bar code scanners, cameras, cell phones, cellular phones, car audio systems, communication devices, computer components, computers, credit cards, depth finders, digital cameras, digital versatile discs (DVDs), electronic books, electronic games and game systems, emergency locator transmitters (ELTs), emergency position-indicating radio beacons (EPIRBs), fish finders, global positioning system (GPS), home security systems, image play back devices, media players, mobile computers, mobile phones, MP3 players, music players, notebook computers, pagers, palm pilots, personal computers, personal digital assistants (PDAs), personal locator beacons, portable books, portable electronic devices, portable game consoles, radar displays, radios, remote control device, satellite phones, smart cards, smartphones, speakers, tablets, telephones (e.g. cellular and standard), televisions, video cameras, video players, automobiles, boats, and aircraft.

In some embodiments, MS SBP formulations are used as, or incorporated into, the coating materials of a device. In some embodiments, the coating may be functional, decorative or both. Coatings may be applied to completely cover the surface. Coating may also be applied to partially cover the surface. Devices coated with SBPs may be more biocompatible and/or less-immunogenic.

Antibiotic Materials

In some embodiments, MS SBP formulations may be used as materials due to their antibiotic properties. Such methods may include any of those described in European Patent Number EP3226835 and Mane et al. (2017) Scientific Reports 7:15531, the contents of each of which are herein incorporated by reference in their entirety. These antibiotic properties may be a general property of SBPs. In some embodiments, SBPs materials with antibiotic properties may include antibiotic cargo. In some embodiments, SBP materials may include antibiotic wound-healing materials (e.g., see Babu et al. (2017) J Colloid Interface Sci 513:62-72, the contents of which are herein incorporated by reference in their entirety).

Synthetic Materials

In some embodiments, MS SBP formulations are combined with synthetic materials. Such SBPs may be used to form scaffolds (e.g., see Lo et al. (2017) J Tissue Eng Regen Med doi.10.1002/term.2616, the contents of which are herein incorporated by reference in their entirety). In some embodiments, SBPs described herein are utilized to coat other materials. Such SBPs may include any of those described in Ai et al. (2017) International Journal of Nanomedicine 12:7737-7750, the contents of which are herein incorporated by reference in their entirety. In some embodiments, SBPs include plastics (e.g. thermoplastics, bioplastics, polyethylene, ultra-high-molecular-weight polyethylene, polypropylene, polystyrene, and polyvinyl chloride). In some embodiments, SBPs include plastic replacements. In some embodiments, SBPs include electronic materials or insulators.

In some embodiments, SBPs include polyolefins, polymers, and/or particles. In some embodiments, SBP materials may be prepared and used according to the methods of preparation and use described in European Patent Numbers EP3226835, EP3242967, and EP2904133, United States Publication Numbers US20170333351 and US20170340575, and Cheng et al. (2017) ACS Appl Mater Interfaces doi.10.1021/acsami.7b13460, the contents of each of which are herein incorporated by reference in their entireties.

In some embodiments, MS SBP formulations may be used as a plastic replacement in various products. Conventional plastic is made from petroleum products, primarily oil. It does not biodegrade and is harmful to the environment. MS SBP formulations are an attractive alternative to synthetic plastics due to their biocompatibility and biodegradability. As a non-limiting example, SBPs may be used as a plastic replacement in the production of water bottles and food containers. As another non-limiting example, MS SBP formulations may be used as a plastic replacement in the preparation of coating materials on a fabric or a cloth. Coatings used on apparels, such as a waterproof jacket or athletic shirt, are generally made of synthetic polymers and may release micro-plastic particles into water during a wash cycle. Using MS SBP formulations in replacement of synthetic polymers may help eliminate this problem.

Nanomaterials

In some embodiments, MS SBP formulations include nanomaterials (e.g. nanoparticles, nanofibrils, nanostructures, and nanofibers), as taught in International Patent Application Publication No. WO2017192227, Xiong el al., and Babu et al. (Xiong el al. (2017) ACS Nano 11(12): 12008-12019; Babu et al. (2017) J Colloid Interface Sci 513:62-72), the contents of each of which are herein incorporated by reference in their entirety. In some embodiments, the nanoparticles may include excipients. In some embodiments, the nanoparticles may include, but are not limited to, any of those excipients listed in Table 1, above.

Cosmetics

In some embodiments, MS SBP formulations are or used in the preparation of cosmetics. In some embodiments, SBPs are active substances in said cosmetics, e.g., as taught in U.S. Pat. No. 6,280,747 and United States Publication Number US20040170590, the contents of each of which are herein incorporated by reference in their entirety. In some embodiments, SBPs are added as a thickening agent, e.g., as taught in United States Publication Number US20150079012, the contents of which are herein incorporated by reference in their entirety. In some embodiments, cosmetics may incorporate SBPs for stabilization and/or preservation of cosmetic components (e.g., see Li el al.

(2017) Biomacromolecules 19(9):2900-2905, the contents of which are herein incorporated by reference in their entirety). In some embodiments, MS SBP formulations may be incorporated into cosmetics as a lubricant. In some embodiments, MS SBP formulations may be used as a plastic replacement in the preparation of cosmetics. As a non-limiting example, MS SBP formulations may be formatted as microbeads to be used in replacement of plastic microbeads in facial scrubs and toothpastes. Examples of cosmetics include, but are not limited to, shampoos, conditioners, lotions, foundations, concealers, eye shadows, powders, lipsticks, lip glosses, ointments, mascara, gels, sprays, eye liners, liquids, solids, eyebrow mascaras, eyebrow gels, hairspray, moisturizers, dyes, minerals, perfumes, colognes, rouges, natural cosmetics, synthetic cosmetics, soaps, cleansers, deodorants, creams, towelettes, bath oils, bath salts, body butters, nail polish, hand sanitizer, primers, plumpers, balms, contour powders, bronzers, setting sprays, and setting powders.

Thickening Agents

In some embodiments, MS SBP formulations may be or may be combined with thickening agents. As used herein, the term "thickening agent" refers to a substance used to increase viscosity of another material, typically without altering any properties of the other material. In some embodiments, SBP thickening agents may be used in paints, inks, explosives, cosmetics, foods, or beverages.

In some embodiments, SBP thickening agents may be used in products for human consumption (e.g., as taught in United States Publication No. US20150079012, the contents of which are herein incorporated by reference in their entirety). SBP biocompatibility, biodegradability, and low toxicity make SBPs attractive tools for thickening materials designed for human consumption. In some embodiments, SBP thickening agents may be used to increase the viscosity of a food item. Examples of food items include, but are not limited to, puddings, soups, sauces, gravies, yogurts, oatmeals, chilis, gumbos, chocolates, and stews. In some embodiments, SBP thickening agents may be used to increase the viscosity of beverages. Examples of beverages include, but are not limited to, shakes, drinkable yogurts, milks, creams, sports drinks, protein shakes, diet supplement beverages, and coffee creamers.

In some embodiments, SBP thickening agents may be added to cosmetics (e.g., as taught in United States Publication Number US20150079012, the contents of which are herein incorporated by reference in their entirety. Such cosmetic products may include, but are not limited to, shampoos, conditioners, lotions, foundations, concealers, eye shadows, powders, lipsticks, lip glosses, ointments, mascara, gels, sprays, eye liners, liquids, solids, eyebrow mascaras, eyebrow gels, hairspray, moisturizers, dyes, minerals, perfumes, colognes, rouges, natural cosmetics, synthetic cosmetics, soaps, cleansers, deodorants, creams, towelettes, bath oils, bath salts, body butters, nail polish, hand sanitizer, primers, plumpers, balms, contour powders, bronzers, setting sprays, and setting powders.

Military Applications

In some embodiments, SBP formulations may be used in military applications. For example, SBP formulations may be incorporated in military fabrics. Such fabrics may be used in items such as, but not limited to, ponchos, tents, uniforms, vests, backpacks, personal protective equipment (PPE), linings, cords, ropes, and cables, webbings, straps and sheaths, helmet coverings, flags, bedsheets and mattress fabrics, ribbons, hats, gloves, masks, boots, suits and belts. As another example, SBP formulations may be used in the manufacture of a military device or gear. Non-limiting examples of military devices or gears include goggles, sunglasses, telescopes, binoculars, monoculars, flashlight, torches, watches, compasses, whistle, shields, knee caps, water bottles, flasks, and cameo face paint.

The details of one or more embodiments of the disclosure are set forth in the accompanying description above. Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

V. Definitions

Linear viscoelastic region: As used herein, the term "linear viscoelastic region" or "LVR" refers to the range in amplitude of deformation in which the shear loss modulus and the shear storage modulus do not vary and the structure of the material does not change.

Phase angle: As used herein, the term "phase angle" refers to the difference in the stress and strain applied to a material during the application of oscillating shear stress. The lag between stress and strain represents a measure of a material's viscoelasticity.

Shear: As used herein, the term "shear" or "shear force" or refers to a force applied to a material that is parallel to the surface of said material.

Shear loss modulus: As used herein, the term "shear loss modulus" or "G"" refers to the measure of a material's ability to dissipate energy, usually in the form of heat.

Shear rate: As used herein, the term "shear rate" refers to the rate of change in a material's strain over time.

Shear storage modulus: As used herein, the term "shear storage modulus" or "G'" refers to the measure of a material's elasticity or reversible deformation as determined by the material's stored energy.

Shear stress: As used herein, the term "shear stress" refers to the force applied parallel to a material divided by the area along the force.

Strain: As used herein, the term "strain" refers to the ratio of displacement of material upon the application of a shear force to the height of the material.

Strain sweep: As used herein, the term "strain sweep" refers to a range of strain measurements over which an experimental parameter may be determined.

Tune: As used herein, the term "tune" refers to the control or modulation of a physical or chemical property. Physical or chemical properties of SBPs may be tuned through the control of silk fibroin molecular weight, silk concentration, the incorporation of excipients, and any other method of control described in the present disclosure.

Viscoelasticity: As used herein, the term "viscoelasticity" refers to the range of viscous and elastic properties of materials under stress.

Viscosity: As used herein, the term "viscosity" refers to a material's ability to resist deformation due to shear forces, and the ability of a fluid to resist flow. It is reflected by the shear stress over the shear rate.

The details of one or more embodiments of the disclosure are set forth in the accompanying description below.

Although any materials and methods similar or equivalent to those described herein can be used in the practice or testing of the present disclosure, the preferred materials and methods are now described. Other features, objects and advantages of the disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which this disclosure belongs. In the case of conflict, the present description will control.

The present disclosure is further illustrated by the following non-limiting examples.

EXAMPLES

Example 1. Silk Fibroin Isolation

Silk yarn, purchased from Jiangsu SOHO International Group, was degummed to remove sericin. 30 grams of cut silk yarn were boiled or heated or degummed at 100° C. in 3 L of deionized (DI) water with 0.02M sodium carbonate with stirring. The yarn was then transferred to a new boiling 0.02M sodium carbonate aqueous solution and boiled at 100° C. with stirring. The total degumming time was discussed in terms of minute boil, or "mb." The total degumming time was 480 minutes, or 480 mb.

Alternatively, Silk yarn, purchased from Jiangsu SOHO International Group, was degummed to remove sericin. 30 grams of cut silk yarn were boiled or heated or degummed at 85° C. in 3 L of deionized (DI) water with 0.5M sodium carbonate with stirring. The total degumming time was 240 minutes or 240 mb. Alternatively, Silk yarn, purchased from Jiangsu SOHO International Group, was degummed to remove sericin. 30 grams of cut silk yarn were boiled or heated or degummed at 90° C. in 3 L of deionized (DI) water with 0.5M sodium carbonate with stirring. The total boiling or degumming time was 120 minutes or 120 mb.

The fibroin was washed in 3×3 L exchanges of 70° C. DI water for 20 minutes each followed by 3×3 L exchanges of room temperature (RT) DI water for 20 minutes each. The silk fibroin was dried overnight, weighed, and dissolved at 20% (w/v) in a 9.3M aqueous solution of lithium bromide (from Sigma-Aldrich, St. Louis, Mo.) for 5 hours at 60° C. The resulting fibroin solution was dialyzed against water (150 mL of fibroin solution against 5 L of water) at room temperature in 3.5 kDa or 50 kDa regenerated cellulose dialysis tubing for 48 hours, with 6 water changes to remove the excess salt. The conductivity was tested and recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and samples of the supernatant were diluted at 1:20 and 1:40 in water or 10 mM phosphate buffer. Samples for a standard curve were prepared for an A280 assay by diluting pre-measured fibroin solutions to 5, 2.5, 1.25, 0.625, 0.3125, and 0 mg/mL in water or 10 mM phosphate buffer. The silk concentration of the 1:20 and 1:40 diluted silk fibroin samples was measured against the standard curve by the absorbance at 280 nm.

The silk fibroin solutions were diluted to a final concentration of 3% (w/v) in 10 mM phosphate buffer (from Sigma Aldrich Fine Chemicals, St. Louis, Mo.), pH 7.4, and/or in 5% sucrose, and/or in water, and they were filtered through a 0.2 µm filter using a vacuum filter unit. 10 mL of each solution was aliquoted into 50 mL conical tubes, snap frozen, or frozen to −80° C., in liquid nitrogen for 10 minutes, transferred for 20 minutes in −80° C., and lyophilized for 72 hours.

Silk yarn, purchased from Jiangsu SOHO International Group, was degummed to remove sericin and modify silk fibroin molecular weight. 20 gramns of cut silk yarn were split into four cotton drawstring bags with 5 grams of silk per bag. The four bags of yarn were then immersed in 2 L of degumming solution at either 0.05 M, 0.1 M, or 0.5 M sodium carbonate. The temperature of the solution was controlled with a ChefSteps Joule Sous Vide (ChefSteps, Seattle, Wash., USA) at either 80, 85, 90° C. A control degumming was performed with four bags of yarn in 0.02 M carbonate at 100° C. Every two hours for each degumming, a bag would be taken from the solution and the pH of the solution would be measured. The silk fibroin in the bag was thoroughly rinsed under DI water and allowed to dry overnight in a fume hood. Table 6 lists the degumming conditions, pH values of the degumming solution at the time the silk fibroin was removed, and the dry weight of the silk fibroin after degumming.

TABLE 6

Silk fibroin degumming conditions, pH values, and dry weights

| Lot # | Silk Degumming Time (hr) | Silk Degumming Sodium Carbonate Concentration (M) | Silk Degumming Temperature (° C.) | Final Degumming Solution pH | Final Silk Fibroin Dry Weight (g) |
|---|---|---|---|---|---|
| 111.2 | 2 | 0.02 | 100 | 10.53 | 3.726 |
| 111.4 | 4 | 0.02 | 100 | 10.52 | 3.515 |
| 111.6 | 6 | 0.02 | 100 | 10.76 | 3.293 |
| 111.8 | 8 | 0.02 | 100 | 11.18 | 3.131 |
| 108A.2 | 2 | 0.05 | 80 | 11.11 | 3.776 |
| 108A.4 | 4 | 0.05 | 80 | 10.77 | 3.737 |
| 108A.6 | 6 | 0.05 | 80 | 10.84 | 3.717 |
| 108A.8 | 8 | 0.05 | 80 | 10.64 | 3.657 |
| 108B.2 | 2 | 0.05 | 85 | 10.77 | 3.870 |
| 108B.4 | 4 | 0.05 | 85 | 10.68 | 3.730 |
| 108B.6 | 6 | 0.05 | 85 | 10.93 | 3.670 |
| 108B.8 | 8 | 0.05 | 85 | 10.75 | 3.500 |
| 108C.2 | 2 | 0.05 | 90 | 10.74 | 3.730 |
| 108C.4 | 4 | 0.05 | 90 | 10.64 | 3.560 |
| 108C.6 | 6 | 0.05 | 90 | 10.91 | 3.390 |
| 108C.8 | 8 | 0.05 | 90 | 10.68 | 3.160 |
| 109A.2 | 7 | 0.1 | 80 | 10.67 | 3.804 |
| 109A.4 | 4 | 0.1 | 80 | 10.58 | 3.726 |
| 109A.6 | 6 | 0.1 | 80 | 11.13 | 3.528 |
| 109A.8 | 8 | 0.1 | 80 | 11.07 | 3.386 |
| 109B.2 | 7 | 0.1 | 85 | 10.76 | 3.684 |
| 109B.4 | 4 | 0.1 | 85 | 10.38 | 3.558 |
| 109B.6 | 6 | 0.1 | 85 | 11.10 | 3.257 |
| 109B.8 | 8 | 0.1 | 85 | 11.04 | 3.073 |
| 1090.2 | 2 | 0.1 | 90 | 10.95 | 3.690 |
| 109C.4 | 4 | 0.1 | 90 | 10.42 | 3.333 |
| 109C.6 | 6 | 0.1 | 90 | 11.02 | 2.755 |
| 109C.8 | 8 | 0.1 | 90 | 10.83 | 2.477 |
| 110A.2 | 2 | 0.5 | 80 | 10.65 | 3.717 |
| 110A.4 | 4 | 0.5 | 80 | 10.98 | 3.459 |
| 110A.6 | 6 | 0.5 | 80 | 11.09 | 2.958 |
| 110A.8 | 8 | 0.5 | 80 | 11.07 | 2.654 |
| 110B.2 | 2 | 0.5 | 85 | 11.05 | 3.443 |
| 110B.4 | 4 | 0.5 | 85 | 10.97 | 2.967 |
| 110B.6 | 6 | 0.5 | 85 | 11.37 | 2.153 |
| 110B.8 | 8 | 0.5 | 85 | 11.30 | 1.891 |
| 110C.2 | 7 | 0.5 | 90 | 10.99 | 3.054 |
| 110C.4 | 4 | 0.5 | 90 | 10.92 | 2.502 |
| 110C.6 | 6 | 0.5 | 90 | 11.34 | 1.785 |
| 110C.8 | 8 | 0.5 | 90 | 11.34 | 0.522 |

The silk fibroin samples were weighed and dissolved at 20% (w/v) in a 9.3M aqueous solution of lithium bromide (from Sigma-Aldrich, St. Louis, Mo.) for 5 hours at 60° C. The resulting fibroin solution was dialyzed against water at 4° C. in 50 kDa regenerated cellulose dialysis tubing for 48 hours, with 6 water changes to remove the excess salt. The conductivity was recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and samples of the supernatant were assessed for silk fibroin concentration via gravimetric analysis. Weigh boats were tared and 50 µL of solution was added onto it. The solution was dried overnight at 60° C. before a final weight was measured. The resulting weight of silk fibroin remaining was used to determine the silk fibroin percentage (w/v).

Silk fibroin solutions were diluted to a final concentration of 5% (w/v) and 50 mM sucrose (from Sigma Aldrich Fine Chemicals, St. Louis, Mo.). If the solution was below 5% (w/v) after dialysis, the solution was diluted as little as possible in order to reach a final concentration of 50 mM sucrose. Ten milliliters of each solution was aliquoted into 50 mL conical tubes, frozen overnight at −80° C., and then stored at −20° C. until use.

Example 2. Silk Fibroin Isolation and Preparation by Gravimetry

Silk yarn, purchased from Jiangsu SOHO International Group, was degummed to remove sericin. 30 grams of cut silk yarn were boiled at 100° C. in 3 L of deionized (DI) water with 0.02M sodium carbonate with stirring. The yarn was then transferred to a new boiling 0.02M sodium carbonate aqueous solution and boiled at 100° C. with stirring. The total degumming time was discussed in terms of minute boil, or "mb." The total degumming time was 480 minutes, or 480 mb.

Alternatively. Silk yarn, purchased from Jiangsu SOHO International Group, was degummed to remove sericin. 30 grams of cut silk yarn were boiled at 85° C. in 3 L of deionized (DI) water with 0.5M sodium carbonate with stirring. The total degumming time was 240 minutes or 240 mb. Alternatively, Silk yarn, purchased from Jiangsu SOHO International Group, was degummed to remove sericin. 30 grams of cut silk yarn were boiled at 90° C. in 3 L of deionized (DI) water with 0.5M sodium carbonate with stirring. The total boiling time was 120 minutes or 120 mb.

The fibroin was washed in 3×3 L exchanges of 70° C. DI water for 20 minutes each followed by 3×3 L exchanges of room temperature (RT) DI water for 20 minutes each. The silk fibroin was dried overnight, weighed, and dissolved at 20% (w/v) in a 9.3M aqueous solution of lithium bromide (from Sigma-Aldrich, St. Louis, Mo.) for 5 hours at 60° C. The resulting fibroin solution was dialyzed against water (150 mL of fibroin solution against 5 L of water) at room temperature in a 3.5 kDa or 50 kDa regenerated cellulose dialysis tubing for 48 hours, with 6 water changes to remove the excess salt. The conductivity was tested and recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and concentration of silk fibroin was determined via gravimetry. The weight of dried silk fibroin remaining was divided by the sample volume to determine the concentration of silk fibroin in solution. Samples of the supernatant were added to pre-tared weigh boats and dried at 60° C. overnight.

The silk fibroin solutions were diluted to a final concentration of 3% (w/v) in 10 mM phosphate buffer (from Sigma Aldrich Fine Chemicals, St. Louis, Mo.), pH 7.4, or to 5% (w/v) silk fibroin in 50 mM sucrose and they were filtered through a 0.2 µm PES filter using a vacuum filter unit. For those solutions diluted in phosphate buffer, 10 mL of each solution was aliquoted into 50 mL conical tubes, snap frozen in liquid nitrogen for 10 minutes, transferred for 20 minutes in −80° C., and lyophilized for 72 hours. For those solutions diluted in sucrose, 10 mL of each solution was aliquoted into 50 mL conical tubes, frozen overnight at −80° C., and then stored at −20° C. Some aliquots were lyophilized. Some aliquots were stored at 2-8° C. prior to freezing at −80° C.

Example 3. Silk Fibroin Isolation and Molecular Weight Determination

Silk yarn, purchased from Jiangsu SOHO International Group, was degummed to remove sericin. 30 grams of cut silk yarn were boiled at 100° C. in 3 L of deionized (DI) water with 0.02M sodium carbonate with stirring. The yarn was then transferred to a new boiling 0.02 M sodium carbonate aqueous solution and boiled at 100° C. with stirring. The total boiling time, or degumming time, was discussed in terms of minute boil, or "mb." The total boiling times ranged from 30-480 mb. The fibroin was dried overnight, weighed, and dissolved at 20% (w/v) in a 9.3 M aqueous solution of lithium bromide (from Sigma-Aldrich, St. Louis, Mo.) for 5 hours at 60° C. The resulting fibroin solution was dialyzed against water at room temperature in 50 kDa regenerated cellulose dialysis tubing for 48 hours, with 6 water changes to remove the excess salt. The conductivity was tested and recorded after each water change with a digital quality tester. When the conductivity was under 5 ppm, the fibroin solution was determined to be ready.

The resulting solution was centrifuged for 20 minutes at 3,900 RPM and 4° C. to remove insoluble particles. The supernatant was collected, and the concentration of silk fibroin was determined via gravimetry. Samples of the supernatant were added to pre-tared weigh boats and dried at 60° C. overnight. The dried weight of silk fibroin was used to determine the concentration in solution. The silk fibroin solutions were diluted to a final concentration of 5% (w/v) in 50 mM sucrose, separated into 10 mL was aliquots in 15 mL conical tubes, and frozen at ≤−20° C.

Silk fibroin molecular weight was determined using a UPLC SEC method. A Waters Acquity H-Class UPLC (Waters, Milford. Mass.) equipped with a Waters BEH 200 Å 1.7 µm, 4.8×150 cm UPLC SEC column was used. Sample temperature was maintained at 4° C. An isocratic flow at 0.3 mL/min of 100 mM Tris-HCl with 400 mM sodium perchlorate, pH 8.0 was used to elute SF from the column. Elution was monitored at 280 nm. Molecular weights were calculated using Waters BEH200 Protein Standard Mix (Waters, Milford, Mass.). Some preparations of 480 mb had an average molecular weight of 30 kDa. Other preparations resulted in molecular weights between 20 kDa and 40 kDa.

The molecular weight of each batch collected was determined by HPLC-SEC. A Waters Acquity H-Class UPLC (Waters, Milford, Mass.) equipped with a Waters BEH 200 Å 1.7 mm, 4.8×300 cm UPLC SEC column (from Waters, Milford, Mass.) was used. Sample temperature was maintained at 4° C. An isocratic flow at 0.3 mL/min of mobile phase (100 mM Tris-HCl with 400 mM sodium perchlorate (Alfa Aesar, Ward Hill, Mass.), pH 8.0 was used to elute SF from the column. Mobile phase was prepared by dissolving 12.1 g of Tris base (VWR, Pittsburgh, Pa.) and 48.1 g of sodium perchlorate (Alfa Aesar. Ward Hill, Mass.) in 800 mL of DI water. The pH was adjusted to 8.0 with 6N HCl. DI water was added to a final volume of 1 L. The solution was sterile filtered through a 0.2 μm polyethersulfone membrane filter. Silk fibroin was diluted to 1% (w/v) in mobile phase after thawing before being run on SEC. Silk fibroin elution was monitored at 280 nm. Molecular weights were calculated using a standard curve prepared from Waters BEH 200 Å Protein SEC Standard Mix (Waters, Milford, Mass.). Table 7 lists these molecular weights for the select batches analyzed.

TABLE 7

SEC measurements of silk fibroin solution formulations

| Lot # | Average MW (kDa) | Average Viscosity at 1 1/s (cP) |
|---|---|---|
| 111.2 | 117.56 | 30.89 |
| 111.4 | 60.74 | 39.00 |
| 111.6 | 42.41 | 76.21 |
| 111.8 | 34.03 | 97.66 |
| 108A.2 | — | — |
| 108A.4 | — | — |
| 108A.6 | — | — |
| 108A.8 | 93.51 | 15.22 |
| 108B.2 | — | — |
| 108B.4 | — | — |
| 108B.6 | — | — |
| 108B.8 | 45.49 | 53.41 |
| 108C.2 | 122.52 | 12.54 |
| 108C.4 | 65.01 | 23.90 |
| 108C.6 | 49.87 | 54.18 |
| 108C.8 | 31.45 | 74.70 |
| 109A.2 | — | — |
| 109A.4 | — | — |
| 109A.6 | — | — |
| 109A.8 | 43.95 | 43.38 |
| 109B.2 | 118.93 | 27.46 |
| 109B.4 | 64.36 | 25.68 |
| 109B.6 | 38.21 | 82.10 |
| 109B.8 | 31.75 | 104.60 |
| 109C.2 | 82.76 | 17.12 |
| 109C.4 | 36.73 | 49.41 |
| 109C.6 | 25.04 | 106.95 |
| 109C.8 | 22.04 | 142.48 |
| 110A.2 | 68.74 | 18.16 |
| 110A.4 | 35.47 | 42.74 |
| 110A.6 | 22.59 | 78.72 |
| 110A.8 | 21.32 | 128.03 |
| 110B.2 | 37.88 | 41.37 |
| 110B.4 | 22.13 | 89.69 |
| 110B.6 | 17.60 | 178.79 |
| 110B.8 | — | — |
| 110C.2 | 24.25 | 99.74 |
| 110C.4 | 17.60 | 140.56 |
| 110C.6 | — | — |
| 110C.8 | — | — |

A decrease in silk fibroin molecular weight was observed over time under each degumming condition. This is a result of the hydrolysis occurring during the degumming process in the basic sodium carbonate buffer. Longer degumming times lead to decreased average silk fibroin MW. Silk fibroin degradation was also observed with increasing sodium carbonate concentration. For example, increasing the sodium carbonate concentration from 0.05 M to 0.5 M while at the same temperature (90° C.) and time (2 hrs.) decreased the average molecular weight of silk fibroin from 122.52 kDa to 24.25 kDa. Temperature also impacted the silk fibroin hydrolysis with increasing temperature leading to lower molecular weights. An example of this was shown with silk that was degummed with 0.5 M sodium carbonate for 2 hrs. The sample at 80° C. showed a molecular weight of 68.74 kDa, while increasing the temperature to 90° C. decreased the molecular weight average of the silk fibroin to 24.35 kDa. These results indicated that by controlling the time of degumming, the sodium carbonate concentration, and the temperature, it is possible to control the hydrolysis of silk fibroin.

Example 4. Formulation of Silk Fibroin Solutions

To prepare the solutions, dry silk fibroin of a designated mb, which had been lyophilized in phosphate buffer, was reconstituted in phosphate buffered saline to afford 30% and 10% (w/v) silk fibroin solutions. Formulations from silk of a 30 mb were prepared from silk fibroin lyophilized with sucrose. Additional dilutions with phosphate buffered saline were performed on the 10% (w/v) silk fibroin solutions to obtain solutions with 5%, 2.5%, 1%, 0.5% and 0.1% (w/v) silk fibroin. The formulations were prepared as described in Table 8. The samples in Table 8 are named by the process used to prepare and formulate each solution. For example, in the sample named "30 mb; sin; 10% SFf; 18% Suc" "30 mb" refers to silk degummed with a 30 minute boil, "sln" refers to the formulation of the sample as a solution, "10% SFf" refers to a formulation with 10% (w/v) silk fibroin, and "18% Suc" refers to a formulation with 18% sucrose (w/v).

TABLE 8

Silk fibroin solution formulations

| Sample | Silk Fibroin Boil Time (mb) | Formulation Silk Concentration (w/v %) | Sample Name |
|---|---|---|---|
| 1A | 30 | 30 | 30mb; sln; 30%SFf |
| 1B | 30 | 10 | 30mb; sln; 10%SFf; 18%Suc |
| 1C | 30 | 5 | 30mb; sln; 5%SFf; 9%Suc |
| 1D | 30 | 2.5 | 30mb; sln; 2.5%SFf; 4.5%Suc |
| 1E | 30 | 1 | 30mb; sln; 1%SFf; 1.8%Suc |
| 1F | 30 | 0.5 | 30mb; sln; 0.5%SFf; 0.9%Suc |
| 1G | 30 | 0.1 | 30mb; sln; 0.1%SFf 0.18%Suc |
| 2A | 90 | 30 | 90mb; sln; 30%SFf |
| 2B | 90 | 10 | 90mb; sln; 10%SFf |
| 2C | 90 | 5 | 90mb; sln; 5%SFf |
| 2D | 90 | 2.5 | 90mb; sln; 2.5%SFf |
| 2E | 90 | 1 | 90mb; sln; 1%SFf |
| 2F | 90 | 0.5 | 90mb; sln; 0.5%SFf |
| 2G | 90 | 0.1 | 90mb;sln; 0.1%SFf |
| 3A | 120 | 30 | 120mb; sln; 30%SFf |
| 3B | 120 | 10 | 120mb; sln; 10%SFf |
| 3C | 120 | 5 | 120mb; sln; 5%SFf |
| 3D | 120 | 2.5 | 120mb; sln; 2.5%SFf |
| 3E | 120 | 1 | 120 mb; sln; 1%SFf |
| 3F | 120 | 0.5 | 120mb; sln; 0.5%SFf |
| 3G | 120 | 0.1 | 120mb; sln; 0.1%SFf |
| 4A | 480 | 30 | 480mb; sln; 30%SFf |
| 4B | 480 | 10 | 480mb; sln; 10%SFf |
| 4C | 480 | 6 | 480mb; sln; 5%SFf |
| 4D | 480 | 2.5 | 480mb; sln; 2.5%SFf |
| 4E | 480 | 1 | 480mb; sln; 1%SFf |
| 4F | 480 | 0.5 | 480mb; sln; 0.5%SFf |
| 4G | 480 | 0.1 | 480mb; sln; 0.1%SFf |

To prepare the following solutions in Table 9, silk fibroin of a designated mb, which had either been frozen in 50 mM sucrose or stored at 4° C. in phosphate buffer, was used. A phosphate buffered saline stock solution containing sodium phosphate dibasic, potassium phosphate monobasic, and sodium chloride was prepared to reach final concentrations of 10 mM phosphate and 125 mM sodium chloride and buffered to pH 7.5. The formulations were prepared as described in Table 6. The samples in Table 9 are named by the process used to prepare and formulate each solution with each degumming process. For example, in the sample named "2% SFf; sln 1.71% Suc; phosphate buffer", "1% SFf" refers to a formulation with 1% (w/v) silk fibroin, "sln" refers to the formulation of the sample as a solution, and "1.71% Suc" refers to a formulation with 1.71% (w/v), or 50 mM, sucrose. All formulations are in a "phosphate buffer" which refers to a vehicle containing final concentrations of 10 mM phosphate and 125 mM sodium chloride at pH 7.5. It is noted that the three variables that differ in the samples are carbonate concentration, temperature, and time duration. By altering these three variables, similar molecular weights can be achieved without having to boil the solution or keep the solution at a high or boiling temperature for a full eight hours.

TABLE 9

Silk Fibroin Formulations (prepared with each SF from Example 1)

| Sample | SF Conc. (%) | Description |
| --- | --- | --- |
| 1 | 2 | 2%SFf; sln; phosphate buffer |
| 2 | 2.5 | 2.5%SFf; sln; phosphate buffer |
| 3 | 3 | 3%SFf; sln; phosphate buffer |
| 4 | 2 | 2%SFf; sln; 1.71%Suc; phosphate buffer |
| 5 | 2.5 | 2.5%SFf; sln; 1.71%Suc; phosphate buffer |
| 6 | 3 | 3%SFf; sln; 1.71%Suc; phosphate buffer |

Example 5. Formulation of Silk Fibroin Solutions with Lyophilized or Freeze-Thaw Silk Fibroin To prepare the solutions, silk fibroin was either reconstituted from a dry state or thawed from a frozen state. Dry silk fibroin of a designated mb, which had been lyophilized in phosphate buffer or sucrose, was reconstituted in phosphate buffered saline to afford 10% (w/v) silk fibroin solutions. Frozen silk fibroin solutions were left at room temperature until completely thawed and then gently mixed before use. Additional dilutions with phosphate buffered saline were performed on the 10% and 5% (w/v) silk fibroin solutions to obtain solutions with 5%, 1%, 0.5%, 0.1%, and 0.05% (w/v) silk fibroin. The formulations were prepared as described in Table 10. The samples in Table 10 are named by the process used to prepare and formulate each solution. For example, in the sample named "90 mb; sn; 5% SFf; 1.7% Suc; frozen" "90 mb" refers to silk degummed with a 90-minute boil, "sln" refers to the formulation of the sample as a solution, "5% SFf" refers to a formulation with 5% (w/v) silk fibroin, "1.7% Suc" refers to a formulation with 1.7% sucrose (w/v), "frozen" refers to the starting silk fibroin stock being frozen, and "lyo" refers to the starting silk fibroin stock being lyophilized.

TABLE 10

Silk fibroin solution formulations prepared with lyophilized or freeze-thaw silk fibroin

| Sample | Silk Fibroin Boil Time (mb) | Silk Concentration (w/v %) | Sample Name |
| --- | --- | --- | --- |
| 1 | 90 | 5 | 90mb; sln; 5%SFf; 1.7%Suc; frozen |
| 2 | 90 | 1 | 90mb; sln; 1%SFf; 0.34%Suc; frozen |
| 3 | 90 | 0.5 | 90mb; sln; 0.5%SFf; 0.17%Suc; frozen |
| 4 | 90 | 0.1 | 90mb; sln; 0.1%SFf; 0.034%Suc; frozen |
| 5 | 90 | 0.05 | 90tnb; sln; 0.05%SFf; 0.017%Suc; frozen |
| 6 | 120 | 5 | 120mb; sln; 5%SFf; 1.7%Suc; frozen |
| 7 | 120 | 1 | 120mb; sln; 1%SFf; 0.34%Suc; frozen |
| 8 | 120 | 0.5 | 120mb; sln; 0.5%SFf; 0.17%Suc; frozen |
| 9 | 120 | 0.1 | 120mb; sln; 0.1%SFf; 0.034%Suc; frozen |
| 10 | 120 | 0.05 | 120mb; sln; 0.05%SFf; 0.017%Suc; frozen |
| 11 | 480 | 5 | 480mb; sln; 5%SFf; 1.7%Suc; frozen |
| 12 | 480 | 1 | 480mb; sln; 1%SFf; 0.34%Suc; frozen |
| 13 | 480 | 0.5 | 480nib; sln; 0.5%SFf; 0.17%Suc; frozen |
| 14 | 480 | 0.1 | 480mb; sln; 0.1%SFf; 0.034%Suc; frozen |
| 15 | 480 | 0.05 | 480mb; sln; 0.05%SFf; 0.017%Suc; frozen |
| 16 | 480 | 5 | 480mb; sln; 5%SFf; 1.7%Suc; lyo |
| 17 | 480 | 1 | 480mb; sln; 1%SFf; 0.34%Suc; lyo |
| 18 | 480 | 0.5 | 480mb; sln; 0.5%SFf; 0.17%Suc; lyo |
| 19 | 480 | 0.1 | 480mb; sln; 0.1%SFf; 0.034%Suc; lyo |
| 20 | 480 | 0.05 | 480nib; sln; 0.05%SFf; 0.017%Suc; lyo |

Example 6. Formulation of Silk Fibroin Solutions with Sucrose, Surfactant, and Borate Buffer To prepare the solutions, silk fibroin of a designated 480 mb (prepared as in Examples 1 or 2), which had been frozen in 50 mM sucrose, was thawed to room temperature. A borate buffer stock solution containing borate, potassium chloride, magnesium chloride, and calcium chloride was prepared and buffered to pH 7.3. A 10% (v/v) polysorbate 80 stock solution was prepared. The formulations and controls (no silk fibroin) were prepared as described in Table 11. The samples in Table 11 are named by the process used to prepare and formulate each solution. For example, in the sample named "480 mb; sln; 1/SFf; 0.34% Suc; borate buffer" "480 mb" refers to silk degummed with a 480-minute boil, "sln" refers to the formulation of the sample as a solution, "1% SFf" refers to a formulation with 1% (w/v) silk fibroin, "0.34% Suc" refers to a formulation with 0.34% (w/v) sucrose, and "0.2% T80" refers to a formulation containing 0.2% (v/v) polysorbate 80. All formulations are in a "borate buffer" which refers to a vehicle containing final concentrations of 99.3 mM borate, 18.8 mM potassium chloride, 0.6 mM magnesium chloride, and 0.5 mM calcium chloride

TABLE 11

Silk Fibroin Formulations with sucrose and borate buffer

| Sample | SF Conc. (%) | Polysorbate 80 Conc. (%) | Description |
| --- | --- | --- | --- |
| 1 | 0 | 0 | 0%SFf; sln; borate buffer |
| 2 | 0 | 0.2 | 0%SFf; sln; borate buffer; 0.2%T80 |
| 3 | 1 | 0 | 480mb; 1%SFf; sln; 0.34%Suc; borate buffer |
| 4 | 1 | 0.2 | 480mb; 1%SFf; sln; 0.34%Suc; borate buffer; 0.2%T80 |

Example 7. Additional Formulation of Silk Fibroin Solutions with Sucrose, Surfactant, and Borate Buffer To prepare the solutions, silk fibroin of a designated 480 mb (prepared as in Examples 1 or 2), which had been frozen in 50 mM sucrose, was thawed to room temperature. A borate buffer stock solution containing borate, potassium chloride, magnesium chloride, and calcium chloride was prepared and buffered to pH 7.3. A 10% (v/v) polysorbate 80 stock solution was prepared. The formulations and controls (no silk fibroin) were prepared as described in Table 12. The samples in Table 12 are named by the process used to prepare and formulate each solution. For example, in the sample named "480 mb; sln; 1% SFf; 0.34% Suc; borate buffer" "480 mb" refers to silk degummed with a 480 minute boil, "sln" refers to the formulation of the sample as a solution, "1% SFf" refers to a formulation with 1% (w/v) silk fibroin, and "0.34% Suc" refers to a formulation with 0.34% (w/v) sucrose. All formulations are in a "borate buffer" which refers to a vehicle containing final concentrations of 99.3 mM borate, 18.8 mM potassium chloride, 0.6 mM magnesium chloride, and 0.5 mM calcium chloride.

TABLE 12

Silk Fibroin Formulations with 480mb and sucrose and borate buffer

| Sample | SF Conc. (%) | Sucrose Conc. (%) | Description |
|---|---|---|---|
| 1 | 5 | 1.71 | 480mb; 5%SFf; sln; 1.71%Suc; borate buffer |
| 2 | 1 | 0.34 | 480mb; 1%SFf; sln; 0.34%Suc; borate buffer |
| 3 | 0.5 | 0.17 | 480mb; 0.5%SFf; sln; 0.17%Suc; borate buffer |
| 4 | 0.1 | 0.03 | 480mb; 0.1%SFf; sln; 0.03%Suc; borate buffer |
| 5 | 0.05 | 0.01 | 480mb; 0.1%SFf; sln; 0.02%Snc; borate buffer |

Example 8. Rheological Measurements of Silk Solutions

Rheological measurements were performed on a Bohlin C-VOR 150 with a 4°/40 mm cone and plate geometry with a 0.5 mm gap. 1.4 mL of each sample were pipetted onto a Peltier plate system that maintained a steady temperature of 25° C. throughout the test. Four tests were un. The first test comprised a strain sweep from 0.1% to 10% strain at 1 Hz over the course of 160 seconds (s), with 50 readings taken. This was to determine the linear viscoelastic region (LVR) of each sample. The second test comprised a strain hold at 5% (or 1% if the LVR was smaller) and 1 Hz for 145 s, with 15 readings taken. The third test comprised a shear rate sweep from 0.1 l/s to 10 l/s over the course of 100 s, followed by a hold at 10 l/s for 20 s, with 70 readings taken. Lastly, a shear rate hold was conducted at 1 l/s for 135 s, with 15 readings taken. The data was then analyzed to determine the average shear storage modulus (the elastic modulus (G')), shear loss modulus (the viscous modulus (G")), phase angle, and viscosity at shear rates of 1 l/s and 10 l/s. The results of the rheology measurements are listed in Table 13 and Table 18.

TABLE 13

Rheology measurements of silk fibroin solution formulations and controls

| Sample | Description | Avg. Viscosity at 1 1/s (cP) | Avg. Viscosity at 10 1/s (cP) | Avg. G' (Pa) | Avg. G" (Pa) | Avg. Phase Angle (°) |
|---|---|---|---|---|---|---|
| — | Refresh Liquigel | 79.90 | 46.29 | 1.69E−01 | 3.46E−01 | 64.05 |
| — | SYSTANE® lubricant eye drop (Alcort) | 20.23 | 12.06 | 2.06E−02 | 7.83E−02 | 75.44 |
| — | SYSTANE® lubricant eye gel (Alcon) | 1073.57 | 549.81 | 2.20E+00 | 3.03E+00 | 53.98 |
| 1B | 10% 30mb | 71.58 | 47.41 | 7.60E−02 | 4.12E−01 | 79.56 |
| 1C | 5% 30mb | 63.99 | 16.37 | 3.96E−01 | 5.67E−01 | 55.19 |
| 1D | 2.5% 30mb | 69.77 | 13.22 | 3.24E−01 | 3.70E−01 | 48.99 |
| 1E | 1% 30mb | 42.44 | 17.32 | 1.33E+01 | 3.57E+00 | 15.15 |
| 1F | 0.5% 30mb | 31.17 | 10.18 | 3.12E−01 | 2.65E−01 | 140.42 |
| 1G | 0.1% 30mb | 233.61 | 36.57 | 1.47E+01 | 3.40E+00 | 13.13 |
| 2B | 10% 90mb | 12.89 | 6.50 | 1.11E−02 | 5.77E−02 | 79.50 |
| 2C | 5% 90mb | 11.51 | 5.36 | 4.28E−02 | 4.36E−02 | 45.40 |
| 2D | 2.5% 90mb | 13.00 | 4.22 | 4.09E−02 | 4.35E−02 | 146.23 |
| 2E | 1% 90mb | 20.36 | 5.92 | 4.79E−02 | 7.50E−02 | 57.45 |
| 2F | 0.5% 90mb | 51.25 | 10.44 | 1.37E+00 | 1.77E+00 | 152.64 |
| 2G | 0.1% mb | 242.98 | 37.12 | 7.15E+00 | 2.47E+00 | 19.06 |
| 3A | 30% 120mb | 148.68 | 125.72 | 2.90E−02 | 8.00E−01 | 87.93 |
| 3B | 10% 120mb | 11.83 | 4.69 | 6.78E−03 | 4.15E−02 | 180.08 |
| 3C | 5% 120mb | 8.74 | 4.15 | 2.77E−02 | 3.71E−02 | 153.00 |
| 3D | 2.5% 120mb | 8.00 | 1.70 | 3.25E−02 | 2.79E−02 | 140.78 |
| 3E | 1% 120mb | 13.23 | 4.58 | 1.10E−02 | 5.23E−02 | 78.14 |
| 3F | 0.5% 120mb | 46.98 | 12.72 | 4.30E−01 | 3.45E−01 | 38.85 |
| 3G | 0.1% 120mb | 469.61 | 74.17 | 6.69E+00 | 3.30E+00 | 126.22 |
| 4A | 30% 480mb | 110.03 | 4.3.84 | 5.76E−01 | 5.30E−01 | 42.89 |
| 4B | 10% 480mb | 55.18 | 12.76 | 3.40E−01 | 2.37E−01 | 135.14 |
| 4C | 5% 480mb | 67.55 | 13.98 | 4.03E−01 | 2.91E−01 | 135.99 |
| 4D | 2.5% 480mb | 77.45 | 15.06 | 4.86E−01 | 3.34E−01 | 34.61 |
| 4E | 1% 480mb | 113.09 | 20.44 | 6.51E−01 | 4.55E−01 | 35.16 |
| 4F | 0.5% 480mb | 255.44 | 36.18 | 2.46E+00 | 1.52E+00 | 131.70 |
| 4G | 0.1% 480mb | 432.52 | 47.05 | 1.37E+01 | 3.30E+00 | 13.52 |
| 5B | 180 mg/mL Sucrose | 10.54 | 2.41 | 6.08E−03 | 3.97E−02 | 81.30 |
| 5E | 18 mg/mL Sucrose | 10.86 | 1.92 | 1.01E−02 | 3.43E−02 | 73.85 |
| 5G | 1.8 mg/mL Sucrose | 14.96 | 9 5 | 9.53E−03 | 3.56E−02 | 74.70 |
| 6 | 1x PBS | 13.41 | 3.03 | 3.26E−02 | 3.55E−02 | 46.66 |

Table 14 provides the standard deviation of rheology measurements in Table 13

TABLE 14

Standard deviations of the rheology measurements of silk fibroin solution formulations and controls

| Sample | Description | Std Dev. Avg. Viscosity at 1 1/s (cP) | Std. Dev. Avg. Viscosity at 10 1/s (cP) | Std. Dev. Avg. G' (Pa) | Std. Dev. Avg. G" (Pa) | Std. Dev. Avg. Phase Angle (°) |
|---|---|---|---|---|---|---|
| — | Refresh Liquigel | 6.07 | 6.84 | 1.35E−02 | 9.89E−03 | 1.81 |
| — | SYSTANE® lubricant eye drop (Alcon) | 7.60 | 6.33 | 8.25E−03 | 6.22E−03 | 5.24 |
| — | SYSTANE® lubricant eye gel (Alcon) | 7.08 | 5.45 | 1.41E−02 | 1.54E−02 | 0.11 |
| 1B | 10% 30mb | 7.17 | 5.61 | 1.26E−02 | 6.37E−03 | 1.68 |
| 1C | 5% 30 mb | 7.94 | 6.65 | 5.69E−02 | 5.06E−02 | 1.72 |

TABLE 14-continued

Standard deviations of the rheology measurements of silk fibroin solution formulations and controls

| Sample | Description | Std. Dev. Avg. Viscosity at 1 1/s (cP) | Std. Dev. Avg. Viscosity at 10 1/s (cP) | Std. Dev. Avg. G' (Pa) | Std. Dev. Avg. G" (Pa) | Std. Dev. Avg. Phase Angle (°) |
|---|---|---|---|---|---|---|
| 1D | 2.5% 30mb | 4.40 | 6.59 | 5.67E−02 | 4.85E−02 | 2.17 |
| 1E | 1% 30mb | 18.27 | 6.03 | 1.38E+00 | 1.97E−01 | 0.68 |
| 1F | 0.5% 30mb | 7.75 | 5.78 | 1.41E−02 | 8.38E−03 | 1.24 |
| 1G | 0.1% 30mb | 13.66 | 6.30 | 1.32E+00 | 1.34E−01 | 0.75 |
| 2B | 10% 90mb | 5.17 | 1.82 | 9.02E−03 | 1.16E−02 | 6.91 |
| 2C | 5% 90mb | 6.03 | 1.33 | 7.01E−03 | 7.83E−03 | 6.04 |
| 2D | 2.5% 90mb | 7.96 | 2.10 | 7.76E−03 | 1.14E−02 | 7.90 |
| 2E | 1% 90mb | 7.18 | 1.63 | 6.50E−03 | 5.90E−03 | 4.02 |
| 2F | 0.5% 90mb | 10.85 | 1.59 | 2.39E−01 | 3.21E−02 | 4.55 |
| 2G | 0.1% 90mb | 39.66 | 1.86 | 4.02E−01 | 5.14E−02 | 0.69 |
| 3A | 30% 120mb | 4.99 | 1.35 | 1.02E−02 | 1.06E−02 | 0.71 |
| 3B | 10% 120mb | 4.28 | 1.06 | 4.27E−03 | 8.25E−03 | 6.47 |
| 3C | 5% 120mb | 3.51 | 1.54 | 8.24E−03 | 8.37E−03 | 12.40 |
| 3D | 2.5% 120mb | 5.11 | 1.25 | 6.70E−03 | 6.08E−03 | 9.61 |
| 3E | 1% 120mb | 3.06 | 1.56 | 7.58E−03 | 8.57E−03 | 7.62 |
| 3F | 0.5% 120mb | 9.42 | 1.60 | 3.59E−02 | 1.11E−02 | 2.53 |
| 3G | 0.1% 120mb | 32.15 | 4.17 | 9.19E−02 | 4.70E−02 | 0.59 |
| 4A | 30% 480mb | 7.24 | 1.89 | 9.07E−02 | 3.09E−02 | 3.21 |
| 4B | 10% 480mb | 4.88 | 1.29 | 4.11E−02 | 1.17E−02 | 2.33 |
| 4C | 5% 480mb | 5.80 | 1.70 | 4.65E−02 | 1.99E−02 | 1.79 |
| 4D | 2.5% 480mb | 5.61 | 1.48 | 4.89E−02 | 1.63E−02 | 1.68 |
| 4E | 1% 480mb | 5.25 | 1.65 | 8.22E−02 | 2.58E−02 | 2.18 |
| 4F | 0.5% 480mb | 8.00 | 1.31 | 2.16E−01 | 6.53E−02 | 1.29 |
| 4G | 0.1% 480mb | 30.88 | 2.73 | 5.66E−01 | 5.21E−02 | 0.44 |
| 5B | 180 mg/mL Sucrose | 5.59 | 1.71 | 4.41E−03 | 1.03E−02 | 5.51 |
| 5E | 18 mg/mL Sucrose | 7.62 | 1.06 | 7.04E−03 | 8.92E−03 | 10.50 |
| 5G | 1.8 mg/mL Sucrose | 7.38 | 1.61 | 5.75E−03 | 7.31E−03 | 10.01 |
| 6 | 1x PBS | 4.56 | 1.14 | 5.57E−03 | 1.01E−02 | 8.93 |

All formulations were observed to demonstrate increased viscosity relative to the controls with sucrose or PBS (samples 5B-6). The viscosities of commercially available dry eye treatments (Refresh Liquigel, SYSTANE® lubricant eye drops (Alcon), and SYSTANE® lubricant eye gel (Alcon)) were also measured as a point of comparison. In general, the solutions prepared from silk fibroin with the longest boiling time (480 mb) and the shortest boil time (30 mb) were more viscous than the other solutions. At higher concentrations, the silk fibroin with a 480 mb and with a 30 mb demonstrated higher viscosities than the other formulations. When the concentration was below 1% (w/v) silk fibroin, the formulations prepared from silk fibroin with longer boiling times demonstrated higher viscosities. A relationship between the concentration of silk fibroin and the viscosity of the solutions was also observed regardless of the boiling time of the silk fibroin. When the silk fibroin concentration was varied between 1-30% (w/v), the viscosity remained consistent among samples prepared from silk fibroin with the same boiling times. When the silk fibroin concentration was between 0.1-0.5%, the solutions demonstrated an increase in viscosity as compared to their more concentrated counterparts. In addition, the storage modulus was higher for formulations with lower concentrations of silk fibroin, and the phase angle was measured to be lower for formulations with lower concentrations of silk fibroin. All of the formulations shear thinned, demonstrating lower viscosities at higher shear rates.

To prepare the solutions for rheological analysis, frozen silk fibroin solutions were thawed at room temperature and gently mixed before use. A borate buffer was prepared at 5× the final desired concentration by dissolving 1500 mg of boric acid, 213 mg of sodium borate decahydrate, 350 mg of potassium chloride, 850 mg of sodium chloride, 32 mg of magnesium chloride hexahydrate, and 20 mg of calcium chloride in DI water to reach 50 mL final. Each silk fibroin solution, after thawing, was diluted with DI water and this 5× borate buffer to reach 1% silk fibroin (w/v) final in 1× borate buffer (which indicates 6 mg/mL boric acid, 0.852 mg/mL sodium borate decahydrate, 1.4 mg/mL potassium chloride, 3.4 mg/mL sodium chloride, 0.128 mg/mL magnesium chloride hexahydrate, and 0.08 mg/mL calcium chloride dihydrate.) Rheological measurements were performed on a Bohlin C-VOR 150 with a 4° C./40 mm cone and plate geometry with a 0.15 mm gap. 1.2 mL of each sample were pipetted onto a Peltier plate system that maintained a steady temperature of 25° C. throughout the test. One test was then run. The test comprised of a pre-shear of 1 1/s for 20 s followed by a shear rate hold at 1 1/s for 90 s, with 30 readings taken. The data was then analyzed to determine the average viscosity. The results of the rheology measurements are listed in Table 15.

TABLE 15

Rheology measurements of silk fibroin solution formulations

| Lot # | Average Viscosity at 1 1/s (cP) | Std. Dev. Of Viscosity at 1 1/s (cP) |
|---|---|---|
| 111.2 | 30.89 | 5.03 |
| 111.4 | 39.00 | 6.11 |
| 111.6 | 76.21 | 6.31 |
| 111.8 | 97.66 | 14.15 |
| 108A.2 | — | — |
| 108A.4 | — | — |
| 108A.6 | — | — |
| 108A.8 | 15.22 | 4.01 |
| 108B.2 | — | — |
| 108B.4 | — | — |
| 108B.6 | — | — |
| 108B.8 | 53.41 | 4.41 |
| 108C.2 | 12.54 | 3.12 |
| 108C.4 | 23.90 | 3.54 |
| 108C.6 | 54.18 | 5.58 |
| 108C.8 | 74.70 | 5.99 |
| 109A.2 | — | — |
| 109A.4 | — | — |
| 109A.6 | — | — |
| 109A.8 | 43.38 | 6.58 |
| 109B.2 | 27.46 | 8.29 |
| 109B.4 | 25.68 | 6.41 |
| 1098.6 | 82.10 | 4.84 |
| 109B.8 | 104.60 | 11.71 |
| 109C.2 | 17.12 | 3.91 |
| 109C.4 | 49.41 | 4.55 |
| 109C.6 | 106.95 | 10.12 |
| 109C.8 | 142.48 | 10.65 |
| 110A.2 | 18 16 | 3.97 |
| 110A.4 | 42.74 | 5.62 |
| 110A.6 | 78.72 | 5.98 |
| 110A.8 | 128.03 | 6.75 |
| 110B.2 | 41.37 | 5.20 |
| 110B.4 | 89.69 | 5.75 |
| 110B.6 | 178.79 | 4.62 |
| 110B.8 | — | — |
| 110C.2 | 99.74 | 4.36 |
| 110C.4 | 140.56 | 10.33 |
| 110C.6 | — | — |
| 110C.8 | — | — |

The viscosity of silk fibroin solutions increased with decreasing molecular weight. This was observed within the same conditions (sodium carbonate concentration and temperature) over the degumming time course. As time increased and molecular weight decreased, viscosity increased. Overall, silk fibroin solutions fell into three ranges. Solutions with average molecular weight ≤34.04 kDa displayed the highest viscosity that ranged from 78.72 to 178.79 centipoise (cPs). Silk fibroin solutions with an average molecular weights that ranged from 35.47 to 60.74 kDa showed slightly lower viscosities which ranged from 39.00 to 82.10 cPs. The lowest viscosity was observed in the solutions with the highest average molecular weights of 64.36 to 122.52 kDa. These solutions displayed viscosities of 12.54 to 30.89 cPs. This effect of lower viscosity silk fibroin solutions which displayed higher viscosity is most likely due to the interfacial partitioning of silk fibroin to the air water interface. The lower molecular weight silk fibroin proteins most likely organize at the air-water interface more efficiently allowing for higher local concentrations and increased local viscosity.

Example 9. Rheological Measurements of Silk Solutions with Lyophilized or Freeze-Thaw Silk Fibroin Rheological measurements were performed on a Bohlin C-VOR 150 with a 4°/40 mm cone and plate geometry with a 0.15 mm gap. 1.2 mL of each sample were pipetted onto a Peltier plate system that maintained a steady temperature of 25° C. throughout the test. Three tests were then run. The first test comprised a strain sweep from 0.1% to 10% strain at 1 Hz over the course of 130 seconds (s), with 40 readings taken. This was to determine the linear viscoelastic region (LVR) of each sample. The second test comprised a strain hold at 5% (or 1% if the LVR was smaller) and 1 Hz for 160 s, with 12 readings taken. The third test comprised a shear rate hold at 1 l/s for 30 s, with 30 readings taken, followed by a hold at 10 l/s for 30 s, with 30 readings taken. The data was then analyzed to determine the average shear storage modulus (the elastic modulus (G')), shear loss modulus (the viscous modulus (G")), phase angle, and viscosity at shear rates of 1 l/s and 10 l/s. The results of the rheology measurements are listed in Table 16 and Table 17.

TABLE 16

Rheology measurements of silk fibroin solution formulations with lyophilized or freeze-thaw silk fibroin, and controls

| Sample | Description | Avg. Viscosity at 1 1/s (cP) | Avg. Viscosity at 10 1/s (cP) | Avg. G' (Pa) | Avg. G" (Pa) | Avg. Phase Angle (°) |
|---|---|---|---|---|---|---|
| 1 | 5% 90mb | 24.21 | 12.23 | 7.89E−02 | 1.79E−01 | 66.03 |
| 2 | 1% 90mb | 36.63 | 14.35 | 9.42E−02 | 1.52E−01 | 57.61 |
| 3 | 0.5% 90mb | 65.94 | 19.57 | 1.86E−01 | 2.62E−01 | 54.71 |
| 4 | 0.1% 90mb | 565.71 | 136.56 | 2.75E+00 | 1.02E+00 | 21.18 |
| 5 | 0.05% 90mb | 492.38 | 79.65 | 9.81E+00 | 2.62E+00 | 15.21 |
| 6 | 5% 120mb | 36.63 | 10.35 | 1.69E−01 | 3.04E−01 | 61.01 |
| 7 | 1% 120mb | 23.09 | 10.90 | 4.52E−02 | 9.52E−02 | 64.35 |
| 8 | 0.5% 120mb | 50.90 | 16.62 | 1.08E−01 | 1.72E−01 | 57.92 |
| 9 | 0.1% 120mb | 302.36 | 43.97 | 1.98E+00 | 1.21E+00 | 31.59 |
| 10 | 0.05% 120mb | 145.83 | 29.29 | 3.79E+00 | 1.25E+00 | 18.32 |
| 11 | 5% 480mb | 54.85 | 16.64 | 1.95E−01 | 2.44E−01 | 51.50 |
| 12 | 1% 480mb | 129.58 | 26.62 | 9.48E−01 | 9.51E−01 | 45.37 |
| 13 | 0.5% 480mb | 117.32 | 21.45 | 8.24E−01 | 7.93E−01 | 44.19 |
| 14 | 0.1% 480mb | 111.52 | 23.66 | 9.07E−01 | 6.55E−01 | 36.39 |
| 15 | 0.05% 480mb | 120.76 | 35.64 | 1.17E+00 | 5.39E−01 | 26.95 |
| 16 | 5% 480mb Lyo | 74.02 | 20.63 | 3.51E−01 | 3.66E−01 | 46.41 |
| 17 | 1% 480mb Lyo | 155.43 | 29.82 | 9.23E−01 | 8.88E−01 | 44.04 |
| 18 | 0.5% 480mb Lyo | 180.84 | 31.41 | 1.25E+00 | 1.09E+00 | 41.36 |
| 19 | 0.1% 480mb Lyo | 127.93 | 36.58 | 1.08E+00 | 1.05E+00 | 47.47 |
| 20 | 0.05% 480mb Lyo | 80.88 | 22.45 | 1.11E+00 | 1.08E+00 | 50.41 |

Table 17 provides the standard deviation of the rheology measurements in Table 16.

TABLE 17

Standard deviations of the rheology measurements of silk fibroin solution formulations and controls

| Sample | Description | Std Dev. Avg. Viscosity at 1 1/s (cP) | Std. Dev. Avg. Viscosity at 10 1/s (cP) | Std. Dev. Avg. G' (Pa) | Std. Dev. Avg. G" (Pa) | Std. Dev. Avg. Phase Angle (°) |
|---|---|---|---|---|---|---|
| 1 | 5% 90mb | 5.62 | 0.37 | 3.18E−02 | 8.32E−02 | 1.36 |
| 2 | 1% 90mb | 12.48 | 2.48 | 5.13E−03 | 4.53E−02 | 6.48 |
| 3 | 0.5% 90 mb | 4.41 | 0.28 | 1.92E−03 | 2.36E−02 | 2.74 |
| 4 | 0.1% 90mb | 102.17 | 5.17 | 1.15E+00 | 2.43E−01 | 3.80 |
| 5 | 0.05% 90mb | 390.47 | 49.59 | 4.17E+00 | 9.28E−01 | 1.13 |
| 6 | 5% 120mb | 8.51 | 0.53 | 2.84E−02 | 4.00E−02 | 0.85 |
| 7 | 1% 120mb | 6.26 | 0.38 | 1.79E−02 | 6.64E−03 | 6.59 |
| 8 | 0.5% 120mb | 4.88 | 0.47 | 2.51E−02 | 3.45E−02 | 0.94 |
| 9 | 0.1% 120mb | 210.48 | 18.49 | 2.20E−01 | 2.42E−02 | 2.17 |
| 10 | 0.05% 120mb | 113.49 | 18.36 | 1.07E+00 | 3.10E−01 | 0.47 |
| 11 | 5% 480mb | 4.75 | 0.19 | 1.61E−02 | 1.96E−02 | 0.01 |
| 12 | 1% 480mb | 21.17 | 3.70 | 1.84E−01 | 1.47E−01 | 1.21 |
| 13 | 0.5% 480mb | 15.19 | 0.71 | 1.02E−02 | 8.08E−02 | 0.52 |
| 14 | 0.1% 480mb | 15.68 | 1.88 | 2.03E−01 | 7.53E−02 | 9.20 |
| 15 | 0.05% 480mb | 93.34 | 29.99 | 6.85E−01 | 1.76E−01 | 7.04 |
| 16 | 5% 480mb Lyo | 0.44 | 0.12 | 1.97E−02 | 1.98E−03 | 1.73 |
| 17 | 1% 480mb Lyo | 3.23 | 3.43 | 4.82E−02 | 3.72E−03 | 1.64 |
| 18 | 0.5% 480mb Lyo | 13.39 | 0.77 | 2.37E−01 | 1.61E−01 | 1.23 |
| 19 | 0.1% 480mb Lyo | 73.44 | 29.03 | 8.81E−01 | 5.87E−01 | 9.63 |
| 20 | 0.05% 480mb Lyo | 49.81 | 8.37 | 1.19E+00 | 8.62E−01 | 13.37 |

The solutions prepared from silk fibroin with the longest boiling time (480 mb) were more viscous than solutions prepared with shorter boil times. At higher concentrations (5%, 1%, and 0.5% (w/v)), the 480 mb silk fibroin solutions demonstrated higher viscosities than the shorter boil time formulations. However, when the concentration of silk fibroin was below 0.5% (w/v), the formulations prepared from shorter boil times demonstrated higher viscosities. A relationship between the concentration of silk fibroin and the viscosity of the solutions was also observed. The general trend showed that the viscosity of the solutions with 5% (w/v) silk fibroin was lower than solutions with 1% (w/v) silk fibroin. At concentrations of 0.1% and 0.05% (w/v) silk fibroin, the viscosities of the 90 mb and 120 mb samples increased, whereas that of the 480 mb samples remained constant. These trends hold for oscillatory properties as well, with the G' and G" values following the viscosity trends. The phase angle displayed lower values with increased viscosity, indicating a more viscous material. The 480 mb samples prepared with lyophilized silk fibroin showed slightly lower viscosities at 5%, 1%, and 0.5% (w/v) silk fibroin than the solutions prepared with frozen silk fibroin stock. The lyophilized solution formulations matched the frozen silk fibroin samples at 0.1% and 0.05% (w/v). All of the formulations shear thinned, demonstrating lower viscosities at higher shear rates.

Example 10. Rheological Measurements Regarding the Interfacial Viscosity of Silk Fibroin Solutions The effect of adding a surfactant on the viscosity properties of silk fibroin solution formulations was assessed. Similar to a surfactant, hydrophobic proteins have been shown to migrate to the air-water boundary, resulting in an increase in the local concentration at this interface. This increase in the local concentration of a protein, such as silk fibroin, can lead to an increase in apparent viscosity. This effect is termed "interfacial viscosity." Incorporation of a surfactant, a molecule that can better and more efficiently associate to the air-water interface, will block the hydrophobic protein association and will negate any increase in viscosity due to the protein buildup at the boundary. We assessed the viscosity properties of silk fibroin formulations with and without the presence of a surfactant using a rotational rheometer.

Rheological measurements were performed on a Bohlin C-VOR 150 with a 4°/40 mm cone and plate geometry with a 0.15 mm gap. 1.2 mL of each sample were pipetted onto a Peltier plate system that maintained a steady temperature of 25° C. throughout the test. The test comprised logarithmic shear rate sweep from 0.01 l/s to 1000 l/s over the course of 606 s with 100 viscosity readings. The test was performed on silk fibroin formulations after their preparation. The formulations tested were prepared using methods described in the previous examples. A standard oil (100 cP) was also evaluated to ensure accuracy of the measurements across this large shear range. The viscosity measurements are listed in Table 18 and Table 19.

TABLE 18

Shear Viscosity of Silk Fibroin Formulations

| Shear Rate (1/s) | 100 cP Oil Std. Viscosity (cP) | 0%SF; sln; borate buffer Average Viscosity (cP) | 480mb; 0%SF; sln; borate buffer; 0.2%T80 Average Viscosity (cP) | 480mb; 1%SFf; sln; 0.34%Suc; borate buffer Average Viscosity (cP) | 480mb; 1%SFf; sln; 0.34%Suc; borate buffer; 0.2%T80 Average Viscosity (cP) |
|---|---|---|---|---|---|
| 0.10 | 137.67 | 26.15 | 12.85 | 470.03 | 27.73 |
| 0.11 | 136.36 | 50.98 | 15.89 | 432.36 | 43.58 |
| 0.13 | 125.49 | 29.37 | 6.47 | 404.69 | 44.84 |
| 0.15 | 70.37 | 26.54 | 7.76 | 356.65 | 36.53 |
| 0.16 | 106.89 | 27.47 | 31.77 | 337.79 | 28.39 |
| 0.18 | 106.75 | 18.73 | 9.84 | 316.25 | 23.51 |
| 0.21 | 112.05 | 22.77 | 24.58 | 285.04 | 28.04 |
| 0.23 | 92.07 | 22.73 | 28.37 | 263.86 | 26.75 |
| 0.26 | 105.37 | 21.92 | 18.64 | 239.22 | 25.60 |
| 0.29 | 100.39 | 24.97 | 12.64 | 230.36 | 30.24 |
| 0.33 | 84.72 | 9.69 | 22.31 | 186.51 | 24.47 |
| 0.37 | 83.06 | 20.69 | 23.15 | 180.08 | 14.57 |
| 0.41 | 89.68 | 17.10 | 17.00 | 158.27 | 15.79 |
| 0.46 | 100.45 | 15.32 | 20.27 | 151.15 | 13.29 |
| 0.52 | 87.69 | 38.20 | 24.42 | 128.86 | 16.82 |

TABLE 18-continued

Shear Viscosity of Silk Fibroin Formulations

| Shear Rate (1/s) | 100 cP Oil Std. Viscosity (cP) | 0%SF; sln; borate buffer Average Viscosity (cP) | 480mb; 0%SF; sln; borate buffer; 0.2%T80 Average Viscosity (cP) | 480mb; 1%SFf; sln; 0.34%Suc; borate buffer Average Viscosity (cP) | 480mb; 1%SFf; sln; 0.34%Suc; borate buffer; 0.2%T80 Average Viscosity (cP) |
|---|---|---|---|---|---|
| 0.59 | 98.09 | 11.24 | 14.67 | 127.66 | 11.09 |
| 0.66 | 96.52 | 8.89 | 18.03 | 114.52 | 5.56 |
| 0.74 | 97.34 | 11.06 | 12.89 | 106.66 | 11.27 |
| 0.83 | 98.63 | 4.54 | 6.75 | 92.54 | 5.40 |
| 0.93 | 95.38 | 6.67 | 7.43 | 83.53 | 8.81 |
| 1.05 | 101.01 | 6.33 | 4.18 | 78.63 | 7.58 |
| 1.18 | 92.76 | 7.82 | 4.52 | 67.05 | 7.37 |
| 1.32 | 94.63 | 6.73 | 5.97 | 62.58 | 6.30 |
| 3.48 | 99.90 | 6.72 | 5.21 | 59.37 | 8.20 |
| 1.67 | 100.40 | 4.79 | 3.91 | 51.99 | 4.71 |
| 1.87 | 102.84 | 3.86 | 5.53 | 47.74 | 3.83 |
| 2.10 | 93.83 | 4.23 | 6.45 | 39.50 | 3.43 |
| 2.36 | 96.82 | 4.01 | 5.81 | 41.94 | 4.20 |
| 2.66 | 99.03 | 6.72 | 3.93 | 35.41 | 4.89 |
| 2.98 | 94.40 | 5.33 | 3.68 | 35.36 | 3.86 |
| 3.35 | 96.11 | 0.50 | 4.35 | 34.85 | 4.08 |
| 3.76 | 96.71 | 3.55 | 5.41 | 29.08 | 4.23 |
| 4.23 | 97.02 | 2.21 | 4.33 | 27.18 | 4.87 |
| 4.75 | 99.08 | 0.95 | 2.55 | 22.68 | 1.61 |
| 5.33 | 104.28 | 2.95 | 2.14 | 23.08 | 3.29 |
| 5.99 | 107.99 | 25.60 | 26.36 | 41.52 | 25.51 |
| 6.73 | 111.10 | 5.88 | 9.62 | 21.58 | 7.56 |
| 7.56 | 97.59 | 3.23 | 3.80 | 16.63 | 3.21 |
| 8.49 | 99.17 | 2.17 | 1.81 | 18.22 | 5.88 |
| 9.54 | 99.03 | 5.64 | 5.74 | 13.38 | 1.57 |
| 10.72 | 102.48 | 2.78 | 3.99 | 15.76 | 3.10 |
| 12.04 | 63.92 | 142.42 | 7.63 | 3.31 | 22.65 |
| 13.53 | 98.09 | 4.35 | 2.71 | 241.74 | 2.13 |
| 15.19 | 98.74 | 1.85 | 4.38 | 11.42 | 3.33 |
| 17.07 | 99.86 | 2.81 | 4.11 | 10.51 | 3.26 |
| 19.07 | 98.95 | 3.38 | 4.35 | 9.39 | 6.58 |
| 21.54 | 97.41 | 3.18 | 2.96 | 9.97 | 3.74 |
| 24.19 | 104.21 | 6.94 | 6.47 | 11.80 | 1.11 |
| 27.18 | 98.30 | 4.27 | 2.99 | 8.54 | 3.52 |
| 30.53 | 98.69 | 3.65 | 3.59 | 8.52 | 4.35 |
| 34.29 | 98.21 | 3.38 | 4.13 | 8.39 | 3.23 |
| 38.52 | 98.29 | 3.50 | 3.80 | 7.28 | 3.88 |
| 43.27 | 98.38 | 3.22 | 3.45 | 7.08 | 3.25 |
| 48.61 | 97.86 | 3.85 | 3.16 | 6.27 | 3.25 |
| 54.60 | 99.51 | 3.36 | 3.42 | 6.12 | 3.54 |
| 61.34 | 327.32 | 5.99 | 7.34 | 9.85 | 7.05 |
| 68.90 | 123.58 | 29.33 | 8.68 | 10.15 | 7.91 |
| 77.40 | 117.30 | 8.22 | 6.40 | 9.54 | 6.55 |
| 86.94 | 117.13 | 8.21 | 6.74 | 11.35 | 8.58 |
| 97.66 | 112.80 | 7.91 | 8.28 | 10.49 | 6.77 |
| 109.71 | 110.36 | 7.44 | 7.57 | 10.42 | 8.22 |
| 123.22 | 106.51 | 7.15 | 8.42 | 10.83 | 8.44 |
| 138.43 | 105.91 | 7.45 | 7.74 | 9.62 | 8.33 |
| 155.50 | 103.33 | 7.24 | 6.80 | 6.40 | 7.41 |
| 174.68 | 102.19 | 7.60 | 8.91 | 9.05 | 8.01 |
| 196.24 | 101.06 | 8.03 | 8.25 | 9.54 | 8.32 |
| 220.42 | 100.93 | 7.96 | 8.04 | 9.17 | 8.11 |
| 247.61 | 99.67 | 7.64 | 7.83 | 9.02 | 8.09 |
| 278.14 | 92.73 | 10.03 | 11.21 | 12.20 | 13.06 |
| 312.44 | 22.66 | 20.41 | 20.35 | 12.57 | 45.20 |
| 350.98 | 105.62 | 17.09 | 18.27 | 8.17 | 9.58 |
| 394.29 | 99.61 | 7.23 | 12.32 | 17.93 | 11.21 |
| 443.08 | 92.48 | 28.72 | 21.22 | 10.89 | 5.05 |
| 497.49 | 92.60 | 9.49 | 23.01 | 16.97 | 21.32 |
| 558.85 | 99.96 | 17.15 | 24.88 | 4.26 | 29.54 |
| 627.73 | 95.56 | 21.40 | 18.93 | 32.16 | 11.94 |
| 705.17 | 85.14 | 1.67 | 8.02 | 6.44 | 5.21 |
| 792.18 | 95.23 | 3.81 | 3.77 | 6.85 | 1.22 |
| 889.90 | 88.54 | 4.51 | 5.69 | 11.00 | 9.08 |
| 999.53 | 91.39 | 11.65 | 6.41 | 12.41 | 11.06 |

TABLE 19

Standard Deviation of Shear Viscosity of Silk Fibroin Formulations

| Shear Rate (1/s) | 0%SFf; sln; borate buffer Standard Deviation (cP) | 0%SF; sln; borate buffer; 0.2%T80 Standard Deviation (cP) | 480mb; 1%SFf; sln; 0.34%Suc; borate buffer Standard Deviation (eP) | 480mb; 1%SF; sln; 0.34%Suc; borate buffer; 0.2%T80 Standard Deviation (cP) |
|---|---|---|---|---|
| 0.10 | 183.21 | 259.48 | 370.04 | 121.43 |
| 0.11 | 113.76 | 28.46 | 397.78 | 379.43 |
| 0.13 | 48.59 | 117.59 | 345.17 | 153.38 |
| 0.15 | 172.35 | 239.23 | 250.15 | 130.21 |
| 0.16 | 274.44 | 79.64 | 356.87 | 269.20 |
| 0.18 | 108.99 | 79.30 | 211.10 | 131.32 |
| 0.23 | 62.00 | 102.73 | 137.40 | 150.49 |
| 0.23 | 174.88 | 59.71 | 246.07 | 212.97 |
| 0.26 | 41.72 | 88.83 | 155.11 | 82.60 |
| 0.29 | 33.42 | 66.11 | 137.49 | 264.30 |
| 0.33 | 44.47 | 14.79 | 164.96 | 30.89 |
| 0.37 | 28.32 | 39.87 | 208.57 | 39.79 |
| 0.41 | 84.89 | 61.00 | 162.86 | 87.22 |
| 0.46 | 61.60 | 33.17 | 119.86 | 12.43 |
| 0.52 | 74.92 | 20.12 | 117.38 | 23.07 |
| 0.59 | 46.31 | 6.54 | 92.01 | 95.79 |
| 0.66 | 12.20 | 18.90 | 101.13 | 49.55 |
| 0.74 | 23.71 | 15.03 | 77.60 | 11.40 |
| 0.83 | 22.47 | 40.76 | 70.79 | 40.35 |
| 0.93 | 14.94 | 23.77 | 40.81 | 24.14 |
| 1.05 | 15.01 | 7.93 | 75.35 | 20.04 |
| 1.18 | 6.46 | 7.53 | 37.63 | 40.49 |
| 1.32 | 24.69 | 3.23 | 59.65 | 36.10 |
| 1.48 | 5.95 | 5.47 | 39.75 | 22.63 |
| 1.67 | 10.29 | 17.84 | 39.72 | 14.55 |
| 1.87 | 17.73 | 9.92 | 32.55 | 14.91 |
| 2.10 | 10.80 | 18.38 | 26.43 | 7.00 |
| 2.36 | 10.97 | 5.47 | 27.16 | 19.05 |
| 2.66 | 8.06 | 7.19 | 15.91 | 8.66 |
| 2.98 | 4.69 | 11.54 | 8.37 | 6.22 |
| 3.35 | 10.58 | 12.60 | 17.45 | 0.82 |
| 3.76 | 10.44 | 5.84 | 7.57 | 8.83 |
| 4.23 | 12.37 | 8.87 | 5.75 | 7.85 |
| 4.75 | 5.90 | 9.31 | 7.37 | 4.44 |
| 5.33 | 1.61 | 11.87 | 17.69 | 5.67 |
| 5.99 | 2.31 | 7.17 | 6.03 | 4.25 |
| 6.73 | 5.34 | 8.04 | 3.08 | 1.72 |
| 7.56 | 7.60 | 1.76 | 9.48 | 2.28 |
| 8.49 | 1.49 | 5.16 | 6.15 | 6.15 |
| 9.54 | 4.67 | 2.76 | 5.88 | 1.95 |
| 10.72 | 5.77 | 3.23 | 1.84 | 2.55 |
| 12.04 | 4.66 | 2.09 | 2.04 | 2.11 |
| 13.53 | 1.37 | 1.29 | 2.55 | 1.63 |
| 15.19 | 2.98 | 3.42 | 5.36 | 2.47 |
| 17.07 | 1.72 | 2.94 | 4.59 | 2.52 |
| 19.17 | 2.58 | 1.77 | 5.37 | 4.18 |
| 21.54 | 1.80 | 1.58 | 6.85 | 3.32 |
| 24.19 | 0.80 | 1.48 | 4.69 | 1.72 |
| 27.18 | 2.55 | 1.89 | 5.21 | 1.48 |
| 30.53 | 1.90 | 0.58 | 4.83 | 2.71 |
| 34.29 | 0.43 | 2.07 | 2.32 | 1.85 |
| 38.52 | 0.70 | 0.67 | 0.98 | 0.82 |
| 43.27 | 1.10 | 2.68 | 5.94 | 1.81 |
| 48.61 | 1.07 | 0.63 | 2.43 | 1.25 |
| 54.60 | 2.98 | 2.07 | 1.49 | 3.06 |
| 61.34 | 4.46 | 8.70 | 6.58 | 5.84 |
| 68.90 | 5.94 | 3.88 | 3.98 | 2.44 |
| 77.40 | 2.75 | 2.41 | 4.45 | 0.96 |
| 86.94 | 1.25 | 0.49 | 2.28 | 0.79 |
| 97.66 | 2 37 | 4.26 | 2.66 | 0.57 |
| 109.71 | 3.43 | 3.01 | 3.25 | 1.72 |
| 123.22 | 232.03 | 2.38 | 3.76 | 17.99 |
| 138.43 | 3.46 | 1.59 | 391.52 | 1.72 |
| 155.50 | 2.03 | 0.43 | 0.47 | 0.45 |
| 174.68 | 0.15 | 0.55 | 0.38 | 0.98 |
| 196.24 | 1.13 | 1.23 | 0.63 | 5.03 |
| 220.42 | 1.17 | 0.38 | 1.10 | 0.31 |
| 247.61 | 3.81 | 3.80 | 4.33 | 1.79 |
| 278.14 | 1.05 | 0.43 | 1.08 | 0.59 |
| 312.44 | 0.32 | 0.08 | 0.55 | 0.75 |
| 350.98 | 0.39 | 0.35 | 0.68 | 0.60 |
| 394.29 | 0.14 | 0.83 | 1.29 | 0.21 |
| 443.08 | 0.23 | 0.41 | 0.92 | 0.71 |
| 497.49 | 1.07 | 0.18 | 1.42 | 0.87 |
| 558.85 | 0.31 | 0.26 | 0.74 | 0.28 |
| 627.73 | 2.30 | 0.40 | 0.93 | 1.17 |
| 705.17 | 40.59 | 0.89 | 1.09 | 1.04 |
| 792.18 | 1.24 | 1.04 | 0.91 | 1.30 |
| 889.90 | 1.61 | 0.20 | 1.74 | 0.69 |
| 999.53 | 1.22 | 1.43 | 0.53 | 0.49 |

The results displayed that silk fibroin formulations without surfactant display shear thinning, reaching viscosities of 470 cP at 0.1 l/s which is reduced to 79 cP at 1 l/s and 13 cP at 10 l/s. When shear rate was increased above 50 cP, the silk fibroin formulation with no surfactant showed viscosity similar to buffer controls (no silk fibroin). When surfactant was added to the silk fibroin formulation, it displayed the same shear viscosity profile as the buffer controls across the entire range of shear rates. Viscosity reached a maximum of 45 cP at a shear rate of 0.13 l/s, which fell below 10 cP at shear rates of 0.6l/s and above. The controls (+/−polysorbate 80) showed the same trends in viscosity over the shear range tested. This increase in viscosity of silk fibroin formulations that was reduced with the addition of a surfactant (polysorbate 80) indicated that silk fibroin in solution possesses interfacial properties that lead to an increase in apparent viscosity.

Example 11. Rheological Measurements of Silk Fibroin Solutions Using Capillary Rheology Capillary rheology was utilized to further understand the interfacial viscosity rheology effects of silk fibroin in solution. Unlike the rotational rheometer, a capillary rheometer has a very low air-water interface. This will greatly reduce if not eliminate interfacial viscosity effects that are observed using other rheologic methods (cone and plate rotational rheology). Samples were evaluated using two tests. First, samples were evaluated using a VROC® microVISC™ capillary viscometer (Rheosense) at 25° C. at 500 l/s shear rate. Samples were then measured on the VROC® Initium automated viscometer (Rheosense) using the B05 chip. Aliquots of 40 μL for each sample were loaded into inserts and then, using a benchtop centrifuge, they were centrifuged at 8000 rpm for 20 seconds to remove any bubbles. The inserts with the sample volume were then placed in capped vials and loaded onto the Initium sample tray. The software w as then programmed to run a shear rate sweep with 5 segments for each sample. The shear rates selected for each sample were determined by logic in the Initium software (3808, 4760, 6427, 16150, and 19040 l/s) All measurements were taken at 25° C. Each viscosity value reported is the average of 10 repeat measurements. The formulations were prepared as described in the previous examples, such as Example 6.

Results showed that silk fibroin solution formulations and buffer controls, in the presence or absence of a surfactant, displayed Newtonian viscosity at shear rates from 500 l/s to 19040 l/s. Borate buffer displayed viscosity that ranged from 0.910 cP to 1.00 cP over this range. The addition of polysorbate 80 to this buffer slightly increased the viscosity (0.931-1.07 cP). The silk fibroin formulations displayed higher viscosity than the buffer controls with the same trends. Silk fibroin without surfactant had a slightly lower viscosity over this shear range than the formulation containing polysorbate 80. Silk fibroin formulations displayed viscosities of 1.05 cP-1.19 cP while the addition of surfactant very slightly increased the viscosity to 1.06 cP-1.31 cP over the same shear range (Table 20 and Table 21).

TABLE 20

Capillary Viscosity of Silk Fibroin Formulations

| Temperature (° C.) | Shear Rate (1/s) | 0%SFf; sln; borate buffer Average Viscosity (cP) | 0%SFf; sln; borate buffer; 0.2%T80 Average Viscosity (cP) | 480mb; 1%SFf; sln; 0.34%Suc; borate buffer Average Viscosity (cP) | 480mb; 1%SFf; sln; 0.34%Suc; borate buffer; 0.2%T80 Average Viscosity (cP) |
|---|---|---|---|---|---|
| 25 | 500   | 1.00 | 1.07 | 1.18 | 1.31 |
| 25 | 3808  | 0.92 | 0.93 | 1.05 | 1.07 |
| 25 | 4759  | 0.92 | 0.94 | 1.06 | 1.07 |
| 25 | 6466  | 0.91 | 0.94 | 1.05 | 1.06 |
| 25 | 10310 | 0.91 | 0.94 | 1.05 | 1.07 |
| 25 | 19040 | 0.92 | 0.93 | 1.05 | 1.06 |

TABLE 21

Standard Deviation of Capillary Viscosity of Silk Fibroin Formulations

| Temperature (° C.) | Shear Rate (1/s) | 0%SFf; sln; borate buffer Standard Deviation | 0%SFf; sln; borate buffer; 0.2%T80 Standard Deviation | 480mb; 1%SFf; sln; 0.34%Suc; borate buffer Standard Deviation | 480mb; 1%SFf; sln; 0.34%Suc; borate buffer; 0.2%T80 Standard Deviation |
|---|---|---|---|---|---|
| 25 | 500   | 0.006 | 0.003 | 0.004 | 0.006 |
| 25 | 3808  | 0.005 | 0.004 | 0.004 | 0.003 |
| 25 | 4759  | 0.006 | 0.003 | 0.002 | 0.004 |
| 25 | 6466  | 0.007 | 0.006 | 0.004 | 0.007 |
| 25 | 10310 | 0.000 | 0.000 | 0.000 | 0.000 |
| 25 | 19040 | 0.001 | 0.001 | 0.004 | 0.003 |

The capillary rheology data is similar to the rotational data at these shear rates greater than or equal to 500 l/s for all of the formulations.

Example 12. Rheological Measurements of Stressed Silk Solutions

Formulations were prepared by dissolving lyophilized silk fibroin, which had been lyophilized in phosphate buffer, into phosphate buffered saline. Rheological measurements were performed on a Bohlin C-VOR 150 with a 4°/40 mm cone and plate geometry with a 0.5 mm gap. 1.4 mL of each sample were pipetted onto a Peltier plate system that maintained a steady temperature of 25° C. throughout the test. Five tests were then run. The first test comprised a strain sweep from 0.1% to 10% strain at 1 Hz over the course of 160 s, with 50 readings taken. This was to determine the linear viscoelastic region (LVR) of each sample. The second test comprised a strain hold at 5% (or 1% if the LVR was smaller) and 1 Hz for 145 s, with 15 readings taken. The third test comprised a shear rate sweep from 0.1 l/s to 10 l/s over the course of 100 s, followed by a hold at 10 l/s for 20 s. 70 readings were taken. Fourth, a shear rate hold was conducted at 1 l/s for 135 s, with 15 readings taken. Lastly, a shear ramp was conducted from 0.01 l/s to 1 l/s over 140 s with 20 readings. The data was then analyzed to determine the average shear storage modulus (G'), shear loss modulus (G"), phase angle, and viscosity at shear rates of 0.1 l/s, 1 l/s, and 10 l/s. The experiments were performed on silk fibroin formulations after their preparation. The formulations were then stressed by incubation at 60° C. overnight, and the samples that did not gel were tested again. The formulations were then stressed by autoclave and the samples that did not gel were tested for a third time. The formulations were stressed to simulate a long shelf-life and terminal sterilization, and to see if the protein maintained rheological integrity. The formulations tested were described in Table 22, and the rheological measurements were listed in Table 23 and Table 24. The samples in the tables are named by the process used to prepare and formulate each solution. For example, in the sample named "480 mb; sln; 1% SFf; 60° C.; Auto" the "80 mb" refers to the silk degummed with a 480-minute boil, "sln" refers to the formulation of the sample as a solution, "1% SFf" refers to a formulation with 1% (w/v) silk fibroin, "60° C." refers to a preparation stressed by incubation at 60° C. overnight, and "Auto" refers to a preparation stressed by incubation at 60° C. overnight followed by autoclave. Table 22 provides characteristics of the formulations containing stressed silk fibroin.

TABLE 22

Silk solution formulations with stressed silk fibroin

| Sample | Description | Stress Condition | 480mb Silk % (w/v) | Sample Name |
|---|---|---|---|---|
| — | REFRESH LIQUIGEL ® lubricant eye gel (Allergan) | None | 0 | REFRESH LIQUIGEL ® lubricant eye gel (Allergan) |
| — | SYSTANE ® lubricant eye drop (Alcon) | None | 0 | SYSTANE ® lubricant eye drop (Alcon) |
| — | SYSTANE ® lubricant eye gel (Alcon) | None | 0 | SYSTANE ® lubricant eye gel (Alcon) |
| 1 | 10% Unstressed | None | 10 | 480mb; sln; 10%SFf |
| 2 | 5% Unstressed | None | 5 | 480mb; sln; 5%SFf |
| 3 | 1% Unstressed | None | 1 | 480mb; sln; 1%SFf |

TABLE 22-continued

Silk solution formulations with stressed silk fibroin

| Sample | Description | Stress Condition | 480mb Silk % (w/v) | Sample Name |
|---|---|---|---|---|
| 4 | 0.5% Unstressed | None | 0.5 | 480mb; sln; 0.5%SFf |
| 5 | 0.1% Unstressed | None | 0.1 | 480mb; sln; 0.1%SFf |
| 6 | 0.05% Unstressed | None | 0.05 | 480mb; sln; 0.05%SFf |
| 7 | 0.01% Unstressed | None | 0.01 | 480mb; sln; 0.01%SFf |
| 8 | 0.005% Unstressed | None | 0.005 | 480mb; sln; 0.005%SFf |
| 9 | 1x PBS | None | 0 | PBS Control |
| — | REFRESH LIQUIGEL ® lubricant eye gel (Allergan) 60° C. | 60° C. Overnight | 0 | REFRESH LIQUIGEL ® lubricant eye gel (Allergan); 60° C. |
| — | SYSTANE ® lubricant eye drop (Alcon)60° C. | 60° C. Overnight | 0 | SYSTANE ® lubricant eye drop (Alcon); 60° C. |
| — | SYSTANE ® lubricant eye gel (Alcon)60° C. | 60° C. Overnight | 0 | SYSTANE ® lubricant eye gel (Alcon) 60° C. |
| 10 | 10% 60° C. | 60° C. Overnight | 10 | 480mb; sln; 10%SFf; 60° C. |
| 11 | 5% 60° C. | 60° C. Overnight | 5 | 480mb; sln; 5%SFf; 60° C. |
| 12 | 1% 60° C. | 60° C. Overnight | 1 | 480mb; sln; 1%SFf; 60° C. |
| 13 | 0.5% 60° C. | 60° C. Overnight | 0.5 | 480mb; sln; 0.5%SFf; 60° C. |
| 14 | 0.1%60° C. | 60° C. Overnight | 0.1 | 480mb; sln; 0.1%SFf; 60° C. |
| 15 | 0.05% 60° C. | 60° C. Overnight | 0.05 | 480mb; sln; 0.05%SFf; 60° C. |
| 16 | 0.01% 60° C. | 60° C. Overnight | 0.01 | 480mb; sln; 0.01%SFf; 60° C. |
| 17 | 0.005% 60° C. | 60° C. Overnight | 0.005 | 480mb; sln; 0.005%SFf; 60° C. |
| 18 | 1x PBS 60° C. | 60° C. Overnight | 0 | PBS control; 60° C. |
| 19 | 1% Autoclave | 60° C. and Autoclave | 1 | 480mb; sln; 1%SFE 60° C.; Auto |
| 20 | 0.5% Autoclave | 60° C. and Autoclave | 0.5 | 480mb; sln; 0.5%SFf; 60° C.; Auto |
| 21 | 0.1% Autoctave | 60° C. and Autoclave | 0.1 | 480mb, sln; 0.1%SFf; 60° C.; Auto |
| 22 | 0.05% Autoclave | 60° C. and Autoclave | 0.05 | 480mb; sln; 0.05%SFf; 60° C.; Auto |
| 23 | 0.01% Autoclave | 60° C. and Autoclave | 0.01 | 480mb; sln; 0.01%SFf; 60° C.; Auto |
| 24 | 0.005% Autoclave | 60° C. and Autoclave | 0.005 | 480mb; sln; 0.005%SFf; 60° C.; Auto |
| 25 | 1x PBS Autoclave | 60° C. and Autoclave | 0 | PBS control; 60° C.; Auto |

Table 23 provides rheological data for the formulations described in Table 22.

TABLE 23

Rheological measurements of silk solutions with stressed silk fibroin

| Sample | Description | Avg. Viscosity at 0.01 1/s (cP) | Avg. Viscosity at 1 1/s (cP) | Avg. Viscosity at 10 1/s (cP) | Avg. G' (Pa) | Avg. G" (Pa) | Avg. Phase Angle (°) |
|---|---|---|---|---|---|---|---|
| — | REFRESH LIQUIGEL ® lubricant eye gel (Allergan) | — | 79.90 | 46.29 | 0.17 | 0.35 | 64.05 |
| — | SYSTANE ® lubricant eye drop (Alcon) | — | 20.23 | 12.06 | 0.02 | 0.08 | 75.44 |
| — | SYSTANE ® lubricant eye gel (Alcon) | — | 1073.57 | 549.81 | 2.20 | 3.03 | 53.98 |
| 1 | 10% Unstressed | 483.28 | 61.29 | 13.90 | 0.18 | 0.19 | 46.54 |
| 2 | 5% Unstressed | 1241.98 | 77.42 | 15.54 | 0.33 | 0.25 | 37.93 |
| 3 | 1% Unstressed | 1211.40 | 152.93 | 24.45 | 0.82 | 0.59 | 36.14 |
| 4 | 0.5% Unstressed | 3168.00 | 164.13 | 23.96 | 0.87 | 0.58 | 34.04 |
| 5 | 0.1% Unstressed | 62996.50 | 848.57 | 71.80 | 6.80 | 2.17 | 17.65 |
| 6 | 0.05% Unstressed | 78834.00 | 1012.95 | 73.62 | 9.55 | 2.21 | 13.07 |
| 7 | 0.01% Unstressed | 42258.50 | 279.10 | 25.40 | 9.80 | 2.00 | 11.63 |
| 8 | 0.005% Unstressed | 13412.20 | 141.06 | 21.93 | 8.61 | 1.58 | 10.48 |
| 9 | 1x PBS | 448.98 | 10.33 | 2.90 | 0.01 | 0.04 | 68.70 |
| — | REFRESH LIQUIGEL ® lubricant eye gel (Allergan) 60° C. | 752.92 | 40.80 | 32.99 | 0.03 | 0.21 | 80.72 |

TABLE 23-continued

Rheological measurements of silk solutions with stressed silk fibroin

| Sample | Description | Avg. Viscosity at 0.01 1/s (cP) | Avg. Viscosity at 1 1/s (cP) | Avg. Viscosity at 10 1/s (cP) | Avg. G' (Pa) | Avg. G" (Pa) | Avg. Phase Angle (°) |
|---|---|---|---|---|---|---|---|
| — | SYSTANE ® lubricant eye drop (Alcon)60° C. | 1581.90 | 16.88 | 10.60 | 0.03 | 0.07 | 70.70 |
| — | SYSTANE ® lubricant eye gel (Alcon)60° C. | 3035.00 | 926.24 | 501.00 | 1.89 | 2.80 | 56.00 |
| 10 | 10% 60° C. | 1586.30 | 62.18 | 13.58 | 0.22 | 0.22 | 45.50 |
| 11 | 5% 60° C. | 1783.60 | 62.33 | 12.19 | 0.25 | 0.21 | 41.18 |
| 12 | 1% 60° C. | 2922.10 | 139.74 | 22.57 | 0.74 | 0.54 | 36.53 |
| 13 | 0.5% 60° C. | 3902.25 | 143.14 | 22.19 | 0.73 | 0.53 | 35.88 |
| 14 | 0.1% 60° C. | 16141.50 | 250.78 | 33.08 | 3.32 | 1.17 | 19.61 |
| 15 | 0.05% 60° C. | 30653.00 | 206.13 | 23.65 | 6.22 | 1.47 | 13.47 |
| 16 | 0.01% 60° C. | 27437.00 | 120.19 | 13.38 | 6.49 | 1.33 | 11.62 |
| 17 | 0.005% 60° C. | 27917.00 | 149.65 | 19.14 | 8.77 | 1.49 | 9.70 |
| 18 | 1x PBS 60° C. | 109.72 | 9.85 | 2.82 | 0.03 | 0.03 | 42.80 |
| 19 | 1% Autoclave | 4274.55 | 141.91 | 21.93 | 0.91 | 0.57 | 32.09 |
| 20 | 0.5% Autoclave | 5146.85 | 150.73 | 23.07 | 1.12 | 0.62 | 29.17 |
| 21 | 0.1% Autoclave | 6566.45 | 110.14 | 14.90 | 1.59 | 0.56 | 20.14 |
| 22 | 0.05% Autoclave | 9674.40 | 182.30 | 24.15 | 4.83 | 1.33 | 15.09 |
| 23 | 0.01% Autoclave | 19294.50 | 113.32 | 11.52 | 4.48 | 0.75 | 9.50 |
| 24 | 0.005% Autoclave | 707.12 | 7.10 | 3.51 | 0.05 | 0.03 | 37.33 |
| 25 | 1x PBS Autoclave | 2833.30 | 83.75 | 14.97 | 0.44 | 0.33 | 36.70 |

Table 24 provides the standard deviations for the rheological measurements described in Table 23.

TABLE 24

Standard deviations of the rheological measurements of silk solutions with stressed silk fibroin

| Sample | Description | Std. Dev. Avg. Viscosity at 0.01 1/s (cP) | Std. Dev. Avg. Viscosity at 1 1/s (cP) | Std. Dev. Avg. Viscosity at 10 1/s (cP) | Std. Dev. Avg. G' (Pa) | Std. Dev. Avg. G" (Pa) | Std. Dev. Avg. Phase Angle (°) |
|---|---|---|---|---|---|---|---|
| — | REFRESH LIQUIGEL ® lubricant eye gel (Allergan) | — | 6.07 | 6.84 | 0.01 | 0.01 | 1.81 |
| — | SYSTANE ® lubricant eye drop (Alcon) | — | 7.60 | 6.33 | 0.01 | 0.01 | 5.24 |
| — | SYSTANE ® lubricant eye gel (Alcon) | — | 7.08 | 5.45 | 0.01 | 0.02 | 0.11 |
| 1 | 10% Unstressed | 0.00 | 5.11 | 0.64 | 0.02 | 0.02 | 5.94 |
| 2 | 5% Unstressed | 1494.72 | 8.11 | 2.23 | 0.09 | 0.04 | 3.45 |
| 3 | 1% Unstressed | 122.90 | 4.47 | 1.07 | 0.11 | 0.00 | 3.52 |
| 4 | 0.5% Unstressed | 561.44 | 9.15 | 0.43 | 0.07 | 0.05 | 0.08 |
| 5 | 0.1% Unstressed | 19771.41 | 7.32 | 14.43 | 0.22 | 0.29 | 1.71 |
| 6 | 0.05% Unstressed | 5313.20 | 174.63 | 19.72 | 0.67 | 0.20 | 0.26 |
| 7 | 0.01% Unstressed | 16087.39 | 130.05 | 17.16 | 0.35 | 0.0.3 | 0.30 |
| 8 | 0.005% Unstressed | 14438.84 | 20.29 | 7.83 | 1.15 | 0.18 | 0.24 |
| 9 | 1x PBS | 0.00 | 3.78 | 1.99 | 0.01 | 0.01 | 12.65 |
| — | REFRESH LIQUIGEL ® lubricant eye gel (Allergan) 60° C. | 0.00 | 5.41 | 1.50 | 0.01 | 0.01 | 2.03 |
| — | SYSTANE ® lubricant eye drop (Alcon)60° C. | 0.00 | 4.63 | 1.96 | 0.01 | 0.01 | 6.10 |
| — | SYSTANE ® lubricant eye gel (Alcon)60° C. | 0.00 | 6.00 | 1.30 | 0.01 | 0.01 | 0.14 |
| 10 | 10% 60° C. | 155.14 | 2.05 | 0.34 | 0.04 | 0.02 | 2.51 |
| 11 | 5% 60° C. | 192.33 | 17.86 | 3.46 | 0.09 | 0.07 | 0,77 |
| 12 | 1% 60° C. | 491.86 | 7.55 | 0.02 | 0.04 | 0.01 | 2.09 |
| 13 | 0.5% 60° C. | 535.77 | 1.70 | 0.52 | 0.03 | 0.03 | 0.41 |
| 14 | 0.1% 60° C. | 2926.71 | 16.47 | 2.71 | 0.50 | 0.16 | 0.31 |
| 15 | 0.05% 60° C. | 15813.74 | 47.39 | 8.45 | 1.12 | 0.11 | 1.34 |

TABLE 24-continued

Standard deviations of the rheological measurements of silk solutions with stressed silk fibroin

| Sample | Description | Std. Dev. Avg. Viscosity at 0.01 1/s (cP) | Std. Dev. Avg. Viscosity at 1 1/s (cP) | Std. Dev. Avg. Viscosity at 10 1/s (cP) | Std. Dev. Avg. G' (Pa) | Std. Dev. Avg. G" (Pa) | Std. Dev. Avg. Phase Angle (°) |
|---|---|---|---|---|---|---|---|
| 16 | 0.01% 60° C. | 20776.21 | 18.64 | 2.47 | 2.82 | 0.59 | 0.03 |
| 17 | 0.005% 60° C. | 7448.66 | 63.16 | 6.20 | 0.75 | 0.06 | 0.42 |
| 18 | 1x PBS 60° C. | 0.00 | 5.20 | 1.19 | 0.01 | 0.01 | 10.68 |
| 19 | 1% Autoclave | 729.80 | 29.98 | 3.22 | 0.24 | 0.19 | 1.97 |
| 20 | 0.5% Autoclave | 525.73 | 6.93 | 1.23 | 0.02 | 0.10 | 3.36 |
| 21 | 0.1% Autoclave | 4329.26 | 115.43 | 14.66 | 0.98 | 0.28 | 2.37 |
| 22 | 0.05% Autoclave | 2750.08 | 75.77 | 9.32 | 2.15 | 0.74 | 1.79 |
| 23 | 0.01% Autoclave | 4848.63 | 23.18 | 0.65 | 0.92 | 0.17 | 0.17 |
| 24 | 0.005% Autoclave | 509.23 | 0.08 | 0.15 | 0.00 | 0.01 | 10.04 |
| 25 | 1x PBS Autoclave | 0.00 | 3.28 | 1.03 | 0.06 | 0.03 | 1.44 |

All of the formulations measured in Table 23 shear thinned, demonstrating lower viscosities at higher shear rates. The observed shear thinning was more pronounced in the silk fibroin formulations than in the corresponding experimental controls, which included commercially available treatments for dry eye (REFRESH LIQUIGEL® lubricant eye gel (Allergan), SYSTANE® lubricant eye drop (Alcon), SYSTANE® lubricant eye gel (Alcon)). At lower shear rates (1 l/s), the silk fibroin formulations exhibited viscosities similar to that of a gel drop. At higher shear rates (10 l/s), the silk fibroin formulations exhibited viscosities similar to that of a liquid drop. The viscosities of the formulations were measured to be higher at lower concentrations of silk fibroin; however, the viscosity peaked when the formulations were between 0.1-0.5% silk fibroin. When the silk fibroin concentration was 0.1% (w/v) or below, the viscosity decreased with the use of stressed silk.

As seen in Table 23, the average shear storage modulus (G') was measured to be higher for formulations with a lower concentration of silk fibroin. When the silk fibroin concentration was 0.1% (w/v) or below, the shear storage modulus was lower for formulations prepared from stressed silk fibroin than from unstressed. The average phase angle was also measured to be lower for formulations with a lower concentration of silk fibroin. For the unstressed formulations and heat stressed formulations (60° C. Overnight), the average shear loss modulus (G") was measured to be higher for formulations with a lower concentration of silk fibroin. When the silk fibroin concentration was below 0.1% (w/v), the average shear loss modulus was lower for formulations prepared from stressed silk fibroin than for formulations prepared from unstressed silk fibroin.

Example 13. Preparation of Fluorescein Isothiocyanate (FITC)-Labeled Silk Fibroin (FITC-SF) Solution Silk fibroin (SF) was labeled with fluorescein isothiocyanate (FITC) for the residence time studies described in the Examples herein. 420 mg of sodium bicarbonate was dissolved in 9 mL of deionized (DI) water. The pH was adjusted to 9.0 using 1 N sodium hydroxide and 1 N hydrochloric acid. A quantity of DI water sufficient to raise the volume to 10 mL was added to prepare a 0.5 M sodium bicarbonate solution.

1.5 M hydroxylamine was prepared by dissolving 262 mg hydroxylamine in 2.0 mL of water. The pH was adjusted to 8.5 using 10 N sodium hydroxide, and a quantity of DI water sufficient to raise the volume to 2.5 mL was added.

Immediately before performing the labeling reaction, FITC (three 10 mg vials, ThermoFisher) was dissolved in 0.5 mL of dimethyl sulfoxide (DMSO; Sigma) resulting in a 20 mg/mL solution of FITC in DMSO.

All buffers and solutions were filtered through 0.2 μm filters under aseptic conditions with the exception of the silk fibroin solution and the FITC in DMSO solution.

A 5% (w/v) silk fibroin solution (480 mb; Batch 88) containing 50 mM sucrose was thawed. 1 mL 0.5 M sodium bicarbonate buffer was added to a vial containing 4 mL of the thawed 5% (w/v) silk fibroin solution. If needed, the pH was adjusted to between 8.5-9.0 using 1N sodium hydroxide. A sample of the silk fibroin solution was retained as a control.

The labeling reaction was performed by adding 1.44 mL FITC in DMSO to 4.5 mL of the silk fibroin solution. The vial was kept protected from light at room temperature (RT) for 2 hours on a rocker resulting in FITC-labeled silk fibroin (FITC-SF).

The control sample of silk fibroin solution was prepared by adding 1.4 mL of DMSO to 4.5 mL of the thawed 5% (w/v) silk fibroin solution. The mixture was incubated at RT for 2 hours on a rocker protected from light.

After the two-hour incubation, 0.6 mL hydroxylamine solution was added to each reaction, and the mixture was placed on a rocker at RT for one hour. The pH was then adjusted to 7.0 using 1 N hydrochloric acid. Each solution was transferred to separate 20 kDa dialysis cassettes. Each solution was protected from light while dialyzed against 4.5 L of water with four complete exchanges at 4° C. over 72 hours. Dialyzed solutions were filtered under aseptic conditions through a 0.2 μm polyethersulfone (PES) filter unit. Final solutions were stored in sterile containers at 4° C. until use.

Example 14. Confirmation of the Conjugation of FITC to Silk Fibroin

High performance liquid chromatography (HPLC) was used to confirm conjugation is successful in the FITC-labeled silk fibroin (FITC-SF) solution. An Agilent 1260 BioInert HPLC system equipped with a Waters X-Bridge Protein BEH SEC, 200 Å, 3.5 μm column was used. An isocratic flow of mobile phase (100 mM Tris-HCl with 400 mM sodium perchlorate, pH 8.5) at 0.86 mL/min was used to lute analytes. Successful FITC labelling of SF was determined by monitoring protein absorbance at 280 nm and FITC emission at 525 nm following excitation at 490 nm. Samples were diluted to 1% (w/v) prior to injection. The data showed overlapping UV and fluorescence profiles for the silk fibroin and FITC-SF, which would represent successful conjugation since the molecular weight of unconjugated FITC is smaller than the silk fibroin (400 Da vs. >6 kDa, respectively) and would elute much later during this analysis.

Example 15. Preparation of Formulations of FITC-SF

Silk fibroin solutions containing varying percentages of FITC-SF were prepared. FITC-SF was prepared as described in Example 13. A frozen stock of 5% (w/v) silk fibroin solution (5% SF) in water was thawed for preparation of these formulations.

Stock solutions, including a 5× Borate Buffer, a 1× Borate Buffer, and a 0.86% (w/v) solution of FITC-SF in water, were prepared. The 5× Borate Buffer was prepared by combining the following: 1.5 g boric acid, 213.1 mg sodium borate decahydrate, 350 mg potassium chloride, 32 mg magnesium chloride hexahydrate, 20 mg calcium chloride dihydrate, and 40 mL DI water. The pH was adjusted to 7.3 using 1 N hydrochloric acid and 1 N sodium hydroxide. A quantity of deionized (DI) water sufficient to raise the volume to 50 mL was added. The 1× Borate Buffer (150 mOsm/L) was prepared by combining 4 mL of the 5× Borate Buffer with 12 mL DI water. The pH was adjusted to 7.3 using 1 N hydrochloric acid and 1 N sodium hydroxide. A quantity of DI water sufficient to raise the volume to 20 mL was added. The FITC-SF solution described in Example 13 was diluted with water to a concentration of 0.86% (w/v) after dialysis.

1% (w/v) silk fibroin solutions were prepared, in which varying percentages of the silk fibroin in solution was FITC-SF. These formulations were prepared by combining volumes of the solutions described below. Table 25 shows the volume of components in each formulation of the resulting 1% (w/v) silk fibroin solution (150 mOsm/L).

TABLE 25

Formulation Volumes

| Sample | % FITC-SF of the 1% SF formulation | 5% Borate buffer [mL] | DI water [mL] | 5% SF [mL] | FITC-SF [mL] |
|---|---|---|---|---|---|
| 289-1 | SF Control | 0.8 | 2.0 | 0.8 | None |
| 289-2 | 40% | 0.8 | 0.5 | 0.48 | 1.850 |
| 289-3 | 30% | 0.8 | 1.0 | 0.56 | 1.387 |
| 289-4 | 20% | 0.8 | 1.5 | 0.64 | 0.924 |
| 289-5 | 10% | 0.8 | 1.75 | 0.72 | 0.462 |

For all the formulations, the pH was adjusted to 7.3 using sodium hydroxide and hydrochloric acid, and DI water sufficient to raise the volume to 4 mL was added. The final product was obtained through filtration with a 0.2 µm syringe filter.

Example 16. Effects of FITC Conjugation on the Viscosity of a Silk Fibroin Formulation A Bholin C-VOR 150 rheometer (Malvern) with a 4°/40 mm cone and plate was used to measure rheology characteristics at 25° C. and a gap of 0.15 mm.

To analyze the complex viscosity of each formulation, thirty samples were put in a strain hold at 5%, each with a delay time of 5 s, an integration time of Is, and a wait time of 4 s. Table 26 provides the oscillation results. As used herein, the term "complex viscosity" refers to viscosity, measured under oscillatory conditions, that is dependent on the percent strain and frequency. "G'" ("G prime") represents the storage modulus, and "G''" ("G double prime") represents the loss modulus.

TABLE 26

Oscillation Data

| Sample | % FITC-SF of the 1% SF formulation | Complex Viscosity [cP] | Standard Deviation | G' [Pa] | Standard Deviation | G'' [Pa] | Standard Deviation |
|---|---|---|---|---|---|---|---|
| 289-1a | 0% | 130.6 | 7.6 | 0.686 | 0.053 | 0.415 | 0.023 |
| 289-1b | 0% | 58.9 | 8.9 | 0.311 | 0.059 | 0.198 | 0.026 |
| Average | 0% | 91 | 35.8 | 0.486 | 0.198 | 0.299 | 0.113 |
| 289-2a | 40% | 45.1 | 7.3 | 0.209 | 0.040 | 0.190 | 0.032 |
| 289-2b | 40% | 29.9 | 6.9 | 0.128 | 0.044 | 0.135 | 0.029 |
| Average | 40% | 37.5 | 10.4 | 0.168 | 0.058 | 0.162 | 0.041 |
| 289-3a | 30% | 83.4 | 9.3 | 0.430 | 0.060 | 0.299 | 0.027 |
| 289-3b | 30% | 97.8 | 12.2 | 0.505 | 0.076 | 0.348 | 0.033 |
| Average | 30% | 90.6 | 12.9 | 0.467 | 0.077 | 0.323 | 0.039 |
| 289-4a | 20% | 184.6 | 15.3 | 0.930 | 0.104 | 0.691 | 0.032 |
| 289-4b | 20% | 34.2 | 6.5 | 0.137 | 0.039 | 0.162 | 0.038 |
| Average | 20% | 143.6 | 69.8 | 0.714 | 0.372 | 0.547 | 0.243 |
| 289-5a | 10% | 122.9 | 81.9 | 0.602 | 0.432 | 0.479 | 0.291 |
| 289-5b | 10% | 247.2 | 38.6 | 1.235 | 0.188 | 0.941 | 0.158 |
| Average | 10% | 185.1 | 89.1 | 0.919 | 0.459 | 0.710 | 0.328 |

Effects of conjugation of FITC to silk fibroin on shear viscosity were also analyzed. Fifteen samples were held at a shear rate of 1 l/s. As used herein, the term "shear viscosity" or "viscosity" refers to the ratio between shear stress and shear rate. Shear viscosity is measured under shear conditions, which means that steady, simple shear in the same direction is applied to the sample. Results are shown in Table 27.

TABLE 27

Shear Viscosity Data

| Sample | %FITC-SF of the 1% SF formalation | Shear Viscosity (cP) | Stand. Dev. |
|---|---|---|---|
| 289-1a | 0% | 76.2 | 11.4 |
| 289-1b | 0% | 50.7 | 4.1 |
| Average | 0% | 63.4 | 15.5 |
| 289-2a | 40% | 39.3 | 5.0 |
| 289-2b | 40% | 33.5 | 4.7 |
| Average | 40% | 36.4 | 5.6 |
| 289-3 | 30% | 61.9 | 5.2 |
| 289-3b | 30% | 85.3 | 6.9 |
| Average | 30% | 73.6 | 13.3 |
| 289-4a | 20% | 91.7 | 11.9 |
| 289-4b | 20% | 23.3 | 6.6 |
| Average | 20% | 46.7 | 33.9 |
| 289-5a | 10% | 35.2 | 3.3 |
| 289-5b | 10% | 98.2 | 4.9 |
| Average | 10% | 66.7 | 12.9 |

Higher percentages of FITC-SF in the formulations was observed to decrease complex viscosity. The complex viscosity, G', G'', and shear viscosity of the samples with 30% FITC-SF were determined to be the most similar to those of the control silk fibroin solution. As a result, silk fibroin solutions in future studies will comprise 30% FITC-SF. 30% FITC-SF was chosen in order to balance maintaining viscosity with effective labeling, because a 10% FITC-SF ration may result in weak labeling.

Example 17. Preparation of Silk Fibroin Formulations for Irritability Analysis in Rabbits The irritability in the eyes of rabbits was compared for silk fibroin formulations with different concentrations and molecular weights of silk fibroin. The materials used in the formulations are shown in Table 28.

TABLE 28

Materials for Silk Fibroin Formulations

| Product | Supplier | Catalog Identifier | Lot Number |
|---|---|---|---|
| Lyophilized LMW Silk-Fibroin (480mb) | Cocoon Biotech | — | Batch #080-3 C |
| Lyophilized LMW Silk-Fibroin (120mb) | Cocoon Biotech | — | Batch #068-C |
| Boric Acid | Fisher | A73-500 | 163991 |
| Sodium Chloride | Sigma | S7653-1KG | SLBS2340V |
| Sodium Borate Decahydrate | Sigma | 31457-100G | BCBS7522V |
| Potassium Chloride | Sigma | 12636-250G | BCBV6226 |
| Magnesium Chloride Hexahydrate | Sigma | M7304-100G | SLBS4877 |
| Calcium Chloride Dihydrate | Fisher | C70-500 | 160760 |

Table 29 described the formulations analyzed in this Example. They were selected based on viscosity and surface tension.

TABLE 29

Silk Fibroin Formulations

| Sample | Description | Silk-Fibroin Boil Time (minutes) | Silk-Fibroin Conc. (%) |
|---|---|---|---|
| 1 | DED Buffer (Vehicle) | N/A | N/A |
| 2 | 1% 480mb in DED Buffer (Silk Fibroin-LMW) | 480 | 1 |
| 3 | 1% 120mb in DED Buffer (Silk Fibroin-HMW) | 120 | 1 |
| 4 | 1% 480mb in DED Buffer with 1% Polyethylene Glycol (Silk Fibroin-LMW with Excipient) | 480 | 1 |

The DED buffer (Vehicle) was prepared by dissolving: 1.2 g boric acid, 170.5 mg sodium borate decahydrate, 680 mg sodium chloride, 280 mg potassium chloride, 25.6 mg magnesium chloride hexahydrate, and 15.9 mg calcium chloride dihydrate in a 250 mL beaker containing 190 mL DI water. The pH was adjusted to 7.3 final using 1 N sodium hydroxide and 1 N hydrochloric acid. A quantity of DI water sufficient to raise the volume to 200 mL was added.

The 1% 480 mb in DED buffer (Silk Fibroin-LMW) formulation was prepared by reconstituting 300 mg of 480 mb silk fibroin to 5% (w/v) by adding 5.7 mL DED buffer. The silk fibroin was allowed to dissolve for 30 minutes or until clear. The solution was diluted to 1% (w/v) silk fibroin by adding 24 mL of DED buffer.

The 1% 120 mb in DED buffer (Silk Fibroin-HMW) formulation was prepared by reconstituting 300 mg of 120 mb silk fibroin to 5% (w/v) by adding 5.7 mL of DED buffer. The silk fibroin was allowed to dissolve for 30 minutes or until clear. The solution was diluted to 1% (w/v) silk fibroin by adding 24 mL of DED buffer.

The 1% 480 mb in DED Buffer with 1% Propylene Glycol (Silk Fibroin-LMW with Excipient) formulation was prepared as follows. Propylene glycol may act as a demulcent. 1.25% propylene glycol in DED buffer was prepared by mixing 0.375 mL propylene glycol with 29.625 mL of DED buffer. One tube (300 mg) of 480 mb silk fibroin was reconstituted to 5% (w/v) by adding 5.7 mL DED buffer. The silk fibroin was allowed to dissolve for 30 minutes or until clear. The solution was diluted to 1% (w/v) SF and 1% propylene glycol by adding 24 mL of 1.25% propylene glycol in DED buffer.

Final formulations were filtered through a 0.2 μm filtration unit with polyethersulfone membranes and stored at 4° C. For each formulation, ten 1.75 mL aliquots were placed in separate sterile 2 mL polypropylene Eppendorf tubes (1 tube/day+3 extra). All samples were stored at 4° C.

Example 18. Rheological Studies of Silk Fibroin Formulations for Irritability Studies Silk fibroin formulations were prepared from the protocol as described in Example 17. Silk fibroin formulations were prepared from silk fibroin lyophilized either in water or in phosphate buffer (PB). The formulations tested were presented in Table 30. Some formulations were prepared with polypropylene glycol (PG). All formulations were prepared in Dry Eye Disease (DED) buffer, a borate buffer comprising 6 mg/mL boric acid, 0.45 mg/mL sodium borate, 3.4 mg/mL sodium chloride, 1.4 mg/mL potassium chloride, 0.06 mg/mL magnesium chloride, and 0.06 mg/mL calcium chloride, pH 7.3.

TABLE 30

Formulations for irritability and rheology studies

| Sample | Description | Silk Lyophilization Buffer | Silk Conc. (%) (w/v) | PG Conc. (%) |
|---|---|---|---|---|
| 254-1 | DED Buffet | — | 0 | 0 |
| 254-2 | 1% 480mb in DED | Water | 1 | 0 |
| 254-3 | 1% 120mb in DED | Water | 1 | 0 |
| 254-4 | 1% 480, 1% PG in DED | Water | 1 | 1 |
| 254-4V | DED Buffer, 1% PG | — | 0 | 1 |
| 254-2PB | 1% 480mb (PB) in DED | PB | 1 | 0 |
| 254-3PB | 1% 120mb (PB) in DED | PB | 1 | 0 |
| 254-4PB | 1% 480 (PB), 1% PG in DED | PB | 1 | 1 |

The rheological properties of the silk fibroin formulations were then analyzed. The experiments were conducted on a Bohlin C-VOR 150 rotational rheometer with a 4°/40 mm cone and plate geometiy, a 0.15 mm gap size, and a temperature of 25° C. The first test comprised a strain sweep from 0.1% to 10% strain at 1 Hz over the course of 160 s, with 50 readings taken. This was to determine the linear viscoelastic region (LVR) of each sample. The second test comprised a strain hold at 5% (or 1% if the LVR was smaller) and 1 Hz for 145 s, with 15 readings taken. The third test comprised a shear ramp from 0.1 l/s to 10 l/s over 100 s, followed by a shear hold for 20 s, for a total time of 120 s, with 70 samples. A fourth/test was also conducted with shear rate of 1 l/s, a time of 135 s and 15 samples. The data from the rheological experiments are presented in Table 31.

TABLE 31

Rheological studies of silk fibroin formulations for irritability studies

| Sample | 254-1 | 254-2 | 254-3 | 254-4 | 254-2PB | 254-3PB | 254-4PB |
|---|---|---|---|---|---|---|---|
| Viscosity at 1 1/s (cP) | 7.07 | 62.85 | 38.95 | 81.96 | 57.78 | 43.14 | 56.30 |
| Viscosity Standard deviation (1 1/s) | 4.25 | 3.23 | 2.64 | 4.59 | 3.45 | 4.29 | 6.03 |
| Viscosity at 10 1/s (cP) | 4.76 | 12.86 | 11.64 | 16.95 | 11.69 | 10.42 | 10.92 |
| Viscosity Standard Deviation (10 1/s) | 5.67 | 5.68 | 6.79 | 6.22 | 1.69 | 1.04 | 1.52 |
| G' (Pa) | 2.24E−02 | 2.41E−01 | 8.76E−02 | 4.39E−01 | 3.07E−01 | 1.48E−01 | 4.24E−01 |
| G' Standard Deviation | 9.10E−03 | 5.26E−02 | 1.87E−02 | 4.72E−02 | 3.72E−02 | 1.66E−02 | 5.22E−02 |
| G" (Pa) | 4.15E−02 | 2.43E−01 | 1.35E−01 | 3.74E−01 | 2.45E−01 | 2.09E−01 | 3.55E−01 |
| G" Standard Deviation | 1.03E−02 | 2.76E−02 | 1.23E−02 | 2.31E−02 | 1.87E−02 | 1.09E−02 | 2.91E−02 |
| Phase Angle (°) | 61.11 | 45.73 | 57.27 | 40.56 | 38.71 | 54.76 | 40.05 |
| Phase Angle Standard Deviation | 13.39 | 3.48 | 5.16 | 1.61 | 1.94 | 2.66 | 1.63 |

All of the formulations showed evidence of shear thinning; the viscosities were measured to be lower at higher shear rates. The formulations with lower molecular weight silk fibroin (480 mb) were more viscous than the formulations with higher molecular weight silk fibroin (120 mb). Preparation from silk fibroin lyophilized in PB did not affect the viscosity of the formulations. Formulations with PG were more viscous than formulations without this excipient. The G' and G" were measured to be lower for formulations with higher molecular weight silk fibroin. G' and G" were also increased by the preparation from silk fibroin lyophilized in PB or formulations with PG. The phase angle was higher for formulations with higher molecular weight silk fibroin.

Example 19. Analysis of Irritability of Silk Fibroin Formulations in Rabbits

Non-GLP ocular irritability/tolerability was evaluated by measuring the effects of topical administration of the silk fibroin formulations described herein in New Zealand White (NZW) Rabbits. Animals received seven days of four times daily (QID) topical administrations of test article or vehicle (bilateral) and underwent full ophthalmic exams at baseline, post the first dose on Day 1, post the last dose on Day 1, post the last dose on Day 4, and post the last dose on Day 8.

Rabbits were individually housed in suspended wire bottom caging in a procedure room. Rabbit Diet 5P25 (lab diet specially formulated per lab animal diet) was provided according to U.S. Department of Agriculture (USDA) guidelines. Filtered tap water or spring water was provided to the animals ad libitum. Environmental controls were set to maintain temperatures 16-22° C. (61-72° F.) with relative humidity between 50±20%. A 12-hour light/12-hour dark cycle was maintained. A staff veterinarian was available as needed throughout the study. Prior to study initiation, the veterinarian released the animals from quarantine.

Animals were assigned to dose groups after a baseline ocular examination. Table 32 provides the group assignments for the 16 animals selected for the study.

TABLE 32

Group Assignments for Animals

| Group | Number of Animals | Silk Fibroin minute boil (mb) | Route | No. of Doses per Day | SF Dose Concentration %(w/v) | Propylene Glycol Dose Concentration (mg/mL) | Dose Volume (µL/eye) |
|---|---|---|---|---|---|---|---|
| 1/Vehicle | 4 | N/A | Topical | QID | 0 | 0 | 40 |
| 2/SilkFibroin-LMW Concentration 1 | 4 | 480 | Topical | QID | 10 | 0 | 40 |
| 3/Silk Fibroin-HMW Concentration 2 | 4 | 120 | Topical | QID | 10 | 0 | 40 |
| 4/SilkFibroin-LMW + 1% PG Formulation | 4 | 480 | Topical | QID | 10 | 10 | 40 |

40 μL of test article or vehicle (bilateral) was administered to the ocular surface of the rabbit using a calibrated micropipette. Care was taken to ensure no dose fell out of the rabbit's eye. QID dosing occurred at approximately 8 am, 11 am, 2 pm, and 4 pm. All times are ±60 minutes.

The weight of each animal was measured on Day 1 and Day 8. Values were rounded to the nearest 0.1 kg. A full ophthalmic exam was performed at baseline, twice on Day 1 (after the first dose and after the fourth dose), Day 4, and Day 8. After all animals were dosed, cage side observations were made for each animal specifically focusing on the eyes. If any indication of ocular pain was observed (squinting, pawing at the eye, or other signs of distress), the technician took the animal out and performed a gross examination of the eye. Gross exams observed the general appearance of the eye (whether or not there is hyperemia, discharge, swelling, squinting, etc.). All exams were 15 minutes post dose.

A hand-held slit-lamp was used to assess anterior abnormalities. If tolerability issues arose, the fundus of the eye was observed using an indirect ophthalmoscope. Prior to posterior examination, animals were dilated with a mydriatic (tropicamide).

Animals underwent full front of the eye exams and a quick vitreal scan via slitlamp. Endpoints included hyperemia, chemosis, discharge, aqueous flare, aqueous cells, presentation of keratic precipitates, and vitritis (as noted via slitlamp). Throughout the study, animals showed no signs of ocular discomfort or pain and the majority of endpoints were scored at zero.

Results indicate the silk fibroin formulations and vehicle are well tolerated in the eyes of New Zealand White rabbits. Results indicate that topical administration of the solution of silk fibroin was tolerated well throughout the duration of the study. Observations and clinical scoring of endpoints maintained baseline levels throughout the entire study. The concentrations of this test article show that it is safe to be administered topically. There were no significant endpoint changes in the hyperemia and discharge evaluations, and the remaining endpoints maintained scores of zero throughout all evaluations. Animals showed no signs of ocular pain or discomfort throughout all dosing time points as well.

Example 20. Ocular Silk Fibroin Residence

Formulation Preparation

To track the residence of the silk fibroin (SF) formulations in the eye, SF formulations were labelled with fluorescent dye, FITC. 5% (w/v) SF, (480 mb) degummed as described above, was prepared in water and 50 mM sucrose. This solution was separated into 5 mL aliquots and frozen to −80° C. to be thawed as needed. FITC labelled silk fibroin (FTC-SF) was prepared as described in Example 13. A 5× stock of the borate (DED) buffer was prepared by combining the following components: 1.5 g boric acid, 213.1 mg sodium borate decahydrate, 350 mg potassium chloride, 32 mg magnesium chloride hexahydrate, 20 mg calcium chloride dihydrate, and 40 mL deionized (DI) water. The pH was adjusted 7.3 using 1 N hydrochloric acid and 1 N sodium hydroxide and brought up to 50 mL with DI water. The 5× stock was prepared so that the final solution of FITC-SF and unlabeled silk fibroin would be in a 1×DED buffer, the contents of which were described in earlier examples. 0.86% (w/v) FITC-SF in water was used to prepare the 30% FITC-SF formulation. A sample of 1% SF in DED with an osmolarity of 150 mOsm/L was prepared by combining 3 mL 5% SF in water, 3 mL 5× borate buffer, and 9 mL DI water in a 20 mL conical tube. The pH was adjusted to 7.3 using 1 N hydrochloric acid and 1 N sodium hydroxide and brought up to 15 mL with DI water. A second sample, a 30% FITC-SF formulation (containing 1% SF in DED with 150 mOsm/L), was also prepared. 5.201 mL 0.86% (w/v) FITC-SF was combined with 2.1 mL 5% (w/v) SF in water, 3.0 mL 5× borate buffer and 4.699 mL DI water. The pH of the solution was adjusted to 7.3 using 1 N hydrochloric acid and 1 N sodium hydroxide and brought up to 15 mL with DI water. The resulting solution has FITC labelled SF and unlabeled SD in the ratio of 3:7. Both formulations were filtered with a 0.2 μm syringe filter.

Rheology of Formulations

The complex viscosity, elastic modulus (G'), viscous modulus (G"), phase angle, and shear viscosity of the formulations to be tested for residence time were measured. The rheological properties were measured on a Bohlin C-VOR 150 rotational rheometer with a 4°/40 mm cone and plate geometry, a gap size of 0.15 mm, a temperature of 25° C., a frequency of 1 Hz. and pre-shear conditions of 1 l/s for 10 s with a 10 second equilibration. The experiment consisted of two tests. The first test involved a strain hold at 5% with 30 samples, each with a delay time of 5 s, an integration time of 1s, and a wait time of 4 s. The second test used a hold at a shear rate of 1 l/s for 15 samples. The results of the experiments are presented in Table 33.

TABLE 33

Rheology data of silk fibroin formulations for residence studies

| | Sample | | | | | | | |
|---|---|---|---|---|---|---|---|---|
| | 1% SF in borate buffer | | | | 30% FITC-SF Formulation | | | |
| Sample | 291-1a | 291-1b | 291-1c | Average | 291-2a | 291-2b | 291-2c | Average |
| Complex viscosity (cP) | 89.64 | 217.01 | 315.31 | 207.32 | 252.18 | 238.09 | 325.11 | 271.79 |
| Complex viscosity standard deviation | 18.48 | 46.29 | 50.70 | 101.52 | 35.54 | 40.71 | 48.58 | 56.39 |
| G' (Pa) | 0.42 | 1.10 | 1.58 | — | 1.13 | 1.08 | 1.50 | — |
| G' standard deviation | 0.11 | 0.28 | 0.31 | — | 0.21 | 0.25 | 0.29 | — |
| G" (Pa) | 0.38 | 0.81 | 1.19 | — | 1.11 | 1.03 | 1.38 | — |
| G" standard deviation | 0.06 | 0.12 | 0.12 | — | 0.11 | 0.12 | 0.14 | — |

TABLE 33-continued

Rheology data of silk fibroin formulations for residence studies

| | Sample | | | | | | | |
|---|---|---|---|---|---|---|---|---|
| | 1% SF in borate buffer | | | | 30% FITC-SF Formulation | | | |
| Sample | 291-1a | 291-1b | 291-1c | Average | 291-2a | 291-2b | 291-2c | Average |
| Phase Angle (°) | 42.95 | 37.14 | 37.44 | 39 18 | 44.94 | 44.44 | 43.05 | 44.14 |
| Phase angle standard deviation | 4.90 | 3.78 | 2.94 | 4.73 | 2.97 | 4.03 | 3.20 | 3.47 |
| Shear Viscosity (cP) | 71.32 | 82.03 | 154.21 | 102.52 | 100.58 | 90.42 | 140.34 | 110.45 |
| Shear viscosity standard deviation | 8.86 | 19.86 | 28.30 | 42.32 | 21.79 | 37.13 | 41.39 | 40.12 |

These results suggested that the incorporation of FITC-SF into the silk fibroin solution formulation produced formulations with similar properties.

Ocular Residence Time

The fluorescence intensity of the formulations was established in vitro. The FITC-SF formulation was diluted 10×, 50×, and 100× in saline solution. 15 µL of the formulations were pipetted onto the end of a wicking strip. The formulations utilized include undiluted FITC-SF and 10×, 50×, and 100× dilutions of the FITC-SF solution in saline. Images of each of the wicking strips were taken through an orange filter with illumination using a cobalt blue light and the fluorescence brightness was analyzed and quantified using Fiji Image software. A segment of the image just adjacent to the end of the wicking strip was used to normalize the background brightness of the images. After brightness correction, a circle was drawn to encompass the end of the wicking strip. The brightness intensity of the wicking strip was then recorded. Two images of each sample were analyzed and averaged to generate the value for each timepoint from each animal. There were 6 animals per timepoint. The results are shown in Table 34.

TABLE 34

Fluorescence intensity

| % FITC-SF Formulation | Dilution | Corrected Intensity Avg. | Standard Deviation |
|---|---|---|---|
| 100 | 0 | 86.1 | 0.8 |
| 10 | 10X | 40.2 | 7.5 |
| 2 | 50X | 17.5 | 3.4 |
| 1 | 100X | 4.2 | 0.1 |
| 0 | 100 (Saline) | 0.0 | 0.1 |

As the concentration of FITC-SF in the formulation decreased, the fluorescence intensity also decreased. The R squared value obtained was 0.935 suggesting a strong correlation between concentration of FITC and fluorescence brightness measured.

To measure the ocular residence time of the FITC-SF formulation, 40 µL of FITC-SF formulation was administered into the lower left lid of each rabbit. Eyes were manually blinked 2-3 times prior to the first sampling (T0). Sampling was performed by placing a wicking strip into the bottom eyelid of the rabbit for 5 sec. to collect ≤5 µL of tears. Images of the wicking strips were taken and the fluorescence was quantified as described above. Sampling was performed at T0, 15 minutes, 30 minutes, 1 hour, 2 hours, and 24 hours. The eyes were also scored clinically for the presence of fluorescence using the Fluorescence Intensity (FI) scale just prior to sampling. Images of the eyes were taken through an orange filter with illumination using a cobalt blue light.

Table 35 shows the Fluorescence Intensity (FI) scale for the tears collected from the fornix of the tear lake.

TABLE 35

Fluorescence Intensity (FI) scale

| Score | Description |
|---|---|
| 0 | No fluorescence |
| 1 | ≤25% fluorescence |
| 2 | ≤50% fluorescence |
| 3 | ≤75% fluorescence |
| 4 | ≥75% fluorescence |

Based on the FI scale in Table 35, the clinical fluorescence score for each time point was calculated as shown in Table 36.

TABLE 36

Clinical Fluorescence Score

| Time (min) | Average | St Dev | SEM |
|---|---|---|---|
| 0 | 4.0 | 0.0 | 0.0 |
| 0.25 | 2.0 | 0.6 | 0.2 |
| 0.5 | 1.3 | 0.8 | 0.2 |
| 1 | 1.0 | 0.6 | 0.2 |
| 2 | 0.2 | 0.4 | 0.1 |
| 24 | 0.0 | 0.0 | 0.0 |

Clinical Fluorescence Score decreased over time indicating that the FITC-SF is cleared from the tear lake over time. The Clinical Fluorescence Score decreased to less than one by 2 hours, indicating that the residence time of the FITC-SF formulations in the eye is ≤2 hours. The reduction in Clinical Fluorescence Score over time was strongly correlated with an R squared value of 0.97.

Images of the wicking strips used to collect the tears from the rabbits were quantified as shown in Table 37. As described above, images were analyzed using Fiji Image software. A segment of the image just adjacent to the end of the wicking strip was used to normalize the brightness of the images. After brightness correction, a circle was drawn to encompass the end of the wicking strip. The brightness intensity of the wicking strip was then recorded. Two images of each sample were analyzed and averaged to generate the value for the timepoint from each animal. There were a total of 6 animals per timepoint.

TABLE 37

Quantified Fluorescence

| Time (hrs) | Intensity Average | Standard Deviation | SEM |
|---|---|---|---|
| 0 | 139.8 | 20.7 | 1.7 |
| 0.25 | 10.1 | 25.1 | 2.1 |
| 0.5 | 97.5 | 14.7 | 1.2 |
| 1 | 93.8 | 20.5 | 1.7 |
| 2 | 86.3 | 6.3 | 0.5 |
| 24 | 89.3 | 4.5 | 0.4 |

Similar to the Clinical Fluorescence Score, the quantified fluorescence decreased over time. A sharp reduction in the quantified fluorescence was observed by 0.5 hours which slowly plateaued over the next hour to reach the values close to the lower limit of detection (86.3) by 2 hours. The lower limit of detection was determined from the dilution study of the fluorescence intensity and was approximately 2% of the initial formulation (a 50× dilution).

Example 21. Tribological Analysis of Silk Fibroin

In this test silk fibroin solutions were analyzed for their lubricating properties by applying a layer of the test sample to a substrate and forcing an upper geometry to slide against it at a number of speeds while under a defined load. Testing was performed using a research rheometer (DHR2, TA Instruments) fitted with a custom 3-balls-on-plate setup with a pliant lower substrate. A tribology assembly was employed that comprised a geometry of 3 glass spheres that slide against a pliant lower substrate, under a defined load of 1 N, onto which the sample has been spread. The rotational angular velocity is ramped from 0.05 rad/s to 20 rad/s, 8 points per decade, with each point maintained for 20 s with the coefficient of friction averaged over the final 15 s. The lower surface was made to hold 25° C. throughout the analysis. This test was performed in triplicate for each sample. The test was performed on silk fibroin formulation 480 mb; 1% SFf; sln; 0.34% Suc; borate buffer. The formulation tested was prepared as described in previous examples. The silk fibroin solution exhibited a clear "stick-slip" behavior across all sliding speeds. Stick-slip behavior is the spontaneous jerking motion that may occur while two objects are sliding over each other.

Example 22. Surface Tension Measurements of Silk Fibroin Solutions Using Dynamic Analysis Surface tension was employed to determine the spreading properties of silk fibroin solutions. The test analyzed the relationship between the volume, density, and shape of the liquid drop suspended from the end of a needle to calculate the surface tension of that liquid. It was performed on a drop shape analyzer (DSA30R, Krüss Scientific) fitted with the pendant drop module. An aliquot of each sample was equilibrated to 25° C. immediately prior to testing. A pendant drop was formed in a cuvette with a saturated atmosphere to minimize evaporation. This drop was imaged, and the surface tension measured every second over a period of 600 s. This test was performed in triplicate for each sample. The tests were performed on silk fibroin formulations after their preparation. Deionized water served as a control. The formulations tested were prepared as described in previous examples. The results of the experiments are displayed in Table 38.

TABLE 38

Surface Tension of Silk Fibroin Solutions

| | Sample 1 Surface Tension (mN/m) | Sample 2 Surface Tension (mN/m) | Sample 3 Surface Tension (mN/m) | Average Surface Tension (mN/m) | RSD (%) | Standard Dev. |
|---|---|---|---|---|---|---|
| DI Water | 71.32 | 71.46 | 71.46 | 71.41 | 0.092 | 0.066 |
| 480mb; 5%SFf sin; 1.71%Suc; borate buffer | 42.48 | 42.15 | 42.08 | 42.24 | 0.412 | 0.174 |
| 480mb; 1%SFf; sln; 0.34%Suc; borate buffer | 44.27 | 44.57 | 44.82 | 44.55 | 0.505 | 0.225 |
| 480mb; 0.5%SPf; sln; 0.17%Suc; borate buffer | 45.80 | 45.99 | 46.03 | 45.94 | 0.218 | 0.100 |
| 480mb; 0.1%SFf; sln; 0.03%Suc; borate buffer | 46.37 | 46.72 | 46.89 | 46.66 | 0.464 | 0.217 |
| 480mb; 0.05%SFf; sln; 0.01%Suc; borate buffer | 49.06 | 49.12 | 49.10 | 49.09 | 0.051 | 0.025 |

Increasing silk fibroin concentration lead to a decrease in calculated surface tension. The presence of 0.05% (w/v) silk fibroin decreased the surface tension to 49.99 mN/m. This is a large decrease from water which displayed a surface tension of 71.41 mN/m. As silk concentration in the samples increased, the surface tension was further decreased reaching a low of 42.24 mN/m with the 5% (w/v) silk fibroin sample (Table 38).

Example 23. Treatment of Dry Eye Disease in Humans

To demonstrate safety and tolerability, optimize a formulation or dose, and show efficacy compared to a placebo, the following study will be performed in humans and animals. Both a single site, open label, placebo controlled safety study and a multi-site, randomized, double-masked, parallel group, placebo or vehicle-controlled, efficacy study will be performed with about 30 subjects and up to 150 patients, respectively. Standardized inclusion and exclusion criteria will be used for enrollment. The subjects will be randomized to a treatment arm after a wash-out or two-week vehicle run-in period.

Treatment arms will be the silk formulation administered four times a day (QID), twice a day (BID), or once a day (QD) compared to a placebo group (patients will serve as their own placebo) and will include between 8-10 subjects per arm. Treatment duration will be one month. The primary endpoint will be safety as measured by visual acuity, slit lamp biomicroscopy of intraocular pressure (IOP), fundoscopy, and adverse event query. The secondary endpoint will be efficacy as measured by corneal fluorescein staining, staining of individual regions of cornea (e.g. inferior, central, superior, nasal, and temporal), conjunctival staining, tear film break-up time, Schirmer's Test, and conjunctival redness. All the results are expected to change from the baseline. Ocular discomfort, such as dryness, grittiness, burning, stinging, etc., and the ocular surface disease index (OSDI) may also be used to characterize the results.

Example 24. Stability of Silk Fibroin Formulations

The stability of multiple silk fibroin formulations may be compared after storage at 4° C. for three weeks, room temperature for three weeks, or 40° C. for one week. A silk fibroin solution was formulated with a concentration of 0.5%, 1%, or 3% (w/v) silk fibroin with either 10 mM phosphate buffer (pH 7.5) or 10 mM borate buffer (pH 7.5) to result in an osmolarity of 150 mOsm/L or 290 mOsm/L. Aggregation was observed to be below 0.1% for all formulations and under all conditions. Silk fibroin formulations maintain their silk fibroin concentration, physical properties, and rheological properties after storage.

Example 25. Preparation of SBP Hydrogel Formulations

Silk was degummed using either a 90 or a 480-minute boil (90 mb and 480 mb), processed as described in Example 1 and lyophilized in 10 mM phosphate buffer (PB). Lyophilized silk fibroin was dissolved in ultrapure water containing Tween-80 to obtain 10, 20, and 30% (w/v) silk fibroin with 0.4% Tween-80. The hydrogels were formed by mixing with a gelling agent (e.g. PEG 4 kDa). 2.5 mL of the silk solution was mixed with 2.5 mL one of the following excipients: (i) 20% P188, (ii) 80% PEG 4 kDa, or (iii) 80% glycerol. 1 N hydrochloric acid was added to the formulations containing 80% PEG 4 kDa, to afford a final concentration of 15 mM hydrochloric acid. The final pH of all formulations was estimated to be approximately 7.4+/−0.1. The SBP hydrogel formulations are summarized in Table 39 below. The samples in Table 39 are named by the process used to prepare and formulate each hydrogel. For example, the sample named "90 mb; hyd; 10% st; 5% SFf; 10% P188f" refers to a formulation where the silk was degummed with a 90-minute boil (90 mb), "hyd" refers to the formulation of the sample as a hydrogel, "10% st" refers to the % (w/v) concentration of the stock solution of silk fibroin, "5% SFf" refers to a formulation with 5% (w/v) final silk fibroin concentration, and "10% P188f" refers to a formulation with 10% P188.

TABLE 39

SBP hydrogel formulations

| No. | Sample name | Boil Time (min) | [Silk] (%) | Excipient name | [Excipient] (%) | [Phosphate Buffer] (mM) |
|---|---|---|---|---|---|---|
| 1 | 90mb; hyd; 10%st; 5%SFf; 10%P188f | 90 | 5 | P188 | 10 | 16.7 |
| 2 | 90mb; hyd; 10%st; 5%SFf; 40%PEG4kf | 90 | 5 | PEG 4k | 40 | 16.7 |
| 3 | 90mb; hyd; 10%st; 5%SFf; 40% Glycf | 90 | 5 | Glycerol | 40 | 16.7 |
| 4 | 90mb; hyd; 20%st; 10%SFf; 10%P188f | 90 | 10 | P188 | 10 | 33.3 |

TABLE 39-continued

SBP hydrogel formulations

| No. | Sample name | Boil Time (min) | [Silk] (%) | Excipient name | [Excipient] (%) | [Phosphate Buffer] (mM) |
|---|---|---|---|---|---|---|
| 5 | 90mb; hyd; 20%st 10%SFf; 40%PEG4kf | 90 | 10 | PEG 4k | 40 | 33.3 |
| 6 | 90mb; hyd; 20%st; SFf; 40%Glyef | 90 | 10 | Glycerol | 40 | 33.3 |
| 7 | 480mb; hyd; 10%st; 5%SFf; 10%P188f | 480 | 5 | P188 | 10 | 16.7 |
| 8 | 480mb; hyd; 10%st; 5%SFf; 40%PEG4kf | 480 | 5 | PEG 4k | 40 | 16.7 |
| 9 | 480mb; hyd; 10%st; 5%SFf; 40% Glycf | 480 | 5 | Glycerol | 40 | 16.7 |
| 10 | 480mb; hyd; 20%st; 10%SFf; 10%P188f | 480 | 10 | P188 | 10 | 33.3 |
| 11 | 480mb; hyd; 20%st; 10%SFf; 40%PEG4kf | 480 | 10 | PEG 4k | 40 | 33.3 |
| 12 | 480mb; hyd; 20%st; 10%SFf 40%Glycf | 480 | 10 | Glycerol | 40 | 33.3 |
| 13 | 480mb; hyd; 30%st; 15%SFf; 10%P188f | 480 | 15 | P188 | 10 | 50 |
| 14 | 480mb; hyd; 30%st; 15%SFf; 40%PEG4kf | 480 | 15 | PEG 4k | 40 | 50 |
| 15 | 480mb; hyd; 30%st; 15%SFf; 40%Glycf | 480 | 15 | Glycerol | 40 | 50 |

Example 26. Freeze Thaw Studies with Varying Silk Fibroin Concentrations and Buffers To date, lyophilization has been utilized for long term storage of silk fibroin. However, this can be costly and time-consuming in product manufacturing. In this study, various silk fibroin concentrations and buffer conditions were examined to test the feasibility of freezing silk fibroin without altering the protein quality. The samples were evaluated using rheology for viscosity and modulus, and size exclusion chromatography (SEC) for molecular weight and aggregation.

This study evaluated the properties of formulations with silk fibroin concentration varied at 1% and 3% (w/v) in phosphate buffer, borate buffer, or phosphate buffered saline, with or without propylene glycol. The formulation in each sample is described in Table 40. In the Table, "PB" is potassium phosphate buffer (from Sigma Aldrich Fine Chemicals, St. Louis, Mo.), pH 7.4; "PBS" is 1× phosphate buffered saline; "DED" is 1× borate buffer as described in Example 15; and "PG" is propylene glycol. The "baseline" measurements were made prior to freezing at −80° C.

The borate buffer stock solution (5×) was prepared by dissolving 3000 mg boric acid, 426.25 mg sodium borate decahydrate, 1700 mg of sodium chloride, 700 mg potassium chloride, 64 mg magnesium chloride hexahydrate, and 40 mg calcium chloride dihydrate in DI water, adjusting pH to 7.3 final using 1 N sodium hydroxide and N hydrochloric acid, and filling up to 100 mL with DI water. The borate buffer was filtered through 0.2 μm polyethersulfone membrane filtration units prior to use. The final formulations contained 1× of this buffer (6 mg/mL boric acid, 0.45 mg/mL sodium borate, 3.4 mg/mL sodium chloride, 1.4 mg/mL potassium chloride, 0.06 mg/mL magnesium chloride, and 0.06 mg/mL calcium chloride, pH 7.3).

TABLE 40

Formulations with varying silk fibroin concentrations and buffers

| Sample No. | Description | Silk % | Buffer | Frozen |
|---|---|---|---|---|
| 82-1 | 3% Water, Baseline | 3 | Water | — |
| 82-1A | 3% Water, Not Frozen | 3 | Water | N |
| 82-1B | 3% Water, Frozen | 3 | Water | Y |
| 82-2 | 3% PB, Baseline | 3 | 10 mM PB | — |
| 82-2A | 3% PB, Not Frozen | 3 | 10 mM PB | N |
| 82-2B | 3% PB, Frozen | 3 | 10 mM PB | Y |
| 82-3 | 3% DED, Baseline | 3 | DED | — |
| 82-3A | 3% DED, Not Frozen | 3 | DED | N |
| 82-3B | 3% DED, Frozen | 3 | DED | Y |

TABLE 40-continued

Formulations with varying silk fibroin concentrations and buffers

| Sample No. | Description | Silk % | Buffer | Frozen |
|---|---|---|---|---|
| 82-4 | 1% PBS, Baseline | 1 | PBS | — |
| 82-4A | 1% PBS, Not Frozen | 1 | PBS | N |
| 82-4 B | 1% PBS, Frozen | 1 | PBS | Y |
| 82-5 | 1% DED, Baseline | 1 | DED | — |
| 82-5A | 1% DED, Not Frozen | 1 | DED | N |
| 82-5B | 1%DED, Frozen | 1 | DED | Y |
| 82-6 | 1% PBS + PG, Baseline | 1 | PBS + 1% PG | — |
| 82-6A | 1% PBS + PG, Not Frozen | 1 | PBS + 1% PG | N |
| 82-6B | 1% PBS + PG, Frozen | 1 | PBS + 1% PG | Y |
| 82-7 | 1% DED + PG, Baseline | 1 | DED + 1% PG | — |
| 82-7A | 1% DED + PG, Not Frozen | 1 | DED + 1% PG | N |
| 82-7B | 1% DED + PG, Frozen | 1 | DED + 1% PG | Y |

The rheology results and the size exclusion chromatography (SEC) results for the solutions are presented in Table 41 and Table 42, respectively, where viscosity, elastic modulus (G') viscous modulus (G") and phase angle were determined. G', G" and phase angle were measured using a Bohlin C-VOR 150 rotational rheometer. The temperature was held constant at 25° C. via a Peltier Plate system, and the gap was held at 0.15 mm. First a strain ramp was applied from 0.0014 to 5% strain with a constant frequency of 1 Hz, with 30 samples taken, each with a delay time of 9 s and an integration time of 1 s. Next a logarithmic shear ramp was applied from 0.00014 to 1 l/s, with holds at 0.00014, 0.001, 0.01, 0.1, and 1 l/s. Overall, the rheological properties did not change significantly following freezing with the exception of the 1% (w/v) silk fibroin in borate buffer with propylene glycol. The molecular weight as measured by SEC did not change following freeze/thaw, nor did the total peak area. Increases in aggregation were observed for all solutions containing borate buffer with the greatest increase in aggregation occurring with the addition of propylene glycol. Given these results, phosphate buffer performed better upon freeze/thaw than borate buffer.

TABLE 41

Rheological properties after freeze thaw

| Sample No. | Frozen | Viscosity (Pa*s) Avg. | Viscosity (Pa*s) Standard Dev. | G' (Pa) Avg. | G' (Pa) Standard Dev. | G" (Pa) Avg. | G" (Pa) Standard Dev. | Phase Angle (°) Avg. | Phase Angle (°) Standard Dev. |
|---|---|---|---|---|---|---|---|---|---|
| 82-1 | — | 65.19 | 2.25 | 4.03E-01 | 0 | 4.47E-01 | 0 | 48.01 | 0 |
| 82-1A | N | 50.91 | 5.69 | 1.45E-01 | 2.66E-02 | 2.53E-01 | 4.07E-02 | 59.73 | 7.91 |
| 82-1B | Y | 49.77 | 5.1 | 1.45E-01 | 9.34E-03 | 2.24E-01 | 1.52E-02 | 57.02 | 2.78 |
| 82-2 | — | 38.18 | 3.17 | 3.28E-01 | 0 | 3.06E-01 | 0 | 43.05 | 0 |
| 82-2A | N | 60.42 | 7.66 | 3.33E-01 | 5.78E-02 | 3.43E-01 | 5.08E-03 | 46.08 | 5.55 |
| 82-2B | Y | 51.63 | 4.71 | 3.19E-01 | 6.16E-02 | 3.07E-01 | 1.44E-02 | 44.22 | 6.25 |
| 82-3 | — | 81.34 | 3.01 | 2.80E-01 | 0 | 3.67E-01 | 0 | 52.73 | 0 |
| 82-3A | N | 79.23 | 1.75 | 3.16E-01 | 4.08E-02 | 3.97E-01 | 1.91E-02 | 51.65 | 2.23 |
| 82-3B | Y | 76.64 | 23.4 | 4.28E-01 | 3.36E-02 | 4.20E-01 | 4.56E-02 | 44.45 | 2.47 |
| 82-4 | — | 93.78 | 4.89 | 5.84E-01 | 0 | 5.13E-01 | 0 | 41.28 | 0 |
| 82-4A | N | 75.67 | 4.05 | 2.93E-01 | 4.79E-02 | 3.25E-01 | 3.87E-02 | 48.08 | 5.01 |
| 82-4B | Y | 62.5 | 9.67 | 3.12E-01 | 5.82E-02 | 3.16E-01 | 1.02E-01 | 44.66 | 4.43 |
| 82-5 | — | 115.1 | 7.78 | 5.66E-01 | 0 | 7.49E-01 | 0 | 52.89 | 0 |
| 82-5A | N | 82.94 | 19.47 | 4.47E-01 | 1.25E-01 | 4.76E-01 | 1.15E-01 | 47.04 | 1.69 |
| 82-5B | Y | 72.05 | 15.33 | 3.17E-01 | 4.23E-02 | 3.53E-01 | 6.76E-02 | 47.83 | 3.86 |
| 82-6 | — | 91.32 | 3.57 | 3.17E-01 | 0 | 4.34E-01 | 0 | 53.85 | 0 |
| 82-6A | N | 64.97 | 5.43 | 2.62E-01 | 1.3 IE-02 | 3.25E-01 | 3.00E-02 | 51.08 | 3.82 |
| 82-6B | Y | 52.32 | 10.46 | 2.03E-01 | 5.77E-02 | 2.70E-01 | 8.27E-02 | 52.86 | 0.99 |
| 82-7 | — | 113.82 | 5.15 | 5.33E-01 | 0 | 6.14E-01 | 0 | 49.04 | 0 |
| 82-7A | N | 87.53 | 24.46 | 4.40E-01 | 1.17E-01 | 4.67E-01 | 9.24E-02 | 46.96 | 2.26 |
| 82-7B | Y | 48.81 | 12.4 | 2.59E-01 | 3.78E-02 | 2.86E-01 | 2.78E-02 | 47.92 | 6.46 |

Example 27. Freeze Thaw Studies with Varying Cryoprotectants

TABLE 42

Molecular weight, peak area and aggregation after freeze thaw

| Sample No. | Frozen | MW (Da) Avg. | MW (Da) Standard Dev. | Peak Area Avg. | Peak Area Standard Dev. | Aggregation (%) Avg. | Aggregation (%) Standard Dev. |
|---|---|---|---|---|---|---|---|
| 82-1 | — | 18218 | 0 | 25183515 | 0 | 0 | 0 |
| 82-1A | N | 18043 | 1190 | 24592650 | 210277 | 0 | 0 |
| 82-1B | Y | 18223 | 1008 | 24541530 | 207449 | 0 | 0 |
| 82-2 | — | 18075 | 0 | 26649930 | 0 | 0 | 0 |
| 82-2A | N | 17943 | 1006 | 26433232 | 96728 | 0 | 0 |
| 82-2B | Y | 18023 | 987 | 26385803 | 9567 | 0 | 0 |
| 82-3 | — | 18123 | 0 | 26161084 | 0 | 0 | 0 |
| 82-3A | N | 18008 | 1069 | 25858311 | 65572 | 0 | 0 |
| 82-3B | Y | 17953 | 1110 | 25937330 | 1196173 | 0.32 | 0.09 |
| 82-4 | — | 18434 | 0 | 8206505 | 0 | 0 | 0 |
| 82-4A | N | 18381 | 1237 | 8102340 | 43772 | 0 | 0 |
| 82-4B | Y | 18375 | 980 | 8008933 | 38407 | 0.04 | 0.01 |
| 82-5 | — | 18627 | 0 | 8590083 | 0 | 0 | 0 |
| 82-5A | N | 18301 | 884 | 8529287 | 16053 | 0 | 0 |
| 82-5B | Y | 18182 | 964 | 8130534 | 115760 | 1.31 | 0.36 |

TABLE 42-continued

Molecular weight, peak area and aggregation after freeze thaw

| Sample No. | Frozen | MW (Da) Avg. | Standard Dev. | Peak Area Avg. | Standard Dev. | Aggregation (%) Avg. | Standard Dev. |
|---|---|---|---|---|---|---|---|
| 82-6 | — | 18603 | 0 | 8191389 | 0 | 0 | 0 |
| 82-6A | N | 18283 | 1139 | 8137815 | 13188 | 0 | 0 |
| 82-6B | Y | 18345 | 1085 | 8130532 | 18074 | 0 | 0 |
| 82-7 | — | 18675 | 0 | 8613387 | 0 | 0 | 0 |
| 82-7A | N | 18262 | 925 | 8527920 | 57162 | 0 | 0 |
| 82-7B | Y | 17305 | 991 | 7919038 | 87323 | 7.27 | 1.7 |

Silk fibroin processing will be more efficient and cheaper if there is no need for lyophilization. Removing a drying condition will require that silk fibroin solutions are stable through a freeze-thaw process. This will allow for aseptic preparation and shipment of silk fibroin from the manufacturing site to the fill/finish facility. This study investigated the effect of silk fibroin concentration as well as cryoprotectants (sucrose and trehalose) on the freeze-thaw stability silk fibroin.

The silk fibroin concentration was varied from 0.5% to 5% (w/v) in 10 mM phosphate buffer and the concentration of each cryoprotect was varied from 10 to 150 mM. The formulation in each sample is described in Table 43. All formulations contained 10 mM phosphate buffer at pH 7.4 and the baseline measurements were made prior to freezing at −80° C. The five 5 mL replicates were prepared for each group in separate 15 cc. conical tubes. In the Table, "SF" refers to silk fibroin.

TABLE 43

Formulations with varying silk fibroin concentrations and cryoprotectants

| Sample No. | Description | Silk Fibroin Conc. (mg/mL) | Cryo-protectant | [Cryo-protectant] mM |
|---|---|---|---|---|
| 83-1 | 0.5% SF in 10 mM phosphate, pH 7.4 | 5 | — | — |
| 83-2 | 1% SF in 10 mM phosphate, pH 7.4 | 10 | — | — |
| 83-3 | 2.5% SF in 10 mM phosphate, pH 7.4 | 25 | — | — |
| 83-4 | 5% SF in 10 mM phosphate, pH 7.4 | 50 | — | — |
| 83-5 | 5% SF, 10 mM sucrose in 10 mM phosphate, pH 7.4 | 50 | Sucrose | 10 |
| 83-6 | 5% SF, 50 mM sucrose in 10 mM phosphate, pH 7.4 | 50 | Sucrose | 50 |
| 83-7 | 5% SF, 100 mM sucrose in 10 mM phosphate, pH 7.4 | 50 | Sucrose | 100 |
| 83-8 | 5% SF, 150 mM sucrose in 10 mM phosphate, pH 7.4 | 50 | Sucrose | 150 |
| 83-9 | 5%SF, 10 mM trehalose in 10 mM phosphate, pH 7.4 | 50 | Trehalose | 10 |
| 83-10 | 5% SF, 50 mM trehalose in 10 mM phosphate, pH 7.4 | 50 | Trehalose | 50 |
| 83-11 | 5% SF, 100 mM trehalose in 10 mM phosphate, pH 7.4 | 50 | Trehalose | 100 |
| 83-12 | 5% SF, 150 mM trehalose in 10 mM phosphate, pH 7.4 | 50 | Trehalose | 150 |

The silk batch number 83 had a concentration of dialyzed silk fibroin of 5.9% as determined using UV-Vis assessment. The phosphate stock buffer (100 mM) was prepared by combining 20 mL of 100 mM monobasic potassium phosphate and 80 mL of 100 mM dibasic potassium phosphate and adjusting the pH to 7.4 using the 100 mM mono or dibasic phosphate solutions. The 1 M sucrose, 67 mM phosphate stock was prepared by dissolving 3.42 g sucrose in 6.7 mL of 100 mM phosphate buffer and filling up to 10 mL with DI water. The 0.67 M sucrose, 67 mM phosphate stock was prepared by dissolving 2.29 g of sucrose in 6.7 mL of 100 mM phosphate buffer and filling up to 10 mL with DI water. The 1 M sucrose stock was prepared by dissolving 3.42 g of sucrose in 6.7 mL of DI water and filling up to 10 mL with DI water. The 1 M trehalose, 67 mM phosphate stock was prepared by dissolving 3.42 g of trehalose in 6.7 mL of 100 mM phosphate buffer and filing up to 10 mL with DI water. The 0.67 M trehalose, 67 mM phosphate stock was prepared by dissolving 3.42 g of trehalose in 6.7 mL of 100 mM phosphate buffer and filing up to 10 mL with DI water. The 1 M trehalose stock was prepared by dissolving 3.42 g of trehalose in 6 mL DI water and filling up to 10 mL with DI water.

Each of the formulations was prepared as follows. Sample 83-1 (0.5% SF in 10 mM phosphate, pH 7.4) was prepared by adding 2.54 mL 5.9% silk fibroin stock, 3 mL 100 mM phosphate. pH 7.4, and 24.46 mL DI water in a 50 cc conical tube. Sample 83-2 (1% SF in 10 mM phosphate, pH 7.4) was prepared by adding 5.08 mL 5.9% silk fibroin stock, 3 mL 100 mM phosphate, pH 7.4, and 21.92 mL DI water in a 50 cc conical tube. Sample 83-3 (2.5% SF in 10 mM phosphate, pH 7.4) was prepared by adding 12.7 mL 5.9% silk fibroin stock, 3 mL 100 mM phosphate, pH 7.4, and 14.3 mL DI water in a 50 cc conical tube. Sample 83-4 (5% SF in 10 mM phosphate, pH 7.4) was prepared by adding 25.4 mL 5.9% silk fibroin stock, 3 mL 100 mM phosphate, pH 7.4, and 1.6 mL DI water in a 50 cc conical tube. Sample 83-5 (5% SF, 10 mM sucrose in 10 mM phosphate, pH 7.4) was prepared by adding 25.4 mL 5.9% silk fibroin stock, 3 mL 100 mM phosphate, pH 7.4, 300 µL 1M sucrose, and 1.3 mL DI water in a 50 cc conical tube. Sample 83-6 (5% SF, 50 mM sucrose in 10 mM phosphate, pH 7.4) was prepared by adding 25.4 mL 5.9% silk fibroin stock, 3 mL 100 mM phosphate, pH 7.4, 1.5 mL 1M sucrose, and 100 µL DI water in a 50 cc conical tube. Sample 83-7 (5% SF, 100 mM sucrose in 10 mM phosphate, pH 7.4) was prepared by adding 25.4 mL 5.9% silk fibroin stock, 4.5 mL 0.67M sucrose, 67 mM phosphate buffer, and 100 µL DI water in a 50 cc conical tube. Sample 83-8 (5% SF, 150 mM sucrose in 10 mM phosphate, pH 7.4) was prepared by adding 25.4 mL 5.9% silk fibroin stock, 4.5 mL 1M sucrose, 67 mM phosphate buffer, and 100 µL DI water in a 50 cc conical tube. Sample 83-9 (5% SF, 10 mM trehalose in 10 mM phosphate, pH 7.4)

was prepared by adding 25.4 mL 5.9% silk fibroin stock, 3 mL 100 mM phosphate, pH 7.4, 300 μL 1M trehalose, and 1.3 mL DI water in a 50 cc conical tube. Sample 83-10 (5% SF, 50 mM trehalose in 10 mM phosphate, pH 7.4) was prepared by adding 25.4 mL 5.9% silk fibroin stock, 3 mL 100 mM phosphate, pH 7.4, 1.5 mL 1M trehalose, and 100 μL DI water in a 50 cc conical tube. Sample 83-11 (5% SF, 100 mM trehalose in 10 mM phosphate, pH 7.4) was prepared by adding 25.4 mL 5.9% silk fibroin stock, 4.5 mL 0.67M trehalose, 67 mM phosphate buffer, and 100 μL DI water in a 50 cc conical tube. Sample 83-12 (5% SF, 150 mM trehalose in 10 mM phosphate, pH 7.4) was prepared by adding 25.4 mL 5.9% silk fibroin stock, 4.5 mL 1M trehalose, 67 mM phosphate buffer, and 100 μL DI water in a 50 cc conical tube.

The rheology results and the size exclusion chromatography (SEC) results are presented in Table 44 and Table 45, respectively. In all conditions, the rheological properties of the silk fibroin solutions remained the same or showed a slight increase following freeze/thaw. The molecular weight by SEC did not change following freeze/thaw however, a very slight increase in aggregation was observed for all samples. When sucrose or trehalose was used as an excipient, aggregation was shown to remain the same or decrease compared the control (no cryoprotectant at 5% w/v).

TABLE 44

Rheological properties after freeze thaw

| Sample No. | Frozen | Viscosity (Pa*s) | | G' (Pa) | | G'' (Pa) | | Phase Angle (°) | |
|---|---|---|---|---|---|---|---|---|---|
| | | Avg. | Standard Dev. | Avg. | Standard Dev. | Avg. | Standard Dev. | Avg. | Standard Dev. |
| 83-1 | — | — | — | — | — | — | — | — | — |
| 83-1 | Y | — | — | — | — | — | — | — | — |
| 83-2 | — | 208.24 | 10.52 | 1.07E+00 | 7.56E-02 | 7.49E-01 | 2.55E-02 | 34.99 | 1.99 |
| 83-2 | Y | 265.7 | 39.98 | 1.32E+00 | 1.21E-01 | 1.01E+00 | 2.54E-01 | 37.1 | 4.24 |
| 83-3 | — | — | — | — | — | — | — | — | — |
| 83-3 | Y | — | — | — | — | — | — | — | — |
| 83-4 | — | 86.71 | 7.93 | 4.11E-01 | 4.73E-02 | 3.57E-01 | 2.74E-02 | 41.11 | 2.41 |
| 83-4 | Y | 120.28 | 15.33 | 5.48E-01 | 6.75E-02 | 5.19E-01 | 7.26E-02 | 43.69 | 1.75 |
| 83-5 | — | 118.53 | 11.54 | 5.74E-01 | 6.46E-02 | 4.73E-01 | 4.48E-02 | 39.57 | 2.35 |
| 83-5 | Y | 122.43 | 34.8 | 5.60E-01 | 1.47E-01 | 5.26E-01 | 1.64E-01 | 43.11 | 2.12 |
| 83-6 | — | — | — | — | — | — | — | — | — |
| 83-6 | Y | 134.4 | 1.76 | 6.40E-01 | 5.47E-02 | 5.47EE01 | 5.07E-02 | 40.67 | 5.03 |
| 83-7 | — | 82.57 | 10.4 | 3.92E-01 | 6.08E-02 | 3.39E-01 | 3.53E-02 | 41.01 | 2.92 |
| 83-7 | Y | 108.28 | 7.24 | 5.04E-01 | 4.65E-02 | 4.55E-01 | 4.39E-02 | 42.28 | 3.87 |
| 83-8 | — | 94.85 | 11.97 | 4.52E-01 | 7.23E-02 | 3.87E-01 | 4.19E-02 | 40.82 | 3.53 |
| 83-8 | Y | 112.06 | 32.05 | 5.22E-01 | 1.57E-01 | 4.71E-01 | 1.28E-01 | 42.43 | 1.1 |
| 83-9 | — | 84.11 | 10.1 | 3.95E-01 | 5.80E-02 | 3.50E-01 | 3.68E-02 | 41.66 | 2.93 |
| 83-9 | Y | 130.05 | 15.31 | 6.09E-01 | 7.05E-02 | 5.43E-01 | 6.83E-02 | 41.88 | 1.4 |
| 83-10 | — | 79.88 | 9.05 | 3.49E-01 | 6.10E-02 | 3.57E-0 | 4.44E-02 | 45.84 | 5.67 |
| 83-10 | Y | 105.12 | 30.49 | 4.74E-01 | 1.36E-01 | 4.58E-01 | 1.40E-01 | 44.22 | 3.07 |
| 83-11 | — | 70.31 | 8.22 | 3.26E-01 | 4.58E-02 | 2.97E-01 | 3.46E-02 | 42.5 | 3.28 |
| 83-11 | Y | 92.24 | 44.09 | 4.36E-01 | 1.95E-01 | 3.79E-01 | 2.00E-01 | 40.63 | 3.51 |
| 83-12 | — | 80.52 | 9.49 | 3.75E-01 | 6.29E-02 | 3.37E-01 | 3.00E-02 | 42.25 | 4.2 |
| 83-12 | Y | 113.08 | 17.18 | 5.32E-01 | 7.895-02 | 4.70E-01 | 7.47E-02 | 41.64 | 0.93 |

TABLE 45

Molecular weight and aggregation after freeze thaw

| Sample No. | Frozen | MW (Da) | | Aggregation (%) | |
|---|---|---|---|---|---|
| | | Avg. | Standard Dev. | Avg. | Standard Dev. |
| 83-1 | — | — | — | — | — |
| 83-1 | Y | 22730 | 166 | 0.17 | 0.01 |
| 83-2 | — | — | — | — | — |
| 83-2 | Y | 22768 | 162 | 0.25 | 0.09 |
| 83-3 | — | — | — | — | — |
| 83-3 | Y | 22659 | 229 | 0.11 | 0.04 |
| 83-4 | — | 23175 | — | 0.00 | — |
| 83-4 | Y | 22688 | 77 | 0.08 | 0.03 |
| 83-5 | — | 23151 | — | 0.00 | — |
| 83-5 | Y | 22491 | 595 | 0.09 | 0.03 |
| 83-6 | — | — | — | — | — |
| 83-6 | Y | 22377 | 408 | 0.08 | 0.05 |
| 83-7 | — | 23004 | — | 0.00 | — |
| 83-7 | Y | 22815 | 503 | 0.07 | 0.01 |
| 83-8 | — | 22955 | — | 0.00 | — |
| 83-8 | Y | 22818 | 224 | 0.07 | 0.05 |
| 83-9 | — | 23175 | — | 0.02 | — |
| 83-9 | Y | 22296 | 648 | 0.06 | 0.04 |
| 83-10 | — | 23102 | — | 0.00 | — |
| 83-10 | Y | 2.2506 | 555 | 0.18 | 0.09 |
| 83-11 | — | 23028 | — | 0.00 | — |
| 83-11 | Y | 22583 | 402 | 0.10 | 0.02 |
| 83-12 | — | 23004 | — | 0.00 | — |
| 83-12 | Y | 22486 | 325 | 0.06 | 0.02 |

EQUIVALENTS AND SCOPE

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure. The present disclosure is further illustrated by the following nonlimiting examples.

The invention claimed is:

1. A silk-based product (SBP) for ocular lubrication comprising processed silk fibroin, and optionally at least one ocular therapeutic agent,
   wherein the processed silk fibroin has been degummed, dissolved in 5-13 M lithium bromide, and stressed by heating the silk fibroin to 60° C. or autoclaving the silk fibroin,
   wherein a 0.05 to 5% w/v solution of the processed silk fibroin has a surface tension of between about 30 mN/m and 60 mN/n, and
   wherein a 0.05 to 5% w/v solution of the processed silk fibroin has a viscosity of between 30-400 cP.

2. The SBP of claim 1, wherein the SBP comprises from about 1% to about 5% (w/v) of silk fibroin.

3. The SBP of claim 1, wherein the SBP comprises one or more excipients.

4. The SBP of claim 3, wherein one or more of the excipients is selected from the group consisting of phosphate buffer, phosphate buffered saline, and sucrose.

5. The SBP of claim 1, wherein the at least one ocular therapeutic agent is a nonsteroidal anti-inflammatory drug (NSAID) or a protein.

6. The SBP of claim 5, wherein the SBP is formulated for ocular administration.

7. A method of treating an ocular indication of a subject comprising administering to the subject the SBP in claim 1.

8. The method of claim 7, wherein the ocular indication is dry eye disease.

9. The method of claim 8, wherein the SBP is administered to the eye.

10. The method of claim 9, wherein the SBP is administered via topical administration and wherein the topical administration of SBP is as drops or sprays.

11. The SBP formulation of claim 6, wherein the silk fibroin is present at a concentration between 0.5% and 5%.

12. The SBP formulation of claim 11, wherein the silk fibroin is in a solution selected from the group consisting of phosphate buffer, borate buffer, and phosphate buffered saline.

13. The SBP formulation of claim 12, wherein the solution further comprises propylene glycol.

14. The SBP formulation of claim 13, wherein the solution comprises propylene glycol at a concentration of 1%.

15. The SBP formulation of claim 12, wherein the solution further comprises sucrose.

16. The SBP formulation of claim 15, wherein the solution comprises sucrose at a concentration selected from the group consisting of 10 mM, 50 mM, 100 mM and 150 mM.

17. The SBP formulation of claim 12, wherein the solution further comprises trehalose.

18. The SBP formulation of claim 17, wherein the solution comprises trehalose at a concentration selected from the group consisting of 10 mM, 50 mM, 100 mM and 150 mM.

* * * * *